US008946460B2

(12) United States Patent  
Petrie et al.

(10) Patent No.: US 8,946,460 B2  
(45) Date of Patent: Feb. 3, 2015

(54) PROCESS FOR PRODUCING POLYUNSATURATED FATTY ACIDS IN AN ESTERIFIED FORM

(71) Applicants: James Robertson Petrie, Goulburn (AU); Surinder Pal Singh, Downer (AU); Robert Charles de Feyter, Monash (AU)

(72) Inventors: James Robertson Petrie, Goulburn (AU); Surinder Pal Singh, Downer (AU); Robert Charles de Feyter, Monash (AU)

(73) Assignees: Commonwealth Scientific and Industrial Research Organisation, Campbell (AU); Grains Research and Development Corporation, Barton (AU); Nuseed Pty Ltd, Laverton (AU)

( * ) Notice: Subject to any disclaimer, the term of this patent is extended or adjusted under 35 U.S.C. 154(b) by 0 days.

(21) Appl. No.: 13/918,392

(22) Filed: Jun. 14, 2013

(65) Prior Publication Data

US 2013/0338387 A1    Dec. 19, 2013

Related U.S. Application Data

(60) Provisional application No. 61/782,680, filed on Mar. 14, 2013, provisional application No. 61/697,676, filed on Sep. 6, 2012, provisional application No. 61/663,344, filed on Jun. 22, 2012, provisional application No. 61/660,392, filed on Jun. 15, 2012.

(51) Int. Cl.
| | |
|---|---|
| *C07C 67/00* | (2006.01) |
| *A23D 9/00* | (2006.01) |
| *C11B 1/00* | (2006.01) |
| *C11C 3/06* | (2006.01) |
| *C11C 3/00* | (2006.01) |

(52) U.S. Cl.
CPC ...... *C11B 1/00* (2013.01); *C11C 3/06* (2013.01); *C11C 3/003* (2013.01)
USPC ............................ 554/124; 554/224; 554/170

(58) Field of Classification Search
None
See application file for complete search history.

(56) References Cited

U.S. PATENT DOCUMENTS

| | | | |
|---|---|---|---|
| 4,399,216 | A | 8/1983 | Axel et al. |
| 5,004,863 | A | 4/1991 | Umbeck |
| 5,104,310 | A | 4/1992 | Saltin |
| 5,159,135 | A | 10/1992 | Umbeck et al. |
| 5,177,010 | A | 1/1993 | Goldman et al. |
| 5,362,865 | A | 11/1994 | Austin |
| 5,416,011 | A | 5/1995 | Hinchee et al. |
| 5,451,513 | A | 9/1995 | Maliga et al. |

(Continued)

FOREIGN PATENT DOCUMENTS

| | | |
|---|---|---|
| AU | 667939 | 1/1994 |
| AU | 776417 | 9/2004 |

(Continued)

OTHER PUBLICATIONS

Gul M.K., et al., Sterols and the phytosterol conent of oil seed rape (*Brassica napus* L.), 2006, Journal of Cell and Molecular Biology, vol. 5, pp. 71-79.*

(Continued)

*Primary Examiner* — Yate K Cutliff
(74) *Attorney, Agent, or Firm* — John P. White; Gary J. Gershik; Cooper & Dunham LLP

(57) ABSTRACT

The present invention relates to a process for producing ethyl esters of polyunsaturated fatty acids, comprising transesterifying triacylglycerols in extracted plant lipid.

43 Claims, 21 Drawing Sheets

(56) References Cited

U.S. PATENT DOCUMENTS

Figure 1:
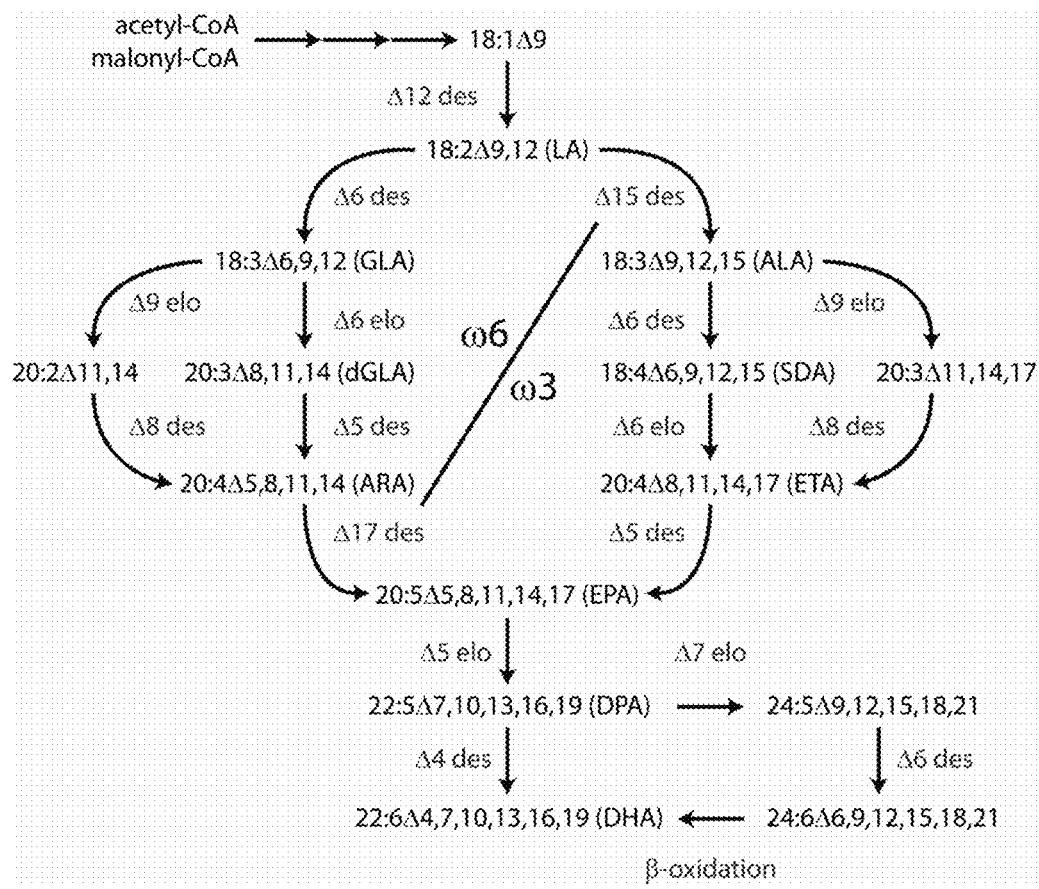

| | | |
|---|---|---|
| 5,463,174 A | 10/1995 | Moloney et al. |
| 5,504,200 A | 4/1996 | Hall et al. |
| 5,518,908 A | 5/1996 | Corbin et al. |
| 5,545,818 A | 8/1996 | McBride et al. |
| 5,569,834 A | 10/1996 | Hinchee et al. |
| 5,589,617 A | 12/1996 | Nehra et al. |
| 5,608,152 A | 3/1997 | Kridl et al. |
| 5,614,393 A | 3/1997 | Thomas et al. |
| 5,663,068 A | 9/1997 | Thomas et al. |
| 5,668,299 A | 9/1997 | Debonte et al. |
| 5,683,898 A | 11/1997 | Yazawa et al. |
| 5,689,050 A | 11/1997 | Thomas et al. |
| 5,789,220 A | 8/1998 | Thomas et al. |
| 5,798,259 A | 8/1998 | Yazawa et al. |
| 5,859,347 A | 1/1999 | Brown et al. |
| 5,877,402 A | 3/1999 | Maliga et al. |
| 5,932,479 A | 8/1999 | Daniell et al. |
| 5,952,544 A | 9/1999 | Browse et al. |
| 5,968,809 A | 10/1999 | Knutzon et al. |
| 5,972,664 A | 10/1999 | Knutzon et al. |
| 6,051,754 A | 4/2000 | Knutzon et al. |
| 6,075,183 A | 6/2000 | Knutzon et al. |
| 6,100,447 A | 8/2000 | Wu et al. |
| 6,136,574 A | 10/2000 | Knutzon et al. |
| 6,140,486 A | 10/2000 | Facciotti et al. |
| 6,194,167 B1 | 2/2001 | Browse et al. |
| 6,342,658 B1 | 1/2002 | DeBonte et al. |
| 6,355,861 B1 | 3/2002 | Thomas et al. |
| 6,372,965 B1 | 4/2002 | Lightner et al. |
| 6,403,349 B1 | 6/2002 | Mukerji et al. |
| 6,410,288 B1 | 6/2002 | Knutzon et al. |
| 6,428,990 B1 | 8/2002 | Mukerji et al. |
| 6,432,684 B1 | 8/2002 | Mukerji et al. |
| 6,459,018 B1 | 10/2002 | Knutzon et al. |
| 6,492,108 B1 | 12/2002 | Hillman et al. |
| 6,541,257 B2 | 4/2003 | Lemaux et al. |
| 6,566,583 B1 * | 5/2003 | Facciotti et al. ............... 800/281 |
| 6,589,767 B1 | 7/2003 | Knutzon et al. |
| 6,620,986 B1 | 9/2003 | McKeon et al. |
| 6,635,451 B2 | 10/2003 | Mukerji et al. |
| 6,677,145 B2 | 1/2004 | Mukerji et al. |
| 6,683,232 B1 | 1/2004 | Thomas et al. |
| 6,686,185 B1 | 2/2004 | Logan et al. |
| 6,825,017 B1 | 11/2004 | Browse et al. |
| 6,825,335 B1 | 11/2004 | Marin et al. |
| 6,838,594 B1 | 1/2005 | Kinney et al. |
| 6,858,416 B2 | 2/2005 | Mukerji et al. |
| 6,864,077 B1 | 3/2005 | Cahoon et al. |
| 6,875,595 B2 | 4/2005 | Kloek et al. |
| 6,884,921 B2 | 4/2005 | Browse et al. |
| 6,897,050 B1 | 5/2005 | Napier |
| 6,913,916 B1 | 7/2005 | Mukerji et al. |
| 6,958,229 B2 | 10/2005 | Suzuki et al. |
| 6,967,243 B2 | 11/2005 | Debonte et al. |
| 7,001,772 B2 | 2/2006 | Roessler et al. |
| 7,045,683 B2 | 5/2006 | Mukerji et al. |
| 7,067,285 B2 | 6/2006 | Mukerji et al. |
| 7,067,722 B2 | 6/2006 | Fillatti |
| 7,070,970 B2 | 7/2006 | Mukerji et al. |
| 7,081,356 B2 | 7/2006 | Putten et al. |
| 7,087,432 B2 | 8/2006 | Qiu et al. |
| 7,091,005 B2 | 8/2006 | Petruhkin et al. |
| 7,109,392 B1 | 9/2006 | Broglie et al. |
| 7,135,614 B1 | 11/2006 | DeBonte et al. |
| 7,135,623 B1 | 11/2006 | Rusing et al. |
| 7,148,336 B2 | 12/2006 | Fillatti |
| 7,179,620 B2 | 2/2007 | Petrukhin et al. |
| 7,179,647 B2 | 2/2007 | Lerchl et al. |
| 7,189,559 B2 | 3/2007 | Damude et al. |
| 7,192,762 B2 | 3/2007 | Macool et al. |
| 7,198,937 B2 | 4/2007 | Xue et al. |
| 7,208,590 B2 | 4/2007 | Mukerji et al. |
| 7,211,418 B2 | 5/2007 | Metz et al. |
| 7,211,656 B2 | 5/2007 | Mukerji et al. |
| 7,214,853 B2 | 5/2007 | Facciotti et al. |
| 7,217,856 B2 | 5/2007 | Weaver et al. |
| 7,220,897 B2 | 5/2007 | Mukerji et al. |
| 7,241,619 B2 | 7/2007 | Mukerji et al. |
| 7,244,563 B2 | 7/2007 | Cahoon et al. |
| 7,247,461 B2 | 7/2007 | Metz et al. |
| 7,256,033 B2 | 8/2007 | Damude et al. |
| 7,262,343 B1 | 8/2007 | DeBonte et al. |
| 7,271,315 B2 | 9/2007 | Metz et al. |
| 7,273,746 B2 | 9/2007 | Yadav et al. |
| 7,402,735 B2 | 7/2008 | Browse et al. |
| 7,411,054 B2 | 8/2008 | Meyers et al. |
| 7,504,259 B2 | 3/2009 | Yadav et al. |
| 7,537,920 B2 | 5/2009 | Renz et al. |
| 7,550,651 B2 | 6/2009 | Damude et al. |
| 7,589,253 B2 | 9/2009 | Green et al. |
| 7,615,679 B2 | 11/2009 | Lerchl et al. |
| 7,619,105 B2 | 11/2009 | Green et al. |
| 7,659,120 B2 | 2/2010 | Yadav et al. |
| 7,709,239 B2 | 5/2010 | Damude et al. |
| 7,714,185 B2 | 5/2010 | Napier et al. |
| 7,736,884 B2 | 6/2010 | Gunnarsson et al. |
| 7,777,098 B2 | 8/2010 | Cirpus et al. |
| 7,807,849 B2 | 10/2010 | Singh et al. |
| 7,834,248 B2 | 11/2010 | Green et al. |
| 7,834,250 B2 | 11/2010 | Singh et al. |
| 7,838,651 B2 | 11/2010 | Picataggio et al. |
| 7,842,852 B2 | 11/2010 | Cirpus et al. |
| 7,855,321 B2 | 12/2010 | Renz et al. |
| 7,871,804 B2 | 1/2011 | Cirpus et al. |
| 7,879,591 B2 | 2/2011 | Damude et al. |
| 7,901,928 B2 | 3/2011 | Yadav et al. |
| 7,932,438 B2 | 4/2011 | Singh et al. |
| 8,071,341 B2 | 12/2011 | Singh et al. |
| 8,084,074 B2 | 12/2011 | Kinney et al. |
| 8,106,226 B2 | 1/2012 | Singh et al. |
| 8,158,392 B1 | 4/2012 | Singh et al. |
| 8,288,572 B2 | 10/2012 | Singh et al. |
| 8,535,917 B2 | 9/2013 | Singh et al. |
| 8,575,377 B2 | 11/2013 | Singh et al. |
| 8,778,644 B2 | 7/2014 | Singh et al. |
| 8,809,559 B2 | 8/2014 | Petrie et al. |
| 8,816,106 B2 | 8/2014 | Damcevski et al. |
| 8,816,111 B2 | 8/2014 | Petrie et al. |
| 2001/0023259 A1 | 9/2001 | Slabas et al. |
| 2002/0009779 A1 | 1/2002 | Meyers et al. |
| 2002/0042933 A1 | 4/2002 | Browse et al. |
| 2002/0065406 A1 | 5/2002 | Meyers et al. |
| 2002/0076786 A1 | 6/2002 | Curtis et al. |
| 2002/0104124 A1 | 8/2002 | Green |
| 2002/0107373 A1 | 8/2002 | Curtis et al. |
| 2002/0108147 A1 | 8/2002 | Thomas et al. |
| 2002/0111307 A1 | 8/2002 | Glucksmann et al. |
| 2002/0115178 A1 | 8/2002 | Meyers et al. |
| 2002/0138874 A1 | 9/2002 | Mukerji et al. |
| 2002/0146784 A1 | 10/2002 | Suzuki et al. |
| 2002/0156254 A1 | 10/2002 | Qiu et al. |
| 2002/0170090 A1 | 11/2002 | Browse et al. |
| 2002/0194641 A1 | 12/2002 | Metz et al. |
| 2003/0033633 A1 | 2/2003 | Lightner et al. |
| 2003/0077747 A1 | 4/2003 | Hillman et al. |
| 2003/0079250 A1 | 4/2003 | Fillatti et al. |
| 2003/0082754 A1 | 5/2003 | Mukerji et al. |
| 2003/0084480 A1 | 5/2003 | Fillatti et al. |
| 2003/0101486 A1 | 5/2003 | Facciotti et al. |
| 2003/0104596 A1 | 6/2003 | Mukerji et al. |
| 2003/0131379 A1 | 7/2003 | DeBonte et al. |
| 2003/0134400 A1 | 7/2003 | Mukerji et al. |
| 2003/0152983 A1 | 8/2003 | Napier et al. |
| 2003/0157144 A1 | 8/2003 | Mukerji et al. |
| 2003/0159164 A1 | 8/2003 | Kopchick et al. |
| 2003/0159173 A1 | 8/2003 | Wolter et al. |
| 2003/0163844 A1 | 8/2003 | Lightner et al. |
| 2003/0163845 A1 | 8/2003 | Mukerji et al. |
| 2003/0166207 A1 | 9/2003 | Roessler et al. |
| 2003/0167525 A1 | 9/2003 | Mukerji et al. |
| 2003/0172398 A1 | 9/2003 | Browsse et al. |
| 2003/0172399 A1 | 9/2003 | Fillatti et al. |
| 2003/0177508 A1 | 9/2003 | Mukerji et al. |
| 2003/0190733 A1 | 10/2003 | Mukerji et al. |

(56) References Cited

U.S. PATENT DOCUMENTS

| | | |
|---|---|---|
| 2003/0196217 A1 | 10/2003 | Mukerji et al. |
| 2004/0009501 A1 | 1/2004 | Curtis et al. |
| 2004/0049805 A1 | 3/2004 | Lerchl et al. |
| 2004/0053234 A1 | 3/2004 | Winther et al. |
| 2004/0053379 A1 | 3/2004 | Lerchl et al. |
| 2004/0067226 A1 | 4/2004 | Petrukhin et al. |
| 2004/0078845 A1 | 4/2004 | Thomas et al. |
| 2004/0086899 A1 | 5/2004 | Winther et al. |
| 2004/0098762 A1 | 5/2004 | Fillatti et al. |
| 2004/0111763 A1 | 6/2004 | Heinz et al. |
| 2004/0157221 A9 | 8/2004 | Curtis et al. |
| 2004/0172682 A1 | 9/2004 | Kinney et al. |
| 2004/0180414 A1 | 9/2004 | Putten et al. |
| 2004/0195512 A1 | 10/2004 | Crosetto et al. |
| 2004/0221335 A1 | 11/2004 | Shewmaker et al. |
| 2004/0224413 A1 | 11/2004 | Cahoon et al. |
| 2004/0235127 A1 | 11/2004 | Metz et al. |
| 2005/0003442 A1 | 1/2005 | Mukerji et al. |
| 2005/0005328 A1 | 1/2005 | Mukerji et al. |
| 2005/0005329 A1 | 1/2005 | Mukerji et al. |
| 2005/0009140 A1 | 1/2005 | Mukerji et al. |
| 2005/0089865 A1 | 4/2005 | Napier et al. |
| 2005/0089879 A1 | 4/2005 | Feussner et al. |
| 2005/0089981 A1 | 4/2005 | Napier et al. |
| 2005/0100995 A1 | 5/2005 | Weaver et al. |
| 2005/0112719 A1 | 5/2005 | Roessler et al. |
| 2005/0164192 A1 | 7/2005 | Graham et al. |
| 2005/0166271 A1 | 7/2005 | Feubner et al. |
| 2005/0214761 A1 | 9/2005 | Lerchl et al. |
| 2005/0262588 A1 | 11/2005 | Dehesh et al. |
| 2005/0262589 A1 | 11/2005 | Fillatti et al. |
| 2005/0262591 A1 | 11/2005 | Debonte et al. |
| 2005/0266440 A1 | 12/2005 | Metz et al. |
| 2005/0273883 A1 | 12/2005 | Metz et al. |
| 2005/0273884 A1 | 12/2005 | Metz et al. |
| 2005/0273885 A1* | 12/2005 | Singh et al. ............... 800/281 |
| 2006/0014268 A1 | 1/2006 | Suzuki et al. |
| 2006/0078973 A1 | 4/2006 | Renz et al. |
| 2006/0094088 A1 | 5/2006 | Picataggio et al. |
| 2006/0094092 A1 | 5/2006 | Damude et al. |
| 2006/0094102 A1 | 5/2006 | Xue et al. |
| 2006/0110806 A1 | 5/2006 | Damude et al. |
| 2006/0115881 A1 | 6/2006 | Damude et al. |
| 2006/0117414 A1 | 6/2006 | Qiu et al. |
| 2006/0156435 A1 | 7/2006 | Ursin et al. |
| 2006/0168687 A1 | 7/2006 | Renz et al. |
| 2006/0174376 A1 | 8/2006 | Renz et al. |
| 2006/0191042 A1 | 8/2006 | Fillatti et al. |
| 2006/0195939 A1 | 8/2006 | Damude et al. |
| 2006/0205047 A1 | 9/2006 | Putten et al. |
| 2006/0206961 A1 | 9/2006 | Cirpus et al. |
| 2006/0206963 A1 | 9/2006 | Voelker et al. |
| 2006/0218668 A1 | 9/2006 | Cirpus et al. |
| 2006/0246556 A1* | 11/2006 | Napier et al. ............... 435/128 |
| 2007/0028326 A1 | 2/2007 | Cirpus et al. |
| 2007/0059730 A1 | 3/2007 | Curtis et al. |
| 2007/0061921 A1 | 3/2007 | Graham et al. |
| 2007/0118929 A1 | 5/2007 | Damude et al. |
| 2007/0163002 A1 | 7/2007 | DeBonte et al. |
| 2007/0192902 A1 | 8/2007 | Qiu et al. |
| 2007/0220634 A1 | 9/2007 | Metz et al. |
| 2007/0224661 A1 | 9/2007 | Cirpus et al. |
| 2007/0238648 A1 | 10/2007 | Brownlie et al. |
| 2007/0244192 A1 | 10/2007 | Metz |
| 2007/0245431 A1 | 10/2007 | Metz et al. |
| 2007/0259355 A1 | 11/2007 | Luy et al. |
| 2007/0261138 A1 | 11/2007 | Graham et al. |
| 2007/0270494 A1 | 11/2007 | Metz et al. |
| 2007/0294790 A1 | 12/2007 | Graham et al. |
| 2008/0005811 A1 | 1/2008 | Metz et al. |
| 2008/0022422 A1 | 1/2008 | Weaver et al. |
| 2008/0057495 A1 | 3/2008 | Ohyama et al. |
| 2008/0063691 A1 | 3/2008 | Ursin et al. |
| 2008/0076166 A1 | 3/2008 | Cirpus et al. |
| 2008/0155705 A1 | 6/2008 | Zank et al. |
| 2008/0160054 A1 | 7/2008 | Heinz et al. |
| 2008/0214667 A1 | 9/2008 | Das et al. |
| 2008/0220143 A1 | 9/2008 | Kinney et al. |
| 2008/0220500 A1 | 9/2008 | Winther et al. |
| 2008/0241133 A1 | 10/2008 | Curtis et al. |
| 2008/0254191 A1 | 10/2008 | Damude et al. |
| 2008/0254195 A1 | 10/2008 | Damude et al. |
| 2008/0260929 A1 | 10/2008 | Ursin et al. |
| 2008/0268539 A1 | 10/2008 | Singh et al. |
| 2009/0093033 A1 | 4/2009 | Luy et al. |
| 2009/0158462 A1 | 6/2009 | Cirpus et al. |
| 2009/0222951 A1 | 9/2009 | Cirpus et al. |
| 2009/0253188 A1 | 10/2009 | Zhu et al. |
| 2009/0320161 A1 | 12/2009 | McGonigle et al. |
| 2010/0088776 A1 | 4/2010 | Bauer et al. |
| 2010/0092640 A1 | 4/2010 | Ursin et al. |
| 2010/0189868 A1 | 7/2010 | Damude et al. |
| 2010/0227924 A1 | 9/2010 | Cirpus et al. |
| 2011/0015415 A1 | 1/2011 | Singh et al. |
| 2011/0016585 A1 | 1/2011 | Periera et al. |
| 2011/0039010 A1 | 2/2011 | Rein et al. |
| 2011/0054198 A1 | 3/2011 | Singh et al. |
| 2011/0059204 A1 | 3/2011 | Jackson et al. |
| 2011/0059496 A1 | 3/2011 | Zhu et al. |
| 2011/0190521 A1 | 8/2011 | Damcevski et al. |
| 2011/0201065 A1 | 8/2011 | Singh et al. |
| 2011/0269983 A1 | 11/2011 | Kinney et al. |
| 2012/0016144 A1 | 1/2012 | Petrie et al. |
| 2012/0041218 A1 | 2/2012 | Singh et al. |
| 2012/0083615 A1 | 4/2012 | Singh et al. |
| 2012/0215018 A1 | 8/2012 | Singh et al. |
| 2013/0060053 A1 | 3/2013 | Singh et al. |
| 2014/0011247 A1 | 1/2014 | Singh at al. |

FOREIGN PATENT DOCUMENTS

| | | |
|---|---|---|
| AU | 776447 | 9/2004 |
| AU | 2007/276257 | 1/2008 |
| AU | 2007276257 | 1/2008 |
| CA | 2092588 | 9/1994 |
| EP | 256223 | 2/1988 |
| EP | 275957 | 7/1988 |
| EP | 256223 | 2/1998 |
| JP | 2000/217582 | 8/2000 |
| JP | 2001/095588 | 4/2001 |
| JP | 2001/145490 | 5/2001 |
| JP | 2001/169780 | 6/2001 |
| JP | 2003/116566 | 4/2003 |
| WO | WO 84/02913 | 8/1984 |
| WO | WO 87/05327 | 9/1987 |
| WO | WO 91/02071 | 2/1991 |
| WO | WO 91/13980 | 9/1991 |
| WO | WO 93/06712 A1 | 4/1993 |
| WO | WO 93/23545 A1 | 11/1993 |
| WO | WO 95/15389 | 6/1995 |
| WO | WO 95/23230 | 8/1995 |
| WO | WO 96/21022 A2 | 7/1996 |
| WO | WO 97/06269 | 2/1997 |
| WO | WO 97/21340 | 6/1997 |
| WO | WO 97/48814 | 12/1997 |
| WO | WO 1997/48814 | 12/1997 |
| WO | WO 98/01565 A1 | 1/1998 |
| WO | WO 98/18952 A1 | 5/1998 |
| WO | WO 98/39468 A1 | 9/1998 |
| WO | WO 98/45461 | 10/1998 |
| WO | WO 98/46763 A1 | 10/1998 |
| WO | WO 98/46764 | 10/1998 |
| WO | WO 98/46764 A1 | 10/1998 |
| WO | WO 98/46765 A1 | 10/1998 |
| WO | WO 98/55625 | 12/1998 |
| WO | WO 98/56239 A1 | 12/1998 |
| WO | WO 99/05265 | 2/1999 |
| WO | WO 99/14314 | 3/1999 |
| WO | WO 99/16890 | 4/1999 |
| WO | WO 99/33958 A2 | 7/1999 |
| WO | WO 99/49050 A2 | 9/1999 |
| WO | WO 99/61602 A1 | 12/1999 |
| WO | WO 99/64614 A2 | 12/1999 |
| WO | WO 99/64616 A2 | 12/1999 |

(56) References Cited

FOREIGN PATENT DOCUMENTS

| | | |
|---|---|---|
| WO | WO 00/12720 A3 | 3/2000 |
| WO | WO 00/20602 A2 | 4/2000 |
| WO | WO 00/20603 A1 | 4/2000 |
| WO | WO 00/21557 A1 | 4/2000 |
| WO | WO 00/40705 A2 | 7/2000 |
| WO | WO 00/42195 A2 | 7/2000 |
| WO | WO 00/052183 | 9/2000 |
| WO | WO 00/53770 | 9/2000 |
| WO | WO 00/55330 A1 | 9/2000 |
| WO | WO 00/75341 A1 | 12/2000 |
| WO | WO 01/02591 A1 | 1/2001 |
| WO | WO 01/04636 A1 | 1/2001 |
| WO | WO 01/14538 | 3/2001 |
| WO | WO 01/14538 A2 | 3/2001 |
| WO | WO 01/20001 | 3/2001 |
| WO | WO 01/38484 | 5/2001 |
| WO | WO 01/38512 | 5/2001 |
| WO | WO 01/38512 A2 | 5/2001 |
| WO | WO 01/44485 A1 | 6/2001 |
| WO | WO 01/59128 | 8/2001 |
| WO | WO 01/66758 A2 | 9/2001 |
| WO | WO 01/70777 | 9/2001 |
| WO | WO 2001/70777 | 9/2001 |
| WO | WO 01/75069 A1 | 10/2001 |
| WO | WO 01/92489 A2 | 12/2001 |
| WO | WO 2001/96363 | 12/2001 |
| WO | WO 02/08401 | 1/2002 |
| WO | WO 02/08401 A2 | 1/2002 |
| WO | WO 02/26946 A2 | 4/2002 |
| WO | WO 02/081668 | 10/2002 |
| WO | WO 02/081668 A3 | 10/2002 |
| WO | WO 02/081702 A1 | 10/2002 |
| WO | WO 02/083869 A3 | 10/2002 |
| WO | WO 02/083870 A2 | 10/2002 |
| WO | WO 02/090493 A2 | 11/2002 |
| WO | WO 02/092540 A2 | 11/2002 |
| WO | WO 02/92540 A1 | 11/2002 |
| WO | WO 03/064596 A2 | 8/2003 |
| WO | WO 03/078639 | 9/2003 |
| WO | WO 03/093482 | 11/2003 |
| WO | WO 03/093482 A2 | 11/2003 |
| WO | WO 03/099216 | 12/2003 |
| WO | WO 03/102138 A2 | 12/2003 |
| WO | WO 2004/005442 | 1/2004 |
| WO | WO 2004/057001 | 7/2004 |
| WO | WO 2004/071467 | 8/2004 |
| WO | WO 2004/071467 A2 | 8/2004 |
| WO | WO 2004/087180 A1 | 10/2004 |
| WO | WO 2004/101757 | 11/2004 |
| WO | WO 2005/007845 A2 | 1/2005 |
| WO | WO 2005/012316 | 2/2005 |
| WO | WO 2005/12316 A2 | 2/2005 |
| WO | WO 2005/80578 A2 | 9/2005 |
| WO | WO 2005/083053 | 9/2005 |
| WO | WO 2005/83053 A2 | 9/2005 |
| WO | WO 2005/83093 A2 | 9/2005 |
| WO | WO 2005/97982 A2 | 10/2005 |
| WO | WO 2005/98033 A1 | 10/2005 |
| WO | WO 2005/103253 | 11/2005 |
| WO | WO 2005/118814 | 12/2005 |
| WO | WO 2006/008099 | 1/2006 |
| WO | WO 2006/019192 | 2/2006 |
| WO | WO 2006/064317 | 6/2006 |
| WO | WO 2006/069936 | 7/2006 |
| WO | WO 2007/005882 A2 | 1/2007 |
| WO | WO 2007/042510 | 4/2007 |
| WO | WO 2007/092460 A2 | 8/2007 |
| WO | WO 2007/127381 | 11/2007 |
| WO | WO 2007/133425 | 11/2007 |
| WO | WO 2007/137788 | 12/2007 |
| WO | WO 2008/009600 A1 | 1/2008 |
| WO | WO 2008/022963 | 2/2008 |
| WO | WO 2008/025068 | 6/2008 |
| WO | WO 2008/128241 | 10/2008 |
| WO | WO 2009/016202 | 2/2009 |
| WO | WO 2009/017821 | 2/2009 |
| WO | WO 2009/129582 | 10/2009 |
| WO | WO 2010/009500 | 1/2010 |
| WO | WO 2010/023202 | 3/2010 |
| WO | WO 2010/057246 | 5/2010 |
| WO | WO2010057246 | * 5/2010 ............ C12N 15/82 |
| WO | WO 2011/146524 | 11/2011 |
| WO | WO 2013/016546 | 1/2013 |
| WO | WO 2013/153404 | 10/2013 |

OTHER PUBLICATIONS

Marekov, I.B., et al., Sterol compositi of rapeseed varieties introduced in Bulgaria, 2009, Bulgarian Journal of AGricultural Science, 15 (No. 2), pp. 119-122.*

Aug. 16, 2013 Notice of Allowance, issued in connection with U.S. Appl. No. 13/651,275.

Marangoni and Rousseau (1995) "Engineering triacylglycerols: The role of interesterification" Trends in Food Science & Technology 6, 329-335.

Petrie et al (2010) "Rapid expression of transgenes driven by seed-specific constructs in leaf tissue: DHA production" Plant Methods 6:8, pp. 1-6.

Petrie et al (2012) "Transgenic production of arachidonic acid in oilseeds" Transgenic Res 21:139-147.

Ruiz-Lopez (2012) "Enhancing the accumulation of omega-3 long chain polyunsaturated fatty acids in transgenic *Arabidopsis thaliana* via iterative metabolic engineering and genetic crossing" Transgenic Res 21:1233-1243.

Sakuradani et al (1999) "Δ6-Fatty acid desaturase from an arachidonic acid-producing *Mortierella* fungus Gene cloning and its heterologous expression in a fungus, *Aspergillus*" Gene 238: 445-453.

Sakuradani et al (2005) "A novel fungal ω3-desaturase with wide substrate specificity from arachidonic acid-producing *Mortierella alpina* 1S-4" Appl Microbiol Biotechnol 66: 648-654.

Speranza and Macedo (2012) "Lipase-mediated production of specific lipids with improved biological and physicochemical properties" Process Biochemistry 47, 1699-1706.

Sperling et al (2001) "Functional Identification of a Δ5-Sphingolipid Desaturase from *Borago officinalis*" Archives of Biochemistry and Biophysics vol. 388, No. 2, pp. 293-298.

Venegas-Calerón et al (2010) "An alternative to fish oils: Metabolic engineering of oil-seed crops to produce omega-3 long chain polyunsaturated fatty acids" Progress in Lipid Research 49, 108-119.

Whitney et al (2003) "Functional characterisation of two cytochrome b5-fusion desaturases from *Anemone leveillei* the unexpected identification of a fatty acid Δ6-desaturase" Planta 217: 983-992.

Zhou et al (2008) "Isolation and functional characterization of two independently-evolved fatty acid Δ12-desaturase genes from insects" Insect Molecular Biology 17(6), 667-676.

Zhou et al (2007) "Isolation and characterization of genes from the marine microalga *Pavlova sauna* encoding three front-end desaturases involved in docosahexaenoic acid biosynthesis" Phytochemistry 68, 785-796.

Mar. 12, 2013 Office Action issued in connection with U.S. Appl. No. 12/310,645.

Mar. 22, 2012 Response filed in connection with U.S. Appl. No. 13/044,984.

May 17, 2012 Office Action issued in connection with U.S. Appl. No. 13/044,984.

Mar. 11, 2013 Office Action issued in connection with U.S. Appl. No. 13/651,275.

Apr. 15, 2013 Response filed in connection with U.S. Appl. No. 13/448,107.

Dec. 7, 2012 Office Action issued in connection with U.S. Appl. No. 13/448,107.

Jan. 7, 2013 Response filed in connection with U.S. Appl. No. 13/448,107.

Jan. 15, 2013 Office Action issued in connection with U.S. Appl. No. 13/448,107.

9, 2013 Notice of Allowance issued in connection with U.S. Appl. No. 13/448,107.

(56) References Cited

OTHER PUBLICATIONS

GenBank accession AAR20444, Periera et al. (2003).
GenBank accession AAV67797, Meyer et al. (2004).
GenBank accession AAV67799, Meyer et al. (2004).
GenBank accession AAV67800, Meyer et al. (2004).
GenBank accession AB094747, Grigoriev et al. (2007).
GenBank accession ABP49078, Li at al. (2007).
GenBank accession AF390174, Qi at al. (2001).
GenBank accession BAD11952, Oura and Kajiwara (2003).
GenBank accession CA158897, Zank at al. (2005).
GenBank accession XP_C01421073 Grigoriev at al. (2007).
Abdullah et al. (1986) "Efficient Plant Regeneration from Rice Protoplasts Through Somatic Embryogenesis" Biotech. 4:1087-90.
Bates at al. (2007) "Incorporation of Newly Synthesized Fatty Acids into Cytosolic Glycerolipids in Pea Leaves Occurs via Acyl Editing" J. Biol. Chem. 282:31206-31216.
Baumberger at al. (2007) "The Polerovirus Silencing Suppressor Po Targets Argonaute Proteins for Degradation" Curr, Biol. 17:1609-1614.
Bligh and Dyer (1959) "Orange-red Flesh in Cod and Haddock" Canadian J. Biochem. 37: 911-917.
Brodersen at al. (2008) "Widespread Translational Inhibition by Plant miRNAs and siRNAs" Science 320:1185-1190.
Brosnan at al. (2007) "Nuclear gene silencing directs reception of long-distance mRNA silencing in *Arabidopsis*" Proc. Natl. Acad. Sci U.S.A. 104:14741-14746.
Chapman et al. (2004) "Transgenic Cotton Plants with Increased Seed Oleic Acid Content" Gen. Dev. 18:1179-1186.
Cheng et al. (1996) "Production of fertile transgenic peanut (*Arachis hypogaea* L.) plants using *Agrobacterium tumefaciens*" Plant Cell Rep. 15:653-657.
Chung et al. (2006) "Effect of 5'UTR introns on gene expression in *Arabidopsis thaliana*" BMC Genomics 7:120.
Clapp (1993) "The 16-Kilodalton N-Terminal Fragment of Human Prolactin Is a Potent Inhibitor of Angiogenesis" Clin. Perinatol. 20:155-168.
Curiel at al. (1992) "High-Efficiency Gene Transfer Mediated by Adenovirus Coupled to DNA-Polylysine Complexes" Hum. Gen. Ther. 3:147-154.
Darji et all (1997) "Oral Somatic Transgene Vaccination Using Attenuated *S. typhimurium*" Cell 91:765-775.
Denic and Weissman (2007) "A Molecular Caliper Mechanism for Determining Very Long-Chain Fatty Acid Length" Cell 130:663-677.
Ding and Voinnet (2007) "Antiviral Immunity Directed by Small RNAs" Cell 130:413-426.
Fennelly et al. (1999) "Mucosal DNA Vaccine Immunization Against Measles with a Highly Attenuated *Shigella flexneri* Vector" J. Immuhol. 162:1603-1610.
Fraser et al. (2004) "Expression of the Isochrysis C18-$\Delta^9$ Polyunsaturated Fatty Acid Specific Elongase Component Alters *Arabidopsis* Glycerolipid Profiles" Plant Physiol 135:859-866.
Gleave (1992) "A versatile binary vector system with a T-DNA organisational structure conducive to efficient integration of cloned DNA into the plant genome" Plant Mol. Biol. 20:1203-1207.
Glevin et al (2003) "Agrobacterium-Mediated Plant Transformation: the Biology behind the 'Gene-Jockeying' Tool" Microbiol. Mol. Biol. Rev. 67:16-37.
Grant et al. (1995) "Transformation of peas (*Pisum sativum* L.) using immature cotyledons" Plant Cell Rep. 15:254-258.
Harayama (1998) "Artificial evolution by DNA shuffling" Trends Biotechnol. 16: 76-82.
Hense et al. (2001) "Eukaryotic expression plasmid transfer from the intracellular bacterium *Listeria* monocytogenes to host cells" Cell Microbiol. 3:599-609.
Hoffman et al (2007) "A Small Membrane-peripheral Region Close to the Active Center Determines Regioselectivity of Membrane-bound Fatty Acid Desaturases from *Aspergillus nidulans*" J. Biol. Chem. 282:26666-26674.

Huang et al. (2004) "How Insulin Binds: the B-Chain a-Helix Contacts the L1 b-Helix of the Insulin Receptor" J. Mol. Biol. 341:529-550.
Lacroix et al. (2008) "Association of the Agrobacterium T-DNA-protein complex with plant nucleosomes" Proc. Natl. Acad. Sci. U.S.A. 105: 15429-15434.
Lu et al. (1993) "High Efficiency Retroviral Mediated Gene Transduction into Single Isolated Immature and 1-Replatable $CD34^{3+}$ Hematopoietic Stem/Progenitor Cells from Human Umbilical Cord Blood" J. Exp. Med. 178:2089-2096.
Matzke et al. (2001) "RNA: Guiding Gene Silencing" Science 293:1086-1083.
Meng et al. (2008) "*Hibiscus chlorotic* ringspot virus coat protein inhibits trans-acting small interfering RNA biogenesis in *Arabidopsis*" J. Gen. Viral. 89:2349-2358.
Niedz et al (1995) "Green fluorescent protein: an in vivo reporter of plant gene expression" Plant Cell Reports. 14:403-406.
Ohlrogge and Jaworski (1997) "Regulation of Fatty Acid Synthesis" 48:109-136.
Petrie et al. (2010) "Isolation and Characterisation of a High-Efficiency Desaturase and Elongases from Microalgae for Transgenic LC-PUEA Production" Mar Biotechnol 12:430-438.
Potenza at al. (2004) "Targeting Transgene Expression in Research, Agricultural, and Environmental Applications: Promoters Used in Plant Transformation" In Vitro Cell Dev Biol.-Plant 40:1-22.
Rose at al. (1998) "Consensus-degenerate hybrid oligonucleotide primers for amplification of distantly related sequences" Nucleic Acids Res. 26:1628-1635.
Saha et al. (2006) "Cytosolic Triacylglycerol Biosynthetic Pathway in Oilseeds. Molecular Cloning and Expression of Peanut Cytosolic Diacylglycerol Acyltransferase" Plant Physiol. 141:1533-1543.
Sayanova et al. (2007) "Cloning and characterization of unusual fatty acid desaturases from *Anemone leveillei*: identification of an acyl-coenzyme a C20 Delta5-desaturase responsible for the synthesis of sciadonic acid" Plant Physiol 144:455-467.
Schubert et al. (2004) "Silencing in *Arabidopsis* T-DNA Transformants: The Predominant Role Of A Gene-Specific RNA Sensing Mechanism versus Position Effects" Plant Cell 16:2561-2572.
Suiyun et al. (2004) "Introgression of salt-tolerance from somatic hybrids between common wheat and *Thinapyrum ponticum*" Plant Science 773-779.
Stalker et al (1988) "Purification and Properties of a Nitrilase Specific for the Herbicide Bromoxynil and Corresponding Nucleotide Sequence Analysis of the *bxn* Gene" J. Biol. Chem. 263:6310-6314.
Thillet et el (1988) "Site-directed Mutagenesis of Mouse Dihydrofolate Reductase" J. Biol. Chem 263:12500-12508.
Toriyama et al. (1986) "Haploid and diploid plant regeneration from protoplasts of anther callus in rice" Theor. Appl. Genet. 205:34.
Tvrdik (2000) "Role of a New Mammalian Gene Family in the Biosynthesis of Very Long Chain Fatty Acids and Sphingolipids" J. Cell Biol. 149:707-718.
Tzfira & Citovsky (2006) "Agrobacterium-mediated genetic transformation of plants: biology and biotechnology" Curt. Opin. Biotech. 17:147-154.
Voinnet et al., (2003) "An enhanced transient expression system in plants based on suppression of gene silencing by the p19 protein of tomato bushy stunt virus" Plant J. 33:949-956.
Watts and Browse (1999b) "A Palmitoyl-CoA-Specific $\Delta 9$ Fatty Acid Desaturase from *Caenorhabditis elegans*" Arch. Biochem. Biophys. 362:175-182.
Yang et al. (2003) "Expression and localization of human lysozyme in the endosperm of transgenic rice" Planta. 216:597-603.
Zhang et al. (2006) "Cucumber mosaic virus-encoded 2b suppressor inhibits *Arabidopsis* Argonautel cleavage activity to counter plant defense" Genes & Development 20:3255-3268.
Zipfel et al. (2006) "Perception of the Bacterial PAMP EF-Tu by the Receptor EFR Restricts Agrobacterium-Mediated Transformation" Cell 125:749-760.
Abbadi, A., et al., (2004) "Biosynthesis Of Very-Long-Chain Polyunsaturated Fatty Acids In Transgenic Oilseeds: Constraints On Their Accumulation," The Plant Cell, 16(10): 2734-3748 al.

(56) References Cited

OTHER PUBLICATIONS

Darnude et al. (2006). Identification of bifunctional delta12/omega3 fatty acid desaturases for improving the ratio of omega3 to omega6 fatty acids in microbes and plants, Proc Natl Acad Sci USA 103: 9446-9451.

Domergue et al. (2002), Cloning and functional characterization of *Phaeodactylum tricornutum* front-end desaturases involved in eicosapentaenoic acid biosynthesis, Eur. J. Biochem. 269:4105-4113.

Domergue et al., (2003), Acyl Carriers Used as Substrates by the Desaturases and Elongases Involved in Very Long-chain Polyunsaturated Fatty Acids Biosynthesis Reconstituted in Yeast, J. Biol. Chem. 278; 35115-35126.

Domergue et al., In vivo characterization of the first acyl-CoA Δ6-desaturase from a member of the plant kingdom, the microalga *Ostreococcus tauri*, Biochem J. 2005, 389, 483-490.

Meyer, A., et al., (2003) Biosynthesis Of Docosahexaenoic Acid in *Euglena gracilis*: Biochemical And Molecular Evidence For The Involvement Of A Δ4-Fatty Acyl Group Desaturase, Biochemistry, 42(32): 9779-9788.

Meyer, A., et al., (2004) Novel Fatty Acid Elongases And Their Use For the Reconstitution Of Docosahexaenoic Acid Biosynthesis, Journal of Lipid Research, 45(10): 1899-1909.

Pereira et al. (2004b) Identification of two novel microalgal enzymes involved in the conversion of the omega3-fatty acid, eicosapentaenoic acid, into docosahexaenoie acid, Biochem. J. 384:357-366.

Petrie et al. (2010a) Metabolic engineering of omega-3 long-chain polyunsaturated fatty acids in plants using an acyl-CoA Delta6-desaturase with omega3-preference from the marine microalga *Micromonas pusilla*, Metab. Eng. 12:233240.

Qi, B., et al., (2002) "Identification Of A cDNA Encoding A Novel C18-Δ9 Polyunsaturated Fatty Acid-Specific Elongating Activity From The Docosahexaenolc Acid(DHA)-Producing Microalga, *Isochrysis galbana*," Federation Of European Biochemical Societies Letters, 510(3): 159-165.

Qiu, X., et al., (2001) "Identification Of A Δ4 Fatty Acid Desaturase From *Thraustochytrium* sp. Involved In The Biosynthesis Of Docosahexanoic Acid By Heterologous Expression In *Saccharomyces cerveisiae* and *Brassica juncea*," The Journal of Biological Chemistry, 276(34): 31561-31566.

Robert et al., Metabolic engineering of *Arabidopsis* to produce nutritionally important DHA in seed oil, Functional Plant Biology, 2005, vol. 32, p. 473-479.

Singh et al. (2005) Metabolic engineering of new fatty acids in plants,Curr. Opin. in Plant Biol. 8:197-203.

Tonon, T., et al., (2003) "Identification Of A Very Long Chain Polyunsaturated Fatty Acid Δ4-Desaturase From The Microalga *Pavlova lutheri*," Federation of European biochemical Societies, 553(3): 440-444.

Wood (2009) A leaf-based assay using interchangeable design principles to rapidly assemble multistep recombinant pathways, Plant Biotechnol J. 7:914-24.

Wu et al. (2005) Stepwise engineering to produce high yields of very long-chain polyunsaturated fatty acids in plants, Nat. Biotech. 23:1013-1017 (Exhibit 16).

Aqaba, M., et al., (2004) "Zebrafish cDNA Encoding Multifunctional Fatty Acid Elongase Involved In Production Of Eicosapentaenoic (20:5n-3) And Docosahexaenoic (22:6n-3) Acids," Marine Biotechnology, 6(3): 251-261.

Armbrust et al. (2004) The genome of the diatom *Thalassiosira pseudonana*: ecology, evolution, and metabolism, Science 306:79-86.

Berberich, T., et al., (1998) "Two Maize Genes Encoding Omega-3 Fatty Acid Desaturase And Their Differential Expression To Temperature," Plant Molecular Biology, 36(2): 297-306.

Broun, F., at al., (1998) "A Bifunctional oleate 12-Hydroxylase: Desaturase From *Lesguerella fendleri*," The Plant Journal, 13(2): 201-210.

Brown et al. (2002) *Limnanthes douglasii* lysophosphatidic acid acyltransferases: immunological quantification, acyl selectivity and functional replacement of the *Escherichia coli* plsC gene, Biochem J. 364:795-805.

Cheng et al. (2010) Towards the production of high levels of eicosapentaenoic acid in transgenic plants: the effects of different host species, genes and promoters, Transgenic Res 19: 221-229.

Cho, H.P., et al., (1999) "Cloning, Expression, And Nutritional Regulation Of The Mammalian Δ-6 Desaturase," The Journal Of Biological Chemistry, 274(1): 471-477.

Cho, H.P., et al., (1999) "Cloning, Expression, And Fatty Acid Regulation Of The Human Δ-5 Desaturase," The Journal Of Biological Chemistry, 274(52): 37335-37339.

Denic and Weissman (2007) A molecular caliper mechanism for determining very long-chain fatty acid length, Cell 130:663-677.

Garcia-Maroto, F., et al., (2002) "Cloning And Molecular Characterization Of The Δ6-Desaturase From Two Echium Plant Species: Production Of GLA By Heterologous Expression In Yeast And Tobacco," Lipids, 37(4): 417-426.

Girke, T., et al., (1998) "Identification of A Novel Δ6-Acyl-Group Desaturase By Targeted Gene Disruption In *Physcomitrella patens*," The Plant Journal, 15(1): 39-48.

Hastings, N., et al., (2001) "A Vertebrate Fatty Acid Desaturase With Δ5 and Δ6 Activities," Proceedings Of The National Academy of Sciences Of The United States Of America, 98(25): 14304-14309.

Hoffman et al., (2008) "Metabolic Engineering of ω3-Very Long Chain Polyunsaturated Fatty Acid Production by an Exclusively Acyl-CoA-dependent Pathway", The Journal of Biological Chemistry, 283:22352-22362.

Hong, H., et al., (2002) "Isolation And Characterization Of A Δ5 FA Desaturase From *Pythium irregulare* by Heterologous Expression in *Saccaromyces cerevisiae* And Oilseed Crops," Lipids, 37(9): 863-868.

Huang, Y., et al., (1999) "Cloning of Δ12-And Δ6-Desaturases From *Mortierella alpina* and Recombinant Production of γ-Linolenic Acid in *Saccharomyces cerevisiae*," Lipids, 34(7): 649-659.

Inagaki, K., et al., (2002) "Identification And Expression Of A Rat Fatty Acid Elongase Involved In The Biosynthesis Of C18 Fatty Acids," Bioscience, Biotechnology, and Biochemistry, 66(3): 613-621.

Kajikawa, M., et al., (2004) "Isolation And Characterization of Δ6-Desaturase, An ELO-Like Enzyme and Δ5-Desaturase From The Liverwort *Marchantia polymorpha* And Production Of Arachidonic And Eicosapentaenoic Acids In The Methylotrophic Yeast *Pichia pastoris*," Plant Molecular Biology, 54: 335-352.

Kajikawa et al. (2006) Isolation and functional characterization of fatty acid delta5-elongase gene from the liverwort *Marchantia polymorpha* L, EBBS Lett 580:149-154.

Knutzon, D.S., et al., (1998) "Identification of Δ5-Desaturase From *Mortierella alpine* By Heterologous Expression In Bakers' Yeast And Canola," The Journal OF Biological Chemistry, 278(45): 29360-29366.

Lassner (1995) Lysophosphatidic acid acyltransferase from meadowfoam mediates insertion of erucic acid at the sn-2 position of triacylglycerol in transgenic rapeseed oil, Plant Physiol. 109:1389-94.

Leonard, A.E., et al., (2000) "cDNA Cloning And Characterization Of Human Δ5-Desaturase Involved In The Biosynthesis of Arachidonic Acid," The Biochemical Journal, 347(Pt 3): 719-724.

Leonard, A.E., et al., (2000) "Cloning Of A Human cDNA Encoding A Novel Enzyme Involved In The Elongation Of Long-Chain Polyunsaturated Fatty Acids," The Biochemical Journal, 350(Pt 3): 765-770.

Meesapyodsuk et al. (2007) Primary structure, regioselectivity, and evolution of the membrane-bound fatty acid desaturases of *Claviceps purpurea*, J Biol Chem 282: 20191-20199.

Michaelson, L.V., et al., (1998) "Isolation Of A Δ5-Fatty Acid Desaturase Gene From *Mortirella alpina*," The Journal Of Biological Chemistry, 273(30): 19055-19059.

Michaelson, L.V., et al., (1998) "Functional Identification Of A Fatty Acid Δ5 Desaturase Gene From *Caenorhabditis elegans*," Federation Of European Biochemical Societies Letters, 439(3): 215-218.

(56) References Cited

OTHER PUBLICATIONS

Napier, J.A., et al., (1998) "Identification Of A *Caenorhabditis elegans* Δ6-Fatty-Acid-Desaturase By Heterologous Expression In *Saccharomyces cerevisiae*," The Biochemical Journal, 330(Pt 2): 611-614.

Parker-Barnes, J.M., et al., (2000) "Identification And Characterization Of An Enzyme Involved In The Elongation Of n-6 And n-3 Polyunsaturated Fatty Acids," Proceedings Of The National Academy Of Sciences Of the United States of America, 97(15): 8284-8289.

Pereira, S.L., at al., (2004) "A Novel omega3-Fatty Acid Desaturase Involved in the Biosynthesis of Eicosapentaenoic Acid," The Biochemical Journal, 378 (Pt 2): 665-671.

Petrie et al. (2012) Transgenic production of arachidonic acid in oilseeds, Transgenic Res. 21:139-147.

Qi et al., (2004) "Production of Very Long Chain Polyunsaturated Omega-3 and Omega-6 Fatty Acids in Plants", Nature Biotechnology 22:739-745 (published online May 16, 2004).

Reddy, A.S., et al., (1993) "Isolation Of A Δ6 -Desaturase Gene From The *Cyanobacterium synechocystis* sp. Strain PCC6803 By Gain-Of-Function Expression in *Anabaena* sp. Strain PCC7120," Plant Molecular Biology, 27: 293-300.

Robert et al. (2009) Isolation and characterisation of a delta5-fatty acid elongase from the marine microalga *Pavlova salina*, Marine Biotech 11:410-418.

Saito, T., et al., (2000) "A Second Functional Δ5 Fatty Acid Desaturase In The Cellular Slime Mould *Diotyosteliurn discoideum*," European Journal of Biochemistry, 267(6): 1813-1818.

Sato et al. (2004) Production of gamma-Linolenic Acid Stearidonic Acid in Seeds of Marker-Free Transgenic Soybean, Crop Sci. 44: 646-652.

Sayanova et al. (2006) A bifunctional Delta12,Delta15-desaturase from *Acanthamoeba castellanii* directs the synthesis of highly unusual n-I series unsaturated fatty acids, J Biol Chem 281: 36533-36541.

Sayanova, O.V., et al., (1997) "Expression Of A Borage Desaturase cDNA Containing An N-Terminal Cytochrome b5 Domain Results In The Accumulation Of High Levels of Δ6-Desaturated Fatty Acids In Transgenic Tobacco," Proceedings Of The National Academy Of Sciences Of The United States Of America, 94(8): 4211-4216.

Sayanova, O.V., et al., (2003) "Identification Of Primula Fatty Acid Δ6-Desaturases with n-3 Substrate Preferences," Federation of European Biochemical Societies, 542: 100-10.

Sayanova et al. (2006) Identification of Primula "front-end" desaturases with distinct n-6 or n-3 substrate preferences, Planta 224:1269-1277.

Singh et al. (2005) Metabolic engineering of new fatty acids in plants, Curr. Opin. in Plant Biol. 8:197-203.

Sperling et al. (2001) Functional identification of a delta8-sphingolipid desaturase from *Borago officinalis*, Arch. Biochm. Biophys. 388:293-8.

Sprecher, H., et al., (1995) "Reevaluation of the Pathways For The Biosynthesis Of Polyunsaturated Fatty Acids," Journal of Lipid Research, 36(12): 2471-2477.

Spychalla, J.P., et al., (1997) "Identification of an animal omega-3 Fatty Acid Desaturase By Heterologous Expression in *Arabidopsis*," Proceedings of the National Academy of Sciences of the United States of America, 94(4) : 1142-1147.

Trautwein, E.A., (2001) "n-3 Fatty Acids—Physiological And Technical Aspects For Their Use In Food," European Journal of Lipid Science and Technology, 103(1): 45-55.

Wallis, J.G. and Browse, J., (1999) "The Δ8-Desaturase Of *Euglena gracilis*: An Alternate Pathway For Synthesis Of 20-Carbon Polyunsaturated Fatty Acids," Archives of Biochemistry and Biophysics, 365(2): 307-316.

Watts, J.L. and Browse, J., (1999) "Isolation And Characterization Of A Δ5-Fatty Acid Desaturase From *Caenorhabditis elegans*," Archives of Biochemistry and Biophysics, 362(1): 175-182.

Zank, T.K., et al., (2002) "Cloning and Functional Characterization of an Enzyme Involved in the Elongation of Δ6-Polyunsaturated Fatty Acids From The Moss *Physcomitrella patens*," The Plant Journal, 31(3): 255-268.

Zhang, Q., at al., (2004) "Identification And Characterization Of A Novel Δ6-Fatty Acid Desaturase Gene *Rhizopus arrhizus*," Federation of European Biochemical Societies Letters, 556(1-3): 81-85.

Zhang et al. (2007a) Identification of a novel bifunctional delta12/delta15 fatty acid desaturase from a basidiomycete, *Coprinus cinereus* TD#822-2, FEBS Letters 581: 315-319.

Zhang et al. (2008) Identification and characterization of a novel yeast omega3-fatty acid desaturase acting on long-chain n-6 fatty acid substrates from *Pichia pastoris*, Yeast 25: 21-27.

Mar. 7, 2012 presentation at the CSIRO Marine and Atmospheric Research. Science Forum, Hobart (poster presentation) at Hobart, Australia, entitled "New Land Plants Containing Long-chain Omega-3 Oils" presented by Peter Nichols, first author, Peter Nichols.

Jun. 8, 2012 presentation at the GOED Exchange at Boston, MA, entitled "An Update from Australia: A Global Leader in Long-Chain Omega-3" presented by Peter Nichols, first author, Peter Nichols, 34 slides.

Jul. 2, 2012 presentation at the Australian Marine Scientists Association, Annual Meeting, 2012 at Hobart, Australia, entitled "New Land Plants With Long-Chain Omega-3 Oils: A journey from marine gene discovery to sustainable sources of health-benefitting oils" presented by Peter Nichols, first author, Peter Nichols, 21 slides.

Jul. 13, 2012 presentation at the 20th International conference on plant lipids at Seville, Spain, entitled "Metabolic engineering plant seeds with fish oil-like levels of DHA" presented by James Petrie, first author, James Petrie, 41 slides.

Jul. 16, 2012 presentation at the Australian Institute of Food Science and Technology, Annual Meeting, 2012 at Adelaide, Australia, entitled "New sustainable land plant sources of long-chain omega-3 oils" presented by Peter Nichols, first author, Peter Nichols, 26 slides.

Aug. 2, 2012 presentation at the UniGateway, Business breakfast series at Melbourne, Australia, entitled "Trends and sustainability of LC omega-3 oils from wild and farmed fish, and Progress with new land plant sources" presented by Peter Nichols, first author, Peter Nichols, 10 slides.

Sep. 26, 2012 presentation at the ComBio—Plants and Human Nutrition Symposium, 2012 at Adelaide, Australia, entitled "Creating Land Plant-Based Sustainable Sources of Essential Long Chain Omega-3 Fatty Acids" presented by Peter Nichols, first author, James Petrie, 24 slides.

Oct. 9, 2012 presentation at the Invited seminar, Department of Plant Science, University of Tasmania at Hobart, Australia, entitled "The Omega-3 Oils story—Sources of Long-chain Omega-3: A Sustainable Future" presented by Peter Nichols, first author, Peter Nichols, 39 slides.

Nov. 14, 2012 presentation at the Novel sources of omega-3, Copenhagen 2012 at Copenhagen, Denmark, entitled "Metabolic engineering plant seeds with fish oil-like levels of DHA" presented by James Petrie, first author, James Petrie, 35 slides.

Mar. 13, 2013 presentation at the Invited seminar, The Biological Club, Hobart at Hobart, Australia, entitled "The Omega-3 Oils story—Sources of Long-chain Omega-3: A Sustainable Future" presented by Peter Nichols, first author, Peter Nichols, 39 slides.

Written Opinion of the International Search Authority, issued Apr. 1, 2010 in connection with PCT International Application Publication No. PCT/AU2009/001488.

International Search Report, issued Apr. 1, 2010 in connection with PCT International Application Publication No. PCT/AU2009/001488.

PCT International Search Report issued Apr. 1, 2010 for WO 2010/057246.

PCT International Preliminary Report on Patentability issued Oct. 25, 2006 for WO 2005/103253.

Supplementary European Search Report issued on Apr. 1, 2008 by the European Patent Office in connection with related International Application No. PCT/AU2005/000571.

(56) References Cited

OTHER PUBLICATIONS

International Search Report issued Jun. 23, 2005 in connection with PCT International Application No. PCT/AU05/000571, filed Apr. 22, 2005.
Requirement for Restriction/Election issued Mar. 5, 2007 in connection with U.S. Appl. No. 11/112,882.
Response to Requirement for Restriction/Election filed May 7, 2007 in connection with U.S. Appl. No. 11/112,882.
Final Office Action issued Oct. 11, 2007 in connection with U.S. Appl. No. 11/112,882.
Response to Non Final Office Action filed Oct. 31, 2007 in connection with U.S. Appl. No. 11/112,882.
Notice of Informal or Non-Responsive Amendment issued Feb. 26, 2008 in connection with U.S. Appl. No. 11/112,882.
Response to Office Action filed Mar. 11, 2008 in connection with U.S. Appl. No. 11/112,882.
Non-Final Office Action issued Jun. 17, 2008 in connection with U.S. Appl. No. 11/112,882.
Response to Non-Final Office Action filed Oct. 17, 2008 in connection with U.S. Appl. No. 11/112,882.
Final Office Action issued Apr. 1, 2009 in connection with U.S. Appl. No. 11/112,882.
Response to Final Office Action filed Jul. 1, 2009 in connection with U.S. Appl. No. 11/112,882.
Notice of Allowance issued Aug. 21, 2009 in connection with U.S. Appl. No. 11/112,882.
Restriction Requirement issued Apr. 30, 2009 in connection with U.S. Appl. No. 11/587,092.
Response to Restriction Requirement filed Jun. 30, 2009 in connection with U.S. Appl. No. 11/587,092.
Non-Final Office Action issued Nov. 17, 2009 in connection with U.S. Appl. No. 11/587,092.
Examiner Interview Summary Record Feb. 22, 2010 in connection with U.S. Appl. No. 11/587,092.
Response to Non-Final Office Action, filed Mar. 17, 2010 in connection with U.S. Appl. No. 11/587,092.
Jul. 2, 2010 Notice of Allowance in connection with U.S. Appl. No. 11/587,092.
Office Action issued by the U.S. Patent Office on Dec. 28, 2010 in connection with U.S. Appl. No. 12/661,978.
Response to Office Action, filed Jan. 25, 2011 in connection with U.S. Appl. No. 12/661,978.
Final Office Action, issued Apr. 18, 2011 in connection with U.S. Appl. No. 12/661,978.
Interview Summary Record, issued May 24, 2011 in connection with U.S. Appl. No. 12/661,978.
Response to Final Office Action, filed Jun. 16, 2011 in connection with U.S. Appl. No. 12/661,978.
Notice of Allowance, issued Sep. 1, 2011 in connection with U.S. Appl. No. 12/661,978.
Non-Final Office Action issued Jan. 5, 2011 in connection with U.S. Appl. No. 12/945,708.
Response to Non-Final Office Action filed Jan. 10, 2011 in connection with U.S. Appl. No. 12/945,708.
Notice of Allowance, issued Feb. 11, 2011 in connection with U.S. Appl. No. 12/945,708.
Accelerated Examination Support Document, filed Apr. 25, 2011 in connection with U.S. Appl. No. 13/093,252.
Pre-Examination Search Document, filed Apr. 25, 2011 in connection with U.S. Appl. No. 13/093,252.
Non-Final Office Action, issued Aug. 30, 2011 in connection with U.S. Appl. No. 13/093,252.
Examiner Interview Summary, issued Sep. 13, 2011 in connection with U.S. Appl. No. 13/093,252.
Amendment in Response to Office Action and Summary of Examiner Interview, filed Sep. 16, 2011 in connection with U.S. Appl. No. 13/093,252.
Notice of Allowance, issued Oct. 7, 2011 in connection with U.S. Appl. No. 13/093,252.
Dec. 5, 2011 Accelerated Examination Support Document, filed in connection with U.S. Appl. No. 13/311,240.
Dec. 5, 2011 Pre-Examination Search Document, filed in connection with U.S. Appl. No. 13/311,240.
Feb. 6, 2012 Communication, filed in connection with U.S. Appl. No. 13/311,240.
Feb. 17, 2012 Notice of Allowance, issued in connection with U.S. Appl. No. 13/311,240.
Feb. 1, 2012 Non-Final Office Action, issued in connection with U.S. Appl. No. 13/243,747.
May 1, 2012 Amendment, filed in connection with U.S. Appl. No. 13/243,747.
Jul. 6, 2012 Notice of Allowance, issued in connection with U.S. Appl. No. 13/243,747.
Dec. 7, 2012 Office Action, issued in connection with U.S. Appl. No. 13/448,107.
May 9, 2013 Notice of Allowance, filed in connection with U.S. Appl. No. 13/448,107.
Mar. 11, 2013 Office Action, issued in connection with U.S. Appl. No. 13/651,275.
Certik M. and Shimizu S., Biosynthesis and regulation of microbial polyunsaturated fatty acid production. J. Biosci Bioeng, 1999; 87(1):1-14.
Damude et al., (2007) "Engineering Oilseed Plants for a Sustainable, Land-Based Source of Long Chain Polyunsaturated Fatty Acids" Lipids, 42:179-185.
Domergue et al., (2003), Acyl Carriers Used as Substrates by the Desaturases and Elongases Involved in Very Long-chian Polyunsaturated Fatty Acids Biosynthesis Reconstituted in Yeast, J. Biol. Chem. 278; 35115-35126.
Hoffmann at al., (2008) "Metabolic Engineering of ω3-Very Long Chain Polyunsaturated Fatty Acid Production by an Exclusively Acyl-CoA-dependent Pathway" The Journal of Biological Chemistry, 283:22352-22362.
Kajikawa M. et al., Isolation and characterization of delta(6)-desaturase, an ELO-like enzyme and delta(5)-desaturase from liverword *Marchantia polymorpha* and production of arachidonic and eicosapentaenoic acids in the methylotrophic yeast *Pichia pastoris*. Plant Mol Biol, 2004; 54(3):335-52.
Marquardt et al., (2000) "cDNA cloning, genomic structure, and chromosomal localization of three members of the human fatty acid desaturase family" Genomics, 66(2):175-83.
Qi et al., (2004) "Production of very long chain polyunsatured omega-3 and omega-6 fatty acids in plants" Nature Biotechnology 22:739-745 (published online May 16, 2004).
Qiu et al. (2001) GenBank Accession No. AF489589, NCBI p. 1.
Qiu, X., et al., (2001) "Identification of a Δ4 Fatty Acid Desaturase from *Thraustochytrium* sp. Involved in the Biosynthesis of Docosahexanoic Acid by Heterologous Expression in *Saccharomyces cerevisiae* and *Brassica juncea*," The Journal of Biological Chemistry, 276(34): 31561-31566.
Sayanova O.V. and Napier J.A., Eicosapentaenoic acid: biosynthetic routes and the potential for synthesis in transgenic plants. Phytochemistry, 2004; 65(2):147-58.
Truksa et al., (2006) "Metabolic Engineering of Plants to Produce Very Long-Chain Polyunsaturated Fatty Acids", Transgenic Research, 15:131-137.
Notification of European publication number issued Jan. 31, 2007 in connection with European Patent Application No. 05733657.0.
Supplementary European Search Report issued Apr. 1, 2008 in connection with European Patent Application No. 05733657.0.
Communication Pursuant to Article 94(3) EPC issued Feb. 12, 2009 in connection with European Patent Application No. 05733657.0.
Response to Communication from the Examining Division, filed Oct. 22, 2009 in connection with European Application No. EP 05733657.0.
Communication from the Examining Division issued by the European Patent Office on Aug. 18, 2010 in connection with European Application No. EP 05733657.0.
Response to Communication from the Examining Division, filed Feb. 3, 2011 in connection with European Application No. EP 05733657.0.

(56) References Cited

OTHER PUBLICATIONS

Communication from the Examining Division issued by the European Patent Office on Apr. 6, 2011 in connection with European Application No. EP 05733657.0.
Examination Report issued Mar. 14, 2012 in connection with corresponding European Patent Application No. 05733657.0.
Oct. 17, 2011 Response to Apr. 6, 2011 Communication from the Examining Division, filed in connection with European Application No. EP05733657.0.
Sep. 24, 2012 Response to Mar. 14, 2012 Communication from the Examining Division, filed in connection with European Application No. EP05733657.0.
Communication from the Examining Division issued by the European Patent Office on Nov. 9, 2012 in connection with European Patent Application No. 05733657.0.
Apr. 5, 2013 Response filed in connection with European Patent Application No. 10184533.7.
European Search Report, issued by the European Patent Office on Jul. 15, 2011 in connection with European Patent Application No. 11155282.4.
Extended European Search Report, issued by the European Patent Office on Oct. 25, 2011 in connection with European Patent Application No. 11155282.4.
Sep. 7, 2012 Amendment after receipt of European Search Report, filed in connection with European Patent Application No. 11155282.4.
Mar. 11, 2013 Office Action, issued in connection with European Patent Application No. 11155282.4.
European Search Report, issued by the European Patent Office on Jul. 15, 2011 in connection with European Patent Application No. 11155364.0.
Extended European Search Report, issued by the European Patent Office on Oct. 25, 2011 in connection with European Patent Application No. 11155364.0.
Sep. 10, 2012 Amendment after receipt of European Search Report, filed in connection with European Patent Application No. 11155364.0.
Feb. 13, 2013 Office Action issued in connection with European Patent Application No. 11155364.0.
European Search Report, issued by the European Patent Office on Oct. 25, 2011 in connection with European Patent Application No. 11155266.7.
Extended European Search Report and Opinion issued Feb. 10, 2012 in connection with corresponding European Divisional Patent Application No. 11155266.7.
Rule 69 EPC Communication issued Mar. 19, 2012 in connection with European Divisional Patent Application No. 11155266.7.
Jan. 3, 2013 Response filed in connection with European Patent Application No. 11155266.7.
Examination Report, issued by the Australian Patent Office on Sep. 6, 2012 in connection with Australian Patent Application No. 2011232757.
Australian Examination Report issued Nov. 16, 2009 in connection with Australian Patent Application No. 2005235627.
Australian Examination Report issued Mar. 14, 2011 in connection with Australian Patent Application No. 2005235627.
Response to Australian Examination Report filed Feb. 25, 2011 in connection with Australian Patent Application No. 2005235627.
Response to Australian Examination Report filed Apr. 19, 2011 in connection with Australian Patent Application No. 2005235627.
Australian Examination Report issued May 16, 2011 in connection with Australian Patent Application No. 2005235627.
Response to Australian Examination Report filed Jun. 14, 2011 in connection with Australian Patent Application No. 2005235627.
Chinese Examination Report issued Apr. 10, 2009 in connection with Chinese Patent Application No. 200580020696.3.
Response to Chinese Examination Report filed Jul. 21, 2009 in connection with Chinese Patent Application No. 200580020696.3.
Chinese Examination Report issued Apr. 30, 2010 in connection with Chinese Patent Application No. 200580020696.3.
Response to Chinese Examination Report filed Sep. 15, 2010 in connection with Chinese Patent Application No. 200580020696.3.
Nov. 30, 2011 Request for Re-Examination filed in connection with Chinese Patent Application No. 200580020696.3, including English language translation of submitted claims.
Aug. 18, 2011 Decision of Rejection issued by the Chinese Patent Office in connection with Chinese Patent Application No. 200580020696.3.
Response to Notification of Re-Examination filed on Oct. 18, 2012 in connection with Chinese Patent Application No. 200580020696,3, including English language filed claims.
Oct. 18, 2012 Request for Reexamination filed in connection with Chinese Patent Application No. 200580020696.3.
Jan. 29, 2013 Office Action issued in connection with Chinese Patent Application No. 201210006139.8.
Brazilian Technical Opinion issued Mar. 1, 2012 in connection with corresponding Brazilian Patent Application No. PI 0510132-8.
Response filed to Brazilian Technical Opinion filed Mar. 29, 2012 in connection with corresponding Brazilian Patent Application No. PI 0510132-8.
Nov. 21, 2011 Examination report issued in connection with Canadian Patent Application No. 2,563,875.
May 22, 2012 Response to Examination Report, filed in connection with Canadian Patent Application No. 2,563,875.
Nov. 23, 2012 Office Action issued in connection with Canadian Patent Application No. 2,563,875.
International Search Report issued Nov. 21, 2007 in connection with International Application No. PCT/AU2007001242, filed Aug. 29, 2007 (CSIRO).
Written Opinion of the International Searching Authority issued Nov. 21, 2007 in connection with International Application No. PCT/A02007001242, filed Aug. 29, 2007 (CSIRO).
Nov. 5, 2013 Office Action, issued in connection with U.S. Appl. No. 13/918,399.
Nov. 1, 2013 Office Action, issued in connection with U.S. Appl. No. 13/129,940.
Nov. 21, 2013 Notice of Allowance, issued in connection with U.S. Appl. No. 14/027,727.
Nov. 6, 2013 Office Action, issued in connection with U.S. Appl. No, 13/913,999.
Jan. 3, 2013 Response, filed in connection with European Patent Application No. 05733657.0.
Dec. 27, 2013 Response, filed in connection with European Patent Application No. 11155282.4.
Dec. 4, 2013 Response, filed in connection with European Patent Application No. 11155364.0.
Jan. 9, 2014 Office Action, issued in connection with Australian Patent Application No. 2013204296.
Nov. 21, 2013 Office Action, issued in connection with Chinese Patent Application No. 201210006139.8.
Nov. 1, 2013 Office Action, issued in connection with Canadian Patent Application No. 2,563,875.
Mar. 29, 2012 Extended European Search Report and Search Opinion issued in connection with European Patent Application No. 09827035.8.
Oct. 29, 2012 Response to European Search Opinion filed in connection with European Patent Application No. 09827035.8.
Jun. 8, 2012 Australian Examination Report issued in connection with Australian Patent Application No. 2009317860.
Jan. 14, 2013 Chinese First Office Action issued in connection with Chinese Patent Application No. 200980154876.9.
Jun. 22, 2011 New Zealand Examination Report issued in connection with New Zealand Patent Application No. 593097.
Dec. 11, 2012 Response to New Zealand Examination Report filed in connection with New Zealand Patent Application No. 593097.
Jan. 3, 2013 New Zealand Examination Report issued in connection with New Zealand Patent Application No. 593097.
Jan. 8, 2013 Response to New Zealand Examination Report filed in connection with New Zealand Patent Application No. 593097.
Supplemental European Search Report and Search Opinion issued Jun. 24, 2010 in connection with European Patent Application No. 07784864.6.

(56) References Cited

OTHER PUBLICATIONS

Response filed to European Search Opinion on Jan. 19, 2011 in connection with European Patent Application No. 07784864.6.
European Examination Report issued Jul. 18, 2011 in connection with European Patent Application No. 07784864.6.
Response filed to European Examination Report on May 15, 2012 in connection with European Patent Application No. 07784864.6.
Australian Examination Report issued Jul. 25, 2012 in connection with Australian Patent Application No. 2007291937.
Zealand Examination Report issued Jul. 29, 2010 in connection with New Zealand Patent Application No. 575809.
Response filed to New Zealand Examination Report filed Dec. 23, 2011 in connection with New Zealand Patent Application No. 575809.
Zealand Examination Report issued Jan. 24, 2012 in connection with New Zealand Patent Application No. 575809.
Chinese Office Action issued May 17, 2011 in connection with Chinese Patent Application No. 200780040245.5, including English Language translation.
, sponse filed to Chinese Office Action on Nov. 30, 2011 in connection with Chinese Patent Application No. 200780040245.5, including English Language translation of claims.
Second Chinese Office Action issued Jun. 6, 2012 in connection with Chinese Patent Application No. 200780040245.5, including English Language translation.
Response filed to Second Chinese Office Action on Oct. 22, 2012 in connection with Chinese Patent Application No. 200780040245.5.
Third Chinese Office Action issued Feb. 17, 2013 in connection with Chinese Patent Application No. 200780040245.5, including English Language translation.
Response filed to Chinese Office Action on Jul. 4, 2013 in connection with. Chinese Patent Application No. 200780040245.5.
Abdullah et al. (1986) "Efficient plant regeneration from rice protoplasts through somatic embryogenesis" Biotechnology, 4, 1087-1090.
Al-Mariri et al. (2002) "*Yersinia enterocolitica* as a Vehicle for a Naked DNA Vaccine Encoding *Brucella abortus* Bacterioferritin or P39 Antigen" Infect. Immun. 70:1915-1923.
Altschul et al. (1997) "Gapped BLAST and PSI-BLAST: a new generation of protein database search programs" Nucleic Acids Research, 25(17), 3389-3402.
Alvarez et al. (2000) "Silencing of HMW glutenins in transgenic wheat expressing extra HMW subunits" Theor Appl Genet 100:319-327.
Badami et al. (1980) "Structure and occurrence of unusual fatty acids in minor seed oils" Prog. Lipid Res., 19, 119-153.
Bates et al. (2007) "Incorporation of Newly Synthesized Fatty Acids into Cytosolic Glycerolipids in Pea Leaves Occurs via Acyl Editing" J. Biol. Chem. 282:31206-31216.
Baumberger et al. (2007) "The Polerovirus Silencing Suppressor P0 Targets ARGONAUTE Proteins for Degradation" Curr. Biol. 17:1609-1614.
Beclin et al. (2002) "A Branched Pathway for Transgene-Induced RNA Silencing in Plants" Curr. Biol. 12:684-688.
Bligh and Dyer, (1959) "Orange-red Flesh in Cod and Haddock" J. Fish. Res. Bd. Canada, 16(4):449-452.
Bortolamiol et al. (2007) "The Polerovirus F Box Protein P0 Targets ARGONAUTE1 to Suppress RNA Silencing" Euro. J. Biochm. 267:85-96.
Bouvier (2000) "Identification of neoxanthin synthase as a carotenoid" Eur J. Biochem. 267:6346-6352.
Brodersen et al. (2008) "Widespread Translational Inhibition by Plant miRNAs and siRNAs" Science 320:1185-1190.
Brosnan et al. (2007) "Nuclear gene silencing directs reception of long-distance mRNA silencing in *Arabidopsis*" Proc. Natl. Acad. Sci U.S.A. 104;14741-14746.
Broun et al. (1998) "A bifunctional oleate 12-hydroxylase: desaturase from *Lesquerella fendleri*" Tthe Plant Journal, 13(2), 201-210.

Cahoon et al. (2001) "Formation of conjugated $\Delta 8, \Delta 10$-double bonds by Al2-oleic-acid desaturase-related enzymes" The Journal of Biological Chemistry, 276(4), 2637-2643.
Cahoon et al. (2000) "Production of fatty acid components of meadowfoam oil in somatic soybean embryos" Plant Physiology, 124, 243-251.
Cahoon et al. (1992) "Expression of a coriander desaturase results in petroselinic acid production in transgenic tobacco" Proc. Natl. Acad. Sci. USA, 89, 11184-11188.
Capecchi (1980) "High Efficiency Transformation by Direct Microinjection of DNA into Cultured Mammalian Cells" Cell 22:479-488.
Chapman et al. (2001) "Transgenic Cotton Plants with Increased Seed Oleic Acid Content" Journal of American Chemists' Chemistry; vol. 78 No. 9, 941-947.
Chen et al. (2004) "Introgression of Salt-Tolerance From Somatic Hybrids Between common Wheat and Thinopyrum Ponticum" Plant Science 167:773-779.
Cheng et al . (1996) "Production of fertile transgenic peanut (*Arachis hypogaea* L.) plants using *Agrobacterium tumefaciens*" Plant Cell Reports, 15, 653-657.
Chikwamba et al. (2003) "Localization of a bacterial protein in starch granules of transgenic maize kernels" Proc. Natl. Acad. Sci. U.S.A. 100:11127-11132.
Chung et al. (2006) "Effect of 5'UTR introns on gene expression in *Arabidopsis thaliana*" BMC Cenomics 7:120.
Clapp et al. (1993) "The 16-Kilodalton N-Terminal Fragment of Human Prolactin is a Potent Inhibitor of Angiogenesis" Endocrinology, 133(3):1292-1299.
Coutu et al. (2007) "pORE: a modular binary vector series suited for both monocot and dicot plant transformation" Transgenic Res. 16: 771-781.
Cripps (1990) "The $\Delta 12$-desaturase from the house cricket, *Acheta domesticus* (orthoptera: gryllidae): characterization and form of the substrate" Archives of Biochemistry and Biophysics, 278(1), 46-51.
Dec. 7, 2012 Office Action, issued in connection with U.S. Appl. No. 13/498,107.
Jan. 7, 2013 Response, filed in connection with U.S. Appl. No. 13/448,107.
Jan. 15, 2013 Office Action, issued in connection with U.S. Appl. No. 13/448,107.
Apr. 15, 2013 Response, filed in connection with U.S. Appl. No. 13/448,107.
2013 Notice of Allowance, filed in connection with U.S. Appl. No. 13/448,107.
Jun. 11, 2013 Response, filed in connection with U.S. Appl. No. 13/651,275.
Aug. 16, 2013 Notice of Allowance, issued U.S. Appl. No. 13/651,275 in connection with Feb. 25, 2014.
Sep. 6, 2013 Response to Australian Examination report, filed in connection with Australian Patent Application No. 2011232757.
Aug. 13, 2013 Response to Chinese Office Action, filed in connection with Chinese Patent Application No. 2012100061398.
Aug. 12, 2013 Response, filed in connection with U.S. Appl. No. 12/310,645.
Oct. 22, 2013 Office Action, issued in connection with U.S. Appl. No. 12/310,645.
Jul. 17, 2013 Response, filed in connection with U.S. Appl. No. 13/044,984.
Jul. 26, 2013 Advisory Action, issued in connection with U.S. Appl. No. 13/044,984.
Aug. 7, 2012 Response, filed in connection with U.S. Appl. No. 13/044,984.
Dec. 2, 2013 Office Action, issued in connection with U.S. Appl. No. 13/044,984.
International Preliminary Report on Patentability, issued May 24, 2011 in connection with PCT International Application Publication No. PCT/AU2009/001488.
Petrie et al. (2013) "Engineered oilseed crops with fish oil DHA levels" Inform, 24(10):648-652.
Dec. 6, 2013 International Search Report, issued in connection with PCT International Patent Application No. PCT/AU2013/000639.

(56) References Cited

OTHER PUBLICATIONS

Dec. 6, 2013 Written Opinion of the International Searching Authority, issued in connection with PCT International Patent Application No. PCT/AU2013/000639.

Chen et al. (2010) "Missa Is a Highly Efficient in Vivo DNA Assembly Method for Plant Multiple-Gene Transformation" Plant Physiology, vol. 153, pp. 41-51.

Hu et al. (2008) "Microalgal triacylglycerols as feedstocks for biofuel production: perspectives and advances" The Plant Journal, 54, 621-639.

Lenihan-Geels et al. (2013) "Alternative Sources of Omega-3 Fats: Can We Find a Sustainable Substitute for Fish?" Nutrients, 5, 1301-1315.

Lin et al. (2003) "Efficient linking and transfer of multiple genes by a multigene assembly and transformation vector system" PNAS, 100(10): 5962-5967.

Petrie et al. (2011) "Expanding the docosahexaenoic acid food web for sustainable production: engineering lower plant pathways into higher plants" AoB Plants Article plr011 (doi:10.1093/aobpla/plr011).

Petrie et al. (2012) "Metabolic Engineering Plant Seeds with Fish Oil-Like Levels of DHA" PLoS One, vol. 7, No. 10, e49165.

Petrie et al. (2010) "Rapid expression of transgenes driven by seed-specific constructs in leaf tissue: DHA production" Plant Methods 6:8 (pp. 1-6).

Robert et al. (2009) "Isolation and Characterisation of a Δ5- fatty Acid Elongase from the Marine Microalga *Pavlova sauna*" Mar Biotechnol, 11:410-418.

Ruiz-Lopez et al. (2012) "Enhancing the accumulation of omega-3 long chain polyunsaturated fatty acids in transgenic *Arabidopsis thaliana* via iterative metabolic engineering and genetic crossing" Transgenic Res, 21:1233-1243.

Ryckebosch et al. (2012) "Microalgae as an alternative source of omega-3 long chain polyunsaturated fatty acids" Lipid Technology, 24(6): 128-130.

Untergasser et al. (2012) "One-Step Agrobacterium Mediated Transformation of Eight Genes Essential for Rhizobium Symbiotic Signaling Using the Novel Binary Vector System pHUGE" PLoS One, vol. 7, No. 10, e47885.

Wu et al. (2005) "Stepwise engineering to produce high yields of very long-chain polyunsaturated fatty acids in plants" Nature Biotechnology, 23(8):1013-1017.

Zhou et al. (2007) "Isolation and characterization of genes from the marine microalga *Pavlova sauna* encoding three front-end desaturases involved in docosahexaenoic acid biosynthesis" Phytochemistry 68, 785-796.

United Kingdom Application No. GB 1206483.8, filed Apr. 12, 2012 (Rothamsted Research LTD).

United Kingdom Application No. GB 1222184.2, filed Dec. 10, 2012 (Rothamsted Research LTD).

Crombie et al. (1984) "Origins of conjugated triene fatty acids. The biosynthesis of calendic acid by *Calendula officinalis*" J. Chem. Soc., Chem. Commun., 15, 953-955.

Crombie & Holloway (1985) "The biosynthesis of calendic acid, octadeca-(8E,10E,12Z)-trienoic acid, by developing marigold seeds: origins of (E,E,Z) and (Z,E,Z) conjugated triene acids in higher plants" J. Chem. Soc. Perkin Trans. 1, 2425-2434.

Cuperus & Derksen (1996) "High value-added applications from vernolic acid" In J. Janick (Ed.), Progress in new crops (pp. 354-356). Alexandria, VA: ASHS Press.

Curiel et al. (1992) "High-Efficiency Gene Transfer Mediated by Adenovirus Coupled to DNA-Polylysine Complexes" Hum. Gen. Ther. 3:147-154.

Darji et al. (1997) "Oral Somatic Transgene Vaccination Using Attenuated *S. typhimurium*" Cell 91:765-775.

de Renobales et al. (1987) "Biosynthesis of linoleic acid in insects" Trends in Biochemical Sciences, 12, 364-366.

Ding & Voinett (2007) "Antiviral Immunity Directed by Small RNAs" Cell 130:413-426.

Dobson & Christie (2002) "Mass spectrometry of fatty acid derivatives" Eur. J. Lipid Sci. Technol., 104, 36-43.

Dunoyer et al. (2004) "Probing the MicroRNA and Small Interfering RNA Pathways with Virus-Encoded Suppressors of RNA Silencing" The Plant Cell 16:1235-1250.

Eglitis et al. (1988) "Retroviral Vectors for Introduction of Genes into Mammalian Cells" Biotechniques 6:608-614.

Eigenheer et al (2002) "Isolation and molecular characterization of *Musca domestica* delta-9 desaturase sequences" Insect Molecular Biology 11(6):533-542.

Fay & Richli (1991) "Location of double bonds in polyunsaturated fatty acids by gas chromatography—mass spectrometry after 4,4-dimethyloxazoline derivatization" Journal of Chromatography, 541, 89-98.

Fennelly et al. (1999) "Mucosal DNA Vaccine Immunization Against Measles with a Highly Attenuated *Shigella flexneri* Vector" J. Immunol. 162:1603-1610.

Fraser et al. (2004) "Expression of the Isochrysis C18-Δ9 Polyunsaturated Fatty Acid Specific Elongase Component Alters *Arabidopsis* Glycerolipid Profiles" Plant Physiol. 135:859-866.

Fritsche et al, (1999) "Isolation and characterization of a calendic acid producing (8,11)-linoleoyl desaturase" FEBS Letters, 462, 249-253.

Fuji et al. (2007) "*Arabidopsis* Vacuolar Sorting Mutants (green fluorescent seed) Can Be Identified Efficiently by Secretion of Vacuole-Targeted Green Fluorescent Protein in Their Seeds" Plant Cell 19:597-609.

Fujimura et al. (1985) "Regeneration of Rice Plants from Protoplasts" Plant Tissue Culture Lett. 2:74.

Cleave (1992) "A versatile binary vector system with a T-DNA organisational structure conducive to efficient integration of cloned DNA into the plant genome" Plant Mol. Biol. 20:1203-1207.

Glevin et al. (2003) "Agrobacterium-Mediated Plant Transformation: the Biology behind the 'Gene-Jockeying' Tool" Microbiol. Mol. Biol. Rev. 67:16-37.

Glick et al. (2008) "Interaction with host SGS3 is required for suppression of RNA silencing by tomato yellow leaf curl virus V2 protein" Proc. Natl. Acad. Sci U.S.A. 105:157-161.

Graham et al. (1973) "Transformation of Rat Cells by DNA of Human Adenovirus 5" Virology 54:536-539.

Grant at al. (1995) "Transformation of peas (*Pisani sativum* L.) using immature cotyledons" Plant Cell Reports, 15, 254-258.

Grillot-Courvalin (1999) "Bacteria as gene delivery vectors for mammalian cells" Curr. Opin. Biotech. 10:477-481.

Hamilton and Baulcombe (1999) "A Species of Small Antisense RNA in Posttranscriptional Gene Silencing in Plants" Science 286:950-952.

Hao et al. (2002) "Acyl-CoA Z9- and Z10-desaturase genes from a New Zealand leafroller moth species" Planotortrix octo. Insect Biochemistry and Molecular Biology, 32, 961-966.

Harayama, S. (1998). Artificial evolution by DNA shuffling. Trends in Biotechnology, 16(2), 76-82.

Hense at al. (2001) "Eukaryotic expression plasmid transfer from the intracellular bacterium *Listeria monocytogenes* to host cells" Cell Microbiol. 3:599-609.

Hoffman et al. (2007) "A Small Membrane-peripheral Region Close to the Active Center Determines Regioselectivity of Membrane-bound Fatty Acid Desaturases from *Aspergillus nidulans*" J. Biol. Chem. 282:26666-26674.

Horiguchi et al., (1998) "Developmental Regulation Of Genes For Microsome And Plastid Omega-3 Fatty Acid Desaturases In Wheat (*Triticum aestivum* L.)," Plant and Cell Physiology, 39(5): 540-544.

Horvath et al. (2000) "The production of recombinant proteins in transgenic barley grains" Proc. Natl. Acad. Sci. U.S.A. 97:1914-1919.

Huang et al. (2004) "How Insulin Binds: the B-Chain a-Helix Contacts the L1 b-Helix of the Insulin Receptor" J. Mol. Biol. 341:529-550.

Johansen and Carrington (2001) "Silencing on the Spot. Induction and Suppression of RNA Silencing in the Agrobacterium-Mediated Transient Expression System" Plant Physiol. 126-930-938.

(56) References Cited

OTHER PUBLICATIONS

Kang et al. (2008) "Coexpression of Elo-like Enzyme and Δ4-Desaturases Derived from *Thraustochytrium aureum* ATCC 34304 and the Production of DHA and DPA in *Pichia pastoris*" 13:483-490.

Kasschau et al. (2003) "P1/HC-Pro, a Viral Suppressor of RNA Silencing, Interferes with *Arabidopsis* Development and miRNA Function" Devel. Cell 4:205-217.

Khozin et al. (1997) "Elucidation of the Biosynthesis of Eicosapentaenoic Acid in the Microalga *Porphyridium cruentum*" Plant Physiol. 114:223-230.

Kleiman, R., & Spencer, G. F. (Jan. 1982). Search for new industrial oils: XVI. umbelliflorae- seed oils rich in petroselinic acid. Journal of the American Oil Chemists' Society, 59(1), 29-38.

Knipple et al. (2002) "Evolution of the integral membrane desaturase gene family in moths and flies" Genetics, 162, 1737-1752.

Koziel et al. (1996) "Optimizing expression of transgenes with an emphasis on post-transcriptional events" Plant Mol. Biol. 32:393-405.

Kunik et al. (2001) "Genetic transformation of HeLa cells by Agrobacterium" Proc. Natl. Acad. Sci. U.S.A. 98:1871-1876.

Lacroix et al. (2008) "Association of the Agrobacterium T-DNA— protein complex with plant nucleosomes" Proc. Natl. Acad. Sci. U.S.A. 105: 15429-15434.

Lechtenberg et al. (2003) "Neither inverted repeat T-DNA configurations nor arrangements of tandemly repeated transgenes are sufficient to trigger transgene silencing" Plant J. 507-517.

Lewis et al. (2000) "Evaluation of extraction methods for recovery of fatty acids from lipid-producing microheterotrophs" Journal of Microbiological Methods, 43, 107-116.

Lewsey et al. (2007) "Selective targeting of miRNA-regulated plant development by a viral counter-silencing protein" Plant J. 50:240-252.

Lindbo et al. (1993) "Induction of a Highly Specific Antiviral State in Transgenic Plants: Implications for Regulation of Gene Expression and Virus Resistance" Plant Cell 5:1749-1759.

Lu et al. (1993) "High Efficiency Retroviral Mediated Gene Transduction into Single Isolated Immature and Replatable CD343+ Hematopoietic Stem/Progenitor Cells from Human Umbilical Cord Blood" J. Exp. Med. 178:2089-2096.

Mallory et al (2002) "The amplicon-plus system for high-level expression of transgenes in plants" Nat. Biotech. 20:622-625.

Matzke et al. (2001) "RNA: Guiding Gene Silencing" Science 293:1080-1083.

Meng et al. (2008) "*Hibiscus chlorotic* ringspot virus coat protein inhibits trans-acting small interfering RNA biogenesis in *Arabidopsis*" J. Gen. Virol. 89:2349-2358.

Moreau et al. (1998) "Lipid Trafficking in Plant Cells" Progress Lip. Res. 37:371-391.

Mortimer et al. (1986) "Genealogy of principal strains of the yeast genetic stock center" Genetics, 113, 35-43.

Moto et al. (2004) "Involvement of a bifunctional fatty-acyl desaturase in the biosynthesis of the silkmoth, *Bombyx mori*, sex pheromone" PNAS, 101(23), 8631-8636.

Murata & Wade (1995) "Acyl-lipid desaturases and their importance in the tolerance and acclimatization to cold of cyanobacteria" Biochem. J., 308, 1-8.

Napier (2007) "The Production of Unusual Fatty Acids in Transgenic Plants" Ann. Rev. Plant. Biol. 58:295-319.

Niedz et al (1995) "Green fluorescent protein: an in vivo reporter of plant gene expression" Plant Cell Reports 14:403-406.

Nishizawa et al. (2003) "A C-terminal sequence of soybean b-conglycinin a' subunit acts as a vacuolar sorting determinant in seed cells" Plant J. 34:647-659.

Ohlrogge and Browse (1995) "Lipid Biosynthesis" Plant Cell 7:957-970.

Ohlrogge and Jaworski (1997) Regulation of Fatty Acid Synthesis. Annu Rev Plant Physiol Plant Mol Biol. 48:109-136.

Ow et al. (1986) "Transient and Stable Expression of the Firefly Luciferase Gene in Plant Cells and Transgenic Plants" Science 234:856-859.

Park and Jeong (2005) "Cloning and Functional Expression of cDNA Encoding Pheromone Δ9 Acyl-CoA Desaturase of the Tobacco Cutworm, *Spodoptera litura* (Lepidoptera: Noctuidae)" Entomological Research, 35(4):253-263.

Passorn et al (1999) "Heterologous Expression of *Mucor rouxii* Δ12-Desaturase Gene in *Saccharomyces cerevisiae*" Biochemical and Biophysical Research Communications 263, 47-51.

Pereira et al. (2004) "Identification of two novel microalgal enzymes involved in the conversion of the ω3-fatty acid, eloosapentaenoic acid, into docosahexaenoic acid" Biochem. J.

Potenza et al. (2004) "Targeting Transgene Expression in Research, Agricultural, and Environmental Applications: Promoters Used in Plant Transformation" In Vitro Cell Dev Biol-Plant 40:1-22.

Qiu et al. (2001) "Identification and analysis of a gene from *Calendula officinalis* encoding a fatty acid conjugase" Plant Physiology, 125, 847-855.

Riddervold et al. (2002) "Biochemical and molecular characterizaton of house cricket (*Acheta domesticus*, Orthoptera: Gryllidee) Δ9 desaturase" Insect Biochemistry and Molecular Biology 32, 1731-1740.

Rodriguez et al. (2004) "Expression and evolution of Δ9 and Δ11 desaturase genes in the moth *Spodoptera littoralis*" Insect Biochemistry and Molecular Biology, 34, 1315-1328.

Rose et al. (1998) "Consensus-degenerate hybrid oligonucleotide primers for amplification of distantly related sequences" Nucleic Acids Res. 26:1628-1635.

Saha et al. (2006) "Cytosolic Triacylglycerol Biosynthetic Pathway in Oilseeds. Molecular Cloning and Expression of Peanut Cytosolic Diacylglycerol Acyltransferase" Plant Physiol. 141: 1533-1543.

Sayanova et al., (2012) "The role of delta (6)-desaturase acyl- carrier specificity in the efficient synthesis of long-chain polyunsaturated fatty acids in transgenic plants" Plant Biotechnology Journal, 10:195-206.

Serra et al. (2006) "All desaturases of *Trichoplusia* ni and *Spodoptera littoralis* exhibit dual catalytic behavior" Insect Biochemistry and Molecular Biology, 36, 822-825.

Shanklin & Cahoon (1998) "Desaturation and related modifications of fatty acids" Annu. Rev. Plant Physiol. Plant Mol. Biol., 49, 611-641.

Smith (1971) "Occurrence of unusual fatty acids in plants" Progress in the Chemistry of Fats and Other Lipids, 11, 137, 139-177.

Smith et al. (2003) "Heterologous expression of a fatty acid hydroxylase gene in developing seeds of *Arabidopsis thaliana*" Planta, 217, 507-516.

Stalker et al. (1988) "Purification and Properties of a Nitrilase Specific for the Herbicide Bromoxynil and Corresponding Nucleotide Sequence Analysis of the bxn Gene" J. Biol. Chem. 263:6310-6314.

Stanley-Samuelson et al. (1998) "Fatty Acids in Insects: Composition, Metabolism, and Biological Significance" Archives of Insect Biochemistry and Physiology 9:1-33.

Stukey et al. (1990) "The OLE1 gene of *Saccharomyces cerevisiae* encodes the Δ9 fatty acid desaturase and can be functionally replaced by the rat stearoyl-CoA desaturase gene" The Journal of Biological Chemistry, 265(33), 20144-20149.

Stymne & Appelqvist (1978) "The biosynthesis of linoleate from oleoyl-CoA via oleoyl-phosphatidylcholine in microsomes of developing safflower seeds" Eur. J. Biochem, 90, 223-229.

Suiyun al. (2004) "Introgression of salt-tolerance from somatic hybrids between common wheat and *Thinopyrum ponticum*" Plant Science 773-779.

Thompson et al. (1997) "The CLUSTAL_X windows interface: flexible strategies for multiple sequence alignment aided by quality analysis tools" Nucleic Acids Research, 25(24), 4876-4882.

Thillet et al (1988) "Site-directed Mutagenesis of Mouse Dihydrofolate Reductase" J. Biol. Chem 263:12500-12508.

Torlyama et al. (1986) "Haploid and diploid plant regeneration from protoplasts of anther callus in rice" Theor App? Genet, 73:16-19.

Tzfira & Citovsky (2006) "Agrobacterium-mediated genetic transformation of plants: biology and biotechnology" Curr. Opin. Biotech. 17:147-154.

(56) References Cited

OTHER PUBLICATIONS

Voinnet et al. (2003) "An enhanced transient expression system in plants based on suppression of gene silencing by the p19 protein of tomato bushy stunt virus" Plant J. 33:949-956.
Wada et al (1993) "The desA Gene of the *Cyanobacterium synechocystis* sp. Strain PCC6803 Is the Structural Gene for Δ12 Desaturase" Journal of Bacteriology 175(18):6056-6058.
Wagner et al. (1992) "Coupling of adenovirus to transferrin-polylysine/DNA complexes greatly enhances receptor-mediated gene delivery and expression of transfected genes" Proc. Natl. Acad. Sci. USA 89:6099-6103.
Wang and Hildebrand (1988) "Biosynthesis and Regulation of Linolenic Acid in Higher Plants" Plant Physiol. Biochem. 26(6), 777-792.
Watts and Browse (1999) "A Palmitoyl-CoA-Specific Δ9 Fatty Acid Desaturase from *Caenorhabditis elegans*" Arch. Biochem. Biophys. 362:175-182.
Whittle et al. (2005) "A multifunctional acyl-acyl carrier protein desaturase from *Hedera helix* L. (English ivy) can synthesize 16- and 18-carbon monoene and diene products" The Journal of Biological Chemistry, 280(31), 28169-28176.
Yang at al. (2003) "Expression and localization cif human lysozyme in the endosperm of transgenic rice" Planta 216:597-603.
Zhang at al. (2006) "cucumber mosaic virus-encoded 2b suppressor inhibits *Arabidopsis* Argonautel cleavage activity to counter plant defense" Genes & Development 20:3255-3268.
Zhou at al. (2005) "Heterologous production of GLA and SDA by expression of an *Echium plantagineum* Δ6-desaturase gene" Plant Science, 170, 665-673.
Zipfel at al. (2006) "Perception of the Bacterial PAMP EF-Tu by the Receptor EFR Restricts Agrobacterium-Mediated Transformation" Cell 125:749-760.
Genbank accession AAF19262, Benveniste (1998).
Genbank accession AAL37626, Qi et al. (2001).
GenBank accession AAM09687, Qiu at al. (2001).
GenBank accession AAR20444, Periera at al. (2003).
GenBank accession AAT85661, Kajikawa et al. (2004).
GenBank accession AAV67797, Meyer at al. (2004).
GenBank accession AAV67799, Meyer at al. (2004).
GenBank accession AAV67800, Meyer at al. (2004).
GenBank accession AAW70157, Domergue and Heinz (2004).
GenBank accession AAW70159, Domergue and Heinz (2004).
GenBank accession AAX14505, Tonon et al. (2004).
GenBank accession AAY15135, Zhou et al. (2005).
GenBank accession AAY15136, Zhou et al. (2005).
GenBank accession ABC18313, Huang and Jiang (2005).
GenBank accession ABC18314, Huang and Jiang (2005).
GenBank accession ABL63813, Zhang et al. (2006).
GenBank accession ABL96295, Zhou et al. (2006).
Genbank accession ABL96296, Zhou et al. (2006).
GenBank accession ABO94747, Grigoriev et al. (2007).
GenBank accession ABP49078, Li et al. (2007).
GenBank accession ABR67690, Niu et al. (2007).
GenBank accession AY746357, Domergue and Heinz (2004).
GenBank accession BAD11952, Lura and Kajiwara (2003).
Genbank accession BAD91495, Sakuradani et al. (2004).
GenBank accession CAD58540, Napier et al. (2002).
GenBank accession CAI58897, Zank et al. (2005).
GenBank accession CAJ30869, Cirpus et al. (2005).
GenBank accession CAL23339, Cirpus et al. (2006).
GenBank accession CAL55414, (2012).
GenBank accession CAM55882, Cirpus (2006).
GenBank accession EDQ92231, Kuo et al. (2007).
GenBank accession XP_001416454, Grigoriev et al. (2007).
GenBank accession XP_001421073 Grigoriev et al. (2007).
Apr. 22, 2014 Notice of Allowance, issued in connection with U.S. Appl. No. 13/918,399.
May 13, 2014 International Preliminary Report on Patentability, issued in connection with PCT International Patent Application No. PCT/AU2013/000639.

Apr. 15, 2014 Demand for International Preliminary Examination, including substitute claim pp. 164-186, filed in connection with PCT International Patent Application No. PCT/AU2013/000639.
Response to Office Action, filed Mar. 22, 2012 in connection with U.S. Appl. No. 13/044,984.
Final Office Action, issued May 17, 2012 in connection with U.S. Appl. No. 13/044,984.
Mar. 12, 2013 Office Action, issued in connection with U.S. Appl. No. 12/310,645.
Abbadi, A., et al., (2001) "Transgenic Oilseeds As Sustainable Source Of Nutritionally Relevant C20 And C22 Polyunsaturated Fatty Acids?" European Journal Of Lipid Science And Technology, 103(2): 106-113.
The *C. Elegans* Sequencing Consortium, (1998) "Genome Sequence Of The Nematode *C. elegans*: A Platform For Investigating Biology," Science, 282(5396): 2012-2018.
Akiyama, H., et al., (1998) "A Novel Plasmid Recombination Mechanism Of The Marine *Cyanobacterium synechococcus* sp. PCC7002," DNA Research, 5(6): 327-334.
Akiyama, H., et al., (1998) "Nucleotide Sequence Of Plasmid pAQ1 Of Marine *Cyanobacterium synechococcus* sp. PCC7002," DNA Research, 5(2): 127-129.
Bäumlein, H., et al., (1992) "Cis-Analysis Of A Seed Protein Gene Promoter: The Conservative RY Repeat CATGCATC Within The Legumin Box Is Essential For Tissue-Specific Expression Of A Legumin Gene," The Plant Journal, 2(2): 233-239.
Bäumlein, H., et al., (1991) "A Novel Seed Protein Gene From *Viola faba* Is Developmentally Regulated In Transgenic *Arabidopsis* Plants," Molecular And General Genetics, 225(3): 459-467.
Beaudoin, F., et al., (2000) "Heterologous Reconstitution In Yeast Of The Polyunsaturated Fatty Acid Biosynthetic Pathway," Proceedings Of The National Academy Of Sciences Of The United States Of America, 97(12): 6421-6426.
Bolch, C.J.S., et al., (1999) "Genetic, Morphological, And Toxicological Variation Among Globally Distributed Strains of *Nodularia* (Cyanobacteria)," Journal of Phycology, 35(2): 339-355.
Bolch, C.J.S., et al., (1999) "Genetic Variation Among Strains Of The Toxic Dinoflagellate *Gymnodinium catenatum* (Dinophyceae)," Journal of Phycology, 35: 356-367.
Brown, M.R., et al., (1997) "Nutritional Properties Of Microalgae For Mariculture," Aquaculture, 151(1): 315-331.
Browse, J.A. and Slack, C.R., (1981) "Catalase Stimulates Linoleate Desaturase Activity In Microsomes From Developing Linseed Cotyledons," Federation Of European Biochemical Societies Letters, 131(1): 111-114.
Chinain, M., et al., "Intraspecific Variation In The Dinoflagellate *Gambierdiscus toxicus* (Dinophyceae). I. Isozyme Analysis," Journal of Phycology, 33: 36-43, (1997).
Clough, S.J. and Bent, A.F., (1998) "Floral Dip: A Simplified Method for Agrobacterium-Mediated Transformation of *Arabidopsis thaliana*," 16(6); 735-743.
Coleman, A.W., (1977) "Sexual And Genetic Isolation In The Cosmopolitan Algal Species Pandorina Morum," American Journal of Botany, 64(3): 361-368.
Dafny-Yelin et al., Delivery of Multiple Transgenes to Plant Cells, Plant Physiology, Dec. 2007, vol. 145, pp. 1118-11128.
Domergue, F., et al., (2003) "New Insight Into *Phaeodactylum tricornutum* Fatty Acid Metabolism. Cloning And Functional Characterization Of Plastidial and Microsomal Δ12-Fatty Acid Desaturases," Plant Physiology, 131(4): 1648-1660.
Drexler, H., et al., (2003) "Metabolic Engineering Of Fatty Acids For Breeding Of New Oilseed Crops: Strategies, Problems And First Results," Journal Of Plant Physiology, 160(7): 779-802.
Dunstan, G.A., et al., (1994) "Essential Polyunsaturated Fatty Acids From 14 Species Of Diatom (Bacillariophyceae)," Phytochemistry, 35(1): 155-161.
Gallagher, J.C., (1980) "Population Genetics Of *Skeletonema costatum* (Bacillariophyceae) In Narragansett Bay," Journal of Phycology, (16)3: 464-474.
Guil-Guerrero, J.L., et al., (2000) "Occurrence And Characterization Of Oils Rich In γ-Linolenic Acid Part I: Echium Seeds From *Macaronesia*," Phytochemistry, 53(4): 451-456.

(56) References Cited

OTHER PUBLICATIONS

Halpin, Gene stacking in transgenic plants—the challenge for 21st century plant biotechnology, Plant Biotechnology Journal (2005, 3, pp. 141-155).
Haseloff, J. and Gerlach, W.L., (1988) "Simple RNA Enzymes With New And Highly Specific Endoribonuclease Activities," Nature, 334: 585-591.
Horiguchi, G., et al., (1998) "Developmental Regulation Of Genes For Microsome And Plastid Omega-3 Fatty Acid Desaturases In Wheat (*Triticum aestivum* L.)," Plant and Cell Physiology, 39(5): 540-544.
Ikeda, K., et al., (2002) "Transformation Of The Fresh Water *Cyanobacterium synechococcus* PCC7942 With The Shuttle-Vector pAQ-EX1 Developed For The Marine *Cyanobacterium synechococcus* PCC7002," World Journal of Microbiology & Biotechnology, 18(1): 55-56.
Jones, A.V.M. and Harwood, J.L., (1980) "Desaturation of Linoleic Acid From Exogenous Lipids by Isolated Chloroplasts," The Biochemical Journal, 190(3): 851-854.
Lee, M., et al., (1998) "Identification Of Non-theme Diiron Proteins That Catalyze Triple Bond And Epoxy Group Formation," Science, 280(5365): 915-918.
Leonard, A.E., et al., (2002) "Identification and Expression of Mammalian Long-Chain PUFA Elongation Enzymes," Lipids, 37(8): 733-740.
Lo, J., et al., (2003) "15,000 Unique Zebrafish EST Clusters and Their Future Use In Microarray For Profiling Expression Patterns During Embryogenesis," Genome Research Letter, 13(3): 455-466.
Mansour, M.P., et al., (1999) "The Fatty Acid And Sterol Composition Of Five Marine Dinoflagellates," Journal of Phycology, 35(4): 710-720.
Medlin, L.K., et al., (1996) "Genetic Characterization of *Emiliania huxleyi* (Haptophyta)," Journal of Marine Systems, 9: 13-31.
Metz, J.G., et al., (2001) "Production of Polyunsaturated Fatty Acids by Polyketide Synthases in Both Prokaryotes and Eukaryotes," Science, 293(5528) : 290-293.
Mitchell, A.G. and Martin, C., (1995) "A Novel Cytochrome b5-Like Domain Is Linked To The Carboxyl Terminus Of The *Saccharomyces cerevisiae* Δ-9 Fatty Acid Desaturase," The Journal Of Biological Chemistry, 270(50): 29766-29772.
Morita, N., et al., (2000) "Biosynthesis Of Fatty Acids In The Docosahexaenoic Acid-Producing Bacterium *Moritella marina* Strain MP-1," Biochemical Society Transactions, 28(6): 943-945.
Napier, J.A., et al., (1999) "A Growing Family Of Cytochrome b5-Domain Fusion Proteins," Trends In Plant Science, 4(1): 2-4.
Napier, J.A., et al., (1999) "Plant Desaturases: Harvesting The Fat Of The Land," Current Opinion In Plant Biology, 2(2): 123-127.
Needleman, S. B., & Wunsch, C. D. (1970). A general method applicable to the search for similarities in the amino acid sequence of two proteins. J. Mol. Biol., 48, 443-453.
Perriman, R., et al., (1992) "Extended Target-Site Specificity for a Hammerhead Ribozyme," Gene, 113(2): 157-163.
Sakuradani, F., et al., (1999) "Δ6-Fatty Acid Desaturase From An Arachidonic Acid-Producing *Mortierella* Fungus. Gene Cloning And Its Heterologous Expression In A Fungus, *Aspergillus*," Gene, 238(2): 445-453.
Sayanova, O.V., et al., (1999) "Histidine-41 Of The Cytochrome b5 Domain Of The Borage Δ6 Fatty Acid Desaturase Is Essential For Enzyme Activity," Plant Physiology, 121(2): 641-646..
Shippy, R., et al., (1999) "The Hairpin Ribozyme—Discovery, Mechanism, And Development For Gene Therapy," Molecular Biotechnology, 12(1): 117-129.
Simopoulos, A.P., (2000) "Symposium: Role Of Poultry Products In Enriching The Human Diet With N-3 PUFA," Poultry Science, 79: 961-970.
Singh, S., et al., (2001) "Transgenic Expression Of A Δ12-Epoxygenase Gene in *Arabidopsis* Seeds Inhibits Accumulation Of Linoleic Acid," Planta, 212: 872-879.

Slater et al., Metabolic engineering of *Arabidopsis* and *Brassica* for poly(3-hydroxybutyrate-co-3-hydroxyvalerate) copolymer production, Nature Biotechnology, Oct. 1999, vol. 12, 1011-1016.
Smith, N.A., et al., (2000) "Total Silencing By Intron-Spliced Hairpin RNAs," Nature, 407(6802): 319-320.
Sperling, P., et al., (2000) "A Bifunctional ΔA-Fatty Acyl Acetylenase/Desaturase From The Moss *Ceratodon purpureus*," European Journal of Biochemistry, 267(12): 3801-3811.
Sperling, P. and Heinz, E., (2001) "Desaturases Fused To Their Electron Donor," European Journal Of Lipid Science And Technology, 103(3): 158-180.
Stålberg, K., et al., (1993) "Deletion Analysis Of A 2S Seed Storage Protein Promoter Of *Brassica napus* In Transgenic Tobacco," Plant Molecular Biology, 23(4): 671-683.
Takeyama, H., et al., (1997) "Expression Of The Eicosapentaenoic Acid Synthesis Gene Cluster From *Shewanella* sp. In A Transgenic Marine Cyanobacterium, *Synechococcus* sp.," Microbiology, 143(Pt 8): 2725-2731.
Tanaka, M., et al., (1999) "Isolation Of Clustered Genes That Are Notably Homologous To The Eicosapentaenoic Acid Biosynthesis Gene Cluster From The Docosaehexaenoic Acid-Producing Bacterium *Vibrio marinus* Strain MP-1," Biotechnology Letters, 21(11): 939-945.
Tsevegsuren et al., (2003) "Isomers of hexadecenoic and hexadecadienoic acids in *Androspace septentrionalis* (Primulaceae) seed oil" Lipids 38(11):1173-1178.
Tvrdik, P., et al., (2000) "Role of a New Mammalian Gene Family In The Biosynthesis Of Very Long Chain Fatty Acids And Sphingolipids," The Journal of Cell Biology, 149(3); 707-717.
Valvekens, D., et al., (1988) "*Agrobacterium tumefaciens*—Mediated Transformation Of *Arabidopsis thaliana* Root Explants By Using Kanamycin Selection," Proceedings Of the National Academy of Sciences of the United States of America, 85(15) 5536-5540.
van de Loo, F. J., Broun, P., Turner, S., & Somerville, C. (Jul. 1995). An oleate 12-hydroxylase from *Ricinus communis* L. is a fatty acyl desaturase homolog. Proc. Natl. Acad. Sci. USA, 92, 6743-6747.
Volkman, J.K., et al., (1989) "Fatty Acid and Lipid Composition Of 10 Species Of Microalgae Used In Mariculture," Journal of Experimental Marine Biology and Ecology, 128(3): 219-240.
Wang, M.B., et al., (1997) "Intron-Mediated Improvement Of A Selectable Marker Gene For Plant Transformation Using *Agrobacterium tumefaciens*," Journal of Genetics & Breeding, 51: 325-334.
Waterbury, J.B. and Willey, J.M., (1988) "Isolation and Growth of Marine Planktonic Cyanobacteria," Methods of Enzymology, 167: 100-105.
Waterhouse, P.M., et al., (1998) "Virus Resistance And Gene Silencing In Plants Can Be Induced By Simultaneous Expression Of Sense And Antisense RNA," Proceedings of the National Academy of Sciences of the United States of America, 95(23): 13959-13964.
Williams, J.G.K. and Szalay, A.A., (1983) "Stable Integration of Foreign DNA Into The Chromosome Of The *Cyanobacterium synechococcus* R2," Gene, 24(1): 37-51.
Whitney, H., et al., (2003) "Functional Characterization of Two Cytochrome b5-Fusion Desaturases From *Anemone leveillei*: The Unexpected Identification Of A Fatty Acid Δ6-Desaturase," Planta, 217(6): 983-992.
Wolff, R. L., et al., (1999) "Arachidonic Eicosapentaenoic, and Biosynthetically Related Fatty Acids in the Seed Lipids from a Primitive Gymnosperm, Agathis Robusta" Lipids, 34(10):1083-1097.
Yazawa, K., (1996) "Production Of Eicosapentaenoic Acid From Marine Bacteria," Lipids, 31: S297-300.
R., et al., (2000) "Production of Eicosapentaenoic Acid By A Recombinant Marine *Cyanobacterium, Synechococcus* sp.," Lipids, 35(10): 1061-1064.
Zhou, X. and Christie, P.J., (1997) "Suppression Of Mutant Phenotypes Of The *Agrobacterium tumefaciens* VirB11 ATPase Overproduction Of VirB Proteins," Journal of Bacteriology, 179(18): 5835-5842.
Meyer et al. (2003) GenBank Accession No. AY278558, NCBI, pp. 1-2.
Tonon et al. (2003) GenBank Accession No. AY332747, NCBI, pp. 1-2.

(56) References Cited

OTHER PUBLICATIONS

Qiu et al. (2001) GenBank Accession No. AF489589, NCBI, pp. 1-2.
Thurmond et al. (2001) GenBank Accession No. AF391543, NCBI, pp. 1-2.
Cho et al. (1999) GenBank Accession No. AF199596, NCBI, pp. 1-2.
Sanger Institute. (2003) GenBank Accession No. NM_069350, NCBI, pp. 1-4.
Knutzon et al. (1998) GenBank Accession No. AF067654, NCBI, pp. 1-2.
Hong et al. (2001) GenBank Accession No. AF419297, NCBI, pp. 1-2.
Saito et al. (1999) GenBank Accession No. AB022097, NCBI, pp. 1-2.
Domergue et al. (2002) GenBank Accession No. AY082392, NCBI, pp. 1-2.
Qiu et al. (2003) GenBank Accession No. AF489588, NCBI, pp. 1-2.
Kajikawa et al. (2004) GenBank Accession No. AY583465, NCBI, pp. 1-2.
GenBank Accession No. NM_013402, NCBI, pp. 1-6, (2008).
GenBank Accession No. NM 019699, NCBI, pp. 1-3, (1999).
Swinburne et al. (1998) GenBank Accession No. 270271, NCBI, pp. 1-11.
Sayanova et al. (1996) GenBank Accession No. U79010, NCBI, pp. 1-2.
Maroto et al. (2001) GenBank Accession No. AY055117, NCBI, pp. 1-2.
Maroto et al. (2001) GenBank Accession No. AY055118, NCBI, pp. 1-2.
Sayanova et al. (2003) GenBank Accession No. AY234127, NCBI, pp. 1-2.
Sayanova et al. (2003) GenBank Accession No. AF536525, NCBI, pp. 1-2.
Sperling et al. (1999) GenBank Accession No. AJ250735, NCBI, pp. 1-2.
Kajikawa et al. (2004) GenBank Accession No. AY583463, NCBI, pp. 1-2.
Knutzon et al. (1998) GenBank Accession No. AF110510, NCBI, pp. 1-2.
Kobayashi et al. (1998) GenBank Accession No. AB020032, NCBI, pp. 1-2.
Qui et al. (2001) GenBank Accession No. AF419296, NCBI, pp. 1-2.
Aki et al. (2000) GenBank Accession No. AB052086, NCBI, pp. 1-2.
Zhang et al. (2003) GenBank Accession No. AY320288, NCBI, pp. 1-2.
Domergue et al. (2002) GenBank Accession No. AY082393, NCBI, pp. 1-2.
Reddy et al. (1993) GenBank Accession No. L11421, NCBI, pp. 1-2.
Hastings et al. (2000) GenBank Accession No. AF309556, NCBI, pp. 1-2.
Wallis et al. (1991) GenBank Accession No. AF139720, NCBI, pp. 1-2.
Libisch et al. (1999) GenBank Accession No. AF13372B, NCBI, pp. 1-2.
(2003) GenBank Accession No. NM 069288, NCBI, pp. 1-3.
Zank et al. (2002) GenBank Accession No. AF428243, NCBI, pp. 1-2.
Kajikawa et al. (2004) GenBank Accession No. AY583464, NCBI, pp. 1-2.
Chaung et al. (1999) GenBank Accession No. AF206662, NCBI, pp. 1-2.
Cirpues et al. (2003) GenBank Accession No. AX951565, NCBI, pp. 1.
Heinz et al. (2001) GenBank Accession No. AX214454, NCBI, pp. 1.
Leonard et al. (2000) GenBank Accession No. AF231981, NCBI, pp. 1-2.
Aki et al. (2001) GenBank Accession No. AB071985, NCBI, pp. 1-2.
Aki et al. (2001) GenBank Accession No. AB071986, NCBI, pp. 1-2.
Tvrdik et al. (1999) GenBank Accession No. AF170907, NCBI, pp. 1-2.
Tvrdik et al. (1999) GenBank Accession No. AF170908, NCBI, pp. 1-2.
Agaba et al. (2004) GenBank Accession No. AF532782, NCBI, pp. 1-2.
Lo et al. (2003) GenBank Accession No. NM_199532, NCBI, pp. 1-2.
Wilkinson et al. (1996) GenBank Accession No. 268749, NCBI, pp. 1-8.
Mukerji et al. (2002) GenBank Accession No. AX464802, NCBI, pp. 1.
Qi et al. (2001) GenBank Accession No. AF390174, NCBI, pp. 1-2.
File History of U.S. Patent No. 7,807,849, Singh et al., issued Oct. 5, 2010 (U.S. Appl. No. 11/112,882, filed Apr. 22, 2005).
File History of U.S. Patent Application Publication No. 2011/0015415, Singh, et al., published Jan. 20, 2011 (U.S. Appl. No. 12/661,978, filed Mar. 26, 2010).
File History of U.S. Patent Application Publication No. 2012-0041218, Singh et al., published Feb. 16, 2012, (U.S. Appl. No. 13/243,747, filed Sep. 23, 2011).
File History of U.S. Patent No. 7,834,250, Singh et al., issued Nov. 16, 2010 (U.S. Appl. No. 11/587,092, filed Oct. 20, 2006).
File History of U.S. Patent No. 7,932,438, Singh et al., issued (U.S. Appl. No. 12/945,708, filed Nov. 12, 2010).
File History of U.S. Patent Application Publication No. 2011/0201065, Singh et al., published Aug. 18, 2011 (U.S. Appl. No. 13/093,252, filed Apr. 25, 2011).
File History of U.S. Patent No. 8,158,392, Singh et al., issued Apr. 17, 2012 (U.S. Appl. No. 13/311,240, filed Sep. 23, 2011).
File History of U.S. Patent Application Publication No. 2011/0190521, Damcevski et al., published Aug. 4, 2011 (U.S. Appl. No. 12/310,645, filed Feb. 16, 2011).
File History of U.S. Appl. No. 12/989,405, Zhou et al., filed May 16, 2011.
File History of U.S. Patent No. 7,589,253, Green et al., issued Sep. 15, 2009 (U.S. Appl. No. 09/981,124, filed Oct. 17, 2011).
File History of U.S. Patent No. 7,834,248, Green et al., issued Nov. 16, 2010 (U.S. Appl. No. 11/699,817, filed Jan. 30, 2007).
File History of U.S. Patent Application No. 2012-0016144, Singh et al., Jan. 19, 2012 (U.S. Appl. No. 13/129,940, filed Sep. 30, 2011).

\* cited by examiner

A)

B)

PROCESS FOR PRODUCING POLYUNSATURATED FATTY ACIDS IN AN ESTERIFIED FORM

CROSS-REFERENCE TO RELATED APPLICATIONS

This application claims benefit of U.S. Provisional Patent Application No. 61/782,680, filed Mar. 14, 2013, U.S. Provisional Patent Application No. 61/697,676, filed Sep. 6, 2012, U.S. Provisional Patent Application No. 61/663,344, filed Jun. 22, 2012, and U.S. Provisional Patent Application No. 61/660,392, filed Jun. 15, 2012, the entire contents of each of which are hereby incorporated by reference into the subject application.

REFERENCE TO SEQUENCE LISTING

This application incorporates-by-reference nucleotide and/or amino acid sequences which are present in the file named "130614_2251_84199_B_Sequence_Listing_REB.txt," which is 369 kilobytes in size, and which was created Jun. 14, 2013 in the IBM-PC machine format, having an operating system compatibility with MS-Windows, which is contained in the text file filed Jun. 14, 2013 as part of this application.

FIELD OF THE INVENTION

The present invention relates to a process for producing ethyl esters of polyunsaturated fatty acids, comprising transesterifying triacylglycerols in extracted plant lipid.

BACKGROUND OF THE INVENTION

Omega-3 long-chain polyunsaturated fatty acids (LC-PUFA) are now widely recognized as important compounds for human and animal health. These fatty acids may be obtained from dietary sources or by conversion of linoleic (LA, 18:2ω6) or α-linolenic (ALA, 18:3ω3) fatty acids, both of which are regarded as essential fatty acids in the human diet. While humans and many other vertebrate animals are able to convert LA or ALA, obtained from plant sources to C22 they carry out this conversion at a very low rate. Moreover, most modern societies have imbalanced diets in which at least 90% of polyunsaturated fatty acids (PUFA) are of the ω6 fatty acids, instead of the 4:1 ratio or less for ω6:ω3 fatty acids that is regarded as ideal (Trautwein, 2001). The immediate dietary source of LC-PUFAs such as eicosapentaenoic acid (EPA, 20:5ω3) and docosahexaenoic acid (DHA, 22:6ω3) for humans is mostly from fish or fish oil. Health professionals have therefore recommended the regular inclusion of fish containing significant levels of LC-PUFA into the human diet. Increasingly, fish-derived LC-PUFA oils are being incorporated into food products and in infant formula, for example. However, due to a decline in global and national fisheries, alternative sources of these beneficial health-enhancing oils are needed.

Flowering plants, in contrast to animals, lack the capacity to synthesise polyunsaturated fatty acids with chain lengths longer than 18 carbons. In particular, crop and horticultural plants along with other angiosperms do not have the enzymes needed to synthesize the longer chain ω3 fatty acids such as EPA, docosapentaenoic acid (DPA, 22:5ω3) and DHA that are derived from ALA. An important goal in plant biotechnology is therefore the engineering of crop plants which produce substantial quantities of LC-PUFA, thus providing an alternative source of these compounds.

LC-PUFA Biosynthesis Pathways

Biosynthesis of LC-PUFAs in organisms such as microalgae, mosses and fungi usually occurs as a series of oxygen-dependent desaturation and elongation reactions (FIG. 1). The most common pathway that produces EPA in these organisms includes a Δ6-desaturation, Δ6-elongation and Δ5-desaturation (termed the Δ6-desaturation pathway) whilst a less common pathway uses a Δ9-elongation, Δ8-desaturation and Δ5-desaturation (termed the Δ9-desaturation pathway). These consecutive desaturation and elongation reactions can begin with either the ω6 fatty acid substrate LA, shown schematically as the upper left part of FIG. 1 (ω6) or the ω3 substrate ALA through to EPA, shown as the lower right part of FIG. 1 (ω3). If the initial Δ6-desaturation is performed on the ω6 substrate LA, the LC-PUFA product of the series of three enzymes will be the ω6 fatty acid ARA. LC-PUFA synthesising organisms may convert ω6 fatty acids to ω3 fatty acids using an ω3-desaturase, shown as the Δ17-desaturase step in FIG. 1 for conversion of arachidonic acid (ARA, 20:4ω6) to EPA. Some members of the ω3-desaturase family can act on a variety of substrates ranging from LA to ARA. Plant ω3-desaturases often specifically catalyse the Δ15-desaturation of LA to ALA, while fungal and yeast ω3-desaturases may be specific for the Δ17-desaturation of ARA to EPA (Pereira et al., 2004a; Zank et al., 2005). Some reports suggest that non-specific ω3-desaturases may exist which can convert a wide variety of ω6 substrates to their corresponding ω3 products (Zhang et al., 2008).

The conversion of EPA to DHA in these organisms occurs by a Δ5-elongation of EPA to produce DPA, followed by a Δ4-desaturation to produce DHA (FIG. 1). In contrast, mammals use the so-called "Sprecher" pathway which converts DPA to DHA by three separate reactions that are independent of a Δ4-desaturase (Sprecher et al., 1995).

The front-end desaturases generally found in plants, mosses, microalgae, and lower animals such as *Caenorhabditis elegans* predominantly accept fatty acid substrates esterified to the sn-2 position of a phosphatidylcholine (PC) substrate. These desaturases are therefore known as acyl-PC, lipid-linked, front-end desaturases (Domergue et al., 2003). In contrast, higher animal front-end desaturases generally accept acyl-CoA substrates where the fatty acid substrate is linked to CoA rather than PC (Domergue et al., 2005). Some microalgal desaturases and one plant desaturase are known to use fatty acid substrates esterified to CoA (Table 2).

Each PUFA elongation reaction consists of four steps catalysed by a multi-component protein complex: first, a condensation reaction results in the addition of a 2C unit from malonyl-CoA to the fatty acid, resulting in the formation of a β-ketoacyl intermediate. This is then reduced by NADPH, followed by a dehydration to yield an enoyl intermediate. This intermediate is finally reduced a second time to produce the elongated fatty acid. It is generally thought that the condensation step of these four reactions is substrate specific whilst the other steps are not. In practice, this means that native plant elongation machinery is capable of elongating PUFA providing that the condensation enzyme (typically called an 'elongase') specific to the PUFA is introduced, although the efficiency of the native plant elongation machinery in elongating the non-native PUFA substrates may be low. In 2007 the identification and characterisation of the yeast elongation cycle dehydratase was published (Denic and Weissman, 2007).

PUFA desaturation in plants, mosses and microalgae naturally occurs to fatty acid substrates predominantly in the acyl-PC pool whilst elongation occurs to substrates in the acyl-CoA pool. Transfer of fatty acids from acyl-PC molecules to a CoA carrier is performed by phospholipases (PLAs) whilst the transfer of acyl-CoA fatty acids to a PC carrier is performed by lysophosphatidyl-choline acyltransferases (LPCATs) (FIG. 21) (Singh et al., 2005).

Engineered Production of LC-PUFA

Most LC-PUFA metabolic engineering has been performed using the aerobic Δ6-desaturation/elongation pathway. The biosynthesis of γ-linolenic acid (GLA, 18:3ω6) in tobacco was first reported in 1996 using a Δ6-desaturase from the cyanobacterium *Synechocystis* (Reddy and Thomas, 1996). More recently, GLA has been produced in crop plants such as safflower (73% GLA in seedoil; Knauf et al., 2006) and soybean (28% GLA; Sato et al., 2004). The production of LC-PUFA such as EPA and DHA involves more complicated engineering due to the increased number of desaturation and elongation steps involved. EPA production in a land plant was first reported by Qi et al. (2004) who introduced genes encoding a Δ9-elongase from *Isochrysis galbana*, a Δ8-desaturase from *Euglena gracilis* and a Δ5-desaturase from *Mortierella alpina* into *Arabidopsis* yielding up to 3% EPA. This work was followed by Abbadi et al. (2004) who reported the production of up to 0.8% EPA in flax seed using genes encoding a Δ6-desaturase and Δ6-elongase from *Physcomitrella patens* and a Δ5-desaturase from *Phaeodactylum tricornutum*.

The first report of DHA production, and to date the highest levels of VLC-PUFA production reported, was in WO 04/017467 where the production of 3% DHA in soybean embryos is described, but not seed, by introducing genes encoding the *Saprolegnia diclina* Δ6-desaturase, *Mortierella alpina* Δ6-desaturase, *Mortierella alpina* Δ5-desaturase, *Saprolegnia diclina* Δ4-desaturase, *Saprolegnia diclina* Δ17-desaturase, *Mortierella alpina* Δ6-elongase and *Pavlova lutheri* Δ5-elongase. The maximal EPA level in embryos also producing DHA was 19.6%, indicating that the efficiency of conversion of EPA to DHA was poor (WO 2004/071467). This finding was similar to that published by Robert et al. (2005), where the flux from EPA to DHA was low, with the production of 3% EPA and 0.5% DHA in *Arabidopsis* using the *Danio rerio* Δ5/6-desaturase, the *Caenorhabditis elegans* Δ6-elongase, and the *Pavlova salina* Δ5-elongase and Δ4-desaturase. Also in 2005, Wu et al. published the production of 25% ARA, 15% EPA, and 1.5% DHA in *Brassica juncea* using the *Pythium irregulare* Δ6-desaturase, a Thraustochytrid Δ5-desaturase, the *Physcomitrella patens* Δ6-elongase, the *Calendula officianalis* Δ12-desaturase, a Thraustochytrid Δ5-elongase, the *Phytophthora infestans* Δ17-desaturase, the *Oncorhyncus mykiss* LC-PUFA elongase, a Thraustochytrid Δ4-desaturase and a Thraustochytrid LPCAT (Wu et al., 2005). Summaries of efforts to produce oil-seed crops which synthesize ω3 LC-PUFAs is provided in Venegas-Caleron et al. (2010) and Ruiz-Lopez et al. (2012). As indicated by Ruiz-Lopez et al. (2012), results obtained to date for the production of DHA in transgenic plants has been no where near the levels seen in fish oils.

There therefore remains a need for more efficient production of LC-PUFA in recombinant cells, in particular of DHA in seeds of oilseed plants.

SUMMARY OF THE INVENTION

The present inventors have identified methods and plants for producing lipid with high levels of DHA.

In a first aspect, the present invention provides extracted plant lipid, comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of DHA in the total fatty acid content of the extracted lipid is about 7% to 20%.

In an embodiment, the extracted lipid has one or more or all of the following features i) the level of palmitic acid in the total fatty acid content of the extracted lipid is between about 2% and 18%, between about 2% and 16%, or between about 2% and 15%, ii) the level of myristic acid (C14:0) in the total fatty acid content of the extracted lipid is less than about 6%, less than about 3%, less than about 2%, or less than about 1%, iii) the level of oleic acid in the total fatty acid content of the extracted lipid is between about 1% and about 30%, between about 3% and about 30%, between about 6% and about 30%, between 1% and about 20%, between about 30% and about 60%, between about 45% to about 60%, or is about 30%, iv) the level of linoleic acid (LA) in the total fatty acid content of the extracted lipid is between about 4% and about 35%, between about 4% and about 20%, or between about 4% and 17%, v) the level of α-linolenic acid (ALA) in the total fatty acid content of the extracted lipid is between about 4% and about 40%, between about 7% and about 40%, between about 10% and about 35%, between about 20% and about 35%, between about 4% and about 16%, or between about 2% and about 16%, vi) the level of γ-linolenic acid (GLA) in the total fatty acid content of the extracted lipid is less than about 4%, less than about 3%, less than about 2%, less than about 1%, less than about 0.5%, between 0.05% and about 7%, between 0.05% and about 4%, between 0.05% and about 3%, or between 0.05% and about 2%, vii) the level of stearidonic acid (SDA) in the total fatty acid content of the extracted lipid is less than about 7%, less than about 6%, less than about 4%, less than about 3%, between about 0.05% and about 7%, between about 0.05% and about 6%, between about 0.05% and about 4%, between about 0.05% and about 3%, or between 0.05% and about 2%, viii) the level of eicosatetraenoic acid (ETA) in the total fatty acid content of the extracted lipid is less than about 6%, less than about 5%, less than about 4%, less than about 1%, less than about 0.5%, between about 0.05% and about 6%, between about 0.05% and about 5%, between about 0.05% and about 4%, between about 0.05% and about 3%, or between about 0.05% and about 2%, ix) the level of eicosatrienoic acid (ETrA) in the total fatty acid content of the extracted lipid is less than about 4%, less than about 2%, less than about 1%, between about 0.05% and about 4%, between about 0.05% and about 3%, between about 0.05% and about 2%, or between about 0.05% and about 1%, x) the level of eicosapentaenoic acid (EPA) in the total fatty acid content of the extracted lipid is less than about 4%, less than about 3%, less than about 2%, between about 0.05% and about 10%, between about 0.05% and about 5%, between about 0.05% and about 3%, or between about 0.05% and about 2%.

xi) the level of docosapentaenoic acid (DPA) in the total fatty acid content of the extracted lipid is less than about 4%, less than about 3%, less than about 2%, between about 0.05% and about 8%, between about 0.05% and about 5%, between about 0.05% and about 3%, or between about 0.05% and about 2%, xii) the level of DHA in the total fatty acid content of the extracted lipid is about 8%, about 9%, about 10%, about 11%, about 12%, about 13%, about 14%, about 15%, about 16%, about 17%, about 18%, between about 8% and 20%, between about 10% and 20%, between about 11% and 20%, between about 10% and about 16%, or between about 14% and 20%, xiii) the lipid comprises ω6-docosapentaenoic acid (22:5$^{\Delta 4,7,10,13,16}$) in its fatty acid content, xiv) the lipid is essentially free of ω6-docosapentaenoic acid (22:5$^{\Delta 4,7,10,13,16}$) in its fatty acid content, xv) the lipid is essentially free of SDA, EPA and ETA in its fatty acid content, xvi) the level of total saturated fatty acids in the total fatty acid content of the extracted lipid is between about 4% and about 25%, between about 4% and about 20%, between about 6% and about 20%, between about 4% and about 60%, between about 30% and about 60%, or between about 45% and about 60%, xvii) the level of total monounsaturated fatty acids in the total fatty acid content of the extracted lipid is between about 4% and about 35%, between about 8% and about 25%, or between 8% and about 22%, xviii) the level of total polyunsaturated fatty acids in the total fatty acid content of the extracted lipid is between about 20% and about 75%, between about 50% and about 75%, or between about 60% and about 75%, xix) the level of total ω6 fatty acids in the total fatty acid content of the extracted lipid is between about 35% and about 50%, between about 20% and about 35%, between about 6% and 20%, less than about 20%, less than about 16%, less than about 10%, between about 1% and about 16%, between about 2% and about 10%, or between about 4% and about 10%, xx) the level of new ω6 fatty acids in the total fatty acid content of the extracted lipid is less than about 10%, less than about 8%, less than about 6%, less than about 4%, between about 1% and about 20%, between about 1% and about 10%, between about 0.5% and about 8%, or between about 0.5% and 4%, xxi) the level of total ω3 fatty acids in the total fatty acid content of the extracted lipid is between 36% and about 65%, between about 40% and about 60%, between about 20% and about 35%, between about 10% and about 20%, about 25%, about 30%, about 35% or about 40%, xxii) the level of new ω3 fatty acids in the total fatty acid content of the extracted lipid is between about 9% and about 33%, between about 10% and about 20%, between about 20% and about 30%, between about 12% and about 25%, about 13%, about 15%, about 17% or about 20%, xxiii) the ratio of total ω6 fatty acids:total ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 1.0, about 0.1 or about 0.2, xxiv) the ratio of new ω6 fatty acids:new ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 0.1, about 0.2 or about 1.0, xxv) the fatty acid composition of the lipid is based on an efficiency of conversion of oleic acid to LA by Δ12-desaturase of at least about 60%, at least about 70%, at least about 80%, between about 60% and about 98%, between about 70% and about 95%, or between about 75% and about 90%, xxvi) the fatty acid composition of the lipid is based on an efficiency of conversion of ALA to SDA by Δ6-desaturase of at least about 30%, at least about 40%, at least about 50%, at least about 60%, at least about 70%, between about 30% and about 70%, between about 35% and about 60%, or between about 50% and about 70%, xxvii) the fatty acid composition of the lipid is based on an efficiency of conversion of SDA to ETA acid by Δ6-elongase of at least about 60%, at least about 70%, at least about 75%, between about 60% and about 95%, between about 70% and about 88%, or between about 75% and about 85%, xxviii) the fatty acid composition of the lipid is based on an efficiency of conversion of ETA to EPA by Δ5-desaturase of at least about 60%, at least about 70%, at least about 75%, between about 60% and about 99%, between about 70% and about 99%, or between about 75% and about 98%, xxix) the fatty acid composition of the lipid is based on an efficiency of conversion of EPA to DPA by Δ5-elongase of at least about 80%, at least about 85%, at least about 90%, between about 50% and about 95%, or between about 85% and about 95%, xxx) the fatty acid composition of the lipid is based on an efficiency of conversion of DPA to DHA by Δ4-desaturase of at least about 80%, at least about 90%, at least about 93%, between about 50% and about 95%, between about 80% and about 95%, or between about 85% and about 95%, xxxi) the fatty acid composition of the lipid is based on an efficiency of conversion of oleic acid to DHA of at least about 10%, at least about 15%, at least about 20%, between about 10% and about 50%, between about 10% and about 30%, or between about 10% and about 25%, xxxii) the fatty acid composition of the lipid is based on an efficiency of conversion of LA to DHA of at least about 15%, at least about 20%, at least about 22%, at least about 25%, between about 15% and about 50%, between about 20% and about 40%, or between about 20% and about 30%, xxxiii) the fatty acid composition of the lipid is based on an efficiency of conversion of ALA to DHA of at least about 17%, at least about 22%, at least about 24%, between about 17% and about 55%, between about 22% and about 35%, or between about 24% and about 35%, xxxiv) the total fatty acid in the extracted lipid has less than 1% C20:1, xxxv) the triacylglycerol (TAG) content of the lipid is at least about 70%, at least about 80%, at least about 90%, at least 95%, between about 70% and about 99%, or between about 90% and about 99%, xxxvi) the lipid comprises diacylglycerol (DAG), xxxvii) the lipid comprises less than about 10%, less than about 5%, less than about 1%, or between about 0.001% and about 5%, free (non-esterified) fatty acids and/or phospholipid, or is essentially free thereof, xxxviii) at least 70%, or at least 80%, of the DHA esterified in the form of TAG is in the sn-1 or sn-3 position of the TAG, xxxix) the most abundant DHA-containing TAG species in the lipid is DHA/18:3/18:3 (TAG 58:12), and xl) the lipid comprises tri-DHA TAG (TAG 66:18).

In another embodiment, the extracted lipid is in the form of an oil, wherein at least about 90%, or least about 95%, at least about 98%, or between about 95% and about 98%, by weight of the oil is the lipid.

In a preferred embodiment, the lipid or oil, preferably a seedoil, has the following features: in the total fatty acid content of the lipid or oil, the level of DHA is between about 7% and 20%, the level of palmitic acid is between about 2% and about 16%, the level of myristic acid is less than about 6%, the level of oleic acid is between about 1% and about 30%, the level of LA is between about 4% and about 35%, ALA is present, GLA is present, the level of SDA is between about 0.05% and about 7%, the level of ETA is less than about 4%, the level of EPA is between about 0.05% and about 10%, the level of DPA is between about 0.05% and about 8%, the level of total saturated fatty acids in the total fatty acid content of the extracted lipid is between about 4% and about 25%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the ratio of total ω6 fatty acids:total ω3 fatty acids in the fatty acid content of the extracted lipid is between about 0.05 and about 3.0, the ratio of new ω6 fatty acids:new ω3 fatty acids in the fatty acid content of the extracted lipid is between about 0.03 and about 3.0, preferably less than about 0.50, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of EPA to DPA by Δ5-elongase of between about 50% and about 95%, an efficiency of conversion of DPA to DHA by Δ4-desaturase of between about 50% and about 95%, an efficiency of conversion of oleic acid to DHA of at least about 10%, and the triacylglycerol (TAG) content of the lipid is at least about 70%, and optionally the lipid is essentially free of cholesterol and/or the lipid comprises tri-DHA TAG (TAG 66:18).

In a more preferred embodiment, the lipid or oil, preferably a seedoil, has the following features: in the total fatty acid content of the lipid, the level of DHA is between about 7% and 20%, the level of palmitic acid is between about 2% and about 16%, the level of myristic acid is less than about 2%, the level of oleic acid is between about 1% and about 30%, the level of LA is between about 4% and about 35%, the level of ALA is between about 7% and about 40%, the level of GLA is less than about 4%, the level of SDA is between about 0.05% and about 7%, the level of ETA is less than about 4%, the level of ETrA is between about 0.05% and about 4%, the level of EPA is between about 0.05% and about 10%, the level of DPA is between about 0.05% and about 8%, the level of total saturated fatty acids in the total fatty acid content of the extracted lipid is between about 4% and about 25%, the level of total monounsaturated fatty acids in the total fatty acid content of the extracted lipid is between about 4% and about 35%, the level of total polyunsaturated fatty acids in the total fatty acid content of the extracted lipid is between about 20% and about 75%, the level of new ω6 fatty acids in the total fatty acid content of the extracted lipid is between about 0.5% and about 10%, the level of total ω3 fatty acids in the total fatty acid content of the extracted lipid is between 36% and about 75%, the level of new ω3 fatty acids in the total fatty acid content of the extracted lipid is between about 9% and about 33%, the ratio of total ω6 fatty acids:total ω3 fatty acids in the fatty acid content of the extracted lipid is between about 0.05 and about 3.0, the ratio of new ω6 fatty acids:new ω3 fatty acids in the fatty acid content of the extracted lipid is between about 0.03 and about 3.0, the fatty acid composition of the lipid is based on: an efficiency of conversion of oleic acid to LA by Δ12-desaturase of at least about 60%, an efficiency of conversion of SDA to ETA acid by Δ6-elongase of at least about 60%, an efficiency of conversion of ETA to EPA by Δ5-desaturase of at least about 60%, an efficiency of conversion of EPA to DPA by Δ5-elongase of between about 50% and about 95%, an efficiency of conversion of DPA to DHA by Δ4-desaturase of between about 50% and about 95%, an efficiency of conversion of oleic acid to DHA of at least about 10%, an efficiency of conversion of LA to DHA of at least about 15%, an efficiency of conversion of ALA to DHA of at least about 17%, and the total fatty acid content in the extracted lipid has less than 1% C20:1, the triacylglycerol (TAG) content of the lipid is at least about 70%, the lipid is essentially free of cholesterol, and the lipid comprises tri-DHA TAG (TAG 66:18). Preferably, the lipid or oil is canola oil and/or has not been treated with a transesterification process after it was extracted from the plant or plant part. In a particular embodiment, the lipid or canola oil may subsequently be treated to convert the fatty acids in the oil to alkyl esters such as methyl or ethyl esters. Further treatment may be applied to enrich the lipid or oil for the DHA.

In an embodiment, the lipid or oil, preferably a seedoil, has the following features: in the total fatty acid content of the lipid, the level of DHA is between about 7% and 20%, the level of palmitic acid is between about 2% and about 16%, the level of myristic acid is less than about 2%, the level of oleic acid is between about 30% and about 60%, preferably between about 45% and about 60%, the level of LA is between about 4% and about 20%, the level of ALA is between about 2% and about 16%, the level of GLA is less than about 3%, the level of SDA is less than about 3%, the level of ETA is less than about 4%, the level of ETrA less than about 2%, the level of EPA is less than about 4%, the level of DPA is less than about 4%, the level of total saturated fatty acids in the total fatty acid content of the extracted lipid is between about 4% and about 25%, the level of total monounsaturated fatty acids in the total fatty acid content of the extracted lipid is between about 30% and about 60%, or between about 40% and about 60%, the level of total polyunsaturated fatty acids in the total fatty acid content of the extracted lipid is between about 20% and about 75%, the level of new ω6 fatty acids in the total fatty acid content of the extracted lipid is between about 0.5% and about 10%, the level of total ω3 fatty acids in the total fatty acid content of the extracted lipid is between about 10% and about 20%, the level of new ω3 fatty acids in the total fatty acid content of the extracted lipid is between about 9% and about 20%, the ratio of total ω6 fatty acids:total ω3 fatty acids in the fatty acid content of the extracted lipid is between about 0.05 and about 3.0, preferably less than about 0.50, the ratio of new ω6 fatty acids:new ω3 fatty acids in the fatty acid content of the extracted lipid is between about 0.03 and about 3.0, the triacylglycerol (TAG) content of the lipid is at least about 70%, the lipid is essentially free of cholesterol, and the lipid comprises tri-DHA TAG (TAG 66:18). Preferably, the lipid or oil is essentially free of SDA, EPA and ETA and/or is canola oil and/or has not been treated with a transesterification process after it was extracted from the plant or plant part. In a particular embodiment, the lipid or canola oil may subsequently be treated to convert the fatty acids in the oil to alkyl esters such as methyl or ethyl esters. Further treatment may be applied to enrich the lipid or oil for the DHA.

In a further preferred embodiment, the lipid or oil, preferably a seedoil, has the following features: in the total fatty acid content of the lipid or oil, the level of DHA is between about 7% and 20%, the level of palmitic acid is between about 2% and about 16%, the level of myristic acid is less than about 6%, the level of oleic acid is between about 1% and about 30%, the level of LA is between about 4% and about 35%, ALA is present, GLA is present, the level of SDA is between about 0.05% and about 7%, the level of ETA is less than about 6%, the level of EPA is between about 0.05% and about 10%, the level of DPA is between about 0.05% and about 8%.

In a further embodiment, the extracted lipid further comprises one or more sterols, preferably plant sterols.

In another embodiment, the extracted lipid is in the form of an oil, and comprises less than about 10 mg of sterols/g of oil, less than about 7 mg of sterols/g of oil, between about 1.5 mg and about 10 mg of sterols/g of oil, or between about 1.5 mg and about 7 mg of sterols/g of oil.

Examples of sterols which can be in the extracted lipid include, but are not necessarily limited to, one or more or all of campesterol/24-methylcholesterol, Δ5-stigmasterol, eburicol, β-sitosterol/24-ethylcholesterol, Δ5-avenasterol/isofucosterol, Δ7-stigmasterol/stigmast-7-en-3β-ol, and Δ7-avenasterol.

In an embodiment, the plant species is one listed in Table 26, such as canola, and the level of sterols are about the same as that listed in Table 26 for that particular plant species.

In an embodiment, the extracted lipid comprises less than about 0.5 mg of cholesterol/g of oil, less than about 0.25 mg of cholesterol/g of oil, between about 0 mg and about 0.5 mg of cholesterol/g of oil, or between about 0 mg and about 0.25 mg of cholesterol/g of oil, or which is essentially free of cholesterol.

In a further embodiment, the lipid is an oil, preferably oil from an oilseed. Examples of such oils include, but are not limited to, *Brassica* sp. oil such as canola oil, *Gossypium hirsutlum* oil, *Linum usitatissimum* oil, *Helianthus* sp. oil, *Carthamus tinctorius* oil, *Glycine max* oil, *Zea mays* oil, *Arabidopsis thaliana* oil, *Sorghum bicolor* oil, *Sorghum vulgare* oil, *Avena sativa* oil, *Trifolium* sp. oil, *Elaesis guineenis* oil, *Nicotiana benthamiana* oil, *Hordeum vulgare* oil, *Lupinus angustifolius* oil, *Oryza sativa* oil, *Oryza glaberrima* oil, *Camelina sativa* oil, *Crambe abyssinica* oil, *Miscanthus× giganteus* oil, or *Miscanthus sinensis* oil.

Also provided is extracted plant lipid, preferably extracted canola seedoil, comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein lipid has the following features in the total fatty acid content of the lipid;

i) the level of DHA is about 3%, about 4%, about 5%, about 6% or about 7%,
ii) the level of palmitic acid is between about 2% and about 16%,
iii) the level of myristic acid is less than about 2%,
iv) the level of oleic acid is between about 30% and about 60%, preferably between about 45% and about 60%,
v) the level of LA is between about 4% and about 20%,
vi) the level of ALA is between about 2% and about 16%,
vii) the level of GLA is less than about 4%,
viii) the level of SDA is less than about 6%, or less than about 4%,
ix) the level of ETA is less than about 6%, or less than about 4%,
x) the level of ETrA less than about 1%,
xi) the level of EPA is less than about 10% and/or the level of EPA is 0.5-2.0 fold the level of DHA,
xii) the level of DPA is less than about 4%,
xiii) the level of total saturated fatty acids in the total fatty acid content of the extracted lipid is between about 4% and about 25%,
xiv) the level of total monounsaturated fatty acids in the total fatty acid content of the extracted lipid is between about 30% and about 70%,
xv) the level of total polyunsaturated fatty acids in the total fatty acid content of the extracted lipid is between about 15% and about 75%, preferably between about 15% and about 30%,
xvi) the level of new ω6 fatty acids in the total fatty acid content of the extracted lipid is between about 0.5% and about 10%,
xvii) the level of total ω3 fatty acids in the total fatty acid content of the extracted lipid is between about 10% and about 20%,
xviii) the level of new ω3 fatty acids in the total fatty acid content of the extracted lipid is between about 3% and about 20%,
xix) the ratio of total ω6 fatty acids:total ω3 fatty acids in the fatty acid content of the extracted lipid is between about 0.05 and about 3.0, preferably less than about 0.50,
xx) the ratio of new ω6 fatty acids:new ω3 fatty acids in the fatty acid content of the extracted lipid is between about 0.03 and about 3.0,
xxi) the triacylglycerol (TAG) content of the lipid is at least about 70%, and
xxii) the lipid is essentially free of cholesterol. In an embodiment, the lipid comprises tri-DHA TAG (TAG 66:18). More preferably, the lipid is essentially free of SDA and ETA, and/or has not been treated with a transesterification process after it was extracted from the plant or plant part.

In another aspect, provided is extracted plant lipid, comprising fatty acids in an esterified form, the fatty acids comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is between 7% and 20%, (ii) the level of palmitic acid in the total fatty acid content of the extracted lipid is between 2% and 16%, (iii) the level of myristic acid (C14:0) in the total fatty acid content of the extracted lipid is less than 6%, (iv) the level of oleic acid in the total fatty acid content of the extracted lipid is between 1% and 30% or between 30% and 60%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids: total ω3 fatty acids in the fatty acid content of the extracted lipid is between 1.0 and 3.0 or between 0.1 and 1, (x) the triacylglycerol (TAG) content of the lipid is at least 70%, and (xi) at least 70% of the DHA esterified in the form of TAG is in the sn-1 or sn-3 position of the TAG. In an embodiment, one or more or all of the following features
   i) the level of palmitic acid in the total fatty acid content of the extracted lipid is between 2% and 15%,
   ii) the level of myristic acid (C14:0) in the total fatty acid content of the extracted lipid is less than 1%,
   iii) the level of oleic acid in the total fatty acid content of the extracted lipid is between about 3% and about 30%, between about 6% and about 30%, between 1% and about 20%, between about 45% and about 60%, or is about 30%,
   iv) the level of linoleic acid (LA) in the total fatty acid content of the extracted lipid is between about 4% and about 20%, or between about 4% and 17%,
   v) the level of α-linolenic acid (ALA) in the total fatty acid content of the extracted lipid is between about 7% and about 40%, between about 10% and about 35%, between about 20% and about 35%, or between about 4% and 16%,
   vi) the level of γ-linolenic acid (GLA) in the total fatty acid content of the extracted lipid is less than 4%, less than about 3%, less than about 2%, less than about 1%, less than about 0.5%, between 0.05% and 7%, between 0.05% and 4%, or between 0.05% and about 3%, or between 0.05% and about 2%,
   vii) the level of stearidonic acid (SDA) in the total fatty acid content of the extracted lipid is less than about 4%, less than about 3%, between about 0.05% and about 7%, between about 0.05% and about 4%, between about 0.05% and about 3%, or between 0.05% and about 2%,
   viii) the level of eicosatetraenoic acid (ETA) in the total fatty acid content of the extracted lipid is less than about 4%, less than about 1%, less than about 0.5%, between about 0.05% and about 5%, between about 0.05% and about 4%, between about 0.05% and about 3%, or between about 0.05% and about 2%,
   ix) the level of eicosatrienoic acid (ETrA) in the total fatty acid content of the extracted lipid is less than about 2%, less than about 1%, between 0.05% and 4%, between 0.05% and 3%, or between 0.05% and about 2%, or between 0.05% and about 1%,
   x) the level of eicosapentaenoic acid (EPA) in the total fatty acid content of the extracted lipid is less than 4%, less than about 3%, less than about 2%, between 0.05% and 10%, between 0.05% and 5%, or between 0.05% and about 3%, or between 0.05% and about 2%,
   xi) the level of docosapentaenoic acid (DPA) in the total fatty acid content of the extracted lipid is less than 4%, less than about 3%, less than about 2%, between 0.05% and 8%, between 0.05% and 5%, or between 0.05% and about 3%, or between 0.05% and about 2%,
   xii) the level of DHA in the total fatty acid content of the extracted lipid is about 8%, about 9%, about 10%, about 11%, about 12%, about 13%, about 14%, about 15%, about 16%, about 17%, about 18%, between about 8% and 20%, between about 10% and 20%, between 11% and 20%, between about 10% and about 16%, or between about 14% and 20%,
   xiii) the lipid comprises ω6-docosapentaenoic acid (22:5$^{\Delta4,7,10,13,16}$) in its fatty acid content,
   xiv) the lipid is essentially free of ω6-docosapentaenoic acid (22:5$^{\Delta4,7,10,13,16}$) in its fatty acid content,
   xv) the lipid is essentially free of SDA, EPA and ETA in its fatty acid content,
   xvi) the level of total saturated fatty acids in the total fatty acid content of the extracted lipid is between about 4% and about 20%, or between about 6% and about 20%,
   xvii) the level of total monounsaturated fatty acids in the total fatty acid content of the extracted lipid is between about 4% and about 35%, between about 8% and about 25%, or between 8% and about 22%,
   xviii) the level of total polyunsaturated fatty acids in the total fatty acid content of the extracted lipid is between about 20% and about 75%, between about 50% and about 75%, or between about 60% and about 75%,
   xix) the level of total ω6 fatty acids in the total fatty acid content of the extracted lipid is between about 35% and about 50%, between about 20% and about 35%, between about 6% and 20%, less than 20%, less than about 16%, less than about 10%, between about 1% and about 16%, between about 2% and about 10%, or between about 4% and about 10%,
   xx) the level of new ω6 fatty acids in the total fatty acid content of the extracted lipid is less than about 10%, less than about 8%, less than about 6%, less than 4%, between about 1% and about 20%, between about 1% and about 10%, between about 0.5% and about 8%, or between about 0.5% and 4%,
   xxi) the level of total ω3 fatty acids in the total fatty acid content of the extracted lipid is between 36% and about 65%, between 40% and about 60%, between about 20% and about 35%, between about 10% and about 20%, about 25%, about 30%, about 35% or about 40%,
   xxii) the level of new ω3 fatty acids in the total fatty acid content of the extracted lipid is between 9% and about 33%, between about 10% and about 20%, between about 20% and about 30%, between about 12% and about 25%, about 13%, about 15%, about 17% or about 20%,
   xxiii) the ratio of total ω6 fatty acids:total ω3 fatty acids in the fatty acid content of the extracted lipid is between about 0.1 and about 0.5, less than about 0.50, less than about 0.40, less than about 0.30, less than about 0.20, less than about 0.15, about 1.0, about 0.1 or about 0.2,
   xxiv) the ratio of new ω6 fatty acids:new ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 0.1, about 0.2 or about 1.0,
   xxv) the fatty acid composition of the lipid is based on an efficiency of conversion of oleic acid to DHA of at least about 10%, at least about 15%, at least about 20%, between about 10% and about 50%, between about 10% and about 30%, or between about 10% and about 25%,
   xxvi) the fatty acid composition of the lipid is based on an efficiency of conversion of LA to DHA of at least about 15%, at least about 20%, at least about 22%, at least about 25%, between about 15% and about 50%, between about 20% and about 40%, or between about 20% and about 30%,
   xxvii) the fatty acid composition of the lipid is based on an efficiency of conversion of ALA to DHA of at least about 17%, at least about 22%, at least about 24%, between about 17% and about 55%, between about 22% and about 35%, or between about 24% and about 35%,
   xxviii) the total fatty acid in the extracted lipid has less than 1% C20:1,
   xxix) the triacylglycerol (TAG) content of the lipid is at least about 80%, at least about 90%, at least 95%, between about 70% and about 99%, or between about 90% and about 99%,
   xxx) the lipid comprises diacylglycerol (DAG), xxxi) the lipid comprises less than about 10%, less than about 5%, less than about 1%, or between about 0.001% and about 5%, free (non-esterified) fatty acids and/or phospholipid, or is essentially free thereof, xxxii) at least 80%, of the DHA esterified in the form of TAG is in the sn-1 or sn-3 position of the TAG, xxxiii) the most abundant DHA-containing TAG species in the lipid is DHA/18:3/18:3 (TAG 58:12), and xxxiv) the lipid comprises tri-DHA TAG (TAG 66:18).

With specific regard to the above aspect, in an embodiment i) the lipid is in the form of an oil, wherein the oil comprises one or more sterols such as one or more or all of campesterol, Δ5-stigmasterol, eburicol, β-sitosterol, Δ5-avenasterol, Δ7-stigmasterol and Δ7-avenasterol, and optionally the oil comprises less than 10 mg of sterols/g of oil and/or the oil is essentially free of cholesterol, and/or ii) the lipid is in the form of an oil from an oilseed such as oilseed is a *Brassica* sp oilseed or canola seed.

In another aspect, the present invention provides a process for producing extracted plant lipid, comprising the steps of i) obtaining a plant part comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of eicosapentaenoic acid (EPA), stearidonic acid (SDA), docosapentaenoic acid (DPA) and eicosatetraenoic acid (ETA), wherein the level of DHA in the total fatty acid content of extractable lipid in the plant part is about 7% to 20%, and ii) extracting lipid from the plant part, wherein the level of DHA in the total fatty acid content of the extracted lipid is about 7% to 20%.

In a preferred embodiment, the extracted lipid has one or more of the features defined above.

In an embodiment, wherein the plant part is a seed, preferably an oilseed. Examples of such seeds include, but are not limited to, *Brassica* sp., *Gossypium hirsutum*, *Linum usitatissimum*, *Helianthus* sp., *Carthamus tinctorius*, *Glycine max*, *Zea mays*, *Arabidopsis thaliana*, *Sorghum bicolor*, *Sorghum vulgare*, *Avena sativa*, *Trifblium* sp., *Elaesis guineenis*, *Nicotiana benthamiana*, *Hordeum vulgare*, *Lupinus angustifolius*, *Oryza sativa*, *Oryza glaberrima*, *Camelina sativa*, or *Crambe abyssinica*, preferably a *Brassica napus*, *B. juncea* or *C. sativa* seed.

In another embodiment, the seed comprises at least about 18 mg, at least about 22 mg, at least about 26 mg, between about 18 mg and about 100 mg, between about 22 mg and about 70 mg, or between about 24 mg and about 50 mg, of DHA per gram of seed.

In a further embodiment, the plant part comprises exogenous polynucleotides encoding one of the following sets of enzymes;

i) an ω3-desaturase, a Δ6-desaturase, a Δ5-desaturase, a Δ4-desaturase, a Δ6-elongase and a Δ5-elongase, ii) a Δ15-desaturase, a Δ6-desaturase, a Δ5-desaturase, a Δ4-desaturase, a Δ6-elongase and a Δ5-elongase, iii) a Δ12-desaturase, a Δ6-desaturase, a Δ5-desaturase, a Δ4-desaturase, a Δ6-elongase and an Δ5-elongase, iv) a Δ12-desaturase, a ω3-desaturase or a Δ15-desaturase, a Δ6-desaturase, a Δ5-desaturase, a Δ4-desaturase, a Δ6-elongase and an Δ5-elongase, v) an ω3-desaturase, a Δ8-desaturase, a Δ5-desaturase, a Δ4-desaturase, a Δ9-elongase and an Δ5-elongase, vi) a Δ15-desaturase, a Δ8-desaturase, a Δ5-desaturase, a Δ4-desaturase, a Δ9-elongase and a Δ5-elongase, vii) a Δ12-desaturase, a Δ8-desaturase, a Δ5-desaturase, a Δ4-desaturase, a Δ9-elongase and an Δ5-elongase, or viii) a Δ12-desaturase, a ω3-desaturase or a Δ15-desaturase, a Δ8-desaturase, a Δ5-desaturase, a Δ4-desaturase, a Δ9-elongase and an Δ5-elongase, and wherein each polynucleotide is operably linked to one or more promoters that are capable of directing expression of said polynucleotides in a cell of the plant part.

In yet a further embodiment, the plant part has one or more or all of the following features i) the Δ12-desaturase converts oleic acid to linoleic acid in one or more cells of the plant with an efficiency of at least about 60%, at least about 70%, at least about 80%, between about 60% and about 98%, between about 70% and about 95%, or between about 75% and about 90%, ii) the ω3-desaturase converts ω6 fatty acids to ω3 fatty acids in one or more cells of the plant with an efficiency of at least about 65%, at least about 75%, at least about 85%, between about 65% and about 95%, between about 75% and about 95%, or between about 80% and about 95%, iii) the Δ6-desaturase converts ALA to SDA in one or more cells of the plant with an efficiency of at least about 30%, at least about 40%, at least about 50%, at least about 60%, at least about 70%, between about 30% and about 70%, between about 35% and about 60%, or between about 50% and about 70%, iv) the Δ6-desaturase converts linoleic acid to γ-linolenic acid in one or more cells of the plant with an efficiency of less than about 5%, less than about 2.5%, less than about 1%, between about 0.1% and about 5%, between about 0.5% and about 2.5%, or between about 0.5% and about 1%, v) the Δ6-elongase converts SDA to ETA in one or more cells of the plant with an efficiency of at least about 60%, at least about 70%, at least about 75%, between about 60% and about 95%, between about 70% and about 88%, or between about 75% and about 85%, vi) the Δ5-desaturase converts ETA to EPA in one or more cells of the plant with an efficiency of at least about 60%, at least about 70%, at least about 75%, at least about 80%, at least about 90%, between about 60% and about 99%, between about 70% and about 99%, or between about 75% and about 98%, vii) the Δ5-elongase converts EPA to DPA in one or more cells of the plant with an efficiency of at least about 80%, at least about 85%, at least about 90%, between about 50% and about 95%, or between about 85% and about 95%, viii) the Δ4-desaturase converts DPA to DHA in one or more cells of the plant with an efficiency of at least about 80%, at least about 90%, at least about 93%, between about 50% and about 95%, between about 80% and about 95%, or between about 85% and about 95%, ix) the efficiency of conversion of oleic acid to DHA in one or more cells of the plant part is at least about 10%, at least about 15%, at least about 20%, between about 10% and about 50%, between about 10% and about 30%, or between about 10% and about 25%, x) the efficiency of conversion of LA to DHA in one or more cells of the plant part is at least about 15%, at least about 20%, at least about 22%, at least about 25%, between about 15% and about 50%, between about 20% and about 40%, or between about 20% and about 30%, xi) the efficiency of conversion of ALA to DHA in one or more cells of the plant part is at least about 17%, at least about 22%, at least about 24%, between about 17% and about 55%, between about 22% and about 35%, or between about 24% and about 35%, xii) one or more cells of the plant part comprise at least about 15%, at least about 20%, between about 15% and about 30%, or between about 22.5% and about 27.5%, more ω3 fatty acids than corresponding cells lacking the exogenous polynucleotides, xiii) the Δ6-desaturase preferentially desaturates α-linolenic acid (ALA) relative to linoleic acid (LA), xiv) the Δ6-elongase also has Δ9-elongase activity, xv) the Δ12-desaturase also has Δ15-desaturase activity, xvi) the Δ6-desaturase also has Δ8-desaturase activity, xvii) the Δ8-desaturase also has Δ6-desaturase activity or does not have Δ6-desaturase activity, xviii) the Δ15-desaturase also has ω3-desaturase activity on GLA, xix) the ω3-desaturase also has Δ15-desaturase activity on LA, xx) the ω3-desaturase desaturates both LA and/or GLA, xxi) the ω3-desaturase preferentially desaturates GLA relative to LA, xxii) the level of DHA in the plant part is based on an efficiency of conversion of oleic acid to DHA in the plant part of at least about 10%, at least about 15%, at least about 20%, between about 10% and about 50%, between about 15% and about 30%, or between about 20% and about 25%, xxiii) the level of DHA in the plant part is based on an efficiency of conversion of LA to DHA in the plant part of at least about 15%, at least about 20%, at least about 22%, between about 15% and about 60%, between about 20% and about 40%, or between about 22% and about 30%, xxiv) the level of DHA in the plant part is based on an efficiency of conversion of ALA to DHA in the plant part of at least about 17%, at least about 22%, at least about 24%, between about 17% and about 65%, between about 22% and about 35%, or between about 24% and about 35% xxx) one or more or all of the desaturases have greater activity on an acyl-CoA substrate than a corresponding acyl-PC substrate, xxxi) the Δ6-desaturase has greater Δ6-desaturase activity on ALA than LA as fatty acid substrate, xxxii) the Δ6-desaturase has greater Δ6-desaturase activity on ALA-CoA as fatty acid substrate than on ALA joined to the sn-2 position of PC as fatty acid substrate, xxxiii) the Δ6-desaturase has at least about a 2-fold greater Δ6-desaturase activity, at least 3-fold greater activity, at least 4-fold greater activity, or at least 5-fold greater activity, on ALA as a substrate compared to LA, xxxiv) the Δ6-desaturase has greater activity on ALA-CoA as fatty acid substrate than on ALA joined to the sn-2 position of PC as fatty acid substrate, xxxv) the Δ6-desaturase has at least about a 5-fold greater Δ6-desaturase activity or at least 10-fold greater activity, on ALA-CoA as fatty acid substrate than on ALA joined to the sn-2 position of PC as fatty acid substrate, xxxvi) the desaturase is a front-end desaturase, xxxvii) the Δ6-desaturase has no detectable Δ5-desaturase activity on ETA.

In yet a further embodiment, the plant part has one or more or all of the following features i) the Δ12-desaturase comprises amino acids having a sequence as provided in SEQ ID NO:10, a biologically active fragment thereof, or an amino acid sequence which is at least 50% identical to SEQ ID NO:10, ii) the ω3-desaturase comprises amino acids having a sequence as provided in SEQ ID NO:12, a biologically active fragment thereof, or an amino acid sequence which is at least 50% identical to SEQ ID NO:12, iii) the Δ6-desaturase comprises amino acids having a sequence as provided in SEQ ID NO:16, a biologically active fragment thereof, or an amino acid sequence which is at least 50% identical to SEQ ID NO:16, iv) the Δ6-elongase comprises amino acids having a sequence as provided in SEQ ID NO:25, a biologically active fragment thereof such as SEQ ID NO:26, or an amino acid sequence which is at least 50% identical to SEQ ID NO:25 and/or SEQ ID NO:26, v) the Δ5-desaturase comprises amino acids having a sequence as provided in SEQ ID NO:30, a biologically active fragment thereof, or an amino acid sequence which is at least 50% identical to SEQ ID NO:30, vi) the Δ5-elongase comprises amino acids having a sequence as provided in SEQ ID NO:37, a biologically active fragment thereof, or an amino acid sequence which is at least 50% identical to SEQ ID NO:37, vii) the Δ4-desaturase comprises amino acids having a sequence as provided in SEQ ID NO:41, a biologically active fragment thereof, or an amino acid sequence which is at least 50% identical to SEQ ID NO:41.

In an embodiment, the plant part further comprises an exogenous polynucleotide encoding a diacylglycerol acyltransferase (DGAT), monoacylglycerol acyltransferase (MGAT), glycerol-3-phosphate acyltransferase (GPAT), 1-acyl-glycerol-3-phosphate acyltransferase (LPAAT) preferably an LPAAT which can use a C22 polyunsaturated fatty acyl-CoA substrate, acyl-CoA:lysophosphatidylcholine acyltransferase (LPCAT), phospholipase $A_2$(PLA$_2$), phospholipase C(PLC), phospholipase D (PLD), CDP-choline diacylglycerol choline phosphotransferase (CPT), phoshatidylcholine diacylglycerol acyltransferase (PDAT), phosphatidylcholine:diacylglycerol choline phosphotransferase (PDCT), acyl-CoA synthase (ACS), or a combination of two or more thereof.

In another embodiment, the plant part further comprises an introduced mutation or an exogenous polynucleotide which down regulates the production and/or activity of an endogenous enzyme in a cell of the plant part selected from FAE1, DGAT, MGAT, GPAT, LPAAT, LPCAT, PLA$_2$, PLC, PLD, CPT, PDAT, a thioesterase such as FATB, or a Δ12-desaturase, or a combination of two or more thereof.

In a further embodiment, at least one, or all, of the promoters are seed specific promoters. In an embodiment, at least one, or all, of the promoters have been obtained from oil biosynthesis or accumulation genes such as oleosin, or from seed storage protein genes such as conlinin.

In another embodiment, the promoter(s) directing expression of the exogenous polynucleotides encoding the Δ4-desaturase and the Δ5-elongase initiate expression of the polynucleotides in developing seed of the plant part before, or reach peak expression before, the promoter(s) directing expression of the exogenous polynucleotides encoding the Δ12-desaturase and the ω3-desaturase.

In a further embodiment, the exogenous polynucleotides are covalently linked in a DNA molecule, preferably a T-DNA molecule, integrated into the genome of cells of the plant part and preferably where the number of such DNA molecules integrated into the genome of the cells of the plant part is not more than one, two or three, or is two or three.

In yet another embodiment, the plant comprises at least two different, exogenous polynucleotides each encoding a Δ6-desaturase which have the same or different amino acid sequences.

In a further embodiment, the total oil content of the plant part comprising the exogenous polynucleotides is at least about 40%, or at least about 50%, or at least about 60%, or at least about 70%, or between about 50% and about 80% of the total oil content of a corresponding plant part lacking the exogenous polynucleotides. In these embodiments, the maximum oil content may be about 100% of the oil content of a corresponding wild-type plant part.

In another embodiment, the lipid is in the form of an oil, preferably a seedoil from an oilseed, and wherein at least about 90%, or about least 95%, at least about 98%, or between about 95% and about 98%, by weight of the lipid is triacylglycerols.

In a further embodiment, the process further comprises treating the lipid to increase the level of DHA as a percentage of the total fatty acid content. For example, the treatment is transesterification. For example, the lipid such as canola oil may be treated to convert the fatty acids in the oil to alkyl esters such as methyl or ethyl esters, which may then be fractionated to enrich the lipid or oil for the DHA.

Further, provided is a process for producing extracted plant lipid, comprising the steps of
i) obtaining a plant part, preferably canola seed, comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of eicosapentaenoic acid (EPA), stearidonic acid (SDA), docosapentaenoic acid (DPA) and eicosatetraenoic acid (ETA), wherein the level of DHA in the total fatty acid content of extractable lipid in the plant part is about 3%, about 4%, about 5%, about 6% or about 7%, and
ii) extracting lipid from the plant part,
wherein the extracted lipid has the following features in the total fatty acid content of the lipid;
i) the level of DHA is about 3%, about 4%, about 5%, about 6% or about 7%,
ii) the level of palmitic acid is between about 2% and about 16%,
iii) the level of myristic acid is less than about 2%,
iv) the level of oleic acid is between about 30% and about 60%, preferably between about 45% and about 60%,
v) the level of LA is between about 4% and about 20%,
vi) the level of ALA is between about 2% and about 16%,
vii) the level of GLA is less than about 4%,
viii) the level of SDA is less than about 6%, or less than about 4%,
ix) the level of ETA is less than about 6%, or less than about 4%,
x) the level of ETrA less than about 1%,
xi) the level of EPA is less than about 10% and/or the level of EPA is 0.5-2.0 fold the level of DHA,
xii) the level of DPA is less than about 4%,
xiii) the level of total saturated fatty acids in the total fatty acid content of the extracted lipid is between about 4% and about 25%,
xiv) the level of total monounsaturated fatty acids in the total fatty acid content of the extracted lipid is between about 30% and about 70%,
xv) the level of total polyunsaturated fatty acids in the total fatty acid content of the extracted lipid is between about 15% and about 75%, preferably between about 15% and about 30%,
xvi) the level of new ω6 fatty acids in the total fatty acid content of the extracted lipid is between about 0.5% and about 10%,
xvii) the level of total ω3 fatty acids in the total fatty acid content of the extracted lipid is between about 10% and about 20%,
xviii) the level of new ω3 fatty acids in the total fatty acid content of the extracted lipid is between about 3% and about 20%,
xix) the ratio of total ω6 fatty acids:total ω3 fatty acids in the fatty acid content of the extracted lipid is between about 0.05 and about 3.0, preferably less than about 0.50,
xx) the ratio of new ω6 fatty acids:new ω3 fatty acids in the fatty acid content of the extracted lipid is between about 0.03 and about 3.0,
xxi) the triacylglycerol (TAG) content of the lipid is at least about 70%, and
xxii) the lipid is essentially free of cholesterol. In an embodiment, the lipid comprises tri-DHA TAG (TAG 66:18). More preferably, the lipid is essentially free of SDA and ETA, and/or has not been treated with a transesterification process after it was extracted from the plant or plant part.

Also provided is a process for producing extracted plant lipid, comprising the steps of
i) obtaining a plant part comprising lipid, the lipid comprising fatty acids in an esterified form, the fatty acids comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is between 7% and 20%, (ii) the level of palmitic acid in the total fatty acid content of the extracted lipid is between 2% and 16%, (iii) the level of myristic acid (C14:0) in the total fatty acid content of the extracted lipid is less than 6%, (iv) the level of oleic acid in the total fatty acid content of the extracted lipid is between 1% and 30% or between 30% and 60%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids: total ω3 fatty acids in the fatty acid content of the extracted lipid is between 1.0 and 3.0 or between 0.1 and 1, (x) the triacylglycerol (TAG) content of the lipid is at least 70%, and (xi) at least 70% of the DHA esterified in the form of TAG is in the sn-1 or sn-3 position of the TAG.
%, and
ii) extracting lipid from the plant part, wherein the level of DHA in the total fatty acid content of the extracted lipid is about 7% to 20%.

Also provided is lipid, or oil comprising the lipid, produced using a process of the invention.

In another aspect, the present invention provides a process for producing ethyl esters of polyunsaturated fatty acids, the process comprising transesterifying triacylglycerols in extracted plant lipid, wherein the extracted plant lipid comprises fatty acids esterified in the form, the fatty acids comprising oleic acid, palmitic acid, ω6 fatty acids which comprise linoleic acid (LA), ω3 fatty acids which comprise α-linolenic acid (ALA), and docosahexaenoic acid (DHA), and optionally one or more of stearidonic acid (SDA), eicosapentaenoic acid (EPA), docosapentaenoic acid (DPA) and eicosatetraenoic acid (ETA), wherein the level of DHA in the total fatty acid content of the extracted lipid is about 7% to 20%, thereby producing the ethyl esters.

In a preferred embodiment, the extracted lipid has one or more of the features defined above.

In another aspect, the present invention provides a process for producing ethyl esters of polyunsaturated fatty acids, the process comprising transesterifying triacylglycerols in extracted plant lipid, wherein the extracted plant lipid comprises fatty acids esterified in the form of the triacylglycerols, the fatty acids comprising oleic acid, palmitic acid, ω6 fatty acids which comprise linoleic acid (LA), ω3 fatty acids which comprise α-linolenic acid (ALA) and docosahexaenoic acid (DHA), and one or more of stearidonic acid (SDA), eicosapentaenoic acid (EPA), docosapentaenoic acid (DPA) and eicosatetraenoic acid (ETA), wherein (i) the level of DHA in the total fatty acid content of the extracted lipid is about 3%, about 4%, about 5%, about 6% or between 7% and 20%, (ii) the level of palmitic acid in the total fatty acid content of the extracted lipid is between 2% and 16%, (iii) the level of myristic acid (C14:0) in the total fatty acid content of the extracted lipid is less than 6%, (iv) the level of oleic acid in the total fatty acid content of the extracted lipid is between 1% and 30% or between 30% and 60%, (v) the level of linoleic acid (LA) in the total fatty acid content of the extracted lipid is between 4% and 35%, (vi) the level of α-linolenic acid (ALA) in the total fatty acid content of the extracted lipid is between 4% and 40%, (vii) the level of eicosatrienoic acid (ETrA) in the total fatty acid content of the extracted lipid is less than 4%, (viii) the level of total saturated fatty acids in the total fatty acid content of the extracted lipid is between 4% and 25%, (ix) the ratio of total ω6 fatty acids:total to 3 fatty acids in the fatty acid content of the extracted lipid is between 1.0 and 3.0 or between 0.1 and 1, (x) the triacylglycerol (TAG) content of the lipid is at least 70%, and (xi) at least 70% of the DHA esterified in the form of TAG is in the sn-1 or sn-3 position of the TAG, thereby producing the ethyl esters. In an embodiment, the extracted plant lipid has one or more or all of the following features i) the level of palmitic acid in the total fatty acid content of the extracted lipid is between 2% and 15%,
ii) the level of myristic acid (C14:0) in the total fatty acid content of the extracted lipid is less than 1%,
xxxv) the level of oleic acid in the total fatty acid content of the extracted lipid is between about 3% and about 30%, between about 6% and about 30%, between 1% and about 20%, between about 45% and about 60%, or is about 30%,
xxxvi) the level of linoleic acid (LA) in the total fatty acid content of the extracted lipid is between about 4% and about 20%, or between about 4% and about 17%,
xxxvii) the level of α-linolenic acid (ALA) in the total fatty acid content of the extracted lipid is between about 7% and about 40%, between about 10% and about 35%, between about 20% and about 35%, or between about 4% and 16%,
xxxviii) the level of γ-linolenic acid (GLA) in the total fatty acid content of the extracted lipid is less than 4%, less than about 3%, less than about 2%, less than about 1%, less than about 0.5%, between 0.05% and 7%, between 0.05% and 4%, or between 0.05% and about 3%, or between 0.05% and about 2%,
xxxix) the level of stearidonic acid (SDA) in the total fatty acid content of the extracted lipid is less than about 4%, less than about 3%, between about 0.05% and about 7%, between about 0.05% and about 4%, between about 0.05% and about 3%, or between 0.05% and about 2%,
xl) the level of eicosatetraenoic acid (ETA) in the total fatty acid content of the extracted lipid is less than about 4%, less than about 1%, less than about 0.5%, between about 0.05% and about 5%, between 0.05% and about 4%, between about 0.05% and about 3%, or between about 0.05% and about 2%,
xli) the level of eicosatrienoic acid (ETrA) in the total fatty acid content of the extracted lipid is less than about 2%, less than about 1%, between 0.05% and 4%, between 0.05% and 3%, or between 0.05% and about 2%, or between 0.05% and about 1%,
xlii) the level of eicosapentaenoic acid (EPA) in the total fatty acid content of the extracted lipid is less than 4%, less than about 3%, less than about 2%, between 0.05% and 10%, between 0.05% and 5%, or between 0.05% and about 3%, or between 0.05% and about 2%,
xliii) the level of docosapentaenoic acid (DPA) in the total fatty acid content of the extracted lipid is less than 4%, less than about 3%, less than about 2%, between 0.05% and 8%, between 0.05% and 5%, or between 0.05% and about 3%, or between 0.05% and about 2%,
xliv) the level of DHA in the total fatty acid content of the extracted lipid is about 8%, about 9%, about 10%, about 11%, about 12%, about 13%, about 14%, about 15%, about 16%, about 17%, about 18%, between about 8% and 20%, between about 10% and 20%, between about 11% and 20%, between about 10% and about 16%, or between about 14% and 20%,
xlv) the lipid comprises ω6-docosapentaenoic acid (22:5$^{\Delta 4,7,10,13,16}$) in its fatty acid content,
xlvi) the lipid is essentially free of ω6-docosapentaenoic acid (22:5$^{\Delta 4,7,10,13,16}$) in its fatty acid content,
xlvii) the lipid is essentially free of SDA, EPA and ETA in its fatty acid content,
xlviii) the level of total saturated fatty acids in the total fatty acid content of the extracted lipid is between about 4% and about 20%, or between about 6% and about 20%,
xlix) the level of total monounsaturated fatty acids in the total fatty acid content of the extracted lipid is between about 4% and about 35%, between about 8% and about 25%, or between 8% and about 22%,
l) the level of total polyunsaturated fatty acids in the total fatty acid content of the extracted lipid is between about 20% and about 75%, between about 50% and about 75%, or between about 60% and about 75%, li) the level of total ω6 fatty acids in the total fatty acid content of the extracted lipid is between about 35% and about 50%, between about 20% and about 35%, between about 6% and 20%, less than 20%, less than about 16%, less than about 10%, between about 1% and about 16%, between about 2% and about 10%, or between about 4% and about 10%,
lii) the level of new ω6 fatty acids in the total fatty acid content of the extracted lipid is less than about 10%, less than about 8%, less than about 6%, less than 4%, between about 1% and about 20%, between about 1% and about 10%, between about 0.5% and about 8%, or between about 0.5% and 4%,
liii) the level of total ω3 fatty acids in the total fatty acid content of the extracted lipid is between 36% and about 65%, between 40% and about 60%, between about 20% and about 35%, between about 10% and about 20%, about 25%, about 30%, about 35% or about 40%,
liv) the level of new ω3 fatty acids in the total fatty acid content of the extracted lipid is between 9% and about 33%, between about 10% and about 20%, between about 20% and about 30%, between about 12% and about 25%, about 13%, about 15%, about 17% or about 20%,
lv) the ratio of total ω6 fatty acids:total ω3 fatty acids in the fatty acid content of the extracted lipid is between about 0.1 and about 0.5, less than about 0.50, less than about 0.40, less than about 0.30, less than about 0.20, less than about 0.15, about 1.0, about 0.1 or about 0.2, lvi) the ratio of new ω6 fatty acids:new ω3 fatty acids in the fatty acid content of the extracted lipid is between about 1.0 and about 3.0, between about 0.1 and about 1, between about 0.1 and about 0.5, less than about 0.50, less than about 0.40, less than about 0.30, less than about 0.20, less than about 0.15, about 0.1, about 0.2 or about 1.0, lvii) the fatty acid composition of the lipid is based on an efficiency of conversion of oleic acid to DHA of at least about 10%, at least about 15%, at least about 20%, between about 10% and about 50%, between about 10% and about 30%, or between about 10% and about 25%, lviii) the fatty acid composition of the lipid is based on an efficiency of conversion of LA to DHA of at least about 15%, at least about 20%, at least about 22%, at least about 25%, between about 15% and about 50%, between about 20% and about 40%, or between about 20% and about 30%, lix) the fatty acid composition of the lipid is based on an efficiency of conversion of ALA to DHA of at least about 17%, at least about 22%, at least about 24%, between about 17% and about 55%, between about 22% and about 35%, or between about 24% and about 35%, lx) the total fatty acid in the extracted lipid has less than 1% C20:1, lxi) the triacylglycerol (TAG) content of the lipid is at least about 80%, at least about 90%, at least 95%, between about 70% and about 99%, or between about 90% and about 99%, lxii) the lipid comprises diacylglycerol (DAG), lxiii) the lipid comprises less than about 10%, less than about 5%, less than about 1%, or between about 0.001% and about 5%, free (non-esterified) fatty acids and/or phospholipid, or is essentially free thereof, lxiv) at least 80%, of the DHA esterified in the form of TAG is in the sn-1 or sn-3 position of the TAG, lxv) the most abundant DHA-containing TAG species in the lipid is DHA/18:3/18:3 (TAG 58:12), and lxvi) the lipid comprises tri-DHA TAG (TAG 66:18).

With specific regard to the above aspect, in an embodiment one or more or all of the following apply i) the lipid is in the form of an oil, wherein the oil comprises one or more sterols such as one or more or all of campesterol, Δ5-stigmasterol, eburicol, β-sitosterol, Δ5-avenasterol, Δ7-stigmasterol and Δ7-avenasterol, and optionally the oil comprises less than 10 mg of sterols/g of oil and/or the oil is essentially free of cholesterol, ii) the lipid is in the form of an oil from an oilseed such as oilseed is a *Brassica* sp oilseed or canola seed, iii) the level of DHA in the total fatty acid content of the extracted plant lipid is about 3%, about 4%, about 5%, about 6%, or is between 7% and 20%.

In a further aspect, the present invention provides a chimeric genetic construct comprising in order a first gene, a second gene, a third gene, a fourth gene, a fifth gene and a sixth gene which are all covalently linked on a single DNA molecule, wherein the first, second and third genes are joined together as a first gene cluster and the fourth, fifth and sixth genes are joined together as a second gene cluster, wherein each gene comprises a promoter, a coding region and a transcription terminator and/or polyadenylation region such that each promoter is operably linked to the coding region and transcription terminator and/or polyadenylation region, wherein each promoter is independently identical or different to the other promoters such that the DNA molecule comprises three, four, five or six different promoters, wherein one or more or all of the promoters are heterologous with respect to the coding region to which it is operably linked, wherein the direction of transcription of the first gene is away from the third gene and opposite to the direction of transcription of the third gene, wherein the direction of transcription of the fourth gene is away from the sixth gene and opposite to the direction of transcription of the sixth gene, wherein the direction of transcription of the second gene is the same as for the first gene or the third gene, wherein the direction of transcription of the fifth gene is the same as for the fourth gene or the sixth gene, wherein the transcription terminator and/or polyadenylation region of the second gene is spaced apart from the promoter of the first or third genes, whichever is closer, by a first spacer region of between about 0.2 and about 3.0 kilobases, wherein the first gene cluster is spaced apart from the second gene cluster by a second spacer region of between about 1.0 and about 10.0 kilobases, and wherein the transcription terminator and/or polyadenylation region of the fifth gene is spaced apart from the promoter of the fourth or sixth genes, whichever is closer, by a third spacer region of between about 0.2 and about 3.0 kilobases.

In an embodiment, the DNA molecule comprises a seventh gene which is spaced apart from the first gene cluster or the second gene cluster, whichever is closer, by a spacer region of between about 1.0 and about 10.0 kilobases.

In another embodiment, the DNA molecule comprises two or more different transcription terminator and/or polyadenylation regions.

In yet a further embodiment, at least one of the spacer regions comprises a matrix attachment region (MAR).

In a further embodiment, the DNA molecule comprises right and left border regions flanking the genes and is a T-DNA molecule.

In another embodiment, the genetic construct is in an *Agrobacterium* cell or is integrated into the genome of a plant cell.

In a preferred embodiment, at least one of the genes encodes a fatty acid desaturase or a fatty acid elongase.

In another embodiment, the genetic construct comprises genes encoding a set of enzymes as defined herein, and/or wherein one or more of the genes encode an enzyme as defined herein.

In a further aspect, the present invention provides an isolated and/or exogenous polynucleotide comprising:

i) a sequence of nucleotides selected from any one of SEQ ID NOs: 1 to 9, 11, 14, 18, 22, 23, 28, 34, 35, 39 or 45, and/or ii) a sequence of nucleotides which are at least 95% identical or 99% identical to one or more of the sequences set forth in SEQ ID NOs: 1 to 9, 11, 14, 18, 22, 23, 28, 34, 35, 39 or 45.

In a particularly preferred embodiment, the isolated and/or exogenous polynucleotide comprises:

i) a sequence of nucleotides of SEQ ID NO: 2, and/or ii) a sequence of nucleotides which are at least 95% identical or 99% identical to the sequence set forth in SEQ ID NO: 2.

In another aspect, the present invention provides a vector or genetic construct comprising the polynucleotide of the invention and/or the genetic construct of the invention.

In an embodiment, the sequence of nucleotides selected from any one of SEQ ID NOs: 11, 14, 18, 22, 23, 28, 34, 35, 39 or 45, or the sequence of nucleotides which is at least 95% identical or 99% identical to one or more of the sequences set forth in SEQ ID NOs: 11, 14, 18, 22, 23, 28, 34, 35, 39 or 45, is operably linked to a promoter.

In a further aspect, the present invention provides a host cell comprising exogenous polynucleotides encoding one of the following sets of enzymes;

i) an ω3-desaturase, a Δ6-desaturase, a Δ5-desaturase, a Δ4-desaturase, a Δ6-elongase and a Δ5-elongase, ii) a Δ15-desaturase, a Δ6-desaturase, a Δ5-desaturase, a Δ4-desaturase, a Δ6-elongase and a Δ5-elongase, iii) a Δ12-desaturase, a Δ6-desaturase, a Δ5-desaturase, a Δ4-desaturase, a Δ6-elongase and an Δ5-elongase, iv) a Δ12-desaturase, a ω3-desaturase or a Δ15-desaturase, a Δ6-desaturase, a Δ5-desaturase, a Δ4-desaturase, a Δ6-elongase and an Δ5-elongase, v) an ω3-desaturase, a Δ8-desaturase, a Δ5-desaturase, a Δ4-desaturase, a Δ9-elongase and an Δ5-elongase, vi) a Δ15-desaturase, a Δ8-desaturase, a Δ5-desaturase, a Δ4-desaturase, a Δ9-elongase and a Δ5-elongase, vii) a Δ12-desaturase, a Δ8-desaturase, a Δ5-desaturase, a Δ4-desaturase, a Δ9-elongase and an Δ5-elongase, or viii) a Δ12-desaturase, a ω3-desaturase or a Δ15-desaturase, a Δ8-desaturase, a Δ5-desaturase, a Δ4-desaturase, a Δ9-elongase and an Δ5-elongase, and wherein each polynucleotide is operably linked to one or more promoters that are capable of directing expression of said polynucleotides in the cell.

In an embodiment, the cell comprises lipid as defined above, or wherein one or more or all of the desaturases or elongases have one or more of the features as defined above.

In another aspect, the present invention provides a host cell comprising i) a first exogenous polynucleotide encoding a Δ12-desaturase which comprises amino acids having a sequence as provided in SEQ ID NO:10, a biologically active fragment thereof, or an amino acid sequence which is at least 50% identical to SEQ ID NO:10, and ii) a second exogenous polynucleotide encoding a ω3-desaturase which comprises amino acids having a sequence as provided in SEQ ID NO:12, a biologically active fragment thereof, or an amino acid sequence which is at least 50% identical to SEQ ID NO:12, wherein each polynucleotide is operably linked to one or more promoters that are capable of directing expression of said polynucleotides in the cell.

In a further aspect, the present invention provides a host cell comprising one or more of the polynucleotide of the invention, the genetic construct of the invention, or the vector or genetic construct of the invention.

In an embodiment, the cell is in a plant, in a plant part and/or is a mature plant seed cell.

In an embodiment, the plant or plant seed is an oilseed plant or an oilseed, respectively.

Also provided is a transgenic non-human organism comprising a cell of the invention. Preferably, the transgenic non-human organism is a transgenic plant, preferably an oilseed plant or *Arabidopsis thaliana*. In an embodiment, the plant is a *Brassica* plant, preferably *B. napus* or *B. juncea*, or a plant other than *Arabidopsis thaliana*.

In another aspect, the present invention provides an oilseed plant comprising a) lipid in its seed, the lipid comprising fatty acids in an esterified form, and b) exogenous polynucleotides encoding one of the following sets of enzymes;

i) a Δ12-desaturase, a fungal ω3-desaturase and/or fungal Δ15-desaturase, a Δ6-desaturase, a Δ5-desaturase, a Δ4-desaturase, a Δ6-elongase and an Δ5-elongase, or ii) a Δ12-desaturase, a fungal ω3-desaturase and/or fungal Δ15-desaturase, a Δ8-desaturase, a Δ5-desaturase, a Δ4-desaturase, a Δ9-elongase and an Δ5-elongase, wherein each polynucleotide is operably linked to one or more seed-specific promoters that are capable of directing expression of said polynucleotides in developing seed of the plant, wherein the fatty acids comprise oleic acid, palmitic acid, ω6 fatty acids which comprise linoleic acid (LA) and γ-linolenic acid (GLA), ω3 fatty acids which comprise α-linolenic acid (ALA), stearidonic acid (SDA), docosapentaenoic acid (DPA) and docosahexaenoic acid (DHA), and optionally eicosapentaenoic acid (EPA) and/or eicosatetraenoic acid (ETA), and wherein the level of DHA in the total fatty acid content of the lipid is about 7% to 20%.

Examples of oilseed plants include, but are not limited to, *Brassica* sp., *Gossypium hirsutum*, *Linum usitatissimum*, *Helianthus* sp., *Carthamus tinctorius*, *Glycine max*, *Zea mays*, *Arabidopsis thaliana*, *Sorghum bicolor*, *Sorghum vulgare*, *Avena sativa*, *Trifolium* sp., *Elaesis guineensis*, *Nicotiana benthamiana*, *Hordeum vulgare*, *Lupinus angustifolius*, *Oryza sativa*, *Oryza glaberrima*, *Camelina sativa*, or *Crambe abyssinica*. In an embodiment, the oilseed plant is a canola, *Glycine max*, *Camelina sativa* or *Arabidopsis thaliana* plant. In an alternate embodiment, the oilseed plant is other than *A. thaliana*.

In an embodiment, one or more of the desaturases is capable of using an acyl-CoA substrate. In a preferred embodiment, one or more of the Δ6-desaturase, Δ5-desaturase, Δ4-desaturase and Δ8-desaturase, if present, is capable of using an acyl-CoA substrate, preferably each of the i) Δ6-desaturase, Δ5-desaturase and Δ4-desaturase or ii) Δ5-desaturase, Δ4-desaturase and Δ8-desaturase is capable of using an acyl-CoA substrate. In an embodiment, a Δ12-desaturase and/or an ω3-desaturase is capable of using an acyl-CoA substrate. The acyl-CoA substrate is preferably an ALA-CoA, ETA-CoA, DPA-CoA, ETrA-CoA, LA-CoA, GLA-CoA, or ARA-CoA.

In an embodiment, mature, harvested seed of the plant has a DHA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed. The maximum DHA content may be about 80 to about 100 mg per gram seed, or about 80 mg or about 100 mg per gram seed.

In a further aspect, the present invention provides a *Brassica napus*, *B. juncea* or *Camelina sativa* plant which is capable of producing seed comprising DHA, wherein mature, harvested seed of the plant has a DHA content of at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed. The maximum DHA content may be about 80 to about 100 mg per gram seed, or about 80 mg or about 100 mg per gram seed.

In another aspect, the present invention provides plant cell of a plant of the invention comprising the exogenous polynucleotides.

Also provided is a plant part, preferably a seed, which has one or more of the following features i) is from a plant of the invention, ii) comprises lipid as defined herein, iii) can be used in a process of the invention, iv) comprises a genetic construct of the invention, or v) comprises a set of exogenous polynucleotides as defined herein.

In yet another aspect, the present invention provides mature, harvested *Brassica napus, B. juncea* or *Camelina sativa* seed comprising DHA and a moisture content of between about 4% and about 15% by weight, wherein the DHA content of the seed at least about 28 mg per gram seed, preferably at least about 32 mg per gram seed, at least about 36 mg per gram seed, at least about 40 mg per gram seed, more preferably at least about 44 mg per gram seed or at least about 48 mg per gram seed. The maximum DHA content may be about 80 to about 100 mg per gram seed, or about 80 mg or about 100 mg per gram seed.

In an embodiment, the cell of the invention, the transgenic organism of the invention, the oilseed plant of the invention, the *Brassica napus, B. juncea* or *Camelina sativa* plant of the invention, the plant part of the invention, or the seed of the invention, which can be used to produce extracted lipid comprising one or more or all of the features defined herein.

In yet a further aspect, the present invention provides a method of producing a cell of the invention, the method comprising a) introducing into the cell, preferably a cell which is not capable of synthesising a LC-PUFA, the gene construct of the invention, the isolated and/or exogenous polynucleotide of the invention, the vector or genetic construct of the invention, one or more of the combinations of exogenous polynucleotides defined herein, b) optionally, expressing the genes or polynucleotide(s) in the cell;

c) optionally, analysing the fatty acid composition of the cell, and d) optionally, selecting a cell which express the genes or polynucleotide(s).

In an embodiment, the lipid in the cell has one or more of the features defined herein.

In another embodiment, the gene construct, the isolated and/or exogenous polynucleotide, the vector, the genetic construct or combinations of exogenous polynucleotides, become stably integrated into the genome of the cell.

In a further embodiment, the cell is a plant cell, and the method further comprises the step of regenerating a transformed plant from the cell of step a).

In another embodiment, the genes and/or exogenous polynucleotide(s) are expressed transiently in the cell.

Also provided is a cell produced using a method of the invention.

In another aspect, the present invention provides a method of producing seed, the method comprising, a) growing a plant of the invention, or a plant which produces a part as defined herein, preferably in a field as part of a population of at least 1000 such plants or in an area of at least 1 hectare planted at a standard planting density, b) harvesting seed from the plant or plants, and c) optionally, extracting lipid from the seed, preferably to produce oil with a total DHA yield of at least 60 kg DHA/hectare.

In an embodiment, the plant, plant cell, plant part or seed of the invention has one or more of the following features i) the oil is as defined herein, ii) the plant part or seed is capable of being used in a process of the invention, iii) the exogenous polynucleotides are comprised in a genetic construct of the invention, iv) the exogenous polynucleotides comprise an exogenous polynucleotide of the invention, v) the plant cell is a cell of the invention, and vi) the seed was produced according to the method of the invention.

In another aspect, the present invention provides a method of producing one or more fatty acid desaturases and/or fatty acid elongases, or one or more fatty acid desaturases and one or more fatty acid elongases, the method comprising expressing in a cell or cell free expression system the gene construct of the invention, the isolated and/or exogenous polynucleotide of the invention, the vector or genetic construct of the invention, one or more of the combinations of exogenous polynucleotides defined herein, preferably in a developing oilseed in an oilseed plant in the field.

In a further aspect, the present invention provides lipid, or oil, produced by, or obtained from, using the process of the invention, the cell of the invention, the transgenic organism of the invention, the oilseed plant of the invention, the *Brassica napus, B. juncea* or *Camelina sativa* plant of the invention, the plant part of the invention, the seed of the invention, or the plant, plant cell, plant part or seed of the invention.

In an embodiment, the lipid or oil is obtained by extraction of oil from an oilseed. Examples of oil from oilseeds include, but are not limited to, canola oil (*Brassica napus, Brassica rapa* ssp.), mustard oil (*Brassica juncea*), other *Brassica* oil, sunflower oil (*Helianthus annus*), linseed oil (*Linum usitatissimum*), soybean oil (*Glycine max*), safflower oil (*Carthamus tinctorius*), corn oil (*Zea mays*), tobacco oil (*Nicotiana tabacum*), peanut oil (*Arachis hypogaea*), palm oil, cottonseed oil (*Gossypium hirsutum*), coconut oil (*Cocos nucifera*), avocado oil (*Persea americana*), olive oil (*Olea europaea*), cashew oil (*Anacardium occidentale*), macadamia oil (*Macadamia intergrifolia*), almond oil (*Prunus amygdalus*) or *Arabidopsis* seed oil (*Arabidopsis thaliana*).

In a further aspect, the present invention provides fatty acid produced by, or obtained from, using the process of the invention, the cell of the invention, the transgenic organism of the invention, the oilseed plant of the invention, the *Brassica napus, B. juncea* or *Camelina sativa* plant of the invention, the plant part of the invention, the seed of the invention, or the plant, plant cell, plant part or seed of the invention. Preferably the fatty acid is DHA. The fatty acid may be in a mixture of fatty acids having a fatty acid composition as described herein. In an embodiment, the fatty acid is non-esterified.

Also provided is seedmeal obtained from seed of the invention. Preferred seedmeal includes, but not necessarily limited to, *Brassica napus, B. juncea, Camelina sativa* or *Glyvcine max* seedmeal. In an embodiment, the seedmeal comprises an exogenous polynucleotide(s) and/or genentic constructs as defined herein.

In another aspect, the present invention provides a composition comprising one or more of a lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, or the seedmeal of the invention. In embodiments, the composition comprises a carrier suitable for pharmaceutical, food or agricultural use, a seed treatment compound, a fertiliser, another food or feed ingredient, or added protein or vitamins.

Also provided is feedstuffs, cosmetics or chemicals comprising one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica*

*napus, B. juncea* or *Camelina sativa* plant of the invention, the plant part of the invention, the seed of the invention, the plant, plant cell, plant part or seed of the invention, the seedmeal of the invention, or the composition of the invention.

In another aspect, the present invention provides a method of producing a feedstuff, the method comprising mixing one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, or the composition of the invention, with at least one other food ingredient.

In another aspect, the present invention provides a method of treating or preventing a condition which would benefit from a PUFA, the method comprising administering to a subject one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, the composition of the invention, or the feedstuff of the invention.

Examples of conditions which would benefit from a PUFA include, but are not limited to, cardiac arrhythmia's, angioplasty, inflammation, asthma, psoriasis, osteoporosis, kidney stones, AIDS, multiple sclerosis, rheumatoid arthritis, Crohn's disease, schizophrenia, cancer, foetal alcohol syndrome, attention deficit hyperactivity disorder, cystic fibrosis, phenylketonuria, unipolar depression, aggressive hostility, adrenoleukodystophy, coronary heart disease, hypertension, diabetes, obesity, Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or an ocular disease.

Also provided is the use of one or more of the lipid or oil of the invention, the fatty acid of the invention, the genetic construct of the invention, the isolated and/or exogenous polynucleotide of the invention, the vector or genetic construct of the invention, the cell according of the invention, the transgenic organism of the invention, the oilseed plant of the invention, the *Brassica napus, B. juncea* or *Camelina sativa* plant of the invention, the plant part of the invention, the seed of the invention, the plant, plant cell, plant part or seed of the invention, the seedmeal of the invention, the composition of the invention, or the feedstuff of the invention for the manufacture of a medicament for treating or preventing a condition which would benefit from a PUFA. The production of the medicament may comprise mixing the oil of the invention with a pharmaceutically acceptable carrier, for treatment of a condition as described herein. The method may comprise firstly purifying the oil and/or transesterification, and/or fractionation of the oil to increase the level of DHA. In a particular embodiment, the method comprises treating the lipid or oil such as canola oil to convert the fatty acids in the oil to alkyl esters such as methyl or ethyl esters. Further treatment such as fractionation or distillation may be applied to enrich the lipid or oil for the DHA. In a preferred embodiment, the medicament comprises ethyl esters of DHA. In an even more preferred embodiment, the level of ethyl esters of DHA in the medicament is between 30% and 50%. The medicament may further comprise ethyl esters of EPA, such as between 30% and 50% of the total fatty acid content in the medicament. Such medicaments are suitable for administration to human or animal subjects for treatment of medical conditions as described herein.

In another aspect, the present invention provides a method of trading seed, comprising obtaining seed of the invention, and trading the obtained seed for pecuniary gain.

In an embodiment, obtaining the seed comprises cultivating plants of the invention and/or harvesting the seed from the plants.

In another embodiment, obtaining the seed further comprises placing the seed in a container and/or storing the seed.

In a further embodiment, obtaining the seed further comprises transporting the seed to a different location.

In yet another embodiment, the method further comprises transporting the seed to a different location after the seed is traded.

In a further embodiment, the trading is conducted using electronic means such as a computer.

In yet a further aspect, the present invention provides a process of producing bins of seed comprising:

a) swathing, windrowing and/or or reaping above-ground parts of plants comprising seed of the invention, b) threshing and/or winnowing the parts of the plants to separate the seed from the remainder of the plant parts, and c) sifting and/or sorting the seed separated in step b), and loading the sifted and/or sorted seed into bins, thereby producing bins of seed.

In an embodiment, where relevant, the lipid or oil, preferably seedoil, of, or useful for, the invention has fatty levels about those provided in a Table in the Examples section, such as seed 14 of Table 16.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Aerobic DHA biosynthesis pathways.

Figure 2:
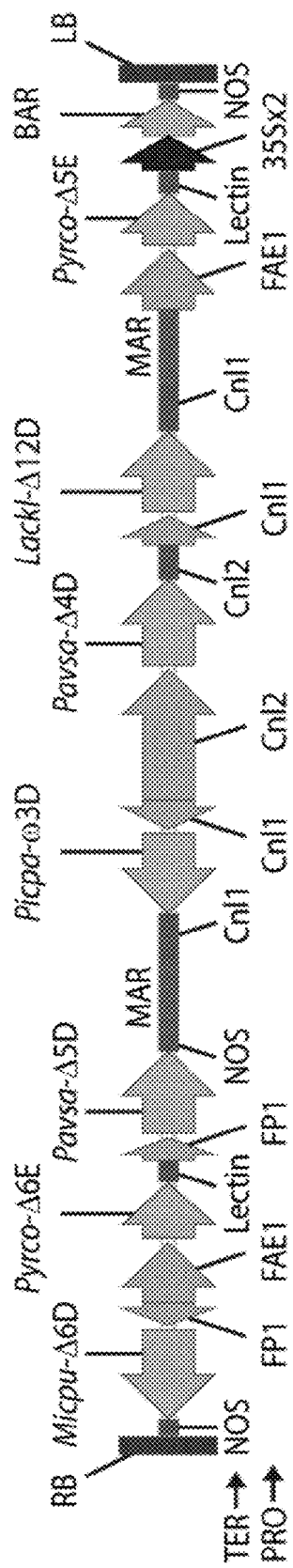

FIG. 2. Map of the T-DNA insertion region between the left and right borders of pJP3416-GA7. RB denotes right border; LB, left border; TER, transcription terminator/polyadenylation region; PRO, promoter; Coding regions are indicated above the arrows, promoters and terminators below the arrows. Micpu-Δ6D, *Micromonas pusilla* Δ6-desaturase; Pyrco-Δ6E, *Pyramimonas cordata* Δ6-elongase; Pavsa-Δ5D, *Pavlova salina* Δ5-desaturase; Picpa-ω3D, *Pichia pastoris*

ω3-desaturase; Pavsa-Δ4D, *P. salina* Δ4-desaturase; Lackl-Δ12D, *Lachancea kluyveri* Δ12-desaturase; Pyrco-Δ5E, *Pyramimonas cordata* Δ5-elongase. NOS denotes the *Agrobacterium tumefaciens* nopaline synthase transcription terminator/polyadenylation region; FP1, *Brassica napus* truncated napin promoter; FAE1, *Arabidopsis thaliana* FAE1 promoter; Lectin, *Glycine max* lectin transcription terminator/polyadenylation region; Cnl1 and Cnl2 denotes the *Linum usitatissimum* conlinin1 or conlinin2 promoter or terminator. MAR denotes the Rb7 matrix attachment region from *Nicotiana tabacum*.

Figure 3:
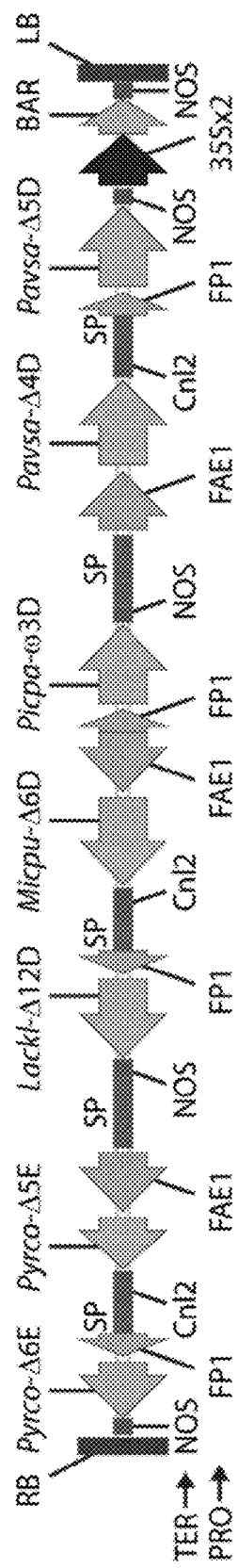

FIG. 3. Map of the T-DNA insertion region between the left and right borders of pJP3404. Labels are as in FIG. 2.

Figure 4:
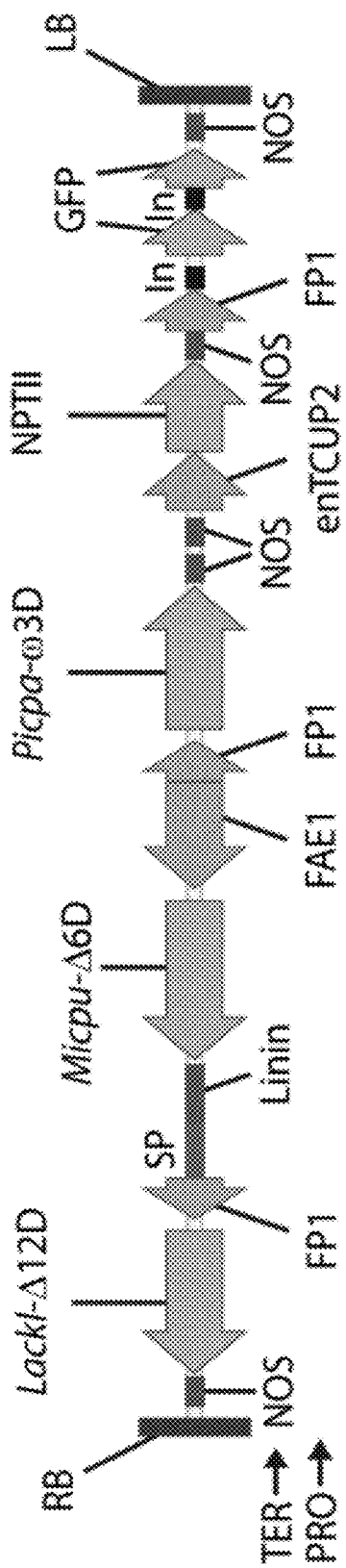

FIG. 4. Map of the insertion region between the left and right borders of pJP3367. Labels are as in FIG. 2.

Figure 5:
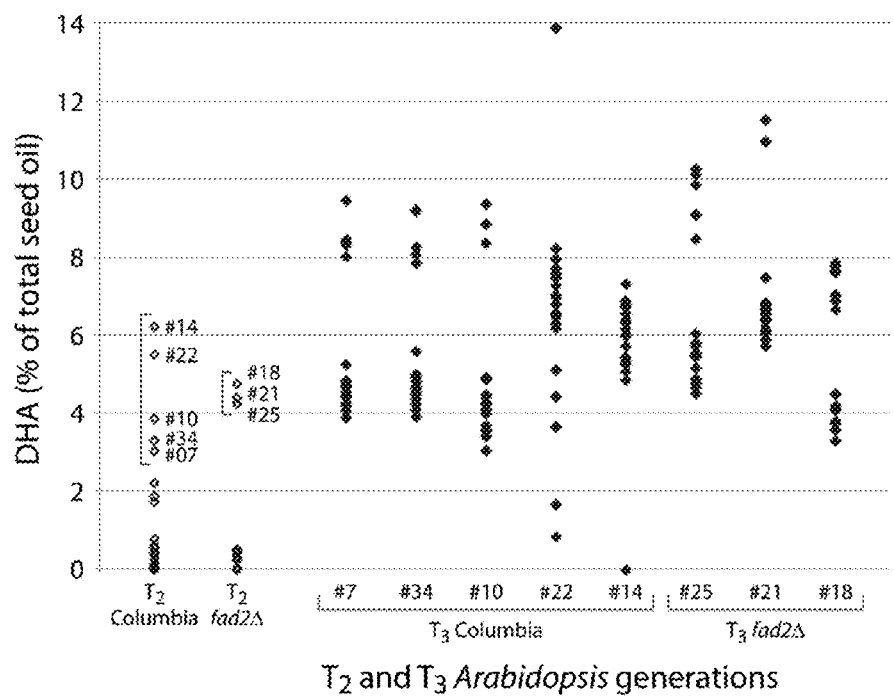

FIG. 5. DHA levels as a percentage of total fatty acids in seed lipid from multiple independent transgenic *Arabidopsis thaliana* seeds in both the $T_2$ and $T_3$ generations. The bracketed $T_2$ events were taken to $T_3$. Events from both the Columbia and fad2 mutant *A. thaliana* backgrounds are shown.

Figure 6:
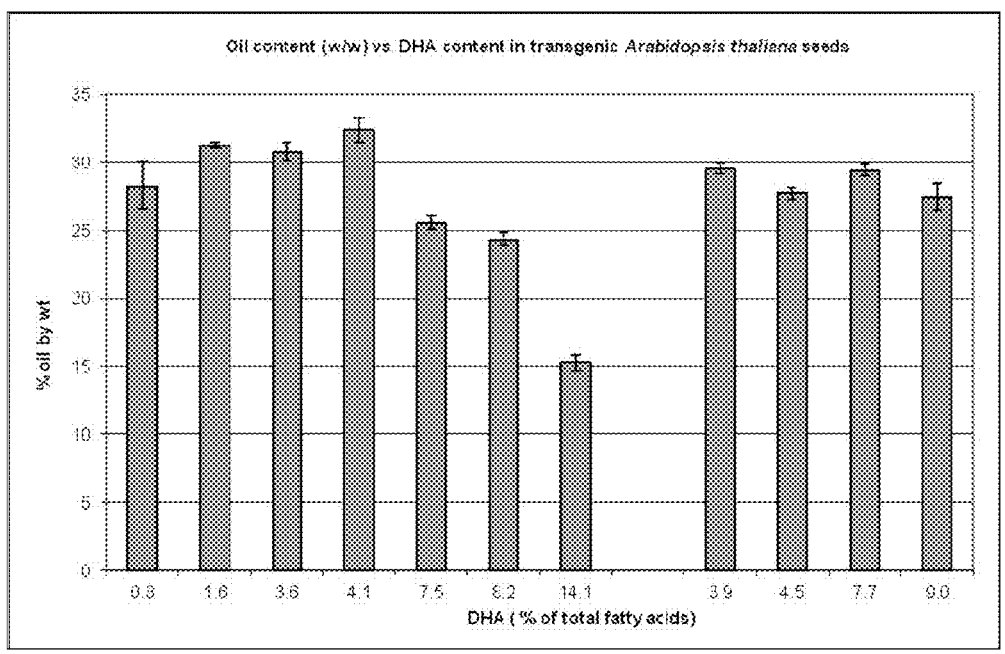

FIG. 6. Oil content (w/w) vs. DHA content, as a percentage of total fatty acid content of lipid from transgenic *Arabidopsis thaliana* seeds.

Figure 7:
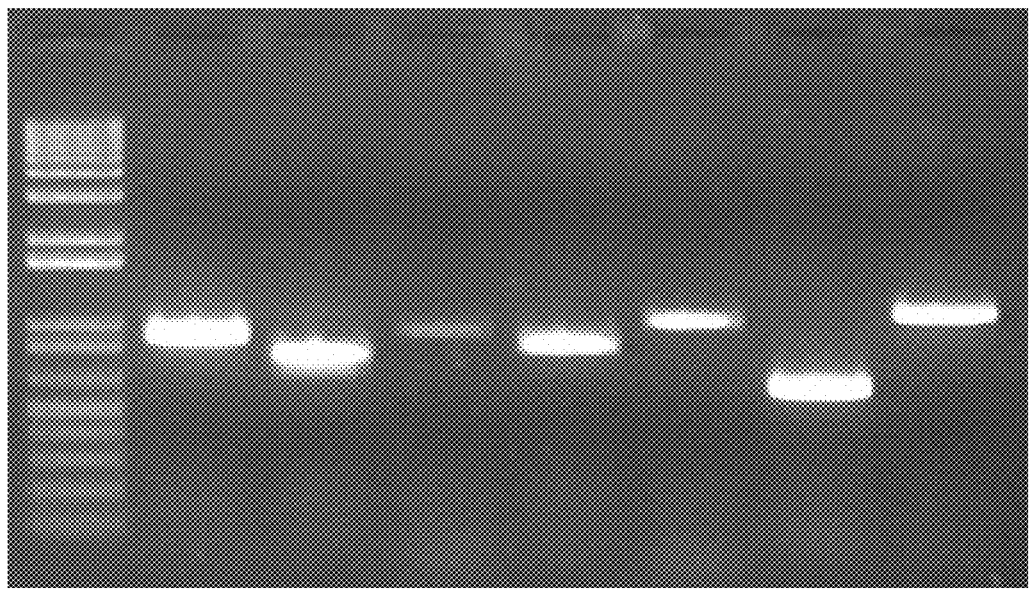

FIG. 7. Representative RT-PCR gel showing the low expression of the Δ6-desaturase gene relative to the other transgenes in the T-DNA of *B. napus* embryos transformed using pJP3416-GA7. Lanes from the left show RT-PCR products: 1, DNA size markers; lane 2, Δ12 desaturase; lane 3, ω3-desaturase; lane 4, Δ6-desaturase (low expression); lane 5, Δ6-elongase; lane 6, Δ5-desaturase; lane 7, Δ5-elongase; lane 8, Δ4-desaturase.

Figure 8:
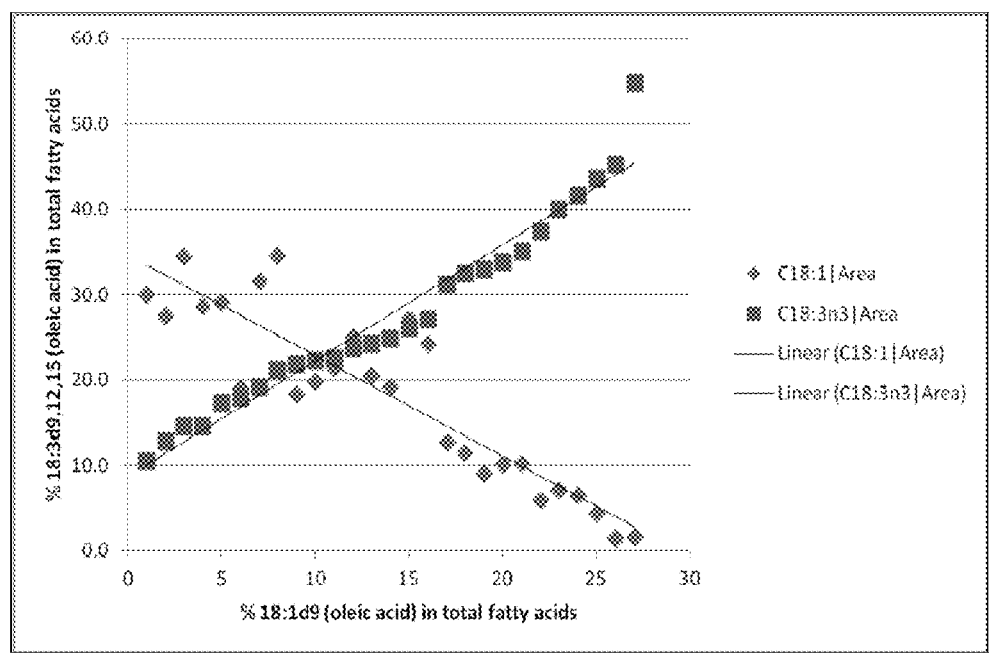

FIG. 8. Percentage of ALA plotted against percentage of oleic acid, each as a percentage of total fatty acids in lipid obtained from transgenic 35S:LEC2 *Brassica napus* somatic embryos.

Figure 9:
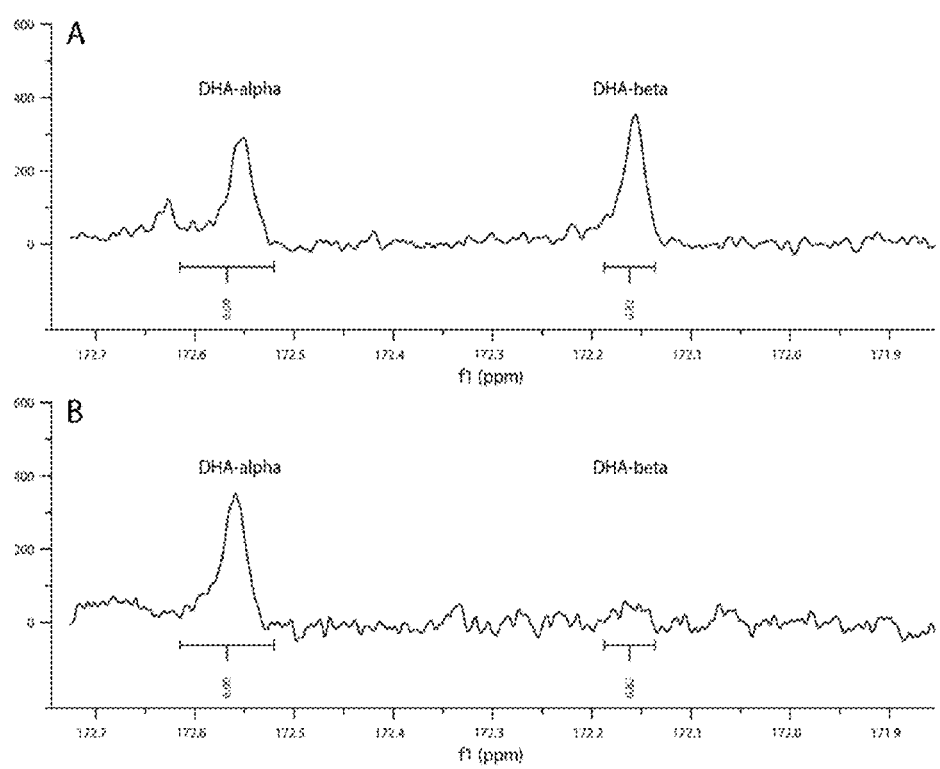

FIG. 9. Positional distribution analysis by NMR on A) Tuna oil and, B) transgenic DHA *Arabidopsis* seed oil. The peaks labelled 'DHA-alpha' represent the amount of DHA present at the sn-1 and sn-3 positions of TAG (with no positional preference this would equal 66% of total DHA) whilst the peaks labelled 'DHA-beta' represent the amount of DHA present at the sn-2 position of TAG (with no preference this would equal 33% of DHA).

Figure 10:
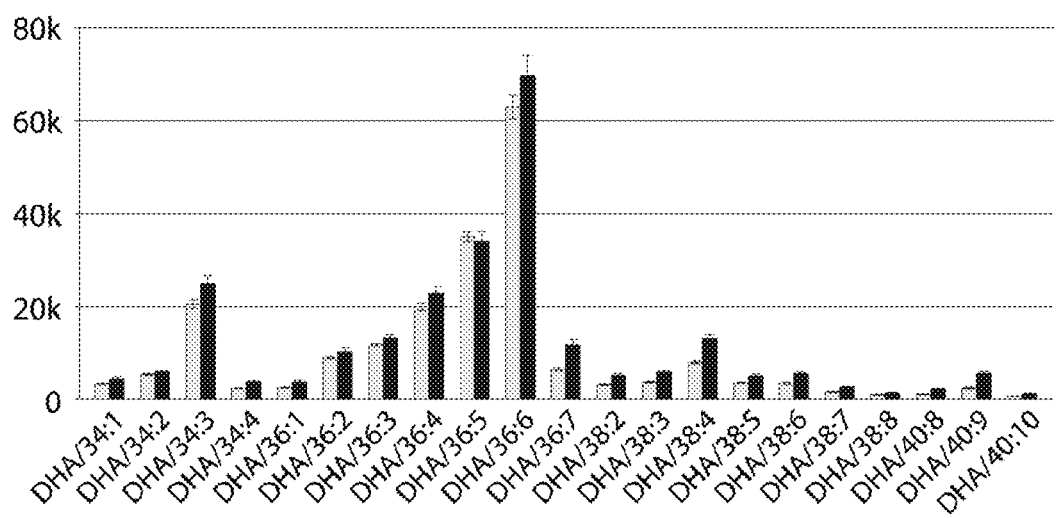

FIG. 10. LC-MS analysis of major DHA-containing triacylglycerol species in transgenic *A. thaliana* developing (grey) and mature (black) seeds. The number following the DHA denotes the total number of carbon atoms and total number of double bonds in the other two fatty acids. Therefore DHA/34:1 can also be designated TAG 56:7, etc.

Figure 11:
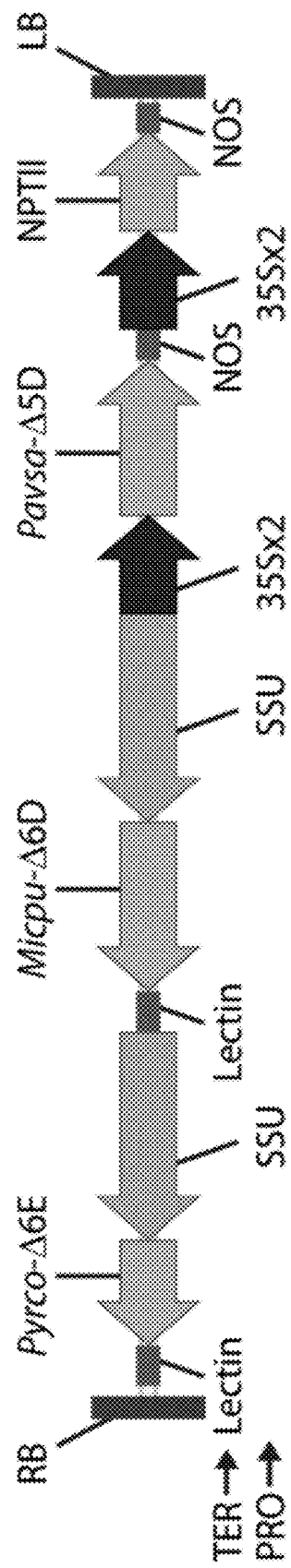

FIG. 11. Map of the T-DNA insertion region between the left and right borders of pORE04+11ABGBEC_Cowpea_EPA_insert. Labels are as in FIG. 2; SSU, *Arabidopsis thaliana* rubisco small subunit promoter.

Figure 12:
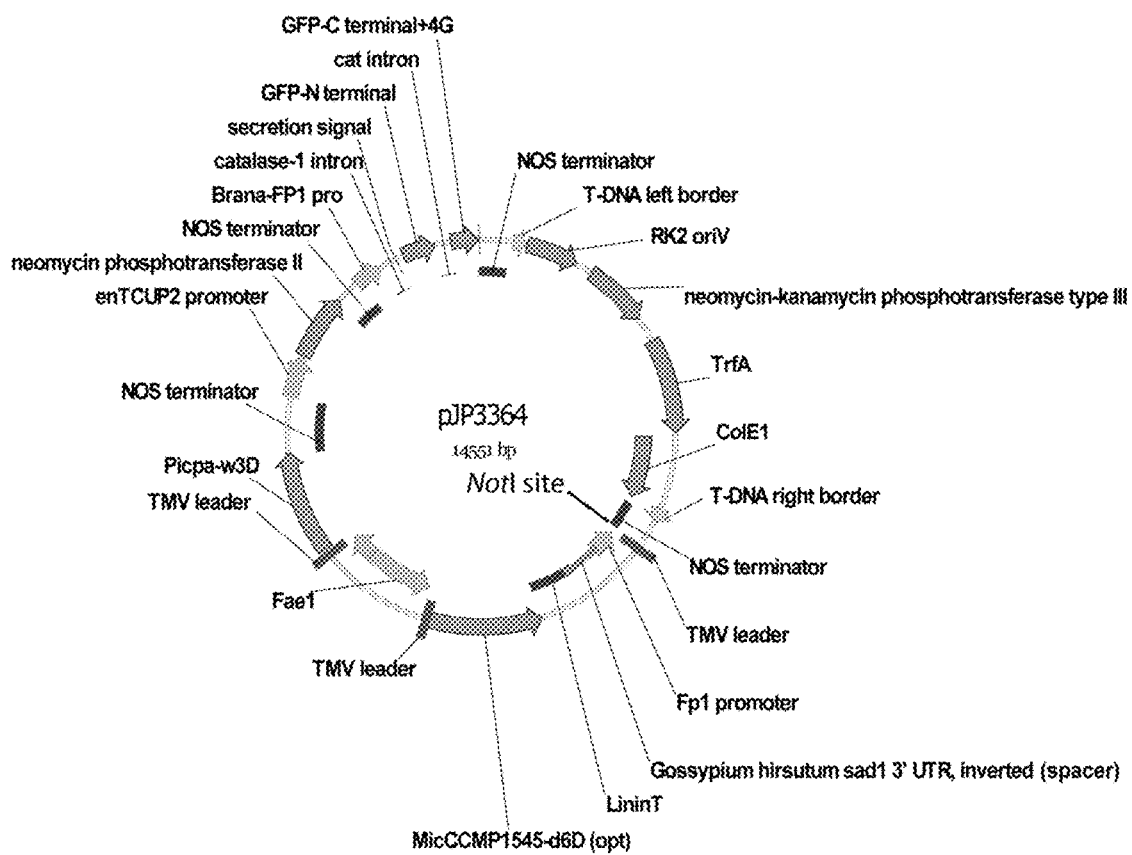

FIG. 12. Map of the binary vector pJP3364 showing the NotI restriction site into which the candidate Δ12-desaturases were cloned.

Figure 13:
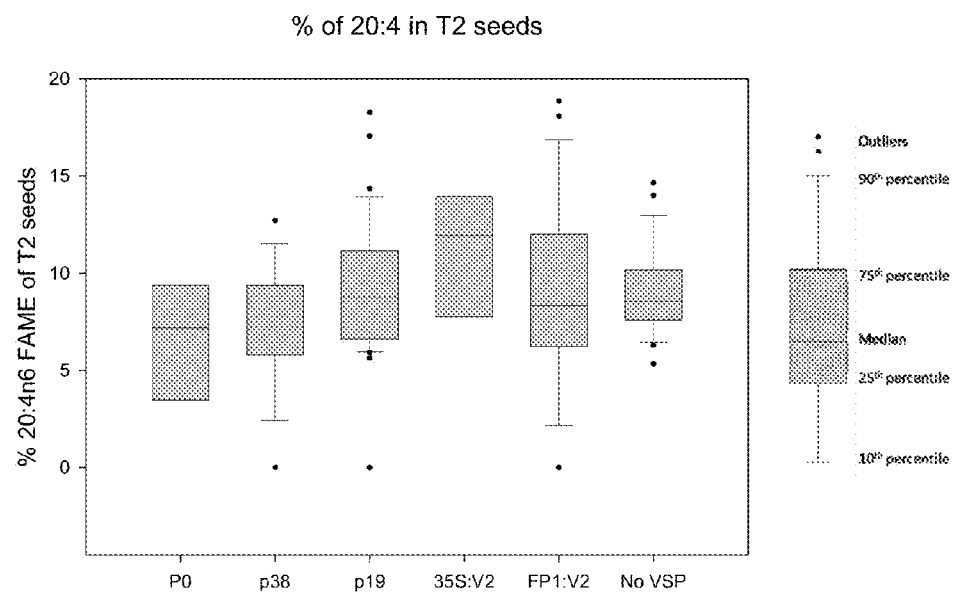

FIG. 13. BoxPlot generated using SigmaPlot showing the percentage of fatty acid 20:4ω6 (ARA) in seed lipid of *Arabidopsis* T2 seed populations transformed with pFN045-pFN050. The boundary of each box closest to zero indicates the 25th percentile, a line within each box marks the median, and the boundary of each box farthest from zero indicates the 75th percentile. Error bars shown above and below each box indicate the 90th and 10th percentiles.

Figure 14:
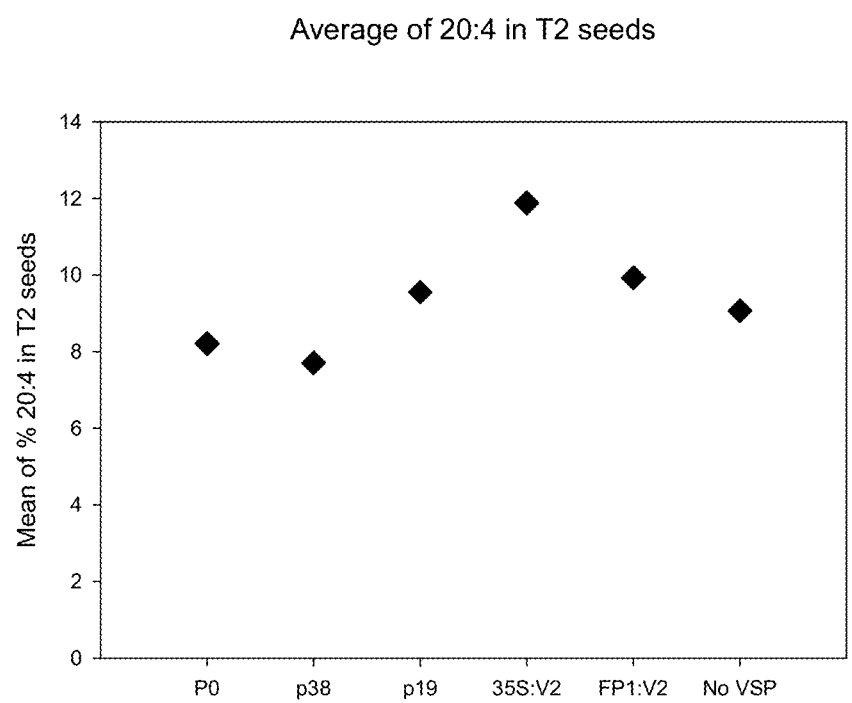

FIG. 14. Average level of ARA as a percentage of the total fatty acid content in seed lipid of *Arabidopsis* T2 seed transformed with pFN045-pFN050.

Figure 15:
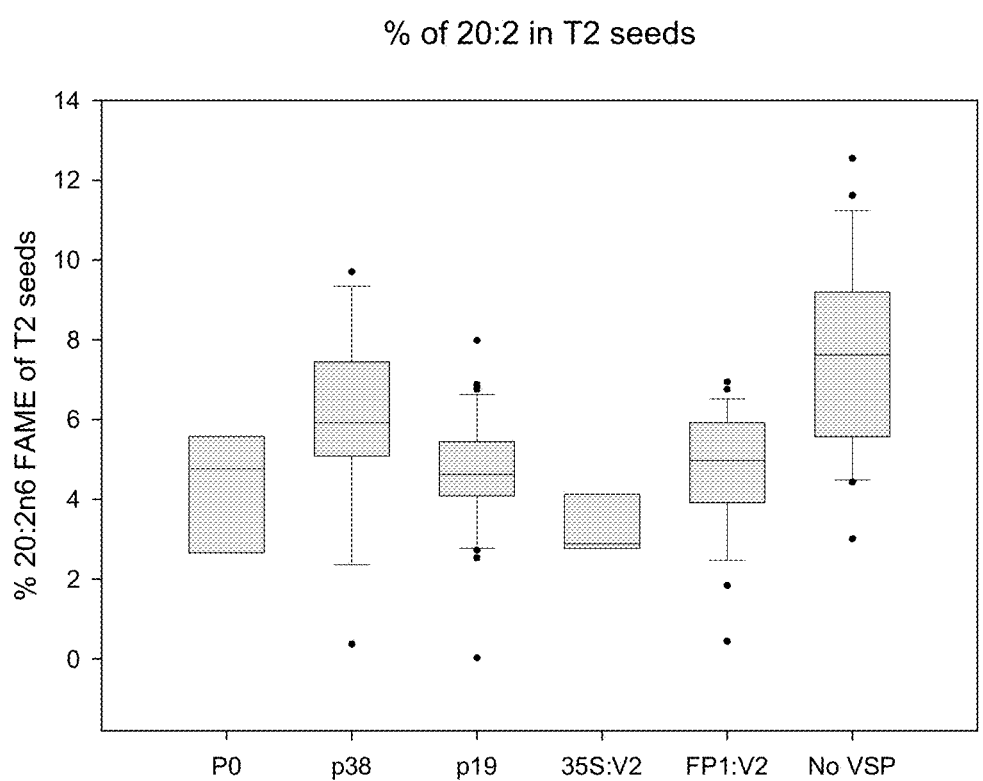

FIG. 15. BoxPlot showing the percentage of fatty acid 20:2ω6 (EDA) in seed lipid of *Arabidopsis* T2 seed populations transformed with pFN045-pFN050. The BoxPlot represents values as described in FIG. 13.

Figure 16:
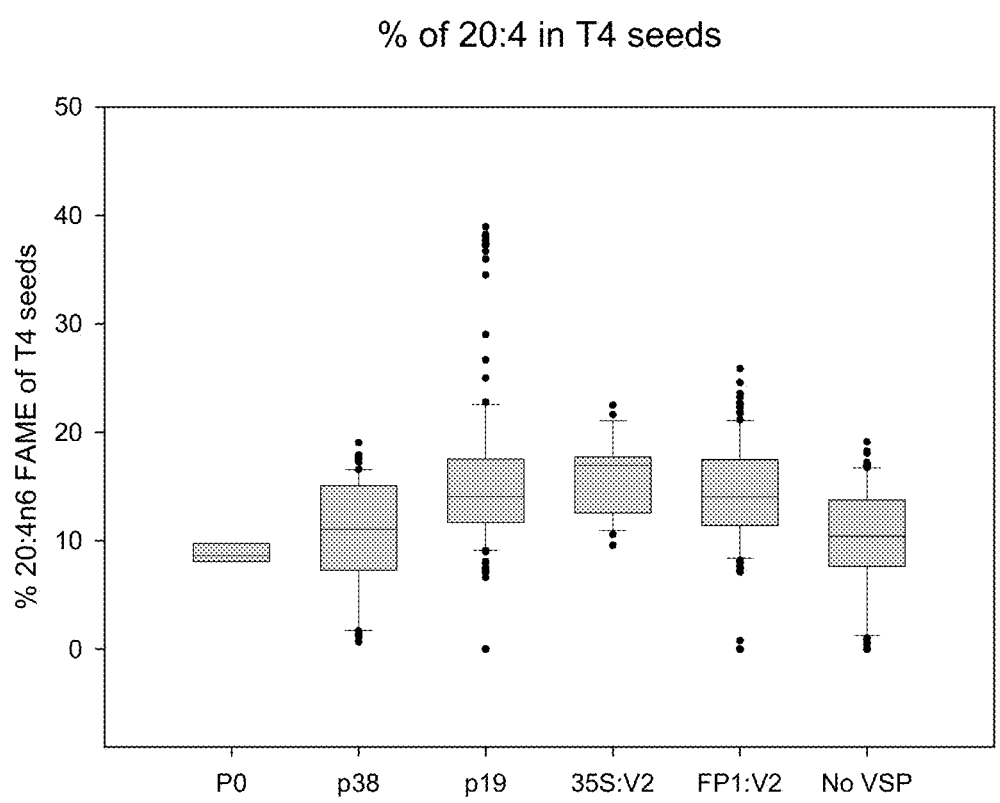

FIG. 16. BoxPlot showing the percentage of ARA in seed lipid of *Arabidopsis* T4 seed populations transformed with pFN045-pFN050. The BoxPlot represents values as described in FIG. 13.

Figure 17:
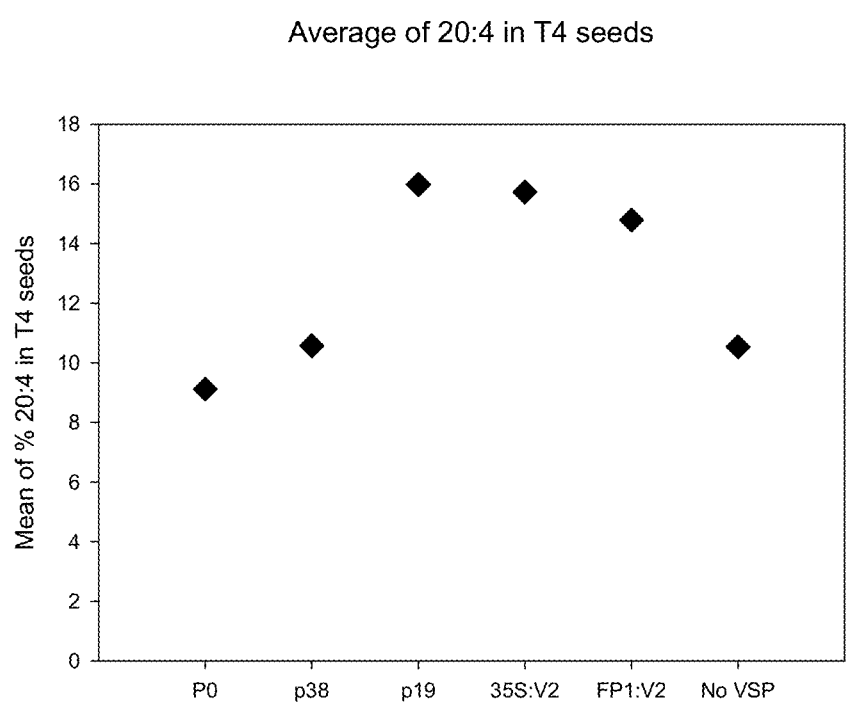

FIG. 17. Average level of ARA as a percentage of the total fatty acid content in seed lipid of *Arabidopsis* T4 seed populations transformed with pFN045-pFN050.

Figure 18:
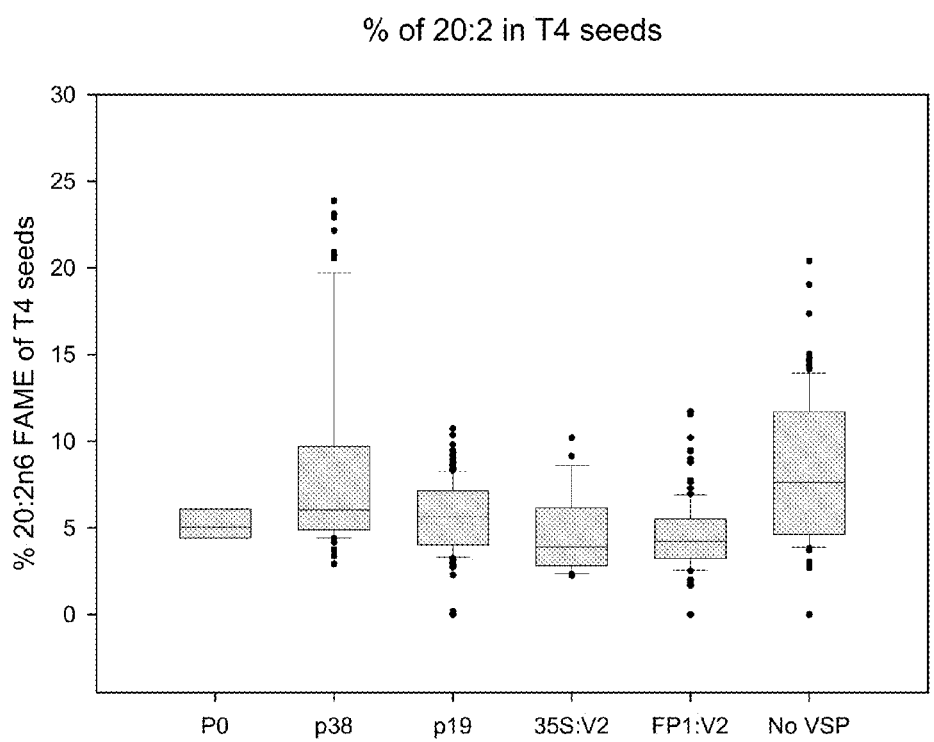

FIG. 18. BoxPlot showing the percentage of EDA in seed lipid of *Arabidopsis* T4 seed populations transformed with pFN045-pFN050. The BoxPlot represents values as described in FIG. 13.

Figure 19:
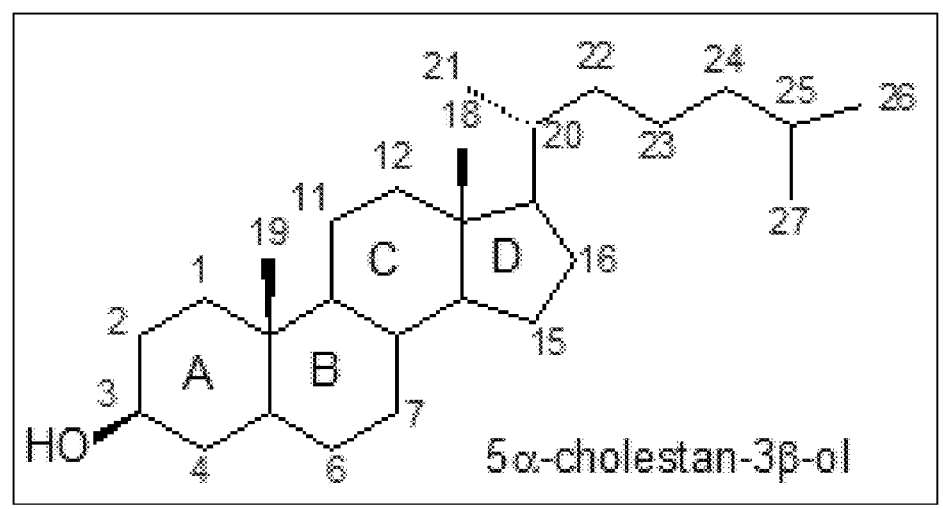
Figure 19:
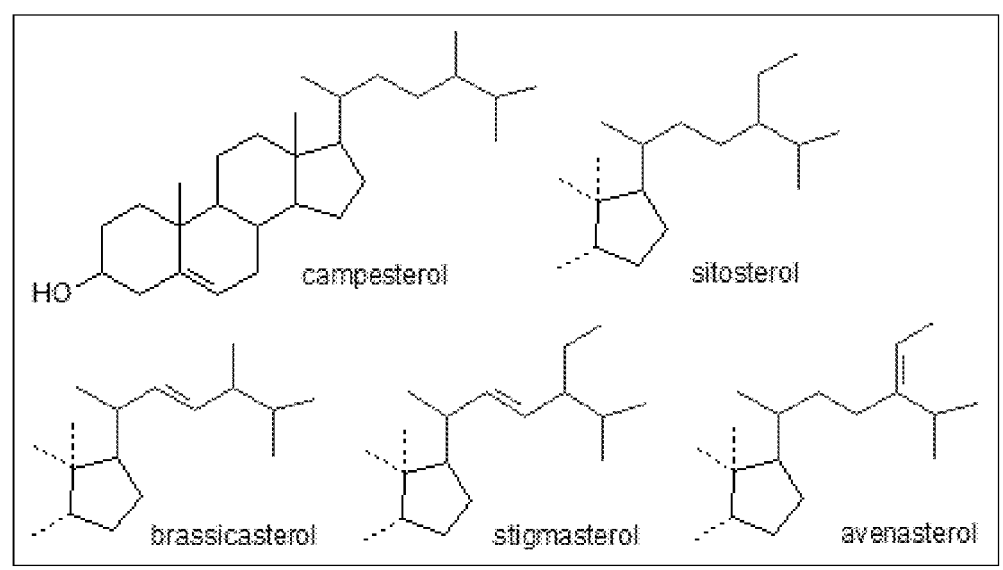

FIG. 19. (A) Basic phytosterol structure with ring and side chain numbering. (B) Chemical structures of some of the phytosterols.

Figure 20:
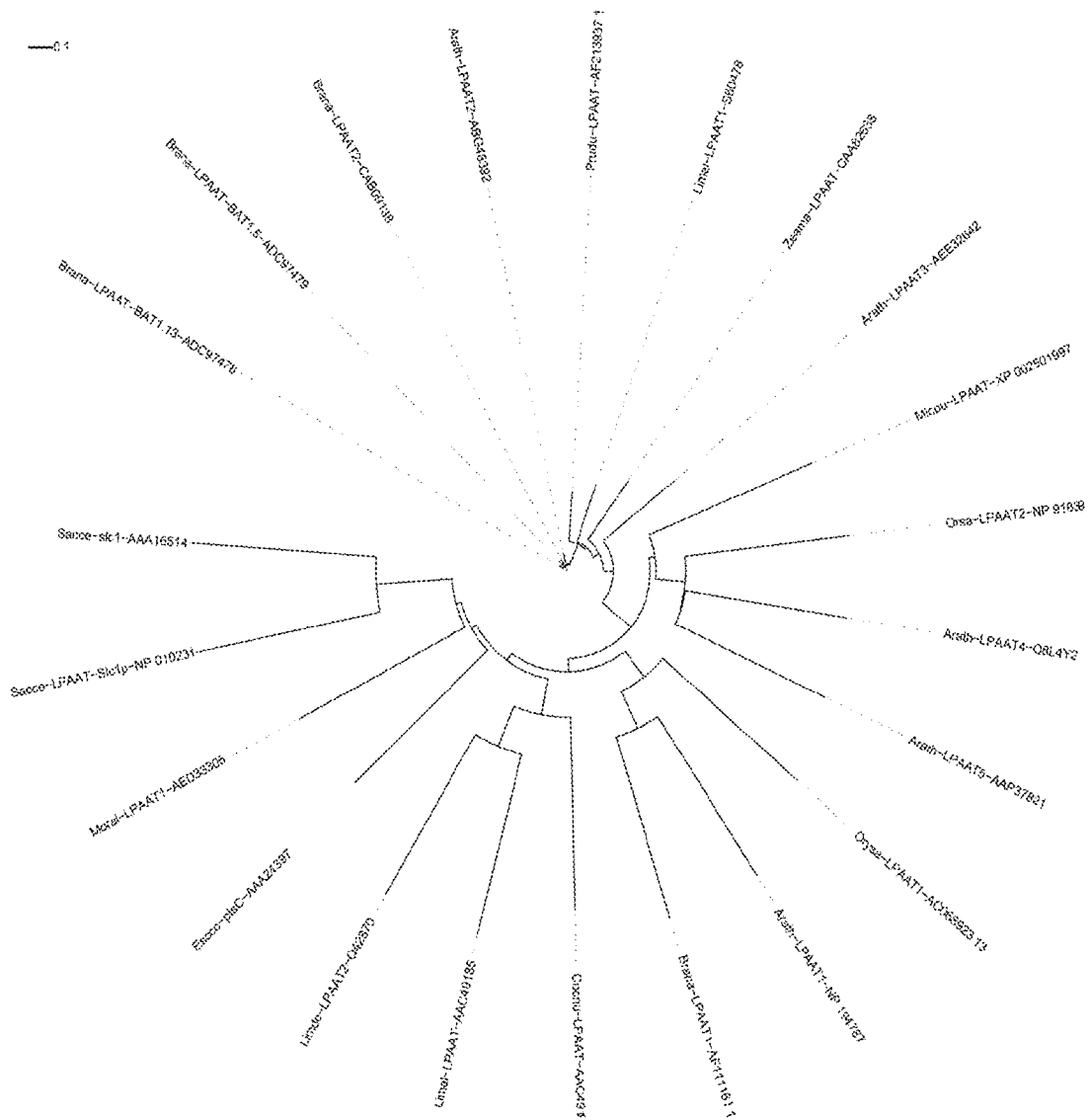

FIG. 20. Phylogenetic tree of known LPAATs.

Figure 21:
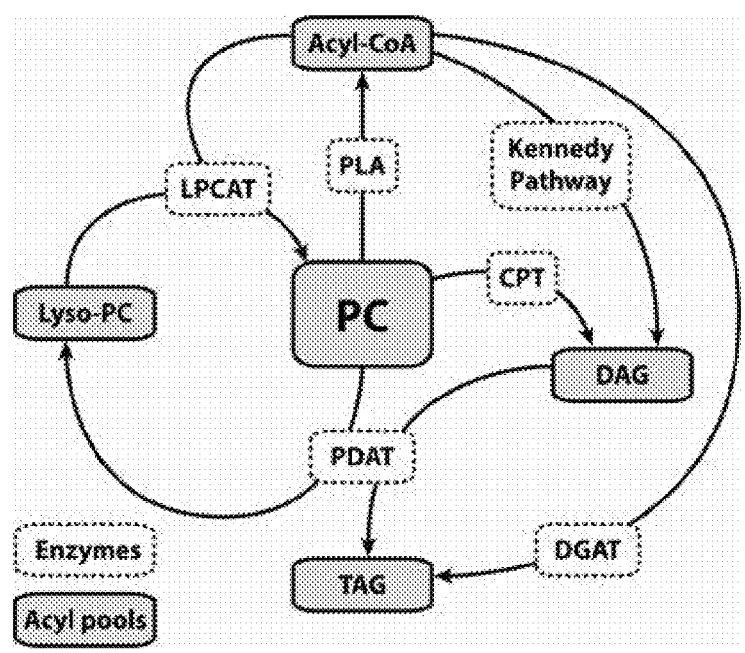

FIG. 21. The various acyl exchange enzymes which transfer fatty acids between PC, CoA pools, and TAG pools. Adapted from Singh et al. (2005).

KEY TO THE SEQUENCE LISTING

SEQ ID NO:1—pJP3416-GA7 nucleotide sequence.
SEQ ID NO:2—pGA7-mod_B nucleotide sequence.
SEQ ID NO:3—pGA7-mod_C nucleotide sequence.
SEQ ID NO:4—pGA7-mod_D nucleotide sequence.
SEQ ID NO:5—pGA7-mod_E nucleotide sequence.
SEQ ID NO:6—pGA7-mod_F nucleotide sequence.
SEQ ID NO:7—pGA7-mod_G nucleotide sequence.
SEQ ID NO:8—pORE04+11ABGBEC_Cowpea_EPA_insert nucleotide sequence.
SEQ ID NO:9—Codon-optimized open reading frame for expression of *Lachancea kluyveri* Δ12 desaturase in plants.
SEQ ID NO:10—*Lachancea kluyveri* Δ12-desaturase.
SEQ ID NO:11—Codon-optimized open reading frame for expression of *Pichia pastoris* ω3 desaturase in plants.
SEQ ID NO:12—*Pichia pastoris* ω3 desaturase.
SEQ ID NO: 13—Open reading frame encoding *Micromonas pusilla* Δ6-desaturase.
SEQ ID NO: 14—Codon-optimized open reading frame for expression of *Micromonas pusilla* Δ6-desaturase in plants (version 1).
SEQ ID NO:15—Codon-optimized open reading frame for expression of *Micromonas pusilla* Δ6-desaturase in plants (version 2).
SEQ ID NO: 16—*Micromonas pusilla* Δ6-desaturase.
SEQ ID NO:17—Open reading frame encoding *Ostreococcus lucimarinus* Δ6-desaturase.
SEQ ID NO: 18—Codon-optimized open reading frame for expression of *Ostreococcus lucimarinus* Δ6-desaturase in plants.
SEQ ID NO: 19—*Ostreococcus lucimarinus* Δ6-desaturase.
SEQ ID NO:20—*Ostreococcus tauri* Δ6-desaturase.
SEQ ID NO:21—Open reading frame encoding *Pyramimonas cordata* Δ6-elongase.
SEQ ID NO:22—Codon-optimized open reading frame for expression of *Pyramimonas cordata* Δ6-elongase in plants (truncated at 3' end and encoding functional elongase) (version 1).
SEQ ID NO:23—Codon-optimized open reading frame for expression of *Pyramimonas cordata* Δ6-elongase in plants (truncated at 3' end and encoding functional elongase) (version 2).

SEQ ID NO:24—Codon-optimized open reading frame for expression of *Pyramimonas cordata* Δ6-elongase in plants (truncated at 3' end and encoding functional elongase) (version 3).
SEQ ID NO:25—*Pyramimonas cordata* Δ6-elongase.
SEQ ID NO:26—Truncated *Pyramimonas cordata* Δ6-elongase.
SEQ ID NO:27—Open reading frame encoding *Pavlova salina* Δ5-desaturase.
SEQ ID NO:28—Codon-optimized open reading frame for expression of *Pavlova salina* Δ5-desaturase in plants (version 1).
SEQ ID NO:29—Codon-optimized open reading frame for expression of *Pavlova salina* Δ5-desaturase in plants (version 2).
SEQ ID NO:30—*Pavlova salina* Δ5-desaturase.
SEQ ID NO:31—Open reading frame encoding *Pyramimonas cordata* Δ5-desaturase.
SEQ ID NO:32—*Pyramimonas cordata* Δ5-desaturase.
SEQ ID NO:33—Open reading frame encoding *Pyramimonas cordata* Δ5-elongase.
SEQ ID NO:34—Codon-optimized open reading frame for expression of *Pyramimonas cordata* Δ5-elongase in plants (version 1).
SEQ ID NO:35—Codon-optimized open reading frame for expression of *Pyramimonas cordata* Δ5-elongase in plants (version 2).
SEQ ID NO:36—Codon-optimized open reading frame for expression of *Pyramimonas cordata* Δ5-elongase in plants (version 3).
SEQ ID NO:37—*Pyramimonas cordata* Δ5-elongase.
SEQ ID NO:38—Open reading frame encoding *Pavlova salina* Δ4-desaturase.
SEQ ID NO:39—Codon-optimized open reading frame for expression of *Pavlova salina* Δ4-desaturase in plants (version 1).
SEQ ID NO:40-Codon-optimized open reading frame for expression of *Pavlova salina* Δ4-desaturase in plants (version 2).
SEQ ID NO:41—*Pavlova salina* Δ4-desaturase.
SEQ ID NO:42—Open reading frame encoding *Isochrysis galbana* Δ9-elongase.
SEQ ID NO:43—*Isochrysis galbana* Δ9-elongase.
SEQ ID NO:44—Open reading frame encoding *Emiliania huxleyi* CCMP1516 Δ9-elongase.
SEQ ID NO:45—Codon-optimized open reading frame for expression of *Emiliania huxleyi* Δ9-elongase in plants.
SEQ ID NO:46—*Emiliania huxleyi* CCMP1516 Δ9-elongase.
SEQ ID NO:47—Open reading frame encoding *Pavlova pinguis* Δ9-elongase.
SEQ ID NO:48—*Pavlova pinguis* Δ9-elongase.
SEQ ID NO:49—Open reading frame encoding *Pavlova salina* Δ9-elongase.
SEQ ID NO:50—*Pavlova salina* Δ9-elongase.
SEQ ID NO:51—Open reading frame encoding *Pavlova salina* Δ8-desaturase.
SEQ ID NO:52—*Pavlova salina* Δ8-desaturase.
SEQ ID NO:53—P19 viral suppressor.
SEQ ID NO:54—V2 viral suppressor.
SEQ ID NO:55—P38 viral suppressor.
SEQ ID NO:56—Pe-P0 viral suppressor.
SEQ ID NO:57—RPV-P0 viral suppressor.
SEQ ID NO:58—Open reading frame encoding P19 viral suppressor.
SEQ ID NO:59—Open reading frame encoding V2 viral suppressor.
SEQ ID NO:60—Open reading frame encoding P38 viral suppressor.
SEQ ID NO:61—Open reading frame encoding Pe-P0 viral suppressor.
SEQ ID NO:62—Open reading frame encoding RPV-P0 viral suppressor.
SEQ ID NO: 63—*Arabidopsis thaliana* LPAAT2.
SEQ ID NO: 64—*Limnanthes alba* LPAAT.
SEQ ID NO: 65—*Saccharomyces cerevisiae* LPAAT.
SEQ ID NO: 66—*Micromonas pusilla* LPAAT.
SEQ ID NO: 67—*Mortierella alpina* LPAAT.
SEQ ID NO: 68—*Braccisa napus* LPAAT.
SEQ ID NO: 69—*Brassica napus* LPAAT.
SEQ ID NO: 70—*Phytophthora infestans* ω3 desaturase.
SEQ ID NO: 71—*Thalassiosira pseudonana* ω3 desaturase.
SEQ ID NO: 72—*Pythium irregulare* ω3 desaturase.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, fatty acid synthesis, transgenic plants, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), Ed Harlow and David Lane (editors), Antibodies: A Laboratory Manual, Cold Spring Harbour Laboratory, (1988), and J. E. Coligan et al. (editors), Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term "about", unless stated to the contrary, refers to +/−10%, more preferably +/−5%, more preferably +/−1% of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

As used herein, the terms "extracted plant lipid" and "isolated plant lipid" refer to a lipid composition which has been extracted from, for example by crushing, a plant or part thereof such as seed. The extracted lipid can be a relatively crude composition obtained by, for example, crushing a plant seed, or a more purified composition where most, if not all, of one or more or each of the water, nucleic acids, proteins and carbohydrates derived from the plant material have been removed. Examples of purification methods are described below. In an embodiment, the extracted or isolated plant lipid comprises at least about 60%, at least about 70%, at least about 80%, at least about 90%, or at least about 95% (w/w) lipid by weight of the composition. The lipid may be solid or liquid at room temperature, when liquid it is considered to be an oil. In an embodiment, extracted lipid of the invention has not been blended with another lipid such as DHA not produced by another source (for example, DHA from fish oil). In an embodiment, following extraction the ratio of one or more or all of, oleic acid to DHA, palmitic acid to DHA, linoleic acid to DHA, and total ω6 fatty acids:total ω3 fatty acids, has not been significantly altered (for example, no greater than a 10% or 5% alteration) when compared to the ratio in the intact seed or cell. In an another embodiment, the extracted plant lipid has not been exposed to a procedure, such as hydrogenation or fractionation, which may alter the ratio of one or more or all of, oleic acid to DHA, palmitic acid to DHA, linoleic acid to DHA, and total ω6 fatty acids:total ω3 fatty acids, when compared to the ratio in the intact seed or cell. When the extracted plant lipid of the invention is comprised in an oil, the oil may further comprise non-fatty acid molecules such as sterols.

As used herein, the terms "extracted plant oil" and "isolated plant oil" refer to a substance or composition comprising extracted plant lipid or isolated plant lipid and which is a liquid at room temperature. The oil is obtained from a plant or part thereof such as seed. The extracted or isolated oil can be a relatively crude composition obtained by, for example, crushing a plant seed, or a more purified composition where most, if not all, of one or more or each of the water, nucleic acids, proteins and carbohydrates derived from the plant material have been removed. The composition may comprise other components which may be lipid or non-lipid. In an embodiment, the oil composition comprises at least about 60%, at least about 70%, at least about 80%, at least about 90%, or at least about 95% (w/w) extracted plant lipid. In an embodiment, extracted oil of the invention has not been blended with another oil such as DHA not produced by another source (for example, DHA from fish oil). In an embodiment, following extraction, the ratio of one or more or all of, oleic acid to DHA, palmitic acid to DHA, linoleic acid to DHA, and total ω6 fatty acids:total ω3 fatty acids, has not been significantly altered (for example, no greater than a 10% or 5% alteration) when compared to the ratio in the intact seed or cell. In an another embodiment, the extracted plant oil has not been exposed to a procedure, such as hydrogenation or fractionation, which may alter the ratio of one or more or all of, oleic acid to DHA, palmitic acid to DHA, linoleic acid to DHA, and total ω6 fatty acids:total to 3 fatty acids, when compared to the ratio in the intact seed or cell. Extracted plant oil of the invention may comprise non-fatty acid molecules such as sterols.

As used herein, an "oil" is a composition comprising predominantly lipid and which is a liquid at room temperature. For instance, oil of the invention preferably comprises at least 75%, at least 80%, at least 85% or at least 90% lipid by weight. Typically, a purified oil comprises at least 90% triacylglycerols (TAG) by weight of the lipid in the oil. Minor components of an oil such as diacylglycerols (DAG), free fatty acids (FFA), phospholipid and sterols may be present as described herein.

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (ω) end contains 3 hydrogens (CH3—) and each carbon within the chain contains 2 hydrogens (—CH2-).

"Unsaturated fatty acids" are of similar form to saturated fatty acids, except that one or more alkene functional groups exist along the chain, with each alkene substituting a singly-bonded "—CH2-CH2-" part of the chain with a doubly-bonded "—CH═CH—" portion (that is, a carbon double bonded to another carbon). The two next carbon atoms in the chain that are bound to either side of the double bond can occur in a cis or trans configuration.

As used herein, the term "monounsaturated fatty acid" refers to a fatty acid which comprises at least 12 carbon atoms in its carbon chain and only one alkene group (carbon-carbon double bond) in the chain. As used herein, the terms "polyunsaturated fatty acid" or "PUFA" refer to a fatty acid which comprises at least 12 carbon atoms in its carbon chain and at least two alkene groups (carbon-carbon double bonds).

As used herein, the terms "long-chain polyunsaturated fatty acid" and "LC-PUFA" refer to a fatty acid which comprises at least 20 carbon atoms in its carbon chain and at least two carbon-carbon double bonds, and hence include VLC-PUFAs. As used herein, the terms "very long-chain polyunsaturated fatty acid" and "VLC-PUFA" refer to a fatty acid which comprises at least 22 carbon atoms in its carbon chain and at least three carbon-carbon double bonds. Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid. In a further embodiment, the long-chain polyunsaturated fatty acid is selected from the group consisting of; arachidonic acid (ARA, 20:4Δ5,8,11,14; ω6), eicosatetraenoic acid (ETA, 20:4Δ8,11,14,17, ω3), eicosapentaenoic acid (EPA, 20:5Δ5,8,11,14,17; ω3), docosapentaenoic acid (DPA, 22:5Δ7,10,13,16,19, ω3), or docosahexaenoic acid (DHA, 22:6Δ4,7,10,13,16,19, ω3). The LC-PUFA may also be dihomo-γ-linoleic acid (DGLA) or eicosatrienoic acid (ETrA, 20:3Δ11,14,17, ω3). It would readily be apparent that the LC-PUFA that is produced according to the invention may be a mixture of any or all of the above and may include other LC-PUFA or derivatives of any of these LC-PUFA. In a preferred embodiment, the ω3 fatty acids are at least DHA, preferably, DPA and DHA, or EPA, DPA and DHA.

Furthermore, as used herein the terms "long-chain polyunsaturated fatty acid" and "very long-chain polyunsaturated fatty acid" refer to the fatty acid being in a free state (non-esterified) or in an esterified form such as part of a triglyceride, diacylglyceride, monoacylglyceride, acyl-CoA bound or other bound form. The fatty acid may be esterified as a phospholipid such as a phosphatidylcholine (PC), phosphatidylethanolamine, phosphatidylserine, phosphatidylglycerol, phosphatidylinositol or diphosphatidylglycerol forms. Thus, the LC-PUFA may be present as a mixture of forms in the lipid of a cell or a purified oil or lipid extracted from cells, tissues or organisms. In preferred embodiments, the invention provides oil comprising at least 75% or at least 85% triacylglycerols, with the remainder present as other forms of lipid such as those mentioned, with at least said triacylglycerols comprising the LC-PUFA. The oil may subsequently be further purified or treated, for example by hydrolysis with a strong base to release the free fatty acids, or by distillation or the like.

As used herein, "total ω6 fatty acids" or "total ω6 fatty acid content" or the like refers to the sum of all the ω6 fatty acids, esterified and non-esterified, in the extracted lipid, oil, recombinanat cell, plant part or seed, as the context determines, expressed as a percentage of the total fatty acid content. These ω6 fatty acids include (if present) LA, GLA, DGLA, ARA, EDA and ω6-DPA, and exclude any ω3 fatty acids and monounsaturated fatty acids.

As used herein, "new ω6 fatty acids" or "new ω6 fatty acid content" or the like refers to the sum of all the ω6 fatty acids excluding LA, esterified and non-esterified, in the extracted lipid, oil, recombinant cell, plant part or seed, as the context determines, expressed as a percentage of the total fatty acid content. These new ω6 fatty acids are the fatty acids that are produced in the cells, plants, plant parts and seeds of the invention by the expression of the genetic constructs (exogenous polynucleotides) introduced into the cells, and include (if present) GLA, DGLA, ARA, EDA and ω6-DPA, but exclude LA and any ω3 fatty acids and monounsaturated fatty acids. Exemplary total ω6 fatty acid contents and new ω6 fatty acid contents are determined by conversion of fatty acids in a sample to FAME and analysis by GC, as described in Example 1.

As used herein, "total ω3 fatty acids" or "total ω3 fatty acid content" or the like refers to the sum of all the ω3 fatty acids, esterified and non-esterified, in the extracted lipid, oil, recombinanat cell, plant part or seed, as the context determines, expressed as a percentage of the total fatty acid content. These ω3 fatty acids include (if present) ALA, SDA, ETrA, ETA, EPA, DPA and DHA, and exclude any ω6 fatty acids and monounsaturated fatty acids.

As used herein, "new ω3 fatty acids" or "new ω3 fatty acid content" or the like refers to the sum of all the ω3 fatty acids excluding ALA, esterified and non-esterified, in the extracted lipid, oil, recombinanat cell, plant part or seed, as the context determines, expressed as a percentage of the total fatty acid content. These new ω3 fatty acids are the fatty acids that are produced in the cells, plants, plant parts and seeds of the invention by the expression of the genetic constructs (exogenous polynucleotides) introduced into the cells, and include (if present) SDA, ETrA, ETA, EPA, DPA and DHA, but exclude ALA and any ω6 fatty acids and monounsaturated fatty acids. Exemplary total ω3 fatty acid contents and new ω3 fatty acid contents are determined by conversion of fatty acids in a sample to FAME and analysis by GC, as described in Example 1.

The desaturase, elongase and acyl transferase proteins and genes encoding them that may be used in the invention are any of those known in the art or homologues or derivatives thereof. Examples of such genes and encoded protein sizes are listed in Table 1. The desaturase enzymes that have been shown to participate in LC-PUFA biosynthesis all belong to the group of so-called "front-end" desaturases.

As used herein, the term "front-end desaturase" refers to a member of a class of enzymes that introduce a double bond between the carboxyl group and a pre-existing unsaturated part of the acyl chain of lipids, which are characterized structurally by the presence of an N-terminal cytochrome b5 domain, along with a typical fatty acid desaturase domain that includes three highly conserved histidine boxes (Napier et al., 1997).

Activity of any of the elongases or desaturases for use in the invention may be tested by expressing a gene encoding the enzyme in a cell such as, for example, a yeast cell, a plant cell or preferably in somatic embryos or transgenic plants, and determining whether the cell, embryo or plant has an increased capacity to produce LC-PUFA compared to a comparable cell, embryo or plant in which the enzyme is not expressed.

In one embodiment one or more of the desaturases and/or elongases for use in the invention can purified from a microalga, i.e. is identical in amino acid sequence to a polypeptide which can be purified from a microalga.

Whilst certain enzymes are specifically described herein as "bifunctional", the absence of such a term does not necessarily imply that a particular enzyme does not possess an activity other than that specifically defined.

Desaturases

As used herein, the term "desaturase" refers to an enzyme which is capable of introducing a carbon-carbon double bond into the acyl group of a fatty acid substrate which is typically in an esterified form such as, for example, acyl-CoA esters. The acyl group may be esterified to a phospholipid such as phosphatidylcholine (PC), or to acyl carrier protein (ACP), or in a preferred embodiment to CoA. Desaturases generally may be categorized into three groups accordingly. In one embodiment, the desaturase is a front-end desaturase.

As used herein, a "Δ4-desaturase" refers to a protein which performs a desaturase reaction that introduces a carbon-carbon double bond at the $4^{th}$ carbon-carbon bond from the carboxyl end of a fatty acid substrate. The "Δ4-desaturase" is at least capable of converting DPA to DHA. The desaturation step to produce DHA from DPA is catalysed by a Δ4-desaturase in organisms other than mammals, and a gene encoding this enzyme has been isolated from the freshwater protist species *Euglena gracilis* and the marine species *Thraustochytrium* sp. (Qiu et al., 2001; Meyer et al., 2003). In one embodiment, the Δ4-desaturase comprises amino acids having a sequence as provided in SEQ ID NO:41, or a *Thraustochytrium* sp. Δ4-desaturase, a biologically active fragment thereof, or an amino acid sequence which is at least 80% identical to SEQ ID NO:41.

TABLE 1

Cloned genes involved in LC-PUFA biosynthesis

| Enzyme | Type of organism | Species | Accession Nos. | Protein size (aa's) | References |
|---|---|---|---|---|---|
| Δ4-desaturase | Protist | *Euglena gracilis* | AY278558 | 541 | Meyer et al., 2003 |
| | Algae | *Pavlova lutherii* | AY332747 | 445 | Tonon et al, 2003 |
| | | *Isochrysis galbana* | AAV33631 | 433 | Pereira et al., 2004b |
| | | *Pavlova salina* | AAY15136 | 447 | Zhou et al., 2007 |
| | Thraustochytrid | *Thraustochytrium aureum* | AAN75707 AAN75708 AAN75709 AAN75710 | 515 | N/A |
| | | *Thraustochytrium* sp. ATCC21685 | AAM09688 | 519 | Qiu et al. 2001 |
| Δ5-desaturase | Mammals | *Homo sapiens* | AF199596 | 444 | Cho et al., 1999b; Leonard et al., 2000b |
| | Nematode | *Caenorhabditis elegans* | AF11440, NM_069350 | 447 | Michaelson et al., 1998b; Watts and Browse, 1999b |
| | Fungi | *Mortierella alpina* | AF067654 | 446 | Michaelson et al., 1998a; Knutzon et al., 1998 |
| | | *Pythium irregulare* | AF419297 | 456 | Hong et al., 2002a |
| | | *Dictyostelium discoideum* | AB022097 | 467 | Saito et al., 2000 |
| | | *Saprolegnia diclina* | | 470 | WO02081668 |
| | Diatom | *Phaeodactylum tricornutum* | AY082392 | 469 | Domergue et al., 2002 |
| | Algae | *Thraustochytrium* sp | AF489588 | 439 | Qiu et al., 2001 |
| | | *Thraustochytrium aureum* | | 439 | WO02081668 |
| | | *Isochrysis galbana* | | 442 | WO02081668 |
| | Moss | *Marchantia polymorpha* | AY583465 | 484 | Kajikawa et al., 2004 |
| Δ6-desaturase | Mammals | *Homo sapiens* | NM_013402 | 444 | Cho et al., 1999a; Leonard et al., 2000 |
| | | *Mus musculus* | NM_019699 | 444 | Cho et al., 1999a |
| | Nematode | *Caenorhabditis elegans* | Z70271 | 443 | Napier et al., 1998 |
| | Plants | *Borago officinales* | U79010 | 448 | Sayanova et al., 1997 |
| | | *Echium* | AY055117 AY055118 | | Garcia-Maroto et al., 2002 |
| | | *Primula vialii* | AY234127 | 453 | Sayanova et al., 2003 |
| | | *Anemone leveillei* | AF536525 | 446 | Whitney et al., 2003 |
| | Mosses | *Ceratodon purpureus* | AJ250735 | 520 | Sperling et al., 2000 |
| | | *Marchantia polymorpha* | AY583463 | 481 | Kajikawa et al., 2004 |
| | | *Physcomitrella patens* | CAA11033 | 525 | Girke et al., 1998 |
| | Fungi | *Mortierella alpina* | AF110510 AB020032 | 457 | Huang et al., 1999; Sakuradani et al., 1999 |
| | | *Pythium irregulare* | AF419296 | 459 | Hong et al., 2002a |
| | | *Mucor circinelloides* | AB052086 | 467 | NCBI* |
| | | *Rhizopus* sp. | AY320288 | 458 | Zhang et al., 2004 |
| | | *Saprolegnia diclina* | | 453 | WO02081668 |
| | Diatom | *Phaeodactylum tricornutum* | AY082393 | 477 | Domergue et al., 2002 |
| | Bacteria | *Synechocystis* | L11421 | 359 | Reddy et al., 1993 |
| | Algae | *Thraustochytrium aureum* | | 456 | WO02081668 |
| Bifunctional Δ5/Δ6-desaturase | Fish | *Danio rerio* | AF309556 | 444 | Hastings et al., 2001 |
| C20 Δ8-desaturase | Algae | *Euglena gracilis* | AF139720 | 419 | Wallis and Browse, 1999 |
| | Plants | *Borago officinales* | AAG43277 | 446 | Sperling et al., 2001 |
| Δ6-elongase | Nematode | *Caenorhabditis elegans* | NM_069288 | 288 | Beaudoin et al., 2000 |
| | Mosses | *Physcomitrella patens* | AF428243 | 290 | Zank et al., 2002 |
| | | *Marchantia polymorpha* | AY583464 | 290 | Kajikawa et al., 2004 |
| | Fungi | *Mortierella alpina* | AF206662 | 318 | Parker-Barnes et al., 2000 |
| | Algae | *Pavlova lutherii*** | | 501 | WO 03078639 |
| | | *Thraustochytrium* | AX951565 | 271 | WO 03093482 |
| | | *Thraustochytrium* sp** | AX214454 | 271 | WO 0159128 |
| PUFA-elongase | Mammals | *Homo sapiens* | AF231981 | 299 | Leonard et al., 2000b; Leonard et al., 2002 |
| | | *Rattus norvegicus* | AB071985 | 299 | Inagaki et al., 2002 |
| | | *Rattus norvegicus*** | AB071986 | 267 | Inagaki et al., 2002 |
| | | *Mus musculus* | AF170907 | 279 | Tvrdik et al., 2000 |
| | | *Mus musculus* | AF170908 | 292 | Tvrdik et al., 2000 |
| | Fish | *Danio rerio* | AF532782 | 291 (282) | Agaba et al., 2004 |
| | | *Danio rerio*** | NM_199532 | 266 | Lo et al., 2003 |
| | Worm | *Caenorhabditis elegans* | Z68749 | 309 | Abbott et al., 1998; Beaudoin et al., 2000 |
| | Algae | *Thraustochytrium aureum*** | AX464802 | 272 | WO 0208401-A2 |
| | | *Pavlova lutherii*** | | 320 | WO 03078639 |
| Δ9-elongase | Algae | *Isochrysis galbana* | AF390174 | 263 | Qi et al., 2002 |
| | | *Euglena gracilis* | | 258 | WO 08/128241 |
| Δ5-elongase | Algae | *Ostreococcus tauri* | AAV67798 | 300 | Meyer et al., 2004 |
| | | *Pyramimonas cordata* | | 268 | WO 2010/057246 |
| | | *Pavlova* sp. CCMP459 | AAV33630 | 277 | Pereira et al., 2004b |
| | | *Pavlova salina* | AAY15135 | 302 | Robert et al., 2009 |

TABLE 1-continued

Cloned genes involved in LC-PUFA biosynthesis

| Enzyme | Type of organism | Species | Accession Nos. | Protein size (aa's) | References |
|---|---|---|---|---|---|
| | Diatom | Thalassiosira pseudonana | AAV67800 | 358 | Meyer et al., 2004 |
| | Fish | Oncorhynchus mykiss | CAM55862 | 295 | WO 06/008099 |
| | Moss | Marchantia polymorpha | BAE71129 | 348 | Kajikawa et al., 2006 |

*http://www.ncbi.nlm.nih.gov/
**Function not proven/not demonstrated

As used herein, a "Δ5-desaturase" refers to a protein which performs a desaturase reaction that introduces a carbon-carbon double bond at the $5^{th}$ carbon-carbon bond from the carboxyl end of a fatty acid substrate. Examples of Δ5-desaturases are listed in Ruiz-Lopez et al. (2012) and Petrie et al. (2010a) and in Table 1 herein. In one embodiment, the Δ5-desaturase comprises amino acids having a sequence as provided in SEQ ID NO:30, a biologically active fragment thereof, or an amino acid sequence which is at least 80% identical to SEQ ID NO:30. In another embodiment, the Δ5-desaturase comprises amino acids having a sequence as provided in SEQ ID NO:32, a biologically active fragment thereof, or an amino acid sequence which is at least 53% identical to SEQ ID NO:32. In another embodiment, the Δ5-desaturase is from Thraustochytrium sp or Emiliania huxleyi.

activity on ALA to produce octadecatetraenoic acid (stearidonic acid, SDA, 18:4Δ6,9,12,15, ω3) with an efficiency of at least 30%, more preferably at least 40%, or most preferably at least 50% when expressed from an exogenous polynucleotide in a recombinant cell such as a plant cell, or at least 35% when expressed in a yeast cell. In one embodiment, the Δ6-desaturase has greater activity, for example, at least about a 2-fold greater Δ6-desaturase activity, on ALA than LA as fatty acid substrate. In another embodiment, the Δ6-desaturase has greater activity, for example, at least about 5 fold greater Δ6-desaturase activity or at least 10-fold greater activity, on ALA-CoA as fatty acid substrate than on ALA joined to the sn-2 position of PC as fatty acid substrate. In a further embodiment, the Δ6-desaturase has activity on both fatty acid substrates ALA-CoA and on ALA joined to the sn-2 position of PC.

TABLE 2

Desaturases demonstrated to have activity on an acyl-CoA substrate

| Enzyme | Type of organism | Species | Accession Nos. | Protein size (aa's) | References |
|---|---|---|---|---|---|
| Δ6-desaturase | Algae | Mantoniella squamata | CAQ30479 | 449 | Hoffmann et al., 2008 |
| | | Ostreococcus tauri | AAW70159 | 456 | Domergue et al., 2005 |
| | | Micromonas pusilla | EEH58637 | | Petrie et al., 2010a (SEQ ID NO: 13) |
| Δ5-desaturase | Algae | Mantoniella squamata | CAQ30478 | 482 | Hoffmann et al., 2008 |
| | Plant | Anemone leveillei | N/A | | Sayanova et al., 2007 |
| ω3-desaturase | Fungi | Pythium aphanidermatum | FW362186.1 | 359 | Xue et al., 2012; WO2008/054565 |
| | Fungi (oomycete) | Phytophthora sojae | FW362214.1 | 363 | Xue et al., 2012; WO2008/054565 |
| | Fungi (oomycete) | Phytophthora ramorum | FW362213.1 | 361 | Xue et al., 2012; WO2008/054565 |

As used herein, a "Δ6-desaturase" refers to a protein which performs a desaturase reaction that introduces a carbon-carbon double bond at the $6^{th}$ carbon-carbon bond from the carboxyl end of a fatty acid substrate. Examples of Δ6-desaturases are listed in Ruiz-Lopez et al. (2012) and Petrie et al. (2010a) and in Table 1 herein. Preferred Δ6-desaturases are from Micromonas pusilla, Pythium irregulare or Ostreocococus taurii.

In an embodiment, the Δ6-desaturase is further characterised by having at least two, preferably all three and preferably in a plant cell, of the following: i) greater Δ6-desaturase activity on α-linolenic acid (ALA, 18:3Δ9,12,15, ω3) than linoleic acid (LA, 18:2Δ9,12, ω6) as fatty acid substrate; ii) greater Δ6-desaturase activity on ALA-CoA as fatty acid substrate than on ALA joined to the sn-2 position of PC as fatty acid substrate; and iii) Δ8-desaturase activity on ETrA. Examples of such Δ6-desaturases are provided in Table 2.

In an embodiment the Δ6-desaturase has greater activity on an ω3 substrate than the corresponding ω6 substrate and has In one embodiment, the Δ6-desaturase has no detectable Δ5-desaturase activity on ETA. In another embodiment, the Δ6-desaturase comprises amino acids having a sequence as provided in SEQ ID NO:16, SEQ ID NO:19 or SEQ ID NO:20, a biologically active fragment thereof, or an amino acid sequence which is at least 77% identical to SEQ ID NO:16, SEQ ID NO:19 or SEQ ID NO:20. In another embodiment, the Δ6-desaturase comprises amino acids having a sequence as provided in SEQ ID NO:19 or SEQ ID NO:20, a biologically active fragment thereof, or an amino acid sequence which is at least 67% identical to one or both of SEQ ID NO:19 or SEQ ID NO:20. The Δ6-desaturase may also have Δ8-desaturase activity.

As used herein, a "Δ8-desaturase" refers to a protein which performs a desaturase reaction that introduces a carbon-carbon double bond at the $8^{th}$ carbon-carbon bond from the carboxyl end of a fatty acid substrate. The Δ8-desaturase is at least capable of converting ETrA to ETA. Examples of Δ8-desaturases are listed in Table 1. In one embodiment, the Δ8-desaturase comprises amino acids having a sequence as provided in SEQ ID NO:52, a biologically active fragment thereof; or an amino acid sequence which is at least 80% identical to SEQ ID NO:52.

As used herein, an "ω3-desaturase" refers to a protein which performs a desaturase reaction that introduces a carbon-carbon double bond at the 3rd carbon-carbon bond from the methyl end of a fatty acid substrate. A ω3-desaturase therefore may convert LA to ALA and GLA to SDA (all C18 fatty acids), or DGLA to ETA and/or ARA to EPA (C20 fatty acids). Some ω3-desaturases (group I) have activity only on C18 substrates, such as plant and cyanobacterial ω3-desaturases. Such ω3-desaturases are also Δ15-desaturases. Other ω3-desaturases have activity on C20 substrates with no activity (group II) or some activity (group III) on C18 substrates. Such ω3-desaturases are also Δ17-desaturases. Preferred ω3-desaturases are group III type which convert LA to ALA, GLA to SDA, DGLA to ETA and ARA to EPA, such as the *Pichia pastoris* ω3-desaturase (SEQ ID NO: 12). Examples of ω3-desaturases include those described by Pereira et al. (2004a) (*Saprolegnia diclina* ω3-desaturase, group II), Horiguchi et al. (1998), Berberich et al. (1998) and Spychalla et al. (1997) (*C. elegans* ω3-desaturase, group III). In a preferred embodiment, the ω3-desaturase is a fungal ω3-desaturase. As used herein, a "fungal ω3-desaturase" refers to an ω3-desaturase which is from a fungal source, including an oomycete source, or a variant thereof whose amino acid sequence is at least 95% identical thereto. Genes encoding numerous ω3-desaturases have been isolated from fungal sources such as, for example, from *Phytophthora infestans* (Accession No. CAJ30870, WO2005083053; SEQ ID NO: 70), *Saprolegnia diclina* (Accession No. AAR20444, Pereira et al., 2004a & U.S. Pat. No. 7,211,656), *Pythium irregulare* (WO2008022963, Group II; SEQ ID NO: 72), *Mortierella alpina* (Sakuradani et al., 2005; Accession No. BAD91495; WO2006019192), *Thalassiosira pseudonana* (Armbrust et al., 2004; Accession No. XP_002291057; WO2005012316, SEQ ID NO: 71), *Lachancea kluyveri* (also known as *Saccharomyces kluyveri*; Oura et al., 2004; Accession No. AB118663). Xue et al. (2012) describes ω3-desaturases from the oomycetes *Pythium aphanidermatum*, *Phytophthora sojae*, and *Phytophthora ramorum* which were able to efficiently convert ω6 fatty acid substrates to the corresponding ω3 fatty acids, with a preference for C20 substrates, i.e. they had stronger Δ17-desaturase activity than Δ15-desaturase activity. These enzymes lacked Δ12-desaturase activity, but could use fatty acids in both acyl-CoA and phospholipid fraction as substrates.

In a more preferred embodiment, the fungal ω3-desaturase is the *Pichia pastoris* (also known as *Komzagataella pastoris*) ω3-desaturase/Δ15-desaturase (Zhang et al., 2008; Accession No. EF116884; SEQ ID NO: 12), or a polypeptide which is at least 95% identical thereto.

In an embodiment, the ω3-desaturase is at least capable of converting one of ARA to EPA, DGLA to ETA, GLA to SDA, both ARA to EPA and DGLA to ETA, both ARA to EPA and GLA to SDA, or all three of these.

In one embodiment, the ω3-desaturase has Δ17-desaturase activity on a C20 fatty acid which has at least three carbon-carbon double bonds, preferably ARA. In another embodiment, the ω3-desaturase has Δ15-desaturase activity on a C18 fatty acid which has three carbon-carbon double bonds, preferably GLA. Preferably, both activities are present.

As used herein, a "Δ12-desaturase" refers to a protein which performs a desaturase reaction that introduces a carbon-carbon double bond at the $12^{th}$ carbon-carbon bond from the carboxyl end of a fatty acid substrate. Δ12-desaturases typically convert either oleoyl-phosphatidylcholine or oleoyl-CoA to linoleoyl-phosphatidylcholine (18:1-PC) or linoleoyl-CoA (18:1-CoA), respectively. The subclass using the PC linked substrate are referred to as phospholipid-dependent Δ12-desaturases, the latter subclass as acyl-CoA dependent Δ12-desaturases. Plant and fungal Δ12-desaturases are generally of the former sub-class, whereas animal Δ12-desaturases are of the latter subclass, for example the Δ12-desaturases encoded by genes cloned from insects by Zhou et al. (2008). Many other Δ12-desaturase sequences can be easily identified by searching sequence databases.

As used herein, a "Δ15-desaturase" refers to a protein which performs a desaturase reaction that introduces a carbon-carbon double bond at the $15^{th}$ carbon-carbon bond from the carboxyl end of a fatty acid substrate. Numerous genes encoding Δ15-desaturases have been cloned from plant and fungal species. For example, U.S. Pat. No. 5,952,544 describes nucleic acids encoding plant Δ15-desaturases (FAD3). These enzymes comprise amino acid motifs that were characteristic of plant Δ15-desaturases. WO200114538 describes a gene encoding soybean FAD3. Many other Δ15-desaturase sequences can be easily identified by searching sequence databases.

As used herein, a "Δ17-desaturase" refers to a protein which performs a desaturase reaction that introduces a carbon-carbon double bond at the $17^{th}$ carbon-carbon bond from the carboxyl end of a fatty acid substrate. A Δ17-desaturase is also regarded as an ω3-desaturase if it acts on a C20 substrate to introduce a desaturation at the ω3 bond.

In a preferred embodiment, the Δ12-desaturase and/or Δ15-desaturase is a fungal Δ12-desaturase or fungal Δ15-desaturase. As used herein, a "fungal Δ12-desaturase" or "a fungal Δ15-desaturase" refers to a Δ12-desaturase or Δ15-desaturase which is from a fungal source, including an oomycete source, or a variant thereof whose amino acid sequence is at least 95% identical thereto. Genes encoding numerous desaturases have been isolated from fungal sources. U.S. Pat. No. 7,211,656 describes a Δ12 desaturase from *Saprolegnia diclina*. WO2009016202 describes fungal desaturases from *Helobdella robusta, Laccaria hicolor, Lottia gigantea, Microcoleus chthonoplastes, Monosiga brevicollis, Mycosphaerella fijiensis, Mycospaerella graminicola, Naegleria gruben, Nectria haematococca, Nematostella vectensis, Phycomyces blakesleeanus, Trichoderma resii, Physcomitrella patens, Postia placenta, Selaginella moellendorffii* and *Microdochium nivale*. WO2005/012316 describes a Δ12-desaturase from *Thalassiosira pseudonana* and other fungi. WO2003/099216 describes genes encoding fungal Δ12-desaturases and Δ15-desaturases isolated from *Neurospora crassa, Aspergillus nidulans, Botrytis cinerea* and *Mortierella alpina*. WO2007133425 describes fungal Δ15 desaturases isolated from: *Saccharomyces kluyveri, Mortierella alpina, Aspergillus nidulans, Neurospora crassa, Fusarium graminearum, Fusarium moniliforme* and *Magnaporthe grisea*. A preferred Δ12 desaturase is from *Phytophthora sojae* (Ruiz-Lopez et al., 2012).

A distinct subclass of fungal Δ12-desaturases, and of fungal Δ15-desaturases, are the bifunctional fungal Δ12/Δ15-desaturases. Genes encoding these have been cloned from *Fusarium monoliforme* (Accession No. DQ272516, Damude et al., 2006), *Acanthamoeba castellanii* (Accession No. EF017656, Sayanova et al., 2006), *Perkinsus marinus* (WO2007042510), *Claviceps purpurea* (Accession No. EF536898, Meesapyodsuk et al., 2007) and *Coprinus cinereus* (Accession No. AF269266, Zhang et al., 2007).

In another embodiment, the ω3-desaturase has at least some activity on, preferably greater activity on, an acyl-CoA substrate than a corresponding acyl-PC substrate. As used herein, a "corresponding acyl-PC substrate" refers to the fatty acid esterified at the sn-2 position of phosphatidylcholine (PC) where the fatty acid is the same fatty acid as in the acyl-CoA substrate. For example, the acyl-CoA substrate may be ARA-CoA and the corresponding acyl-PC substrate is sn-2 ARA-PC. In an embodiment, the activity is at least two-fold greater. Preferably, the ω3-desaturase has at least some activity on both an acyl-CoA substrate and its corresponding acyl-PC substrate and has activity on both C18 and C20 substrates. Examples of such ω3-desaturases are known amongst the cloned fungal desaturases listed above.

In a further embodiment, the ω3-desaturase comprises amino acids having a sequence as provided in SEQ ID NO:12, a biologically active fragment thereof, or an amino acid sequence which is at least 60% identical to SEQ ID NO:12, preferably at least 90% or at least 95% identical to SEQ ID NO: 12.

In yet a further embodiment, a desaturase for use in the present invention has greater activity on an acyl-CoA substrate than a corresponding acyl-PC substrate. In another embodiment, a desaturase for use in the present invention has greater activity on an acyl-PC substrate than a corresponding acyl-CoA substrate, but has some activity on both substrates. As outlined above, a "corresponding acyl-PC substrate" refers to the fatty acid esterified at the sn-2 position of phosphatidylcholine (PC) where the fatty acid is the same fatty acid as in the acyl-CoA substrate. In an embodiment, the greater activity is at least two-fold greater. In an embodiment, the desaturase is a Δ5 or Δ6-desaturase, or an ω3-desaturase, examples of which are provided, but not limited to, those listed in Table 2. To test which substrate a desaturase acts on, namely an acyl-CoA or an acyl-PC substrate, assays can be carried out in yeast cells as described in Domergue et al. (2003) and (2005). Acyl-CoA substrate capability for a desaturase can also be inferred when an elongase, when expressed together with the desaturase, has an enzymatic conversion efficiency in plant cells of at least about 90% where the elongase catalyses the elongation of the product of the desaturase. On this basis, the Δ5-desaturase and Δ4-desaturases expressed from the GA7 construct (Examples 2 and 3) and variants therefor (Example 5) are capable of desaturating their respective acyl-CoA substrates, ETA-CoA and DPA-CoA.

Elongases

Biochemical evidence suggests that the fatty acid elongation consists of 4 steps: condensation, reduction, dehydration and a second reduction. In the context of this invention, an "elongase" refers to the polypeptide that catalyses the condensing step in the presence of the other members of the elongation complex, under suitable physiological conditions. It has been shown that heterologous or homologous expression in a cell of only the condensing component ("elongase") of the elongation protein complex is required for the elongation of the respective acyl chain. Thus, the introduced elongase is able to successfully recruit the reduction and dehydration activities from the transgenic host to carry out successful acyl elongations. The specificity of the elongation reaction with respect to chain length and the degree of desaturation of fatty acid substrates is thought to reside in the condensing component. This component is also thought to be rate limiting in the elongation reaction.

As used herein, a "Δ5-elongase" is at least capable of converting EPA to DPA. Examples of Δ5-elongases include those disclosed in WO2005/103253. In one embodiment, the Δ5-elongase has activity on EPA to produce DPA with an efficiency of at least 60%, more preferably at least 65%, more preferably at least 70% or most preferably at least 80% or 90%. In a further embodiment, the Δ5-elongase comprises an amino acid sequence as provided in SEQ ID NO:37, a biologically active fragment thereof, or an amino acid sequence which is at least 47% identical to SEQ ID NO:37. In a further embodiment, the Δ6-elongase is from *Ostreococcus taurii* or *Ostreococcus lucimarinus* (US2010/088776).

As used herein, a "Δ6-elongase" is at least capable of converting SDA to ETA. Examples of Δ6-elongases include those listed in Table 1. In one embodiment, the elongase comprises amino acids having a sequence as provided in SEQ ID NO:25, a biologically active fragment thereof (such as the fragment provided as SEQ ID NO:26), or an amino acid sequence which is at least 55% identical to one or both of SEQ ID NO:25 or SEQ ID NO:26. In an embodiment, the Δ6-elongase is from *Physcomitrella patens* (Zank et al., 2002; Accession No. AF428243) or *Thalassiosira pseudonana* (Ruiz-Lopez et al., 2012).

As used herein, a "Δ9-elongase" is at least capable of converting ALA to ETrA. Examples of Δ9-elongases include those listed in Table 1. In one embodiment, the Δ9-elongase comprises amino acids having a sequence as provided in SEQ ID NO:43, a biologically active fragment thereof, or an amino acid sequence which is at least 80% identical to SEQ ID NO:43. In another embodiment, the Δ9-elongase comprises amino acids having a sequence as provided in SEQ ID NO:46, a biologically active fragment thereof, or an amino acid sequence which is at least 81% identical to SEQ ID NO:46. In another embodiment, the Δ9-elongase comprises amino acids having a sequence as provided in SEQ ID NO:48, a biologically active fragment thereof, or an amino acid sequence which is at least 50% identical to SEQ ID NO:48. In another embodiment, the Δ9-elongase comprises amino acids having a sequence as provided in SEQ ID NO:50, a biologically active fragment thereof, or an amino acid sequence which is at least 50% identical to SEQ ID NO:50. In a further embodiment, the Δ9-elongase has greater activity on an ω6 substrate than the corresponding ω3 substrate, or the converse.

As used herein, the term "has greater activity on an ω6 substrate than the corresponding ω3 substrate" refers to the relative activity of the enzyme on substrates that differ by the action of an ω3 desaturase. Preferably, the ω6 substrate is LA and the ω3 substrate is ALA.

An elongase with Δ6-elongase and Δ9-elongase activity is at least capable of (i) converting SDA to ETA and (ii) converting ALA to ETrA and has greater Δ6-elongase activity than Δ9-elongase activity. In one embodiment, the elongase has an efficiency of conversion on SDA to produce ETA which is at least 50%, more preferably at least 60%, and/or an efficiency of conversion on ALA to produce ETrA which is at least 6% or more preferably at least 9%. In another embodiment, the elongase has at least about 6.5 fold greater Δ6-elongase activity than Δ9-elongase activity. In a further embodiment, the elongase has no detectable Δ5-elongase activity Other Enzymes As used herein, the term "1-acyl-glycerol-3-phosphate acyltransferase" (LPAAT), also termed lysophosphatidic acid-acyltransferase or acylCoA-lysophosphatidate-acyltransferase, refers to a protein which acylates sn-1-acyl-glycerol-3-phosphate (sn-1 G-3-P) at the sn-2 position to form phosphatidic acid (PA). Thus, the term "1-acyl-glycerol-3-phosphate acyltransferase activity" refers to the acylation of (sn-1 G-3-P) at the sn-2 position to produce PA (EC 2.3.1.51). Preferred LPAATs are those that can use a polyunsaturated C22 acyl-CoA as substrate to transfer the polyunsaturated C22 acyl group to the sn-2 position of LPA, forming PA. Such LPAATs are exemplified in Example 13 and can be tested as described therein. In an embodiment, an LPAAT useful for the invention comprises amino acids having a sequence as provided in any one of SEQ ID NOs: 63 to 69, a biologically active fragment thereof, or an amino acid sequence which is at least 40% identical to any one or more of SEQ ID NOs: 63 to 69. In a preferred embodiment, an LPAAT useful for the invention comprises amino acids having a sequence as provided in any one of SEQ ID NOs: 64, 65 and 67, a biologically active fragment thereof, or an amino acid sequence which is at least 40% identical to any one or more of SEQ ID NOs: 64, 65 and 67.

As used herein, the term "diacylglycerol acyltransferase" (EC 2.3.1.20; DGAT) refers to a protein which transfers a fatty acyl group from acyl-CoA to a diacylglycerol substrate to produce a triacylglycerol. Thus, the term "diacylglycerol acyltransferase activity" refers to the transfer of acyl-CoA to diacylglycerol to produce triacylglycerol. There are three known types of DGAT referred to as DGAT1, DGAT2 and DGAT3 respectively. DGAT1 polypeptides typically have 10 transmembrane domains, DGAT2 typically have 2 transmembrane domains, whilst DGAT3 is typically soluble. Examples of DGAT1 polypeptides include polypeptides encoded by DGAT1 genes from *Aspergillus fumigatus* (Accession No. XP_755172), *Arabidopsis thaliana* (CAB44774), *Ricinus communis* (AAR11479), *Vernicia fordii* (ABC94472), *Vernonia galamensis* (ABV21945, ABV21946), *Euonymus alatus* (AAV31083), *Caenorhabditis elegans* (AAF82410), *Rattus norvegicus* (NP_445889), *Homo sapiens* (NP_036211), as well as variants and/or mutants thereof. Examples of DGAT2 polypeptides include polypeptides encoded by DGAT2 genes from *Arabidopsis thaliana* (Accession No. NP_566952), *Ricinus communis* (AAY16324), *Vernicia fordii* (ABC94474), *Mortierella ramanniana* (AAK84179), *Homo sapiens* (Q96PD7, Q58HT5), *Bos taurus* (Q70VD8), *Mus musculus* (AAK84175), *Micromonas* CCMP1545, as well as variants and/or mutants thereof. Examples of DGAT3 polypeptides include polypeptides encoded by DGAT3 genes from peanut (*Arachis hypogaea*, Saha, et al., 2006), as well as variants and/or mutants thereof.

Polypeptides/Peptides

The term "recombinant" in the context of a polypeptide refers to the polypeptide when produced by a cell, or in a cell-free expression system, in an altered amount or at an altered rate, compared to its native state if it is produced naturally. In one embodiment the cell is a cell that does not naturally produce the polypeptide. However, the cell may be a cell which comprises a non-endogenous gene that causes an altered amount of the polypeptide to be produced. A recombinant polypeptide of the invention includes polypeptides in the cell, tissue, organ or organism, or cell-free expression system, in which it is produced i.e. a polypeptide which has not been purified or separated from other components of the transgenic (recombinant) cell in which it was produced, and polypeptides produced in such cells or cell-free systems which are subsequently purified away from at least some other components.

The terms "polypeptide" and "protein" are generally used interchangeably.

A polypeptide or class of polypeptides may be defined by the extent of identity (% identity) of its amino acid sequence to a reference amino acid sequence, or by having a greater % identity to one reference amino acid sequence than to another. The % identity of a polypeptide to a reference amino acid sequence is typically determined by GAP analysis (Needleman and Wunsch, 1970; GCG program) with parameters of a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length. The polypeptide or class of polypeptides may have the same enzymatic activity as, or a different activity than, or lack the activity of, the reference polypeptide. Preferably, the polypeptide has an enzymatic activity of at least 10%, at least 50%, at least 75% or at least 90%, of the activity of the reference polypeptide.

As used herein a "biologically active" fragment is a portion of a polypeptide defined herein which maintains a defined activity of a full-length reference polypeptide, for example possessing desaturase and/or elongase activity or other enzyme activity. Biologically active fragments as used herein exclude the fill-length polypeptide. Biologically active fragments can be any size portion as long as they maintain the defined activity. Preferably, the biologically active fragment maintains at least 10%, at least 50%, at least 75% or at least 90%, of the activity of the full length protein.

With regard to a defined polypeptide or enzyme, it will be appreciated that % identity figures higher than those provided herein will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence variants/mutants of the polypeptides of the defined herein can be prepared by introducing appropriate nucleotide changes into a nucleic acid defined herein, or by in vitro synthesis of the desired polypeptide. Such variants/mutants include, for example, deletions, insertions or substitutions of residues within the amino acid sequence. A combination of deletion, insertion and substitution can be made to arrive at the final construct, provided that the final peptide product possesses the desired enzyme activity.

Mutant (altered) peptides can be prepared using any technique known in the art. For example, a polynucleotide defined herein can be subjected to in vitro mutagenesis or DNA shuffling techniques as broadly described by Harayama (1998). Products derived from mutated/altered DNA can readily be screened using techniques described herein to determine if they possess, for example, desaturase or elongase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites which are not conserved amongst naturally occurring desaturases or elongases. These sites are preferably substituted in a relatively conservative manner in order to maintain enzyme activity. Such conservative substitutions are shown in Table 3 under the heading of "exemplary substitutions".

In a preferred embodiment a mutant/variant polypeptide has only, or not more than, one or two or three or four conservative amino acid changes when compared to a naturally occurring polypeptide. Details of conservative amino acid changes are provided in Table 3. As the skilled person would be aware, such minor changes can reasonably be predicted not to alter the activity of the polypeptide when expressed in a recombinant cell.

Polypeptides can be produced in a variety of ways, including production and recovery of natural polypeptides or recombinant polypeptides according to methods known in the art. In one embodiment, a recombinant polypeptide is produced by culturing a cell capable of expressing the polypeptide under conditions effective to produce the polypeptide, such as a host cell defined herein. A more preferred cell to produce the polypeptide is a cell in a plant, especially in a seed in a plant.

Polynucleotides

The invention also provides and/or uses polynucleotides which may be, for example, a gene, an isolated polynucleotide, a chimeric genetic construct such as a T-DNA molecule, or a chimeric DNA. It may be DNA or RNA of genomic or synthetic origin, double-stranded or single-stranded, and combined with carbohydrate, lipids, protein or other materials to perform a particular activity defined herein. The term "polynucleotide" is used interchangeably herein with the term "nucleic acid molecule". By "isolated polynucleotide" we mean a polynucleotide which, if obtained from a natural source, has been separated from the polynucleotide sequences with which it is associated or linked in its native state, or a non-naturally occurring polynucleotide. Preferably, the isolated polynucleotide is at least 60% free, more preferably at least 75% free, and more preferably at least 90% free from other components with which it is naturally associated.

TABLE 3

Exemplary substitutions.

| Original Residue | Exemplary Substitutions |
| --- | --- |
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |

TABLE 3-continued

Exemplary substitutions.

| Original Residue | Exemplary Substitutions |
| --- | --- |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In an embodiment, a polynucleotide of the invention is non-naturally occurring. Examples of non-naturally occurring polynucleotides include, but are not limited to, those that have been mutated (such as by using methods described herein), and polynucleotides where an open reading frame encoding a protein is operably linked to a promoter to which it is not naturally associated (such as in the constructs described herein).

As used herein, the term "gene" is to be taken in its broadest context and includes the deoxyribonucleotide sequences comprising the transcribed region and, if translated, the protein coding region, of a structural gene and including sequences located adjacent to the coding region on both the 5' and 3' ends for a distance of at least about 2 kb on either end and which are involved in expression of the gene. In this regard, the gene includes control signals such as promoters, enhancers, termination and/or polyadenylation signals that are naturally associated with a given gene, or heterologous control signals in which case the gene is referred to as a "chimeric gene". The sequences which are located 5' of the protein coding region and which are present on the mRNA are referred to as 5' non-translated sequences. The sequences which are located 3' or downstream of the protein coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA). Introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, a "chimeric DNA" or "chimeric genetic construct" refers to any DNA molecule that is not a native DNA molecule in its native location, also referred to herein as a "DNA construct". Typically, a chimeric DNA or chimeric gene comprises regulatory and transcribed or protein coding sequences that are not found operably linked together in nature i.e. that are heterologous with respect to each other. Accordingly, a chimeric DNA or chimeric gene may comprise regulatory sequences and coding sequences that are derived from different sources, or regulatory sequences and coding sequences derived from the same source, but arranged in a manner different than that found in nature.

The term "endogenous" is used herein to refer to a substance that is normally present or produced in, for example, an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. Foreign or exogenous genes may be genes that are inserted into a non-native organism, native genes introduced into a new location within the native host, or chimeric genes. A "transgene" is a gene that has been introduced into the genome by a transformation procedure. The terms "genetically modified", "transgenic" and variations thereof include introducing genes into cells by transformation or transduction, mutating genes in cells and altering or modulating the regulation of a gene in a cell or organisms to which these acts have been done or their progeny. A "genomic region" as used herein refers to a position within the genome where a transgene, or group of transgenes (also referred to herein as a cluster), have been inserted into a cell, or an ancestor thereof. Such regions only comprise nucleotides that have been incorporated by the intervention of man such as by methods described herein.

The term "exogenous" in the context of a polynucleotide refers to the polynucleotide when present in a cell in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

As used herein, the term "different exogenous polynucleotides" or variations thereof means that the nucleotide sequence of each polynucleotide are different by at least one, preferably more, nucleotides. The polynucleotides encode RNAs which may or may not be translated to a protein within the cell. In an example, it is preferred that each polynucleotide encodes a protein with a different activity. In another example, each exogenous polynucleotide is less than 95%, less than 90%, or less than 80% identical to the other exogenous polynucleotides. Preferably, the exogenous polynucleotides encode functional proteins/enzymes. Furthermore, it is preferred that the different exogenous polynucleotides are non-overlapping in that each polynucleotide is a distinct region of the, for example, extrachromosomal transfer nucleic acid which does not overlap with another exogenous polynucleotide. At a minimum, each exogenous polynucleotide has a transcription start and stop site, as well as the designated promoter. An individual exogenous polynucleotide may or may not comprise introns.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of the present invention may selectively hybridise, under stringent conditions, to a polynucleotide that encodes a polypeptide of the present invention. As used herein, stringent conditions are those that (1) employ during hybridisation a denaturing agent such as formamide, for example, 50% (v/v) formamide with 0.1% (w/v) bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (2) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2× SSC and 0.1% SDS and/or (3) employ low ionic strength and high temperature for washing, for example, 0.015 M NaCl/ 0.0015 M sodium citrate/0.1% SDS at 50° C.

Polynucleotides of the invention may possess, when compared to naturally occurring molecules, one or more mutations which are deletions, insertions, or substitutions of nucleotide residues. Polynucleotides which have mutations relative to a reference sequence can be either naturally occurring (that is to say, isolated from a natural source) or synthetic (for example, by performing site-directed mutagenesis or DNA shuffling on the nucleic acid as described above). It is thus apparent that polynucleotides of the invention can be either from a naturally occurring source or recombinant. Preferred polynucleotides are those which have coding regions that are codon-optimised for translation in plant cells, as is known in the art.

Recombinant Vectors

One embodiment of the present invention includes a recombinant vector, which comprises at least one polynucleotide molecule defined herein, inserted into any vector capable of delivering the polynucleotide molecule into a host cell. Recombinant vectors include expression vectors. Recombinant vectors contain heterologous polynucleotide sequences, that is, polynucleotide sequences that are not naturally found adjacent to polynucleotide molecules defined herein that preferably are derived from a species other than the species from which the polynucleotide molecule(s) are derived. The vector can be either RNA or DNA and typically is a plasmid. Plasmid vectors typically include additional nucleic acid sequences that provide for easy selection, amplification, and transformation of the expression cassette in prokaryotic cells, e.g., pUC-derived vectors, pSK-derived vectors, pGEM-derived vectors, pSP-derived vectors, pBS-derived vectors, or preferably binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells. The recombinant vector may comprise more than one polynucleotide defined herein, for example three, four, five or six polynucleotides defined herein in combination, preferably a chimeric genetic construct of the invention, each polynucleotide being operably linked to expression control sequences that are operable in the cell of interest. More than one polynucleotide defined herein, for example 3, 4, 5 or 6 polynucleotides, are preferably covalently joined together in a single recombinant vector, preferably within a single T-DNA molecule, which may then be introduced as a single molecule into a cell to form a recombinant cell according to the invention, and preferably integrated into the genome of the recombinant cell, for example in a transgenic plant. Thereby, the polynucleotides which are so joined will be inherited together as a single genetic locus in progeny of the recombinant cell or plant. The recombinant vector or plant may comprise two or more such recombinant vectors, each containing multiple polynucleotides, for example wherein each recombinant vector comprises 3, 4, 5 or 6 polynucleotides.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

When there are multiple promoters present, each promoter may independently be the same or different.

Recombinant molecules such as the chimeric DNAs or genetic constructs may also contain (a) one or more secretory signals which encode signal peptide sequences, to enable an expressed polypeptide defined herein to be secreted from the cell that produces the polypeptide or which provide for localisation of the expressed polypeptide, for example for retention of the polypeptide in the endoplasmic reticulum (ER) in the cell or transfer into a plastid, and/or (b) contain fusion sequences which lead to the expression of nucleic acid molecules as fusion proteins. Examples of suitable signal segments include any signal segment capable of directing the secretion or localisation of a polypeptide defined herein. Recombinant molecules may also include intervening and/or untranslated sequences surrounding and/or within the nucleic acid sequences of nucleic acid molecules defined herein.

To facilitate identification of transformants, the nucleic acid construct desirably comprises a selectable or screenable marker gene as, or in addition to, the foreign or exogenous polynucleotide. By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked. The actual choice of a marker is not crucial as long as it is functional (i.e., selective) in combination with the cells of choice such as a plant cell.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding β-glucuronidase (GUS) enzyme for which various chromogenic substrates are known, a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of the cell, such as the plant cell. Accordingly, the nucleic acid may comprise appropriate elements which allow the molecule to be incorporated into the genome, preferably the right and left border sequences of a T-DNA molecule, or the construct is placed in an appropriate vector which can be incorporated into a chromosome of the cell.

Expression

As used herein, an expression vector is a DNA vector that is capable of transforming a host cell and of effecting expression of one or more specified polynucleotide molecule(s). Preferred expression vectors of the present invention can direct gene expression in yeast and/or plant cells. Expression vectors useful for the invention contain regulatory sequences such as transcription control sequences, translation control sequences, origins of replication, and other regulatory sequences that are compatible with the recombinant cell and that control the expression of polynucleotide molecules of the present invention. In particular, polynucleotides or vectors useful for the present invention include transcription control sequences. Transcription control sequences are sequences which control the initiation, elongation, and termination of transcription. Particularly important transcription control sequences are those which control transcription initiation, such as promoter and enhancer sequences. Suitable transcription control sequences include any transcription control sequence that can function in at least one of the recombinant cells of the present invention. The choice of the regulatory sequences used depends on the target organism such as a plant and/or target organ or tissue of interest. Such regulatory sequences may be obtained from any eukaryotic organism such as plants or plant viruses, or may be chemically synthesized. A variety of such transcription control sequences are known to those skilled in the art. Particularly preferred transcription control sequences are promoters active in directing transcription in plants, either constitutively or stage and/or tissue specific, depending on the use of the plant or parts thereof.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triose-phosphate isomerase promoter, the adenine phosphoribosyl-transferase promoter of *Arabidopsis*, the rice actin I gene promoter, the mannopine synthase and octopine synthase promoters, the Adh promoter, the sucrose synthase promoter, the R gene complex promoter, and the chlorophyll α/β binding protein gene promoter For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are ribulose-1, 5-bisphosphate carboxylase promoters, and Cab promoters.

A variety of plant gene promoters that are regulated in response to environmental, hormonal, chemical, and/or developmental signals, also can be used for expression of genes in plant cells, including promoters regulated by (1) heat, (2) light (e.g., pea RbcS-3A promoter, maize RbcS promoter); (3) hormones, such as abscisic acid, (4) wounding (e.g., WunI); or (5) chemicals, such as methyl jasmonate, salicylic acid, steroid hormones, alcohol, Safeners (WO97/06269), or it may also be advantageous to employ (6) organ-specific promoters.

As used herein, the term "plant seed specific promoter" or variations thereof refer to a promoter that preferentially, when compared to other plant tissues, directs gene transcription in a developing seed of a plant. In an embodiment, the seed specific promoter is expressed at least 5-fold more strongly in the developing seed of the plant relative to the leaves and/or stems of the plant, and is preferably expressed more strongly in the embryo of the developing seed compared to other plant tissues. Preferably, the promoter only directs expression of a gene of interest in the developing seed, and/or expression of the gene of interest in other parts of the plant such as leaves is not detectable by Northern blot analysis and/or RT-PCR. Typically, the promoter drives expression of genes during growth and development of the seed, in particular during the phase of synthesis and accumulation of storage compounds in the seed. Such promoters may drive gene expression in the entire plant storage organ or only part thereof such as the seedcoat, or cotyledon(s), preferably in the embryos, in seeds of dicotyledonous plants or the endosperm or aleurone layer of a seeds of monocotyledonous plants.

Preferred promoters for seed-specific expression include i) promoters from genes encoding enzymes involved in fatty acid biosynthesis and accumulation in seeds, such as desaturases and elongases, ii) promoters from genes encoding seed storage proteins, and iii) promoters from genes encoding enzymes involved in carbohydrate biosynthesis and accumulation in seeds. Seed specific promoters which are suitable are the oilseed rape napin gene promoter (U.S. Pat. No. 5,608, 152), the *Vicia faba* USP promoter (Baumlein et al., 1991), the *Arabidopsis* oleosin promoter (WO98/45461), the *Phaseolus vulgaris* phaseolin promoter (U.S. Pat. No. 5,504, 200), the *Brassica* Bce4 promoter (WO91/13980) or the legumin LeB4 promoter from *Vicia faba* (Baumlein et al., 1992), and promoters which lead to the seed-specific expression in monocots such as maize, barley, wheat, rye, rice and the like. Notable promoters which are suitable are the barley lpt2 or lpt1 gene promoter (WO95/15389 and WO95/23230) or the promoters described in WO99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998), Potenza et al. (2004), US20070192902 and US20030159173. In an embodiment, the seed specific promoter is preferentially expressed in defined parts of the seed such as the embryo, cotyledon(s) or the endosperm. Examples of such specific promoters include, but are not limited to, the FP1 promoter (Ellerstrom et al., 1996), the pea legumin promoter (Perrin et al., 2000), the bean phytohemagglutnin promoter (Perrin et al., 2000), the conlinin 1 and conlinin 2 promoters for the genes encoding the flax 2S storage proteins (Cheng et al., 2010), the promoter of the FAE1 gene from *Arabidopsis thaliana*, the BnGLP promoter of the globulin-like protein gene of *Brassica napus*, the LPXR promoter of the peroxiredoxin gene from *Linum usitatissimum*.

The 5' non-translated leader sequence can be derived from the promoter selected to express the heterologous gene sequence of the polynucleotide of the present invention, or preferably is heterologous with respect to the coding region of the enzyme to be produced, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene or a flax conlinin gene are commonly used in this capacity. The 3' transcribed, non-translated regions containing the polyadenylate signal of *Agrobacterium* tumor-inducing (Ti) plasmid genes are also suitable.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules defined herein include, but are not limited to, integration of the polynucleotide molecule into one or more host cell chromosomes, addition of stability sequences to mRNAs, substitutions or modifications of transcription control signals (e.g., promoters, operators, enhancers), substitutions or modifications of translational control signals (e.g., ribosome binding sites, Shine-Dalgamo sequences), modification of polynucleotide molecules to correspond to the codon usage of the host cell, and the deletion of sequences that destabilize transcripts.

Recombinant Cells

The invention also provides a recombinant cell, preferably a recombinant plant cell, which is a host cell transformed with one or more recombinant molecules, such as the polynucleotides, chimeric genetic constructs or recombinant vectors defined herein. The recombinant cell may comprise any combination thereof, such as two or three recombinant vectors, or a recombinant vector and one or more additional polynucleotides or chimeric DNAs. Suitable cells of the invention include any cell that can be transformed with a polynucleotide, chimeric DNA or recombinant vector of the invention, such as for example, a molecule encoding a polypeptide or enzyme described herein. The cell is preferably a cell which is thereby capable of being used for producing LC-PUFA. The recombinant cell may be a cell in culture, a cell in vitro, or in an organism such as for example a plant, or in an organ such as for example a seed or a leaf. Preferably, the cell is in a plant or plant part, more preferably in the seed of a plant.

Host cells into which the polynucleotide(s) are introduced can be either untransformed cells or cells that are already transformed with at least one nucleic acid molecule. Such nucleic acid molecules may be related to LC-PUFA synthesis, or unrelated. Host cells of the present invention either can be endogenously (i.e., naturally) capable of producing proteins defined herein, in which case the recombinant cell derived therefrom has an enhanced capability of producing the polypeptides, or can be capable of producing such proteins only after being transformed with at least one polynucleotide of the invention. In an embodiment, a recombinant cell of the invention has a enhanced capacity to synthesize a long chain polyunsaturated fatty acid. As used herein, the term "cell with an enhanced capacity to synthesize a long chain polyunsaturated fatty acid" is a relative term where the recombinant cell of the invention is compared to the host cell lacking the polynucleotide(s) of the invention, with the recombinant cell producing more long chain polyunsaturated fatty acids, or a greater concentration of LC-PUFA such as DHA (relative to other fatty acids), than the native cell. The cell with an enhanced capacity to synthesize another product, such as for example another fatty acid, a lipid, a carbohydrate such as starch, an RNA molecule, a polypeptide, a pharmaceutical or other product has a corresponding meaning.

Host cells of the present invention can be any cell capable of producing at least one protein described herein, and include bacterial, fungal (including yeast), parasite, arthropod, animal and plant cells. The cells may be prokaryotic or eukaryotic. Preferred host cells are yeast and plant cells. In a preferred embodiment, the plant cell is a seed cell, in particular a cell in a cotyledon or endosperm of a seed. In one embodiment, the cell is an animal cell or an algal cell. The animal cell may be of any type of animal such as, for example, a non-human animal cell, a non-human vertebrate cell, a non-human mammalian cell, or cells of aquatic animals such as, fish or crustacea, invertebrates, insects, etc. The cells may be of an organism suitable for a fermentation process. As used herein, the term the "fermentation process" refers to any fermentation process or any process comprising a fermentation step. Examples of fermenting microorganisms include fungal organisms, such as yeast. As used herein, "yeast" includes *Saccharomyces* spp., *Saccharomyces cerevisiae*, *Saccharomyces carlbergensis*, *Candida* spp., *Kluveromyces* spp. *Pichia* spp., *Hansenula* spp., *Trichoderma* spp., *Lipomyces starkey*, and *Yarrowia lipolytica*. Preferred yeast include strains of the *Saccharomyces* spp., and in particular, *Saccharomyces cerevisiae*.

Transgenic Plants

The invention also provides a plant comprising a cell of the invention, such as a transgenic plant comprising one or more polynucleotides of the invention. The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. The term "plant part" refers to all plant parts that comprise the plant DNA, including vegetative structures such as, for example, leaves or stems, roots, floral organs or structures, pollen, seed, seed parts such as an embryo, endosperm, scutellum or seed coat, plant tissue such as, for example, vascular tissue, cells and progeny of the same, as long as the plant part synthesizes lipid according to the invention.

A "transgenic plant", "genetically modified plant" or variations thereof refers to a plant that contains a gene construct ("transgene") not found in a wild-type plant of the same species, variety or cultivar. Transgenic plants as defined in the context of the present invention include plants and their progeny which have been genetically modified using recombinant techniques to cause production of the lipid or at least one polypeptide defined herein in the desired plant or plant organ. Transgenic plant cells and transgenic plant parts have corresponding meanings. A "transgene" as referred to herein has the normal meaning in the art of biotechnology and includes a genetic sequence which has been produced or altered by recombinant DNA or RNA technology and which has been introduced into a cell of the invention, preferably a plant cell. The transgene may include genetic sequences derived from a plant cell which may be of the same species, variety or cultivar as the plant cell into which the transgene is introduced or of a different species, variety or cultivar, or from a cell other than a plant cell. Typically, the transgene has been introduced into the cell, such as a plant, by human manipulation such as, for example, by transformation but any method can be used as one of skill in the art recognizes.

The terms "seed" and "grain" are used interchangeably herein. "Grain" refers to mature grain such as harvested grain or grain which is still on a plant but ready for harvesting, but can also refer to grain after imbibition or germination, according to the context. Mature grain or seed commonly has a moisture content of less than about 18-20%. "Developing seed" as used herein refers to a seed prior to maturity, typically found in the reproductive structures of the plant after fertilisation or anthesis, but can also refer to such seeds prior to maturity which are isolated from a plant.

As used herein, the term "obtaining a plant part" or "obtaining a seed" refers to any means of obtaining a plant part or seed, respectively, including harvesting of the plant parts or seed from plants in the field or in containment such as a greenhouse or growth chamber, or by purchase or receipt from a supplier of the plant parts or seed. The seed may be suitable for planting i.e. able to germinate and produce progeny plants, or alternatively has been processed in such a way that it is no longer able to germinate, e.g. cracked, polished or milled seed which is useful for food or feed applications, or for extraction of lipid of the invention.

As used herein, the term "plant storage organ" refers to a part of a plant specialized to storage energy in the form of, for example, proteins, carbohydrates, fatty acids and/or oils. Examples of plant storage organs are seed, fruit, tuberous roots, and tubers. A preferred plant storage organ of the invention is seed.

As used herein, the term "phenotypically normal" refers to a genetically modified plant or plant organ, particularly a storage organ such as a seed, tuber or fruit of the invention not having a significantly reduced ability to grow and reproduce when compared to an unmodified plant or plant organ. In an embodiment, the genetically modified plant or plant organ which is phenotypically normal comprises an exogenous polynucleotide encoding a silencing suppressor operably linked to a plant storage organ specific promoter and has an ability to grow or reproduce which is essentially the same as an isogenic plant or organ not comprising said polynucleotide. Preferably, the biomass, growth rate, germination rate, storage organ size, seed size and/or the number of viable seeds produced is not less than 90% of that of a plant lacking said exogenous polynucleotide when grown under identical conditions. This term does not encompass features of the plant which may be different to the wild-type plant but which do not effect the usefulness of the plant for commercial purposes such as, for example, a ballerina phenotype of seedling leaves.

Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. The plants may be vegetables or ornamental plants. The plants of the invention may be: corn (*Zea mays*), canola (*Brassica napus, Brassica rapa* ssp.), mustard (*Brassica juncea*), flax (*Linum usitatissimum*), alfalfa (*Medicago sativa*), rice (*Oryza sativa*), rye (*Secale cerale*), sorghum (*Sorghum bicolour, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citrus tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, or barley.

In a preferred embodiment, the plant is an angiosperm.

In an embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, sorghum, flax (linseed) or sugar beet. Furthermore, the oilseed plant may be other *Brassicas*, cotton, peanut, poppy, mustard, castor bean, sesame, safflower, or nut producing plants. The plant may produce high levels of oil in its fruit, such as olive, oil palm or coconut. Horticultural plants to which the present invention may be applied are lettuce, endive, or vegetable *brassicas* including cabbage, broccoli, or cauliflower. The present invention may be applied in tobacco, cucurbits, carrot, strawberry, tomato, or pepper.

In a further preferred embodiment, the non-transgenic plant used to produce a transgenic plant of the invention produces oil, especially in the seed, which has i) less than 20%, less than 10% or less than 5% 18:2 fatty acids and/or ii) less than 10% or less than 5% 18:3 fatty acids.

In a preferred embodiment, the transgenic plant is homozygous for each and every gene that has been introduced (transgene) so that its progeny do not segregate for the desired phenotype. The transgenic plant may also be heterozygous for the introduced transgene(s), preferably uniformly heterozygous for the transgene, such as for example in F1 progeny which have been grown from hybrid seed. Such plants may provide advantages such as hybrid vigour, well known in the art.

Where relevant, the transgenic plants may also comprise additional transgenes encoding enzymes involved in the production of LC-PUFAs such as, but not limited to, a Δ6-desaturase, a Δ9-elongase, a Δ8-desaturase, a Δ6-elongase, a Δ5-desaturase, an ω3-desaturase, a Δ4-desaturase, a Δ5-elongase, diacylglycerol acyltransferase, LPAAT, a Δ17-desaturase, a Δ15-desaturase and/or a Δ12 desaturase. Examples of such enzymes with one of more of these activities are known in the art and include those described herein. In specific examples, the transgenic plant at least comprises exogenous polynucleotides encoding;

a) a Δ4-desaturase, a Δ5-desaturase, a Δ6-desaturase, a Δ5-elongase and a Δ6-elongase, b) a Δ4-desaturase, a Δ5-desaturase, a Δ8-desaturase, a Δ5-elongase and a Δ9-elongase, c) a Δ4-desaturase, a Δ5-desaturase, a Δ6-desaturase, a Δ5-elongase, a Δ6-elongase, and a Δ15-desaturase, d) a Δ4-desaturase, a Δ5-desaturase, a Δ8-desaturase, a Δ5-elongase, a Δ9-elongase, and a Δ15-desaturase, e) a Δ4-desaturase, a Δ5-desaturase, a Δ6-desaturase, a Δ5-elongase, a Δ6-elongase, and a Δ17-desaturase, or f) a Δ4-desaturase, a Δ5-desaturase, a Δ8-desaturase, a Δ5-elongase, a Δ9-elongase, and a Δ17-desaturase.

In an embodiment, the exogenous polynucleotides encode set of polypeptides which are a *Pythium irregulare* Δ6-desaturase, a *Thraustochytrid* Δ5-desaturase or an *Emiliana huxleyi* Δ5-desaturase, a *Physcomitrella patens* Δ6-elongase, a *Thraustochytrid* Δ5-elongase or an *Ostreoccus tauri* Δ5-elongase, a *Phytophthora infestans* ω3-desaturase or a *Pythium irregulare* ω3-desaturase, and a *Thraustochytrid* Δ4-desaturase.

In an embodiment, plants of the invention are grown in the field, preferably as a population of at least 1,000 or 1,000,000 plants that are essentially the same, or in an area of at least 1 hectare. Planting densities differ according to the plant species, plant variety, climate, soil conditions, fertiliser rates and other factors as known in the art. For example, canola is typically grown at a planting density of 1.2-1.5 million plants per hectare. Plants are harvested as is known in the art, which may comprise swathing, windrowing and/or reaping of plants, followed by threshing and/or winnowing of the plant material to separate the seed from the remainder of the plant parts often in the form of chaff. Alternatively, seed may be harvested from plants in the field in a single process, namely combining.

Transformation of Plants

Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

As used herein, the terms "stably transforming", "stably transformed" and variations thereof refer to the integration of the exogenous nucleic acid molecules into the genome of the cell such that they are transferred to progeny cells during cell division without the need for positively selecting for their presence. Stable transformants, or progeny thereof, can be selected by any means known in the art such as Southern blots on chromosomal DNA or in situ hybridization of genomic DNA.

*Agrobacterium*-mediated transfer is a widely applicable system for introducing genes into plant cells because DNA can be introduced into cells in whole plant tissues or plant organs or explants in tissue culture, for either transient expression or for stable integration of the DNA in the plant cell genome. The use of *Agrobacterium*-mediated plant integrating vectors to introduce DNA into plant cells is well known in the art (see, for example, U.S. Pat. Nos. 5,177,010, 5,104,310, 5,004,863 or 5,159,135) including floral dipping methods using *Agrobacterium* or other bacteria that can transfer DNA into plant cells. The region of DNA to be transferred is defined by the border sequences, and the intervening DNA (T-DNA) is usually inserted into the plant genome. Further, the integration of the T-DNA is a relatively precise process resulting in few rearrangements. In those plant varieties where *Agrobacterium*-mediated transformation is efficient, it is the method of choice because of the facile and defined nature of the gene transfer. Preferred *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO99/05265).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

A transgenic plant formed using *Agrobacterium* or other transformation methods typically contains a single genetic locus on one chromosome. Such transgenic plants can be referred to as being hemizygous for the added gene(s). More preferred is a transgenic plant that is homozygous for the added gene(s); i.e., a transgenic plant that contains two added genes, one gene at the same locus on each chromosome of a chromosome pair. A homozygous transgenic plant can be obtained by self-fertilising a hemizygous transgenic plant, germinating some of the seed produced and analyzing the resulting plants for the gene of interest.

It is also to be understood that two different transgenic plants that contain two independently segregating exogenous genes or loci can also be crossed (mated) to produce offspring that contain both sets of genes or loci. Selfing of appropriate F1 progeny can produce plants that are homozygous for both exogenous genes or loci. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Enhancing Exogenous RNA Levels and Stabilized Expression

Silencing Suppressors

In an embodiment, a cell, plant or plant part of the invention comprises an exogenous polynucleotide encoding a silencing suppressor protein.

Post-transcriptional gene silencing (PTGS) is a nucleotide sequence-specific defense mechanism that can target both cellular and viral mRNAs for degradation PTGS occurs in plants or fungi stably or transiently transformed with foreign (heterologous) or endogenous DNA and results in the reduced accumulation of RNA molecules with sequence similarity to the introduced nucleic acid.

It has widely been considered that co-expression of a silencing suppressor with a transgene of interest will increase the levels of RNA present in the cell transcribed from the transgene. Whilst this has proven true for cells in vitro, significant side-effects have been observed in many whole plant co-expression studies. More specifically, as described in Mallory et al. (2002), Chapman et al. (2004), Chen et al. (2004), Dunoyer et al. (2004), Zhang et al. (2006), Lewsey et al. (2007) and Meng et al. (2008) plants expressing silencing suppressors, generally under constitutive promoters, are often phenotypically abnormal to the extent that they are not useful for commercial production.

Recently, it has been found that RNA molecule levels can be increased, and/or RNA molecule levels stabilized over numerous generations, by limiting the expression of the silencing suppressor to a seed of a plant or part thereof (WO2010/057246). As used herein, a "silencing suppressor protein" or SSP is any polypeptide that can be expressed in a plant cell that enhances the level of expression product from a different transgene in the plant cell, particularly over repeated generations from the initially transformed plant. In an embodiment, the SSP is a viral silencing suppressor or mutant thereof. A large number of viral silencing suppressors are known in the art and include, but are not limited to P19, V2, P38, Pe-Po and RPV-P0. In an embodiment, the viral silencing suppressor comprises amino acids having a sequence as provided in any one of SEQ ID NOs 53 to 57, a biologically active fragment thereof, or an amino acid sequence which is at least 50% identical to any one or more of SEQ ID NOs 53 to 57 and which has activity as a silencing suppressor.

As used herein, the terms "stabilising expression", "stably expressed", "stabilised expression" and variations thereof refer to level of the RNA molecule being essentially the same or higher in progeny plants over repeated generations, for example at least three, at least five or at least 10 generations, when compared to isogenic plants lacking the exogenous polynucleotide encoding the silencing suppressor. However, this term(s) does not exclude the possibility that over repeated generations there is some loss of levels of the RNA molecule when compared to a previous generation, for example not less than a 10% loss per generation.

The suppressor can be selected from any source e.g. plant, viral, mammal etc. See WO2010/057246 for a list of viruses from which the suppressor can be obtained and the protein (eg B2, P14 etc) or coding region designation for the suppressor from each particular virus. Multiple copies of a suppressor may be used. Different suppressors may be used together (e.g., in tandem).

RNA Molecules

Essentially any RNA molecule which is desirable to be expressed in a plant seed can be co-expressed with the silencing suppressor. The encoded polypeptides may be involved in metabolism of oil, starch, carbohydrates, nutrients, etc., or may be responsible for the synthesis of proteins, peptides, fatty acids, lipids, waxes, oils, starches, sugars, carbohydrates, flavors, odors, toxins, carotenoids. hormones, polymers, flavonoids. storage proteins, phenolic acids, alkaloids, lignins, tannins, celluloses, glycoproteins, glycolipids, etc, preferably the biosynthesis or assembly of TAG.

In a particular example, the plants produced increased levels of enzymes for oil production in plants such as Brassicas, for example canola or sunflower, safflower, flax, cotton, soya bean, *Camelina* or maize.

Levels of LC-PUFA Produced

The levels of the LC-PUFA or combination of LC-PUFAs that are produced in the recombinant cell or plant part such as seed are of importance. The levels may be expressed as a composition (in percent) of the total fatty acid that is a particular LC-PUFA or group of related LC-PUFA, for example the ω3 LC-PUFA or the ω6 LC-PUFA, or the VLC-PUFA, or other which may be determined by methods known in the art. The level may also be expressed as a LC-PUFA content, such as for example the percentage of LC-PUFA in the dry weight of material comprising the recombinant cells, for example the percentage of the weight of seed that is LC-PUFA. It will be appreciated that the LC-PUFA that is produced in an oilseed may be considerably higher in terms of LC-PUFA content than in a vegetable or a grain that is not grown for oil production, yet both may have similar LC-PUFA compositions, and both may be used as sources of LC-PUFA for human or animal consumption.

The levels of LC-PUFA may be determined by any of the methods known in the art. In a preferred method, total lipid is extracted from the cells, tissues or organisms and the fatty acid converted to methyl esters before analysis by gas chromatography (GC). Such techniques are described in Example 1. The peak position in the chromatogram may be used to identify each particular fatty acid, and the area under each peak integrated to determine the amount. As used herein, unless stated to the contrary, the percentage of particular fatty acid in a sample is determined as the area under the peak for that fatty acid as a percentage of the total area for fatty acids in the chromatogram. This corresponds essentially to a weight percentage (w/w). The identity of fatty acids may be confirmed by GC-MS. Total lipid may be separated by techniques known in the art to purify fractions such as the TAG fraction. For example, thin-layer chromatography (TLC) may be performed at an analytical scale to separate TAG from other lipid fractions such as DAG, acyl-CoAs or phospholipid in order to determine the fatty acid composition specifically of TAG.

In one embodiment, the sum total of ARA, EPA, DPA and DHA in the fatty acids in the extracted lipid is between about 7% and about 25% of the total fatty acids in the cell. In a further embodiment, the total fatty acid in the cell has less than 1% C20:1. In preferred embodiments, the extractable TAG in the cell comprises the fatty acids at the levels referred to herein. Each possible combination of the features defining the lipid as described herein is also encompassed.

The level of production of LC-PUFA in the recombinant cell, plant or plant part such as seed may also be expressed as a conversion percentage of a specific substrate fatty acid to one or more product fatty acids, which is also referred to herein as a "conversion efficiency" or "enzymatic efficiency". This parameter is based on the fatty acid composition in the lipid extracted from the cell, plant, plant part or seed, i.e., the amount of the LC-PUFA formed (including other LC-PUFA derived therefrom) as a percentage of one or more substrate fatty acids (including all other fatty acids derived therefrom). The general formula for a conversion percentage is: 100×(the sum of percentages of the product LC-PUFA and all products derived therefrom)/(the sum of the percentages of the substrate fatty acid and all products derived therefrom). With regard to DHA, for example, this may be expressed as the ratio of the level of DHA (as a percentage in the total fatty acid content in the lipid) to the level of a substrate fatty acid (e.g. OA, LA, ALA, SDA, ETA or EPA) and all products other than DHA derived from the substrate. The conversion percentage or efficiency of conversion can be expressed for a single enzymatic step in a pathway, or for part or the whole of a pathway.

Specific conversion efficiencies are calculated herein according to the formulae:

$OA$ to $DHA$=100×(% $DHA$)/(sum % for $OA, LA, GLA, DGLA, ARA, EDA, ALA, SDA, ETrA, ETA, EPA, DPA$ and $DHA$).     1

$LA$ to $DHA$=100×(% $DHA$)/(sum % for $LA, GLA, DGLA, ARA, EDA ALA, SDA, ETrA, ETA, EPA, DPA$ and $DHA$).     2

$ALA$ to $DHA$=100×(% $DHA$)/(sum % for $ALA, SDA, ETrA, ETA, EPA, DPA$ and $DHA$).     3

$EPA$ to $DHA$=100×(% $DHA$)/(sum % for $EPA, DPA$ and $DHA$).     4

$DPA$ to $DHA$(Δ4-desaturase efficiency)=100×(% $DHA$)/(sum % for $DPA$ and $DHA$).     5

Δ12-desaturase efficiency=100×(sum % for $LA, GLA, DGLA, ARA, EDA, ALA, SDA, ETrA, ETA, EPA, DPA$ and $DHA$)/(sum % for $OA, LA, GLA, DGLA, ARA, EDA, ALA, SDA, ETrA, ETA, EPA, DPA$ and $DHA$).     6

ω3-desaturase efficiency=100×(sum % for $ALA, SDA, ETrA, ETA, EPA, DPA$ and $DHA$)/(sum % for $LA, GLA, DGLA, ARA, EDA, ALA, SDA, ETrA, ETA, EPA, DPA$ and $DHA$).     7

$OA$ to $ALA$=100×(sum % for $ALA, SDA, ETrA, ETA, EPA, DPA$ and $DHA$)/(sum % for $OA, LA, GLA, DGLA, ARA, EDA, ALA, SDA, ETrA, ETA, EPA, DPA$ and $DHA$).     8

Δ6-desaturase efficiency(on ω3 substrate $ALA$)=100× (sum % for $SDA, ETA, EPA, DPA$ and $DHA$)/(% $ALA, SDA, ETrA, ETA, EPA, DPA$ and $DHA$).     9

Δ6-elongase efficiency(on ω3 substrate $SDA$)=100× (sum % for $ETA, EPA, DPA$ and $DHA$)/(sum % for $SDA, ETA, EPA, DPA$ and $DHA$).     10

Δ5-desaturase efficiency(on ω3 substrate $ETA$)=100× (sum % for $EPA, DPA$ and $DHA$)/(sum % for $ETA, EPA, DPA$ and $DHA$).     11

Δ5-elongase efficiency(on ω3 substrate $EPA$)=100× (sum % for $DPA$ and $DHA$)/(sum % for $EPA, DPA$ and $DHA$).     12

The fatty acid composition of the lipid, preferably seedoil, of the invention, is also characterised by the ratio of ω6 fatty acids:ω3 fatty acids in the total fatty acid content, for either total ω6 fatty acids:total ω3 fatty acids or for new ω6 fatty acids:new ω3 fatty acids. The terms total ω6 fatty acids, total ω3 fatty acids, new ω6 fatty acids and new ω3 fatty acids have the meanings as defined herein. The ratios are calculated from the fatty acid composition in the lipid extracted from the cell, plant, plant part or seed, in the manner as exemplified herein. It is desirable to have a greater level of ω3 than ω6 fatty acids in the lipid, and therefore an ω6:ω3 ratio of less than 1.0 is preferred. A ratio of 0.0 indicates a complete absence of the defined ω6 fatty acids; a ratio of 0.03 was achieved as described in Example 6. Such low ratios can be achieved through the combined use of a Δ6-desaturase which has an ω3 substrate preference together with an ω3-desaturase, particularly a fungal ω3-desaturase such as the *Pichia pastoris* ω3-desaturase as exemplified herein.

The yield of LC-PUFA per weight of seed may also be calculated based on the total oil content in the seed and the % DHA in the oil. For example, if the oil content of canola seed is about 40% (w/w) and about 12% of the total fatty acid content of the oil is DHA, the DHA content of the seed is about 4.8% or about 48 mg per gram of seed. As described in Example 2, the DHA content of *Arabidopsis* seed having about 9% DHA, which has a lower oil content than canola, was about 25 mg/g seed. At a DHA content of about 7%, canola seed or *Camelina sativa* seed has a DHA content of about 28 mg per gram of seed. The present invention therefore provides *Brassica napus*, *B. juncea* and *Camelina sativa* plants, and seed obtained therefrom, comprising at least about 28 mg DHA per gram seed. The seed has a moisture content as is standard for harvested mature seed after drying down (4-15% moisture). The invention also provides a process for obtaining oil, comprising obtaining the seed and extracting the oil from the seed, and uses of the oil and methods of obtaining the seed comprising harvesting the seeds from the plants according to the invention.

The amount of DHA produced per hectare can also be calculated if the seed yield per hectare is known or can be estimated. For example, canola in Australia typically yields about 2.5 tonnes seed per hectare, which at 40% oil content yields about 1000 kg of oil. At 12% DHA in the total oil, this provides about 120 kg of DHA per hectare. If the oil content is reduced by 50%, this still provides about 60 kg DHA/ha.

Evidence to date suggests that some desaturases expressed heterologously in yeast or plants have relatively low activity in combination with some elongases. This may be alleviated by providing a desaturase with the capacity of to use an acyl-CoA form of the fatty acid as a substrate in LC-PUFA synthesis, and this is thought to be advantageous in recombinant cells particularly in plant cells. A particularly advantageous combination for efficient DHA synthesis is a fungal ω3-desaturase, for example such as the *Pichia pastoris* ω3-desaturase (SEQ ID NO: 12), with a Δ6-desaturase which has a preference for ω3 acyl substrates such as, for example, the *Micromonas pusilla* Δ6-desaturase (SEQ ID NO: 13), or variants thereof which have at least 95% amino acid sequence identity.

As used herein, the term "essentially free" means that the composition (for example lipid or oil) comprises little (for example, less than about 0.5%, less than about 0.25%, less than about 0.1%, or less than about 0.01%) or none of the defined component. In an embodiment, "essentially free" means that the component is undetectable using a routine analytical technique, for example a specific fatty acid (such as ω6-docosapentaenoic acid) cannot be detected using gas chromatography as outlined in Example 1.

Production of Oils

Techniques that are routinely practiced in the art can be used to extract, process, and analyze the oils produced by cells, plants, seeds, etc of the instant invention. Typically, plant seeds are cooked, pressed, and extracted to produce crude oil, which is then degummed, refined, bleached, and deodorized. Generally, techniques for crushing seed are known in the art. For example, oilseeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

In an embodiment, the majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures. As used herein, the term "purified" when used in connection with lipid or oil of the invention typically means that that the extracted lipid or oil has been subjected to one or more processing steps of increase the purity of the lipid/oil component. For example, a purification step may comprise one or more or all of the group consisting of: degumming, deodorising, decolourising, drying and/or fractionating the extracted oil. However, as used herein, the term "purified" does not include a transesterification process or other process which alters the fatty acid composition of the lipid or oil of the invention so as to increase the DHA content as a percentage of the total fatty acid content. Expressed in other words, the fatty acid composition of the purified lipid or oil is essentially the same as that of the unpurified lipid or oil.

Degumming

Degumming is an early step in the refining of oils and its primary purpose is the removal of most of the phospholipids from the oil, which may be present as approximately 1-2% of the total extracted lipid. Addition of ~2% of water, typically containing phosphoric acid, at 70-80° C. to the crude oil results in the separation of most of the phospholipids accompanied by trace metals and pigments. The insoluble material that is removed is mainly a mixture of phospholipids and triacylglycerols and is also known as lecithin. Degumming can be performed by addition of concentrated phosphoric acid to the crude seedoil to convert non-hydratable phosphatides to a hydratable form, and to chelate minor metals that are present. Gum is separated from the seedoil by centrifugation.

Alkali Refining

Alkali refining is one of the refining processes for treating crude oil, sometimes also referred to as neutralization. It usually follows degumming and precedes bleaching. Following degumming, the seedoil can treated by the addition of a sufficient amount of an alkali solution to titrate all of the fatty acids and phosphoric acids, and removing the soaps thus formed. Suitable alkaline materials include sodium hydroxide, potassium hydroxide, sodium carbonate, lithium hydroxide, calcium hydroxide, calcium carbonate and ammonium hydroxide. This process is typically carried out at room temperature and removes the free fatty acid fraction. Soap is removed by centrifugation or by extraction into a solvent for the soap, and the neutralised oil is washed with water. If required, any excess alkali in the oil may be neutralized with a suitable acid such as hydrochloric acid or sulphuric acid.

Bleaching

Bleaching is a refining process in which oils are heated at 90-120° C. for 10-30 minutes in the presence of a bleaching earth (0.2-2.0%) and in the absence of oxygen by operating with nitrogen or steam or in a vacuum. This step in oil processing is designed to remove unwanted pigments (carotenoids, chlorophyll, gossypol etc), and the process also removes oxidation products, trace metals, sulphur compounds and traces of soap.

Deodorization

Deodorization is a treatment of oils and fats at a high temperature (200-260° C.) and low pressure (0.1-1 mm Hg). This is typically achieved by introducing steam into the seedoil at a rate of about 0.1 ml/minute/100 ml of seedoil. After about 30 minutes of sparging, the seedoil is allowed to cool under vacuum. The seedoil is typically transferred to a glass container and flushed with argon before being stored under refrigeration. This treatment improves the colour of the seedoil and removes a majority of the volatile substances or odorous compounds including any remaining free fatty acids, monoacylglycerols and oxidation products.

Winterisation

Winterization is a process sometimes used in commercial production of oils for the separation of oils and fats into solid (stearin) and liquid (olein) fractions by crystallization at sub-ambient temperatures. It was applied originally to cottonseed oil to produce a solid-free product. It is typically used to decrease the saturated fatty acid content of oils.

Transesterification

Transesterification is a process that exchanges the fatty acids within and between TAGs or transfers the fatty acids to another alcohol to form an ester, initially by releasing fatty acids from the TAGs either as free fatty acids or as fatty acid esters, usually fatty acid methyl esters or ethyl esters. When combined with a fractionation process, transesterification can be used to modify the fatty acid composition of lipids (Marangoni et al., 1995). Transesterification can use either chemical (e.g. strong acid or base catalysed) or enzymatic means, the latter using lipases which may be position-specific (sn-1/3 or sn-2 specific) for the fatty acid on the TAG, or having a preference for some fatty acids over others (Speranza et al, 2012). The fatty acid fractionation to increase the concentration of LC-PUFA in an oil can be achieved by any of the methods known in the art, such as, for example, freezing crystallization, complex formation using urea, molecular distillation, supercritical fluid extraction and silver ion complexing. Complex formation with urea is a preferred method for its simplicity and efficiency in reducing the level of saturated and monounsaturated fatty acids in the oil (Gamez et al., 2003). Initially, the TAGs of the oil are split into their constituent fatty acids, often in the form of fatty acid esters, by hydrolysis under either acid or base catalysed reaction conditions, whereby one mol of TAG is reacted with at least 3 mol of alcohol (e.g. ethanol for ethyl esters or methanol for methyl esters) with excess alcohol used to enable separation of the formed alkyl esters and the glycerol that is also formed, or by lipases. These free fatty acids or fatty acid esters, which are usually unaltered in fatty acid composition by the treatment, may then be mixed with an ethanolic solution of urea for complex formation. The saturated and monounsaturated fatty acids easily complex with urea and crystallize out on cooling and may subsequently be removed by filtration. The non-urea complexed fraction is thereby enriched with LC-PUFA.

Feedstuffs

The present invention includes compositions which can be used as feedstuffs. For purposes of the present invention, "feedstuffs" include any food or preparation for human or animal consumption which when taken into the body (a) serve to nourish or build up tissues or supply energy; and/or (b) maintain, restore or support adequate nutritional status or metabolic function. Feedstuffs of the invention include nutritional compositions for babies and/or young children such as, for example, infant formula, and seedmeal of the invention.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term "carrier" is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, protein, carbohydrate, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borage oil, fungal oil, black current oil, soy oil, and mono- and diglycerides. Examples of such carbohydrates include (but are not limited to): glucose, edible lactose, and hydrolyzed starch. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

The genus *Saccharomyces* spp is used in both brewing of beer and wine making and also as an agent in baking, particularly bread. Other yeasts such as oleaginous yeast including, for example, *Yarrowia* spp, are also useful in LC-PUFA production. Yeasts may be used as an additive in animal feed, such as in aquaculture. It will be apparent that genetically engineered yeast strains can be provided which are adapted to synthesise LC-PUFA as described herein. These yeast strains, or LC-PUFA produced therein, can then be used in food stuffs and in wine and beer making to provide products which have enhanced fatty acid content.

Additionally, fatty acids produced in accordance with the present invention or host cells transformed to contain and express the subject genes may also be used as animal food supplements to alter an animal's tissue, egg or milk fatty acid composition to one more desirable for human or animal consumption. Examples of such animals include sheep, cattle, horses, poultry such as chickens and the like.

Furthermore, feedstuffs of the invention can be used in aquaculture to increase the levels of fatty acids in fish or crustaceans such as, for example, prawns for human or animal consumption. Preferred fish are salmon.

Preferred feedstuffs of the invention are the plants, seed and other plant parts such as leaves and stems which may be used directly as food or feed for humans or other animals. For example, animals may graze directly on such plants grown in the field or be fed more measured amounts in controlled feeding. The invention includes the use of such plants and plant parts as feed for increasing the LC-PUFA levels in humans and other animals.

Compositions

The present invention also encompasses compositions, particularly pharmaceutical compositions, comprising one or more of the fatty acids and/or resulting oils produced using the methods of the invention.

A pharmaceutical composition may comprise one or more of the fatty acids and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, fatty acids produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant fatty acid(s).

For intravenous administration, the fatty acids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a fatty acid produced according to the subject invention may be used as the sole "active" ingredient in a cosmetic composition.

EXAMPLES

Example 1

Materials and Methods

Expression of Genes in Plant Cells in a Transient Expression System

Exogenous genetic constructs were expressed in plant cells in a transient expression system essentially as described by Voinnet et al. (2003) and Wood et al. (2009). Plasmids containing a coding region to be expressed from a strong constitutive promoter such as the CaMV 35S promoter were introduced into *Agrobacterium tumefaciens* strain AGL1. A chimeric gene 35S:p19 for expression of the p19 viral silencing suppressor was separately introduced into AGL1, as described in WO 2010/057246. The recombinant *Agrobacterium* cells were grown at 28° C. in LB broth supplemented with 50 mg/L kanamycin and 50 mg/L rifampicin to stationary phase. The bacteria were then pelleted by centrifugation at 5000 g for 15 min at room temperature before being resuspended to OD600=1.0 in an infiltration buffer containing 10 mM MES pH 5.7, 10 mM $MgCl_2$ and 100 µM acetosyringone. The cells were then incubated at 28° C. with shaking for 3 hours before equal volumes of *Agrobacterium* cultures containing 35S:p19 and the test chimeric construct(s) of interest were mixed prior to infiltration into leaf tissue. The plants were typically grown for a further five days after infiltration before leaf discs were taken and freeze-dried for GC analysis of the fatty acids.

Fatty acid methyl esters (FAME) of total leaf lipids in freeze-dried samples were produced by incubating the samples in methanol/HCl/dichloromethane (10/1/1 v/v) solution for 2 hours at 80° C. together with a known amount of hexadecanoic acid as an internal standard. FAMEs were extracted in hexane/DCM, concentrated to a small volume in hexane and injected into a GC. The amount of individual and total fatty acids present in the lipid fractions were quantified on the basis of the known amount of internal standard.

Gas Chromatography (GC) Analysis of Fatty Acids

FAME were analysed by gas chromatography using an Agilent Technologies 7890A GC (Palo Alto, Calif., USA) equipped with a 30 m SGE-BPX70 column (70% cyanopropyl polysilphenylene-siloxane, 0.25 mm inner diameter, 0.25 mm film thickness), an FID, a split/splitless injector and an Agilent Technologies 7693 Series auto sampler and injector. Helium was used as the carrier gas. Samples were injected in split mode (50:1 ratio) at an oven temperature of 150° C. After injection, the oven temperature was held at 150° C. for 1 min then raised to 210° C. at 3° C. $min^{-1}$, again raised to 240° C. at 50° C. $min^{-1}$ and finally holding for 1.4 min at 240° C. Peaks were quantified with Agilent Technologies ChemStation software (Rev B.04.03 (16), Palo Alto, Calif., USA) based on the response of the known amount of the external standard GLC-411 (Nucheck) and C17:0-ME internal standard.

Liquid Chromatography-Mass Spectrometry (LC-MS) Analysis of Lipids

Total lipids were extracted from freeze-dried developing seeds, twelve days after flowering (daf), and mature seeds after adding a known amount of tri-C17:0-TAG as an internal quantitation standard. The extracted lipids were dissolved into 1 mL of 10 mM butylated hydroxytoluene in butanol:methanol (1:1 v/v) per 5 mg dry material and analysed using an Agilent 1200 series LC and 6410b electrospray ionisation triple quadrupole LC-MS. Lipids were chromatographically separated using an Ascentis Express RP-Amide column (50 min×2.1 mm, 2.7 µm, Supelco) operating a binary gradient with a flow rate of 0.2 mL/min. The mobile phases were: A. 10 mM ammonium formate in $H_2O$:methanol:tetrahydrofuran (50:20:30 v/v/v); B. 10 mM ammonium formate in $H_2O$:methanol:tetrahydrofuran (5:20:75, v/v/v). Multiple reaction monitoring (MRM) lists were based on the following major fatty acids: 16:0, 18:0, 18:1, 18:2, 18:3, 18:4, 20:1, 20:2, 20:3, 20:4, 20:5, 22:4, 22:5, 22:6 using a collision energy of 30 V and fragmentor of 60 V. Individual MRM TAG was identified based on ammoniated precursor ion and product ion from neutral loss of 22:6. TAG was quantified using a 10 µM tristearin external standard.

Determination of Seed Fatty Acid Profile and Oil Content

Where seed oil content was to be determined, seeds were dried in a desiccator for 24 h and approximately 4 mg of seed was transferred to a 2 ml glass vial containing Teflon-lined screw cap. 0.05 mg triheptadecanoin dissolved in 0.1 ml toluene was added to the vial as internal standard.

Seed FAME were prepared by adding 0.7 ml of 1N methanolic HCl (Supelco) to the vial containing seed material, vortexed briefly and incubated at 80° C. for 2 h. After cooling to room temperature, 0.3 ml of 0.9% NaCl (w/v) and 0.1 ml hexane was added to the vial and mixed well for 10 min in Heidolph Vibramax 110. The FAME was collected into 0.3 ml glass insert and analysed by GC with a flame ionization detector (FID) as mentioned earlier.

The peak area of individual FAME were first corrected on the basis of the peak area responses of known amount of the same FAMEs present in a commercial standard GLC-411 (NU-CHEK PREP, INC., USA). GLC-411 contains equal amounts of 31 fatty acids (% by wt), ranging from C8:0 to C22:6. In case of fatty acids, which were not present in the standard, the inventors took the peak area responses of the most similar FAME. For example, peak area response of FAMEs of 16:1d9 was used for 16:1d7 and FAME response of C22:6 was used for C22:5. The corrected areas were used to calculate the mass of each FAME in the sample by comparison to the internal standard mass. Oil is stored mainly in the form of TAG and its weight was calculated based on FAME weight. Total moles of glycerol was determined by calculating moles of each FAMES and dividing total moles of FAMEs by three. TAG was calculated as the sum of glycerol and fatty acyl moieties using a relation: % oil by weight=100× ((41×total mol FAME/3)+(total g FAME−(15×total mol FAME)))/g seed, where 41 and 15 are molecular weights of glycerol moiety and methyl group, respectively.

Analysis of the Sterol Content of Oil Samples

Samples of approximately 10 mg of oil together with an added aliquot of C24:0 monol as an internal standard were saponified using 4 mL 5% KOH in 80% MeOH and heating for 2 h at 80° C. in a Teflon-lined screw-capped glass tube. After the reaction mixture was cooled, 2 mL of Milli-Q water were added and the sterols were extracted into 2 mL of hexane:dichloromethane (4:1 v/v) by shaking and vortexing. The mixture was centrifuged and the sterol extract was removed and washed with 2 mL of Milli-Q water. The sterol extract was then removed after shaking and centrifugation. The extract was evaporated using a stream of nitrogen gas and the sterols silylated using 200 mL of BSTFA and heating for 2 h at 80° C.

For GC/GC-MS analysis of the sterols, sterol-OTMSi derivatives were dried under a stream of nitrogen gas on a heat block at 40° C. and then re-dissolved in chloroform or hexane immediately prior to GC/GC-MS analysis. The sterol-OTMS derivatives were analysed by gas chromatography (GC) using an Agilent Technologies 6890A GC (Palo Alto, Calif., USA) fitted with an Supelco Equity™-1 fused silica capillary column (15 m×0.1 mm i.d., 0.1 µm film thickness), an FID, a split/splitless injector and an Agilent Technologies 7683B Series auto sampler and injector. Helium was the carrier gas. Samples were injected in splitless mode at an oven temperature of 120° C. After injection, the oven temperature was raised to 270° C. at 10° C. min$^{-1}$ and finally to 300° C. at 5° C. min$^{-1}$. Peaks were quantified with Agilent Technologies ChemStation software (Palo Alto, Calif., USA). GC results are subject to an error of ±5% of individual component areas.

GC-mass spectrometric (GC-MS) analyses were performed on a Finnigan Thermoquest GCQ GC-MS and a Finnigan Thermo Electron Corporation GC-MS; both systems were fitted with an on-column injector and Thermoquest Xcalibur software (Austin, Tex., USA). Each GC was fitted with a capillary column of similar polarity to that described above. Individual components were identified using mass spectral data and by comparing retention time data with those obtained for authentic and laboratory standards. A full procedural blank analysis was performed concurrent to the sample batch.

RT-PCR Conditions

Reverse transcription-PCR (RT-PCR) amplification was typically carried out using the Superscript III One-Step RT-PCR system (Invitrogen) in a volume of 25 µL using 10 pmol of the forward primer and 30 µmol of the reverse primer, $MgSO_4$ to a final concentration of 2.5 mM, 400 ng of total RNA with buffer and nucleotide components according to the manufacturer's instructions. Typical temperature regimes were: 1 cycle of 45° C. for 30 minutes for the reverse transcription to occur; then 1 cycle of 94° C. for 2 minutes followed by 40 cycles of 94° C. for 30 seconds, 52° C. for 30 seconds, 70° C. for 1 minute; then 1 cycle of 72° C. for 2 minutes before cooling the reaction mixtures to 5° C.

Production of *B. napus* Somatic Embryos by Induction with 35S-LEC2

*B. napus* (cv. Oscar) seeds were sterilized using chlorine gas as described by (Attila Kereszt et al., 2007). Sterilized seeds were germinated on ½ strength MS media (Murashige and Skoog, 1962) with 0.8% agar adjusted to pH 5.8, and grown at 24° C. under fluorescent lighting (50 µE/m²s) with a 18/6 h (light/dark) photoperiod for 6-7 days. Cotyledonary petioles with 2-4 mm stalk length were isolated aseptically from these seedlings and used as explants. Cultures of the transformed *A. tumefaciens* strain AGL1, one harbouring a seed specific binary vector and a second with a 35S-LEC2 construct were inoculated from single colonies from fresh plates and grown in 10 mL of LB medium with appropriate antibiotics and grown overnight at 28° C. with agitation at 150 rpm. The bacterial cells were collected by centrifugation at 4000 rpm for 5 minutes, washed with MS media containing 2% sucrose and re-suspended in 10 mL of the same medium and grown with antibiotics for selection as appropriate for 4 hours after the addition of acetosyringone to 100 µM. Two hours before addition to the plant tissues, spermidine was added to a final concentration of 1.5 mM and the final density of the bacteria adjusted to OD 600 nm=0.4 with fresh medium. The two bacterial cultures, one carrying the seed specific construct and other carrying 35S-AtLEC2, were mixed in 1:1 to 1:1.5 ratios.

Freshly-isolated *B. napus* cotyledonary petioles were infected with 20 mL *A. tumefaciens* cultures for 6 minutes. The cotyledonary petioles were blotted on sterile filter paper to remove excess *A. tumefaciens* and then transferred to co-cultivation media (MS media with 1 mg/L TDZ, 0.1 mg/L NAA, 100 µM acetosyringone supplemented with L-cysteine (50 mg/L), ascorbic acid (15 mg/L) and MES (250 mg/l)). The plates were sealed with micro-pore tape and incubated in the dark at 24° C. for 48 hrs. The co-cultivated explants were transferred to pre-selection media (MS containing 1 mg/L TDZ, 0.1 mg/L NAA, 3 mg/L $AgNO_3$, 250 mg/L cefotaxime and 50 mg/L timentin) and cultured for 4-5 days at 24° C. with a 16 h/8 h photoperiod. The explants were then transferred to selection media (MS containing 1 mg/L TDZ, 0.1 mg/L NAA, 3 mg/L $AgNO_3$, 250 mg/L cefotaxime and 50 mg/L timentin) according to the selectable marker gene on the seed specific vector and cultured for 2-3 weeks at 24° C. with a 16 h/8 h photoperiod. Explants with green embryogenic callus were transferred to hormone free MS media (MS with 3 mg/L $AgNO_3$, 250 mg/L cefotaxime, 50 mg/L timentin and the selection agent) and cultured for another 2-3 weeks. Torpedo or cotyledonary stage embryos isolated from surviving explants on the selection medium were analysed for fatty acid composition in their total lipid using GC.

Example 2

Stable Expression of Transgenic DHA Pathways in Arabidopsis thaliana Seeds

Binary Vector Construction

The binary vectors pJP3416-GA7 and pJP3404 each contained seven heterologous fatty acid biosynthesis genes, encoding 5 desaturases and 2 elongases, and a plant selectable marker between the left and right border repeats of the T-DNA present in each vector (FIGS. 2 and 3). SEQ ID NO:1 provides the nucleotide sequence of the T-DNA region of pJP3416-GA7 from the right to left border sequences. Both genetic constructs contained plant codon-optimised genes encoding a *Lachancea kluyveri* Δ12-desaturase (comprising nucleotides 14143-16648 of SEQ ID NO:1), a *Pichia pastoris* ω3-desaturase (comprising nucleotides 7654-10156 of SEQ ID NO:1), a *Micromonas pusilla* Δ6-desaturase (comprising nucleotides 226-2309 of SEQ ID NO: 1), *Pavlova salina* Δ5- and Δ4-desaturases (comprising nucleotides 4524-6485 and 10157-14142 of SEQ ID NO:1, respectively) and *Pyramimonas cordata* Δ6- and Δ5-elongases (comprising nucleotides 2310-4523 and 17825-19967 of SEQ ID NO:1, respectively). The specific regions of the T-DNA (Orientation: right to left border sequences) region of the binary vector pJP3416-GA7 with respect to SEQ ID NO:1 are as follows:

Nucleotides 1-163: Right border; 480-226, *Agrobacterium tumefaciens* nopaline synthase terminator (TER_NOS); 1883-489, *Micromonas pusilla* Δ6-desaturase; 2309-1952, *Brassica napus* truncated napin promoter (PRO_FP1); 2310-3243, *Arabidopsis thaliana* FAE1 promoter (PRO_FAE1); 3312-4181, *Pyramimonas cordata* Δ6-elongase; 4190-4523, *Glycine max* lectin terminator (TER_Lectin); 4524-4881, PRO_FP1; 4950-6230: *Pavlova salina* Δ5-desaturase; 6231-6485: TER_NOS; 7653-6486, *Nicotiana tabacum* Rb7 matrix attachment region (MAR); 8387-7654, *Linum* usitatissimum conlinin1 terminator (TER_Cnl1); 9638-8388, *Pichia pastoris* ω3-desaturase; 10156-9707, *Linum usitatissimum* conlinin1 promoter (PRO_Cnl1); 10157-12189, *Linum usitatissimum* conlinin1 promoter; 12258-13604, *Pavlova salina* Δ4-desaturase; 13605-14142, *Linum usitatissimum* conlinin2 terminator; 14143-14592, PRO_Cnl1; 14661-15914, *Lachancea kluyveri* Δ12-desaturase; 15915-16648, TER_Cnl1; 17816-16649, MAR; 17825-18758, PRO_FAE1; 18827-19633, *Pyramimonas cordata* Δ5-elongase; 19634-19967, TER_Lectin; 19990-20527, Cauliflower mosaic virus 35S promoter with duplicated enhancer region; 20537-21088, *Streptomyces* viridochromogenes phosphinothricin-N-acetyltransferase; 21097-21349, TER_NOS; 21367-21527, Left border.

The seven coding regions in the constructs were each under the control of a seed specific promoter—three different promoters were used, namely the truncated *Brassica napus* napin promoter (pBnFP1), the *Arabidopsis thaliana* FAE1 promoter (pAtFAE1) and the *Linum usitatissimum* conlinin 1 promoter (pLuCnl1). The seven fatty acid biosynthesis genes together coded for an entire DHA synthesis pathway that was designed to convert 18:1$^{Δ9}$ (oleic acid) through to 22:6$^{Δ4,7,10,13,16,19}$ (DHA). Both binary vectors contained a BAR plant selectable marker coding region operably linked to a Cauliflower Mosaic Virus (CaMV) 35S promoter with duplicated enhancer region and *A. tumefaciens* nos3' polyadenylation region-transcription terminator. The plant selectable marker was situated adjacent to the left border of the T-DNA region, therefore distally located on the T-DNA with respect to the orientation of T-DNA transfer into the plant cells. This increased the likelihood that partial transfer of the T-DNA, which would be likely to not include the selectable marker gene, would not be selected. pJP3416-GA7 and pJP3404 each contained an RiA4 origin of replication from *Agrobacterium rhizogenes* (Hamilton, 1997).

pJP3416-GA7 was generated by synthesising the DNA region corresponding to nucleotides 226-19975 of SEQ ID NO:1 (GA7 region) and inserting this region into the recipient binary vector pJP3416 at the PspOMI site. Each fatty acid biosynthetic gene on GA7 included a Tobacco Mosaic Virus 5' untranslated region (5'UTR) sequence which was operably linked to each coding region, between the promoter and the translation initiation ATG, to maximise translation efficiency of the mRNAs produced from the genes. The GA7 construct also included two *Nicotiana tabacum* Rb7 matrix attachment region (MAR) sequences, as described by Hall et al. (1991). MAR sequences, sometimes termed nuclear attachment regions, are known to bind specifically to the nuclear matrix in vitro and may mediate binding of chromatin to the nuclear matrix in vivo. MARs are thought to function to reduce transgene silencing. In pJP3416-GA7 the MARs were also inserted and positioned within the T-DNA region in order to act as DNA spacers to insulate transgenic expression cassettes. The pJP3416 vector prior to insertion of the GA7 region contained only the plant selectable marker cassette between the borders.

The genetic construct pJP3404 was made by sequential restriction enzyme-based insertions in which gene cassettes were added to the binary vector, pJP3367, which comprised genes for production of SDA in seeds. This construct contained genes encoding the *L. kluvveri* Δ12-desaturase and *P. pastoris* ω3-desaturase, both expressed by the *B. napus* truncated napin promoter (FP1), and the *M. pusilla* Δ6-desaturase expressed by the *A. thaliana* FAE1 promoter (FIG. 4). First, the *A. thaliana* FAD2 intron was flanked by EcoRI sites and cloned into the pJP3367 MfeI site to generate pJP3395. A fragment containing the *P. cordata* Δ6- and Δ5-elongase cassettes driven by the FAE1 and FP1 promoters, respectively, was cloned into the KasI site of pJP3395 to generate pJP3398. pJP3399 was then generated by replacing the RK2 origin of replication in pJP3398 with a RiA4 origin of replication. The final binary vector, pJP3404, was generated by cloning a SbfI-flanked fragment containing the *P. salina* Δ5- and Δ4-desaturase cassettes driven by the FP1 and FAE1 promoters, respectively, into the SbfI site of pJP3399.

*A. Thaliana* Transformation and Analysis of Fatty Acid Composition

The chimeric vectors were introduced into *A. tumefaciens* strain AGL1 and cells from cultures of the transformed *Agrobacterium* used to treat *A. thaliana* (ecotypes Columbia and a fad2 mutant) plants using the floral dip method for transformation (Clough and Bent, 1998). After maturation, the $T_1$ seeds from the treated plants were harvested and plated onto MS plates containing PPT for selection of plants containing the BAR selectable marker gene. Surviving, healthy $T_1$ seedlings were transferred to soil. After growth of the plants to maturity and allowing for self-fertilisation, $T_2$ seeds from these plants were harvested and the fatty acid composition of their seed lipid analysed by GC analysis as described in Example 1.

The data for the DHA level in the seed lipids are shown in FIG. 5 (lanes labelled $T_2$) for 13 transformants using pJP3416-GA7 into the Columbia genetic background, and for six transformants using the Jad2 mutant. The pJP3416-GA7 construct resulted in the production of slightly higher levels of DHA, as a percentage of total fatty acid content, on average than the pJP3404 construct. Table 4 shows the fatty acid composition of total seed lipid from the $T_2$ lines with the highest DHA levels. The calculated conversion efficiencies for each enzymatic step in the production of DHA from oleic acid in the same seeds are shown in Table 5. Conversion efficiencies were calculated as (% products×100)/(% remaining substrate+% products), thereby expressed as a percentage.

The highest observed level of DHA produced in the pJP3416-GA7 $T_2$ transformed lines was 6.2%, additionally with 0.5% EPA and 0.2% DPA (line #14). These $T_2$ seeds were still segregating for the transgene i.e. were not yet uniformly homozygous. Compiled data from the total seed lipid profiles from independent transgenic seed (Table 4) are shown in Table 6. The level of ω3 fatty acids produced as a result of the transgenes in these seeds (total new ω3 fatty acids, excluding the level of ALA which was produced endogenously in the Columbia background) was 10.7% while the level of ω6 fatty acids (total new ω6 fatty acids but excluding $18:2^{\Delta 9,12}$) was 1.5%. This represents an extremely favourable ration of new ω3 fatty acids:new ω06 fatty acids, namely 7.3:1.

$T_2$ seeds of selected lines transformed with pJP3416-GA7, namely for lines designated 7, 10, 14, 22 and 34 in the Columbia background and for lines designated 18, 21 and 25 in the fad2 mutant background, were plated onto MS media containing PPT for selection of transgenic seedlings in vitro. Twenty PPT-resistant seedlings for each line were transferred to soil and grown to maturity after self-fertilisation. These plants were highly likely to be homozygous for the selectable marker gene, and therefore for at least one T-DNA insertion in the genome of the plants. $T_3$ seed from these plants were harvested and analysed for fatty acid composition in their seedoil by GC. The data are shown in Table 7. This analysis revealed that the pJP3416-GA7 construct generated higher levels of the ω3 LC-PUFA DHA in $T_3$ seeds of the homozygous plants than in the segregating $T_2$ seed. Up to about 13.9% DHA was observed in the $T_3$ pJP3416-GA7 transformed line designated 22.2 in the Columbia background, increased from about 5.5% in the hemizygous $T_2$ seed, with a sum level of about 24.3% of new ω3 fatty acids as a percentage of the total fatty acids in the seed lipid content. New ω6 fatty acids were at a level of 1.1% of total fatty acids, representing a very favourable ratio of new ω3 fatty acids:new ω6 fatty acids, namely about 22:1. Similarly, transformants in the fad2 mutant background yielded 20.6% as a sum of new ω3 fatty acids, including 11.5% DHA, as a percentage of the total fatty acids in the seed lipid content.

TABLE 4

Fatty acid composition of total seed lipid from independent transgenic $T_2$ *Arabidopsis* seeds with DHA levels at the higher end of the observed range.

|  | pJP3404_Col_#1 | pJP3404_FAD2_#31 | GA7_Col_#7 | GA7_Col_#34 | GA7_Col_#2 | GA7_Col_#10 |
|---|---|---|---|---|---|---|
| 16:0 | 9.6 | 7.8 | 8.7 | 8.2 | 8.7 | 8.6 |
| 18:0 | 2.9 | 3.9 | 3.7 | 3.9 | 3.6 | 3.3 |
| 18:1d11 | 2.2 | 1.8 | 2.0 | 1.9 | 2.0 | 2.3 |
| 20:0 | 1.6 | 2.3 | 2.0 | 2.0 | 2.1 | 1.6 |
| 20:1d13 | 2.2 | 1.8 | 1.6 | 1.5 | 1.7 | 1.6 |
| 20:1d9/d11 | 13.0 | 15.9 | 16.1 | 16.1 | 16.3 | 15.0 |
| 22:1d13 | 1.1 | 1.2 | 1.1 | 1.1 | 1.3 | 1.0 |
| Other minor | 1.9 | 1.5 | 1.5 | 1.4 | 1.5 | 1.3 |
| 18:1d9 | 10.8 | 14.0 | 10.6 | 10.6 | 10.1 | 11.1 |
| 18:2ω6 | 28.9 | 28.3 | 16.4 | 16.1 | 18.2 | 13.7 |
| 18:3ω3 | 16.6 | 14.9 | 29.6 | 29.6 | 27.5 | 32.4 |
| 18:3ω6 | 0.7 | 0.5 | 0.1 | 0.1 | 0.1 | 0.1 |
| 20:2ω6 | 1.6 | 1.5 | 1.1 | 1.2 | 1.3 | 1.0 |
| 20:3ω6 | 0.0 | 0.0 | 0.0 | 0.0 | 0.0 | 0.0 |
| 20:4ω6 | 0.0 | 0.0 | 0.0 | 0.0 | 0.0 | 0.0 |
| 22:4ω6 | 1.6 | 0.6 | 0.3 | 0.3 | 0.3 | 0.4 |
| 22:5ω6 | 0.1 | 0.1 | 0.0 | 0.0 | 0.0 | 0.0 |
| 18:4ω3 | 1.0 | 0.5 | 1.2 | 1.1 | 1.1 | 1.5 |
| 20:3ω3 | 0.0 | 0.0 | 0.0 | 0.6 | 0.0 | 0.0 |
| 20:4ω3 | 0.4 | 0.6 | 0.6 | 0.7 | 0.5 | 0.8 |
| 20:5ω3 | 0.2 | 0.2 | 0.3 | 0.3 | 0.3 | 0.3 |
| 22:5ω3 | 0.0 | 0.2 | 0.2 | 0.2 | 0.2 | 0.2 |
| 22:6ω3 | 3.6 | 2.4 | 3.0 | 3.1 | 3.3 | 3.9 |

|  | GA7_Col_#22 | GA7_Col_#14 | GA7_FAD2_#25 | GA7_FAD2_#21 | GA7_FAD2_#18 |
|---|---|---|---|---|---|
| 16:0 | 8.3 | 9.7 | 7.2 | 8.5 | 7.5 |
| 18:0 | 3.4 | 3.6 | 3.2 | 3.9 | 3.0 |
| 18:1d11 | 2.3 | 2.7 | 1.9 | 2.0 | 1.8 |
| 20:0 | 1.6 | 1.8 | 1.6 | 2.2 | 1.5 |
| 20:1d13 | 1.5 | 1.7 | 1.5 | 1.7 | 1.4 |
| 20:1d9/d11 | 13.9 | 13.5 | 18.3 | 15.9 | 17.0 |
| 22:1d13 | 1.0 | 1.0 | 1.0 | 1.3 | 1.2 |
| Other minor | 1.6 | 1.7 | 1.6 | 1.4 | 1.6 |
| 18:1d9 | 10.0 | 7.7 | 26.0 | 8.2 | 20.9 |
| 18:2ω6 | 13.7 | 11.4 | 6.6 | 16.6 | 4.3 |
| 18:3ω3 | 30.4 | 32.8 | 21.9 | 27.7 | 30.1 |
| 18:3ω6 | 0.2 | 0.1 | 0.1 | 0.2 | 0.1 |
| 20:2ω6 | 1.0 | 1.0 | 0.4 | 1.4 | 0.4 |
| 20:3ω6 | 0.0 | 0.0 | 0.0 | 0.0 | 0.0 |
| 20:4ω6 | 0.0 | 0.0 | 0.0 | 0.0 | 0.0 |
| 22:4ω6 | 0.5 | 0.4 | 0.5 | 0.4 | 0.4 |
| 22:5ω6 | 0.0 | 0.0 | 0.0 | 0.0 | 0.0 |

TABLE 4-continued

Fatty acid composition of total seed lipid from independent transgenic T₂
Arabidopsis seeds with DHA levels at the higher end of the observed range.

| | | | | | |
|---|---|---|---|---|---|
| 18:4ω3 | 2.7 | 2.7 | 1.9 | 1.8 | 1.7 |
| 20:3ω3 | 0.6 | 0.7 | 0.0 | 0.8 | 0.6 |
| 20:4ω3 | 0.8 | 0.4 | 1.0 | 0.8 | 0.8 |
| 20:5ω3 | 0.7 | 0.5 | 0.6 | 0.4 | 0.5 |
| 22:5ω3 | 0.2 | 0.2 | 0.3 | 0.3 | 0.3 |
| 22:6ω3 | 5.5 | 6.2 | 4.3 | 4.4 | 4.8 |

'Col' refers to the Columbia ecotype and 'FAD2' to the fad2 mutant ecotype.
'GA7' refers to transformation with the T-DNA of the pJP3416-GA7 vector, pJP3404 with the T-DNA of the pJP3404 vector.
20:1n-9 and 20:1n-11 fatty acids were not resolved in the GC analysis.
"Other minor" fatty acids include 14:0, 16:1n7, 16:1n9, 16:1n13t, 16:2n6, 16:3n3, i18:0, 18:1n5, 20:1n5, 22:0, 22:1n7, 22:1n11/n13, 24:0, 24:1n9.

TABLE 5

Conversion efficiencies of the individual enzymatic steps for production of DHA from oleic acid, observed in total seed lipid from independent transgenic seed as for Table 4.

| | | pJP3404_Col_#1 | pJP3404_FAD2_#31 | GA7_Col_#7 | GA7_Col_#34 | GA7_Col_#2 | GA7_Col_#10 |
|---|---|---|---|---|---|---|---|
| | d12-des | 69.6% | 62.5% | 66.4% | 66.6% | 66.7% | 67.5% |
| | d15-des | 39.8% | 37.8% | 66.1% | 66.8% | 62.3% | 72.1% |
| Omega-6 | d6-des | 4.5% | 2.5% | 0.7% | 0.7% | 0.7% | 0.9% |
| | (d9-elo) | 3.1% | 3.1% | 2.2% | 2.3% | 2.4% | 1.8% |
| | d6-elo | 71.4% | 56.9% | 83.3% | 83.4% | 83.0% | 84.7% |
| | d5-des | 100.0% | 100.0% | 100.0% | 100.0% | 100.0% | 100.0% |
| | d5-elo | 100.0% | 97.8% | 100.0% | 100.0% | 100.0% | 100.0% |
| | d4-des | 6.2% | 13.0% | 0.0% | 0.0% | 0.0% | 0.0% |
| Omega-3 | d6-des | 23.9% | 21.0% | 15.2% | 15.4% | 16.4% | 17.1% |
| | (d9-elo) | 0.0% | 0.0% | 0.0% | 1.8% | 0.0% | 0.0% |
| | d6-elo | 80.6% | 86.6% | 77.7% | 79.6% | 79.4% | 77.5% |
| | d5-des | 93.7% | 92.1% | 91.7% | 91.4% | 91.5% | 92.6% |
| | d5-elo | 93.7% | 92.1% | 91.7% | 91.4% | 91.5% | 92.6% |
| | d4-des | 100.0% | 90.6% | 94.8% | 94.0% | 95.3% | 94.4% |

| | | GA7_Col_#22 | GA7_Col_#14 | GA7_FAD2_#25 | GA7_FAD2_#21 | GA7_FAD2_#18 |
|---|---|---|---|---|---|---|
| | d12-des | 70.2% | 72.7% | 45.9% | 69.5% | 53.7% |
| | d15-des | 72.7% | 77.2% | 79.7% | 66.0% | 88.1% |
| Omega-6 | d6-des | 1.3% | 1.0% | 1.6% | 1.1% | 1.1% |
| | (d9-elo) | 1.8% | 1.7% | 1.2% | 2.7% | 0.9% |
| | d6-elo | 70.3% | 74.5% | 85.5% | 66.1% | 88.0% |
| | d5-des | 100.0% | 100.0% | 100.0% | 100.0% | 100.0% |
| | d5-elo | 100.0% | 100.0% | 100.0% | 100.0% | 100.0% |
| | d4-des | 0.0% | 0.0% | 0.0% | 0.0% | 0.0% |
| Omega-3 | d6-des | 24.7% | 23.6% | 27.1% | 21.9% | 21.0% |
| | (d9-elo) | 2.0% | 2.2% | 0.0% | 2.6% | 2.1% |
| | d6-elo | 72.7% | 73.0% | 76.7% | 77.4% | 79.2% |
| | d5-des | 89.6% | 92.4% | 88.0% | 91.8% | 91.0% |
| | d5-elo | 89.6% | 92.4% | 88.0% | 91.8% | 91.0% |
| | d4-des | 95.8% | 96.9% | 93.1% | 92.9% | 94.2% |

TABLE 6

Compiled data from the total seed lipid profiles from independent transgenic seed shown in Table 2. Calculations do not include the 'minor fatty acids' in Table 4.

| Parameter | pJP3404_Col_#1 | pJP3404_FAD2_#31 | GA7_Col_#7 | GA7_Col_#34 | GA7_Col_#2 | GA7_Col_#10 |
|---|---|---|---|---|---|---|
| total w3 (% of total FA) | 21.8 | 18.8 | 34.9 | 35.6 | 32.9 | 39.1 |
| total w6 (% of total FA) | 32.9 | 31.0 | 17.9 | 17.7 | 19.9 | 15.2 |
| w3/w6 ratio | 0.66 | 0.61 | 1.95 | 2.01 | 1.65 | 2.57 |
| w6/w3 ratio | 1.51 | 1.65 | 0.51 | 0.50 | 0.60 | 0.39 |
| total novel w3 (% of total FA) | 5.2 | 3.9 | 5.3 | 6.0 | 5.4 | 6.7 |
| total novel w6 (% of total FA) | 4.0 | 2.7 | 1.5 | 1.6 | 1.7 | 1.5 |
| novel w3/w6 ratio | 1.30 | 1.44 | 3.53 | 3.75 | 3.18 | 4.47 |
| novel w6/w3 ratio | 0.77 | 0.69 | 0.28 | 0.27 | 0.31 | 0.22 |
| OA to EPA efficiency | 4.8% | 3.5% | 4.3% | 4.4% | 4.7% | 5.4% |
| OA to DHA efficiency | 4.5% | 3.0% | 3.7% | 3.8% | 4.1% | 4.8% |
| LA to EPA efficiency | 6.9% | 5.6% | 6.6% | 6.8% | 7.2% | 8.1% |

TABLE 6-continued

Compiled data from the total seed lipid profiles from independent transgenic seed shown in Table 2. Calculations do not include the 'minor fatty acids' in Table 4.

| | | | | | | |
|---|---|---|---|---|---|---|
| LA to DHA efficiency | 6.6% | 4.8% | 5.7% | 5.8% | 6.3% | 7.2% |
| ALA to EPA efficiency | 17.4% | 14.9% | 10.0% | 10.1% | 11.6% | 11.3% |
| ALA to DHA efficiency | 16.5% | 12.8% | 8.6% | 8.7% | 10.0% | 10.0% |
| total saturates | 14.1 | 14.0 | 14.4 | 14.1 | 14.4 | 13.5 |
| total monounsaturates | 29.3 | 34.7 | 31.4 | 31.2 | 31.4 | 31.0 |
| total polyunsaturates | 54.7 | 49.8 | 52.8 | 53.3 | 52.8 | 54.3 |
| total C20 | 17.4 | 20 | 19.7 | 20.4 | 20.1 | 18.7 |
| total C22 | 6.4 | 4.5 | 4.6 | 4.7 | 5.1 | 5.5 |
| C20/C22 ratio | 2.72 | 4.44 | 4.28 | 4.34 | 3.94 | 3.40 |

| Parameter | GA7_Col_#22 | GA7_Col_#14 | GA7_FAD2_#25 | GA7_FAD2_#21 | GA7_FAD2_#18 |
|---|---|---|---|---|---|
| total w3 (% of total FA) | 40.9 | 43.5 | 30.0 | 36.2 | 38.8 |
| total w6 (% of total FA) | 15.4 | 12.9 | 7.6 | 18.6 | 5.2 |
| w3/w6 ratio | 2.66 | 3.37 | 3.95 | 1.95 | 7.46 |
| w6/w3 ratio | 0.38 | 0.30 | 0.25 | 0.51 | 0.13 |
| total novel w3 (% of total FA) | 10.5 | 10.7 | 8.1 | 8.5 | 8.7 |
| total novel w6 (% of total FA) | 1.7 | 1.5 | 1.0 | 2.0 | 0.9 |
| novel w3/w6 ratio | 6.18 | 7.13 | 8.10 | 4.25 | 9.67 |
| novel w6/w3 ratio | 0.16 | 0.14 | 0.12 | 0.24 | 0.10 |
| OA to EPA efficiency | 7.9% | 8.8% | 6.3% | 6.4% | 6.7% |
| OA to DHA efficiency | 6.8% | 7.9% | 5.2% | 5.5% | 5.8% |
| LA to EPA efficiency | 11.4% | 12.2% | 13.8% | 9.3% | 12.7% |
| LA to DHA efficiency | 9.8% | 11.0% | 11.4% | 8.0% | 10.9% |
| ALA to EPA efficiency | 15.6% | 15.9% | 17.3% | 14.1% | 14.4% |
| ALA to DHA efficiency | 13.4% | 14.3% | 14.3% | 12.2% | 12.4% |
| total saturates | 13.3 | 15.1 | 12.0 | 14.6 | 12.0 |
| total monounsaturates | 28.7 | 26.6 | 48.7 | 29.1 | 42.3 |
| total polyunsaturates | 56.3 | 56.4 | 37.6 | 54.8 | 44.0 |
| total C20 | 18.5 | 17.8 | 21.8 | 21 | 20.7 |
| total C22 | 7.2 | 7.8 | 6.1 | 6.4 | 6.7 |
| C20/C22 ratio | 2.57 | 2.28 | 3.57 | 3.28 | 3.09 |

TABLE 7

Fatty acid composition of total seed lipid from independent transgenic $T_3$ and $T_4$ Arabidopsis progeny seeds obtained from plant lines as in Table 3. The error shown in the $T_4$ generation denotes the SD of n = 10.

| | GA7_Col_7.2 | GA7_Col_34.2 | GA7_Col_10.13 | GA7_Col_22.2 | GA7_Col_14.19 |
|---|---|---|---|---|---|
| 16:0 | 9.8 | 9.0 | 9.5 | 11.2 | 10.4 |
| 18:0 | 4.0 | 3.8 | 4.2 | 3.4 | 3.5 |
| 18:1n7 | 2.0 | 1.9 | 2.2 | 2.9 | 2.5 |
| 20:0 | 2.2 | 1.9 | 1.7 | 1.4 | 2.3 |
| 20:1d13 | 1.4 | 1.3 | 1.2 | 1.6 | 2.5 |
| 20:1d9/11 | 13.6 | 14.7 | 12.4 | 9.5 | 13.0 |
| 22:1d13 | 1.2 | 1.2 | 0.8 | 0.6 | 1.6 |
| Other minor | 1.8 | 1.5 | 1.5 | 2.1 | 2.6 |
| 18:1d9 | 5.5 | 6.7 | 6.8 | 4.6 | 6.9 |
| 18:2ω6 | 7.5 | 7.9 | 7.4 | 5.6 | 14.8 |
| 18:3ω3 | 33.7 | 33.7 | 36.1 | 31.5 | 26.1 |
| 18:3ω6 | 0.2 | 0.2 | 0.2 | 0.4 | 0.1 |
| 20:2ω6 | 1.0 | 1.0 | 0.7 | 0.7 | 1.4 |
| 20:3ω6 | 0 | 0 | 0 | 0 | 0 |
| 20:4ω6 | 0 | 0 | 0 | 0 | 0 |
| 22:4ω6 | 0 | 0 | 0 | 0 | 0 |
| 22:5ω6 | 0 | 0 | 0 | 0 | 0 |
| 18:4ω3 | 3.1 | 2.6 | 3.0 | 5.3 | 3.3 |
| 20:3ω3 | 1.4 | 1.3 | 1.2 | 1.3 | 1.2 |
| 20:4ω3 | 0.7 | 0.6 | 0.6 | 0.9 | 0.2 |
| 20:5ω3 | 0.9 | 0.9 | 0.7 | 1.9 | 0.8 |
| 22:5ω3 | 0.7 | 0.6 | 0.6 | 1.0 | 0.4 |
| 22:6ω3 | 9.5 | 9.2 | 9.4 | 13.9 | 6.6 |

| | GA7_FAD2-25.10 | GA7_FAD2-21.2 | GA7_FAD2-18.14 | $T_4$Col_22.2 (mean ± SD) | $T_4$Col_22.2 best line |
|---|---|---|---|---|---|
| 16:0 | 8.1 | 10.7 | 7.7 | 10.6 ± 0.9 | 12.2 |
| 18:0 | 3.5 | 3.8 | 3.3 | 3.5 ± 0.4 | 3.6 |
| 18:1n7 | 1.7 | 2.2 | 1.6 | 2.3 ± 0.2 | 2.6 |
| 20:0 | 1.8 | 2.0 | 1.9 | 1.9 ± 0.3 | 2.0 |
| 20:1d13 | 1.2 | 1.4 | 1.3 | 1.6 ± 0.2 | 1.9 |

TABLE 7-continued

Fatty acid composition of total seed lipid from independent transgenic T₃ and
T₄ Arabidopsis progeny seeds obtained from plant lines as in Table 3. The error shown
in the T₄ generation denotes the SD of n = 10.

| | | | | | |
|---|---|---|---|---|---|
| 20:1d9/11 | 15.7 | 12.4 | 18.4 | 11.7 ± 1.7 | 9.5 |
| 22:1d13 | 1.0 | 1.1 | 1.5 | 0.9 ± 0.1 | 0.8 |
| Other minor | 1.7 | 1.9 | 1.6 | 1.9 ± 0.1 | 2.3 |
| 18:1d9 | 11.3 | 4.2 | 11.5 | 4.6 ± 1.0 | 3.3 |
| 18:2ω6 | 5.8 | 8.9 | 5.6 | 5.3 ± 0.9 | 4.3 |
| 18:3ω3 | 28.3 | 28.9 | 30.8 | 31.0 ± 1.1 | 29.5 |
| 18:3ω6 | 0.3 | 0.6 | 0.1 | 0.4 ± 0.1 | 0.4 |
| 20:2ω6 | 0.6 | 1.2 | 0.6 | 0.9 ± 0.1 | 0.9 |
| 20:3ω6 | 0 | 0 | 0 | | |
| 20:4ω6 | 0 | 0 | 0 | | |
| 22:4ω6 | 0 | 0 | 0 | 0.1 ± 0.0 | 0.1 |
| 22:5ω6 | 0 | 0 | 0 | | |
| 18:4ω3 | 3.7 | 5.2 | 2.6 | 4.8 ± 0.9 | 5.5 |
| 20:3ω3 | 1.1 | 1.3 | 1.3 | 1.5 ± 0.2 | 1.7 |
| 20:4ω3 | 1.7 | 0.9 | 0.9 | 0.8 ± 0.2 | 0.8 |
| 20:5ω3 | 1.2 | 1.0 | 0.8 | 1.5 ± 0.3 | 1.8 |
| 22:5ω3 | 0.8 | 0.6 | 0.5 | 1.1 ± 0.2 | 1.5 |
| 22:6ω3 | 10.3 | 11.5 | 7.9 | 13.3 ± 1.6 | 15.1 |

Enzymatic conversion efficiencies for each enzyme step in the pathway for production of DHA from oleic acid are shown in Table 8 for the T₃ seeds with the higher DHA levels. The Δ12-desaturase conversion efficiency in seeds of line 22.2 was 81.6% and the ω3-desaturase efficiency was 89.1%, both of them remarkably high and indicating that these fungal (yeast) enzymes were able to function well in developing seeds. The activities of the other exogenous enzymes in the DHA pathway were similarly high for ω3 substrates with the Δ6-desaturase acting at 42.2% efficiency, Δ6-elongase at 76.8%, Δ5-desaturase at 95.0%, Δ5-elongase at 88.7% and Δ4-desaturase at 93.3% efficiency. The Δ6-desaturase activity on the ω6 substrate LA was much lower, with the Δ6-desaturase acting at only 0.7% conversion efficiency on LA.

GLA was present at a level of only 0.4% and was the only new ω6 product aside from 20:2ω6 detected in the T₃ seeds with the highest DHA content. Compiled data from the total seed lipid profiles from independent transgenic seed (Table 7) are shown in Table 9. This data for the line with the greatest DHA level included a total ω6 FA (including LA) to total ω3 FA (including ALA) ratio of 0.10. The new ω6 FA (excluding LA) to new ω3 FA (excluding ALA) ratio in the lipid of this line was 0.05. Total polyunsaturated fatty acid levels were more than 50% in these lines, and greater than 60% in at least 4 of the lines. Overall conversion efficiencies were calculated to be: OA to EPA=21.8%, OA to DHA=18.0%, LA to EPA=26.9%, LA to DHA=22.2%, ALA to EPA=30.1%, ALA to DHA=24.9%.

TABLE 8

Conversion efficiencies of the individual enzymatic steps for the production of DHA from oleic acid, observed in total seed lipid from transgenic T₃ Arabidopsis seeds as in Table 7.

| | | GA7_Col_7.2 | GA7_Col_34.2 | GA7_Col_10.13 | GA7_Col_22.2 | GA7_Col_14.19 |
|---|---|---|---|---|---|---|
| | d12-des | 75.4% | 73.1% | 75.7% | 81.6% | 73.4% |
| | d15-des | 85.3% | 84.4% | 86.2% | 89.1% | 70.2% |
| Omega-6 | d6-des | 0.3% | 0.3% | 0.3% | 0.7% | 0.3% |
| | (d9-elo) | 1.7% | 1.7% | 1.2% | 1.2% | 2.6% |
| | d6-elo | | | | | |
| | d5-des | | | | | |
| | d5-elo | | | | | |
| | d4-des | | | | | |
| Omega-3 | d6-des | 30.7% | 29.3% | 28.2% | 42.2% | 30.2% |
| | (d9-elo) | 2.7% | 2.7% | 2.3% | 2.4% | 3.0% |
| | d6-elo | 79.0% | 81.1% | 79.0% | 76.8% | 70.9% |
| | d5-des | 94.0% | 94.6% | 94.5% | 95.0% | 97.9% |
| | d5-elo | 91.9% | 91.7% | 93.6% | 88.7% | 89.5% |
| | d4-des | 93.2% | 93.7% | 94.4% | 93.3% | 93.7% |

| | | GA7_FAD2-25.10 | GA7_FAD2-21.2 | GA7_FAD2-18.14 | T₄ Col_22.2 (mean) | T₄ Col_22.2 best line |
|---|---|---|---|---|---|---|
| | d12-des | 66.6% | 78.5% | 63.1% | 67.6% | 82.7% |
| | d15-des | 87.5% | 82.2% | 87.6% | 81.0% | 90.9% |
| Omega-6 | d6-des | 0.6% | 1.0% | 0.2% | 1.3% | 0.7% |
| | (d9-elo) | 1.1% | 2.0% | 1.3% | 1.6% | 1.5% |
| | d6-elo | | | | | |
| | d5-des | | | | | |
| | d5-elo | | | | | |
| | d4-des | | | | | |

TABLE 8-continued

Conversion efficiencies of the individual enzymatic steps for the production of DHA from oleic acid, observed in total seed lipid from transgenic $T_3$ *Arabidopsis* seeds as in Table 7.

| Omega-3 | d6-des | 38.5% | 40.0% | 29.2% | 41.0% | 45.7% |
|---|---|---|---|---|---|---|
| | (d9-elo) | 2.3% | 2.7% | 2.9% | 2.8% | 3.1% |
| | d6-elo | 79.2% | 73.2% | 79.1% | 77.5% | 77.7% |
| | d5-des | 87.8% | 93.3% | 91.1% | 95.0% | 95.8% |
| | d5-elo | 89.9% | 92.2% | 91.6% | 90.8% | 90.2% |
| | d4-des | 92.5% | 95.0% | 93.9% | 92.2% | 90.9% |

TABLE 9

Compiled data from the total seed lipid profiles from independent transgenic seed shown in Table 5. Calculations do not include the 'minor fatty acids' in Table 7.

| Parameter | GA7-Col_7.2 | GA7-Col_34.2 | GA7-Col_10.13 | GA7-Col_22.2 | GA7-Col_14.19 |
|---|---|---|---|---|---|
| total w3 (% of total FA) | 50.0 | 48.9 | 51.6 | 55.8 | 38.6 |
| total w6 (% of total FA) | 8.7 | 9.1 | 8.3 | 6.7 | 16.3 |
| w3/w6 ratio | 5.75 | 5.37 | 6.22 | 8.33 | 2.37 |
| w6/w3 ratio | 0.17 | 0.19 | 0.16 | 0.12 | 0.42 |
| total novel w3 (% of total FA) | 16.3 | 15.2 | 15.5 | 24.3 | 12.5 |
| total novel w6 (% of total FA) | 1.2 | 1.2 | 0.9 | 1.1 | 1.5 |
| novel w3/w6 ratio | 13.58 | 12.67 | 17.22 | 22.09 | 8.33 |
| novel w6/w3 ratio | 0.07 | 0.08 | 0.06 | 0.05 | 0.12 |
| OA to EPA efficiency | 14.1% | 13.3% | 13.4% | 21.8% | 10.2% |
| OA to DHA efficiency | 12.0% | 11.4% | 11.8% | 18.0% | 8.6% |
| LA to EPA efficiency | 18.9% | 18.4% | 17.9% | 26.9% | 14.2% |
| LA to DHA efficiency | 16.2% | 15.9% | 15.7% | 22.2% | 12.0% |
| ALA to EPA efficiency | 22.2% | 21.9% | 20.7% | 30.1% | 20.2% |
| ALA to DHA efficiency | 19.0% | 18.8% | 18.2% | 24.9% | 17.1% |
| total saturates | 16.0 | 14.7 | 15.4 | 16.0 | 16.2 |
| total monounsaturates | 23.7 | 25.8 | 23.4 | 19.2 | 26.5 |
| total polyunsaturates | 58.7 | 58.0 | 59.9 | 62.5 | 54.9 |
| total C20 | 19 | 19.8 | 16.8 | 15.9 | 19.1 |
| total C22 | 11.4 | 11 | 10.8 | 15.5 | 8.6 |
| C20/C22 ratio | 1.67 | 1.80 | 1.56 | 1.03 | 2.22 |

| Parameter | GA7-FAD2-25.10 | GA7-FAD2-21.2 | GA7-FAD2-18.14 | $T_4$ Col_22.2 (mean ± SD) | $T_4$ Col_22.2 best line |
|---|---|---|---|---|---|
| total w3 (% of total FA) | 47.1 | 49.4 | 44.8 | 54.0 | 55.9 |
| total w6 (% of total FA) | 6.7 | 10.7 | 6.3 | 6.7 | 5.7 |
| w3/w6 ratio | 7.03 | 4.62 | 7.11 | 8.06 | 9.81 |
| w6/w3 ratio | 0.14 | 0.22 | 0.14 | 0.12 | 0.10 |
| total novel w3 (% of total FA) | 18.8 | 20.5 | 14.0 | 23.0 | 26.4 |
| total novel w6 (% of total FA) | 0.9 | 1.8 | 0.7 | 1.4 | 1.4 |
| novel w3/w6 ratio | 20.89 | 11.39 | 20.00 | 16.43 | 18.86 |
| novel w6/w3 ratio | 0.05 | 0.09 | 0.05 | 0.06 | 0.05 |
| OA to EPA efficiency | 15.0% | 16.8% | 11.2% | 20.4% | 24.5% |
| OA to DHA efficiency | 12.6% | 14.8% | 9.6% | 17.1% | 20.1% |
| LA to EPA efficiency | 22.9% | 21.8% | 18.0% | 26.2% | 29.9% |
| LA to DHA efficiency | 19.1% | 19.1% | 15.5% | 21.9% | 24.5% |
| ALA to EPA efficiency | 26.1% | 26.5% | 20.5% | 29.4% | 32.9% |
| ALA to DHA efficiency | 21.9% | 23.3% | 17.6% | 24.6% | 27.0% |
| total saturates | 13.4 | 16.5 | 12.9 | 16.0 | 17.8 |
| total monounsaturates | 30.9 | 21.3 | 34.3 | 21.1 | 18.1 |
| total polyunsaturates | 53.8 | 60.1 | 51.1 | 60.7 | 61.6 |
| total C20 | 21.5 | 18.2 | 23.3 | 18 | 16.6 |
| total C22 | 12.1 | 13.2 | 9.9 | 15.4 | 17.5 |
| C20/C22 ratio | 1.78 | 1.38 | 2.35 | 1.17 | 0.95 |

$T_3$ seeds from the pJP3416-GA7 line 22.2 in the Columbia background, which were progeny from $T_2$ line 22, were sown directly to soil and the fatty acid composition of mature seed from the resultant $T_3$ plants analysed by GC. The average DHA level of these seeds was 13.3%±1.6 (n=10) as a percentage of total fatty acids in the seed lipid. As shown in Table 6 (right hand column), the line with the highest level of DHA contained 15.1% DHA in the total fatty acids of the seed lipid. The enzymatic conversion efficiencies are shown in Table 8 for each step in the production of DHA from oleic acid.

The total ω6 FA (including LA) to ω3 FA (including ALA) ratio in the line with the highest DHA level was 0.102. The new ω6 FA (excluding LA) to new ω3 FA (excluding ALA) ratio in the line with the highest DHA level was 0.053. The level of total saturated fatty acids was about 17.8% and the level of monounsaturated fatty acids was about 18.1%. The level of total ω6-fatty acids was about 5.7% and the level of ω3-fatty acids was about 55.9%. Overall conversion efficiencies were calculated to be: OA to EPA=24.5%, OA to DHA=20.1%, LA to EPA=29.9%, LA to DHA=24.5%, ALA to EPA=32.9%, ALA to DHA=27.0%. Total omega-3 fatty acids were found to accumulate to 55.9% of total fatty acids whereas omega-6 fatty acids were 5.7% of the total profile.

Southern blot hybridisation analysis was performed. The results showed that the high-accumulating DHA lines were either single- or double-copy for the T-DNA from the pJP3416-GA7 construct with the exception of transgenic line Columbia#22, which had three T-DNA insertions in the genome of the *Arabidopsis* plant. The T5 generation seed was also analysed and found to have up to 13.6% DHA in the total seed lipids. The GA7 construct was found to be stable across multiple generations in terms of DHA production capability.

Determination of Oil Content in Transgenic *A. Thaliana* DHA Lines

The oil content of transgenic *A. thaliana* seeds with various levels of DHA was determined by GC as described in Example 1. The data are shown in FIG. 6, graphing the oil content (% oil by weight of seed) against the DHA content (as a percentage of total fatty acids). Up to 26.5 mg of DHA per gram of seed was observed (Table 10). The oil content of the transgenic *Arabidopsis* seeds was found to be negatively correlated with DHA content. The amount of DHA per weight of seed was greater in the transformed seeds with a DHA level of about 9% relative to the seeds with about 14% DHA. Whether this would be true for seeds other than *Arabidopsis* has not been determined.

TABLE 10

Proportion and amount of DHA in GA7-transformed *Arabidopsis* seeds.

| | DHA content (% of TFA) | Oil content (% oil per g seeds) | DHA content per weight (mg/g seed) |
|---|---|---|---|
| GA7/col 22.2-1 | 14.2 | 14.89 | 20.2 |
| GA7/col 22.2-2 | 14.3 | 15.02 | 20.5 |
| GA7/col 22.2-3 | 14.0 | 15.92 | 21.2 |
| GA7/col 10.15-1 | 8.7 | 30.23 | 25.06 |

TABLE 10-continued

Proportion and amount of DHA in GA7-transformed *Arabidopsis* seeds.

| | DHA content (% of TFA) | Oil content (% oil per g seeds) | DHA content per weight (mg/g seed) |
|---|---|---|---|
| GA7/col 10.15-2 | 8.6 | 31.25 | 25.77 |
| GA7/col 10.15-3 | 8.8 | 31.70 | 26.49 |

Example 3

Stable Expression of a Transgenic DHA Pathway in *Camelina sativa* Seeds

The binary vector pJP3416-GA7 as described above was introduced into *A. tumefaciens* strain AGL1 and cells from a culture of the transformed *Agrobacterium* used to treat *C. sativa* flowering plants using a floral dip method for transformation (Lu and Kang, 2008). After growth and maturation of the plants, the $T_1$ seeds from the treated plants were harvested, sown onto soil and the resultant plants treated by spraying with the herbicide BASTA to select for plants which were transgenic for, and expressing, the bar selectable marker gene present on the T-DNA of pJP3416-GA7. Surviving $T_1$ plants which were tolerant to the herbicide were grown to maturity after allowing them to self-fertilise, and the resultant $T_2$ seed harvested. Five transgenic plants were obtained, only three of which contained the entire T-DNA.

Lipid was extracted from a pool of approximately twenty seeds from each of the three plants that contained the entire T-DNA. Two of the pooled samples contained very low, barely detectable levels of DHA, but the third pool contained about 4.7% DHA (Table 12). Therefore, lipid was extracted from 10 individual $T_2$ seeds from this plant and the fatty acid composition analysed by GC. The fatty acid composition data of the individual seeds for this transformed line is also shown in Table 11. Compiled data from the total seed lipid profiles (Table 11) are shown in Table 12.

TABLE 11

Fatty acid composition of total seed lipids from transgenic $T_2$ *Camelina sativa* seeds transformed with the T-DNA from pJP3416-GA7. The fatty acid composition is shown for a pooled seed batch (FD5.46) and for 10 single seeds ranked (left to right) from highest to lowest DHA.

| Fatty acid | FD5.46 pooled | #2 | #4 | #8 | #7 | #9 | #1 | #3 | #5 | #6 | #10 |
|---|---|---|---|---|---|---|---|---|---|---|---|
| 14:0 | 0 | 0.2 | 0.2 | 0.1 | 0.2 | 0.2 | 0.2 | 0.2 | 0.1 | 0.2 | 0.2 |
| 16:0 | 11.6 | 12.1 | 12.3 | 12.1 | 13.2 | 12.3 | 12.8 | 11.9 | 11.4 | 11.5 | 11.7 |
| 16:1 | 0.2 | 0.0 | 0.1 | 0.1 | 0.0 | 0.2 | 0.0 | 0.2 | 0.2 | 0.2 | 0.2 |
| 16:3 | 0.3 | 0 | 0.0 | 0.0 | 0.0 | 0.0 | 0.0 | 0.0 | 0.0 | 0.0 | 0.0 |
| 18:0 | 3.7 | 3.3 | 3.2 | 3.2 | 3.0 | 3.1 | 3.2 | 3.3 | 3.1 | 3.2 | 3.2 |
| 18:1 | 10.8 | 8.0 | 8.0 | 8.6 | 8.5 | 9.4 | 11.0 | 10.2 | 8.3 | 9.4 | 8.6 |
| 18:1d11 | 1.7 | 1.3 | 1.4 | 1.4 | 1.7 | 1.4 | 1.5 | 1.3 | 1.3 | 1.3 | 1.3 |
| 18:2 | 24.7 | 18.2 | 19.5 | 19.2 | 18.5 | 20.1 | 23.8 | 32.2 | 30.3 | 29.8 | 31.6 |
| 18:3ω3 | 27.4 | 26.7 | 26.6 | 27.3 | 28.9 | 28.2 | 27.4 | 28.3 | 29.2 | 29.5 | 28.2 |
| 18:3ω6 | 0.2 | 1.4 | 0.3 | 0.3 | 0.4 | 0.2 | 0.5 | 0.0 | 0.5 | 0.4 | 0.6 |
| 20:0 | 1.6 | 1.4 | 1.3 | 1.4 | 1.2 | 1.4 | 1.4 | 1.8 | 2.1 | 1.9 | 2.0 |
| 18:4ω3 | 2.2 | 6.8 | 6.4 | 5.7 | 7.2 | 5.7 | 4.1 | 0.0 | 0.0 | 0.0 | 0.0 |
| 20:1d11 | 5.3 | 4.4 | 4.6 | 4.8 | 3.3 | 4.1 | 3.5 | 4.4 | 6.1 | 5.8 | 5.5 |
| 20:1iso | 0.4 | 0.3 | 0.3 | 0.3 | 0.3 | 0.3 | 0.0 | 0.5 | 0.6 | 0.5 | 0.5 |
| 20:2ω6 | 0.8 | 0.8 | 0.9 | 0.8 | 0.6 | 0.8 | 0.7 | 1.3 | 1.5 | 1.4 | 1.4 |
| 20:3ω3 | 0.6 | 0.8 | 0.8 | 0.8 | 0.7 | 0.8 | 0.7 | 0.6 | 0.7 | 0.7 | 0.6 |
| 22:0 | 0.4 | 0.5 | 0.5 | 0.5 | 0.4 | 0.5 | 0.5 | 0.6 | 0.6 | 0.6 | 0.6 |
| 20:4ω3 | 0.2 | 0.3 | 0.3 | 0.3 | 0.4 | 0.4 | 0.5 | 0.0 | 0.0 | 0.0 | 0.0 |
| 22:1 | 1.1 | 1.1 | 1.2 | 1.1 | 0.5 | 0.9 | 0.8 | 1.6 | 2.2 | 1.9 | 2.0 |
| 20:5ω3 | 0.7 | 1.3 | 1.6 | 1.5 | 1.6 | 1.1 | 1.7 | 0.0 | 0.0 | 0.0 | 0.1 |
| 22:2ω6 | 0.1 | 0.0 | 0.0 | 0.0 | 0.0 | 0.0 | 0.0 | 0.2 | 0.3 | 0.2 | 0.2 |
| 22:4ω6 + 22:3ω3 | 0.3 | 0.2 | 0.3 | 0.3 | 0.0 | 0.3 | 0.0 | 0.4 | 0.6 | 0.5 | 0.5 |
| 24:0 | 0.3 | 0.3 | 0.3 | 0.3 | 0.0 | 0.3 | 0.0 | 0.4 | 0.4 | 0.4 | 0.4 |

TABLE 11-continued

Fatty acid composition of total seed lipids from transgenic T$_2$ *Camelina sativa* seeds transformed with the T-DNA from pJP3416-GA7. The fatty acid composition is shown for a pooled seed batch (FD5.46) and for 10 single seeds ranked (left to right) from highest to lowest DHA.

| Fatty acid | FD5.46 pooled | # 2 | # 4 | # 8 | # 7 | # 9 | # 1 | # 3 | # 5 | # 6 | # 10 |
|---|---|---|---|---|---|---|---|---|---|---|---|
| 24:1 | 0.3 | 0.4 | 0.4 | 0.3 | 0.0 | 0.3 | 0.0 | 0.5 | 0.6 | 0.5 | 0.5 |
| 22:5ω3 | 0.3 | 1.1 | 1.2 | 1.1 | 1.1 | 0.9 | 0.8 | 0.0 | 0.0 | 0.0 | 0.0 |
| 22:6ω3 | 4.7 | 9.0 | 8.5 | 8.3 | 8.3 | 7.1 | 4.9 | 0.0 | 0.0 | 0.0 | 0.0 |

TABLE 12

Compiled data from the total seed lipid profiles from transgenic seed shown in Table 11. Calculations do not include the 'minor fatty acids' in Table 11.

| Parameter | FD5.46 pooled | # 2 | # 4 | # 8 | # 7 | # 9 | # 1 | # 3 | # 5 | # 6 | # 10 |
|---|---|---|---|---|---|---|---|---|---|---|---|
| total w3 (% of total FA) | 36.1 | 46 | 45.4 | 45 | 48.2 | 44.2 | 40.1 | 28.9 | 29.9 | 30.2 | 28.9 |
| total w6 (% of total FA) | 25.8 | 20.4 | 20.7 | 20.3 | 19.5 | 21.1 | 25 | 33.7 | 32.6 | 31.8 | 33.8 |
| w3/w6 ratio | 1.40 | 2.25 | 2.19 | 2.22 | 2.47 | 2.09 | 1.60 | 0.86 | 0.92 | 0.95 | 0.86 |
| w6/w3 ratio | 0.71 | 0.44 | 0.46 | 0.45 | 0.40 | 0.48 | 0.62 | 1.17 | 1.09 | 1.05 | 1.17 |
| total novel w3 (% of total FA) | 8.1 | 18.5 | 18 | 16.9 | 18.6 | 15.2 | 12 | 0 | 0 | 0 | 0.1 |
| total novel w6 (% of total FA) | 1.1 | 2.2 | 1.2 | 1.1 | 1 | 1 | 1.2 | 1.5 | 2.3 | 2 | 2.2 |
| novel w3/w6 ratio | 7.36 | 8.41 | 15.00 | 15.36 | 18.60 | 15.20 | 10.00 | | | | 0.05 |
| novel w6/w3 ratio | 0.14 | 0.12 | 0.07 | 0.07 | 0.05 | 0.07 | 0.10 | | | | 22.00 |
| OA to EPA efficiency | 8.2% | 15.6% | 15.5% | 15.1% | 15.1% | 12.8% | 10.5% | 0.0% | 0.0% | 0.0% | 0.1% |
| OA to DHA efficiency | 6.7% | 12.3% | 11.6% | 11.5% | 11.4% | 10.0% | 7.0% | 0.0% | 0.0% | 0.0% | 0.0% |
| LA to EPA efficiency | 9.2% | 17.2% | 17.1% | 16.7% | 16.2% | 13.9% | 11.4% | 0.0% | 0.0% | 0.0% | 0.2% |
| LA to DHA efficiency | 7.6% | 13.6% | 12.9% | 12.7% | 12.3% | 10.9% | 7.5% | 0.0% | 0.0% | 0.0% | 0.0% |
| ALA to EPA efficiency | 15.8% | 24.8% | 24.9% | 24.2% | 22.8% | 20.6% | 18.5% | 0.0% | 0.0% | 0.0% | 0.3% |
| ALA to DHA efficiency | 13.0% | 19.6% | 18.7% | 18.4% | 17.2% | 16.1% | 12.2% | 0.0% | 0.0% | 0.0% | 0.0% |
| total saturates | 17.6 | 17.8 | 17.8 | 17.6 | 18 | 17.8 | 18.1 | 18.2 | 17.7 | 17.8 | 18.1 |
| total monounsaturates | 19.8 | 15.5 | 16 | 16.6 | 14.3 | 16.6 | 16.8 | 18.7 | 19.3 | 19.6 | 18.6 |
| total polyunsaturates | 62.5 | 66.6 | 66.4 | 65.6 | 67.7 | 65.6 | 65.1 | 63 | 63.1 | 62.5 | 63.2 |
| total C20 | 9.6 | 9.3 | 9.8 | 9.9 | 8.1 | 8.9 | 8.5 | 8.6 | 11 | 10.3 | 10.1 |
| total C22 | 5.4 | 10.3 | 10 | 9.7 | 9.4 | 8.3 | 5.7 | 0.6 | 0.9 | 0.7 | 0.7 |
| C20/C22 ratio | 1.78 | 0.90 | 0.98 | 1.02 | 0.86 | 1.07 | 1.49 | 14.33 | 12.22 | 14.71 | 14.43 |

DHA was present in six of the 10 individual seeds. The four other seeds did not have DHA and were presumed to be null segregants which did not have the T-DNA, based on hemizygosity of the T-DNA insertion in the parental plant. Extracted lipid from the single seed with the highest level of DHA had 9.0% DHA while the sum of the percentages for EPA, DPA and DHA was 11.4%. The sum of the percentages for the new ω3 fatty acids produced in this seed as a result of the transformation (SDA, ETrA, ETA, EPA, DPA, DHA) was 19.3% whilst the corresponding sum for the new ω6 fatty acids (GLA, EDA, DGLA, ARA and any ω6 elongation products) was 2.2%-only GLA and EDA were detected as new ω6 fatty acids. The total ω6 FA (including LA) to ω3 FA (including ALA) ratio was found to be 0.44. The new ω6 FA (excluding LA) to new ω3 FA (excluding ALA) ratio in the seed with the highest DHA level was 0.12. The level of total saturated fatty acids was about 17.8% and the level of monounsaturated fatty acids was about 15.5%. The level of total ω6-fatty acids was about 20.4% and the level of ω3-fatty acids was about 46%. Overall conversion efficiencies were calculated to be: OA to EPA=15.6%, OA to DHA=12.3%, LA to EPA=17.2%, LA to DHA=13.6%, ALA to EPA=24.8%, ALA to DHA=19.6%.

Homozygous seed from this line was obtained in the T4 generation. Up to 10.3% DHA was produced in event FD5-46-18-110 with an average of 7.3% DHA observed across the entire T4 generation.

Homozygous seed was planted out across several glasshouses to generate a total of over 600 individual plants. Oil is being extracted from the seed using a variety of methods including soxhlet, acetone and hexane extractions.

Since the number of independently transformed lines of *C. sativa* obtained as described above was low, further experiments to transform *C. sativa* with pJP3416-GA7 are performed. The inventors predict that DHA levels of greater than 10% as a percentage of total fatty acids in seed oil will be achieved in further transformed lines, and plants which are homozygous for the T-DNA to 20% DHA. Twenty *C. sativa* GA7_modH events were generated and seed is being analysed for DHA content. Three GA7_modB events were generated and analysis of the T1 seed from event CMD17.1 revealed a pooled seed DHA content of 9.8%. The highest single seed DHA value was found to be 13.5%.

Example 4

Stable Expression of Transgenic DHA Pathways in *Brassica napus* Seeds

*B. Napus* Transformation and Analysis of Fatty Acid Composition Using Single Vector The binary vector pJP3416-GA7 was used to generate transformed *Brassica napus* plants and seeds from the plants. The vector pJP3416-GA7 as described above was introduced into *Agrobacterium tumefaciens* strain AGL1 via standard electroporation procedures. Cultures of the transgenic *Agro*- bacterium cells were grown overnight at 28° C. in LB medium with agitation at 150 rpm. The bacterial cells were collected by centrifugation at 4000 rpm for 5 minutes, washed with Winans AB medium (Winans, 1988) and re-suspended in 10 mL of Winans AB medium (pH 5.2) and growth continued overnight in the presence of kanamycin (50 mg/L), rifampicin (25 mg/L) and 100 μM acetosyringone. Two hours before infection of the Brassica cells, spermidine (120 mg/L) was added and the final density of the bacteria adjusted to an OD 600 nm of 0.3-0.4 with fresh AB media. Freshly isolated cotyledonary petioles from 8-day old *Brassica napus* seedlings grown on ½ MS (Murashige and Skoog, 1962) or hypocotyl segments preconditioned by 3-4 days on MS media with 1 mg/L thidiazuron (TDZ) and 0.1 mg/L α-naphthaleneacetic acid (NAA) were infected with 10 mL *Agrobacterium* cultures for 5 minutes. The explants infected with *Agrobacterium* were then blotted on sterile filter paper to remove the excess *Agrobacterium* and transferred to co-cultivation media (MS media with 1 mg/L TDZ, 0.1 mg/L NAA and 100 μM acetosyringone) supplemented with or without different antioxidants (L-cysteine 50 mg/L and ascorbic 15 mg/L). All the plates were sealed with parafilm and incubated in the dark at 23-24° C. for 48 hrs.

The treated explants were then washed with sterile distilled water containing 500 mg/L cefotaxime and 50 mg/L timentin for 10 minutes, rinsed in sterile distilled water for 10 minutes, blotted dry on sterile filter paper, transferred to pre-selection media (MS containing 1 mg/L TDZ, 0.1 mg/L NAA, 20 mg/L adenine sulphate (ADS), 1.5 mg/L AgNO$_3$, 250 mg/L cefotaxime and 50 mg/L timentin) and cultured for five days at 24° C. with a 16 h/8 h photoperiod. They were then transferred to selection media (MS containing 1 mg/L TDZ, 0.1 mg/L NAA, 20 mg/L ADS, 1.5 mg/L AgNO$_3$, 250 mg/L cefotaxime and 50 mg/L timentin) with 1.5 mg/L glufosinate ammonium as the agent for selection of transformed cells, and cultured for 4 weeks at 24° C. with 16 h/8 h photoperiod with a biweekly subculture on to the same media. Explants with green callus were transferred to shoot initiation media (MS containing 1 mg/L kinetin, 20 mg/L ADS, 1.5 mg/L AgNO$_3$, 250 mg/L cefotaxime, 50 mg/L timentin and 1.5 mg/L glufosinate ammonium) and cultured for another 2-3 weeks. Shoots emerging from the resistant explants were transferred to shoot elongation media (MS media with 0.1 mg/L gibberelic acid, 20 mg/L ADS, 1.5 mg/L AgNO$_3$, 250 mg/L cefotaxime and 1.5 mg/L glufosinate ammonium) and cultured for another two weeks. Healthy shoots 2-3 cm long were selected and transferred to rooting media (½ MS containing 1 mg/L NAA, 20 mg/L ADS, 1.5 mg/L AgNO$_3$ and 250 mg/L cefotaxime) and cultured for 2-3 weeks. Well established shoots with roots were transferred to pots containing seedling raising mix and grown in a growth cabinet for two weeks and subsequently transferred to a glasshouse. Approximately 40 ($T_0$) plants transformed with the GA7 construct were obtained by this method.

Plants were grown to maturity after being allowed to self-fertilise. Seeds obtained from transformed plants were analysed for fatty acid composition in their seedoil as described in Example L. Data for a transformed line with the highest DHA level are shown in Table 13. DHA levels on average were significantly lower in the seedoil of the *B. napus* seeds transformed with the T-DNA from pJP3416-GA7 than in *A. thaliana* seeds (Example 2) or *Camelina* seeds (Example 3) transformed with the same construct. The highest level of DHA in approximately 40 lines was found to be 1.52% with the majority of the transgenic lines having detectable DHA. It was noted that there was a substantial accumulation of ALA, about 35% of the total fatty acids, in these seeds which was not being converted efficiently to SDA or following products in the pathway.

Fatty acid profile analysis of single *B. napus* seeds from a $T_1$ event, CT125-2, was performed to better determine the amount of DHA produced in transgenic seeds. Seeds were found to contain between 0% (null seeds) and 8.5% DHA (Table 13).

Some of the seeds from the plant line CT116 as well as other transgenic lines showing DHA production were sown to produce progeny plants. RT-PCR was performed on total RNA isolated from developing embryos from these plants in order to determine why the GA7 construct performed poorly for DHA production relative to transgenic *A. thaliana* and *C. sativa* having the same construct, and poorly relative to the combination of the genes on pJP3115 and pJP3116 (below). RT-PCR was performed on total RNA using a one-step RT-PCR kit (Invitrogen) and gene-specific primers targeting each transgene. This confirmed that each of the genes in the GA7 construct was expressed well in the *B. napus* transformants except for the Δ6-desaturase which was poorly expressed in the majority of transformed seeds. The other genes from this construct functioned well in both *B. napus* and *A. thaliana* seeds, for example the Δ12- and Δ115-desaturases which functioned to produce increased levels of LA and ALA in the seeds whilst decreasing oleic acid levels. A representative RT-PCR gel is shown in FIG. 7 which clearly shows the low expression of the Δ6-desaturase relative to the other transgenes from pJP3416-GA7.

Transgenic plants and seed which are homozygous for the transgenes are generated by planting out progeny from the lines with the highest DHA.

TABLE 13

Fatty acid composition as a percentage of total fatty acids in seedoil from independent $T_1$ *Brassica napus* seed transformed with pJP3416-GA7, lines CT116-11 and CT-125-2 compared to wild-type (untransformed) control. 22:6ω3 is DHA. Data from single CT125-2 *B. napus* seeds is denoted by 'SS'.

|  | Control | CT116-11 | CT125-2 | CT125-2 #2 SS | CT125-2 #3 SS | CT125-2 #10 SS |
|---|---|---|---|---|---|---|
| 14:0 | 0.1 | 0.2 | 0.1 | 0.1 | 0.1 | 0.1 |
| 16:0 | 4.3 | 7.2 | 5.2 | 6.5 | 4.7 | 7.7 |
| 16:1 | 0.2 | 0.5 | 0.4 | 0.3 | 0.3 | 0.8 |
| 16:3 | 0.2 | 0.2 | 0.2 | 0.1 | 0.2 | 0.2 |
| 18:0 | 2.1 | 2.2 | 2.4 | 2.3 | 2.3 | 2.8 |
| 18:1d9 | 59.1 | 27.0 | 38.1 | 34.0 | 19.3 | 14.8 |
| 18:1d11 | 3.7 | 6.6 | 4.2 | 4.4 | 4.3 | 9.6 |
| 18:2 | 19.7 | 14.1 | 16.6 | 13.9 | 10.2 | 10.2 |
| 18:3ω3 | 8.3 | 35.2 | 27.7 | 34.1 | 49.5 | 37.9 |
| 20:0 | 0.6 | 0.5 | 0.6 | 0.4 | 0.3 | 0.7 |
| 18:4ω3 | 0.0 | 0.9 | 0.3 | 0.5 | 0.6 | 2.6 |
| 20:1d11 | 1.2 | 1.1 | 1.0 | 1.0 | 0.8 | 0.6 |
| 20:1isO |  | 0.2 |  | 0.1 |  | 0.2 |
| 20:2ω6 | 0.1 | 0.1 | 0.1 | 0.1 | 0.1 | 0.1 |
| 20:3ω3 |  | 1.3 | 0.7 | 0.8 | 1.6 | 0.9 |
| 22:0 | 0.3 | 0.4 | 0.3 | 0.1 | 0.1 | 0.4 |
| 20:4ω3 |  | 0.1 | 0.3 | 0.4 | 0.6 | 0.5 |
| 22:1 |  |  |  |  |  |  |
| 20:5ω3 |  |  |  |  | 0.1 | 0.3 |
| 22:3ω3 |  |  |  |  | 0.1 |  |
| 24:0 | 0.2 | 0.4 | 0.3 | 0.1 | 0.1 | 0.3 |
| 24:1 | 0.1 | 0.3 | 0.1 | 0.1 | 0.2 | 0.1 |
| 22:5ω3 |  | 0.1 | 0.1 | 0.1 | 0.1 | 0.5 |
| 22:6ω3 |  | 1.52 | 1.2 | 1.3 | 2.7 | 8.5 |

B. Napus Transformation and Analysis of Fatty Acid Composition Using Two Vectors In another experiment in B. napus and as an alternative format for introducing the transgenes, the binary vectors pJP3115 and pJP3116 as described in WO 2010/057246 were used to separately generate transformed B. napus plants and transformed seeds were obtained from the plants. The T-DNA on pJP3115 comprised chimeric genes encoding the Crepis palestina Δ12-desaturase, Micromonas pusilla Δ6-desaturase, Pyramimonas cordata Δ6-elongase and Pavlova salina Δ5-desaturase and the T-DNA on pJP3116 contained chimeric genes encoding Perilla frutescens Δ15-desaturase, Pyramimonas cordata Δ5-elongase and Pavlova salina Δ4-desaturase. The two T-DNAs, when present together and expressed in developing seeds, formed a 7-gene pathway for producing DHA from endogenously produced oleic acid. These vectors were introduced into Agrobacterium tumefaciens strain AGL1 via standard electroporation procedures and the transformed cells used independently to transform B. napus using the method as described above to generate stably transformed $T_0$ plants. 29 pJP3115 and 19 pJP3116 transformants were obtained and these plants were grown to maturity and seeds obtained after self-fertilisation were analysed for fatty acid composition in their seedoil. Transformation with the T-DNA from pJP3115 was expected to result in EPA production from endogenously produced ALA whilst transformation with the T-DNA from pJP3116 was expected to result in increased ALA production from LA. Several plants were identified which displayed these phenotypes. The majority of events displayed a decreased OA/increased LA phenotype due to Δ12 desaturation with a low level of EPA production. Up to 2.6% EPA was observed in pJP31115 transgenic pooled seed. Similarly, the majority of pJP3116 events were found to have an elevated ALA phenotype due to Δ15-desaturase activity. Up to 18.5% ALA was found in pooled seed transformed with the T-DNA from pJP3116.

$T_1$ plants from the lines with the highest levels of EPA and ALA were crossed and the progeny seed (F1) from 24 recovered events analysed for DHA content. DHA was found in 17 of these events with up to 1.9% DHA found in pooled seed from these events. Single-seed analysis was performed to determine the range of DHA production—the data are shown in Table 14. A large range of DHA levels were observed in the crossed progeny, probably due to the hemizygous nature of the T-DNAs in the parental plants, so that some seeds did not receive both T-DNAs. Up to 6.7% DHA was observed in total seed lipid.

TABLE 14

Fatty acid composition as a percentage of total fatty acids in seedoil from B. napus F1 single seeds that were from a cross of plants transgenic for the T-DNA from pJP3115 with plants transgenic for the T-DNA from pJP3116. B1, B2 and B4 designate events. 0.0 = not detectable by the GC method.

|  | B1.1 | B1.2 | B1.3 | B1.4-g | B1.5-g | B2.1 | B2.2 | B2.3g | B2.4g | B2.5g | B3.1 | B3.2 |
|---|---|---|---|---|---|---|---|---|---|---|---|---|
| 14:0 | 0.1 | 0.1 | 0.1 | 0.2 | 0.2 | 0.1 | 0.1 | 0.2 | 0.2 | 0.1 | 0.1 | 0.1 |
| 16:0 | 6.6 | 6.4 | 4.5 | 12.3 | 7.9 | 5.1 | 5.0 | 10.1 | 8.5 | 6.8 | 5.3 | 7.2 |
| 16:1 | 0.4 | 0.5 | 0.2 | 1.0 | 0.6 | 0.4 | 0.4 | 0.6 | 1.1 | 0.5 | 0.5 | 0.6 |
| 16:3 | 0.1 | 0.1 | 0.1 | 0.1 | 0.1 | 0.1 | 0.1 | 0.1 | 0.2 | 0.1 | 0.1 | 0.2 |
| 18:0 | 2.3 | 2.6 | 2.2 | 1.6 | 2.9 | 2.9 | 3.4 | 2.2 | 1.8 | 2.9 | 3.4 | 2.4 |
| 18:1 | 34.1 | 39.3 | 46.9 | 14.9 | 20.7 | 41.6 | 46.3 | 14.4 | 23.4 | 38.3 | 43.6 | 32.0 |
| 18:1d11 | 4.6 | 5.8 | 2.7 | 6.8 | 6.2 | 3.8 | 4.9 | 5.9 | 8.7 | 4.5 | 5.5 | 5.1 |
| 18:2 | 33.6 | 30.7 | 30.4 | 29.2 | 34.4 | 31.7 | 27.7 | 33.2 | 23.9 | 33.3 | 27.9 | 33.4 |
| 18:3ω6 | 0.2 | 0.3 | 0.1 | 0.4 | 0.4 | 0.2 | 0.2 | 0.7 | 0.1 | 0.2 | 0.2 | 0.3 |
| 18:3ω3 | 10.3 | 7.1 | 7.7 | 18.7 | 14.9 | 8.2 | 5.9 | 14.8 | 28.1 | 6.3 | 7.3 | 10.0 |
| 20:0 | 0.6 | 0.7 | 0.6 | 0.5 | 0.7 | 0.8 | 0.9 | 0.6 | 0.4 | 0.7 | 0.9 | 0.7 |
| 18:4ω3 | 0.2 | 0.1 | 0.1 | 0.8 | 0.5 | 0.2 | 0.2 | 0.8 | 0.0 | 0.2 | 0.2 | 0.2 |
| 20:1d11 | 1.0 | 1.1 | 1.1 | 0.7 | 0.8 | 1.1 | 1.1 | 0.5 | 0.9 | 1.1 | 1.1 | 0.9 |
| 20:1iso | 0.1 | 0.1 | 0.0 | 0.1 | 0.1 | 0.1 | 0.1 | 0.1 | 0.3 | 0.1 | 0.1 | 0.1 |
| 20:2ω6 | 0.4 | 0.3 | 0.2 | 0.5 | 0.5 | 0.4 | 0.3 | 0.4 | 0.5 | 0.5 | 0.3 | 0.5 |
| 20:3ω6 | 0.0 | 0.0 | 0.0 | 0.0 | 0.0 | 0.0 | 0.0 | 0.0 | 0.0 | 0.0 | 0.0 | 0.0 |
| 20:4ω6 | 0.0 | 0.0 | 0.0 | 0.0 | 0.0 | 0.0 | 0.0 | 0.1 | 0.0 | 0.0 | 0.0 | 0.0 |
| 20:3ω3 | 1.8 | 1.6 | 1.1 | 2.8 | 2.1 | 1.1 | 1.0 | 2.7 | 0.7 | 1.4 | 0.9 | 1.6 |
| 22:0 | 0.3 | 0.4 | 0.3 | 0.3 | 0.4 | 0.4 | 0.5 | 0.3 | 0.3 | 0.4 | 0.5 | 0.4 |
| 20:4ω3 | 0.3 | 0.2 | 0.2 | 0.4 | 0.4 | 0.1 | 0.1 | 0.5 | 0.0 | 0.2 | 0.1 | 0.2 |
| 22:1 | 0.0 | 0.0 | 0.0 | 0.0 | 0.0 | 0.0 | 0.0 | 0.0 | 0.0 | 0.0 | 0.0 | 0.0 |
| 20:5ω3 | 0.0 | 0.0 | 0.0 | 0.1 | 0.1 | 0.0 | 0.0 | 0.2 | 0.0 | 0.0 | 0.0 | 0.0 |
| 22:2ω6 | 0.0 | 0.0 | 0.0 | 0.0 | 0.0 | 0.0 | 0.0 | 0.0 | 0.0 | 0.0 | 0.0 | 0.0 |
| 22:4ω6 | 0.1 | 0.2 | 0.1 | 0.2 | 0.2 | 0.1 | 0.1 | 0.4 | 0.2 | 0.2 | 0.1 | 0.2 |
| 24:0 | 0.3 | 0.4 | 0.2 | 0.2 | 0.3 | 0.3 | 0.3 | 0.3 | 0.4 | 0.4 | 0.4 | 0.3 |
| 22:5ω6 | 0.1 | 0.2 | 0.1 | 0.2 | 0.3 | 0.1 | 0.1 | 0.5 | 0.0 | 0.2 | 0.1 | 0.2 |
| 24:1 | 0.2 | 0.2 | 0.2 | 0.3 | 0.3 | 0.2 | 0.2 | 0.3 | 0.3 | 0.2 | 0.2 | 0.2 |
| 22:5ω3 | 0.7 | 0.7 | 0.3 | 2.1 | 1.6 | 0.3 | 0.4 | 3.2 | 0.0 | 0.5 | 0.4 | 1.2 |
| 22:6ω3 | 1.4 | 1.0 | 0.5 | 5.5 | 3.9 | 0.8 | 0.7 | 6.7 | 0.0 | 1.1 | 0.8 | 2.0 |

TABLE 15

Compiled data from the total seed lipid profiles from transgenic seed shown in Table 14. Calculations do not include the 'minor fatty acids' in Table 14.

| Parameter | B1.1 | B1.2 | B1.3 | B1.4-g | B1.5-g | B2.1 | B2.2 | B2.3g | B2.4g | B2.5g | B3.1 |
|---|---|---|---|---|---|---|---|---|---|---|---|
| total w3 (% of total FA) | 4.6 | 3.9 | 2.3 | 12.1 | 9 | 2.7 | 2.6 | 14.8 | 0.8 | 3.6 | 2.6 |
| total w6 (% of total FA) | 44.5 | 38.5 | 38.5 | 48.8 | 50.3 | 40.5 | 34.1 | 49.4 | 52.7 | 40.5 | 35.7 |
| w3/w6 ratio | 0.10 | 0.10 | 0.06 | 0.25 | 0.18 | 0.07 | 0.08 | 0.30 | 0.02 | 0.09 | 0.07 |

TABLE 15-continued

Compiled data from the total seed lipid profiles from transgenic seed shown in Table 14. Calculations do not include the 'minor fatty acids' in Table 14.

| Parameter | B1.1 | B1.2 | B1.3 | B1.4-g | B1.5-g | B2.1 | B2.2 | B2.3g | B2.4g | B2.5g | B3.1 |
|---|---|---|---|---|---|---|---|---|---|---|---|
| w6/w3 ratio | 9.67 | 9.87 | 16.74 | 4.03 | 5.59 | 15.00 | 13.12 | 3.34 | 65.88 | 11.25 | 13.73 |
| total novel w3 (% of total FA) | 2.6 | 2 | 1.1 | 8.9 | 6.5 | 1.4 | 1.4 | 11.4 | 0 | 2 | 1.5 |
| total novel w6 (% of total FA) | 10.5 | 7.5 | 7.9 | 19.1 | 15.4 | 8.4 | 6.1 | 15.8 | 28.3 | 6.7 | 7.5 |
| novel w3/w6 ratio | 0.25 | 0.27 | 0.14 | 0.47 | 0.42 | 0.17 | 0.23 | 0.72 | 0.00 | 0.30 | 0.20 |
| novel w6/w3 ratio | 4.04 | 3.75 | 7.18 | 2.15 | 2.37 | 6.00 | 4.36 | 1.39 | | 3.35 | 5.00 |
| OA to EPA efficiency | 2.5% | 2.1% | 0.9% | 10.1% | 6.9% | 1.3% | 1.3% | 12.8% | | 1.9% | 1.4% |
| OA to DHA efficiency | 1.7% | 1.2% | 0.6% | 7.2% | 4.8% | 0.9% | 0.8% | 8.5% | | 1.3% | 1.0% |
| LA to EPA efficiency | 4.3% | 4.0% | 2.0% | 12.6% | 9.4% | 2.5% | 3.0% | 15.7% | | 3.6% | 3.1% |
| LA to DHA efficiency | 2.9% | 2.4% | 1.2% | 9.0% | 6.6% | 1.9% | 1.9% | 10.4% | | 2.5% | 2.1% |
| ALA to EPA efficiency | 47.7% | 44.7% | 36.4% | 68.1% | 65.9% | 44.0% | 45.8% | 72.1% | | 47.1% | 50.0% |
| ALA to DHA efficiency | 31.8% | 26.3% | 22.7% | 48.7% | 45.9% | 32.0% | 29.2% | 47.9% | | 32.4% | 33.3% |
| total saturates | 10.2 | 10.6 | 7.9 | 15.1 | 12.4 | 9.6 | 10.2 | 13.7 | 11.6 | 11.3 | 10.6 |
| total monounsaturates | 40.4 | 47 | 51.1 | 23.8 | 28.7 | 47.2 | 53 | 21.8 | 34.7 | 44.7 | 51 |
| total polyunsaturates | 49.2 | 42.5 | 40.9 | 61 | 59.4 | 43.3 | 36.8 | 64.3 | 53.7 | 44.2 | 38.4 |
| total C20 | 4.2 | 4 | 3.2 | 5.1 | 4.7 | 3.6 | 3.5 | 5.1 | 2.8 | 4 | 3.4 |
| total C22 | 2.6 | 2.5 | 1.3 | 8.3 | 6.4 | 1.7 | 1.8 | 11.1 | 0.5 | 2.4 | 1.9 |
| C20/C22 ratio | 1.62 | 1.60 | 2.46 | 0.61 | 0.73 | 2.12 | 1.94 | 0.46 | 5.60 | 1.67 | 1.79 |

Compiled data from the total lipid profiles (Table 14) are shown in Table 15. From the data in Table 15, the total ω6 FA (including LA) to ω3 FA (including ALA) ratio in the seed with the highest level of DHA was 3.34. The new ω06 FA (excluding LA) to new ω3 FA (excluding ALA) ratio was 1.39. The level of total saturated fatty acids was about 13.7% and the level of monounsaturated fatty acids was about 21.8%. The level of total ω6-fatty acids was about 46.4% and the level of ω3-fatty acids was about 14.8%. Overall conversion efficiencies were calculated to be: OA to EPA=12.8%, OA to DHA=8.5%, LA to EPA=15.7%, LA to DHA=10.4%, ALA to EPA=72.1%, ALA to DHA=47.9%. The reduced efficiency of the ω6 fatty acids to ω3 fatty acids conversion observed in this experiment with the combination of the pJP3115 and pJP3116 was thought to be due to a lower efficiency of the plant Δ15-desaturase compared to the fungal Δ15/ω3 desaturase (Examples 2 and 3) when combined with the genes for conversion of ALA to DHA.

Progeny from DHA-containing lines which are homozygous for all of the introduced transgenes are generated for analysis.

Example 5

Modifications to T-DNAs Encoding DHA Pathways in Plant Seeds

In order to improve the DHA production level in *B. napus* beyond the levels described in Example 4, the binary vectors pJP3416-GA7-modA, pJP3416-GA7-modB, pJP3416-GA7-modC, pJP3416-GA7-modD, pJP3416-GA7-modE and pJP3416-GA7-modF were constructed as follows. These binary vectors were variants of the pJP3416-GA7 construct described in Example 2 and were designed to further increase the synthesis of DHA in plant seeds, particularly by improving Δ6-desaturase and Δ6-elongase functions. SDA had been observed to accumulate in some seed transformed with the GA7 construct due to a relatively low elongation efficiency compared to the Δ5-elongase, so amongst other modifications, the two elongase gene positions were switched in the T-DNA.

The two elongase coding sequences in pJP3416-GA7 were switched in their positions on the T-DNA to yield pJP3416-GA7-modA by first cloning a new *P. cordata* Δ6-elongase cassette between the SbfI sites of pJP3416-GA7 to replace the *P. cordata* Δ5-elongase cassette. This construct was further modified by exchanging the FP1 promoter driving the *M. pusilla* Δ6-desaturase with a conlinin Cnl2 promoter (pLuCnl2) to yield pJP3416-GA7-modB. This modification was made in an attempt to increase the Δ6-desaturase expression and thereby enzyme efficiency. It was thought that the Cnl2 promoter might yield higher expression of the transgene in *B. napus* than the truncated napin promoter. pJP3416-GA7-modC was produced by adding a second *M. pusilla* Δ6-desaturase cassette with slightly different codon usage (SEQ ID NO:15) and driven by the FP1 promoter, which was inserted at the PmeI site just inside the right border of pJP3416-GA7-modB. The second Δ6-desaturase cassette was added to both pJP3416-GA7-modB and pJP3416-GA7-modF in order to increase the Δ6-desaturase expression level and extend the time period during seed development for expression of Δ6-desaturase by the use of multiple promoters. Different codon usages were used in the two nucleotide sequences to result in the translation of the same protein sequence without risking co-suppression from similar coding regions within the same T-DNA. pJP3416-GA7-modD and pJP3416-GA7-modE were similar variants in which a third MAR sequence, corresponding to nucleotides 16649-17816 of SEQ ID NO: 1, was added to pJP3416-GA7 and pJP3416-GA7-modB, respectively, at the PmeI site. pJP3416-GA7-modF was produced by adding a second *M. pusilla* Δ6-desaturase cassette containing the native Δ6-desaturase nucleotide sequence and driven by the FP1 promoter at the PmeI site at the right border of pJP3416-GA7-modB. pJP3416-GA7-modG was made by first replacing the *M. pusilla* Δ6-desaturase cassette with a Cnl2:*P. cordata* Δ5-elongase cassette by restriction cloning at the AscI-PacI sites. pJP3416-GA7-modG was then made by replacing the original FAE1:*P. cordata* Δ5-elongase cassette with a FAE1:*M. pusilla* Δ6-desaturase cassette by restriction cloning at the SbfI sites. The nucleotide sequences of the T-DNAs from each of these genetic constructs are shown as: pJP3416-GA7-modB (SEQ ID NO:2), pJP3416-GA7-modC (SEQ ID NO:3), pJP3416-GA7-modD (SEQ ID NO:4), pJP3416-GA7-modE (SEQ ID NO:5), pJP3416-GA7-modF (SEQ ID NO:6) and pJP3416-GA7-modG (SEQ ID NO:7).

The binary vectors pJP3416-GA7-modB, pJP3416-GA7-modC, pJP3416-GA7-modD, pJP3416-GA7-modE, pJP3416-GA7-modF and pJP3416-GA7-modG are used to generate transformed *Brassica* somatic embryos and *Bras-* sica napus, Camelina sativa and Arabidopsis thaliana plants and progeny seeds. Data for pJP3416-GA7-modB are shown in the next Example.

Eight transgenic pJP3416-GA7-modB A. thaliana events and 15 transgenic pJP3416-GA7-modG A. thaliana events were generated. Between 3.4% and 7.2% DHA in pooled pJP3416-GA7-modB seed was observed and between 0.6 and 4.1% DHA in pooled T2 pJP3416-GA7-modG seed was observed. Several of the highest pJP3416-GA7-modB events were sown out on selectable media and surviving seedlings taken to the next generation. Seed is being analysed for DHA content. Since the pooled T1 seeds represented populations that were segregating for the transgenes and included any null segregants, it is expected that the homozygous seeds from progeny plants will have increased levels of DHA, up to 20% of the total fatty acid content in the seed oil. The other modified constructs were used to transform A. thaliana. Although only a small number of transformed lines were obtained, none yielded higher levels of DHA than the modB construct.

The pJP3416-GA7-modB construct was also used to generate transformed B. napus plants of cultivar Oscar and in a breeding line designated NX005. Ten independent transformed plants (T0) were obtained so far for the Oscar transformation, and 20 independent lines for NX005. Seed (T1 seed) was harvested from these transgenic lines. Pools of seed were tested for levels of DHA in the seed oil, and two lines which showed the highest levels were selected, these were designated lines CT132.5 (in cultivar Oscar) and CT133.15 (in NX005). Twenty seeds from CT132.5 and 11 seeds from CT133.15 were imbibed and, after two days, oil was extracted from a half cotyledon from each of the individual seeds. The other half cotyledons with embryonic axes were kept and cultured on media to maintain the specific progeny lines. The fatty acid composition in the oil was determined; the data is shown in Table 16 for CT132.5. The DHA level in ten of the 20 seeds analysed was in the range of 7-20% of the total fatty acid content as determined by the GC analysis. Other seeds had less than 7% DHA and may have contained a partial (incomplete) copy of the T-DNA from pJP3416-GA7-modB. The transgenic line appeared to contain multiple transgene insertions that were genetically unlinked. The seeds of transgenic line CT133.15 exhibited DHA levels in the range 0-5%. Seeds with no DHA were likely to be null segregants. These data confirmed that the modB construct performed well for DHA production in canola seed.

The pJP3416-GA7-modB and pJP3416-GA7-modF constructs were also used to generate transformed Camelina sativa plants. At least 24 independent transformed plants (T0) were obtained and examined in more detail by progeny analysis. Seed (T1 seed) was harvested from these transgenic lines. Pools of seed were tested for levels of DHA in the seed oil, and 6 lines which showed the highest levels of DHA (between 6% and 9%) were selected. The DHA levels in 20 T1 seeds from each line were analysed-most seeds exhibited DHA levels in the range of 6-14% of the total fatty acid content as determined by the GC analysis. The fatty acid composition in the oil was determined; the data is shown in Table 17 for several transgenic seeds. These data confirmed that the modB and modF constructs both performed well for DHA production in Camelina seed.

TABLE 16

Fatty acid profiles of half cotyledons of germinating T1 transgenic B. napus seeds containing the modB construct. Up to 18.1% DHA was observed with numerous samples containing greater than 10% DHA.

| Seed | 14:0 | 16:0 | 16:1d3? | 16:1 | 16:3 | 18:0 | 18:1 | 18:1d11 | 18:2 | 18:3n6 | 18:3n3 | 20:0 | 18:4n3 | C20:1d11 | 20:1d13 |
|---|---|---|---|---|---|---|---|---|---|---|---|---|---|---|---|
| 1 | 0.1 | 4.2 | 0.1 | 0.1 | 0.2 | 1.8 | 29.9 | 2.5 | 9.9 | 0.1 | 38.4 | 0.5 | 0.8 | 1.0 | 0.0 |
| 2 | 0.1 | 4.7 | 0.1 | 0.1 | 0.2 | 4.0 | 23.0 | 2.3 | 7.4 | 0.3 | 29.3 | 1.0 | 4.3 | 1.1 | 0.0 |
| 3 | 0.1 | 3.7 | 0.2 | 0.1 | 0.2 | 1.8 | 55.1 | 1.9 | 4.7 | 0.2 | 15.2 | 0.8 | 1.8 | 1.4 | 0.0 |
| 4 | 0.1 | 4.6 | 0.2 | 0.2 | 0.2 | 2.9 | 22.1 | 1.8 | 6.6 | 0.4 | 26.5 | 1.0 | 7.2 | 1.0 | 0.0 |
| 5 | 0.1 | 4.0 | 0.1 | 0.1 | 0.2 | 1.7 | 27.4 | 2.1 | 8.1 | 0.3 | 26.4 | 0.6 | 2.8 | 1.0 | 0.0 |
| 6 | 0.1 | 3.5 | 0.1 | 0.1 | 0.2 | 1.6 | 59.8 | 2.0 | 4.3 | 0.1 | 18.5 | 0.6 | 0.5 | 1.3 | 0.0 |
| 7 | 0.1 | 6.0 | 0.3 | 0.3 | 0.3 | 1.7 | 16.6 | 2.6 | 23.9 | 1.0 | 23.2 | 0.6 | 5.4 | 0.8 | 0.0 |
| 8 | 0.1 | 4.9 | 0.1 | 0.1 | 0.2 | 2.7 | 12.9 | 1.4 | 11.7 | 0.3 | 34.3 | 0.9 | 5.0 | 0.9 | 0.0 |
| 9 | 0.1 | 3.9 | 0.1 | 0.1 | 0.1 | 2.4 | 41.6 | 1.7 | 21.5 | 0.0 | 23.4 | 0.7 | 0.0 | 1.2 | 0.0 |
| 10 | 0.1 | 3.7 | 0.2 | 0.1 | 0.1 | 2.1 | 30.9 | 1.7 | 19.2 | 0.4 | 23.6 | 0.7 | 2.1 | 1.1 | 0.0 |
| 11 | 0.1 | 5.7 | 0.4 | 0.3 | 0.2 | 3.8 | 41.2 | 2.4 | 26.7 | 2.1 | 7.2 | 1.3 | 0.3 | 1.2 | 0.0 |
| 12 | 0.1 | 4.6 | 0.0 | 0.1 | 0.2 | 2.4 | 25.5 | 1.7 | 16.1 | 0.3 | 28.9 | 0.8 | 3.9 | 1.1 | 0.0 |
| 13 | 0.1 | 4.3 | 0.1 | 0.1 | 0.1 | 4.2 | 19.4 | 1.6 | 9.2 | 0.1 | 45.5 | 1.0 | 0.2 | 1.1 | 0.0 |
| 14 | 0.1 | 6.3 | 0.2 | 0.2 | 0.2 | 4.0 | 10.5 | 2.3 | 8.4 | 0.3 | 31.1 | 1.3 | 3.9 | 0.8 | 0.0 |
| 15 | 0.1 | 5.1 | 0.1 | 0.2 | 0.2 | 3.3 | 16.8 | 2.4 | 11.2 | 0.3 | 28.8 | 1.0 | 4.5 | 0.9 | 0.0 |
| 16 | 0.1 | 4.4 | 0.1 | 0.1 | 0.2 | 4.0 | 16.2 | 1.5 | 11.6 | 0.2 | 33.5 | 0.9 | 2.8 | 1.1 | 0.0 |
| 17 | 0.2 | 7.2 | 0.2 | 0.2 | 0.2 | 4.9 | 15.0 | 2.1 | 8.9 | 0.3 | 25.9 | 1.4 | 5.1 | 0.9 | 0.0 |
| 18 | 0.1 | 4.0 | 0.1 | 0.1 | 0.2 | 2.3 | 64.8 | 1.2 | 7.2 | 0.1 | 12.5 | 1.0 | 3.5 | 1.5 | 0.0 |
| 19 | 0.1 | 3.9 | 0.1 | 0.1 | 0.2 | 4.6 | 36.9 | 1.7 | 7.1 | 0.2 | 28.6 | 1.2 | 1.8 | 1.2 | 0.0 |
| 20 | 0.1 | 4.8 | 0.1 | 0.1 | 0.2 | 6.0 | 18.5 | 1.2 | 12.8 | 0.2 | 34.8 | 1.4 | 2.4 | 1.1 | 0.0 |

| Seed | C20:2n6 | C20:3n3 | C22:0 | 20:4n3 | 20:5n3 | 22:3n3 | C24:0 | C24:1 | 22:5n3 | C22:6n3 |
|---|---|---|---|---|---|---|---|---|---|---|
| 1 | 0.1 | 2.1 | 0.3 | 2.8 | 0.3 | 0.1 | 0.2 | 0.2 | 0.5 | 3.9 |
| 2 | 0.1 | 1.9 | 0.4 | 6.9 | 1.0 | 0.0 | 0.3 | 0.1 | 1.7 | 9.5 |
| 3 | 0.1 | 0.3 | 0.5 | 11.3 | 0.0 | 0.0 | 0.3 | 0.2 | 0.0 | 0.0 |
| 4 | 0.1 | 0.8 | 0.5 | 11.2 | 1.9 | 0.0 | 0.2 | 0.2 | 1.7 | 8.7 |
| 5 | 0.1 | 1.5 | 0.3 | 7.6 | 1.5 | 0.0 | 0.1 | 0.1 | 1.8 | 12.2 |
| 6 | 0.0 | 0.7 | 0.3 | 6.0 | 0.0 | 0.0 | 0.2 | 0.1 | 0.0 | 0.0 |
| 7 | 0.2 | 0.6 | 0.4 | 2.6 | 1.1 | 0.0 | 0.3 | 0.3 | 1.7 | 9.9 |
| 8 | 0.2 | 2.4 | 0.5 | 4.1 | 1.3 | 0.0 | 0.2 | 0.2 | 1.8 | 13.8 |
| 9 | 0.1 | 2.2 | 0.4 | 0.0 | 0.0 | 0.1 | 0.3 | 0.2 | 0.0 | 0.0 |
| 10 | 0.1 | 1.5 | 0.4 | 3.6 | 0.6 | 0.0 | 0.2 | 0.1 | 0.7 | 6.9 |
| 11 | 0.2 | 0.3 | 0.8 | 4.8 | 0.0 | 0.0 | 0.6 | 0.3 | 0.0 | 0.0 |
| 12 | 0.1 | 1.9 | 0.4 | 3.9 | 0.6 | 0.0 | 0.2 | 0.0 | 1.1 | 6.2 |
| 13 | 0.1 | 5.2 | 0.4 | 2.6 | 0.3 | 0.2 | 0.2 | 0.1 | 0.4 | 3.4 |
| 14 | 0.1 | 2.3 | 0.6 | 4.6 | 1.8 | 0.1 | 0.3 | 0.2 | 2.5 | 18.1 |

TABLE 16-continued

Fatty acid profiles of half cotyledons of germinating T1 transgenic B. napus seeds containing the modB construct. Up to 18.1% DHA was observed with numerous samples containing greater than 10% DHA.

| | | | | | | | | | | |
|---|---|---|---|---|---|---|---|---|---|---|
| 15 | 0.1 | 2.1 | 0.6 | 3.2 | 1.5 | 0.1 | 0.3 | 0.1 | 1.8 | 15.1 |
| 16 | 0.2 | 3.7 | 0.4 | 4.6 | 0.7 | 0.1 | 0.3 | 0.1 | 1.3 | 12.1 |
| 17 | 0.0 | 1.6 | 0.8 | 4.9 | 2.1 | 0.0 | 0.6 | 0.3 | 2.2 | 15.0 |
| 18 | 0.1 | 0.0 | 0.7 | 0.0 | 0.0 | 0.0 | 0.5 | 0.2 | 0.0 | 0.0 |
| 19 | 0.1 | 1.4 | 0.5 | 4.3 | 0.4 | 0.0 | 0.4 | 0.1 | 0.8 | 4.3 |
| 20 | 0.1 | 3.4 | 0.6 | 3.2 | 0.4 | 0.1 | 0.3 | 0.1 | 0.7 | 7.6 |

TABLE 17

Fatty acid profiles of T1 transgenic C. sativa seeds containing the modB or modF constructs

| | C14:0 | C16:0 | C16:1 | C18:0 | C18:1 | C18:1d11 | C18:2 | C18:3n6 | C18:3n3 | C20:0 |
|---|---|---|---|---|---|---|---|---|---|---|
| 123-8 | 0.1 | 7.3 | 0.0 | 5.2 | 7.9 | 1.0 | 7.7 | 0.7 | 29.9 | 2.3 |
| 123-12 | 0.1 | 8.3 | 0.0 | 5.3 | 7.2 | 1.2 | 8.7 | 0.9 | 27.2 | 2.5 |
| 5-8 | 0.1 | 8.3 | 0.1 | 3.5 | 9.4 | 1.3 | 8.1 | 1.1 | 29.0 | 1.0 |
| 5-9 | 0.1 | 8.1 | 0.0 | 3.5 | 9.4 | 1.2 | 8.4 | 1.2 | 29.2 | 1.0 |
| 17-10 | 0.1 | 8.7 | 0.1 | 4.1 | 8.4 | 1.3 | 5.5 | 1.2 | 26.1 | 1.6 |
| 17-26 | 0.1 | 8.8 | 0.1 | 5.5 | 5.0 | 1.3 | 7.6 | 0.9 | 27.8 | 2.7 |

| | 18:4n3 | C20:1d11 | 20:1d13 | C20:2n6 | C20:3n6 | C20:4n6 | C20:3n3 | C22:0 | 20:4n3 |
|---|---|---|---|---|---|---|---|---|---|
| 123-8 | 6.0 | 7.1 | 0.4 | 0.7 | 0.0 | 0.0 | 0.9 | 0.4 | 1.3 |
| 123-12 | 5.7 | 6.9 | 0.5 | 0.7 | 0.0 | 0.1 | 0.9 | 0.5 | 1.5 |
| 5-8 | 9.3 | 7.9 | 0.4 | 0.6 | 0.0 | 0.0 | 0.8 | 0.2 | 0.4 |
| 5-9 | 9.0 | 8.1 | 0.3 | 0.6 | 0.0 | 0.0 | 0.8 | 0.2 | 0.5 |
| 17-10 | 11.8 | 7.2 | 0.3 | 0.0 | 0.4 | 0.03 | 0.8 | 0.3 | 0.4 |
| 17-26 | 10.1 | 6.2 | 0.3 | 0.0 | 0.7 | 0.03 | 1.1 | 0.6 | 0.5 |

| | C22:1 | 20:5n3 | C22:2n6 | 22:3n3 | C24:0 | C24:1 | 22:5n3 | C22:6n3 |
|---|---|---|---|---|---|---|---|---|
| 123-8 | 1.0 | 4.6 | 0.0 | 0.1 | 0.2 | 0.3 | 1.5 | 13.3 |
| 123-12 | 1.2 | 5.0 | 0.0 | 0.1 | 0.2 | 0.4 | 1.5 | 13.2 |
| 5-8 | 0.8 | 3.4 | 0.0 | 0.1 | 0.2 | 0.4 | 0.9 | 12.6 |
| 5-9 | 0.8 | 3.5 | 0.0 | 0.1 | 0.1 | 0.3 | 0.9 | 12.6 |
| 17-10 | 0.7 | 5.5 | 0.0 | 0.0 | 0.2 | 0.3 | 1.3 | 13.5 |
| 17-26 | 1.0 | 4.7 | 0.1 | 0.1 | 0.3 | 0.4 | 1.0 | 13.1 |

The inventors considered that, in general, the efficiency of rate-limiting enzyme activities in the DHA pathway can be greater in multicopy T-DNA transformants compared to single-copy T-DNA transformants, or can be increased by inserting into the T-DNA multiple genes encoding the enzyme which might be limiting in the pathway. Evidence for the possible importance of multi-copy transformants was seen in the *Arabidopsis* seeds transformed with the GA7 construct (Example 2), where the highest yielding DHA event had three T-DNAs inserted into the host genome. The multiple genes can be identical, or preferably are different variants that encode the same polypeptide, or are under the control of different promoters which have overlapping expression patterns. For example, increased expression could be achieved by expression of multiple Δ6-desaturase coding regions, even where the same protein is produced. In pJP3416-GA7-modF and pJP3416-GA7-modC, for instance, two versions of the *M. pusilla* Δ6-desaturase were present and expressed by different promoters. The coding sequences had different codon usage and therefore different nucleotide sequences, to reduce potential silencing or co-suppression effects but resulting in the production of the same protein.

Example 6

Activity of Seed-Specific Constructs in Somatic Embryos

In order to establish a rapid assay system which was predictive of expression of genetic constructs in seeds under the control of seed-specific promoters, a somatic embryo system was set up for *Brassica napus*. This used a vector to express the LEC2 transcription factor which is involved in initiation of somatic embryogenesis. As a demonstration, the binary vectors 35S:LEC2 and pJP107 (Petrie et al., 2010a and b) were introduced into *Agrobacterium tumefaciens* strain AGL1 via standard electroporation and the *Agrobacterium* transformants used to co-transform *Brassica napus* by co-cultivation. The T-DNA region of pJP107 contained genes encoding the *Isochrysis galbana* Δ9-elongase, *P. salina* Δ8-desaturase and *P. salina* Δ5-desaturase with each gene expressed by a seed-specific promoter. A control transformation used the 35S:LEC2 vector alone. 35S:LEC2 expression resulted in the generation of somatic embryos in tissue culture directly from the transformed *B. napus* callus tissue as described in Example 1.

Fatty acid analysis showed that the seed-specific genes on the T-DNA of the construct pJP107 were expressed in the transgenic somatic embryos in the presence of the co-transformed LEC2 gene and functioned to produce ARA ($20:4^{\Delta 5,8,11,14}$) from LA and EPA ($20:5^{\Delta 5,8,11,14,17}$) from ALA. The data for three co-transformed somatic embryos are shown in Table 18 and the fatty acid composition of each compared to the fatty acid composition of seed oil from *Brassica napus* seed which was transgenic for, and expressing, the T-DNA of pJP107 (Petrie et al., 2010a and b). Similar total percentages of ARA and the intermediate fatty acids EDA ($20:2\omega 6$) and DGLA ($20:3\omega 6$), as well as conversion efficiencies, were observed in somatic embryo tissue when compared with stably-transformed seed profiles. Similar results were observed in the fatty acid compositions of the stable $T_2$ transgenic seed and somatic embryos: ω6 fatty acids were at a level of 26.6% and 25.6% (on average), respectively, whilst ARA levels were found to be 9.7% and 10.6% (on average), respectively.

When 35S:LEC2 alone was introduced and the somatic embryos analysed in a time-course, the fatty acid profile was found to change to a more embryo-like profile with $18:3^{\Delta 9,12,15}$ decreasing and $18:1^{\Delta 9}$ increasing in an inversely correlated manner (FIG. 8). These results indicated that the somatic embryos were indeed becoming seed-like in character and the genes on the T-DNA from pJP107 were expressed. This demonstrated that the somatic embryo system allowed a rapid characterisation of transgenic seed-specific constructs in *B. napus* without requiring the full process of producing a transgenic plant and, from that, mature seed.

to DHA=9.7%, 24.2%; LA to EPA=15.4%, 30.7%; LA to DHA=10.7%, 25.0%; ALA to EPA=22.1%, 33.3%; ALA to DHA=15.3%, 27.0%. These efficiencies were similar, or greater than in the case of #284, to those observed for the $T_3$ pJP3416-GA7 *Arabidopsis* lines which indicated that the pJP3416-GA7-modB vector was capable of functioning well in *B. napus* cells. The SDA level was below 3.0%, indicating that the Δ6-elongase was performing even better than the GA7 construct. The individual enzyme efficiencies achieved in #284 were: Δ12-desaturase, 97.4%; ω3-desaturase, 92.3%; Δ6-desaturase, 38.2%; Δ6-elongase, 88.2%; Δ5-desaturase, 98.8%; Δ5-elongase, 94.1%; and Δ4-desaturase, 86.3%. Total saturates were 21.2%, total monounsaturates were 10.2%, total polyunsaturates were 68.6%.

The inventors believe this was the highest level of DHA achieved in *B. napus* cells to date, except for further data described below. This also demonstrated that the modification in pJP3416-GA7-modB relative to pJP3416-GA7 was effective in increasing the level of expression of the Δ6-desaturase gene. The binary vectors pJP3416-GA7, pJP3416-GA7-modA, pJP3416-GA7-modC, pJP3416-GA7-modD, pJP3416-GA7-modE and pJP3416-GA7-modF as described above are co-transformed with 35S:LEC2 to generate transformed *B. napus* somatic embryos. Up to 7.0% DHA was observed in modD embryos, 9.9% in modE embryos, 8.3% in modF embryos and 3.6% in a small number of modG embryos.

TABLE 18

Fatty acid composition of lipid obtained from *Brassica napus* somatic embryos generated by co-transforming pJP107 with 35S:LEC2, compared to the control untransformed (WT) and $T_2$ seeds transformed with pJP107. Individual enzymatic conversion efficiencies are shown in brackets after the relevant enzymatic steps. D9-Elo is Δ9-elongase, D8-Des is Δ8-desaturase and D5-Des is Δ5-desaturase.

| | WT | T2 pJP107 transgenic seed | LEC2: #45 | LEC2: #57 | LEC2: #58 |
|---|---|---|---|---|---|
| $18:1^{\Delta 9}$ | 57.2 | 45.7 | 3.8 | 2.5 | 1.9 |
| $18:2^{\Delta 9,12}$ | 19.1 | 8.7 | 10 | 10.6 | 10 |
| $18:3^{\Delta 9,12,15}$ | 10.2 | 4.1 | 22.5 | 27.5 | 24.2 |
| $20:2^{\Delta 11,14}$ | | 7.1 ± 1.9 (67% D9-elo) | 5.2 (61.8% D9-elo) | 3.7 (56.7% D9-elo) | 4.6 (61.8% D9-elo) |
| $20:3^{\Delta 8,11,14}$ | | 1.1 ± 0.2 (60% D8-des) | 0.4 (67% D8-des) | 0.2 (73% D8-des) | 0.4 (73% D8-des) |
| $20:4^{\Delta 5,8,11,14}$ | | 9.7 ± 0.9 (90% D5-des) | 10.6 (98% D5-des) | 10 (96% D5-des) | 11.2 (97% D5-des) |
| $20:3^{\Delta 11,14,17}$ | | 4.0 ± 0.8 | 9.9 | 5.5 | 7.3 |
| $20:4^{\Delta 8,11,14,17}$ | | 0.3 ± 0.1 | 0.4 | 0.3 | 0.4 |
| $20:5^{\Delta 5,8,11,14,17}$ | | 2.4 ± 0.2 | 7.6 | 6.4 | 7.9 |
| Total new | | 24.6 | 34.1 | 26.1 | 31.8 |

Using the same system to generate somatic embryos, *Brassica napus* cells were transformed separately with pJP3416-GA7-modB and pJP3416-GA7-modD. 42 embryos were obtained, 18 for modB and 24 for modD. Total lipid was extracted from the embryos and analysed for fatty acid composition. The embryos contained between 0% and up to 16.9% DHA (Table 19). The results with 0% DHA was presumed to be due to integration of only a partial T-DNA or an insertion into a transcriptionally silent region of the genome. The total ω3 FA (including ALA) to total ω6 FA (including LA) ratio was found to be 2.3 for embryo #270 and 11.96 for embryo #284. The total ω6 FA (including LA) to total ω3 FA (including ALA) ratio was 0.08 for #284. The new ω6 FA (excluding LA) to new ω3 FA (excluding ALA) ratio was 0.03 for #284. Overall conversion efficiencies were calculated to be: (for embryos #270, #284) OA to EPA=14.0%, 29.8%; OA

TABLE 19

Fatty acid composition of oil from *Brassica napus* somatic embryos #270 and #284 generated by co-transforming the seed-specific DHA acid construct pJP3416-GA7-modB with 35S:LEC2, and #286 and #289 (pJP3416-GA7-modD).

| | #270 | #284 | #286 | #289 |
|---|---|---|---|---|
| 14:0 | 0.3 | 0.2 | 0.2 | 0.2 |
| 16:0 | 14.0 | 15.7 | 17.2 | 16.6 |
| 16:1d9 | 0.7 | 0.4 | 0.8 | 0.8 |
| 16:3 | 0.5 | 0.6 | 1.1 | 1.3 |
| 18:0 | 2.6 | 2.4 | 2.5 | 2.5 |
| 18:1d9 | 6.6 | 1.8 | 1.5 | 1.1 |
| 18:1d11 | 6.3 | 6.8 | 6.5 | 6.7 |
| 18:2 | 18.9 | 4.5 | 10.0 | 9.8 |
| 18:3ω6 | 0.7 | 0.8 | 0.3 | 0.3 |

TABLE 19-continued

Fatty acid composition of oil from Brassica napus somatic embryos #270 and #284 generated by co-transforming the seed-specific DHA acid construct pJP3416-GA7-modB with 35S:LEC2, and #286 and #289 (pJP3416-GA7-modD).

|         | #270 | #284 | #286 | #289 |
|---------|------|------|------|------|
| 18:3ω3  | 33.0 | 37.2 | 42.0 | 41.5 |
| 20:0    | 0.9  | 0.9  | 0.8  | 0.8  |
| 18:4ω3  | 1.9  | 2.8  | 3.6  | 4.5  |
| 20:1d11 | 0.2  | 0.1  | 0.1  | 0.1  |
| 20:2ω6  | 0.1  | 0.1  | 0.1  | 0.2  |
| 20:3ω3  | 0.5  | 0.0  | 0.5  | 0.6  |
| 22:0    | 0.8  | 1.5  | 0.6  | 0.7  |
| 20:4ω3  | 0.2  | 0.9  | 0.7  | 0.7  |
| 20:5ω3  | 0.7  | 0.2  | 0.3  | 0.3  |
| 22:2ω6  | 0.0  | 1.2  | 0.0  | 0.0  |
| 22:3ω3  | 0.0  | 0.1  | 0.0  | 0.1  |
| 24:0    | 0.8  | 1.0  | 1.0  | 1.0  |
| 24:1    | 0.8  | 1.0  | 0.7  | 0.9  |
| 22:5ω3  | 2.4  | 2.7  | 3.2  | 3.0  |
| 22:6ω3  | 7.0  | 16.9 | 6.1  | 6.4  |

Example 7

Analysis of TAG from Transgenic *A. thaliana* Seeds Producing DHA

The positional distribution of DHA on the TAG from the transformed *A. thaliana* seed was determined by NMR. Total lipid was extracted from approximately 200 mg of seed by first crushing them under hexane before transferring the crushed seed to a glass tube containing 10 mL hexane. The tube was warmed at approximately 55° C. in a water bath and then vortexed and centrifuged. The hexane solution was removed and the procedure repeated with a further 4×10 mL. The extracts were combined, concentrated by rotary evaporation and the TAG in the extracted lipid purified away from polar lipids by passage through a short silica column using 20 mL of 7% diethyl ether in hexane. Acyl group positional distributions on the purified TAG were determined quantitatively as previously described (Petrie et al., 2010a and b).

The analysis showed that the majority of the DHA in the total seed oil was located at the sn-1/3 positions of TAG with little found at the sn-2 position (FIG. 9). This was in contrast to TAG from ARA producing seeds which demonstrated that 50% of the ARA (20:4$^{\Delta5,8,11,14}$) was located at the sn-2 position of transgenic canola oil whereas only 33% would be expected in a random distribution (Petrie et al., 2012).

Positional distribution of DHA in the TAG from the *B. napus* seeds transformed with pJP3416-GA7 or with the combination of pJP3115 and pJP3116 is determined by essentially the same method.

The total lipid from transgenic *A. thaliana* seeds was also analysed by triple quadrupole LC-MS to determine the major DHA-containing triacylglycerol (TAG) species (FIG. 10). The most abundant DHA-containing TAG species was found to be DHA-18:3-18:3 (TAG 58:12; nomenclature not descriptive of positional distribution) with the second-most abundant being DHA-18:3-18:2 (TAG 58:11). Tri-DHA TAG (TAG 66:18) was observed in total seed oil, albeit at low but detectable levels. Other major DHA-containing TAG species included DHA-34:3 (TAG 56:9), DHA-36:3 (TAG 58:9), DHA-36:4 (TAG 58:10), DHA-36:7 (TAG 58:13) and DHA-38:4 (TAG 60:10). The identities of the two major DHA-containing TAG were further confirmed by Q-TOF MS/MS.

Example 8

Predicting DHA Production in *B. Napus* Seeds

Efficient production of DHA in *Arabidopsis* seeds at a 15% level using the GA7 genetic construct was demonstrated in Example 2. The same construct in *Brassica napus* seeds produced only about 1.5% DHA in many (but not all) of the transformants, primarily due to the poor expression of the Δ6-desaturase gene of GA7 in this species (Example 4). Based on the realisation that modifications to the GA7 construct would overcome the Δ6-desaturase gene expression problem (see Example 5, as demonstrated in Example 6), calculations were performed to determine the likely fatty acid profile of *B. napus* transgenic seeds expressing the genes from a variant of pJP3416-GA7, where each transgene-encoded enzyme was performing as efficiently as was observed in *A. thaliana* with the GA7 construct. The predicted fatty acid compositions for three calculations (#1, #2, #3) are shown in Table 20. This was based on a wild-type (non-transformed) fatty acid composition for *B. napus* that included 59% oleic acid, 20% LA and 8% ALA. The three predicted partial fatty acid profiles shown in the lower half of the table were based on the conversion efficiencies for each enzymatic step shown in the upper half of the table. In prediction #2, a combination of Δ12-desaturation at 75% efficiency, Δ15-desaturation at 75%, Δ6-desaturation at 35%, Δ6-elongation at 80%, Δ5-desaturation at 90%, Δ5-elongation at 90% and Δ4-desaturation at 90% would result in the production of approximately 10% DHA in a typical canola transgenic seed. These efficiencies were all lower or about equal to the individual efficiencies seen in *Arabidopsis*, so prediction #2 represented a conservative estimate. The conversion efficiencies listed in #3 were approximations based on the efficient conversions seen in *A. thaliana* transformed with pJP3416-GA7. DHA was predicted to be produced at about 15% of the total fatty acid content in seedoil produced in *B. napus* seed, a result that mirrored the most efficient production levels observed in *A. thaliana*. Insertion of multiple T-DNAs in the homozygous state is expected to raise the DHA level to 20% in *B. napus*.

TABLE 20

Predicted fatty acid composition for selected fatty acids as a percentage of total fatty acid content in seedoil from *Brassica napus* transformed with a DHA pathway construct, based on observed enzymatic efficiencies in transgenic *Arabidopsis*. The enzymes are listed in order in the pathway for producing DHA from oleic acid. des = desaturase, elo = elongase. Predicted fatty acid compositions #1, #2 and #3 are based on the efficiencies in the upper half of the Table.

|            | WT  | #1  | #2  | #3  |
|------------|-----|-----|-----|-----|
| Enzyme     |     |     |     |     |
| d12-des    |     | 70% | 75% | 80% |
| d15-des    |     | 70% | 75% | 80% |
| d6-des (ω3)|     | 30% | 35% | 40% |
| d6-elo     |     | 80% | 80% | 90% |
| d5-des     |     | 80% | 90% | 90% |
| d5-elo     |     | 80% | 90% | 90% |
| d4-des     |     | 80% | 90% | 90% |
| Fatty acid |     |     |     |     |
| 18:1d9     | 59% | 26% | 22% | 18% |
| 18:2ω6     | 20% | 19% | 17% | 14% |
| 18:3ω6     |     | 1%  | 2%  | 3%  |
| 18:3ω3     | 8%  | 30% | 32% | 34% |
| 18:4ω3     |     | 3%  | 3%  | 2%  |
| 20:4ω3     |     | 2%  | 1%  | 2%  |

TABLE 20-continued

Predicted fatty acid composition for selected fatty acids as a percentage of total fatty acid content in seedoil from Brassica napus transformed with a DHA pathway construct, based on observed enzymatic efficiencies in transgenic Arabidopsis. The enzymes are listed in order in the pathway for producing DHA from oleic acid. des = desaturase, elo = elongase. Predicted fatty acid compositions #1, #2 and #3 are based on the efficiencies in the upper half of the Table.

|        | WT | #1 | #2  | #3  |
|--------|----|----|-----|-----|
| 20:5ω3 |    | 2% | 1%  | 2%  |
| 22:5ω3 |    | 1% | 1%  | 2%  |
| 22:6ω3 |    | 5% | 10% | 15% |

Example 9

Stable Expression of a Transgenic EPA Pathway in Plant Leaf

Binary Vector Construction

A binary vector, pORE04+11ABGBEC_Cowpea_E-PA_insert (SEQ ID NO:8), was designed for introduction of a T-DNA into plants for the synthesis of EPA in leaf tissues. It contained chimeric genes encoding the enzymes: *M. pusilla* Δ6-desaturase (SEQ ID NO:16), *P. cordata* Δ6-elongase (SEQ ID NO:25) and *P. salina* Δ5-desaturase (SEQ ID NO:30), each under the control of the CaMV 35S and *A. thaliana* rubisco small subunit (SSU) promoters (FIG. 9). The binary vector was constructed by synthesising the region 199-10878 of SEQ ID 2 and cloning this into the recipient binary vector pORE04 (Coutu et al., 1997) at the BsiWI and KasI sites. The three fatty acid biosynthesis genes coded for the enzymes required to convert ALA, $18:3^{\Delta9,12,15}$ to EPA, $20:5^{\Delta5,8,11,14,17}$.

Transient Expression of EPA Construct in *N. benthamiana* Leaf Cells

To test that the construct was correct and would express the genes efficiently in leaf tissues, the chimeric vector pORE04+11ABGBEC_Cowpea EPA insert was introduced into *A. tumefaciens* strain AGL1. The chimeric vector 35S:p19 was also introduced into *A. tumefaciens* strain AGL1 as described in Example 1. Cells from cultures of these infiltrated into leaf tissue of *Nicotiana benthamiana* plants in a 24° C. growth room. Several direct comparisons were infiltrated with the samples being compared located on either side of the same leaf. Experiments were performed in triplicate. Following infiltration, the plants were grown for a further five days before leaf discs were taken for fatty acid profile analysis by GC as described in Example 1. GC analysis revealed that the EPA vector was functioning to produce EPA in *Nicotiana benthamiana* leaf (Table 21) with the highest level of EPA found to be 10.7% of total leaf lipids.

*Nicotiana Tabacum* Stable Transformation

The chimeric vector pORE04+11ABGBEC_Cowpea_E-PA_insert was used to stably transform *Nicotiana tabacum*. The vector was introduced into *A. tumefaciens* strain AGL1 via standard electroporation procedure. The transformed cells were grown on solid LB media supplemented with kanamycin (50 mg/L) and rifampicin (25 mg/L) and incubated at 28° C. for two days. A single colony was used to initiate fresh culture. Following 48 h vigorous culture, the cells were collected by centrifugation at 2,000×g and the supernatant was removed. The cells were resuspended in fresh solution containing 50% LB and 50% MS medium at the density of $OD_{600}$=0.5.

TABLE 21

Fatty acid composition of total leaf lipid from transgenic *Nicotiana benthamiana* (transient) and *Nicotiana tabacum* (stable primary transformant) events with the highest EPA levels from each experiment.

|         |        | N. benthamiana | N. tabacum |
|---------|--------|----------------|------------|
|         | 14:0   | 0.1            | 0.1        |
|         | 16:0   | 18.5           | 17.8       |
|         | 16:1w13t | 2.2          | 3.8        |
|         | 16:1d9 | 0.1            | 0          |
|         | 16:3   | 6.2            | 5.7        |
|         | 18:0   | 3.4            | 3.2        |
|         | 18:1d11| 0.3            | 0.3        |
|         | 20:0   | 0.5            | 0.5        |
|         | 22:0   | 0.2            | 0.3        |
|         | 24:0   | 0.1            | 0.4        |
|         | 18:1   | 2.9            | 1.6        |
|         | 18:2ω6 | 12.6           | 14.5       |
| Omega-6 | 18:3ω6 | 2.3            | 2.9        |
|         | 20:2ω6 | 0.0            | 0.0        |
|         | 20:3ω6 | 0.1            | 0.0        |
|         | 20:4ω6 | 0.3            | 0.7        |
| Omega-3 | 18:3ω3 | 37.1           | 32.4       |
|         | 18:4ω3 | 1.6            | 1.9        |
|         | 20:3ω3 | 0.1            | 0.3        |
|         | 20:4ω3 | 0.3            | 1.1        |
|         | 20:5ω3 | 10.7           | 12.1       |
|         | 22:5ω3 | 0.3            | 0.4        |

Leaf samples of *N. tabacum* cultivar W38 grown in vitro were excised and cut into square sections around 0.5-1 cm² in size with a sharp scalpel while immersed in the *A. tumefaciens* solution. The wounded *N. tabacum* leaf pieces submerged in *A. tumefaciens* were allowed to stand at room temperature for 10 minutes prior to being blotted dry on a sterile filter paper and transferred onto MS plates without supplement. Following a co-cultivation period of two days at 24° C., the explants were washed three times with sterile, liquid MS medium, then blotted dry with sterile filter paper and placed on the selective MS agar supplemented with 1.0 mg/L benzylaminopurine (BAP), 0.25 mg/L indoleacetic acid (IAA), 50 mg/L kanamycin and 250 mg/L cefotaxime. The plates were incubated at 24° C. for two weeks to allow for shoot development from the transformed *N. tabacum* leaf pieces.

To establish rooted transgenic plants in vitro, healthy green shoots were cut off and transferred into 200 mL tissue culture pots containing MS agar medium supplemented with 25 g/L IAA, 50 mg/L kanamycin and 250 mg/L cefotaxime. Transgenic shoots were transferred to soil after rooting and grown to maturity in the glasshouse. Sufficiently large leaf discs were taken from 21 mature transgenic plants from and analysed for fatty acid profile as described in Example 1. All transgenic samples were found to contain EPA (Table 21) with the highest level of EPA in a hemizygous primary transformant found to be 12.1% of total leaf lipids. The leaf samples also contained a small amount (<0.5%) of DPA in their lipid, which resulted from elongation of the EPA by a low level of Δ5-elongation activity of the Δ6-elongase. The total ω3 FA (including ALA) to ω6 FA (including LA) ratio was found to be 2.7. Overall conversion efficiencies were calculated to be: OA to EPA=18.4%, LA to EPA=18.9%, ALA to EPA=25.9%. The production of 12.1% EPA is notable especially since the events were hemizygous primary transformants. The ALA to EPA efficiency in particular is close to that observed in stable seed transformants. It is worth noting that the construct did not contain a Δ12 or Δ15-desaturase to increase the conversion of OA and LA to ALA. Increased efficiencies would be expected with addition of these activities.

Seed from hemizygous transformants is being harvested and sown out to generate homozygous plants.

Seed set in the top EPA lines appeared normal and seed from lines #10 and #17 germinated well to establish the $T_2$ generation. The ratio of EPA to null (no EPA) lines indicated that event #28 was single-locus and the $T_3$ generation of this line was therefore also established. Fatty acid profile analysis of the $T_3$ population indicated that the transgenes were homozygous with no null events found and a stable amount of EPA. The average amount of EPA in the total leaf lipids in the entire $T_3$ population was found to be 9.4%±0.3 (Table 22).

Stable Transformation of Cowpea

The chimeric vector pORE04+1ABGBEC-Cowpea-EPA-insert was transformed into cowpea (*Vigna unguiculata*) as follows. Mature dry seeds are the preferred starting material although seeds harvested from immature pods at maximum fresh weight of seeds can also be used. Dry seeds are threshed by hand to avoid cracking of seed coats and thus reduce contamination with microorganisms.

Dry seeds or immature pods are submerged in 70% ethanol for 2 min and then treated for 30 min in 20% commercial

TABLE 22

Representative fatty acid profiles of total leaf lipids from wildtype (WT) and independent transgenic or transiently-transformed lines (EPA). Species are *Nicotiana benthamiana* (transient transformation), *N. tabacum* (a stably transformed $T_3$ population), *Vigna unguiculata* (stably transformed $T_1$ event). The errors denote standard deviation of multiple samples. Apparent conversion efficiencies shown at the bottom describe the ω3 pathway and are calculated as the sum of product FAs/sum of substrate + product FAs.

|  |  | *N. benthamiana* | | *N. tabacum* | | *V. unguiculata* | |
|---|---|---|---|---|---|---|---|
|  |  | WT | EPA | WT | EPA | WT | EPA |
|  | 16:0 | 17.7 ± 0.1 | 18.7 ± 0.2 | 15.0 ± 0.6 | 16.5 ± 0.5 | 18.0 | 18.2 ± 0.2 |
|  | 16:1ω13t | 3.2 ± 0.1 | 2.2 ± 0 | 3.5 ± 0.1 | 3.0 ± 0.3 | 3.8 | 2.0 ± 0.9 |
|  | 16:3 | 6.8 ± 0.1 | 6.2 ± 0.1 | 5.2 ± 0.5 | 5.4 ± 0.3 | — | — |
|  | 18:0 | 3.1 ± 0 | 3.5 ± 0.3 | 2.2 ± 0.2 | 2.6 ± 0.1 | 1.8 | 4.5 ± 0.4 |
|  | Minor | 1.4 ± 0 | 1.4 ± 0.1 | 3.1 ± 0.4 | 2.5 ± 0.3 | 2.3 | 2.5 ± 0.4 |
|  | OA | 1.7 ± 0.1 | 2.7 ± 0.2 | 1.6 ± 0.3 | 2.1 ± 0.3 | 2.0 | 4.3 ± 1.3 |
|  | LA | 12.5 ± 0.4 | 12.7 ± 0.2 | 17.0 ± 1.1 | 18.0 ± 0.9 | 13.4 | 18.2 ± 3.0 |
|  | ALA | 53.3 ± 0.2 | 37.2 ± 0.2 | 52.2 ± 1.9 | 34.0 ± 0.6 | 58.6 | 38.2 ± 0 |
| Omega-6 | GLA | — | 2.3 ± 0.1 | — | 2.3 ± 0.3 | — | 0.6 ± 0.2 |
|  | 20:2ω6 | 0.1 ± 0 | — | 0.1 ± 0 | 0.1 ± 0 | — | 0.1 ± 0 |
|  | DGLA | 0.1 ± 0 | 0.1 ± 0 | — | — | — | — |
|  | ARA | — | 0.3 ± 0 | — | 0.7 ± 0.1 | — | 0.2 ± 0 |
| Omega-3 | SDA | — | 1.5 ± 0.1 | — | 1.6 ± 0.1 | — | 1.5 ± 0 |
|  | 20:3ω3 | 0.1 ± 0 | 0.1 ± 0 | 0.1 ± 0 | 0.3 ± 0 | 0.1 ± 0 | 1.5 ± 0.1 |
|  | ETA | — | 0.4 ± 0 | — | 1.1 ± 0.1 | — | 0.3 ± 0.2 |
|  | EPA | — | 10.2 ± 0.5 | — | 9.4 ± 0.3 | — | 7.1 ± 0.2 |
|  | DPA | — | 0.3 ± 0.1 | — | 0.4 ± 0 | — | 0.8 ± 0.1 |
| Omega-3 conversion | Δ6-des | | 25% | | 27% | | 20% |
|  | Δ6-elo | | 88% | | 87% | | 85% |
|  | Δ5-des | | 97% | | 90% | | 96% |
|  | Δ5-elo | | 3% | | 4% | | 10% |

Leaf samples of homozygous T3 *N. tabacum* plants were subjected to further biochemical analysis. Total lipids were extracted from freeze-dried leaf material and fractionated by thin-layer chromatography (TLC). EPA was found to be present in *N. tabacum* TAG at up to 30.1% as well as in the polar lipids at 6.3% (Table 23). It was interesting to note that the EPA produced by the transgenic pathway was present in all of the lipid fractions assessed including TAG, MGDG, DGDG, SQDG, PG, PC, PE, PI and PS. All lipid pools contained low levels of novel intermediate or to 6 LC-PUFA fatty acids with the TAG ratio of novel ω3 to ω6 fatty acids being 10:1.

bleach (8.4 g/L sodium hypochlorite final concentration). The seeds are then washed several times with sterile water. Immature seeds are removed aseptically from pods while mature seeds are imbibed overnight. Two different explants can be used for multiple shoot production, ie the embryonic axis and the cotyledon itself, preferably the cotyledon with the bisected embryonic axis attached. The shoot and root tips are removed from the axis before wounding at the cotyledonary node, i.e. the point of attachment of the axis to the cotyledon. From an initial comparison of 19 cultivars and lines, it is now clear that most lines of cowpea can be transformed, the only caveat being that different tissue culture conditions need to be optimised for each line.

TABLE 23

Analysis of young and mature (young|mature) leaf lipid fractions triacylglycerol (TAG), total polar lipid (PL), monogalactosyldiacylglycerol (MGDG), digalactosyldiacylglycerol (DGDG), sulfoquinovosyldiacylglycerol (SQDG), phosphatidylglycerol (PG), phosphatidylcholine (PC), phosphatidylethanolamine (PE), phosphatidylinositol (PI) and phosphatidylserine (PS) from transgenic *Nicotiana tabacum* leaf samples. The errors denote standard deviation of multiple samples. Up to 30% EPA was observed in leaf TAG with EPA also distributed throughout the polar lipids. Differences between young and mature leaf profiles were also observed for several fatty acids.

|   |   |   |   | Chloroplastidic | | | Extra-chloroplastidic | | | | |
|---|---|---|---|---|---|---|---|---|---|---|---|
|   |   | TAG | PL | MGDG | DGDG | SQDG | PG | PC | PE | PI | PS |
|   | 16:0 | 9.8\|18.3 | 17.8\|23.8 | 3.1\|3.2 | 18.0\|16.8 | 48.3\|50.0 | 21.0\|26.4 | 22.9\|30.0 | 24.0\|30.5 | 38.7\|43.3 | 31.9\|36.2 |
|   | 16:1ω13t | 0\|0 | 3.4\|3.1 | 0\|0 | 0\|0 | 0\|0 | 34.0\|32.0 | 0\|0 | 0\|0 | 0\|0 | 1.0\|1.4 |
|   | 16:3 | 0.2\|0.9 | 5.6\|6.4 | 14.8\|19.4 | 1.2\|1.8 | 0.4\|1.2 | 0\|0 | 0\|0 | 0\|0 | 0\|0 | 0\|0 |
|   | 18:0 | 7.3\|3.7 | 2.9\|3.9 | 1.1\|1.2 | 3.5\|3.5 | 5.4\|7.1 | 4.7\|6.9 | 6.6\|9.1 | 11.0\|11.4 | 9.4\|9.3 | 20.2\|19.4 |
|   | Minor | 2.5\|2.9 | 1.4\|2.4 | 1.0\|0.4 | 0.8\|1.0 | 1.9\|2.1 | 1.0\|1.5 | 1.4\|1.6 | 4.9\|4.1 | 6.5\|7.7 | 2.5\|3.7 |
|   | OA | 5.5\|0.8 | 2.8\|1.1 | 0.8\|0.3 | 1.8\|1.0 | 2.7\|1.3 | 5.3\|4.9 | 8.1\|2.9 | 2.5\|1.1 | 2.5\|0.8 | 4.9\|2.3 |
|   | LA | 27.7\|13.7 | 17.3\|12.3 | 8.0\|6.8 | 9.2\|10.5 | 11.7\|8.9 | 17.1\|13.2 | 39.2\|25.2 | 37.9\|28.5 | 22.0\|13.4 | 24.4\|17.1 |
|   | ALA | 9.6\|17.2 | 39.0\|34.4 | 60.3\|51.9 | 61.2\|58.6 | 23.7\|21.5 | 15.7\|14.1 | 7.3\|18.2 | 5.5\|10.5 | 7.6\|10.0 | 4.8\|10.5 |
| Omega-6 | GLA | 2.5\|3.0 | 1.5\|2.1 | 2.1\|3.0 | 1.1\|1.8 | 1.4\|1.9 | 0.2\|0 | 1.8\|2.5 | 1.7\|2.7 | 0.8\|0.9 | 1.1\|1.3 |
|   | 20:2ω6 | 0\|0 | 0.1\|1.1 | 0\|0 | 0\|0 | 0\|0 | 0\|0 | 0\|0 | 0.5\|0 | 0\|0 | 0\|0 |
|   | DGLA | 0\|0 | 0\|0 | 0\|0 | 0\|0 | 0\|0 | 0\|0 | 0\|0 | 0\|0 | 0\|0 | 0\|0 |
|   | ARA | 0.6\|0.9 | 0.1\|0.2 | 0.2\|0.4 | 0\|0 | 0\|0 | 0\|0 | 0.3\|0.3 | 0.4\|0.4 | 0.4\|0.6 | 0\|0.2 |
| Omega-3 | SDA | 4.0\|7.6 | 1.6\|2.0 | 1.7\|2.0 | 0.6\|0.7 | 1.2\|1.2 | 0\|0 | 2.1\|3.6 | 1.3\|2.0 | 0.8\|0.8 | 0.9\|1.6 |
|   | 20:3ω3 | 0.2\|0.3 | 0.1\|0.2 | 0\|0 | 0.2\|0.3 | 0\|0 | 0\|0.1 | 0.2\|0 | 0.3\|0.4 | 0\|0 | 0\|0 |
|   | ETA | 0.9\|0.2 | 0.2\|0.3 | 0\|0.2 | 0\|0.3 | 0\|0 | 0\|0 | 0.2\|0 | 0.4\|0.2 | 0.1\|0.2 | 0\|0 |
|   | EPA | 28.8\|30.1 | 6.1\|6.3 | 6.9\|11.2 | 2.3\|3.6 | 3.4\|4.6 | 1.0\|0.8 | 9.7\|6.4 | 9.1\|7.8 | 11.2\|12.8 | 8.4\|6.2 |
|   | DPA | 0.4\|0.5 | 0\|0 | 0\|0.1 | 0\|0 | 0\|0 | 0\|0 | 0.3\|0.4 | 0.5\|0.4 | 0\|0.2 | 0\|0.1 |

The selectable marker genes, bar or NptII can be used for transformation. The *Agrobacterium tumefaciens* strain AGL1 is the preferred strain for cowpea transformation. *Agrobacterium* containing the pORE04+11 ABGBEC-Cowpea-EPA-insert vector is cultured overnight at 28° C. on a shaker at 180 rpm and the suspension is centrifuged at 8000 g for 10 min and re-suspended in Medium 1 (MS-basic medium diluted one in ten and containing 30 g/l sucrose, 20 mM 2-MES, adjusted to pH 5.6 prior to autoclaving, supplemented with filter sterilized MS-vitamins, 100 mg/l myoinositol, 1.7 mg/l BAP, 0.25 mg/l $GA_3$, 0.2 mM acetosyringone, 250 mg/l Na-thiosulphate, 150 mg/l dithiothreitol and 0.4 g/l L-cysteine). The explants are submerged without shaking in the bacterial suspension for one hour following wounding in the meristematic regions with a scalpel. The treated explants are then blotted on sterile filter paper and transferred to solidified Medium 2 (Medium 1 containing 0.8% agar) overlayed with filter paper. After four days of co-cultivation, explants are transferred to Medium 3 (full strength MS medium, supplemented with 100 mg/l myo-inositol, 150 mg/l timentin, 30 g/L sucrose, 3 mM MES, 1.7 mg/L BAP, 5 mg/L PPT or 25-50 mg/L geneticin or 150 mg/L kanamycin, 0.8 g/L agar and adjusted to pH 5.6) for shoot initiation and selection of transformed shoots. After two weeks the first shoots are visible. The cotyledons are removed from the cotyledonary node region and cultures are transferred to fresh Medium 3. Cultures are transferred to fresh Medium 3 every two weeks following removal of dead and dying tissue. The first four subcultures are on kanamycin selection followed by alternating with geneticin and kanamycin. After six sub-cultures, the surviving green shoots are transferred to Medium 4 (Medium 3 without BAP but supplemented with 0.5 mg/l $GA_3$, 50 mg/l asparagine, 0.1 mg/l 3-indoleacetic acid (IAA), 150 mg/l timentin, and either PPT (10 mg/l), geneticin (50 mg/L) or kanamycin (150 mg/L), for shoot elongation. The shoots are sub-cultured every two weeks until single shoots are more than 1 cm long. These larger shoots are transferred from petri dishes to culture jars (80 mm height) for further growth under selection.

The majority of the regenerated shoots can be rooted in vitro, and the rooted plants are transferred to soil and allowed to establish in a high humidity chamber for 14-21 days before transfer to ambient greenhouse conditions.

To enhance gene transfer to cowpea, co-culture media is supplemented with thiol compounds. The addition of L-cysteine, dithiothreitol, and sodium thiosulfate reduces browning of wounded tissue.

Large numbers of cowpea explants can be processed in a simplified protocol. In brief, the protocol consists of the following steps: imbibition of sterilized mature seeds overnight in water, explants are derived by longitudinally bisecting the seed as a result of which, the split embryonic axis (with shoot and root apices removed) is still attached to the cotyledon, infection with *Agrobacterium* strain AGL1 aided by local wounding in the meristematic regions, co-culture on medium containing thiol compounds over 4 days at 25° C. in light, shoot initiation and elongation on medium containing selective agents, shoots are rooted in vitro and transferred to greenhouse conditions for flowering and seed setting, PCR or enzyme analysis of putative transgenic plants, and screening of next generation progeny by PCR or enzyme activity.

The progeny of transgenic $T_0$ plants are normal in phenotype. The transgenes are transmitted to the progeny and homozygous $T_2$ plants are identified by screening their $T_3$ progeny for enzyme activity or by PCR.

Using this transformation system about 10 transgenic plants are produced per 1000 explants, which is similar to the transformation frequency for other legumes. Depending on the cultivar or line to be transformed, this protocol requires 5-8 months from explant preparation to harvested $T_1$ seeds.

The transformation system is used to introduce the pORE04+11ABGBEC-Cowpea-EPA-insert binary vector into regenerated, transformed cowpea plants.

Modifications to the pORE04+11ABGBEC-Cowpea-EPA-insert binary vector are made in which genes encoding a Δ5-elongase and Δ4-desaturase are added, to provide a genetic construct which confers the ability to further convert the produced EPA to DHA. The construct is transformed into plants for production of DHA in vegetative tissues.

EPA was found to be present in the small number of events surviving chemical selection. The highest line contained 7.1%±0.2 EPA in the total leaf lipids. The rate of transformation was lower than usually experienced for cowpea with only six lines confirmed transgenic. It is, as yet, unknown what caused this effect although it is interesting to note that a larger than usual proportion of transgenic events contained incomplete T-DNA regions. It is possible that the large construct size contributed to the reduced efficiency. The apparent conversion efficiencies of each of the three transgenic enzymes were also calculated (Table 22). Results were broadly similar in all three species with good conversion to EPA after initial Δ6-desaturation of the native ALA. Some Δ5-elongation of EPA to DPA was noted despite the absence of a specific Δ5-elongase. The *P. cordata* Δ6-elongase has previously been shown to have a low level of Δ9-elongase activity (i.e. $18:3^{\Delta 9, 12, 15}$ to $20:3^{\Delta 11, 14, 17}$ conversion) although no Δ5-elongase activity was detected in a yeast assay.

Example 10

Testing Variations of Δ12-Desaturase Genes

Binary Vector Construction

In an attempt to test and compare a series of chimeric Δ12-desaturase genes, several binary vectors were made which were used to transform *A. thaliana* and *B. napus*. The binary vectors pJP3365, pJP3366, pJP3367, pJP3368 and pJP3369 each contained genes that encoded the *P. pastoris* ω3-desaturase (SEQ ID NO:12) and *M. pusilla* Δ6-desaturase (SEQ ID NO:16) enzymes, and one of a series of Δ12-desaturases. The Δ12-desaturases were from *Cryptococcus neoformans* (Accession No. XP_570226 in pJP3365), a version of the *Cryptococcus neoformans* Δ12-desaturase which contained a L151M mutation in an attempt to increase gene activity (in pJP3366), *Lachancea kluyveri* (SEQ ID NO:10 in pJP3367), *Synechocystis* PCC6803 (Accession No. BAA18169 in pJP3368) and *Crepis palaestina* (Accession No. CAA76157, Lee et al., 1998, in pJP3369). The *Crepis* desaturase was the only plant desaturase in the series; the others were fungal enzymes. The vectors were made by inserting a plant codon-optimised protein coding region, except for the *Crepis* palestina Δ12-desaturase which was wildtype, for each Δ12-desaturase into the NotI site of the vector pJP3364 (see FIG. 12), in the orientation operably linked to the FP1 promoter to provide for seed-specific expression of each desaturase. The vector pJP3364 already contained the chimeric genes encoding the *P. pastoris* ω3-desaturase and *M. pusilla* Δ6-desaturase, each under the control of seed-specific promoters (FIG. 12). The combination of the three fatty acid biosynthesis enzymes, namely Δ12-desaturase, ω3-desaturase and Δ6-desaturase, was designed to assemble a pathway to convert oleic acid ($18:1^{\Delta 9}$) to SDA ($18:4^{\Delta 6,9,12,15}$). Assays were therefore carried out to measure the level of SDA production in transformed seeds.

*A. thaliana* and *B. napus* Transformation and Analysis The chimeric binary vectors were introduced into *A. tumefaciens* strain AGL1 and cells from cultures of the transformed *Agrobacterium* used to transform fad2 mutant *A. thaliana* plants using the floral dip method for transformation (Clough and Bent, 1998). After maturation, the $T_1$ seeds from the treated plants were harvested and plated on MS plates containing kanamycin for selection of plantlets having the NptII selectable marker gene present on the T-DNA of each chimeric vector. Surviving $T_1$ seedlings were transferred to soil. After allowing the plants to self-fertilise and growing them to maturity, the $T_2$ seeds from these plants were harvested and the fatty acid composition of seed lipids analysed by GC.

The chimeric vector pJP3367 was also used to transform *B. napus* by the method described in Example 4 to generate 12 transgenic events. SDA was found to range from 0.6% to 2.2% in pooled seed of the plants, and nine individual seeds from the transgenic plant with the highest SDA transgenic plant were analysed for fatty acid composition. Fatty acid composition data from such analysis is shown in Table 24.

The data showed that the Δ12-desaturase activity expressed from each of the T-DNAs in both *A. thaliana* and *B. napus* were unexpectedly low, providing an enzyme conversion efficiency of about 20% rather than the 70-80% seen with the same expression cassette in the GA7 construct (Examples 2 and 3). The reason for this relatively poor expression of the Δ12-desaturase genes from these vectors is unclear but could be related to the position of the genes in the construct as a whole.

In contrast, RT-PCR expression analysis demonstrated that the *P. pastoris* ω3-desaturase and *M. pusilla* Δ6-desaturase genes on the T-DNAs were relatively well expressed in the transformed seed. Table 24 includes the Δ6-desaturase conversion efficiencies in the transformed seeds, which ranged from about 11% to about 25% in the one *B. napus* transformed line. This was considerably higher than the Δ6-desaturase conversion efficiency of about 7% seen in the *B. napus* seeds transformed with the GA7 construct (Example 4).

TABLE 24

Fatty acid composition as a percentage of total fatty acids in seed oil from single seeds from a $T_1$ *Brassica napus* plant transformed with the T-DNA from pJP3367. SDA (18:4ω3) is shown in bold.

| Sample | CT110-3#1 | CT110-3#2 | CT110-3#3 | CT110-3#4 | CT110-3#5 | CT110-3#6 | CT110-3#7 | CT110-3#8 | CT110-3#9 |
|---|---|---|---|---|---|---|---|---|---|
| C14:0 | 0.1 | 0.1 | 0.1 | 0.1 | 0.1 | 0.1 | 0.1 | 0.1 | 0.1 |
| C16:0 | 4.3 | 4.2 | 4.1 | 4.5 | 3.8 | 4.3 | 4.0 | 5.0 | 4.7 |
| 16:1d7 | 0.1 | 0.1 | 0.1 | 0.1 | 0.0 | 0.1 | 0.1 | 0.1 | 0.1 |
| C16:1d9 | 0.2 | 0.2 | 0.2 | 0.2 | 0.2 | 0.2 | 0.2 | 0.3 | 0.3 |
| 16:3 | 0.2 | 0.2 | 0.2 | 0.2 | 0.2 | 0.2 | 0.2 | 0.2 | 0.2 |
| C18:0 | 1.9 | 1.9 | 1.3 | 1.8 | 2.1 | 1.8 | 2.4 | 3.1 | 2.2 |
| C18:1 | 58.1 | 59.4 | 55.5 | 59.1 | 62.1 | 56.0 | 57.2 | 52.0 | 53.2 |
| C18:1d11 | 3.5 | 3.6 | 3.0 | 3.2 | 2.9 | 3.6 | 3.2 | 4.4 | 3.5 |
| C18:2 | 18.4 | 17.1 | 19.2 | 17.3 | 17.4 | 18.7 | 19.0 | 20.3 | 20.2 |
| C18:3ω6 | 0.3 | 0.2 | 0.3 | 0.2 | 0.2 | 0.2 | 0.2 | 0.2 | 0.3 |
| C18:3ω3 | 8.2 | 9.0 | 11.1 | 8.6 | 7.5 | 10.2 | 9.8 | 9.3 | 9.8 |
| C20:0 | 0.5 | 0.5 | 0.4 | 0.5 | 0.6 | 0.5 | 0.6 | 0.7 | 0.6 |

TABLE 24-continued

Fatty acid composition as a percentage of total fatty acids in seed oil from single seeds from a $T_1$ Brassica napus plant transformed with the T-DNA from pJP3367. SDA (18:4ω3) is shown in bold.

| Sample | CT110-3#1 | CT110-3#2 | CT110-3#3 | CT110-3#4 | CT110-3#5 | CT110-3#6 | CT110-3#7 | CT110-3#8 | CT110-3#9 |
|---|---|---|---|---|---|---|---|---|---|
| 18:4ω3 | 2.4 | 2.0 | 2.8 | 2.5 | 1.4 | 2.6 | 1.3 | 2.4 | 3.2 |
| C20:1d11 | 1.1 | 1.1 | 1.2 | 1.2 | 1.2 | 1.1 | 1.2 | 1.1 | 1.1 |
| 20:1iso | 0.03 | 0.03 | 0.03 | 0.03 | 0.01 | 0.03 | 0.02 | 0.03 | 0.02 |
| C20:2ω6 | 0.1 | 0.1 | 0.1 | 0.1 | 0.1 | 0.1 | 0.1 | 0.1 | 0.1 |
| C22:0 | 0.2 | 0.2 | 0.2 | 0.2 | 0.2 | 0.2 | 0.2 | 0.3 | 0.2 |
| C24:0 | 0.1 | 0.1 | 0.1 | 0.2 | 0.1 | 0.1 | 0.2 | 0.3 | 0.2 |
| C24:1 | 0.1 | 0.1 | 0.1 | 0.1 | 0.1 | 0.1 | 0.1 | 0.1 | 0.1 |
| Δ6-des % | 22.9 | 17.9 | 20.3 | 22.8 | 15.8 | 20.2 | 11.7 | 20.9 | 24.9 |

Therefore, to take advantage of the higher Δ6-desaturase conversion efficiencies conferred by the T-DNA from pJP3367, B. napus plants transformed with this T-DNA were crossed to plants transformed with the T-DNA from pJP3416-GA7 (Example 4) to produce progeny plants and seeds carrying both T-DNAs. The fatty acid composition of oil extracted from F1 seeds is analysed by GC for DHA content and other fatty acid contents. Increased DHA levels are observed as a consequence of increased expression of the Δ6-desaturase. Plants which are homozygous for both T-DNAs are produced and should produce higher levels of DHA.

Example 11

Increasing Accumulation of Fatty Acids by Using Silencing Suppressor Proteins

Binary Vector Construction

WO 2010/057246 describes the use of silencing suppressor proteins (SSP) to increase transgene expression in the seeds of plants. To demonstrate that the use of such proteins could enhance and stabilise the production of LC-PUFA in oilseeds over several generations, several SSP were selected for testing, namely V2 (Accession No. GU178820.1), p19 (Accession No. AJ288943.1), p38 (Accession No. DQ286869.1) and P0$^{PE}$ (Accession No. L04573.1). p19 is a suppressor protein from Tomato Bushy Stunt Virus (TBSV) which binds to 21 nucleotide long siRNAs before they guide Argonaute-guided cleavage of homologous RNA (Voinnet et al., 2003). V2, a suppressor protein from Tomato Yellow Leaf Curl Virus (TYLCV), binds to the plant protein SGS3 (Glick et al., 2008), a protein thought to be required for the production of double stranded RNA intermediates from ssRNA substrates (Beclin et al., 2002), or binds to dsRNA structures that have a 5' overhangs (Fukunaga et al., 2009). p38 is a suppressor protein from Turnip Crinkle Virus (TCV) which interferes with plant silencing mechanisms by binding to Dicer and Argonaute proteins (Azevedo et al., 2010). P0 proteins such as P0$^{PE}$ and RPV-P0, from poleroviruses, target Argonaut proteins for enhanced degradation (Baumberger et al., 2007; Bortolamiol et al., 2007, Fusaro et al., 2012). Genetic constructs were therefore prepared for expression of these SSP in plant seed in combination with a set of fatty acid biosynthesis genes for production of ARA (20:4$^{Δ5,8,11,14}$) from LA (18:1$^{Δ9,12}$), as follows.

The fatty acid biosynthesis genes encoding the Isochrysis galbana Δ9-elongase and the Pavlova salina Δ8- and Δ5-desaturases and the bacterial selection marker were obtained on a single DNA fragment from pJP3010 by digestion with PmeI and AvrII giving rise to a 9560 bp fragment. The Δ9-elongase coding region on this fragment was joined to an A. thaliana FAE1 promoter (pAtFAE1) and a conlinin transcription termination/polyadenylation region (LuCnl2-3'). The desaturase coding regions were each joined to a truncated napin FP1 promoter (pBnFP1) and a nos3' transcription termination/polyadenylation region. The three fatty acid biosynthesis genes on this fragment were oriented and spaced in the same manner as in pJP107 (Petrie et al., 2012) and encoded the same proteins as pJP107. The DNA fragment also comprised a pFP1:GFiP:nos3' gene from pCW141 (see WO2010/057246) which encoded a green fluorescent protein (GFP). This screenable marker gene was used as a visual seed-specific marker, allowing simple and non-destructive identification and thereby selection of transgenic seed comprising and expressing the gene.

The PmeI-AvrII fragment was inserted into the PmeI-AvrII site of each of a series of five vectors, each containing a different SSP gene (WO2010/057246), resulting in the genetic constructs designated pFN045, pFN046, pFN047, pFN048 and pFN049. These comprise the genes encoding the SSPs P0$^{PE}$, p38, p19, 35S:V2 and V2, respectively. Each of the SSP genes was under the control of the FP1 promoter and ocs3' transcription termination/polyadenylation region except in the construct pFN048 where the V2 coding region was under the control of the constitutive CaMV 35S promoter. The SSP gene in each case was within the T-DNA region of the constructs, adjacent to the right border (RB) of the T-DNA. A sixth construct, pFN050 which lacked any SSP coding sequence, was made by digesting pFN045 with AhdI and NheI followed by recircularisation with DNA ligase to delete the FP1:P0$^{PE}$ gene. Each of the six constructs comprised an NptII selectable marker gene within the T-DNA and adjacent to the left border of the T-DNA. All of the constructs had an RK2 origin of replication for maintenance of the plasmids in Agrobacterium.

Transformation of A. thaliana with ARA Expression Vectors in Combination with SSPs To transform the genotype MC49 of Arabidopsis, which is a fad2/fae1 double mutant with high linoleic acid levels in its seed lipid, plants were treated by the floral dip method (Clough and Bent, 1998) with A. tumefaciens strain GV3101 separately transformed with each of the six constructs pFN045-pFN050. The treated plants were grown to maturity and $T_1$ seeds harvested from them were plated on MS media containing kanamycin to select for transformed $T_1$ plants. Screening for GFP expression in the seed was also used as a visual marker for transformed $T_1$ seeds. The seedlings which survived on MS/Kan plates or which were obtained from GFP-positive seeds were transferred to soil and grown to maturity for $T_2$ seeds. The numbers of transformed plants obtained were 5, 14, 32, 8, 23 and 24 for the transformations with pFN045, pFN046, pFN047, pFN048, pFN049 and pFN050, respectively. It was discovered at this stage that the gene encoding p38 in pFN046 was not functional and therefore plants transformed with the vector pFN046 were considered as additional controls i.e. essentially the same as for pFN050.

About 100 pooled $T_2$ seeds were taken from each transformed plant for fatty acid composition determination of seed lipid by FAME preparation and GC analysis. Six $T_2$ seedlings from each transgenic line were also grown to produce $T_3$ seeds.

The fatty acid composition in total lipid extracted from the $T_2$ seeds was determined using GC. The analysis showed a range of levels of ARA and the intermediates EDA (20:2ω6) and DGLA (20:3ω6) in the $T_2$ populations. The data for ARA is shown in FIGS. 13 and 14.

FIG. 13 shows a box-plot analysis of the ARA level in the lipid of the populations of the $T_2$ seeds. It was evident that the median ($50^{th}$ percentile) level of ARA in the populations of seeds which contained the FP1:p19 and 35S:V2 genes in addition to the ARA biosynthetic genes was significantly higher than in seeds containing the defective FP1:p38 gene or the control T-DNA from pFP050 which did not contain an SSP gene. The average ARA levels for seeds transformed with genes encoding p19 and V2 were greater than for seeds transformed with the p38 gene or those without an SSP (FIG. 14). One FP1:p19 and two FP1:V2 lines exhibited about 19%, 20% and 23% ARA, respectively. These were outliers and therefore not included in the calculations for the box-plot analysis. Fewer plants transformed with the T-DNAs comprising the genes FP1:$P0^{PE}$ and 35S:V2 survived compared to the other constructs; it is thought that these genes could be detrimental to plant health in the MC49 background.

Not only were the ARA levels significantly different among the constructs, the levels in seed lipid of the first intermediate of the pathway from LA to ARA, namely EDA (20:20ω6), was observed to be lower in lines expressing either V2 or p19 than in seeds lacking an SSP or containing the p38 construct (FIG. 15). In $T_3$ seeds, one population containing the construct expressing p19 exhibited 38% ARA as a percentage of total fatty acids in the seed lipid.

A range of transgenic $T_3$ lines were progressed to the $T_4$ generation. The levels of ARA in the $T_4$ seeds expressing V2 were either the same as compared to the previous generation, or indeed exhibited increased levels compared to their T3 parents (FIG. 16). The lines expressing p19 showed more varied ARA levels. The ARA level was decreased in some lines while in others it was the same or increased compared to the T3 parents. In contrast, the lines containing the defective p38 gene or lacking an SSP generally showed a decline in the level of ARA and an increase in the levels of intermediates (FIG. 18). In some of these lines, ARA was reduced to about 1% and levels of EDA had increased to about 20%. The mean levels of ARA in $T_4$ seeds were higher for lines expressing p19 and V2 compared to lines expressing p38 or lacking an SSP (FIG. 17).

This experiment showed that the expression of an SSP in seeds of a transgenic plant along with additional genes for a LC-PUFA biosynthetic pathway not only increased the level of production of the desired fatty acid in the first generation of progeny, but also stabilised the level of the fatty acid production in later generations such as the third or fourth generation of progeny. The increased fatty acid production was accompanied by decreased levels of intermediate fatty acids in the biosynthetic pathway. The SSP's p19 and V2 expressed from seed-specific promoters were preferred. The construct designed to express the p38 SSP was defective and no useful data were obtained with this construct. The V2 SSP and its homologs from other viruses are thought to be particularly preferred because they allow maximal expression of the biosynthetic pathway genes and the simultaneous silencing of other genes in the same cells in the developing seed.

Example 12

Assaying Sterol Content and Composition in Oils

The phytosterols from 12 vegetable oil samples purchased from commercial sources in Australia were characterised by GC and GC-MS analysis as O-trimethylsilyl ether (OTMSi-ether) derivatives as described in Example 1. Sterols were identified by retention data, interpretation of mass spectra and comparison with literature and laboratory standard mass spectral data. The sterols were quantified by use of a 5β(H)-Cholan-24-ol internal standard. The basic phytosterol structure and the chemical structures of some of the identified sterols are shown in FIG. 19 and Table 25.

The vegetable oils analysed were from: sesame (*Sesamum indicum*), olive (*Olea europaea*), sunflower (*Helianthus annus*), castor (*Ricinus communis*), canola (*Brassica napus*), safflower (*Carthamus tinctorius*), peanut (*Arachis hypogaea*), flax (*Linum usitatissimum*) and soybean (*Glycine max*). In decreasing relative abundance, across all of the oil samples, the major phytosterols were: β-sitosterol (range 28-55% of total sterol content), Δ5-avenasterol (isofucosterol) (3-24%), campesterol (2-33%), Δ5-stigmasterol (0.7-18%), Δ7-stigmasterol (1-18%) and Δ7-avenasterol (0.1-5%). Several other minor sterols were identified, these were: cholesterol, brassicasterol, chalinasterol, campestanol and eburicol. Four C29:2 and two C30:2 sterols were also detected, but further research is required to complete identification of these minor components. In addition, several other unidentified sterols were present in some of the oils but due to their very low abundance, the mass spectra were not intense enough to enable identification of their structures.

The sterol contents expressed as mg/g of oil in decreasing amount were: canola oil (6.8 mg/g), sesame oil (5.8 mg/g), flax oil (4.8-5.2 mg/g), sunflower oil (3.7-4.1 mg/g), peanut oil (3.2 mg/g), safflower oil (3.0 mg/g), soybean oil (3.0 mg/g), olive oil (2.4 mg/g), castor oil (1.9 mg/g). The % sterol compositions and total sterol content are presented in Table 26.

TABLE 25

IUPAC/systematic names of identified sterols.

| Sterol No. | Common name(s) | IUPAC/Systematic name |
|---|---|---|
| 1 | cholesterol | cholest-5-en-3β-ol |
| 2 | brassicasterol | 24-methylcholesta-5,22E-dien-3β-ol |
| 3 | chalinasterol/24-methylene cholesterol | 24-methylcholesta-5,24(28)E-dien-3β-ol |
| 4 | campesterol/24-methyl-cholesterol | 24-methylcholest-5-en-3β-ol |
| 5 | campestanol/24-methyl-cholestanol | 24-methylcholestan-3β-ol |
| 7 | Δ5-stigmasterol | 24-ethylcholesta-5,22E-dien-3β-ol |
| 9 | ergost-7-en-3β-ol | 24-methylcholest-7-en-3β-ol |
| 11 | eburicol | 4,4,14-trimthylergosta-8,24(28)-dien-3β-ol |

TABLE 25-continued

IUPAC/systematic names of identified sterols.

| Sterol No. | Common name(s) | IUPAC/Systematic name |
|---|---|---|
| 12 | β-sitosterol/24-ethylcholesterol | 24-ethylcholest-5-en-3β-ol |
| 13 | D5-avenasterol/isofucosterol | 24-ethylcholesta-5,24(28)Z-dien-3β-ol |
| 19 | D7-stigmasterol/stigmast-7-en-3b-ol | 24-ethylcholest-7-en-3β-ol |
| 20 | D7-avenasterol | 24-ethylcholesta 7,24(28)-dien-3β-ol |

Among all the seed oil samples, the major phytosterol was generally β-sitosterol (range 30-57% of total sterol content). There was a wide range amongst the oils in the proportions of the other major sterols: campesterol (2-17%), Δ5-stigmasterol (0.7-18%), Δ5-avenasterol (4-23%), Δ7-stigmasterol (1-18%). Oils from different species had a different sterol profile with some having quite distinctive profiles. In the case of canola oil, it had the highest proportion of campesterol (33.6%), while the other species samples generally had lower levels, e.g. up to 17% in peanut oil. Safflower oil had a relatively high proportion of Δ7-stigmasterol (18%), while this sterol was usually low in the other species oils, up to 9% in sunflower oil. Because they were distinctive for each species, sterol profiles can therefore be used to help in the identification of specific vegetable or plant oils and to check their genuineness or adulteration with other oils.

TABLE 26

Sterol content and composition of assayed plant oils.

| Sterol number* | Sterol common name | Sesame | Olive | Sunflower | Sunflower cold-pressed | Castor | Canola | Safflower | Safflower cold-pressed | Peanut | Flax (linseed) | Flax (linseed) | Soybean |
|---|---|---|---|---|---|---|---|---|---|---|---|---|---|
| 1 | cholesterol | 0.2 | 0.8 | 0.2 | 0.0 | 0.1 | 0.3 | 0.2 | 0.1 | 0.2 | 0.4 | 0.4 | 0.2 |
| 2 | brassicasterol | 0.1 | 0.0 | 0.0 | 0.0 | 0.3 | 0.1 | 0.0 | 0.0 | 0.0 | 0.2 | 0.2 | 0.0 |
| 3 | chalinasterol/24-methylene cholesterol | 1.5 | 0.1 | 0.3 | 0.1 | 1.1 | 2.4 | 0.2 | 0.1 | 0.9 | 1.5 | 1.4 | 0.8 |
| 4 | campesterol/24-methylcholesterol | 16.2 | 2.4 | 7.4 | 7.9 | 8.4 | 33.6 | 12.1 | 8.5 | 17.4 | 15.7 | 14.4 | 16.9 |
| 5 | campestanol/24-methylcholestanol | 0.7 | 0.3 | 0.3 | 0.1 | 0.9 | 0.2 | 0.8 | 0.8 | 0.3 | 0.2 | 0.2 | 0.7 |
| 6 | C29:2* | 0.0 | 0.0 | 0.1 | 0.2 | 0.0 | 0.1 | 0.5 | 0.5 | 0.0 | 1.2 | 1.3 | 0.1 |
| 7 | Δ5-stigmasterol | 6.4 | 1.2 | 7.4 | 7.2 | 18.6 | 0.7 | 7.0 | 4.6 | 6.9 | 5.1 | 5.8 | 17.6 |
| 8 | unknown | 0.5 | 1.3 | 0.7 | 0.6 | 0.8 | 0.7 | 0.7 | 1.3 | 0.4 | 0.7 | 0.6 | 1.3 |
| 9 | ergost-7-en-3β-ol | 0.1 | 0.1 | 1.9 | 1.8 | 0.2 | 0.4 | 2.7 | 4.0 | 1.4 | 1.4 | 1.4 | 1.0 |
| 10 | unknown | 0.0 | 1.3 | 0.9 | 0.8 | 1.2 | 0.9 | 1.8 | 0.7 | 1.2 | 0.7 | 0.5 | 0.7 |
| 11 | eburicol | 1.6 | 1.8 | 4.1 | 4.4 | 1.5 | 1.0 | 1.9 | 2.9 | 1.2 | 3.5 | 3.3 | 0.9 |
| 12 | β-sitosterol/24-ethylcholesterol | 55.3 | 45.6 | 43.9 | 43.6 | 37.7 | 50.8 | 40.2 | 35.1 | 57.2 | 29.9 | 28.4 | 40.2 |
| 13 | Δ5-avenasterol/isofucosterol | 8.6 | 16.9 | 7.2 | 4.1 | 19.3 | 4.4 | 7.3 | 6.3 | 5.3 | 23.0 | 24.2 | 3.3 |
| 14 | triterpenoid alcohol | 0.0 | 2.4 | 0.9 | 1.1 | 0.0 | 0.0 | 1.6 | 1.9 | 0.0 | 0.0 | 0.0 | 0.9 |
| 15 | triterpenoid alcohol | 0.0 | 0.0 | 0.7 | 0.6 | 0.0 | 0.0 | 2.8 | 1.8 | 0.0 | 0.0 | 0.3 | 0.0 |
| 16 | C29:2* | 0.0 | 0.5 | 0.7 | 0.7 | 1.5 | 1.2 | 2.8 | 1.9 | 2.0 | 1.0 | 0.7 | 0.5 |
| 17 | C29:2* | 1.0 | 0.9 | 2.3 | 2.4 | 0.6 | 0.4 | 1.3 | 1.9 | 0.9 | 1.0 | 1.0 | 1.0 |
| 18 | C30:2* | 0.0 | 0.0 | 0.0 | 0.0 | 1.9 | 0.0 | 0.0 | 0.0 | 0.0 | 0.0 | 0.0 | 0.0 |
| 19 | Δ7-stigmasterol/stigmast-7-en-3β-ol | 2.2 | 7.1 | 9.3 | 10.9 | 2.3 | 0.9 | 10.5 | 18.3 | 1.1 | 7.9 | 8.7 | 5.6 |
| 20 | Δ7-avenasterol | 1.3 | 0.1 | 4.0 | 3.6 | 0.6 | 0.2 | 2.0 | 4.7 | 0.7 | 0.4 | 0.4 | 0.6 |
| 21 | unknown | 0.7 | 7.1 | 0.9 | 0.8 | 0.0 | 0.4 | 0.3 | 0.4 | 0.0 | 3.0 | 3.6 | 0.0 |
| 22 | unknown | 0.3 | 0.0 | 0.3 | 0.9 | 0.0 | 0.0 | 1.2 | 1.3 | 0.2 | 0.1 | 0.0 | 0.3 |
| 23 | unknown | 0.2 | 0.2 | 0.3 | 0.3 | 0.2 | 0.1 | 0.3 | 0.2 | 0.2 | 0.1 | 0.2 | 0.5 |
| 24 | unknown | 0.0 | 3.1 | 0.9 | 1.3 | 0.6 | 0.4 | 0.2 | 0.4 | 0.7 | 1.7 | 1.9 | 0.8 |
| 25 | unknown | 0.9 | 0.4 | 0.3 | 0.5 | 0.3 | 0.1 | 0.5 | 0.7 | 0.3 | 0.1 | 0.1 | 0.6 |
| 26 | C30:2 | 2.2 | 6.0 | 4.6 | 5.7 | 1.4 | 0.6 | 1.0 | 1.2 | 1.2 | 1.2 | 1.1 | 5.2 |
| 27 | unknown | 0.0 | 0.4 | 0.4 | 0.3 | 0.3 | 0.2 | 0.1 | 0.2 | 0.3 | 0.1 | 0.0 | 0.3 |
| | Sum | 100.0 | 100.0 | 100.0 | 100.0 | 100.0 | 100.0 | 100.0 | 100.0 | 100.0 | 100.0 | 100.0 | 100.0 |
| | Total sterol (mg/g oil) | 5.8 | 2.4 | 4.1 | 3.7 | 1.9 | 6.8 | 3.2 | 3.0 | 3.2 | 4.8 | 5.2 | 3.0 |

C29:2* and and C30:2* denotes a C29 sterol with two double bonds and a C30 sterol with two double bonds, respectively Two samples each of sunflower and safflower were compared, in each case one was produced by cold pressing of seeds and unrefined, while the other was not cold-pressed and refined. Although some differences were observed, the two sources of oils had similar sterol compositions and total sterol contents, suggesting that processing and refining had little effect on these two parameters. The sterol content among the samples varied three-fold and ranged from 1.9 mg/g to 6.8 mg/g. Canola oil had the highest and castor oil the lowest sterol content.

Example 13

Increasing Accumulation of DHA at the sn-2 TAG Position

The present inventors considered that DHA accumulation at the sn-2 position in TAG could be increased by co-expressing an 1-acyl-glycerol-3-phosphate acyltransferase (LPAAT) together with the DHA biosynthesis pathway such as conferred by the GA7 construct or its variants. Preferred LPAATs are those which can act on polyunsaturated C22 fatty acyl-CoA as substrate, resulting in increased insertion of the polyunsaturated C22 chain at the sn-2 position of LPA to form PA, relative to the endogenous LPAAT. Cytoplasmic LPAAT enzymes often display varied substrate preferences, particularly where the species synthesises and accumulates unusual fatty acids in TAG. A LPAAT2 from *Limnanthes douglasii* was shown to use erucoyl-CoA (C22:1-CoA) as a substrate for PA synthesis, in contrast to an LPAAT1 from the same species that could not utilise the C22 substrate (Brown et al., 2002).

Known LPAATs were considered and a number were selected for testing, including some which were not expected to increase DHA incorporation at the sn-2 position, as controls. The known LPAATs included: *Arabidopsis thaliana* LPAAT2: (SEQ ID NO: 63, Accession No. ABG48392, Kim et al., 2005), *Limnanthes alba* LPAAT (SEQ ID NO: 64, Accession No. AAC49185, Lassner et al., 1995), Saccharomyces cerevisiae Slc1p (SEQ ID NO: 65, Accession No. NP_010231, Zou et al., 1997), *Mortierella alpina* LPAATI (SEQ ID NO: 67, Accession No. AED33305; U.S. Pat. No. 7,879,591) and *Brassica napus* LPAATs (SEQ ID NO: 68 and SEQ ID NO:69, Accession Nos ADC97479 and ADC97478 respectively). These were chosen to cover three groups of LPAAT enzymes: 1) control plant seed LPAATs with typically low activity on unusual long-chain polyunsaturated fatty acids (including the *Arabidopsis* and *Brassica* LPAATs), 2. LPAATs that had previously been demonstrated to act on C22 fatty acids by using C22 acyl-CoA as substrate, in this case erucic acid C22:1 (including the *Limnanthes* and *Saccharomyces* LPAATs), 3. LPAATs which the inventors considered likely to be able to utilise long-chain polyunsaturated fatty acids such as EPA and DHA as substrates (including the *Mortierella* LPAAT).

The *Arabidopsis* LPAAT2 (also designated LPAT2) is an endoplasmic reticulum-localised enzyme shown to have activity on C16 and C18 substrates, however activity on C20 or C22 substrates was not tested (Kim et al., 2005). *Limnanthes alba* LPAAT2 was demonstrated to insert a C22:1 acyl chain into the sn-2 position of PA, although the ability to use DHA as a substrate was not tested (Lassner et al., 1995). The selected *S. cerevisiae* LPAAT Slc1p was shown to have activity using 22:1-CoA in addition to 18:1-CoA as substrates, indicating a broad substrate specificity with respect to chain length (Zou et al., 1997). Again, DHA-CoA and other LC-PUFAs were not tested as substrates. The *Mortierella* LPAAT had previously been shown to have activity on EPA and DHA fatty acid substrates in transgenic *Yarrowia lipolytica* (U.S. Pat. No. 7,879,591).

Additional LPAATs were identified by the inventors. *Micromonas pusilla* is a microalga that produces and accumulates DHA in its oil, although the positional distribution of the DHA on TAG in this species has not been confirmed. The *Micromonas pusilla* LPAAT (SEQ ID NO: 66, Accession No. XP_002501997) was identified by searching the *Micromonas pusilla* genomic sequence using the *Arabidopsis* LPAAT2 as a BLAST query sequence. Several candidate sequences emerged and the sequence XP 002501997 was synthesised for testing as a likely LPAAT enzyme with activity on C22 LC-PUFA. The *Ricinus communis* LPAAT was annotated as a putative LPAAT in the castor genome sequence (Chan et al., 2010). Four candidate LPAATs from the castor genome were synthesised and tested in crude leaf lysates of infiltrated *N. benthamiana* leaf tissue. The candidate sequence described here showed LPAAT activity.

A number of candidate LPAATs were aligned with known LPAATs on a phylogenetic tree (FIG. 20). It was noted that the putative *Micromonas* LPAAT did not cluster with the putative C22 LPAATs but was a divergent sequence.

As an initial test of various LPAATs for their ability to use DHA-CoA as substrate, chimeric genetic constructs are made for constitutive expression of exogenous LPAATs in *N. benthamiana* leaves, each under the control of the 35S promoter, as follows: 35S:Arath-LPAAT2 (*Arabidopsis* ER LPAAT); 35S:Ricco-LPAAT2; 35S:Limal-LPAAT (*Limnanthes alba* LPAAT); 35S:Sacce-Slc1p (*S. cerevisiae* LPAAT); 35S:Micpu-LPAAT (*Micromonas pusilla* LPAAT); 35S: Moral-LPAATI (*Mortierella alpina* LPAAT). A 35S:p19 construct lacking an exogenous LPAAT is used as a control in the experiment. Each of these constructs is introduced via *Agrobacterium* into *N. benthamiana* leaves as described in Example 1, and 5 days after infiltration, the treated leaf zones are excised and ground to make leaf lysates. Each lysate includes the exogenous LPAAT as well as the endogenous enzymes for synthesizing LPA. In vitro reactions are set up by separately adding $^{14}$C-labelled-OA, -LA or -ALA (C18 substrates), -ARA (a C20 substrate) and -DHA (C22) to the lysates, in triplicate. Reactions are incubated at 25° C. and the level of incorporation of the $^{14}$C labelled fatty acids into PA determined by TLC. The ability of each LPAAT to use DHA relative to ARA and the C18 fatty acids is calculated. The meadowfoam, *Mortierella* and *Saccharomyces* LPAATs were found to have activity on DHA substrate, with radiolabelled PA appearing for these but not the other LPAATs. All LPAATs were confirmed active by a similar oleic acid feed.

To test LPAAT activity in seeds, several of the protein coding sequences or LPAATs are inserted into a binary vector under the control of a conlinin (pLuCnl1) promoter. The resultant genetic constructs containing the chimeric genes, Cnl1:Arath-LPAAT (negative control), Cnl1:Limal-LPAAT, Cnl:Sacce-Slc1p, and Cnl1:Moral-LPAAT, respectively, are then used transform *B. napus* and *A. thaliana* plants to generate stable transformants expressing the LPAATs in a seed-specific manner. The transformed plants having the Cnl1: LPAAT constructs are crossed with plants expressing the GA7 construct or its variants (Example 5) which produce DHA in the seed to result in increased incorporation of DHA at the sn-2 position of TAG. The constructs are also used to transform *B. napus*, *C. sativa* and *A. thaliana* plants that already contain the GA7 construct and variants thereof (Examples 2 to 5) to generate progeny carrying both the parental and LPAAT genetic constructs. Increased incorporation of DHA at the sn-2 position of TAG is expected relative to the incorporation in plants lacking the LPAAT encoding transgenes. Oil content is also improved in the seeds, particularly for seeds producing higher levels of DHA, counteracting the trend seen in *Arabidopsis* seed as described in Example 2.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/660,392 filed 15 Jun. 2012, U.S. 61/663,344 filed 22 Jun. 2012, U.S. 61/697,676 filed 6 Sep. 2012 and U.S. 61/782,680 filed 14 Mar. 2013, the entire contents of each of which are incorporated herein by reference.

All publications discussed and/or referenced herein are incorporated herein in their entirety.

This application incorporates herein by reference U.S. 61/660,392 filed 15 Jun. 2012, U.S. 61/663,344 filed 22 Jun. 2012 and U.S. 61/697,676 filed 6 Sep. 2012.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

References
Abbadi et al. (2004) Plant Cell 16: 2734-2748.
Abbott et al. (1998) Science 282:2012-2018.
Abdullah et al. (1986) Biotech. 4:1087.
Agaba et al. (2004) Marine Biotechnol. (NY) 6:251-261.
Alvarez et al. (2000) Theor Appl Genet 100:319-327.
Armbrust et al. (2004) Science 306:79-86.
Attila Kereszt et al. (2007) Nature Protocols 2:948-952.
Baumberger et al. (2007) Curr. Biol. 17:1609-1614.
Baumlein et al. (1991) Mol. Gen. Genet. 225:459-467.
Baumlein et al. (1992) Plant J. 2:233-239.
Beaudoin et al. (2000) Proc. Natl. Acad. Sci. U.S.A. 97:6421-6426.
Beclin et al. (2002) Curr. Biol. 12:684-688.
Berberich. et al. (1998) Plant Mol. Biol. 36:297-306.
Bortolamiol et al. (2007) Curt. Biol. 17:1615-1621.
Broun et al. (1998) Plant J. 13:201-210.
Brown et al. (2002) Biochem J. 364:795-805.
Chapman et al. (2004) Gen. Dev. 18:1179-1186.
Chen et al. (2004) The Plant Cell 16:1302-1313.
Cheng et al. (1996) Plant Cell Rep. 15:653-657.
Cheng et al. (2010) Transgenic Res 19: 221-229.
Chikwamba et al. (2003) Proc. Natl. Acad. Sci. U.S.A. 100: 11127-11132.
Cho et al. (1999a) J. Biol. Chem. 274:471-477.
Cho et al. (1999b) J. Biol. Chem. 274:37335-37339.
Clough and Bent (1998) Plant J. 16:735-43.
Coutu et al. (2007) Transgenic Res. 16: 771-781.
Damude et al. (2006). Proc Natl Acad Sci USA 103: 9446-9451.
Denic and Weissman (2007) Cell 130:663-677.
Domergue et al (2002) Eur. J. Biochem. 269:4105-4113.
Domergue et al. (2002) Eur. J. Biochem. 269:4105-4113.
Domergue et al. (2003) J. Biol. Chem. 278: 35115-35126.
Domergue et al. (2005) Biochem. J. 1389: 483-490.
Dunoyer et al. (2004) The Plant Cell 16:1235-1250.
Ellerstrom et al. (1996) Plant Mol. Biol. 32:1019-1027.
Fujimura et al. (1985) Plant Tissue Culture Lett. 2:74.
Fukunaga (2009) EMBO J. 28:545-55.
Gamez et al. (2003) Food Res International 36: 721-727.
Garcia-Maroto et al. (2002) Lipids 37:417-426.
Girke et al. (1998) Plant J. 15:39-48.
Glick et al. (2008) Proc. Natl. Acad. Sci. U.S.A. 105-157-161.
Grant et al. (1995) Plant Cell Rep. 15:254-258.
Hall et al. (1991) Proc. Natl. Acad. Sci. USA 88:9320-9324
Hamilton and Baulcombe (1999) Science 286:950-952.
Hamilton et al. (1997) Gene 200:107-16.
Harayama (1998). Trends Biotechnol. 16: 76-82.
Hastings et al. (2001) Proc. Natl. Acad. Sci. U.S.A. 98:14304-14309.
Hinchee et al. (1988) Biotechnology 6:915-922.
Hoffmann et al. (2008) J. Biol. Chem. 283:22352-22362.
Hong et al. (2002a) Lipids 37:863-868.
Horiguchi et al. (1998) Plant Cell Physiol. 39:540-544.
Horvath et al. (2000) Proc. Natl. Acad. Sci. U.S.A. 97:1914-1919.
Huang et al. (1999) Lipids 34:649-659.
Inagaki et al. (2002) Biosci. Biotechnol. Biochem. 66:613-621.
Johansen and Carrington (2001) Plant Physiol. 126-930-938.
Kajikawa et al. (2004) Plant Mol. Biol. 54:335-52.
Kajikawa et al. (2006) FEBS Lett 580:149-154.
Kim et al. (2005) Plant Cell. 2005 1073-89.
Knutzon et al. (1998) J. Biol Chem. 273:29360-6.
Koziel et al. (1996) Plant Mol. Biol. 32:393-405.
Lassner (1995) Plant Physiol. 109:1389-94.
Leonard et al. (2000) Biochem. J. 347:719-724.
Leonard et al. (2000b) Biochem. J. 350:765-770.
Leonard et al. (2002) Lipids 37:733-740.
Lewsey et al. (2007) Plant J. 50:240-252.
Lo et al. (2003) Genome Res. 13:455-466.
Lu and Kang (2008) Plant Cell Rep. 27:273-8.
Mallory et al. (2002) Nat. Biotech. 20:622-625.
Marangoni et al. (1995) Trends in Food Sci. Technol. 6: 329-335.
Meesapyodsuk et al. (2007) J Biol Chem 282: 20191-20199.
Meng et al. (2008) J. Gen. Virol. 89:2349-2358.
Meyer et al. (2003) Biochem. 42:9779-9788.
Meyer et al. (2004) Lipid Res 45:1899-1909.
Michaelson et al. (1998a) J. Biol. Chem. 273:19055-19059.
Michaelson et al. (1998b) FEBS Lett. 439:215-218.
Murashige and Skoog (1962) Physiologia Plantarum 15:473-497.
Napier et al. (1998) Biochem. J. 330:611-614.
Needleman and Wunsch (1970) J. Mol. Biol. 48:443-453.
Niedz et al. (1995) Plant Cell Reports 14:403.
Ow et al. (1986) Science 234:856-859.
Parker-Barnes et al. (2000) Proc. Natl. Acad. Sci. USA 97:8284-8289.
Pereira et al. (2004a) Biochem. J. 378:665-671.
Pereira et al. (2004b) Biochem. J. 384:357-366.
Perrin et al. (2000) Mol Breed 6:345-352.
Petrie et al. (2010a) Metab. Eng. 12:233-240.
Petrie et al. (2010b) Plant Methods 11:6:8.
Petrie et al. (2012) Transgenic Res. 21:139-147.
Potenza et al. (2004) In Vitro Cell Dev Biol—Plant 40:1-22.
Prasher et al (1985) Biochem. Biophys. Res. Commun. 127: 31-36.
Qi et al. (2002) FEBS Lett. 510:159-165.
Qi et al. (2004) Nat. Biotech. 22: 739-745.
Qiu et al. (2001) J. Biol. Chem. 276:31561-31566.
Reddy and Thomas (1996) Nat. Biotech. 14:639-642.
Reddy et al. (1993) Plant Mol. Biol. 22:293-300.
Robert et al. (2005) Func. Plant Biol. 32:473-479.
Robert et al. (2009) Marine Biotech 11:410-418.
Ruiz-Lopez et al. (2012) Transgenic Res. 21:139-147.

Saha et al. (2006) Plant Physiol. 141:1533-1543.
Saito et al. (2000) Eur. J. Biochem. 267:1813-1818.
Sakuradani et al. (1999) Gene 238:445-453.
Sato et al. (2004) Crop Sci. 44: 646-652.
Sakuradani et al. (2005) Appl. Microbiol. Biotechnol. 66:648-654.
Sayanova et al. (2006) J Biol Chem 281: 36533-36541.
Sayanova et al. (1997) Proc. Natl. Acad. Sci. U.S.A. 94:4211-4216.
Sayanova et al. (2003) FEBS Lett. 542:100-104.
Sayanova et al. (2006) Planta 224:1269-1277.
Sayanova et al. (2007) Plant Physiol 144:455-467.
Singh et al. (2005) Curr. Opin. in Plant Biol. 8:197-203.
Speranza et al. (2012) Process Biochemistry (In Press).
Sperling et al. (2000) Eur. J. Biochem. 267:3801-3811.
Sperling et al. (2001) Arch. Biochm. Biophys. 388:293-8.
Sprecher et al. (1995) J. Lipid Res. 36:2471-2477.
Spychalla et al., (1997) Proc. Natl. Acad. Sci. U.S.A. 94:1142-1147.
Stalker et al. (1998) J. Biol. Chem. 263:6310-6314.
Thillet et al. (1988) J. Biol. Chem. 263:12500-12508.
Tonon et al. (2003) FEBS Lett. 553:440-444.
Toriyama et al. (1986) Theor. Appl. Genet. 205:34.
Trautwein (2001) European J. Lipid Sci. and Tech. 103:45-55.
Tvrdik (2000) J. Cell Biol. 149:707-718.
Venegas-Caleron et al. (2010) Prog. Lipid Res. 49:108-119.
Voinnet et al. (2003) Plant J. 33:949-956.
Wallis and Browse (1999) Arch. Biochem. Biophys. 365:307-316.
Watts and Browse (1999b) Arch. Biochem. Biophys. 362: 175-182.
Weiss et al. (2003) Int. J. Med. Microbiol. 293:95:106.
Whitney et al. (2003) Planta 217:983-992.
Winans (1988) J. Bacteriol. 170:4047-54.
Wood (2009) Plant Biotechnol J. 7:914-24.
Wu et al. (2005) Nat. Biotech. 23:1013-1017.
Yang et al. (2003) Planta 216:597-603.
Zank et al. (2002) Plant J. 31:255-268.
Zank et al. (2005) WO 2005/012316
Zhang et al. (2004) FEBS Lett. 556:81-85.
Zhang et al. (2006) 20:3255-3268.
Zhang et al. (2007a) FEBS Letters 581: 315-319.
Zhang et al. (2008) Yeast 25: 21-27.
Zhou et al. (2007) Phytochem. 68:785-796.
Zhou et al. (2008) Insect Mol Biol 17: 667-676.
Zou et al. (1997) Plant Cell. 9:909-23.

The invention claimed is:

1. A process for producing polyunsaturated fatty acids in an esterified form, the process comprising hydrolyzing or trans-esterifying the polyunsaturated fatty acids in triacylglycerols (TAG) in extracted plant lipid whose total fatty acid content comprises
   (a) a total monounsaturated fatty acid content which comprises oleic acid,
   (b) a total saturated fatty acid content which comprises palmitic acid and, if present, myristic acid (C14:0),
   (c) a total ω6 fatty acid content which comprises linoleic acid (LA),
   (d) a total ω3 fatty acid content which comprises α-linolenic acid (ALA), docosahexaenoic acid (DHA) and one or more of stearidonic acid (SDA), eicosapentaenoic acid (EPA), docosapentaenoic acid (DPA) and eicosatetraenoic acid (ETA),
   (e) less than 1% myristic acid (C14:0), and
   (f) less than 4% eicosatrienoic acid (ETrA),
   wherein
   (i) a level of DHA of between 7% and 20% is present in the total fatty acid content of the extracted plant lipid, wherein at least 70% of the DHA is esterified at the sn-1 or sn-3 position of the TAG,
   (ii) a level of palmitic acid between 2% and 16% is present in the total fatty acid content of the extracted plant lipid,
   (iii) a level of oleic acid between 1% and 60% is present in the total fatty acid content of the extracted plant lipid,
   (iv) a level of linoleic acid (LA) between 4% and 35% is present in the total fatty acid content of the extracted plant lipid,
   (v) a level of α-linolenic acid (ALA) between 4% and 40% is present in the total fatty acid content of the extracted plant lipid,
   (vi) the total saturated fatty acid content of the extracted plant lipid is between 4% and 25% of the total ratty acid content,
   (vii) the ratio of the total ω6 fatty acid content to the total ω3 fatty acid content of the extracted plant lipid is between 0.1 and 3.0, and
   (viii) at least 70% of the total fatty acid content of the extracted plant lipid is esterified in the form of TAG, thereby producing the polyunsaturated fatty acids in an esterified form.

2. The process of claim 1 in which the extracted plant lipid has one or more or all of the following features
   i) a level of palmitic acid between 2% and 15% is present in the total fatty acid content of the extracted plant lipid,
   ii) a level of oleic acid between about 3% and about 30%, is present in the total fatty acid content of the extracted plant lipid,
   iii) a level of linoleic acid (LA) between 4% and about 20% is present in the total fatty acid content of the extracted plant lipid,
   iv) a level of α-linolenic acid (ALA) between about 10% and about 35% is present in the total fatty acid content of the extracted plant lipid,
   v) a level of γ-linolenic acid (GLA) less than 4% is present in the total fatty acid content of the extracted plant lipid,
   vi) a level of stearidonic acid (SDA) between 0.05% and about 7% is present in the total fatty acid content of the extracted plant lipid,
   vii) a level of eicosatetraenoic acid (ETA) between 0.05% and about 4% is present in the total fatty acid content of the extracted plant lipid,
   viii) a level of eicosatrienoic acid (ETrA) between 0.05% and about 2% is present in the total fatty acid content of the extracted plant lipid,
   ix) the extracted plant lipid comprises ω6-docosapentaenoic acid ($22:5^{\Delta4,7,10,13,16}$) in its total fatty acid content,
   x) a level of SDA of less than about 0.1%, EPA of less than about 0.1% and ETA of less than about 0.1% in its total fatty acid content,
   xi) the total saturated fatty acid content in the extracted plant lipid is between about 4% and about 20% of the total fatty acid content,
   xii) the total monounsaturated fatty acid content in the extracted plant lipid is between about 4% and about 35% of the total fatty acid content,
   xiii) the extracted plant lipid comprises a total polyunsaturated fatty acid content comprising the total ω6 fatty acid content and the total ω3 fatty acid content, wherein the total polyunsaturated fatty acid content in the extracted plant lipid is between about 20% and about 75% of the total fatty acid content,
   xiv) the total ω6 fatty acid content in the extracted plant lipid is less than 20% of the total fatty acid content, xv) the extracted plant lipid comprises new ω6 fatty acids in the total ω6 fatty acid content, wherein the level of new ω6 fatty acids in the extracted plant lipid is less than about 10% of the total fatty acid content, xvi) the total ω3 fatty acid content in the extracted plant lipid is between 36% and about 65% of the total fatty acid content, xvii) the extracted plant lipid comprises new ω3 fatty acids in the total ω3 fatty acid content, wherein the level of new ω3 fatty acids in the extracted plant lipid is between 9% and about 33% of the total fatty acid content, xviii) the ratio of the total ω6 fatty acid content to the total ω3 fatty acid content in the extracted plant lipid is between about 0.1 and about 0.5, xix) the extracted plant lipid comprises new ω3 fatty acids in the total ω3 fatty acid content and new ω6 fatty acids in the total ω6 fatty acid content, wherein the ratio of the new ω6 fatty acids to the new ω3 fatty acids in the extracted plant lipid is between about 0.1 and about 1, xx) the extracted plant lipid has a fatty acid composition based on an efficiency of conversion of oleic acid to DHA of at least about 10%, xxi) the extracted plant lipid has a fatty acid composition based on an efficiency of conversion of LA to DHA of at least about 15%, xxii) the extracted plant lipid has a fatty acid composition based on an efficiency of conversion of ALA to DHA of at least about 17%, xxiii) the total fatty acid content in the extracted plant lipid has less than 1% C20:1, xxiv) at least about 80% of the total fatty acid content of the extracted plant lipid is esterified in the form of TAG, xxv) the extracted plant lipid comprises diacylglycerol (DAG), xxvi) the extracted plant lipid comprises less than about 10% free (non-esterified) fatty acids and/or phospholipid, and xxvii) the extracted plant lipid comprises tri-DHA TAG (TAG 66:18).

3. The process of claim 1, wherein the extracted plant lipid is in the form of an oil, and wherein the oil comprises one or more sterols.

4. The process of claim 3, wherein the oil comprises less than 10 mg of sterols/g of oil.

5. The process of claim 3, wherein the oil comprises one or more or all of campesterol, Δ5-stigmasterol, eburicol, β-sitosterol, Δ5-avenasterol, Δ7-stigmasterol, and Δ7-avenasterol.

6. The process of claim 3, wherein the oil has a level of cholesterol of less than about 0.5% by weight.

7. The process of claim 1, wherein the extracted plant lipid is in the form of an oil from an oilseed.

8. The process of claim 7, wherein the oilseed is a *Brassica* sp. oilseed or a *Camelina sativa* oilseed.

9. The process of claim 7, wherein the oilseed is canola seed.

10. The process of claim 8 in which the extracted plant lipid has one or more or all of the following features
   i) a level of palmitic acid between 2% and 15% is present in the total fatty acid content of the extracted plant lipid,
   ii) a level of oleic acid between about 3% and about 30% is present in the total fatty acid content of the extracted plant lipid,
   iii) a level of linoleic acid (LA) between 4% and about 20% is present in the total fatty acid content of the extracted plant lipid,
   iv) a level of α-linolenic acid (ALA) is present in the total fatty acid content of the extracted plant lipid,
   v) a level of γ-linolenic acid (GLA) less than 4% is present in the total fatty acid content of the extracted plant lipid,
   vi) a level of stearidonic acid (SDA) between 0.05% and about 4% is present in the total fatty acid content of the extracted plant lipid,
   vii) a level of eicosatetraenoic acid (ETA) between 0.05% and about 4% is present in the total fatty acid content of the extracted plant lipid,
   viii) a level of eicosatrienoic acid (ETrA) between 0.05% and about 2% is present in the total fatty acid content of the extracted plant lipid,
   ix) the extracted plant lipid comprises ω6-docosapentaenoic acid ($22:5^{\Delta4,7,10,13,16}$) in its total fatty acid content,
   x) a level of SDA of less than about 0.1%, EPA of less than about 0.1% and ETA of less than about 0.1% in its total fatty acid content,
   xi) the total saturated fatty acid content in the extracted plant lipid is between about 4% and about 20% of the total fatty acid content,
   xii) the total monounsaturated fatty acid content in the extracted plant lipid is between about 4% and about 35% of the total fatty acid content,
   xiii) the extracted plant lipid comprises a total polyunsaturated fatty acid content comprising the total ω6 fatty acid content and the total ω3 fatty acid content, wherein the total polyunsaturated fatty acid content in the extracted plant lipid is between about 20% and about 75% of the total fatty acid content,
   xiv) the total ω6 fatty acid content in the extracted plant lipid is less than 20% of the total fatty acid content,
   xi) the extracted plant lipid comprises new ω6 fatty acids in the total ω6 fatty acid content, wherein the level of new ω6 fatty acids in the extracted plant lipid is less than about 10% of the total fatty acid content,
   xvi) the total ω3 fatty acid content in the extracted plant lipid is between 36% and about 65% of the total fatty acid content,
   xvii) the extracted plant lipid comprises new ω3 fatty acids in the total ω3 fatty acid content, wherein the level of new ω3 fatty acids in the extracted plant lipid is between 9% and about 33% of the total fatty acid content,
   xviii) the ratio of the total ω6 fatty acid content to the total ω3 fatty acid content in the extracted plant lipid is between about 0.1 and about 0.5,
   xix) the extracted plant lipid comprises new ω3 fatty acids in the total ω3 fatty acid content and new ω6 fatty acids in the total ω6 fatty acid content, wherein the ratio of the new ω6 fatty acids to the new ω3 fatty acids in the extracted plant lipid is between about 0.1 and about 1,
   xx) the extracted plant lipid has a fatty acid composition based on an efficiency of conversion of oleic acid to DHA of at least about 10%,
   xxi) the extracted plant lipid has a fatty acid composition based on an efficiency of conversion of LA to DHA of at least about 15%,
   xxii) the extracted plant lipid has a fatty acid composition based on an efficiency of conversion of ALA to DHA of at least about 17%,
   xxiii) the total fatty acid content in the extracted plant lipid has less than 1% C20:1,
   xxiv) at least about 80% of the total fatty acid content of the extracted plant lipid is esterified in the form of TAG,
   xxv) the extracted plant lipid comprises diacylglycerol (DAG), xxvi) the extracted plant lipid comprises less than about 10% free (non-esterified) fatty acids and/or phospholipid, and xxvii) the extracted plant lipid comprises tri-DHA TAG (TAG 66:18).

11. The process of claim 8, wherein the oil comprises less than 10 mg of sterols/g of oil.

12. The process of claim 8, wherein the oil comprises one or more or all of campesterol, Δ5-stigmasterol, eburicol, β-sitosterol, Δ5-avenasterol, Δ7-stigmasterol, and Δ7-avenasterol.

13. The process of claim 8, wherein the oil has a level of cholesterol of less than about 0.5% by weight.

14. The process of claim 1, wherein the polyunsaturated fatty acids in an esterified form are ethyl esters of the polyunsaturated fatty acids.

15. The process of claim 14 in which the extracted plant lipid has one or more or all of the following features i) a level of palmitic acid between 2% and 15% is present in the total fatty acid content of the extracted plant lipid, ii) a level of oleic acid between about 3% and about 30% is present in the total fatty acid content of the extracted plant lipid, iii) a level of linoleic acid (LA) between 4% and about 20% is present in the total fatty acid content of the extracted plant lipid, iv) a level of α-linolenic acid (ALA) between about 10% and about 35% is present in the total fatty acid content of the extracted plant lipid, v) a level of γ-linolenic acid (GLA) less than 4% is present in the total fatty acid content of the extracted plant lipid, vi) a level of stearidonic acid (IDA) between 0.05% and about 4% is present in the total fatty acid content of the extracted plant lipid, vii) a level of eicosatetraenoic acid (ETA) between 0.05% and about 4% is present in the total fatty acid content of the extracted plant lipid, viii) a level of eicosatrienoic acid (ETrA) between 0.05% and about 2% is present in the total fatty acid content of the extracted plant lipid, ix) the extracted plant lipid comprises ω6-docosapentaenoic acid ($22:5^{\Delta4,7,10,13,16}$) in its total fatty acid content, x) a level of IDA of less than about 0.1%, EPA of less than about 0.1% and ETA of less than about 0.1% in its total fatty acid content, xi) the total saturated fatty acid content in the extracted plant lipid is between about 4% and about 20% of the total fatty acid content, xii) the total monounsaturated fatty acid content in the extracted plant lipid is between about 4% and about 35% of the total fatty acid content, xiii) the extracted plant lipid comprises a total polyunsaturated fatty acid content comprising the total ω6 fatty acid content and the total ω3 fatty acid content, wherein the total polyunsaturated fatty acid content in the extracted plant lipid is between about 20% and about 75% of the total fatty acid content, xiv) the total ω6 fatty acid content in the extracted plant lipid is less than 20% of the total fatty acid content, xv) the extracted plant lipid comprises new ω6 fatty acids in the total ω6 fatty acid content, wherein the level of new ω6 fatty acids in the extracted plant lipid is less than about 10% of the total fatty acid content, xvi) the total ω3 fatty acid content in the extracted plant lipid is between 36% and about 65% of the total fatty acid content, xvii) the extracted plant lipid comprises new ω3 fatty acids in the total ω3 fatty acid content, wherein the level of new ω3 fatty acids in the extracted plant lipid is between 9% and about 33% of the total fatty acid content, xviii) the ratio of the total ω6 fatty acid content to the total ω3 fatty acid content in the extracted plant lipid is between about 0.1 and about 0.5, xix) the extracted plant lipid comprises new ω3 fatty acids in the total ω3 fatty acid content and new ω6 fatty acids in the total ω6 fatty acid content, wherein the ratio of the new ω6 fatty acids to the new ω3 fatty acids in the extracted plant lipid is between about 0.1 and about 1, xx) the extracted plant lipid has a fatty acid composition based on an efficiency of conversion of oleic acid to DHA of at least about 10%, xxi) the extracted plant lipid has a fatty acid composition based on an efficiency of conversion of LA to DHA of at least about 15%, xxii) the extracted plant lipid has a fatty acid composition based on an efficiency of conversion of ALA to DHA of at least about 17%, xxiii) the total fatty acid content in the extracted plant lipid has less than 1% C20:1, xxiv) at least about 80% of the total fatty acid content of the extracted plant lipid is esterified in the form of TAG, xxv) the extracted plant lipid comprises diacylglycerol (DAG), and xxvi) the extracted plant lipid comprises less than about 10% free (non-esterified) fatty acids and/or phospholipid, and xxvii) the extracted plant lipid comprises tri-DHA TAG (TAG 66:18).

16. The process of claim 14, wherein the extracted plant lipid is in the form of an oil, and wherein the oil comprises one or more sterols.

17. The process of claim 16, wherein the oil comprises less than 10 mg of sterols/g of oil.

18. The process of claim 16, wherein the oil comprises one or more or all of campesterol, Δ5-stigmasterol, eburicol, β-sitosterol, Δ5-avenasterol, Δ7-stigmasterol, and Δ7-avenasterol.

19. The process of claim 16, wherein the oil has a level of cholesterol of less than about 0.5% by weight.

20. The process of claim 14, wherein the extracted plant lipid is in the form of an oil from an oilseed.

21. The process of claim 20, wherein the oilseed is a *Brassica* sp. oilseed or a *Camelina sativa* oilseed.

22. The process of claim 1, wherein a level of eicosapentaenoic acid (EPA) of less than 4% is present in the total fatty acid content of the extracted plant lipid.

23. The process of claim 1, wherein a level of docosapentaenoic acid (DPA) of between 0.05% and 8% is present in the total fatty acid content of the extracted plant lipid.

24. The process of claim 1, wherein the extracted plant lipid comprises less than 0.1% ω6-docosapentaenoic acid ($22:5^{\Delta4,7,10,13,16}$) in its fatty acid content.

25. The process of claim 1, wherein at least 80% of the DHA esterified in the form of TAG is at the sn-1 or sn-3 position of the TAG.

26. The process of claim 1, wherein the most abundant DHA-containing TAG species in the extracted plant lipid is DHA/18:3/18:3 (TAG 58:12).

27. The process of claim 1, wherein a level of docosahexaenoic acid (DHA) of between 8% and 20% is present in the total fatty acid content of the extracted plant lipid.

28. The process of claim 1, wherein a level of docosahexaenoic acid (DHA) of between 10% and 20% is present in the total fatty acid content of the extracted plant lipid.

29. The process of claim 1, wherein level of docosahexaenoic acid (DHA) of between 11% and 20% is present in the total fatty acid content of the extracted plant lipid.

30. A process for producing polyunsaturated fatty acids in an esterified form, the process comprising hydrolyzing or transesterifying the polyunsaturated fatty acids in triacylglycerols (TAG) in extracted plant lipid whose total fatty acid content comprises
  (a) a total monounsaturated fatty acid content which comprises oleic acid,
  (b) a total saturated fatty acid content which comprises palmitic acid and, if present, myristic acid (C14:0),
  (c) a total ω6 fatty acid content which comprises linoleic ad (LA),
  (d) a total ω3 fatty acid content which comprises e linolenic acid (ALA) and docosahexaenoic acid (DHA),
  (e) less than 1% myristic acid (G14:0), and
  (f) less than 4% eicosatrienoic acid (ETrA),
  wherein
  (i) a level of DHA of about 3%, about 4%, about 5% or about 6% is present in the total fatty acid content of the extracted plant lipid, wherein at least 70% of the DHA is esterified at the sn-1 or sn-3 position of the TAG,
  (ii) a level of palmitic acid between 2% and 16% is present in the total fatty acid content of the extracted plant lipid,
  (iii) a level of oleic acid between 1% and 60% is present in the total fatty acid content of the extracted plant lipid,
  (iv) a level of linoleic acid (LA) between 4% and 35% is present in the total fatty acid content of the extracted plant lipid,
  (v) a level of α-linolenic acid (ALA) between 4% and 40% is present in the total fatty acid content of the extracted plant lipid,
  (vi) the total saturated fatty acid content of the extracted plant lipid is between 4% and 25% of the total fatty acid content,
  (vii) the ratio of the total ω6 fatty acid content to the total ω3fatty acid content of the extracted plant lipid is between 0.1 and 3.0, and
  (viii) at least 70% of the total fatty acid content of the extracted plant lipid is esterified at the form of TAG, thereby producing the polyunsaturated fatty acids in an esterified form.

31. The process of claim 30 in which the extracted plant lipid has one or more or all of the following features
  i) a level of palmitic acid between 2% and 15% is present in the total fatty acid content of the extracted plant lipid,
  ii) a level of oleic acid between about 3% and about 30% is present in the total fatty acid content of the extracted plant lipid,
  iii) a level of linoleic acid (LA) between about 4% and about 20% is present in the total fatty acid content of the extracted plant lipid,
  iv) a level of α-linolenic acid (ALA) between about 10% and about 35% is present in the total fatty acid content of the extracted plant lipid,
  v) a level of γ-linolenic acid (GLA) less than 4% is present in the total fatty acid content of the extracted plant lipid,
  vi) a level of stearidonic acid (SDA) between 0.05% and about 7% is present in the total fatty acid content of the extracted plant lipid,
  vii) a level of eicosatetraenoic acid (ETA) between 0.05% and about 4% is present in the total fatty acid content of the extracted plant lipid,
  viii) a level of eicosatrienoic acid (ETrA) between 0.05% and about 2% is present in the total fatty acid content of the extracted plant lipid,
  ix) the extracted plant lipid comprises ω6-docosapentaenoic acid ($22:5^{66\ 4,7,10,13,16}$) in its total fatty acid content,
  x) a level of SDA of less than about 0.1%, EPA of less than about 0.1% and ETA of less than about 0.1% in its total fatty acid content,
  xi) the total saturated fatty acid content in the extracted plant lipid is between about 4% and about 20% of the total fatty acid content,
  xii) the total monounsaturated fatty acid content in the extracted plant lipid is between about 4% and about 35% of the total fatty acid content,
  xiii) the extracted plant lipid comprises a total polyunsaturated fatty acid content comprising the total ω6 fatty acid content and the total ω3 fatty acid content, wherein the total polyunsaturated fatty acid content in the extracted plant lipid is between about 20% and about 75% of the total fatty acid content,
  xiv) the total ω6 fatty acid content in the extracted plant lipid is less than 20% of the total fatty acid content,
  xv) the extracted plant lipid comprises new ω6 fatty acids in the total ω6 fatty acid content, wherein the level of new ω6 fatty acids in the extracted plant lipid is less than about 10% of the total fatty acid content,
  xvi) the total ω3 fatty acid content in the extracted plant lipid is between 36% and about 65% of the total fatty acid content,
  xvii) the extracted plant lipid comprises new ω3 fatty acids in the total ω3 fatty acid content, wherein the level of new ω3 fatty acids in the extracted plant lipid is between 9% and about 33% of the total fatty acid content,
  xviii) the ratio of the total ω6 fatty acid content to the total ω3fatty acid content in the extracted plant lipid is between about 0.1and about 0.5,
  xix) the extracted plant lipid comprises new ω3 fatty acids in the total ω3 fatty acid content and new ω6 fatty acids in the total ω6 fatty acid content, wherein the ratio of the new ω6fatty acids to the new ω3 fatty acids in the extracted plant lipid is between about 0.1 and about 1,
  xx) the extracted plant lipid has a fatty acid composition based on an efficiency of conversion of oleic acid to DHA of at least about 10%,
  xxi) the extracted plant lipid has a fatty acid composition based on an efficiency of conversion of LA to DHA of at least about 15%,
  xxii) the extracted plant lipid has a fatty acid composition based on an efficiency of conversion of ALA to DHA of at least about 17%,
  xxiii) the total fatty acid content in the extracted plant lipid has less than 1% C20:1,
  xxiv) at least about 80% of the total fatty acid content of the extracted plant lipid is esterified in the form of TAG,
  xxv) the extracted plant lipid comprises diacylglycerol (DAG),
  xxvi) the extracted plant lipid comprises less than about 10% free (non-esterified) fatty acids and/or phospholipid, and
  xxvii) the extracted plant lipid comprises tri-DHA TAG (TAG 66:18).

32. The process of claim 30, wherein the extracted plant lipid is in the form of an oil, and wherein the oil comprises one or more sterols.

33. The process of claim 32, wherein the oil comprises less than 10 mg of sterols/g of oil.

34. The process of claim 32, wherein the oil comprises one or more or all of campesterol, Δ5-stigmasterol, eburicol, β-sitosterol, Δ5-avenasterol, Δ7-stigmasterol, and Δ7-avenasterol.

35. The process of claim 32, wherein the oil is has a level of cholesterol of less than about 0.5% by weight.

36. The process of claim 30, wherein the extracted plant lipid is in the form of an oil from an oilseed.

37. The process of claim 36, wherein the oilseed is a *Brassica* sp oilseed or a *Camelina sativa* oilseed.

38. The process of claim 36, wherein the oilseed is canola seed.

39. The process of claim 30, wherein a level of oleic acid between 30% and 60% is present in the total fatty acid content of the extracted plant lipid.

40. The process of claim 30, wherein the polyunsaturated fatty acids in an esterified form are ethyl esters of the polyunsaturated fatty acids.

41. The process of claim 40, wherein a level of oleic acid between 30% and 60% is present in the total fatty acid content of the extracted plant lipid.

42. The process of claim 1 which comprises transesterifying the polyunsaturated fatty acids in TAG in the extracted plant lipid.

43. The process of claim 30 which comprises transesterifying the polyunsaturated fatty acids in TAG in the extracted plant lipid.

* * * * *

SEQUENCE LISTING

```
<160> NUMBER OF SEQ ID NOS: 72

<210> SEQ ID NO 1
<211> LENGTH: 21527
<212> TYPE: DNA
<213> ORGANISM: Artificial Sequence
<220> FEATURE:
<223> OTHER INFORMATION: pJP3416-GA7 nucleotide sequence.

<400> SEQUENCE: 1
tcctgtggtt ggcatgcaca tacaaatgga cgaacggata aaccttttca cgcccttta      60 aatatccgat tattctaata aacgctcttt tctcttaggt ttacccgcca atatatcctg    120
tcaaacactg atagtttaaa ctgaaggcgg gaaacgacaa tctgctagtg gatctcccag    180
tcacgacgtt gtaaaacggg cgccccgcgg aaagcttgcg gccgcccgat ctagtaacat    240
agatgacacc gcgcgcgata atttatccta gtttgcgcgc tatattttgt tttctatcgc    300
gtattaaatg tataattgcg ggactctaat cataaaaacc catctcataa ataacgtcat    360
gcattacatg ttaattatta cgtgcttaac gtaattcaac agaaattata tgataatcat    420
cgcaagaccg gcaacaggat tcaatcttaa gaaactttat tgccaaatgt ttgaacgatc    480
ggcgcgcctc attagtgagc cttctcagcc tttccgttaa cgtagtagtg ctgtcccacc    540
ttatcaaggt tagagaaagt agccttccaa gcaccgtagt aagagagcac cttgtagttg    600
agtccccact tcttagcgaa aggaacgaat cttctgctaa cctcaggctg tctgaattga    660
ggcatatcag ggaagaggtg gtggataacc tgacagttaa ggtatcccat aagccagttc    720
acgtatcctc tagaaggatc gatatcaacg gtgtgatcaa cagcgtagtt aacccaagaa    780
aggtgcttat cagatggaac aacagggagg tgagtatgag aagtagagaa gtgagcgaaa    840
aggtacatgt aagcgatcca gtttccgaaa gtgaaccacc agtaagcaac aggccaagag    900
tatccagtag caagcttgat aacagcggtt ctaacaacat gagaaacgag catccaagaa    960
gcctcttcgt agttcttctt acggagaact tgtctagggt ggagaacgta gatccagaaa   1020
gcttgaacaa gaagtccaga ggtaacagga acgaaagtcc aagcttgaag tctagcccaa   1080
```

```
gctctagaga atcctctagg tctgttatcc tcaacagcag tgttgaagaa agccacagca    1140
ggagtggtat caagatccat atcgtgtcta accttttgag gggtagcatg gtgcttgtta    1200
tgcatctggt tccacatctc accagaagta gaaagtccga atccacaagt catagcctga    1260
agtctcttgt ccacgtaaac agatccggta agagagttat gtccaccctc atgttgaacc    1320
catccacatc tagctccgaa gaaagcaccg taaacaacag aagcaatgat agggtatcca    1380
gcgtacataa gagcagttcc aagagcgaat gtagcaagaa gctcgagaag tctgtaagcc    1440
acatgggtga tagaaggctt gaagaatcca tctctctcaa gctcagcacg ccatctagcg    1500
aaatcctcaa gcataggagc atcctcagac tcagatctct tgatctcagc aggtctagaa    1560
ggcaaagctc taagcatctt ccaagccttg agagaacgca tgtggaattc tttgaaagcc    1620
tcagtagcat cagcaccagt gttagcaagc atgtagaaga tcacagatcc accagggtgc    1680
ttgaagttag tcacatcgta ctcaacgtcc tcaactctaa cccatctagt ctcgaaagta    1740
gcagcaagct catgaggctc aagagtctta agatcaacag gagcagtaga agcatcccta    1800
gcatcaagag cctcagcaga agatttagac ctggtaagtg gagatctagg agaagatctt    1860
ccatcagtct taggagggca catggtatgg taattgtaaa tgtaattgta atgttgtttg    1920
ttgtttgttg ttgttggtaa ttgttgtaaa agatcctcgt gtatgttttt aatcttgttt    1980
gtatcgatga gttttggttt gagtaaagag tgaagcggat gagttaattt ataggctata    2040
aaggagattt gcatggcgat cacgtgtaat aatgcatgca cgcatgtgat tgtatgtgtg    2100
tgctgtgaga gagaagctct taggtgtttg aagggagtga caagtggcga agaaaaacaa    2160
ttctccgcgg ctgcatgcta tgtgtaacgt gtagctaatg ttctggcatg gcatcttatg    2220
aacgattctt tttaaaaaca aggtaaaaac ttaacttcat aaaattaaaa aaaaaacgt    2280
ttactaagtt ggtttaaaag gggatgagac tagtagattg gttggttggt ttccatgtac    2340
cagaaggctt accctattag ttgaaagttg aaactttgtt ccctactcaa ttcctagttg    2400
tgtaaatgta tgtatatgta atgtgtataa aacgtagtac ttaaatgact aggagtggtt    2460
cttgagaccg atgagagatg ggagcagaac taaagatgat gacataatta agaacgaatt    2520
tgaaaggctc ttaggtttga atcctattcg agaatgtttt tgtcaaagat agtggcgatt    2580
ttgaaccaaa gaaaacattt aaaaaatcag tatccggtta cgttcatgca aatagaaagt    2640
ggtctaggat ctgattgtaa ttttagactt aaagagtctc ttaagattca atcctggctg    2700
tgtacaaaac tacaaataat atattttaga ctatttggcc ttaactaaac ttccactcat    2760
tatttactga ggttagagaa tagacttgcg aataaacaca ttcccgagaa atactcatga    2820
tcccataatt agtcagaggg tatgccaatc agatctaaga acacacattc cctcaaattt    2880
taatgcacat gtaatcatag tttagcacaa ttcaaaaata atgtagtatt aaagacagaa    2940
atttgtagac ttttttttgg cgttaaaaga agactaagtt tatacgtaca ttttattta    3000
agtggaaaac cgaaattttc catcgaaata tatgaattta gtatatatat ttctgcaatg    3060
tactattttg ctattttggc aactttcagt ggactactac tttattacaa tgtgtatgga    3120
tgcatgagtt tgagtataca catgtctaaa tgcatgcttt gtaaaacgta acggaccaca    3180
aaagaggatc catacaaata catctcatag cttcctccat tattttccga cacaaacaga    3240
gcattttaca acaattacca acaacaacaa acaacaaaca acattacaat tacatttaca    3300
attaccatac catggaattc gcccagcctc ttgttgctat ggctcaagag caatacgctg    3360
ctatcgatgc tgttgttgct cctgctatct tctctgctac tgattctatc ggatggggac    3420
ttaagcctat ctcttctgct actaaggact tgcctcttgt tgagtctcct acacctctca    3480
```

```
tcctttcttt gcttgcttac ttcgctatcg ttggatctgg actcgtttac agaaaggttt    3540
tccctagaac cgtgaaggga caagatccat tccttttgaa ggctcttatg cttgctcaca    3600
acgtgttcct tatcggactt tctctttaca tgtgcctcaa gcttgtgtac gaggcttacg    3660
ttaacaagta ctctttctgg ggaaacgctt acaaccctgc tcaaactgag atggctaagg    3720
ttatctggat cttctacgtg agcaagatct acgagttcat ggataccttc atcatgctcc    3780
tcaagggaaa tgttaaccag gttagcttcc ttcacgttta ccatcacgga tctatctctg    3840
gaatctggtg gatgattact tacgctgctc ctggtggtga tgcttacttc tctgctgctc    3900
ttaactcttg ggttcacgtg tgtatgtaca cctactattt tatggctgcc gtgcttccta    3960
aggacgagaa aactaagaga aagtacctct ggtggggaag ataccttact caaatgcaga    4020
tgttccagtc cttcatgaac cttctccagg ctgtttacct tctctactct tcatctcctt    4080
accctaagtt tatcgctcag ctcctcgtgg tgtacatggt tactcttctc atgcttttcg    4140
gaaacttcta ctacatgaag caccacgcta gcaagtgatg aggcgcgccg ggccgccgcc    4200
atgtgacaga tcgaaggaag aaagtgtaat aagacgactc tcactactcg atcgctagtg    4260
attgtcattg ttatatataa taatgttatc tttcacaact tatcgtaatg catgtgaaac    4320
tataacacat taatcctact tgtcatatga taacactctc cccatttaaa actcttgtca    4380
atttaaagat ataagattct ttaaatgatt aaaaaaaata tattataaat tcaatcactc    4440
ctactaataa attattaatt attatttatt gattaaaaaa atacttatac taatttagtc    4500
tgaatagaat aattagattc tagtctcatc cccttttaaa ccaacttagt aaacgttttt    4560 tttttttaatt ttatgaagtt aagttttttac cttgtttttta aaaagaatcg ttcataagat    4620
gccatgccag aacattagct acacgttaca catagcatgc agccgcggag aattgttttt    4680
cttcgccact tgtcactccc ttcaaacacc taagagcttc tctctcacag cacacacata    4740
caatcacatg cgtgcatgca ttattacacg tgatcgccat gcaaatctcc tttatagcct    4800
ataaattaac tcatccgctt cactctttac tcaaaccaaa actcatcgat acaaacaaga    4860
ttaaaaacat acacgaggat cttttacaac aattaccaac aacaacaaac aacaaacaac    4920
attacaatta catttacaat taccatacca tgcctccaag ggactcttac tcttatgctg    4980
ctcctccttc tgctcaactt cacgaagttg atactcctca agagcacgac aagaaagagc    5040
ttgttatcgg agatagggct tacgatgtta ccaacttcgt taagagacac cctggtggaa    5100
agatcattgc ttaccaagtt ggaactgatg ctaccgatgc ttacaagcag ttccatgtta    5160
gatctgctaa ggctgacaag atgcttaagt ctcttccttc tcgtcctgtt cacaagggat    5220
actctccaag aagggctgat cttatcgctg atttccaaga gttcaccaag caacttgagg    5280
ctgagggaat gttcgagcct tctcttcctc atgttgctta cagacttgct gaggttatcg    5340
ctatgcatgt tgctggtgct gctcttatct ggcatggata cactttcgct ggaatcgcta    5400
tgcttggagt tgttcaggga agatgtggat ggcttatgca tgagggtgga cattactctc    5460
tcactggaaa cattgctttc gacagagcta tccaagttgc ttgttacgga cttggatgtg    5520
gaatgtctgg tgcttggtgg cgtaaccagc ataacaagca ccatgctact cctcaaaagc    5580
ttcagcacga tgttgatctt gataccctc ctctcgttgc tttccatgag agaatcgctg    5640
ctaaggttaa gtctcctgct atgaaggctt ggctttctat gcaagctaag cttttcgctc    5700
ctgttaccac tcttccttgtt gctcttggat ggcagcttta ccttcatcct agacacatgc    5760
tcaggactaa gcactacgat gagcttgcta tgctcggaat cagatacgga cttgttggat    5820
```

```
accttgctgc taactacggt gctggatacg ttctcgcttg ttaccttctt tacgttcagc    5880
ttggagctat gtacatcttc tgcaacttcg ctgtttctca tactcacctc cctgttgttg    5940
agcctaacga gcatgctact tgggttgagt acgctgctaa ccacactact aactgttctc    6000
catcttggtg gtgtgattgg tggatgtctt accttaacta ccagatcgag caccacccttt  6060
acccttctat gcctcaattc agacacccta agatcgctcc tagagttaag cagcttttcg    6120
agaagcacgg acttcactac gatgttagag atacttcga ggctatggct gatactttcg     6180
ctaaccttga taacgttgcc catgctcctg agaagaaaat gcagtaatga gatcgttcaa    6240
acatttggca ataaagtttc ttaagattga atcctgttgc cggtcttgcg atgattatca    6300
tataatttct gttgaattac gttaagcacg taataattaa catgtaatgc atgacgttat    6360
ttatgagatg ggtttttatg attagagtcc cgcaattata catttaatac gcgatagaaa    6420
acaaaatata gcgcgcaaac taggataaat tatcgcgcgc ggtgtcatct atgttactag    6480
atcggtcgat taaaaatccc aattatattt ggtctaattt agtttggtat tgagtaaaac    6540
aaattcgaac caaaccaaaa tataaatata tagtttttat atatatgcct ttaagacttt    6600
ttatagaatt ttcttttaaaa aatatctaga aatatttgcg actcttctgg catgtaatat    6660
ttcgttaaat atgaagtgct ccatttttat taactttaaa taattggttg tacgatcact    6720
ttcttatcaa gtgttactaa aatgcgtcaa tctctttgtt cttccatatt catatgtcaa    6780
aatctatcaa aattcttata tatcttttc gaatttgaag tgaaatttcg ataatttaaa     6840
attaaataga acatatcatt atttaggtat catattgatt tttatactta attactaaat    6900
ttggttaact ttgaaagtgt acatcaacga aaaattagtc aaacgactaa aataaataaa    6960
tatcatgtgt tattaagaaa attctcctat aagaatattt taatagatca tatgtttgta    7020
aaaaaaatta atttttacta acacatatat ttacttatca aaaatttgac aaagtaagat    7080
taaaataata ttcatctaac aaaaaaaaaa ccagaaaatg ctgaaaaccc ggcaaaaccg    7140
aaccaatcca aaccgatata gttggtttgg tttgattttg atataaaccg aaccaactcg    7200
gtccatttgc accccctaatc ataatagctt taatatttca agatattatt aagttaacgt   7260
tgtcaatatc ctggaaattt tgcaaaatga atcaagccta tatggctgta atatgaatttt  7320
aaaagcagct cgatgtggtg gtaatatgta atttacttga ttctaaaaaa atatcccaag    7380
tattaataat ttctgctagg aagaaggtta gctacgattt acagcaaagc cagaatacaa    7440
agaaccataa agtgattgaa gctcgaaata tacgaaggaa caaatatttt taaaaaaata    7500
cgcaatgact tggaacaaaa gaaagtgata tattttttgt tcttaaacaa gcatcccctc    7560
taaagaatgg cagttttcct ttgcatgtaa ctattatgct cccttcgtta caaaaatttt    7620
ggactactat tgggaacttc ttctgaaaat agtgatagaa cccacacgag catgtgcttt    7680
ccatttaatt ttaaaaacca agaaacatac atacataaca ttccatcagc ctctctctct    7740
ttttattacg gttaatgact taaaacacat cttattatcc catccttaac acctagcagt    7800
gtctttatac gatctcatcg atcaccactt caaaaccatg cagactgctg ctgcccctgg    7860
agctggcatc ggctaggctg ggtgccgcac tgtcccggaa ggtccctagc gacttgttta    7920
gattgatggg accacctctc aacttcctgc tgctgtccct gctgctggat gtcctgcctc    7980
atctggccga ttgcacgctc cagtccctg catgtgcact cgctcctcaa ttgcttaaga    8040
tcatcgcagc agctatcgaa gtgctggctc tgttgccctc ctccacggcc ttggttgtag    8100
tagtagctgc cgccgccctt ctggactttt tcccacagga accgccgaat aattcgatag    8160
aaccacacga gcatgtgctt tcatttattt taaaaaccaa gaaacataca taacatttca    8220
```

```
tcagcctctc tctctctctc tctctctctc tctctctctc tctctcttta      8280
ttacagctgt tacactaact taaaacacat tcatctcatt attattatta ttatccatcc      8340
ttaacaccta gcagtgtctt tgtacgatct cataatcgat caccccttca tcaggtatcc      8400
ttaggcttca ctccaacgtt gttgcagtta cggaacatgt acaccactc atggttctca      8460 acgaactggc aagatctcca agttttccaa aggctaaccc acatgttctc atcggtgtgt      8520
ctgtagtgct ctcccataac tttcttgatg cactcggtag cttctctagc atggtagaat      8580
gggatccttg aaacgtagtg atggagcaca tgagtctcga tgatgtcatg aagatgatt      8640 ccgaggattc cgaactctct atcgatagta gcagcagcac ccttagcgaa agtccactct      8700
tgagcatcgt aatgaggcat agaagaatcg gtgtgctgaa ggaaggtaac gaaaacaagc      8760
cagtggttaa caaggatcca aggacagaac catgtgatga agtaggcca gaatccgaaa      8820 accttgtaag cggtgtaaac agaagtgagg gtagcaagga ttccaagatc agaagaacg      8880 atgtaccagt agtccttctt atcgaaaaca gggctagaag gccagtagtg agacttgaag      8940
aacttagaaa caccagggta aggttgtcca gtagcgttag tagcaaggta aagagaaagt      9000
cctccaagct gttggaacaa gagagcgaaa acagagtaga taggagtttc ctcagcgata      9060
tcgtgaaggc tggtaacttg gtgcttctct ttgaattcct cggcggtgta aggaacgaaa      9120
accatatctc tggtcatgtg tccagtagcc ttatggtgct tagcatgaga gaacttccag      9180
ctgaagtaag gaaccataac aagagagtgg agaacccatc caacggtatc gttaacccat      9240
ccgtagttag agaaagcaga atgtccacac tcatgtccaa ggatccagat tccgaatccg      9300
aaacaagaga tagaacac gtaagcagac caagcagcga atctaaggaa ttcgttaggg      9360
agaagaggga tgtaggtaag tccaacgtaa gcgatagcag agatagccac gatatctctc      9420
accacgtaag acatagactt cacgagagat ctctcgtaac agtgcttagg gatagcgtca      9480
aggatatcct tgatggtgta atctggcacc ttgaaaacgt ttccgaaggt atcgatagcg      9540
gtcttttgct gcttgaaaga tgcaacgttt ccagaacgcc taacggtctt agtagatccc      9600
tcaaggatct cagatccaga cacggtaacc ttagacatgg tatggtaatt gtaaatgtaa      9660
ttgtaatgtt gtttgttgtt tgttgttgtt ggtaattgtt gtaaaatttt tggtggtgat      9720
tggttcttta aggtgtgaga gtgagttgtg agttgtgtgg tgggtttggt gagattgggg      9780
atggtgggtt tatatagtgg agactgagga atggggtcgt gagtgttaac tttgcatggg      9840
ctacacgtgg gttcttttgg gcttacacgt agtattattc atgcaaatgc agccaataca      9900
tatacggtat tttaataatg tgtgggaata caatatgccg agtattttac taattttggc      9960
aatgacaagt gtacatttgg attatcttac ttggcctctc ttgctttaat ttggattatt     10020
tttattctct taccttggcc gttcatattc acatccctaa aggcaagaca gaattgaatg     10080
gtggccaaaa attaaaacga tggatatgac ctacatagtg taggatcaat taacgtcgaa     10140
ggaaaatact gattctctca agcatacgga caagggtaaa taacatagtc accagaacat     10200
aataaacaaa aagtgcagaa gcaagactaa aaaaattagc tatggacatt caggttcata     10260
ttggaaacat cattatccta gtcttgtgac catccttcct cctgctctag ttgagaggcc     10320
ttgggactaa cgagaggtca gttgggatag cagatcctta tcctggacta gcctttctgg     10380
tgtttcagag tcttcgtgcc gccgtctaca tctatctcca ttaggtctga agatgactct     10440
tcacaccaac gacgtttaag gtctctatcc tactcctagc ttgcaatacc tggcttgcaa     10500
tacctggagc atcgtgcacg atgattggat actgtggagg aggagtgttt gctgatttag     10560
```

```
agctcccggt tgggtgattt gacttcgatt tcagtttagg cttgttgaaa ttttcaggt    10620
tccattgtga agcctttaga gcttgagctt ccttccatgt taatgccttg atcgaatact    10680
cctagagaaa agggaagtcg atctctgagt attgaaatcg aagtgcacat tttttttcaa    10740
cgtgtccaat caatccacaa acaaagcaga agacaggtaa tctttcatac ttatactgac    10800
aagtaatagt cttaccgtca tgcataataa cgtctcgttc cttcaagagg ggttttccga    10860
catccataac gacccgaagc ctcatgaaag cattagggaa gaactttttgg ttcttcttgt    10920
catggccttt ataggtgtca gccgagctcg ccaattcccg tccgactggc tccgcaaaat    10980
attcgaacgg caagttatgg acttgcaacc ataactccac ggtattgagc aggacctatt    11040
gtgaagactc atctcatgga gcttcagaat gtggttgtca gcaaaccaat gaccgaaatc    11100
catcacatga cggacgtcca gtgggtgagc gaaacgaaac aggaagcgcc tatctttcag    11160
agtcgtgagc tccacaccgg attccggcaa ctacgtgttg ggcaggcttc gccgtattag    11220
agatatgttg aggcagaccc atctgtgcca ctcgtacaat tacgagagtt gtttttttg    11280
tgattttcct agtttctcgt tgatggtgag ctcatattct acatcgtatg gtctctcaac    11340
gtcgtttcct gtcatctgat atcccgtcat ttgcatccac gtgcgccgcc tcccgtgcca    11400
agtccctagg tgtcatgcac gccaaattgg tggtggtgcg ggctgccctg tgcttcttac    11460
cgatgggtgg aggttgagtt tggggggtctc cgcggcgatg gtagtgggtt gacggtttgg    11520
tgtgggttga cggcattgat caatttactt cttgcttcaa attctttggc agaaaacaat    11580
tcattagatt agaactggaa accagagtga tgagacggat taagtcagat tccaacagag    11640
ttacatctct taagaaataa tgtaaccccct ttagacttta tatatttgca attaaaaaaa    11700
taatttaact tttagacttt atatatagtt ttaataacta agtttaaccca ctctattatt    11760
tatatcgaaa ctatttgtat gtctcccctc taaataaact tggtattgtg tttacagaac    11820
ctataatcaa ataatcaata ctcaactgaa gtttgtgcag ttaattgaag ggattaacgg    11880
ccaaaatgca ctagtattat caaccgaata gattcacact agatggccat ttccatcaat    11940
atcatcgccg ttcttcttct gtccacatat cccctctgaa acttgagaga cacctgcact    12000
tcattgtcct tattacgtgt tacaaaatga aacccatgca tccatgcaaa ctgaagaatg    12060
gcgcaagaac ccttcccctc catttcttat gtggcgacca tccatttcac catctcccgc    12120
tataaaacac ccccatcact tcacctagaa catcatcact acttgcttat ccatccaaaa    12180
gataccccact tttacaacaa ttaccaacaa caacaaacaa caaacaacat tacaattaca    12240
tttacaatta ccataccatg ccacctagcg ctgctaagca aatgggagct tctactggtg    12300
ttcatgctgg tgttactgac tcttctgctt tcaccagaaa ggatgttgct gatagacctg    12360
atctcaccat cgttggagat tctgtttacg atgctaaggc tttcagatct gagcatcctg    12420
gtggtgctca tttcgtttct ttgttcggag gaagagatgc tactgaggct ttcatggaat    12480
accatagaag ggcttggcct aagtctagaa tgtctagatt ccacgttgga tctcttgctt    12540
ctactgagga acctgttgct gctgatgagg gataccttca actttgtgct aggatcgcta    12600
agatggtgcc ttctgttttct tctggattcg ctcctgcttc ttactgggtt aaggctggac    12660
ttatccttgg atctgctatc gctcttgagg cttacatgct ttacgctgga aagagacttc    12720
tcccttctat cgttcttgga tggcttttcg ctcttatcgg tcttaacatc cagcatgatg    12780
ctaaccatgg tgctttgtct aagtctgctt ctgttaacct tgctcttgga ctttgtcagg    12840
attggatcga aggatctatg atcctttggc ttcaagagca tgttgttatg caccacctcc    12900
acactaacga tgttgataag gatcctgatc aaaaggctca cggtgctctt agactcaagc    12960
```

```
ctactgatgc ttggtcacct atgcattggc ttcagcatct ttaccttttg cctggtgaga    13020
ctatgtacgc tttcaagctt ttgttcctcg acatctctga gcttgttatg tggcgttggg    13080
agggtgagcc tatctctaag cttgctggat acctctttat gccttctttg cttctcaagc    13140
ttaccttctg ggctagattc gttgcttttgc ctctttacct tgctccttct gttcatactg    13200
ctgtgtgtat cgctgctact gttatgactg gatctttcta cctcgctttc ttcttcttca    13260
tctcccacaa cttcgagggt gttgcttctg ttggacctga tggatctatc acttctatga    13320
ctagaggtgc tagcttcctt aagagacaag ctgagacttc ttctaacgtt ggaggacctc    13380
ttcttgctac tcttaacggt ggactcaact accaaattga gcatcacttg ttccctagag    13440
ttcaccatgg attctaccct agacttgctc ctcttgttaa ggctgagctt gaggctagag    13500
gaatcgagta caagcactac cctactatct ggtctaacct tgcttctacc ctcagacata    13560
tgtacgctct tggaagaagg cctagatcta aggctgagta atgacaagct tatgtgacgt    13620
gaaataataa cggtaaaata tatgtaataa taataataat aaagccacaa agtgagaatg    13680
aggggaaggg gaaatgtgta atgagccagt agccggtggt gctaattttg tatcgtattg    13740
tcaataaatc atgaattttg tggttttat gtgttttttt aaatcatgaa ttttaaattt    13800
tataaaataa tctccaatcg gaagaacaac attccatatc catgcatgga tgtttcttta    13860
cccaaatcta gttcttgaga ggatgaagca tcaccgaaca gttctgcaac tatccctcaa    13920 aagcttttaaa atgaacaaca aggaacagag caacgttcca aagatcccaa acgaaacata    13980
ttatctatac taatactata ttattaatta ctactgcccg gaatcacaat ccctgaatga    14040
ttcctattaa ctacaagcct tgttggcggc ggagaagtga tcggcgcggc gagaagcagc    14100
ggactcggag acgaggcctt ggaagatctg agtcgaacgg gcagaatcag tatttccctt    14160
cgacgttaat tgatcctaca ctatgtaggt catatccatc gttttaattt ttggccacca    14220
ttcaattctg tcttgccttt agggatgtga atatgaacgg ccaaggtaag agaataaaaa    14280
taatccaaat taaagcaaga gaggccaagt aagataatcc aaatgtacac ttgtcattgc    14340
caaaattagt aaaatactcg gcatattgta ttcccacaca ttattaaaat accgtatatg    14400
tattggctgc atttgcatga ataatactac gtgtaagccc aaaagaaccc acgtgtagcc    14460
catgcaaagt taacactcac gaccccattc ctcagtctcc actatataaa cccaccatcc    14520
ccaatctcac caaacccacc acacaactca caactcactc tcacaccta aagaaccaat    14580 caccaccaaa aattttacaa caattaccaa caacaacaaa caacaaacaa cattacaatt    14640
acatttacaa ttaccatacc atgagcgctg ttaccgttac tggatctgat cctaagaaca    14700
gaggatcttc tagcaacacc gagcaagagg ttccaaaagt tgctatcgat accaacggaa    14760
acgtgttctc tgttcctgat ttcaccatca aggacatcct tggagctatc cctcatgagt    14820
gttacgagag aagattggct acctctctct actacgtgtt cagagatatc ttctgcatgc    14880
ttaccaccgg ataccttacc cataagatcc tttaccctct cctcatctct tacacctcta    14940
acagcatcat caagttcact ttctgggccc tttacactta cgttcaagga cttttcggaa    15000
ccggaatctg ggttctcgct catgagtgtg gacatcaagc tttctctgat tacggaatcg    15060
tgaacgattt cgttggatgg acccttcact cttaccttat ggttccttac ttcagctgga    15120
agtactctca tggaaagcac cataaggcta ctggacacat gaccagagat atggttttcg    15180
ttcctgccac caaagaggaa ttcaagaagt ctaggaactt cttcggtaac ctcgctgagt    15240
actctgagga ttctccactt agaacccttt acgagcttct tgttcaacaa cttggaggat    15300
```

```
ggatcgctta cctcttcgtt aacgttacag gacaacctta ccctgatgtt ccttcttgga   15360
aatggaacca cttctggctt acctctccac ttttcgagca aagagatgct ctctacatct   15420
tcctttctga tcttggaatc ctcacccagg gaatcgttct tactctttgg tacaagaaat   15480
tcggaggatg gtccctttc atcaactggt tcgttcctta catctgggtt aaccactggc   15540
tcgttttcat cacattcctt cagcacactg atcctactat gcctcattac aacgctgagg   15600
aatggacttt cgctaagggt gctgctgcta ctatcgatag aaagttcgga ttcatcggac   15660
ctcacatctt ccatgatatc atcgagactc atgtgcttca ccactactgt tctaggatcc   15720
cattctacaa cgctagacct gcttctgagg ctatcaagaa agttatggga aagcactaca   15780
ggtctagcga cgagaacatg tggaagtcac tttggaagtc tttcaggtct tgccaatacg   15840
ttgacggtga taacggtgtt ctcatgttcc gtaacatcaa caactgcgga gttggagctg   15900
ctgagaagta atgaaggggt gatcgattat gagatcgtac aaagacactg ctaggtgtta   15960
aggatggata ataataataa taatgagatg aatgtgtttt aagttagtgt aacagctgta   16020
ataaagagag agagagagag agagagagag agagagagag agagagagag agagaggctg   16080
atgaaatgtt atgtatgttt cttggttttt aaaataaatg aaagcacatg ctcgtgtggt   16140
tctatcgaat tattcggcgg ttcctgtggg aaaaagtcca aagggccgc cgcagctact   16200 actacaacca aggccgtgga ggagggcaac agagccagca cttcgatagc tgctgcgatg   16260
atcttaagca attgaggagc gagtgcacat gcagggact ggagcgtgca atcggccaga   16320
tgaggcagga catccagcag cagggacagc agcaggaagt tgagaggtgg tcccatcaat   16380
ctaaacaagt cgctagggac cttccgggac agtgcggcac ccagcctagc cgatgccagc   16440
tccaggggca gcagcagtct gcatggtttt gaagtggtga tcgatgagat cgtataaaga   16500
cactgctagg tgttaaggat gggataataa gatgtgtttt aagtcattaa ccgtaataaa   16560
aagagagaga ggctgatgga atgttatgta tgtatgtttc ttggttttta aaattaaatg   16620
gaaagcacat gctcgtgtgg gttctatctc gattaaaaat cccaattata tttggtctaa   16680
tttagtttgg tattgagtaa aacaaattcg aaccaaacca aaatataaat atatagtttt   16740
tatatatatg cctttaagac tttttataga atttctttta aaaatatct agaaatattt   16800 gcgactcttc tggcatgtaa tatttcgtta aatatgaagt gctccatttt tattaacttt   16860
aaataattgg ttgtacgatc actttcttat caagtgttac taaatgcgt caatctcttt   16920 gttcttccat attcatatgt caaatctat caaaattctt atatatcttt ttcgaatttg   16980
aagtgaaatt tcgataattt aaaattaaat agaacatatc attatttagg tatcatattg   17040 attttttatac ttaattacta aatttggtta actttgaaag tgtacatcaa cgaaaaatta   17100
gtcaaacgac taaaataaat aaatatcatg tgttattaag aaaattctcc tataagaata   17160
ttttaataga tcatatgttt gtaaaaaaaa ttaattttta ctaacacata tatttactta   17220
tcaaaaattt gacaaagtaa gattaaaata atattcatct aacaaaaaaa aaaccagaaa   17280
atgctgaaaa cccggcaaaa ccgaaccaat ccaaaccgat atagttggtt tggtttgatt   17340
ttgatataaa ccgaaccaac tcggtccatt tgcaccccta atcataatag ctttaatatt   17400
tcaagatatt attaagttaa cgttgtcaat atcctggaaa ttttgcaaaa tgaatcaagc   17460
ctatatggct gtaatatgaa tttaaaagca gctcgatgtg gtggtaatat gtaatttact   17520
tgattctaaa aaaatatccc aagtattaat aatttctgct aggaagaagg ttagctacga   17580
tttacagcaa agccagaata caaagaacca taaagtgatt gaagctcgaa atatacgaag   17640
gaacaaatat ttttaaaaaa atacgcaatg acttggaaca aagaaagtg atatatttt    17700
```

```
tgttcttaaa caagcatccc ctctaaagaa tggcagtttt cctttgcatg taactattat  17760
gctcccttcg ttacaaaaat tttggactac tattgggaac ttcttctgaa aatagtcctg  17820
caggctagta gattggttgg ttggtttcca tgtaccagaa ggcttaccct attagttgaa  17880
agttgaaact ttgttcccta ctcaattcct agttgtgtaa atgtatgtat atgtaatgtg  17940
tataaaacgt agtacttaaa tgactaggag tggttcttga gaccgatgag agatgggagc  18000
agaactaaag atgatgacat aattaagaac gaatttgaaa ggctcttagg tttgaatcct  18060
attcgagaat gttttgtca aagatagtgg cgattttgaa ccaaagaaaa catttaaaaa  18120
atcagtatcc ggttacgttc atgcaaatag aaagtggtct aggatctgat tgtaatttta  18180
gacttaaaga gtctcttaag attcaatcct ggctgtgtac aaaactacaa ataatatatt  18240
ttagactatt tggccttaac taaacttcca ctcattattt actgaggtta gagaatagac  18300
ttgcgaataa acacattccc gagaaatact catgatccca taattagtca gagggtatgc  18360
caatcagatc taagaacaca cattccctca aattttaatg cacatgtaat catagtttag  18420
cacaattcaa aaataatgta gtattaaaga cagaaatttg tagactttt tttggcgtta  18480 aaagaagact aagtttatac gtacatttta ttttaagtgg aaaaccgaaa ttttccatcg  18540
aaatatatga atttagtata tatatttctg caatgtacta ttttgctatt ttggcaactt  18600
tcagtggact actactttat tacaatgtgt atggatgcat gagtttgagt atacacatgt  18660
ctaaatgcat gctttgtaaa acgtaacgga ccacaaaaga ggatccatac aaatacatct  18720
catagcttcc tccattatttt tccgacacaa acagagcatt ttacaacaat taccaacaac  18780
aacaaacaac aaacaacatt acaattacat ttacaattac cataccatgg cctctatcgc  18840
tatccctgct gctcttgctg gaactcttgg atacgttacc tacaatgtgg ctaaccctga  18900
tatcccagct tctgagaaag ttcctgctta cttcatgcag gttgagtact ggggacctac  18960
tatcggaact attggatacc tcctcttcat ctacttcgga aagcgtatca tgcagaacag  19020
atctcaacct ttcggactca agaacgctat gctcgtttac aacttctacc agaccttctt  19080
caacagctac tgcatctacc tttttcgttac ttctcatagg gctcagggac ttaaggtttg  19140
gggaaacatc cctgatatga ctgctaactc ttggggaatc tctcaggtta tctggcttca  19200
ctacaacaac aagtacgttg agcttctcga caccttcttc atggtgatga ggaagaagtt  19260
cgaccagctt tctttccttc acatctacca ccacactctt ctcatctggt catggttcgt  19320
tgttatgaag cttgagcctg ttggagattg ctacttcgga tcttctgtta acaccttcgt  19380
gcacgtgatc atgtactctt actacggact tgctgctctt ggagttaact gtttctggaa  19440
gaagtacatc acccagatcc agatgcttca gttctgtatc tgtgcttctc actctatcta  19500
caccgcttac gttcagaata ccgctttctg gcttccttac cttcaactct gggttatggt  19560
gaacatgttc gttctcttcg ccaacttcta ccgtaagagg tacaagtcta agggtgctaa  19620
gaagcagtga taagggccgc cgccatgtga cagatcgaag gaagaaagtg taataagacg  19680
actctcacta ctcgatcgct agtgattgtc attgttatat ataataatgt tatcttttcac 19740 aacttatcgt aatgcatgtg aaactataac acattaatcc tacttgtcat atgataacac  19800
tctccccatt taaaactctt gtcaatttaa agatataaga ttctttaaat gattaaaaaa  19860
aatatattat aaattcaatc actcctacta ataaattatt aattattatt tattgattaa  19920
aaaaatactt atactaattt agtctgaata gaataattag attctagcct gcagggcggc  19980
cgcggatccc atggagtcaa agattcaaat agaggaccta acagaactcg ccgtaaagac  20040
```

```
tggcgaacag ttcatacaga gtctcttacg actcaatgac aagaagaaaa tcttcgtcaa    20100
catggtggag cacgcacac  ttgtctactc caaaaatatc aaagatacag tctcagaaga    20160
ccaaagggca attgagactt tcaacaaag  ggtaatatcc ggaaacctcc tcggattcca    20220
ttgcccagct atctgtcact ttattgtgaa gatagtggaa aaggaaggtg gctcctacaa    20280
atgccatcat tgcgataaag gaaaggccat cgttgaagat gcctctgccg acagtggtcc    20340
caaagatgga ccccccaccca cgaggagcat cgtggaaaaa aagacgttc  caaccacgtc    20400
ttcaaagcaa gtggattgat gtgatatctc cactgacgta agggatgacg cacaatccca    20460
ctatccttcg caagaccctt cctctatata aggaagttca tttcatttgg agagaacacg    20520
ggggactgaa ttaaatatga gccctgagag gcgtcctgtt gaaatcagac ctgctactgc    20580
tgctgatatg gctgctgttt gtgatatcgt gaaccactac atcgagactt ctaccgttaa    20640
cttcagaact gagcctcaaa ctcctcaaga gtggatcgat gatcttgaga gactccaaga    20700
tagataccct tggcttgttg ctgaggttga gggtgttgtt gctggaatcg cttacgctgg    20760
accttggaag gctagaaacg cttacgattg gactgttgag tctaccgttt acgtttcaca    20820
cagacatcag agacttggac ttggatctac cctttacact caccttctca gtctatgga     20880
agctcaggga ttcaagtctg ttgttgctgt tatcggactc cctaacgatc cttctgttag    20940
acttcatgag gctcttggat acactgctag aggaactctt agagctgctg gatacaagca    21000
cggtggatgg catgatgttg gattctggca aagagatttc gagcttcctg ctcctcctag    21060
acctgttaga ccagttactc agatctgaat ttgcgtgatc gttcaaacat ttggcaataa    21120
agtttcttaa gattgaatcc tgttgccggt cttgcgatga ttatcatata atttctgttg    21180
aattacgtta agcatgtaat aattaacatg taatgcatga cgttatttat gagatgggtt    21240
tttatgatta gagtcccgca attatacatt taatacgcga tagaaaacaa atatagcgc     21300
gcaaactagg ataaattatc gcgcgcggtg tcatctatgt tactagatca ctagtgatgt    21360
acggttaaaa ccaccccagt acattaaaaa cgtccgcaat gtgttattaa gttgtctaag    21420
cgtcaatttg tttacaccac aatatatcct gccaccagcc agccaacagc tccccgaccg    21480
gcagctcggc acaaaatcac cactcgatac aggcagccca tcagtcc                  21527
```

<210> SEQ ID NO 2
<211> LENGTH: 23512
<212> TYPE: DNA
<213> ORGANISM: Artificial Sequence
<220> FEATURE:
<223> OTHER INFORMATION: pGA7- mod_B nucleotide sequence

<400> SEQUENCE: 2

```
tcctgtggtt ggcatgcaca tacaaatgga cgaacggata aacctttca cgcccttta      60
aatatccgat tattctaata aacgctcttt tctcttaggt ttacccgcca atatatcctg   120
tcaaacactg atagtttaaa ctgaaggcgg gaaacgacaa tctgctagtg gatctcccag   180
tcacgacgtt gtaaaacggg cgccccgcgg aaagcttgcg gccgcggtac cgcccgttcg   240
actcagatct tccaaggcct cgtctccgag tccgctgctt ctcgccgcgc cgatcacttc   300
tccgccgcca acaaggcttg tagttaatag gaatcattca gggattgtga ttccgggcag   360
tagtaattaa taatatagta ttagtataga taatatgttt cgtttgggat ctttggaacg   420
ttgctctgtt ccttgttgtt catttttaaag cttttgaggg atagttgcag aactgttcgg   480
tgatgcttca tcctctcaag aactagattt gggtaaagaa acatccatgc atggatatgg   540
aatgttgttc ttccgattgg agattatttt ataaaattta aaattcatga tttaaaaaaa   600
```

```
cacataaaaa ccacaaaatt catgatttat tgacaatacg atacaaaatt agcaccaccg    660
gctactggct cattacacat ttcccttcc cctcattctc actttgtggc tttattatta    720
ttattattac atatatttta ccgttattat ttcacgtcac ataagcttgt taattaatca    780
ttagtgagcc ttctcagcct ttccgttaac gtagtagtgc tgtcccacct tatcaaggtt    840
agagaaagta gccttccaag caccgtagta agagagcacc ttgtagttga gtccccactt    900
cttagcgaaa ggaacgaatc ttctgctaac ctcaggctgt ctgaattgag gcatatcagg    960
gaagaggtgg tggataacct gacagttaag gtatcccata agccagttca cgtatcctct   1020
agaaggatcg atatcaacgg tgtgatcaac agcgtagtta acccaagaaa ggtgcttatc   1080
agatggaaca acagggaggt gagtatgaga agtagagaag tgagcgaaaa ggtacatgta   1140
agcgatccag tttccgaaag tgaaccacca gtaagcaaca ggccaagagt atccagtagc   1200
aagcttgata acagcggttc taacaacatg agaaacgagc atccaagaag cctcttcgta   1260
gttcttctta cggagaactt gtctagggtg gagaacgtag atccagaaag cttgaacaag   1320
aagtccagag gtaacaggaa cgaaagtcca agcttgaagt ctagcccaag ctctagagaa   1380
tcctctaggt ctgttatcct caacagcagt gttgaagaaa gccacagcag gagtggtatc   1440
aagatccata tcgtgtctaa ccttttgagg ggtagcatgg tgcttgttat gcatctggtt   1500
ccacatctca ccagaagtag aaagtccgaa tccacaagtc atagcctgaa gtctcttgtc   1560
cacgtaaaca gatccggtaa gagagttatg tccaccctca tgttgaaccc atccacatct   1620
agctccgaag aaagcaccgt aaacaacaga agcaatgata gggtatccag cgtacataag   1680
agcagttcca agagcgaatg tagcaagaag ctcgagaagt ctgtaagcca catgggtgat   1740
agaaggcttg aagaatccat ctctctcaag ctcagcacgc catctagcga aatcctcaag   1800
cataggagca tcctcagact cagatctctt gatctcagca ggtctagaag gcaaagctct   1860
aagcatcttc caagccttga gagaacgcat gtggaattct ttgaaagcct cagtagcatc   1920
agcaccagtg ttagcaagca tgtagaagat cacagatcca ccagggtgct tgaagttagt   1980
cacatcgtac tcaacgtcct caactctaac ccatctagtc tcgaaagtag cagcaagctc   2040
atgaggctca agagtcttaa gatcaacagg agcagtagaa gcatccttag catcaagagc   2100
ctcagcagaa gatttagacc tggtaagtgg agatctagga gaagatcttc catcagtctt   2160
aggagggcac atggtatggt aattgtaaat gtaattgtaa tgttgtttgt tgtttgttgt   2220
tgttggtaat tgttgtaaaa ttaattaagt gggtatcttt tggatggata agcaagtagt   2280
gatgatgttc taggtgaagt gatggggtg ttttatagcg ggagatggtg aaatggatgg   2340
tcgccacata agaaatggag gggaagggtt cttgcgccat tcttcagttt gcatggatgc   2400
atgggtttca ttttgtaaca cgtaataagg acaatgaagt gcaggtgtct ctcaagtttc   2460
agagggata tgtggacaga agaagaacgg cgatgatatt gatggaaatg gccatctagt   2520
gtgaatctat tcggttgata atactagtgc attttggccg ttaatccctt caattaactg   2580
cacaaacttc agttgagtat tgattatttg attataggtt ctgtaaacac aataccaagt   2640
ttatttagag gggagacata caaatagttt cgatataaat aatagagtgg ttaaacttag   2700
ttattaaaac tatatataaa gtctaaaagt taaattattt ttttaattgc aaatatataa   2760
agtctaaagg ggttacatta tttcttaaga gatgtaactc tgttggaatc tgacttaatc   2820
cgtctcatca ctctggtttc cagttctaat ctaatgaatt gttttctgcc aaagaatttg   2880
aagcaagaag taaattgatc aatgccgtca acccacacca aaccgtcaac ccactaccat   2940
```

```
cgccgcggag accccccaaac tcaacctcca cccatcggta agaagcacag ggcagcccgc    3000
accaccacca atttggcgtg catgacacct agggacttgg cacgggaggc ggcgcacgtg    3060
gatgcaaatg acgggatatc agatgacagg aaacgacgtt gagagaccat acgatgtaga    3120
atatgagctc accatcaacg agaaactagg aaaatcacaa aaaaaacaac tctcgtaatt    3180
gtacgagtgg cacagatggg tctgcctcaa catatctcta atacggcgaa gcctgcccaa    3240
cacgtagttg ccggaatccg gtgtggagct cacgactctg aaagataggc gcttcctgtt    3300
tcgtttcgct cacccactgg acgtccgtca tgtgatggat ttcggtcatt ggtttgctga    3360
caaccacatt ctgaagctcc atgagatgag tcttcacaat aggtcctgct caataccgtg    3420
gagttatggt tgcaagtcca taacttgccg ttcgaatatt ttgcggagcc agtcggacgg    3480
gaattggcga gctcggctga cacctataaa ggccatgaca agaagaacca aaagttcttc    3540
cctaatgctt tcatgaggct tcgggtcgtt atggatgtcg gaaaacccct cttgaaggaa    3600
cgagacgtta ttatgcatga cggtaagact attacttgtc agtataagta tgaaagatta    3660
cctgtcttct gctttgtttg tggattgatt ggacacgtta aaaaaaaatg tgcacttcga    3720
tttcaatact cagagatcga cttccctttt ctctaggagt attcgatcaa ggcattaaca    3780
tggaaggaag ctcaagctct aaaggcttca caatggaacc tgaaaaattt caacaagcct    3840
aaactgaaat cgaagtcaaa tcacccaacc gggagctcta aatcagcaaa cactcctcct    3900
ccacagtatc caatcatcgt gcacgatgct ccaggtattg caagccaggt attgcaagct    3960
aggagtagga tagagacctt aaacgtcgtt ggtgtgaaga gtcatcttca gacctaatgg    4020
agatagatgt agacggcggc acgaagactc tgaaacacca gaaaggctag tccaggataa    4080
ggatctgcta tcccaactga cctctcgtta gtcccaaggc ctctcaacta gagcaggagg    4140
aaggatggtc acaagactag gataatgatg tttccaatat gaacctgaat gtccatagct    4200
aattttttta gtcttgcttc tgcactttt gtttattatg ttctggtgac tatgttattt    4260
acccttgtcc gtatgcttga gggtacccta gtagattggt tggttggttt ccatgtacca    4320
gaaggcttac cctattagtt gaaagttgaa actttgttcc ctactcaatt cctagttgtg    4380
taaatgtatg tatatgtaat gtgtataaaa cgtagtactt aaatgactag gagtggttct    4440
tgagaccgat gagagatggg agcagaacta agatgatga cataattaag aacgaatttg    4500
aaaggctctt aggtttgaat cctattcgag aatgttttg tcaaagatag tggcgatttt    4560
gaaccaaaga aaacatttaa aaaatcagta tccggttacg ttcatgcaaa tagaaagtgg    4620
tctaggatct gattgtaatt ttagacttaa agagtctctt aagattcaat cctggctgtg    4680
tacaaaacta caaataatat attttagact atttggcctt aactaaactt ccactcatta    4740
tttactgagg ttagaaata gacttgcgaa taaacacatt cccgagaaat actcatgatc    4800
ccataattag tcagagggta tgccaatcag atctaagaac acacattccc tcaaatttta    4860
atgcacatgt aatcatagtt tagcacaatt caaaaataat gtagtattaa agacagaaat    4920
ttgtagactt ttttttggcg ttaaaagaag actaagttta tacgtacatt ttattttaag    4980
tggaaaaccg aaattttcca tcgaaatata tgaatttagt atatatattt ctgcaatgta    5040
ctattttgct attttggcaa ctttcagtgg actactactt tattacaatg tgtatggatg    5100
catgagtttg agtatacaca tgtctaaatg catgctttgt aaaacgtaac ggaccacaaa    5160
agaggatcca tacaaatata tctccatagct tcctccatta ttttccgaca caaacagagc    5220
attttacaac aattaccaac aacaacaaac aacaaacaac attacaatta catttacaat    5280
taccatacca tggcctctat cgctatccct gctgctcttg ctggaactct tggatacgtt    5340
```

```
acctacaatg tggctaaccc tgatatccca gcttctgaga aagttcctgc ttacttcatg    5400
caggttgagt actggggacc tactatcgga actattggat acctcctctt catctacttc    5460
ggaaagcgta tcatgcagaa cagatctcaa cctttcggac tcaagaacgc tatgctcgtt    5520
tacaacttct accagacctt cttcaacagc tactgcatct accttttcgt tacttctcat    5580
agggctcagg gacttaaggt ttggggaaac atccctgata tgactgctaa ctcttgggga    5640
atctctcagg ttatctggct tcactacaac aacaagtacg ttgagcttct cgacaccttc    5700
ttcatggtga tgaggaagaa gttcgaccag cttttctttcc ttcacatcta ccaccacact    5760
cttctcatct ggtcatggtt cgttgttatg aagcttgagc tgttggagaa ttgctacttc    5820
ggatcttctg ttaacacctt cgtgcacgtg atcatgtact cttactacgg acttgctgct    5880
cttggagtta actgtttctg gaagaagtac atcacccaga tccagatgct tcagttctgt    5940
atctgtgctt ctcactctat ctacaccgct tacgttcaga ataccgcttt ctggcttcct    6000
taccttcaac tctgggttat ggtgaacatg ttcgttctct tcgccaactt ctaccgtaag    6060
aggtacaagt ctaagggtgc taagaagcag tgataaggcg cgcggcgcgc cgggccgccg    6120
ccatgtgaca gatcgaagga agaaagtgta ataagacgac tctcactact cgatcgctag    6180
tgattgtcat tgttatatat aataatgtta tctttcacaa cttatcgtaa tgcatgtgaa    6240
actataacac attaatccta cttgtcatat gataacactc tccccattta aaactcttgt    6300
caatttaaag atataagatt cttaaatga ttaaaaaaaa tatattataa attcaatcac    6360
tcctactaat aaattattaa ttattattta ttgattaaaa aaatacttat actaattag    6420
tctgaataga ataattagat tctagtctca tccccttta aaccaactta gtaaacgttt    6480
ttttttttaa ttttatgaag ttaagttttt accttgtttt taaaaagaat cgttcataag    6540
atgccatgcc agaacattag ctacacgtta cacatagcat gcagccgcgg agaattgttt    6600
ttcttcgcca cttgtcactc ccttcaaaca cctaagagct tctctctcac agcacacaca    6660
tacaatcaca tgcgtgcatg cattattaca cgtgatcgcc atgcaaatct cctttatagc    6720
ctataaatta actcatccgc ttcactcttt actcaaacca aaactcatcg atacaaacaa    6780
gattaaaaac atacacgagg atcttttaca acaattacca acaacaacaa acaacaaaca    6840
acattacaat tacatttaca attaccatac catgcctcca agggactctt actcttatgc    6900
tgctcctcct tctgctcaac ttcacagagt tgatactcct caagagcacg acaagaaaga    6960
gcttgttatc ggagataggg cttacgatgt taccaacttc gttaagagac accctggtgg    7020
aaagatcatt gcttaccaag ttggaactga tgctaccgat gcttacaagc agttccatgt    7080
tagatctgct aaggctgaca agatgcttaa gtctcttcct tctcgtcctg ttcacaaggg    7140
atactctcca agaagggctg atcttatcgc tgatttccaa gagttcacca agcaacttga    7200
ggctgaggga atgttcgagc cttctcttcc tcatgttgct tacagacttg ctgaggttat    7260
cgctatgcat gttgctggtg ctgctcttat ctggcatgga tacactttcg ctggaatcgc    7320
tatgcttgga gttgttcagg aagatgtgg atggcttatg catgagggtg acattactc    7380
tctcactgga aacattgctt tcgacagagc tatccaagtt gcttgttacg gacttggatg    7440
tggaatgtct ggtgcttggt ggcgtaacca gcataacaag caccatgcta ctcctcaaaa    7500
gcttcagcac gatgttgatc ttgataccct tcctctcgtt gctttccatg agagaatcgc    7560
tgctaaggtt aagtctcctg ctatgaaggc ttggctttct atgcaagcta agcttttcgc    7620
tcctgttacc actcttcttg ttgctcttgg atggcagctt taccttcatc ctagacacat    7680
```

```
gctcaggact aagcactacg atgagcttgc tatgctcgga atcagatacg gacttgttgg    7740
ataccttgct gctaactacg gtgctggata cgttctcgct tgttaccttc tttacgttca    7800
gcttggagct atgtacatct tctgcaactt cgctgtttct catactcacc tccctgttgt    7860
tgagcctaac gagcatgcta cttgggttga gtacgctgct aaccacacta ctaactgttc    7920
tccatcttgg tggtgtgatt ggtggatgtc ttaccttaac taccagatcg agcaccacct    7980
ttacccttct atgcctcaat tcagacaccc taagatcgct cctagagtta agcagctttt    8040
cgagaagcac ggacttcact acgatgttag aggatacttc gaggctatgg ctgatacttt    8100
cgctaacctt gataacgttg cccatgctcc tgagaagaaa atgcagtaat gagatcgttc    8160
aaacatttgg caataaagtt tcttaagatt gaatcctgtt gccggtcttg cgatgattat    8220
catataattt ctgttgaatt acgttaagca cgtaataatt aacatgtaat gcatgacgtt    8280
atttatgaga tgggttttta tgattagagt cccgcaatta tacatttaat acgcgataga    8340
aaacaaaata tagcgcgcaa actaggataa attatcgcgc gcggtgtcat ctatgttact    8400
agatcggtcg attaaaaatc ccaattatat ttggtctaat ttagtttggt attgagtaaa    8460
acaaattcga accaaaccaa aatataaata tatagttttt atatatatgc ctttaagact    8520
ttttatagaa ttttctttaa aaaatatcta gaaaatatttg cgactcttct ggcatgtaat    8580
atttcgttaa atatgaagtg ctccatttt attaacttta ataattggt tgtacgatca    8640 cttctttatc aagtgttact aaaatgcgtc aatctctttg ttcttccata ttcatatgtc    8700
aaaatctatc aaaattctta tatatctttt tcgaatttga agtgaaattt cgataattta    8760
aaattaaata gaacatatca ttatttaggt atcatattga tttttatact taattactaa    8820
atttggttaa ctttgaaagt gtacatcaac gaaaaattag tcaaacgact aaaataaata    8880
aatatcatgt gttattaaga aaattctcct ataagaatat tttaatagat catatgtttg    8940
taaaaaaaat taatttttac taacacatat atttacttat caaaaatttg acaaagtaag    9000
attaaaataa tattcatcta acaaaaaaaa aaccagaaaa tgctgaaaac ccggcaaaac    9060
cgaaccaatc caaaccgata tagttggttt ggtttgattt tgatataaac cgaaccaact    9120
cggtccattt gcacccctaa tcataatagc tttaatattt caagatatta ttaagttaac    9180
gttgtcaata tcctggaaat tttgcaaaat gaatcaagcc tatatggctg taatatgaat    9240
ttaaaagcag ctcgatgtgg tggtaatatg taatttactt gattctaaaa aaatatccca    9300
agtattaata atttctgcta ggaagaaggt tagctacgat ttacagcaaa gccagaatac    9360
aaagaaccat aaagtgattg aagctcgaaa tatacgaagg aacaaatatt tttaaaaaaa    9420
tacgcaatga cttggaacaa aagaaagtga tatattttt gttcttaaac aagcatcccc    9480
tctaaagaat ggcagttttc cttttgcatgt aactattatg ctcccttcgt tacaaaaatt    9540
ttggactact attgggaact tcttctgaaa atagtgatag aacccacacg agcatgtgct    9600
ttccatttaa ttttaaaaac caagaaacat acatacataa cattccatca gcctctctct    9660 cttttatta cggttaatga cttaaaacac atcttattat cccatcctta acacctagca    9720
gtgtctttat acgatctcat cgatcaccac ttcaaaacca tgcagactgc tgctgcccct    9780
ggagctggca tcggctaggc tgggtgccgc actgtcccgg aaggtcccta gcgacttgtt    9840
tagattgatg ggaccacctc tcaacttcct gctgctgtcc ctgctgctgg atgtcctgcc    9900
tcatctggcc gattgcacgc tccagtcccc tgcatgtgca ctcgctcctc aattgcttaa    9960
gatcatcgca gcagctatcg aagtgctggc tctgttgccc tcctccacgg ccttggttgt   10020
agtagtagct gccgccgccc ttctggactt tttcccacag gaaccgccga ataattcgat   10080
```

```
agaaccacac gagcatgtgc tttcatttat tttaaaaacc aagaaacata cataacattt    10140
catcagcctc tctctctctc tctctctctc tctctctctc tctctctctt                10200
tattacagct gttacactaa cttaaaacac attcatctca ttattattat tattatccat    10260
ccttaacacc tagcagtgtc tttgtacgat ctcataatcg atcaccccctt catcaggtat   10320 ccttaggctt cactccaacg ttgttgcagt tacggaacat gtacacacca tcatggttct   10380
caacgaactg gcaagatctc caagttttcc aaaggctaac ccacatgttc tcatcggtgt   10440
gtctgtagtg ctctcccata actttcttga tgcactcggt agcttctcta gcatggtaga   10500
atgggatcct tgaaacgtag tgatggagca catgagtctc gatgatgtca tggaagatga   10560
ttccgaggat tccgaactct ctatcgatag tagcagcagc acccttagcg aaagtccact    10620
cttgagcatc gtaatgaggc atagaagaat cggtgtgctg aaggaaggta acgaaaacaa   10680
gccagtggtt aacaaggatc caaggacaga accatgtgat gaaagtaggc cagaatccga   10740
aaaccttgta agcggtgtaa acagaagtga gggtagcaag gattccaaga tcagaaagaa   10800
cgatgtacca gtagtccttc ttatcgaaaa cagggctaga aggccagtag tgagacttga   10860
agaacttaga aacaccaggg taaggttgtc cagtagcgtt agtagcaagg taaagagaaa   10920
gtcctccaag ctgttggaac aagagagcga aaacagagta gataggagtt tcctcagcga   10980
tatcgtgaag gctggtaact tggtgcttct ctttgaattc ctcggcggtg taaggaacga   11040
aaaccatatc tctggtcatg tgtccagtag ccttatggtg cttagcatga gagaacttcc   11100
agctgaagta aggaaccata acaagagagt ggagaaccca tccaacggta tcgttaaccc   11160
atccgtagtt agagaaagca gaatgtccac actcatgtcc aaggatccag attccgaatc   11220
cgaaacaaga gatagagaac acgtaagcag accaagcagc gaatctaagg aattcgttag   11280
ggagaagagg gatgtaggta agtccaacgt aagcgatagc agagatagcc acgatatctc   11340
tcaccacgta agacatagac ttcacgagag atctctcgta acagtgctta gggatagcgt   11400
caaggatatc cttgatggtg taatctggca ccttgaaaac gtttccgaag gtatcgatag   11460
cggtcttttg ctgcttgaaa gatgcaacgt ttccagaacg cctaacggtc ttagtagatc   11520
cctcaaggat ctcagatcca gacacggtaa ccttagacat ggtatggtaa ttgtaaatgt   11580
aattgtaatg ttgtttgttg tttgttgttg ttggtaattg ttgtaaaatt tttggtggtg   11640
attggttctt taaggtgtga gagtgagttg tgagttgtgt ggtgggtttg gtgagattgg   11700
ggatggtggg tttatatagt ggagactgag gaatggggtc gtgagtgtta actttgcatg   11760
ggctacacgt gggttctttt gggcttacac gtagtattat tcatgcaaat gcagccaata   11820
catatacggt attttaataa tgtgtgggaa tacaatatgc cgagtatttt actaattttg   11880
gcaatgacaa gtgtacattt ggattatctt acttggcctc tcttgcttta atttggatta   11940
tttttattct cttaccttgg ccgttcatat tcacatccct aaaggcaaga cagaattgaa   12000
tggtggccaa aaattaaaac gatggatatg acctacatag tgtaggatca attaacgtcg   12060
aaggaaaata ctgattctct caagcatacg gacaagggta aataacatag tcaccagaac   12120
ataataaaca aaaagtgcag aagcaagact aaaaaaatta gctatggaca ttcaggttca   12180
tattggaaac atcattatcc tagtcttgtg accatccttc ctcctgctct agttgagagg   12240
ccttgggact aacgagaggt cagttgggat agcagatcct tatcctggac tagccttttct  12300 ggtgtttcag agtcttcgtg ccgccgtcta catctatctc cattaggtct gaagatgact   12360
cttcacacca acgacgttta aggtctctat cctactccta gcttgcaata cctggcttgc   12420
```

```
aatacctgga gcatcgtgca cgatgattgg atactgtgga ggaggagtgt ttgctgattt    12480
agagctcccg gttgggtgat ttgacttcga tttcagttta ggcttgttga aatttttcag    12540
gttccattgt gaagccttta gagcttgagc ttccttccat gttaatgcct tgatcgaata    12600
ctcctagaga aaagggaagt cgatctctga gtattgaaat cgaagtgcac atttttttc     12660 aacgtgtcca atcaatccac aaacaaagca gaagacaggt aatctttcat acttatactg    12720
acaagtaata gtcttaccgt catgcataat aacgtctcgt tccttcaaga ggggttttcc    12780
gacatccata acgacccgaa gcctcatgaa agcattaggg aagaactttt ggttcttctt    12840
gtcatggcct ttataggtgt cagccgagct cgccaattcc cgtccgactg gctccgcaaa    12900
atattcgaac ggcaagttat ggacttgcaa ccataactcc acggtattga gcaggaccta    12960
ttgtgaagac tcatctcatg gagcttcaga atgtggttgt cagcaaacca atgaccgaaa    13020
tccatcacat gacggacgtc cagtgggtga gcgaaacgaa acaggaagcg cctatctttc    13080
agagtcgtga gctccacacc ggattccggc aactacgtgt tgggcaggct tcgccgtatt    13140
agagatatgt tgaggcagac ccatctgtgc cactcgtaca attacgagag ttgtttttt      13200 tgtgattttc ctagtttctc gttgatggtg agctcatatt ctacatcgta tggtctctca    13260
acgtcgtttc ctgtcatctg atatcccgtc atttgcatcc acgtgcgccg cctcccgtgc    13320
caagtcccta ggtgtcatgc acgccaaatt ggtggtggtg cgggctgccc tgtgcttctt    13380
accgatgggt ggaggttgag tttgggggtc tccgcggcga tggtagtggg ttgacggttt    13440
ggtgtgggtt gacggcattg atcaatttac ttcttgcttc aaattctttg gcagaaaaca    13500
attcattaga ttagaactgg aaaccagagt gatgagacgg attaagtcag attccaacag    13560
agttacatct cttaagaaat aatgtaaccc ctttagactt tatatatttg caattaaaaa    13620
aataatttaa cttttagact ttatatatag ttttaataac taagtttaac cactctatta    13680
tttatatcga aactatttgt atgtctcccc tctaaataaa cttggtattg tgtttacaga    13740
acctataatc aaataatcaa tactcaactg aagtttgtgc agttaattga agggattaac    13800
ggccaaaatg cactagtatt atcaaccgaa tagattcaca ctagatggcc atttccatca    13860
atatcatcgc cgttcttctt ctgtccacat atcccctctg aaacttgaga gacacctgca    13920
cttcattgtc cttattacgt gttacaaaat gaaacccatg catccatgca aactgaagaa    13980
tggcgcaaga acccttcccc tccatttctt atgtggcgac catccatttc accatctccc    14040
gctataaaac accccccatca cttcacctag aacatcatca ctacttgctt atccatccaa    14100 aagatacccca cttttacaac aattaccaac aacaacaaac aacaaacaac attacaatta    14160
catttacaat taccatacca tgccacctag cgctgctaag caaatgggag cttctactgg    14220
tgttcatgct ggtgttactg actcttctgc tttcaccaga aaggatgttg ctgatagacc    14280
tgatctcacc atcgttggag attctgttta cgatgctaag gctttcagat ctgagcatcc    14340
tggtggtgct catttcgttt cttgttcgg aggaagagat gctactgagg ctttcatgga     14400
ataccataga agggcttggc ctaagtctag aatgtctaga ttccacgttg gatctcttgc    14460
ttctactgag gaacctgttg ctgctgatga gggataccct caactttgtg ctaggatcgc    14520
taagatggtg ccttctgttt cttctggatt cgctcctgct tcttactggg ttaaggctgg    14580
acttatcctt ggatctgcta cgctcttga ggcttacatg ctttacgctg gaaagagact     14640
tctcccttct atcgttcttg gatggctttt cgctcttatc ggtcttaaca tccagcatga    14700
tgctaaccat ggtgctttgt ctaagtctgc ttctgttaac cttgctcctg gactttgtca    14760
ggattggatc ggaggatcta tgatcctttg gcttcaagag catgttgtta tgcaccacct    14820
```

```
ccacactaac gatgttgata aggatcctga tcaaaaggct cacggtgctc ttagactcaa   14880
gcctactgat gcttggtcac ctatgcattg gcttcagcat ctttaccttt tgcctggtga   14940
gactatgtac gctttcaagc ttttgttcct cgacatctct gagcttgtta tgtggcgttg   15000
ggagggtgag cctatctcta agcttgctgg atacctcttt atgccttctt tgcttctcaa   15060
gcttaccttc tgggctagat tcgttgcttt gcctctttac cttgctcctt ctgttcatac   15120
tgctgtgtgt atcgctgcta ctgttatgac tggatctttc tacctcgctt tcttcttctt   15180
catctcccac aacttcgagg gtgttgcttc tgttggacct gatggatcta tcacttctat   15240
gactagaggt gctagcttcc ttaagagaca agctgagact tcttctaacg ttggaggacc   15300
tcttcttgct actcttaacg gtggactcaa ctaccaaatt gagcatcact tgttccctag   15360
agttcaccat ggattctacc ctagacttgc tcctcttgtt aaggctgagc ttgaggctag   15420
aggaatcgag tacaagcact accctactat ctggtctaac cttgcttcta ccctcagaca   15480
tatgtacgct cttggaagaa ggcctagatc taaggctgag taatgacaag ttatgtgac    15540 gtgaaataat aacggtaaaa tatatgtaat aataataata ataaagccac aaagtgagaa   15600
tgaggggaag gggaaatgtg taatgagcca gtagccggtg gtgctaattt tgtatcgtat   15660
tgtcaataaa tcatgaattt tgtggttttt atgtgttttt ttaaatcatg aattttaaat   15720
tttataaaat aatctccaat cggaagaaca acattccata tccatgcatg gatgtttctt   15780
tacccaaatc tagttcttga gaggatgaag catcaccgaa cagttctgca actatccctc   15840
aaaagcttta aaatgaacaa caaggaacag agcaacgttc caaagatccc aaacgaaaca   15900
tattatctat actaatacta tattattaat tactactgcc cggaatcaca atccctgaat   15960
gattcctatt aactcaaagc cttgttggcg gcggagaagt gatcggcgcg gcgagaagca   16020
gcggactcgg agacgaggcc ttggaagatc tgagtcgaac gggcagaatc agtattttcc   16080
ttcgacgtta attgatccta cactatgtag gtcatatcca tcgttttaat ttttggccac   16140
cattcaattc tgtcttgcct ttagggatgt gaatatgaac ggccaaggta agagaataaa   16200
aataatccaa attaaagcaa gagaggccaa gtaagataat ccaaatgtac acttgtcatt   16260
gccaaaatta gtaaaatact cggcatattg tattcccaca cattattaaa ataccgtata   16320
tgtattggct gcatttgcat gaataatact acgtgtaagc ccaaaagaac ccacgtgtag   16380
cccatgcaaa gttaacactc acgacccat tcctcagtct ccactatata aacccaccat    16440
ccccaatctc accaaaccca ccacacaact cacaactcac tctcacacct taaagaacca   16500
atcaccacca aaaattttac aacaattacc aacaacaaca acaacaaac aacattacaa    16560 ttacatttac aattaccata ccatgagcgc tgttaccgtt actggatctg atcctaagaa   16620
cagaggatct tctagcaaca ccgagcaaga ggttccaaaa gttgctatcg ataccaacgg   16680
aaacgtgttc tctgttcctg atttcaccat caaggacatc cttggagcta tccctcatga   16740
gtgttacgag agaagattgg ctacctctct ctactacgtg ttcagagata tcttctgcat   16800
gcttaccacc ggatacctta cccataagat cctttaccct ctcctcatct cttacacctc   16860
taacagcatc atcaagttca ctttctgggc cctttacact tacgttcaag acttttcgg    16920 aaccggaatc tgggttctcg ctcatgagtg tggacatcaa gctttctctg attacggaat   16980
cgtgaacgat ttcgttggat ggaccccttca ctcttacctt atggttcctt acttcagctg   17040
gaagtactct catggaaagc accataaggc tactggacac atgaccagag atatggtttt   17100
cgttcctgcc accaaagagg aattcaagaa gtctaggaac ttcttcggta acctcgctga   17160
```

```
gtactctgag gattctccac ttagaaccct ttacgagctt cttgttcaac aacttggagg    17220
atggatcgct tacctcttcg ttaacgttac aggacaacct tacccctgatg ttccttcttg    17280 gaaatggaac cacttctggc ttacctctcc acttttcgag caaagagatg ctctctacat    17340
cttcctttct gatcttggaa tcctcaccca gggaatcgtt cttactcttt ggtacaagaa    17400
attcggagga tggtcccttt tcatcaactg gttcgttcct tacatctggg ttaaccactg    17460
gctcgttttc atcacattcc ttcagcacac tgatcctact atgcctcatt acaacgctga    17520
ggaatggact ttcgctaagg gtgctgctgc tactatcgat agaaagttcg gattcatcgg    17580
acctcacatc ttccatgata tcatcgagac tcatgtgctt caccactact gttctaggat    17640
cccattctac aacgctagac ctgcttctga ggctatcaag aaagttatgg gaaagcacta    17700
caggtctagc gacgagaaca tgtggaagtc actttggaag tctttcaggt cttgccaata    17760
cgttgacggt gataacggtg ttctcatgtt ccgtaacatc aacaactgcg gagttggagc    17820
tgctgagaag taatgaaggg gtgatcgatt atgagatcgt acaaagacac tgctaggtgt    17880
taaggatgga taataataat aataatgaga tgaatgtgtt ttaagttagt gtaacagctg    17940
taataaagag agagagagag agagagagag agagagagag agagagagag agagagaggc    18000
tgatgaaatg ttatgtatgt ttcttggttt ttaaaataaa tgaaagcaca tgctcgtgtg    18060
gttctatcga attattcggc ggttcctgtg ggaaaaagtc cagaagggcc gccgcagcta    18120
ctactacaac caaggccgtg gaggagggca acagagccag cacttcgata gctgctgcga    18180
tgatcttaag caattgagga gcgagtgcac atgcagggga ctggagcgtg caatcggcca    18240
gatgaggcag gacatccagc agcagggaca gcagcaggaa gttgagaggt ggtcccatca    18300
atctaaacaa gtcgctaggg accttccggg acagtgcggc acccagccta gccgatgcca    18360
gctccagggg cagcagcagt ctgcatggtt ttgaagtggt gatcgatgag atcgtataaa    18420
gacactgcta ggtgttaagg atgggataat aagatgtgtt ttaagtcatt aaccgtaata    18480
aaaagagaga gaggctgatg gaatgttatg tatgtatgt tcttggtttt taaaattaaa    18540
tggaaagcac atgctcgtgt gggttctatc tcgattaaaa atcccaatta tatttggtct    18600
aatttagttt ggtattgagt aaaacaaatt cgaaccaaac caaatataaa atatatagtt    18660
tttatatata tgcctttaag acttttttata gaattttctt taaaaaatat ctagaaatat    18720
ttgcgactct tctggcatgt aatatttcgt taaatatgaa gtgctccatt tttattaact    18780
ttaaataatt ggttgtacga tcactttctt atcaagtgtt actaaaatgc gtcaatctct    18840
ttgttcttcc atattcatat gtcaaaatct atcaaaattc ttatatatct ttttcgaatt    18900
tgaagtgaaa tttcgataat ttaaaattaa atagaacata tcattattta ggtatcatat    18960
tgatttttat acttaattac taaatttggt taactttgaa agtgtacatc aacgaaaaat    19020
tagtcaaacg actaaaataa ataaatatca tgtgttatta agaaaattct cctataagaa    19080
tattttaata gatcatatgt ttgtaaaaaa aattaattt tactaacaca tatatttact    19140
tatcaaaaat ttgacaaagt aagattaaaa taatattcat ctaacaaaaa aaaaaccaga    19200
aaatgctgaa aacccggcaa aaccgaacca atccaaaccg atatagttgg tttggtttga    19260
ttttgatata aaccgaacca actcggtcca tttgcacccc taatcataat agctttaata    19320
tttcaagata ttattaagtt aacgttgtca atatcctgga aattttgcaa atgaatcaa    19380 gcctatatgg ctgtaaatatg aatttaaaag cagctcgatg tggtggtaat atgtaattta    19440
cttgattcta aaaaaatatc ccaagtatta ataattctg ctaggaagaa ggttagctac    19500
gatttacagc aaagccagaa tacaaagaac cataaagtga ttgaagctcg aaatatacga    19560
```

```
aggaacaaat attttaaaa aaatacgcaa tgacttggaa caaaagaaag tgatatattt    19620
tttgttctta aacaagcatc ccctctaaag aatggcagtt ttcctttgca tgtaactatt    19680
atgctcccct cgttacaaaa atttggact actattggga acttcttctg aaaatagtcc    19740
tgcaggctag tagattggtt ggttggtttc catgtaccag aaggcttacc ctattagttg    19800
aaagttgaaa ctttgttccc tactcaattc ctagttgtgt aaatgtatgt atatgtaatg    19860
tgtataaaac gtagtactta aatgactagg agtggttctt gagaccgatg agagatggga    19920
gcagaactaa agatgatgac ataattaaga acgaatttga aaggctctta ggtttgaatc    19980
ctattcgaga atgttttgt caaagatagt ggcgattttg aaccaaagaa acatttaaa    20040
aaatcagtat ccggttacgt tcatgcaaat agaaagtggt ctaggatctg attgtaattt    20100
tagacttaaa gagtctctta agattcaatc ctggctgtgt acaaaactac aaataatata    20160
ttttagacta tttggcctta actaaacttc cactcattat ttactgaggt tagagaatag    20220
acttgcgaat aaacacattc ccgagaaata ctcatgatcc cataattagt cagagggtat    20280
gccaatcaga tctaagaaca cacattccct caaatttaa tgcacatgta atcatagttt    20340
agcacaattc aaaaataatg tagtattaaa gacagaaatt tgtagacttt ttttggcgt    20400
taaaagaaga ctaagtttat acgtacattt tattttaagt ggaaaaccga aattttccat    20460
cgaaatatat gaatttagta tatatatttc tgcaatgtac tattttgcta ttttggcaac    20520
tttcagtgga ctactacttt attacaatgt gtatggatgc atgagtttga gtatacacat    20580
gtctaaatgc atgctttgta aaacgtaacg gaccacaaaa gaggatccat acaaatacat    20640
ctcatagctt cctccattat tttccgacac aaacagagca ttttacaaca attaccaaca    20700
acaacaaaca acaaacaaca ttacaattac atttacaatt accataccat ggaatttgct    20760
caacctctcg ttgctatggc tcaagagcag tacgctgcta tcgatgctgt tgttgctcct    20820
gctatcttct ctgctaccga ctctattgga tggggactca agcctatctc ttctgctact    20880
aaggatctcc ctctcgttga atctcctacc cctcttatcc tttctctcct cgcttacttc    20940
gctatcgttg ttctggact cgtttaccgt aaagtgttcc ctagaaccgt taagggacag    21000
gatcctttcc ttctcaaggc tcttatgctc gctcacaacg ttttccttat cggactcagc    21060
ctttacatgt gcctcaagct cgtttacgag gcttacgtga acaagtactc cttctgggga    21120
aacgcttaca accctgctca aaccgagatg gctaaggtga tctggatctt ctacgtgtcc    21180
aagatctacg agttcatgga caccttcatc atgcttctca agggaaacgt taaccaggtt    21240
tccttcctcc atgtttacca ccacggatct atctctggaa tctggtggat gatcacttat    21300
gctgctccag gtggagatgc ttacttctct gctgctctca actcttgggt tcatgtgtgc    21360
atgtacacct actacttcat ggctgctgtt cttcctaagg acgaaaagac caagagaaag    21420
tacctttggt ggggaagata ccttacccag atgcaaatgt tccagttctt catgaacctt    21480
ctccaggctg tttacctcct ctactcttct tctccttacc ctaagttcat tgctcaactc    21540
ctcgttgttt acatggttac cctcctcatg cttttcggaa acttctacta catgaagcac    21600
cacgcttcta agtgataagg gccgccgcca tgtgacagat cgaaggaaga aagtgtaata    21660
agacgactct cactactcga tcgctagtga ttgtcattgt tatatataat aatgttatct    21720
ttcacaactt atcgtaatgc atgtgaaact ataacacatt aatcctactt gtcatatgat    21780
aacactctcc ccatttaaaa ctcttgtcaa tttaaagata taagattctt taaatgatta    21840
aaaaaaatat attataaatt caatcactcc tactaataaa ttattaatta ttatttattg    21900
```

| | |
|---|---|
| attaaaaaaa tacttatact aatttagtct gaatagaata attagattct agcctgcagg | 21960 |
| gcggccgcgg atcccatgga gtcaaagatt caaatagagg acctaacaga actcgccgta | 22020 |
| aagactggcg aacagttcat acagagtctc ttacgactca atgacaagaa gaaaatcttc | 22080 |
| gtcaacatgg tggagcacga cacacttgtc tactccaaaa atatcaaaga tacagtctca | 22140 |
| gaagaccaaa gggcaattga acttttcaa caaagggtaa tatccggaaa cctcctcgga | 22200 |
| ttccattgcc cagctatctg tcactttatt gtgaagatag tggaaaagga aggtggctcc | 22260 |
| tacaaatgcc atcattgcga taaaggaaag gccatcgttg aagatgcctc tgccgacagt | 22320 |
| ggtcccaaag atggacccc acccacgagg agcatcgtgg aaaaagaaga cgttccaacc | 22380 |
| acgtcttcaa agcaagtgga ttgatgtgat atctccactg acgtaaggga tgacgcacaa | 22440 |
| tcccactatc cttcgcaaga cccttcctct atataaggaa gttcatttca tttggagaga | 22500 |
| acacggggga ctgaattaaa tatgagccct gagaggcgtc ctgttgaaat cagacctgct | 22560 |
| actgctgctg atatggctgc tgtttgtgat atcgtgaacc actacatcga gacttctacc | 22620 |
| gttaacttca gaactgagcc tcaaactcct caagagtgga tcgatgatct tgagagactc | 22680 |
| caagatagat acccttggct tgttgctgag gttgagggtg ttgttgctgg aatcgcttac | 22740 |
| gctggacctt ggaaggctag aaacgcttac gattggactg ttgagtctac cgtttacgtt | 22800 |
| tcacacagac atcagagact tggacttgga tctacccttt acactcacct tctcaagtct | 22860 |
| atggaagctc agggattcaa gtctgttgtt gctgttatcg gactccctaa cgatccttct | 22920 |
| gttagacttc atgaggctct tggatacact gctagaggaa ctcttagagc tgctggatac | 22980 |
| aagcacggtg gatggcatga tgttggattc tggcaaagag atttcgagct tcctgctcct | 23040 |
| cctagacctg ttagaccagt tactcagatc tgaatttgcg tgatcgttca acatttggc | 23100 |
| aataaagttt cttaagattg aatcctgttg ccggtcttgc gatgattatc atataatttc | 23160 |
| tgttgaatta cgttaagcat gtaataatta acatgtaatg catgacgtta tttatgagat | 23220 |
| gggttttat gattagagtc ccgcaattat acatttaata cgcgatagaa aacaaaatat | 23280 |
| agcgcgcaaa ctaggataaa ttatcgcgcg cggtgtcatc tatgttacta gatcactagt | 23340 |
| gatgtacggt taaaaccacc ccagtacatt aaaaacgtcc gcaatgtgtt attaagttgt | 23400 |
| ctaagcgtca atttgtttac accacaatat atcctgccac cagccagcca acagctcccc | 23460 |
| gaccggcagc tcggcacaaa atcaccactc gatacaggca gcccatcagt cc | 23512 |

<210> SEQ ID NO 3
<211> LENGTH: 25787
<212> TYPE: DNA
<213> ORGANISM: Artificial Sequence
<220> FEATURE:
<223> OTHER INFORMATION: pGA7- mod_C nucleotide sequence

<400> SEQUENCE: 3

| | |
|---|---|
| tcctgtggtt ggcatgcaca tacaaatgga cgaacggata aacctttca cgccctttta | 60 |
| aatatccgat tattctaata aacgctcttt tctcttaggt ttacccgcca atatatcctg | 120 |
| tcaaacactg atagtttaaa ctgaaggcgg gaaacgacaa tctgctagtg gatctcccag | 180 |
| tcacgacgtt gtaaacggg cgccccgatc tagtaacata tgacaccg cgcgcgataa | 240 |
| tttatcctag tttgcgcgct atattttgtt ttctatcgcg tattaaatgt ataattgcgg | 300 |
| gactctaatc ataaaaaccc atctcataaa taacgtcatg cattacatgt taattattac | 360 |
| gtgcttaacg taattcaaca gaaattatat gataatcatc gcaagaccgg caacaggatt | 420 |
| caatcttaag aaactttatt gccaaatgtt tgaacgatct gcccggaagc ggccaactcg | 480 |

-continued

```
aaaatttaat taatcatcag tgagccttct cagcctttcc gttaacgtag tagtgctgtc    540
caactttgtc gaggttgctg aaagtagcct tccaagcacc gtagtaagag agcaccttgt    600
agttgagtcc ccacttctta gcgaaaggga cgaatcttct tgacacctca ggctgtctga    660
attgaggcat atcagggaag agatggtgga taacctggca gttaaggtat cccataagcc    720
agttaacgta tccacgagaa ggatcgatgt caacggtgtg atcaacagcg tagttaaccc    780
agctaaggtg cttgtcagat ggaacaacag ggaggtgagt gtgagaagta gagaagtgag    840
cgaagaggta catgtaagcg atccagtttc cgaaagtgaa ccaccagtaa gcaacaggcc    900
aagagtatcc ggtagcaagc ttgataacag cggttctaac aacgtgagaa acgagcatcc    960
aagaagcttc ctcgtagttc ttcttcctga gcacctgtct aggatggaga acgtagatcc   1020
agaaagcctg aacgagaagt ccagaagtaa caggaacgaa ggtccaagct tgaagtctag   1080
cccaagctct agagaatccc ctaggtctat tatcctccac agcggtgttg aagaaagcca   1140
cagcaggagt ggtatcaaga tccatgtcgt gtctaacttt ctgaggggta gcatggtgct   1200
tgttatgcat ctggttccac atctctccgc tggtagaaag tccgaatccg caagtcatag   1260
cctgaagtct cttatccacg tacacagatc cggtaagaga gttgtgtcca ccctcatgtt   1320
gaacccatcc acatctagct ccgaagaaag caccgtacac aacgctagca atgatagggt   1380
atccagcgta cataagagcg gttccaagag cgaaagtagc aagaagctcc aaaagacggt   1440
aagcaacatg ggtgatagaa ggcttgaaga atccgtccct ctcaagttca gctctccacc   1500
tagcgaaatc ctcaagcata ggagcatcct cagactcaga tctcttgatc tcagcaggtc   1560
tagaaggcaa agctctaagc atcttccaag ccttgaggct acgcatgtga aattctttga   1620
aagcctcagt agcatcagca ccagtgttag caagcatgta gaagatcacg cttccaccag   1680
gatgtttgaa gttggtcacg tcgtactcaa catcctcaac cctaacccat ctagtctcga   1740
aggtagcagc aagttcatga ggctcaaggg tcttaagatc aacaggagcg gtagaagcat   1800
ccttagcatc aagagcctca gcagatgact tagacctggt gagaggagat ctaggagaag   1860
atcttccatc ggtcttagga ggacacatgg cgcgccgatt ttcgagatgg taattgtaaa   1920
tgtaattgta atgttgtttg ttgtttgttg ttgttggtaa ttgttgtaaa attcgagttg   1980
gccgcttccg gggatcctcg tgtatgtttt taatcttgtt tgtatcgatg agttttggtt   2040
tgagtaaaga gtgaagcgga tgagttaatt tataggctat aaaggagatt tgcatggcga   2100
tcacgtgtaa taatgcatgc acgcatgtga ttgtatgtgt gtgctgtgag agagaagctc   2160
ttaggtgttt gaagggagtg acaagtggcg aagaaaaaca attctccgcg gctgcatgct   2220
atgtgtaacg tgtagctaat gttctggcat ggcatcttat gaacgattct tttaaaaac    2280
aaggtaaaaa cttaacttca taaaattaaa aaaaaaacg tttactaagt tggttttaaa    2340
ggggatgaga ggcgccccgc ggaaagcttg ctagccaatt ggggcccaac gttctcgagt   2400
ttttctagaa ggaaactgaa ggcgggaaac gacaatctgc tagtggatct cccagtcacg   2460
acgttgtaaa acgggcgccc cgcggaaagc ttgcggccgc ggtaccgccc gttcgactca   2520
gatcttccaa ggcctcgtct ccgagtccgc tgcttctcgc cgcgccgatc acttctccgc   2580
cgccaacaag gcttgtagtt aataggaatc attcagggat tgtgattccg ggcagtagta   2640
attaataata tagtattagt atagataata tgtttcgttt gggatctttg aacgttgct    2700
ctgttccttg ttgttcattt taaagctttt gagggatagt tgcagaactg ttcggtgatg   2760
cttcatcctc tcaagaacta gatttgggta aagaaacatc catgcatgga tatggaatgt   2820
```

```
tgttcttccg attggagatt attttataaa atttaaaatt catgatttaa aaaaacacat    2880
aaaaaccaca aaattcatga tttattgaca atacgataca aaattagcac caccggctac    2940
tggctcatta cacatttccc cttcccctca ttctcacttt gtggctttat tattattatt    3000
attacatata ttttaccgtt attatttcac gtcacataag cttgttaatt aatcattagt    3060
gagccttctc agcctttccg ttaacgtagt agtgctgtcc caccttatca aggttagaga    3120
aagtagcctt ccaagcaccg tagtaagaga gcaccttgta gttgagtccc cacttcttag    3180
cgaaaggaac gaatcttctg ctaacctcag gctgtctgaa ttgaggcata tcagggaaga    3240
ggtggtggat aacctgacag ttaaggtatc ccataagcca gttcacgtat cctctagaag    3300
gatcgatatc aacggtgtga tcaacagcgt agttaaccca agaaaggtgc ttatcagatg    3360
gaacaacagg gaggtgagta tgagaagtag agaagtgagc gaaaaggtac atgtaagcga    3420
tccagtttcc gaaagtgaac caccagtaag caacaggcca agagtatcca gtagcaagct    3480
tgataacagc ggttctaaca acatgagaaa cgagcatcca agaagcctct tcgtagttct    3540
tcttacggag aacttgtcta gggtggagaa cgtagatcca gaaagcttga acaagaagtc    3600
cagaggtaac aggaacgaaa gtccaagctt gaagtctagc ccaagctcta gagaatcctc    3660
taggtctgtt atcctcaaca gcagtgttga agaaagccac agcaggagtg gtatcaagat    3720
ccatatcgtg tctaaccttt tgaggggtag catggtgctt gttatgcatc tggttccaca    3780
tctcaccaga agtagaaagt ccgaatccac aagtcatagc ctgaagtctc ttgtccacgt    3840
aaacagatcc ggtaagagag ttatgtccac cctcatgttg aacccatcca catctagctc    3900
cgaagaaagc accgtaaaca acagaagcaa tgatagggta tccagcgtac ataagagcag    3960
ttccaagagc gaatgtagca agaagctcga gaagtctgta agccacatgg gtgatagaag    4020
gcttgaagaa tccatctctc tcaagctcag cacgccatct agcgaaatcc tcaagcatag    4080
gagcatcctc agactcagat ctcttgatct cagcaggtct agaaggcaaa gctctaagca    4140
tcttccaagc cttgagagaa cgcatgtgga attctttgaa agcctcagta gcatcagcac    4200
cagtgttagc aagcatgtag aagatcacag atccaccagg gtgcttgaag ttagtcacat    4260
cgtactcaac gtcctcaact ctaacccatc tagtctcgaa agtagcagca agctcatgag    4320
gctcaagagt cttaagatca acaggagcag tagaagcatc cttagcatca agagcctcag    4380
cagaagattt agacctggta agtggagatc taggagaaga tcttccatca gtcttaggag    4440
ggcacatggt atggtaattg taaatgtaat tgtaatgttg tttgttgttt gttgttgttg    4500
gtaattgttg taaaattaat taagtgggta tcttttggat ggataagcaa gtagtgatga    4560
tgttctaggt gaagtgatgg gggtgtttta tagcgggaga tggtgaaatg gatggtcgcc    4620
acataagaaa tggaggggaa gggttcttgc gccattcttc agtttgcatg gatgcatggg    4680
tttcattttg taacacgtaa taaggacaat gaagtgcagg tgtctctcaa gtttcagagg    4740
ggatatgtgg acagaagaag aacggcgatg atattgatgg aaatggccat ctagtgtgaa    4800
tctattcggt tgataatact agtgcatttt ggccgttaat cccttcaatt aactgcacaa    4860
acttcagttg agtattgatt atttgattat aggttctgta aacacaatac caagtttatt    4920
tagaggggag acatacaaat agtttcgata taaataatag agtggttaaa cttagttatt    4980
aaaactatat ataaagtcta aagttaaat tattttttta attgcaaata tataaagtct    5040
aaaggggtta cattatttct taagagatgt aactctgttg gaatctgact taatccgtct    5100
catcactctg gttccagtt ctaatctaat gaattgtttt ctgccaaaga atttgaagca    5160
agaagtaaat tgatcaatgc cgtcaaccca caccaaaccg tcaacccact accatcgccg    5220
```

-continued

```
cggagacccc caaactcaac ctccacccat cggtaagaag cacagggcag cccgcaccac    5280
caccaatttg gcgtgcatga cacctaggga cttggcacgg gaggcggcgc acgtggatgc    5340
aaatgacggg atatcagatg acaggaaacg acgttgagag accatacgat gtagaatatg    5400
agctcaccat caacgagaaa ctaggaaaat cacaaaaaaa acaactctcg taattgtacg    5460
agtggcacag atgggtctgc ctcaacatat ctctaatacg gcgaagcctg cccaacacgt    5520
agttgccgga atccggtgtg gagctcacga ctctgaaaga taggcgcttc ctgtttcgtt    5580
tcgctcaccc actggacgtc cgtcatgtga tggatttcgg tcattggttt gctgacaacc    5640
acattctgaa gctccatgag atgagtcttc acaataggtc ctgctcaata ccgtggagtt    5700
atggttgcaa gtccataact tgccgttcga atattttgcg gagccagtcg acgggaatt    5760 ggcgagctcg gctgacacct ataaaggcca tgacaagaag aaccaaaagt tcttccctaa    5820
tgctttcatg aggcttcggg tcgttatgga tgtcggaaaa cccctcttga aggaacgaga    5880
cgttattatg catgacggta agactattac ttgtcagtat aagtatgaaa gattacctgt    5940 cttctgctttt gtttgtggat tgattggaca cgttgaaaaa aaatgtgcac ttcgatttca    6000
atactcagag atcgacttcc cttttctcta ggagtattcg atcaaggcat taacatggaa    6060
ggaagctcaa gctctaaagg cttcacaatg gaacctgaaa aatttcaaca agcctaaact    6120
gaaatcgaag tcaaatcacc caaccgggag ctctaaatca gcaaacactc ctcctccaca    6180
gtatccaatc atcgtgcacg atgctccagg tattgcaagc caggtattgc aagctaggag    6240
taggatagag accttaaacg tcgttggtgt gaagagtcat cttcagacct aatggagata    6300
gatgtagacg gcggcacgaa gactctgaaa caccagaaag gctagtccag gataaggatc    6360
tgctatccca actgacctct cgttagtccc aaggcctctc aactagagca ggaggaagga    6420
tggtcacaag actaggataa tgatgttttcc aatatgaacc tgaatgtcca tagctaattt    6480
ttttagtctt gcttctgcac ttttttgttta ttatgttctg gtgactatgt tatttaccct    6540
tgtccgtatg cttgagggta ccctagtaga ttggttggtt ggtttccatg taccagaagg    6600
cttaccctat tagttgaaag ttgaaacttt gttccctact caattcctag ttgtgtaaat    6660
gtatgtatat gtaatgtgta taaaacgtag tacttaaatg actaggagtg gttcttgaga    6720
ccgatgagag atgggagcag aactaaagat gatgacataa ttaagaacga atttgaaagg    6780
ctcttaggtt tgaatcctat tcgagaatgt ttttgtcaaa gatagtggcg attttgaacc    6840
aaagaaaaca tttaaaaaat cagtatccgg ttacgttcat gcaaatagaa agtggtctag    6900
gatctgattg taattttaga cttaaagagt ctcttaagat tcaatcctgg ctgtgtacaa    6960
aactacaaat aatatatttt agactatttg gccttaacta aacttccact cattatttac    7020
tgaggttaga gaatagactt gcgaataaac acattcccga gaaatactca tgatcccata    7080
attagtcaga gggtatgcca atcagatcta agaacacaca ttccctcaaa ttttaatgca    7140
catgtaatca tagtttagca caattcaaaa ataatgtagt attaaagaca gaaatttgta    7200 gactttttttt tggcgttaaa agaagactaa gtttatacgt acattttatt ttaagtggaa    7260
aaccgaaatt ttccatcgaa atatatgaat ttagtatata tatttctgca atgtactatt    7320
ttgctatttt ggcaactttc agtggactac tactttatta caatgtgtat ggatgcatga    7380
gtttgagtat acacatgtct aaatgcatgc tttgtaaaac gtaacggacc acaaaagagg    7440
atccatacaa atacatctca tagcttcctc cattattttc cgacacaaac agagcatttt    7500
acaacaatta ccaacaacaa caaacaacaa acaacattac aattacattt acaattacca    7560
```

```
taccatggcc tctatcgcta tccctgctgc tcttgctgga actcttggat acgttaccta    7620
caatgtggct aaccctgata tcccagcttc tgagaaagtt cctgcttact tcatgcaggt    7680
tgagtactgg ggacctacta tcggaactat tggatacctc ctcttcatct acttcggaaa    7740
gcgtatcatg cagaacagat ctcaaccttt cggactcaag aacgctatgc tcgtttacaa    7800
cttctaccag accttcttca acagctactg catctacctt ttcgttactt ctcatagggc    7860
tcagggactt aaggtttggg gaaacatccc tgatatgact gctaactctt ggggaatctc    7920
tcaggttatc tggcttcact acaacaacaa gtacgttgag cttctcgaca ccttcttcat    7980
ggtgatgagg aagaagttcg accagctttc tttccttcac atctaccacc acactcttct    8040
catctggtca tggttcgttg ttatgaagct tgagcctgtt ggagattgct acttcggatc    8100
ttctgttaac accttcgtgc acgtgatcat gtactcttac tacggacttg ctgctcttgg    8160
agttaactgt ttctggaaga agtacatcac ccagatccag atgcttcagt tctgtatctg    8220
tgcttctcac tctatctaca ccgcttacgt tcagaatacc gctttctggc ttccttacct    8280
tcaactctgg gttatggtga acatgttcgt tctcttcgcc aacttctacc gtaagaggta    8340
caagtctaag ggtgctaaga agcagtgata aggcgcgcgg cgcgccgggc cgccgccatg    8400
tgacagatcg aaggaagaaa gtgtaataag acgactctca ctactcgatc gctagtgatt    8460
gtcattgtta tatataataa tgttatcttt cacaacttat cgtaatgcat gtgaaactat    8520
aacacattaa tcctacttgt catatgataa cactctcccc atttaaaact cttgtcaatt    8580
taaagatata agattcttta aatgattaaa aaaatatat tataaattca atcactccta    8640
ctaataaatt attaattatt atttattgat taaaaaaata cttatactaa tttagtctga    8700
atagaataat tagattctag tctcatcccc ttttaaacca acttagtaaa cgttttttt    8760 tttaattta tgaagttaag ttttaccttt gttttaaaa agaatcgttc ataagatgcc    8820
atgccagaac attagctaca cgttacacat agcatgcagc cgcggagaat tgttttctt    8880 cgccacttgt cactcccttc aaacacctaa gagcttctct ctcacagcac acacatacaa    8940
tcacatgcgt gcatgcatta ttacacgtga tcgccatgca aatctccttt atagcctata    9000
aattaactca tccgcttcac tctttactca aaccaaaact catcgataca aacaagatta    9060
aaaacataca cgaggatctt ttacaacaat taccaacaac aacaaacaac aaacaacatt    9120
acaattacat ttacaattac ataccatgc ctccaaggga ctcttactct tatgctgctc    9180
ctccttctgc tcaacttcac gaagttgata ctcctcaaga gcacgacaag aaagagcttg    9240
ttatcggaga tagggcttac gatgttacca acttcgttaa gagacaccct ggtgaaaga    9300 tcattgctta ccaagttgga actgatgcta ccgatgctta caagcagttc catgttagat    9360
ctgctaaggc tgcaagatg cttaagtctc ttccttctcg tcctgttcac aagggatact    9420
ctccaagaag ggctgatctt atcgctgatt ccaagagtt caccaagcaa cttgaggctg    9480
agggaatgtt cgagccttct cttcctcatg ttgcttacag acttgctgag gttatcgcta    9540
tgcatgttgc tggtgctgct cttatctggc atggatacac tttcgctgga atcgctatgc    9600
ttggagttgt tcagggaaga tgtggatggc ttatgcatga gggtggacat tactctctca    9660
ctggaaacat tgctttcgac agagctatcc aagttgcttg ttacggactt ggatgtggaa    9720
tgtctggtgc ttggtggcgt aaccagcata acaagcacca tgctactcct caaaagcttc    9780
agcacgatgt tgatcttgat acccttcctc tcgttgcttt ccatgagaga atcgctgcta    9840
aggttaagtc tcctgctatg aaggcttggc tttctatgca agctaagctt ttcgctcctg    9900
ttaccactct tcttgttgct cttggatggc agctttacct tcatcctaga cacatgctca    9960
```

```
ggactaagca ctacgatgag cttgctatgc tcggaatcag atacggactt gttggatacc    10020
ttgctgctaa ctacggtgct ggatacgttc tcgcttgtta ccttctttac gttcagcttg    10080
gagctatgta catcttctgc aacttcgctg tttctcatac tcacctccct gttgttgagc    10140
ctaacgagca tgctacttgg gttgagtacg ctgctaacca cactactaac tgttctccat    10200
cttggtggtg tgattggtgg atgtcttacc ttaactacca gatcgagcac cacctttacc    10260
cttctatgcc tcaattcaga caccctaaga tcgctcctag agttaagcag cttttcgaga    10320
agcacggact tcactacgat gttagaggat acttcgaggc tatggctgat actttcgcta    10380
accttgataa cgttgcccat gctcctgaga agaaaatgca gtaatgagat cgttcaaaca    10440
tttggcaata aagtttctta agattgaatc ctgttgccgg tcttgcgatg attatcatat    10500
aatttctgtt gaattacgtt aagcacgtaa taattaacat gtaatgcatg acgttattta    10560
tgagatgggt ttttatgatt agagtcccgc aattatacat ttaatacgcg atagaaaaca    10620
aaatatagcg cgcaaactag gataaattat cgcgcgcggt gtcatctatg ttactagatc    10680
ggtcgattaa aaatcccaat tatatttggt ctaatttagt ttggtattga gtaaaacaaa    10740
ttcgaaccaa accaaaatat aaatatatag tttttatata tatgccttta agacttttta    10800
tagaattttc tttaaaaaat atctagaaat atttgcgact cttctggcat gtaatatttc    10860
gttaaatatg aagtgctcca ttttttattaa ctttaaataa ttggttgtac gatcactttc    10920
ttatcaagtg ttactaaaat gcgtcaatct ctttgttctt ccatattcat atgtcaaaat    10980
ctatcaaaat tcttatatat cttttttcgaa tttgaagtga aatttcgata atttaaaatt    11040
aaatagaaca tatcattatt taggtatcat attgatttt atacttaatt actaaatttg    11100
gttaactttg aaagtgtaca tcaacgaaaa attagtcaaa cgactaaaat aaataaatat    11160
catgtgttat taagaaaatt ctcctataag aatattttaa tagatcatat gtttgtaaaa    11220
aaaattaatt tttactaaca catatattta cttatcaaaa atttgacaaa gtaagattaa    11280
aataatattc atctaacaaa aaaaaaacca gaaaatgctg aaaacccggc aaaaccgaac    11340
caatccaaac cgatatagtt ggtttggttt gattttgata taaaccgaac caactcggtc    11400
catttgcacc cctaatcata atagctttaa tatttcaaga tattattaag ttaacgttgt    11460
caatatcctg gaaattttgc aaaatgaatc aagcctatat ggctgtaata tgaatttaaa    11520
agcagctcga tgtggtggta atatgtaatt tacttgattc taaaaaaata tcccaagtat    11580
taataatttc tgctaggaag aaggttagct acgatttaca gcaaagccag aatacaaaga    11640
accataaagt gattgaagct cgaaatatac gaaggaacaa atatttttaa aaaaatacgc    11700
aatgacttgg aacaaaagaa agtgatatat ttttttgttct taaacaagca tcccctctaa    11760
agaatggcag ttttcctttg catgtaacta ttatgctccc ttcgttacaa aaattttgga    11820
ctactattgg gaacttcttc tgaaaatagt gatagaaccc acacgagcat gtgctttcca    11880
tttaatttta aaaaccaaga aacatacata cataacattc catcagcctc tctctctttt    11940
tattacggtt aatgacttaa aacacatctt attatcccat ccttaacacc tagcagtgtc    12000
tttatacgat ctcatcgatc accacttcaa aaccatgcag actgctgctg ccccctggagc    12060 tggcatcggc taggctgggt gccgcactgt cccggaaggt ccctagcgac ttgtttagat    12120
tgatgggacc acctctcaac ttcctgctgc tgtccctgct gctggatgtc ctgcctcatc    12180
tggccgattg cacgctccag tcccctgcat gtgcactcgc tcctcaattg cttaagatca    12240
tcgcagcagc tatcgaagtg ctggctctgt tgccctcctc cacggccttg gttgtagtag    12300
```

```
tagctgccgc cgcccttctg gacttttcc cacaggaacc gccgaataat tcgatagaac    12360
cacacgagca tgtgctttca tttattttaa aaaccaagaa acatacataa catttcatca    12420
gcctctctct ctctctctct ctctctctct ctctctctct ctctctctct ctctttatta    12480
cagctgttac actaacttaa aacacattca tctcattatt attattatta tccatcctta    12540
acacctagca gtgtctttgt acgatctcat aatcgatcac cccttcatca ggtatcctta    12600
ggcttcactc caacgttgtt gcagttacgg aacatgtaca caccatcatg gttctcaacg    12660
aactggcaag atctccaagt tttccaaagg ctaacccaca tgttctcatc ggtgtgtctg    12720
tagtgctctc ccataacttt cttgatgcac tcggtagctt ctctagcatg gtagaatggg    12780
atccttgaaa cgtagtgatg gagcacatga gtctcgatga tgtcatggaa gatgattccg    12840
aggattccga actctctatc gatagtagca gcagcaccct tagcgaaagt ccactcttga    12900
gcatcgtaat gaggcataga agaatcggtg tgctgaagga aggtaacgaa aacaagccag    12960
tggttaacaa ggatccaagg acagaaccat gtgatgaaag taggccagaa tccgaaaacc    13020
ttgtaagcgg tgtaaacaga agtgagggta gcaaggattc caagatcaga aagaacgatg    13080
taccagtagt ccttcttatc gaaaacaggg ctagaaggcc agtagtgaga cttgaagaac    13140
ttagaaacac cagggtaagg ttgtccagta gcgttagtag caaggtaaag agaaagtcct    13200
ccaagctgtt ggaacaagag agcgaaaaca gagtagatag gagtttcctc agcgatatcg    13260
tgaaggctgg taacttggtg cttctctttg aattcctcgg cggtgtaagg aacgaaaacc    13320
atatctctgg tcatgtgtcc agtagcctta tggtgcttag catgagagaa cttccagctg    13380
aagtaaggaa ccataacaag agagtggaga acccatccaa cggtatcgtt aacccatccg    13440
tagttagaga aagcagaatg tccacactca tgtccaagga tccagattcc gaatccgaaa    13500
caagagatag agaacacgta agcagaccaa gcagcgaatc taaggaattc gttagggaga    13560
agagggatgt aggtaagtcc aacgtaagcg atagcagaga tagccacgat atctctcacc    13620
acgtaagaca tagacttcac gagagatctc tcgtaacagt gcttagggat agcgtcaagg    13680
atatccttga tggtgtaatc tggcaccttg aaaacgtttc cgaaggtatc gatagcggtc    13740
ttttgctgct tgaaagatgc aacgtttcca gaacgcctaa cggtcttagt agatccctca    13800
aggatctcag atccagacac ggtaaccttta gacatggtat ggtaattgta aatgtaattg    13860
taatgttgtt tgttgtttgt tgttgttggt aattgttgta aaattttggg tggtgattgg    13920
ttctttaagg tgtgagagtg agttgtgagt tgtgtggtgg gtttggtgag attggggatg    13980
gtgggtttat atagtggaga ctgaggaatg gggtcgtgag tgttaacttt gcatgggcta    14040
cacgtgggtt ctttttgggct tacacgtagt attattcatg caaatgcagc caatacatat    14100
acggtatttt aataatgtgt gggaatacaa tatgccgagt attttactaa ttttggcaat    14160
gacaagtgta catttggatt atcttacttg gcctctcttg ctttaatttg gattattttt    14220
attctcttac cttggccgtt catattcaca tccctaaagg caagacagaa ttgaatggtg    14280
gccaaaaatt aaaacgatgg atatgaccta catagtgtag gatcaattaa cgtcgaagga    14340
aaatactgat tctctcaagc atacggacaa gggtaaataa catagtcacc agaacataat    14400
aaacaaaaag tgcagaagca agactaaaaa aattagctat ggacattcag gttcatattg    14460
gaaacatcat tatcctagtc ttgtgaccat ccttcctcct gctctagttg agaggccttg    14520
ggactaacga gaggtcagtt gggatagcag atccttatcc tggactagcc tttctggtgt    14580
ttcagagtct tcgtgccgcc gtctacatct atctccatta ggtctgaaga tgactcttca    14640
caccaacgac gtttaaggtc tctatcctac tcctagcttg caataacctgg cttgcaatac    14700
```

```
ctggagcatc gtgcacgatg attggatact gtggaggagg agtgtttgct gatttagagc    14760
tcccggttgg gtgatttgac ttcgatttca gtttaggctt gttgaaattt ttcaggttcc    14820
attgtgaagc ctttagagct tgagcttcct tccatgttaa tgccttgatc gaatactcct    14880
agagaaaagg gaagtcgatc tctgagtatt gaaatcgaag tgcacatttt ttttcaacgt    14940
gtccaatcaa tccacaaaca aagcagaaga caggtaatct ttcatactta tactgacaag    15000
taatagtctt accgtcatgc ataataacgt ctcgttcctt caagagtggt tttccgacat    15060
ccataacgac ccgaagcctc atgaaagcat tagggaagaa cttttggttc ttcttgtcat    15120
ggcctttata ggtgtcagcc gagctcgcca attcccgtcc gactggctcc gcaaaatatt    15180
cgaacggcaa gttatggact tgcaaccata actccacggt attgagcagg acctattgtg    15240
aagactcatc tcatggagct tcagaatgtg gttgtcagca aaccaatgac cgaaatccat    15300
cacatgacgg acgtccagtg ggtgagcgaa acgaaacagg aagcgcctat ctttcagagt    15360
cgtgagctcc acaccggatt ccggcaacta cgtgttgggc aggcttcgcc gtattagaga    15420
tatgttgagg cagacccatc tgtgccactc gtacaattac gagagttgtt ttttttgtga    15480
ttttcctagt ttctcgttga tggtgagctc atattctaca tcgtatggtc tctcaacgtc    15540
gtttcctgtc atctgatatc ccgtcatttg catccacgtg cgccgcctcc cgtgccaagt    15600
ccctaggtgt catgcacgcc aaattggtgg tggtgcgggc tgccctgtgc ttcttaccga    15660
tgggtggagg ttgagtttgg gggtctccgc ggcgatggta gtgggttgac ggtttggtgt    15720
gggttgacgg cattgatcaa tttacttctt gcttcaaatt cttttggcaga aaacaattca    15780 ttagattaga actggaaacc agagtgatga gacggattaa gtcagattcc aacagagtta    15840
catctcttaa gaaataatgt aaccccttta gactttatat atttgcaatt aaaaaaataa    15900
tttaactttt agactttata tatagtttta ataactaagt ttaaccactc tattatttat    15960
atcgaaacta tttgtatgtc tcccctctaa ataaacttgg tattgtgttt acagaaccta    16020
taatcaaata atcaatactc aactgaagtt tgtgcagtta attgaaggga ttaacggcca    16080
aaatgcacta gtattatcaa ccgaatagat tcactagata tggccatttc catcaatatc    16140
atcgccgttc ttcttctgtc cacatatccc ctctgaaact tgagagacac ctgcacttca    16200
ttgtccttat tacgtgttac aaaatgaaac ccatgcatcc atgcaaactg aagaatggcg    16260
caagaaccct tccctccat  ttcttatgtg gcgaccatcc atttcaccat ctcccgctat    16320
aaaacacccc catcacttca cctagaacat catcactact tgcttatcca tccaaaagat    16380
acccactttt acaacaatta ccaacaacaa caaacaacaa acaacattac aattacattt    16440
acaattacca taccatgcca cctagcgctg ctaagcaaat gggagcttct actggtgttc    16500
atgctggtgt tactgactct tctgctttca ccagaaagga tgttgctgat agacctgatc    16560
tcaccatcgt tggagattct gtttacgatg ctaaggcttt cagatctgag catcctggtg    16620
gtgctcattt cgtttctttg ttcggaggaa gagatgctac tgaggctttc atggaatacc    16680
atagaagggc ttggcctaag tctagaatgt ctagattcca cgttggatct cttgcttcta    16740
ctgaggaacc tgttgctgct gatgagggat accttcaact ttgtgctagg atcgctaaga    16800
tggtgccttc tgtttcttct ggattcgctc ctgcttctta ctgggttaag gctgacttca    16860
tccttggatc tgctatcgct cttgaggctt acatgcttta cgctggaaag agacttctcc    16920
cttctatcgt tcttggatgg cttttcgctc ttatcggtct taacatccag catgatgcta    16980
accatggtgc tttgtctaag tctgcttctg ttaaccttgc tcttgacttt tgtcaggatt    17040
```

```
ggatcggagg atctatgatc ctttggcttc aagagcatgt tgttatgcac cacctccaca   17100
ctaacgatgt tgataaggat cctgatcaaa aggctcacgg tgctcttaga ctcaagccta   17160
ctgatgcttg gtcacctatg cattggcttc agcatcttta cctttttgcct ggtgagacta   17220 tgtacgcttt caagcttttg ttcctcgaca tctctgagct tgttatgtgg cgttgggagg   17280
gtgagcctat ctctaagctt gctggatacc tctttatgcc ttctttgctt ctcaagctta   17340
ccttctgggc tagattcgtt gctttgcctc tttaccttgc tccttctgtt catactgctg   17400
tgtgtatcgc tgctactgtt atgactggat ctttctacct cgctttcttc ttcttcatct   17460
cccacaactt cgagggtgtt gcttctgttg gacctgatgg atctatcact tctatgacta   17520
gaggtgctag cttccttaag agacaagctg agacttcttc taacgttgga ggacctcttc   17580
ttgctactct taacggtgga ctcaactacc aaattgagca tcacttgttc cctagagttc   17640
accatggatt ctaccctaga cttgctcctc ttgttaaggc tgagcttgag gctagaggaa   17700
tcgagtacaa gcactaccct actatctggt ctaaccttgc ttctaccctc agacatatgt   17760
acgctcttgg aagaaggcct agatctaagg ctgagtaatg acaagcttat gtgacgtgaa   17820
ataataacgg taaatatat gtaataataa taataataaa gccacaaagt gagaatgagg   17880 ggaagggaa atgtgtaatg agccagtagc cggtggtgct aattttgtat cgtattgtca   17940
ataaatcatg aattttgtgg tttttatgtg tttttttaaa tcatgaattt taaattttat   18000
aaaataatct ccaatcggaa gaacaacatt ccatatccat gcatggatgt ttctttaccc   18060
aaatctagtt cttgagagga tgaagcatca ccgaacagtt ctgcaactat ccctcaaaag   18120 cttaaaatg aacaacaagg aacagagcaa cgttccaaag atcccaaacg aaacatatta   18180
tctatactaa tactatatta ttaattacta ctgcccggaa tcacaatccc tgaatgattc   18240
ctattaacta caagccttgt tggcggcgga gaagtgatcg cgcggcgag aagcagcgga   18300 ctcggagacg aggccttgga agatctgagt cgaacgggca gaatcagtat tttccttcga   18360
cgttaattga tcctacacta tgtaggtcat atccatcgtt ttaattttg gccaccattc   18420 aattctgtct tgcctttagg gatgtgaata tgaacggcca aggtaagaga ataaaaataa   18480
tccaaattaa agcaagagag gccaagtaag ataatccaaa tgtacacttg tcattgccaa   18540
aattagtaaa atactcggca tattgtattc ccacacatta ttaaaatacc gtatatgtat   18600
tggctgcatt tgcatgaata atactacgtg taagcccaaa agaacccacg tgtagcccat   18660
gcaaagttaa cactcacgac cccattcctc agtctccact atataaaccc accatcccca   18720
atctcaccaa acccaccaca caactcacaa ctcactctca caccttaaag aaccaatcac   18780
caccaaaaat tttacaacaa ttaccaacaa caacaaacaa caaacaacat tacaattaca   18840
tttacaatta ccataccatg agcgctgtta ccgttactgg atctgatcct aagaacagag   18900
gatcttctag caacaccgag caagaggttc caaaagttgc tatcgatacc aacggaaacg   18960
tgttctctgt tcctgatttc accatcaagg acatccttgg agctatccct catgagtgtt   19020
acgagagaag attggctacc tctctctact acgtgttcag agatatcttc tgcatgctta   19080
ccaccggata ccttacccat aagatccttt accctctcct catctcttac acctctaaca   19140
gcatcatcaa gttcactttc tgggcccttt acacttacgt tcaaggactt ttcggaaccg   19200
gaatctgggt tctcgctcat gagtgtggac atcaagcttt ctctgattac ggaatcgtga   19260
acgatttcgt tggatggacc cttcactctt accttatggt tccttacttc agctggaagt   19320
actctcatgg aaagcaccat aaggctactg gacacatgac cagagatatg gttttcgttc   19380
ctgccaccaa agaggaattc aagaagtcta ggaacttctt cggtaacctc gctgagtact   19440
```

```
ctgaggattc tccacttaga acccttacg agcttcttgt tcaacaactt ggaggatgga   19500
tcgcttacct cttcgttaac gttacaggac aaccttaccc tgatgttcct tcttggaaat   19560
ggaaccactt ctggcttacc tctccacttt tcgagcaaag agatgctctc tacatcttcc   19620
tttctgatct tggaatcctc acccagggaa tcgttcttac tctttggtac aagaaattcg   19680
gaggatggtc cctttcatc aactggttcg ttccttacat ctgggttaac cactggctcg   19740
ttttcatcac attccttcag cacactgatc ctactatgcc tcattacaac gctgaggaat   19800
ggactttcgc taagggtgct gctgctacta tcgatagaaa gttcggattc atcggacctc   19860
acatcttcca tgatatcatc gagactcatg tgcttcacca ctactgttct aggatcccat   19920
tctacaacgc tagacctgct tctgaggcta tcaagaaagt tatgggaaag cactacaggt   19980
ctagcgacga gaacatgtgg aagtcacttt ggaagtcttt caggtcttgc caatacgttg   20040
acggtgataa cggtgttctc atgttccgta acatcaacaa ctgcggagtt ggagctgctg   20100
agaagtaatg aaggggtgat cgattatgag atcgtacaaa gacactgcta ggtgttaagg   20160
atggataata ataataataa tgagatgaat gtgttttaag ttagtgtaac agctgtaata   20220
aagagagaga gagagagaga gagagagaga gagagagaga gagagagaga gaggctgatg   20280
aaatgttatg tatgtttctt ggttttaaa ataaatgaaa gcacatgctc gtgtggttct   20340
atcgaattat tcggcggttc ctgtgggaaa aagtccagaa gggccgccgc agctactact   20400
acaaccaagg ccgtggagga gggcaacaga gccagcactt cgatagctgc tgcgatgatc   20460
ttaagcaatt gaggagcgag tgcacatgca ggggactgga gcgtgcaatc ggccagatga   20520
ggcaggacat ccagcagcag ggacagcagc aggaagttga gaggtggtcc catcaatcta   20580
aacaagtcgc tagggacctt ccgggacagt gcggcaccca gcctagccga tgccagctcc   20640
aggggcagca gcagtctgca tggttttgaa gtggtgatcg atgagatcgt ataaagacac   20700
tgctaggtgt taaggatggg ataataagat gtgttttaag tcattaaccg taataaaaag   20760
agagagaggc tgatggaatg ttatgtatgt atgtttcttg gtttttaaaa ttaaatggaa   20820
agcacatgct cgtgtgggtt ctatctcgat taaaaatccc aattatattt ggtctaattt   20880
agtttggtat tgagtaaaac aaattcgaac caaaccaaaa tataaatata tagttttat   20940 atatatgcct ttaagacttt ttatagaatt ttctttaaaa aatatctaga aatatttgcg   21000
actcttctgg catgtaatat ttcgttaaat atgaagtgct ccatttttat aactttaaa   21060 taattggttg tacgatcact ttcttatcaa gtgttactaa aatgcgtcaa tctctttgtt   21120
cttccatatt catatgtcaa aatctatcaa aattcttata tatctttttc gaatttgaag   21180
tgaaatttcg ataatttaaa attaaataga acatatcatt atttaggtat catattgatt   21240
tttatactta attactaaat ttggttaact ttgaaagtgt acatcaacga aaaattagtc   21300
aaacgactaa aataaataaa tatcatgtgt tattaagaaa attctcctat aagaatattt   21360
taatagatca tatgtttgta aaaaaaatta attttacta acacatatat ttacttatca   21420
aaaatttgac aaagtaagat taaaataata ttcatctaac aaaaaaaaaa ccagaaaatg   21480
ctgaaaaccc ggcaaaaccg aaccaatcca aaccgatata gttggtttgg tttgattttg   21540
atataaaccg aaccaactcg gtccatttgc accctaatc ataatagctt taatatttca   21600
agatattatt aagttaacgt tgtcaatatc ctggaaattt tgcaaaatga atcaagccta   21660
tatggctgta atatgaattt aaaagcagct cgatgtggtg gtaatatgta atttacttga   21720
ttctaaaaaa atatcccaag tattaataat ttctgctagg aagaaggtta gctacgattt   21780
```

```
acagcaaagc cagaatacaa agaaccataa agtgattgaa gctcgaaata tacgaaggaa    21840
caaatatttt taaaaaaata cgcaatgact tggaacaaaa gaaagtgata tattttttgt    21900
tcttaaacaa gcatcccctc taaagaatgg cagttttcct ttgcatgtaa ctattatgct    21960
cccttcgtta caaaaatttt ggactactat tgggaacttc ttctgaaaat agtcctgcag    22020
gctagtagat tggttggttg gtttccatgt accagaaggc ttaccctatt agttgaaagt    22080
tgaaactttg ttccctactc aattcctagt tgtgtaaatg tatgtatatg taatgtgtat    22140
aaaacgtagt acttaaatga ctaggagtgg ttcttgagac cgatgagaga tgggagcaga    22200
actaaagatg atgacataat taagaacgaa tttgaaaggc tcttaggttt gaatcctatt    22260
cgagaatgtt tttgtcaaag atagtggcga ttttgaacca agaaaaacat ttaaaaaatc    22320
agtatccggt tacgttcatg caaatagaaa gtggtctagg atctgattgt aattttagac    22380
ttaaagagtc tcttaagatt caatcctggc tgtgtacaaa actacaaata atatatttta    22440
gactatttgg ccttaactaa acttccactc attatttact gaggttagag aatagacttg    22500
cgaataaaca cattcccgag aaatactcat gatcccataa ttagtcagag ggtatgccaa    22560
tcagatctaa gaacacacat tccctcaaat tttaatgcac atgtaatcat agtttagcac    22620
aattcaaaaa taatgtagta ttaaagacag aaatttgtag acttttttt ggcgttaaaa    22680 gaagactaag tttatacgta cattttattt taagtggaaa accgaaattt tccatcgaaa    22740
tatatgaatt tagtatatat atttctgcaa tgtactattt tgctattttg gcaactttca    22800
gtggactact actttattac aatgtgtatg gatgcatgag tttgagtata cacatgtcta    22860
aatgcatgct ttgtaaaacg taacggacca caaaagagga tccatacaaa tacatctcat    22920
agcttcctcc attattttcc gacacaaaca gagcatttta caacaattac caacaacaac    22980
aaacaacaaa caacattaca attacattta caattaccat accatggaat ttgctcaacc    23040
tctcgttgct atggctcaag agcagtacgc tgctatcgat gctgttgttg ctcctgctat    23100
cttctctgct accgactcta ttggatgggg actcaagcct atctcttctg ctactaagga    23160
tctccctctc gttgaatctc ctaccccttct tatcctttct ctcctcgctt acttcgctat    23220
cgttggttct ggactcgttt accgtaaagt gttccctaga accgttaagg gacaggatcc    23280
tttccttctc aaggctctta tgctcgctca caacgttttc cttatcggac tcagcccttta    23340 catgtgcctc aagctcgttt acgaggctta cgtgaacaag tactccttct ggggaaacgc    23400
ttacaaccct gctcaaaccg agatggctaa ggtgatctgg atcttctacg tgtccaagat    23460
ctacgagttc atggacaccct tcatcatgct tctcaaggga acgttaacc aggttttcctt    23520 cctccatgtt taccaccacg gatctatctc tggaatctgg tggatgatca cttatgctgc    23580
tccaggtgga gatgcttact ctctgctgc tctcaactct tgggttcatg tgtgcatgta    23640
cacctactac ttcatggctg ctgttcttcc taaggacgaa aagaccaaga gaaagtacct    23700
ttggtgggga agatacccta cccagatgca aatgttccag ttcttcatga accttctcca    23760
ggctgtttac ctcctctact cttcttctcc ttaccctaag ttcattgctc aactcctcgt    23820
tgtttacatg gttaccctcc tcatgctttt cggaaacttc tactacatga agcaccacgc    23880
ttctaagtga taagggccgc cgccatgtga cagatcgaag gaagaaagtg taataagacg    23940
actctcacta ctcgatcgct agtgattgtc attgttatat ataataatgt tatctttcac    24000
aacttatcgt aatgcatgtg aaactataac acattaatcc tacttgtcat atgataacac    24060
tctccccatt taaaactctt gtcaatttaa agatataaga ttcttaaat gattaaaaaa    24120 aatatattat aaattcaatc actcctacta ataaattatt aattattatt tattgattaa    24180
```

```
aaaaatactt atactaattt agtctgaata gaataattag attctagcct gcagggcggc   24240
cgcggatccc atggagtcaa agattcaaat agaggaccta acagaactcg ccgtaaagac   24300
tggcgaacag ttcatacaga gtctcttacg actcaatgac aagaagaaaa tcttcgtcaa   24360
catggtggag cacgacacac ttgtctactc caaaaatatc aaagatacag tctcagaaga   24420
ccaaagggca attgagactt ttcaacaaag gtaatatcc ggaaacctcc tcggattcca    24480
ttgcccagct atctgtcact ttattgtgaa gatagtggaa aaggaaggtg gctcctacaa   24540
atgccatcat tgcgataaag gaaaggccat cgttgaagat gcctctgccg acagtggtcc   24600
caaagatgga ccccccaccca cgaggagcat cgtggaaaaa gaagacgttc caaccacgtc   24660
ttcaaagcaa gtggattgat gtgatatctc cactgacgta agggatgacg cacaatccca   24720
ctatccttcg caagacccctt cctctatata aggaagttca tttcatttgg agagaacacg   24780
ggggactgaa ttaaatatga gccctgagag gcgtcctgtt gaaatcagac ctgctactgc   24840
tgctgatatg gctgctgttt gtgatatcgt gaaccactac atcgagactt ctaccgttaa   24900
cttcagaact gagcctcaaa ctcctcaaga gtggatcgat gatcttgaga gactccaaga   24960
tagataccct tggcttgttg ctgaggttga gggtgttgtt gctggaatcg cttacgctgg   25020
accttggaag gctagaaacg cttacgattg gactgttgag tctaccgttt acgtttcaca   25080
cagacatcag agacttggac ttggatctac cctttacact caccttctca gtctatgga    25140 agctcaggga ttcaagtctg ttgttgctgt tatcggactc cctaacgatc cttctgttag   25200
acttcatgag gctcttggat acactgctag aggaactctt agagctgctg gatacaagca   25260
cggtggatgg catgatgttg gattctggca aagagatttc gagcttcctg ctcctcctag   25320
acctgttaga ccagttactc agatctgaat ttgcgtgatc gttcaaacat ttggcaataa   25380
agtttcttaa gattgaatcc tgttgccggt cttgcgatga ttatcatata atttctgttg   25440
aattacgtta agcatgtaat aattaacatg taatgcatga cgttatttat gagatgggtt   25500
tttatgatta gagtcccgca attatacatt taatacgcga tagaaaacaa atatagcgc    25560 gcaaactagg ataaattatc gcgcgcggtg tcatctatgt tactagatca ctagtgatgt   25620
acggttaaaa ccaccccagt acattaaaaa cgtccgcaat gtgttattaa gttgtctaag   25680
cgtcaatttg tttacaccac aatatatcct gccaccagcc agccaacagc tccccgaccg   25740
gcagctcggc acaaaatcac cactcgatac aggcagccca tcagtcc                25787
```

<210> SEQ ID NO 4
<211> LENGTH: 22824
<212> TYPE: DNA
<213> ORGANISM: Artificial Sequence
<220> FEATURE:
<223> OTHER INFORMATION: pGA7- mod_D nucleotide sequence

<400> SEQUENCE: 4

```
tcctgtggtt ggcatgcaca tacaaatgga cgaacggata aaccttttca cgcccttta      60 aatatccgat tattctaata aacgctcttt tctcttaggt ttacccgcca atatatcctg    120
tcaaacactg atagtttaaa ctgaaggcgg gaaacgacaa tctgctagtg gatctcccag    180
tcacgacgtt gtaaaacggg cgcctcgatt aaaaatccca attatatttg gtctaattta    240
gtttggtatt gagtaaaaca aattcgaacc aaaccaaaat ataaatatat agttttttata  300 tatatgcctt taagcttttt tatagaattt tcttttaaaaa atatctagaa atatttgcga   360
ctcttctggc atgtaatatt tcgttaaata tgaagtgctc cattttttatt aactttaaat   420
```

```
aattggttgt acgatcactt tcttatcaag tgttactaaa atgcgtcaat ctctttgttc    480
ttccatattc atatgtcaaa atctatcaaa attcttatat atcttttttcg aatttgaagt   540 gaaatttcga taatttaaaa ttaaatagaa catatcatta tttaggtatc atattgattt    600
ttatacttaa ttactaaatt tggttaactt tgaaagtgta catcaacgaa aaattagtca    660
aacgactaaa ataaataaat atcatgtgtt attaagaaaa ttctcctata agaatatttt    720
aatagatcat atgtttgtaa aaaaaattaa ttttttactaa cacatatatt tacttatcaa    780
aaatttgaca aagtaagatt aaaataatat tcatctaaca aaaaaaaaac cagaaaatgc    840
tgaaaacccg gcaaaaccga accaatccaa accgatatag ttggtttggt ttgattttga    900
tataaaccga accaactcgg tccatttgca cccctaatca taatagcttt aatatttcaa    960
gatattatta agttaacgtt gtcaatatcc tggaaatttt gcaaaatgaa tcaagcctat   1020
atggctgtaa tatgaattta aaagcagctc gatgtggtgg taatatgtaa tttacttgat   1080
tctaaaaaaa tatcccaagt attaataatt tctgctagga agaaggttag ctacgattta   1140
cagcaaagcc agaatacaaa gaaccataaa gtgattgaag ctcgaaatat acgaaggaac   1200
aaatattttt aaaaaaatac gcaatgactt ggaacaaaag aaagtgatat atttttttgtt  1260 cttaaacaag catcccctct aaagaatggc agttttcctt tgcatgtaac tattatgctc   1320
ccttcgttac aaaaattttg gactactatt gggaacttct tctgaaaata gtggcgcccc   1380
gcggaaagct tgctagccaa ttggggccca acgttctcga gttttctag aaggaaactg    1440 aaggcgggaa acgacaatct gctagtggat ctcccagtca cgacgttgta aaacgggcgc   1500
cccgcggaaa gcttgcggcc gcccgatcta gtaacataga tgacaccgcg cgcgataatt   1560
tatcctagtt tgcgcgctat attttgtttt ctatcgcgta ttaaatgtat aattgcggga   1620
ctctaatcat aaaaacccat ctcataaata acgtcatgca ttcatgtta attattacgt    1680 gcttaacgta attcaacaga aattatatga taatcatcgc aagaccggca acaggattca   1740
atcttaagaa actttattgc caaatgtttg aacgatcggc gcgcctcatt agtgagcctt   1800
ctcagccttt ccgttaacgt agtagtgctg tcccaccttta tcaaggttag agaaagtagc  1860
cttccaagca ccgtagtaag agagcacctt gtagttgagt ccccacttct tagcgaaagg   1920
aacgaatctt ctgctaacct caggctgtct gaattgaggc atatcaggga agaggtggtg   1980
gataacctga cagttaaggt atcccataag ccagttcacg tatcctctag aaggatcgat   2040
atcaacggtg tgatcaacag cgtagttaac ccaagaaagg tgcttatcag atggaacaac   2100
agggaggtga gtatgagaag tagagaagtg agcgaaaagg tacatgtaag cgatccagtt   2160
tccgaaagtg aaccaccagt aagcaacagg ccaagagtat ccagtagcaa gcttgataac   2220
agcggttcta acaacatgag aaacgagcat ccaagaagcc tcttcgtagt tcttcttacg   2280
gagaacttgt ctagggtgga gaacgtagat ccagaaagct tgaacaagaa gtccagaggt   2340
aacaggaacg aaagtccaag cttgaagtct agcccaagct ctagagaatc ctctaggtct   2400
gttatcctca acagcagtgt tgaagaaagc cacagcagga gtggtatcaa gatccatatc   2460
gtgtctaacc ttttgagggg tagcatggtg cttgttatgc atctggttcc acatctcacc   2520
agaagtagaa agtccgaatc cacaagtcat agcctgaagt ctcttgtcca cgtaaacaga   2580
tccggtaaga gagttatgtc caccctcatg ttgaacccat ccacatctag ctccgaagaa   2640
agcaccgtaa acaacagaag caatgatagg gtatccagcg tacataagag cagttccaag   2700
agcgaatgta gcaagaagct cgagaagtct gtaagccaca tgggtgatag aaggcttgaa   2760
gaatccatct ctctcaagct cagcacgcca tctagcgaaa tcctcaagca taggagcatc   2820
```

```
ctcagactca gatctcttga tctcagcagg tctagaaggc aaagctctaa gcatcttcca    2880
agccttgaga gaacgcatgt ggaattcttt gaaagcctca gtagcatcag caccagtgtt    2940
agcaagcatg tagaagatca cagatccacc agggtgcttg aagttagtca catcgtactc    3000
aacgtcctca actctaaccc atctagtctc gaaagtagca gcaagctcat gaggctcaag    3060
agtcttaaga tcaacaggag cagtagaagc atccttagca tcaagagcct cagcagaaga    3120
tttagacctg gtaagtggag atctaggaga agatcttcca tcagtcttag gagggcacat    3180
ggtatggtaa ttgtaaatgt aattgtaatg ttgtttgttg tttgttgttg ttggtaattg    3240
ttgtaaaaga tcctcgtgta tgtttttaat cttgtttgta tcgatgagtt ttggtttgag    3300
taaagagtga agcggatgag ttaatttata ggctataaag gagatttgca tggcgatcac    3360
gtgtaataat gcatgcacgc atgtgattgt atgtgtgtgc tgtgagagag aagctcttag    3420
gtgtttgaag ggagtgacaa gtggcgaaga aaaacaattc tccgcggctg catgctatgt    3480
gtaacgtgta gctaatgttc tggcatggca tcttatgaac gattcttttt aaaaacaagg    3540
taaaaactta acttcataaa attaaaaaaa aaacgtttta ctaagttggt ttaaaagggg    3600
atgagactag tagattggtt ggttggtttc catgtaccag aaggcttacc ctattagttg    3660
aaagttgaaa ctttgttccc tactcaattc ctagttgtgt aaatgtatgt atatgtaatg    3720
tgtataaaac gtagtactta aatgactagg agtggttctt gagaccgatg agagatggga    3780
gcagaactaa agatgatgac ataattaaga acgaatttga aaggctctta ggtttgaatc    3840
ctattcgaga atgttttgt caaagatagt ggcgattttg aaccaaagaa acatttaaa     3900 aaatcagtat ccggttacgt tcatgcaaat agaaagtggt ctaggatctg attgtaattt    3960
tagacttaaa gagtctctta agattcaatc ctggctgtgt acaaaactac aaataatata    4020
ttttagacta tttggcctta actaaacttc cactcattat ttactgaggt tagagaatag    4080
acttgcgaat aaaacacattc ccgagaaata ctcatgatcc cataattagt cagagggtat    4140
gccaatcaga tctaagaaca cacattccct caaatttta tgcacatgta atcatagttt     4200
agcacaattc aaaaataatg tagtattaaa gacagaaatt tgtagacttt tttttggcgt    4260
taaaagaaga ctaagtttat acgtacattt tattttaagt ggaaaaccga aattttccat    4320
cgaaatatat gaatttagta tatatatttc tgcaatgtac tattttgcta ttttggcaac    4380
tttcagtgga ctactacttt attacaatgt gtatggatgc atgagtttga gtatacacat    4440
gtctaaatgc atgctttgta aaacgtaacg gaccacaaaa gaggatccat acaaatacat    4500
ctcatagctt cctccattat tttccgacac aaacagagca ttttacaaca attaccaaca    4560
acaacaaaca acaaacaaca ttacaattac atttacaatt accataccat ggaattcgcc    4620
cagcctcttg ttgctatggc tcaagagcaa tacgctgcta tcgatgctgt tgttgctcct    4680
gctatcttct ctgctactga ttctatcgga tggggactta agcctatctc ttctgctact    4740
aaggacttgc ctcttgttga gtctcctaca cctctcatcc tttctttgct tgcttacttc    4800
gctatcgttg gatctggact cgtttacaga aaggttttcc ctagaaccgt gaagggacaa    4860
gatccattcc ttttgaaggc tcttatgctt gctcacaacg tgttccttat cggactttct    4920
ctttacatgt gcctcaagct tgtgtacgag gcttacgtta caagtactc tttctgggga    4980 aacgcttaca accctgctca aactgagatg gctaaggtta tctggatctt ctacgtgagc    5040
aagatctacg agttcatgga taccttcatc atgctcctca agggaaatgt taaccaggtt    5100
agcttccttc acgtttacca tcacggatct atctctggaa tctggtggat gattacttac    5160
```

```
gctgctcctg gtggtgatgc ttacttctct gctgctctta actcttgggt tcacgtgtgt    5220
atgtacacct actattttat ggctgccgtg cttcctaagg acgagaaaac taagagaaag    5280
tacctctggt ggggaagata ccttactcaa atgcagatgt tccagttctt catgaacctt    5340
ctccaggctg tttaccttct ctactcttca tctccttacc ctaagtttat cgctcagctc    5400
ctcgtggtgt acatggttac tcttctcatg cttttcggaa acttctacta catgaagcac    5460
cacgctagca agtgatgagg cgcgccgggc cgccgccatg tgacagatcg aaggaagaaa    5520
gtgtaataag acgactctca ctactcgatc gctagtgatt gtcattgtta tatataataa    5580
tgttatcttt cacaacttat cgtaatgcat gtgaaactat aacacattaa tcctacttgt    5640
catatgataa cactctcccc atttaaaact cttgtcaatt taaagatata agattcttta    5700
aatgattaaa aaaatatat tataaattca atcactccta ctaataaatt attaattatt    5760
atttattgat taaaaaaata cttatactaa tttagtctga atagaataat tagattctag    5820
tctcatcccc ttttaaacca acttagtaaa cgttttttt tttaattta tgaagttaag    5880 tttttacctt gtttttaaaa agaatcgttc ataagatgcc atgccagaac attagctaca    5940
cgttacacat agcatgcagc cgcggagaat tgttttttctt cgccacttgt cactcccttc    6000
aaacacctaa gagcttctct ctcacagcac acacatacaa tcacatgcgt gcatgcatta    6060
ttacacgtga tcgccatgca aatctccttt atagcctata aattaactca tccgcttcac    6120
tctttactca aaccaaaact catcgataca aacaagatta aaaacataca cgaggatctt    6180
ttacaacaat taccaacaac aacaaacaac aaacaacatt acaattacat ttacaattac    6240
cataccatgc ctccaaggga ctcttactct tatgctgctc ctccttctgc tcaacttcac    6300
gaagttgata ctcctcaaga gcacgacaag aaagagcttg ttatcggaga tagggcttac    6360
gatgttacca acttcgttaa gagacaccct ggtggaaaga tcattgctta ccaagttgga    6420
actgatgcta ccgatgctta caagcagttc catgttagat ctgctaaggc tgacaagatg    6480
cttaagtctc ttccttctcg tcctgttcac aagggatact ctccaagaag ggctgatctt    6540
atcgctgatt tccaagagtt caccaagcaa cttgaggctg agggaatgtt cgagccttct    6600
cttcctcatg ttgcttacag acttgctgag gttatcgcta tgcatgttgc tggtgctgct    6660
cttatctggc atggatacac tttcgctgga atcgctatgc ttggagttgt tcagggaaga    6720
tgtggatggc ttatgcatga gggtggacat tactctctca ctggaaacat tgctttcgac    6780
agagctatcc aagttgcttg ttacggactt ggatgtggaa tgtctggtgc ttggtggcgt    6840
aaccagcata acaagcacca tgctactcct caaaagcttc agcacgatgt tgatcttgat    6900
acccttcctc tcgttgcttt ccatgagaga atcgctgcta aggttaagtc tcctgctatg    6960
aaggcttggc tttctatgca agctaagctt ttcgctcctg ttaccactct tcttgttgct    7020
cttggatggc agctttacct tcatcctaga cacatgctca ggactaagca ctacgatgag    7080
cttgctatgc tcggaatcag atacggactt gttggatacc ttgctgctaa ctacggtgct    7140
ggatacgttc tcgcttgtta ccttctttac gttcagcttg gagctatgta catcttctgc    7200
aacttcgctg tttctcatac tcacctccct gttgttgagc ctaacgagca tgctacttgg    7260
gttgagtacg ctgctaacca cactactaac tgttctccat cttggtggtg tgattggtgg    7320
atgtcttacc ttaactacca gatcgagcac caccttacc cttctatgcc tcaattcaga    7380
caccctaaga tcgctcctag agttaagcag cttttcgaga agcacggact tcactacgat    7440
gttagaggat acttcgaggc tatggctgat actttcgcta accttgataa cgttgcccat    7500
gctcctgaga agaaaatgca gtaatgagat cgttcaaaca tttggcaata agtttcttta    7560
```

```
agattgaatc ctgttgccgg tcttgcgatg attatcatat aatttctgtt gaattacgtt   7620
aagcacgtaa taattaacat gtaatgcatg acgttattta tgagatgggt ttttatgatt   7680
agagtcccgc aattatacat ttaatacgcg atagaaaaca aaatatagcg cgcaaactag   7740
gataaattat cgcgcgcggt gtcatctatg ttactagatc ggtcgattaa aaatcccaat   7800
tatatttggt ctaatttagt ttggtattga gtaaaacaaa ttcgaaccaa accaaaatat   7860
aaatatatag tttttatata tatgccttta agacttttta tagaattttc tttaaaaaat   7920
atctagaaat atttgcgact cttctggcat gtaatatttc gttaaatatg aagtgctcca   7980
tttttattaa ctttaaataa ttggttgtac gatcactttc ttatcaagtg ttactaaaat   8040
gcgtcaatct ctttgttctt ccatattcat atgtcaaaat ctatcaaaat tcttatatat   8100 cttttcgaa tttgaagtga aatttcgata atttaaaatt aaatagaaca tatcattatt   8160
taggtatcat attgattttt atacttaatt actaaatttg gttaactttg aaagtgtaca   8220
tcaacgaaaa attagtcaaa cgactaaaat aaataaatat catgtgttat taagaaaatt   8280
ctcctataag aatattttaa tagatcatat gtttgtaaaa aaaattaatt tttactaaca   8340
catatattta cttatcaaaa atttgacaaa gtaagattaa aataatattc atctaacaaa   8400
aaaaaaacca gaaaatgctg aaaacccggc aaaaccgaac caatccaaac cgatatagtt   8460
ggtttggttt gattttgata taaaccgaac caactcggtc catttgcacc cctaatcata   8520
atagctttaa tatttcaaga tattattaag ttaacgttgt caatatcctg gaaattttgc   8580
aaaatgaatc aagcctatat ggctgtaata tgaatttaaa agcagctcga tgtggtggta   8640
atatgtaatt tacttgattc taaaaaaata tcccaagtat taataatttc tgctaggaag   8700
aaggttagct acgatttaca gcaaagccag aatacaaaga accataaagt gattgaagct   8760
cgaaatatac gaaggaacaa atattttaa aaaaatacgc aatgacttgg aacaaaagaa   8820
agtgatatat ttttgttct taaacaagca tccctctaa agaatggcag ttttcctttg   8880
catgtaacta ttatgctccc ttcgttacaa aaattttgga ctactattgg gaacttcttc   8940 tgaaatagt gatagaaccc acacgagcat gtgctttcca tttaatttta aaaaccaaga   9000
aacatacata cataacattc catcagcctc tctctctttt tattacggtt aatgacttaa   9060
aacacatctt attatcccat ccttaacacc tagcagtgtc tttatacgat ctcatcgatc   9120
accacttcaa aaccatgcag actgctgctg cccctggagc tggcatcggc taggctgggt   9180
gccgcactgt cccggaaggt ccctagcgac ttgtttagat tgatgggacc acctctcaac   9240
ttcctgctgc tgtccctgct gctggatgtc ctgcctcatc tggccgattg cacgctccag   9300 tccctgcat gtgcactcgc tcctcaattg cttaagatca tcgcagcagc tatcgaagtg   9360
ctggctctgt tgccctcctc cacggccttg gttgtagtag tagctgccgc cgcccttctg   9420
gactttttcc cacaggaacc gccgaataat tcgatagaac cacacgagca tgtgctttca   9480
tttattttaa aaaccaagaa acatacataa catttcatca gcctctctct ctctctctct   9540
ctctctctct ctctctctct ctctctctct ctctttatta cagctgttac actaacttaa   9600
aacacattca tctcattatt attattatta tccatcctta acacctagca gtgtctttgt   9660
acgatctcat aatcgatcac cccttcatca ggtatcctta ggcttcactc caacgttgtt   9720
gcagttacgg aacatgtaca caccatcatg gttctcaacg aactggcaag atctccaagt   9780
tttccaaagg ctaacccaca tgttctcatc ggtgtgtctg tagtgctctc ccataacttt   9840
cttgatgcac tcggtagctt ctctagcatg gtagaatggg atccttgaaa cgtagtgatg   9900
```

```
gagcacatga gtctcgatga tgtcatggaa gatgattccg aggattccga actctctatc    9960
gatagtagca gcagcaccct tagcgaaagt ccactcttga gcatcgtaat gaggcataga   10020
agaatcggtg tgctgaagga aggtaacgaa aacaagccag tggttaacaa ggatccaagg   10080
acagaaccat gtgatgaaag taggccagaa tccgaaaacc ttgtaagcgg tgtaaacaga   10140
agtgagggta gcaaggattc caagatcaga agaacgatg taccagtagt ccttcttatc    10200
gaaaacaggg ctagaaggcc agtagtgaga cttgaagaac ttagaaacac cagggtaagg   10260
ttgtccagta gcgttagtag caaggtaaag agaaagtcct ccaagctgtt ggaacaagag   10320
agcgaaaaca gagtagatag gagtttcctc agcgatatcg tgaaggctgg taacttggtg   10380
cttctctttg aattcctcgg cggtgtaagg aacgaaaacc atatctctgg tcatgtgtcc   10440
agtagcctta tggtgcttag catgagagaa cttccagctg aagtaaggaa ccataacaag   10500
agagtggaga acccatccaa cggtatcgtt aacccatccg tagttagaga aagcagaatg   10560
tccacactca tgtccaagga tccagattcc gaatccgaaa caagagatag agaacacgta   10620
agcagaccaa gcagcgaatc taaggaattc gttagggaga gagggatgt aggtaagtcc    10680
aacgtaagcg atagcagaga tagccacgat atctctcacc acgtaagaca tagacttcac   10740
gagagatctc tcgtaacagt gcttagggat agcgtcaagg atatccttga tggtgtaatc   10800
tggcaccttg aaaacgtttc cgaaggtatc gatagcggtc ttttgctgct tgaaagatgc   10860
aacgtttcca gaacgcctaa cggtcttagt agatccctca aggatctcag atccagacac   10920
ggtaacctta gacatggtat ggtaattgta aatgtaattg taatgttgtt tgttgtttgt   10980
tgttgttggt aattgttgta aaattttttgg tggtgattgg ttctttaagg tgtgagagtg   11040
agttgtgagt tgtgtggtgg gtttggtgag attggggatg gtgggtttat atagtggaga   11100
ctgaggaatg gggtcgtgag tgttaacttt gcatgggcta cacgtgggtt cttttgggct   11160
tacacgtagt attattcatg caaatgcagc caatacatat acggtatttt aataatgtgt   11220
gggaatacaa tatgccgagt attttactaa ttttggcaat gacaagtgta catttggatt   11280
atcttacttg gcctctcttg ctttaatttg gattattttt attctcttac cttggccgtt   11340
catattcaca tccctaaagg caagacagaa ttgaatggtg gccaaaaatt aaaacgatgg   11400
atatgaccta catagtgtag gatcaattaa cgtcgaagga aaatactgat tctctcaagc   11460
atacggacaa gggtaaataa catagtcacc agaacataat aaacaaaaag tgcagaagca   11520
agactaaaaa aattagctat ggacattcag gttcatattg gaaacatcat tatcctagtc   11580
ttgtgaccat ccttcctcct gctctagttg agaggcttg ggactaacga gaggtcagtt    11640
gggatagcag atccttatcc tggactagcc tttctggtgt ttcagagtct tcgtgccgcc   11700
gtctacatct atctccatta ggtctgaaga tgactcttca caccaacgac gtttaaggtc   11760
tctatcctac tcctagcttg caatacctgg cttgcaatac ctggagcatc gtgcacgatg   11820
attggatact gtgaggagg agtgtttgct gatttagagc tcccggttgg gtgatttgac    11880
ttcgatttca gtttaggctt gttgaaattt ttcaggttcc attgtgaagc ctttagagct   11940
tgagcttcct tccatgttaa tgccttgatc gaatactcct agagaaaagg gaagtcgatc   12000
tctgagtatt gaaatcgaag tgcacatttt ttttcaacgt gtccaatcaa tccacaaaca   12060
aagcagaaga caggtaatct ttcatactta tactgacaag taatagtctt accgtcatgc   12120
ataataacgt ctcgttcctt caagaggggt tttccgacat ccataacgac ccgaagcctc   12180
atgaaagcat tagggaagaa cttttggttc ttccttgtcat ggcctttata ggtgtcagcc   12240
gagctcgcca attcccgtcc gactggctcc gcaaaatatt cgaacggcaa gttatggact   12300
```

```
tgcaaccata actccacggt attgagcagg acctattgtg aagactcatc tcatggagct    12360
tcagaatgtg gttgtcagca aaccaatgac cgaaatccat cacatgacgg acgtccagtg    12420
ggtgagcgaa acgaaacagg aagcgcctat ctttcagagt cgtgagctcc acaccggatt    12480
ccggcaacta cgtgttgggc aggcttcgcc gtattagaga tatgttgagg cagacccatc    12540
tgtgccactc gtacaattac gagagttgtt ttttttgtga ttttcctagt ttctcgttga    12600
tggtgagctc atattctaca tcgtatggtc tctcaacgtc gtttcctgtc atctgatatc    12660
ccgtcatttg catccacgtg cgccgcctcc cgtgccaagt ccctaggtgt catgcacgcc    12720
aaattggtgg tggtgcgggc tgccctgtgc ttcttaccga tgggtggagg ttgagtttgg    12780
gggtctccgc ggcgatggta gtgggttgac ggtttggtgt gggttgacgg cattgatcaa    12840
tttacttctt gcttcaaatt ctttggcaga aaacaattca ttagattaga actgaaaacc    12900
agagtgatga gacggattaa gtcagattcc aacagagtta catctcttaa gaaataatgt    12960
aaccccttta gactttatat atttgcaatt aaaaaaataa tttaacttttt agactttata    13020 tatagtttta ataactaagt ttaaccactc tattatttat atcgaaacta tttgtatgtc    13080 tccctctaa ataaacttgg tattgtgttt acagaaccta taatcaaata atcaatactc    13140
aactgaagtt tgtgcagtta attgaaggga ttaacggcca aaatgcacta gtattatcaa    13200
ccgaatagat tcacactaga tggccatttc catcaatatc atcgccgttc ttcttctgtc    13260
cacatatccc ctctgaaact tgagagacac ctgcacttca ttgtccttat tacgtgttac    13320
aaaatgaaac ccatgcatcc atgcaaactg aagaatggcg caagaacccct tcccctccat    13380 ttcttatgtg gcgaccatcc atttcaccat ctcccgctat aaaacaccccc catcacttca    13440 cctagaacat catcactact tgcttatcca tccaaaagat acccactttt acaacaatta    13500
ccaacaacaa caaacaacaa acaacattac aattacattt acaattacca taccatgcca    13560
cctagcgctg ctaagcaaat gggagcttct actggtgttc atgctggtgt tactgactct    13620
tctgctttca ccagaaagga tgttgctgat agacctgatc tcaccatcgt tggagattct    13680
gtttacgatg ctaaggcttt cagatctgag catcctggtg gtgctcattt cgtttctttg    13740
ttcggaggaa gagatgctac tgaggctttc atggaatacc atagaagggc ttggcctaag    13800
tctagaatgt ctagattcca cgttggatct cttgcttcta ctgaggaacc tgttgctgct    13860
gatgagggat accttcaact ttgtgctagg atcgctaaga tggtgccttc tgtttcttct    13920
ggattcgctc ctgcttctta ctgggttaag gctggactta ccttggatc tgctatcgct    13980 cttgaggctt acatgcttta cgctggaaag agacttctcc cttctatcgt tcttggatgg    14040
cttttcgctc ttatcggtct taacatccag catgatgcta accatggtgc tttgtctaag    14100
tctgcttctg ttaaccttgc tcttggactt tgtcaggatt ggatcggagg atctatgatc    14160
ctttggcttc aagagcatgt tgttatgcac cacctccaca ctaacgatgt tgataaggat    14220
cctgatcaaa aggctcacgg tgctcttaga ctcaagccta ctgatgcttg gtcacctatg    14280
cattggcttc agcatctttta ccttttgcct ggtgagacta tgtacgcttt caagcttttg    14340
ttcctcgaca tctctgagct tgttatgtgg cgttgggagg gtgagcctat ctctaagctt    14400
gctggatacc tctttatgcc ttctttgctt ctcaagctta ccttctgggc tagattcgtt    14460
gctttgcctc tttaccttgc tccttctgtt catactgctg tgtgtatcgc tgctactgtt    14520
atgactggat cttttctacct cgctttcttc ttcttcatct cccacaactt cgagggtgtt    14580
gcttctgttg gacctgatgg atctatcact tctatgacta gaggtgctag cttccttaag    14640
```

```
agacaagctg agacttcttc taacgttgga ggacctcttc ttgctactct taacggtgga    14700
ctcaactacc aaattgagca tcacttgttc cctagagttc accatggatt ctaccctaga    14760
cttgctcctc ttgttaaggc tgagcttgag gctagaggaa tcgagtacaa gcactaccct    14820
actatctggt ctaaccttgc ttctacccte agacatatgt acgctcttgg aagaaggcct    14880
agatctaagg ctgagtaatg acaagcttat gtgacgtgaa ataataacgg taaaatatat    14940
gtaataataa taataataaa gccacaaagt gagaatgagg ggaagggaa atgtgtaatg    15000 agccagtagc cggtggtgct aattttgtat cgtattgtca ataaatcatg aattttgtgg    15060
tttttatgtg ttttttttaaa tcatgaattt taaattttat aaaataatct ccaatcggaa    15120
gaacaacatt ccatatccat gcatggatgt ttctttaccc aaatctagtt cttgagagga    15180
tgaagcatca ccgaacagtt ctgcaactat ccctcaaaag ctttaaaatg aacaacaagg    15240
aacagagcaa cgttccaaag atcccaaacg aaacatatta tctatactaa tactatatta    15300
ttaattacta ctgcccggaa tcacaatccc tgaatgattc ctattaacta caagccttgt    15360
tggcggcgga gaagtgatcg gcgcggcgag aagcagcgga ctcggagacg aggccttgga    15420
agatctgagt cgaacgggca gaatcagtat tttccttcga cgttaattga tcctacacta    15480
tgtaggtcat atccatcgtt ttaattttg gccaccattc aattctgtct tgcctttagg    15540
gatgtgaata tgaacggcca aggtaagaga ataaaaataa tccaaattaa agcaagagag    15600
gccaagtaag ataatccaaa tgtacacttg tcattgccaa aattagtaaa atactcggca    15660
tattgtattc ccacacatta ttaaaatacc gtatatgtat tggctgcatt tgcatgaata    15720
atactacgtg taagcccaaa agaacccacg tgtagcccat gcaaagttaa cactcacgac    15780
cccattcctc agtctccact atataaaccc accatcccca atctcaccaa acccaccaca    15840
caactcacaa ctcactctca caccttaaag aaccaatcac caccaaaaat tttacaacaa    15900
ttaccaacaa caacaaacaa caaacaacat tacaattaca tttacaatta ccataccatg    15960
agcgctgtta ccgttactgg atctgatcct aagaacagag gatcttctag caacaccgag    16020
caagaggttc caaaagttgc tatcgatacc aacggaaacg tgttctctgt tcctgatttc    16080
accatcaagg acatccttgg agctatccct catgagtgtt acgagagaag attggctacc    16140
tctctctact acgtgttcag agatatcttc tgcatgctta ccaccggata ccttacccat    16200
aagatccttt accctctcct catctcttac acctctaaca gcatcatcaa gttcactttc    16260
tgggcccttt acacttacgt tcaaggactt ttcggaaccg gaatctgggt tctcgctcat    16320
gagtgtggac atcaagcttt ctctgattac ggaatcgtga acgatttcgt tggatggacc    16380
cttcactctt accttatggt tccttacttc agctggaagt actctcatgg aaagcaccat    16440
aaggctactg gacacatgac cagagatatg gtttttcgttc ctgccaccaa agaggaattc    16500
aagaagtcta ggaacttctt cggtaacctc gctgagtact ctgaggattc tccacttaga    16560 acccttacg agcttcttgt tcaacaactt ggaggatgga tcgcttacct cttcgttaac    16620
gttacaggac aaccttaccc tgatgttcct tcttggaaat ggaaccactt ctggcttacc    16680
tctccacttt tcgagcaaag agatgctctc tacatcttcc tttctgatct tggaatcctc    16740
acccagggaa tcgttcttac tctttggtac aagaaattcg gaggatggtc ccttttcatc    16800
aactggttcg ttccttacat ctgggttaac cactggctcg ttttcatcac attccttcag    16860
cacactgatc ctactatgcc tcattacaac gctgaggaat ggacttcgc taagggtgct    16920 gctgctacta tcgatagaaa gttcggattc atcggacctc acatcttcca tgatatcatc    16980
gagactcatg tgcttcacca ctactgttct aggatcccat tctacaacgc tagacctgct    17040
```

```
tctgaggcta tcaagaaagt tatgggaaag cactacaggt ctagcgacga gaacatgtgg   17100
aagtcacttt ggaagtcttt caggtcttgc caatacgttg acggtgataa cggtgttctc   17160
atgttccgta acatcaacaa ctgcggagtt ggagctgctg agaagtaatg aagggggtgat  17220 cgattatgag atcgtacaaa gacactgcta ggtgttaagg atggataata ataataataa  17280
tgagatgaat gtgttttaag ttagtgtaac agctgtaata agagagaga gagagagaga   17340 gagagagaga gagagagaga gagagagaga gaggctgatg aaatgttatg tatgtttctt   17400 ggttttaaa ataaatgaaa gcacatgctc gtgtggttct atcgaattat tcggcggttc    17460
ctgtgggaaa aagtccagaa gggccgccgc agctactact acaaccaagg ccgtggagga   17520
gggcaacaga gccagcactt cgatagctgc tgcgatgatc ttaagcaatt gaggagcgag   17580
tgcacatgca ggggactgga gcgtgcaatc ggccagatga ggcaggacat ccagcagcag   17640
ggacagcagc aggaagttga gaggtggtcc catcaatcta aacaagtcgc tagggacctt   17700
ccgggacagt gcggcaccca gcctagccga tgccagctcc aggggcagca gcagtctgca   17760
tggttttgaa gtggtgatcg atgagatcgt ataaagacac tgctaggtgt taaggatggg   17820
ataataagat gtgttttaag tcattaaccg taataaaaag agagagaggc tgatggaatg   17880
ttatgtatgt atgtttcttg gttttttaaaa ttaaatggaa agcacatgct cgtgtgggtt   17940
ctatctcgat taaaaatccc aattatattt ggtctaattt agtttggtat tgagtaaaac   18000
aaattcgaac caaaccaaaa tataaatata tagttttttat atatatgcct ttaagacttt   18060
ttatagaatt ttcttttaaaa aatatctaga aatatttgcg actcttctgg catgtaatat   18120
ttcgttaaat atgaagtgct ccattttat taactttaaa taattggttg tacgatcact    18180
ttcttatcaa gtgttactaa aatgcgtcaa tctctttgtt cttccatatt catatgtcaa   18240
aatctatcaa aattcttata tatcttttttc gaatttgaag tgaaatttcg ataatttaaa  18300
attaaataga acatatcatt atttaggtat catattgatt tttatactta attactaaat   18360
ttggttaact ttgaaagtgt acatcaacga aaaattagtc aaacgactaa aataaataaa   18420
tatcatgtgt tattaagaaa attctcctat aagaatattt taatagatca tatgtttgta   18480 aaaaaatta atttttacta acacatatat ttacttatca aaaatttgac aaagtaagat    18540
taaaataata ttcatctaac aaaaaaaaa ccagaaaatg ctgaaaaccc ggcaaaaccg    18600
aaccaatcca aaccgatata gttggtttgg tttgattttg atataaaccg aaccaactcg   18660
gtccatttgc acccctaatc ataatagctt taatatttca agatattatt aagttaacgt   18720
tgtcaatatc ctggaaattt tgcaaaatga atcaagccta tatggctgta atatgaattt   18780
aaaagcagct cgatgtggtg gtaatatgta atttacttga ttctaaaaaaa atatcccaag  18840 tattaataat ttctgctagg aagaaggtta gctacgattt acagcaaagc cagaatacaa   18900
agaaccataa agtgattgaa gctcgaaata tacgaaggaa caaatatttt taaaaaaata   18960
cgcaatgact tggaacaaaa gaaagtgata tattttttgt tcttaaacaa gcatcccctc   19020
taaagaatgg cagttttcct ttgcatgtaa ctattatgct cccttcgtta caaaaatttt   19080
ggactactat tgggaacttc ttctgaaaat agtcctgcag gctagtagat tggttggttg   19140
gtttccatgt accagaaggc ttaccctatt agttgaaagt tgaaactttg ttccctactc   19200
aattcctagt tgtgtaaatg tatgtatatg taatgtgtat aaaacgtagt acttaaatga   19260
ctaggagtgg ttcttgagac cgatgagaga tgggagcaga actaaagatg atgacataat   19320
taagaacgaa tttgaaaggc tcttaggttt gaatcctatt cgagaatgtt tttgtcaaag   19380
```

```
atagtggcga ttttgaacca aagaaaacat ttaaaaaatc agtatccggt tacgttcatg   19440
caaatagaaa gtggtctagg atctgattgt aattttagac ttaaagagtc tcttaagatt   19500
caatcctggc tgtgtacaaa actacaaata atatatttta gactatttgg ccttaactaa   19560
acttccactc attatttact gaggttagag aatagacttg cgaataaaca cattcccgag   19620
aaatactcat gatcccataa ttagtcagag ggtatgccaa tcagatctaa gaacacacat   19680
tccctcaaat tttaatgcac atgtaatcat agtttagcac aattcaaaaa taatgtagta   19740
ttaaagacag aaatttgtag acttttttt ggcgttaaaa gaagactaag tttatacgta   19800
cattttattt taagtggaaa accgaaattt tccatcgaaa tatatgaatt tagtatatat   19860
atttctgcaa tgtactattt tgctattttg gcaactttca gtggactact actttattac   19920
aatgtgtatg gatgcatgag tttgagtata cacatgtcta aatgcatgct ttgtaaaacg   19980
taacggacca caaagagga tccatacaaa tacatctcat agcttcctcc attattttcc   20040
gacacaaaca gagcatttta caacaattac caacaacaac aaacaacaaa caacattaca   20100
attacattta caattaccat accatggcct ctatcgctat ccctgctgct cttgctggaa   20160
ctcttggata cgttacctac aatgtggcta accctgatat cccagcttct gagaaagttc   20220
ctgcttactt catgcaggtt gagtactggg gacctactat cggaactatt ggatacctcc   20280
tcttcatcta cttcggaaag cgtatcatgc agaacagatc tcaacctttc ggactcaaga   20340
acgctatgct cgtttacaac ttctaccaga ccttcttcaa cagctactgc atctaccttt   20400
tcgttacttc tcatagggct cagggactta aggtttgggg aaacatccct gatatgactg   20460
ctaactcttg gggaatctct caggttatct ggcttcacta caacaacaag tacgttgagc   20520
ttctcgacac cttcttcatg gtgatgagga agaagttcga ccagctttct ttccttcaca   20580
tctaccacca cactcttctc atctggtcat ggttcgttgt tatgaagctt gagcctgttg   20640
gagattgcta cttcggatct tctgttaaca ccttcgtgca cgtgatcatg tactcttact   20700
acggacttgc tgctcttgga gttaactgtt tctggaagaa gtacatcacc cagatccaga   20760
tgcttcagtt ctgtatctgt gcttctcact ctatctacac cgcttacgtt cagaataccg   20820
ctttctggct tccttacctt caactctggg ttatggtgaa catgttcgtt ctcttcgcca   20880
acttctaccg taagaggtac aagtctaagg gtgctaagaa gcagtgataa gggccgccgc   20940
catgtgacag atcgaaggaa gaaagtgtaa taagacgact ctcactactc gatcgctagt   21000
gattgtcatt gttatatata ataatgttat ctttcacaac ttatcgtaat gcatgtgaaa   21060
ctataacaca ttaatcctac ttgtcatatg ataacactct ccccatttaa aactcttgtc   21120
aatttaaaga tataagattc tttaaatgat taaaaaaat atattataaa ttcaatcact   21180
cctactaata aattattaat tattatttat tgattaaaaa aatacttata ctaatttagt   21240
ctgaatagaa taattagatt ctagcctgca gggcggccgc ggatcccatg gagtcaaaga   21300
ttcaaataga ggacctaaca gaactcgccg taaagactgg cgaacagttc atacagagtc   21360
tcttacgact caatgacaag aagaaaatct tcgtcaacat ggtggagcac gacacacttg   21420
tctactccaa aaatatcaaa gatacagtct cagaagacca agggcaatt gagacttttc   21480 aacaaagggt aatatccgga aacctcctcg gattccattg cccagctatc tgtcacttta   21540
ttgtgaagat agtggaaaag gaaggtggct cctacaaatg ccatcattgc gataaaggaa   21600
aggccatcgt tgaagatgcc tctgccgaca gtggtcccaa agatggaccc ccacccacga   21660
ggagcatcgt ggaaaaagaa gacgttccaa ccacgtcttc aaagcaagtg gattgatgtg   21720
atatctccac tgacgtaagg gatgacgcac aatcccacta tccttcgcaa gacccttcct   21780
```

```
ctatataagg aagttcattt catttggaga gaacacgggg gactgaatta aaatatgagcc    21840 ctgagaggcg tcctgttgaa atcagacctg ctactgctgc tgatatggct gctgtttgtg    21900
atatcgtgaa ccactacatc gagacttcta ccgttaactt cagaactgag cctcaaactc    21960
ctcaagagtg gatcgatgat cttgagagac tccaagatag ataccttggg cttgttgctg    22020
aggttgaggg tgttgttgct ggaatcgctt acgctggacc ttggaaggct agaaacgctt    22080
acgattggac tgttgagtct accgtttacg tttcacacag acatcagaga cttggacttg    22140
gatctaccct ttacactcac cttctcaagt ctatggaagc tcagggattc aagtctgttg    22200
ttgctgttat cggactccct aacgatcctt ctgttagact tcatgaggct cttggataca    22260
ctgctagagg aactcttaga gctgctggat acaagcacgg tggatggcat gatgttggat    22320
tctggcaaag agatttcgag cttcctgctc ctcctagacc tgttagacca gttactcaga    22380
tctgaatttg cgtgatcgtt caaacatttg gcaataaagt ttcttaagat tgaatcctgt    22440
tgccggtctt gcgatgatta tcatataatt tctgttgaat tacgttaagc atgtaataat    22500
taacatgtaa tgcatgacgt tatttatgag atgggttttt atgattagag tcccgcaatt    22560
atacatttaa tacgcgatag aaaacaaaat atagcgcgca aactaggata aattatcgcg    22620
cgcggtgtca tctatgttac tagatcacta gtgatgtacg gttaaaacca ccccagtaca    22680
ttaaaaacgt ccgcaatgtg ttattaagtt gtctaagcgt caatttgttt acaccacaat    22740
atatcctgcc accagccagc caacagctcc ccgaccggca gctcggcaca aaatcaccac    22800
tcgatacagg cagcccatca gtcc                                          22824

<210> SEQ ID NO 5
<211> LENGTH: 24809
<212> TYPE: DNA
<213> ORGANISM: Artificial Sequence
<220> FEATURE:
<223> OTHER INFORMATION: pga7- mod_e nucleotide sequence

<400> SEQUENCE: 5
tcctgtggtt ggcatgcaca tacaaatgga cgaacggata aaccttttca cgcccttta     60 aatatccgat tattctaata aacgctcttt tctcttaggt ttacccgcca atatatcctg   120
tcaaacactg atagtttaaa ctgaaggcgg gaaacgacaa tctgctagtg gatctcccag   180
tcacgacgtt gtaaaacggg cgcctcgatt aaaaatccca attatatttg gtctaattta   240
gtttggtatt gagtaaaaca aattcgaacc aaaccaaaat ataaatatat agttttttata   300 tatatgcctt taagactttt tatagaattt tcttttaaaaa atatctagaa atatttgcga   360
ctcttctggc atgtaatatt tcgttaaata tgaagtgctc catttttatt aactttaaat   420
aattggttgt acgatcactt tcttatcaag tgttactaaa atgcgtcaat ctctttgttc   480
ttccatattc atatgtcaaa atctatcaaa attcttatat atcttttcg aatttgaagt    540 gaaatttcga taatttaaaa ttaaatagaa catatcatta tttaggtatc atattgattt   600
ttatacttaa ttactaaatt tggttaactt tgaaagtgta catcaacgaa aaattagtca   660
aacgactaaa ataaataaat atcatgtgtt attaagaaaa ttctcctata agaatatttt   720
aatagatcat atgtttgtaa aaaaaattaa ttttttactaa cacatatatt tacttatcaa   780
aaatttgaca aagtaagatt aaaataatat tcatctaaca aaaaaaaaac cagaaaatgc   840
tgaaaacccg gcaaaaccga accaatccaa accgatatag ttggtttggt ttgattttga   900
tataaaccga accaactcgg tccatttgca cccctaatca taatagcttt aatatttcaa   960
```

```
gatattatta agttaacgtt gtcaatatcc tggaaatttt gcaaaatgaa tcaagcctat    1020
atggctgtaa tatgaattta aaagcagctc gatgtggtgg taatatgtaa tttacttgat    1080
tctaaaaaaa tatcccaagt attaataatt tctgctagga agaaggttag ctacgattta    1140
cagcaaagcc agaatacaaa gaaccataaa gtgattgaag ctcgaaatat acgaaggaac    1200
aaatatttt aaaaaaatac gcaatgactt ggaacaaaag aaagtgatat attttttgtt    1260
cttaaacaag catccctct aaagaatggc agttttcctt tgcatgtaac tattatgctc    1320
ccttcgttac aaaaattttg gactactatt gggaacttct tctgaaaata gtggcgcccc    1380
gcggaaagct tgctagccaa ttggggccca acgttctcga gttttctag aaggaaactg    1440
aaggcgggaa acgacaatct gctagtggat ctcccagtca cgacgttgta aacgggcgc    1500
cccgcggaaa gcttgcggcc gcggtaccgc ccgttcgact cagatcttcc aaggcctcgt    1560
ctccgagtcc gctgcttctc gccgcgccga tcacttctcc gccgccaaca aggcttgtag    1620
ttaataggaa tcattcaggg attgtgattc cgggcagtag taattaataa tatagtatta    1680
gtatagataa tatgtttcgt ttgggatctt tggaacgttg ctctgttcct tgttgttcat    1740
tttaaagctt ttgagggata gttgcagaac tgttcggtga tgcttcatcc tctcaagaac    1800
tagatttggg taaagaaaca tccatgcatg gatatgaat gttgttcttc cgattggaga    1860
ttatttata aaatttaaaa ttcatgattt aaaaaaacac ataaaaacca caaattcat     1920
gatttattga caatacgata caaaattagc accaccggct actggctcat tacacatttc    1980
cccttcccct cattctcact tgtggctttt attattatta ttattacata tattttaccg    2040
ttattatttc acgtcacata agcttgttaa ttaatcatta gtgagccttc tcagccttc    2100
cgttaacgta gtagtgctgt cccaccttat caaggttaga gaaagtagcc ttccaagcac    2160
cgtagtaaga gagcaccttg tagttgagtc cccacttctt agcgaaagga acgaatcttc    2220
tgctaacctc aggctgtctg aattgaggca tatcagggaa gaggtggtgg ataacctgac    2280
agttaaggta tcccataagc cagttcacgt atcctctaga aggatcgata tcaacggtgt    2340
gatcaacagc gtagttaacc caagaaaggt gcttatcaga tggaacaaca gggaggtgag    2400
tatgagaagt agagaagtga gcgaaaaggt acatgtaagc gatccagttt ccgaaagtga    2460
accaccagta agcaacaggc caagagtatc cagtagcaag cttgataaca gcggttctaa    2520
caacatgaga aacgagcatc caagaagcct cttcgtagtt cttcttacgg agaacttgtc    2580
tagggtggag aacgtagatc cagaaagctt gaacaagaag tccagaggta acaggaacga    2640
aagtccaagc ttgaagtcta gcccaagctc tagagaatcc tctaggtctg ttatcctcaa    2700
cagcagtgtt gaagaaagcc acagcaggag tggtatcaag atccatatcg tgtctaacct    2760
tttgaggggt agcatggtgc ttgttatgca tctggttcca catctcacca gaagtagaaa    2820
gtccgaatcc acaagtcata gcctgaagtc tcttgtccac gtaaacagat ccggtaagag    2880
agttatgtcc accctcatgt tgaacccatc cacatctagc tccgaagaaa gcaccgtaaa    2940
caacagaagc aatgataggg tatccagcgt acataagagc agttccaaga gcgaatgtag    3000
caagaagctc gagaagtctg taagccacat gggtgataga aggcttgaag aatccatctc    3060
tctcaagctc agcacgccat ctagcgaaat cctcaagcat aggagcatcc tcagactcag    3120
atctcttgat ctcagcaggt ctagaaggca aagctctaag catcttccaa gccttgagag    3180
aacgcatgtg gaattctttg aaagcctcag tagcatcagc accagtgtta gcaagcatgt    3240
agaagatcac agatccacca gggtgcttga agttagtcac atcgtactca acgtcctcaa    3300
ctctaaccca tctagtctcg aaagtagcag caagctcatg aggctcaaga gtcttaagat    3360
```

```
caacaggagc agtagaagca tccttagcat caagagcctc agcagaagat ttagacctgg    3420
taagtggaga tctaggagaa gatcttccat cagtcttagg agggcacatg gtatggtaat    3480
tgtaaatgta attgtaatgt tgtttgttgt ttgttgttgt tggtaattgt tgtaaaatta    3540
attaagtggg tatcttttgg atggataagc aagtagtgat gatgttctag gtgaagtgat    3600
gggggtgttt tatagcggga gatggtgaaa tggatggtcg ccacataaga aatggagggg    3660
aagggttctt gcgccattct tcagtttgca tggatgcatg ggtttcattt tgtaacacgt    3720
aataaggaca atgaagtgca ggtgtctctc aagtttcaga ggggatatgt ggacagaaga    3780
agaacggcga tgatattgat ggaaatggcc atcagtgtg aatctattcg gttgataata    3840
ctagtgcatt ttggccgtta atcccttcaa ttaactgcac aaacttcagt tgagtattga    3900
ttatttgatt ataggttctg taaacacaat accaagttta tttagagggg agacatacaa    3960
atagtttcga tataaataat agagtggtta aacttagtta ttaaaactat atataaagtc    4020
taaaagttaa attattttt taattgcaaa tatataaagt ctaaagggt tacattattt    4080 cttaagagat gtaactctgt tggaatctga cttaatccgt ctcatcactc tggtttccag    4140
ttctaatcta atgaattgtt ttctgccaaa gaatttgaag caagaagtaa attgatcaat    4200
gccgtcaacc cacaccaaac cgtcaaccca ctaccatcgc cgcggagacc cccaaactca    4260
acctccaccc atcggtaaga agcacagggc agcccgcacc accaccaatt tggcgtgcat    4320
gacacctagg gacttggcac gggaggcggc gcacgtggat gcaaatgacg ggatatcaga    4380
tgacaggaaa cgacgttgag agaccatacg atgtagaata tgagctcacc atcaacgaga    4440
aactaggaaa atcacaaaaa aaacaactct cgtaattgta cgagtggcac agatgggtct    4500
gcctcaacat atctctaata cggcgaagcc tgcccaacac gtagttgccg gaatccggtg    4560
tggagctcac gactctgaaa gataggcgct tcctgtttcg tttcgctcac ccactggacg    4620
tccgtcatgt gatggatttc ggtcattggt ttgctgacaa ccacattctg aagctccatg    4680
agatgagtct tcacaatagg tcctgctcaa taccgtggag ttatggttgc aagtccataa    4740
cttgccgttc gaatattttg cggagccagt cggacgggaa ttggcgagct cggctgacac    4800
ctataaaggc catgacaaga agaaccaaaa gttcttccct aatgctttca tgaggcttcg    4860
ggtcgttatg gatgtcggaa accccctctt gaaggaacga gacgttatta tgcatgacgg    4920
taagactatt acttgtcagt ataagtatga aagattacct gtcttctgct ttgtttgtgg    4980
attgattgga cacgttgaaa aaaaatgtgc acttcgattt caatactcag agatcgactt    5040
cccttttctc taggagtatt cgatcaaggc attaacatgg aaggaagctc aagctctaaa    5100
ggcttcacaa tggaacctga aaaatttcaa caagcctaaa ctgaaatcga agtcaaatca    5160
cccaaccggg agctctaaat cagcaaacac tcctcctcca cagtatccaa tcatcgtgca    5220
cgatgctcca ggtattgcaa gccaggtatt gcaagctagg agtaggatag agaccttaaa    5280
cgtcgttggt gtgaagagtc atcttcagac ctaatgagga tagatgtaga cggcggcacg    5340
aagactctga aacaccagaa aggctagtcc aggataagga tctgctatcc caactgacct    5400
ctcgttagtc ccaaggcctc tcaactagag caggaggaag gatggtcaca agactaggat    5460
aatgatgttt ccaatatgaa cctgaatgtc catagctaat ttttttagtc ttgcttctgc    5520 acttttttgtt tattatgttc tggtgactat gttatttacc cttgtccgta tgcttgaggg    5580 tacccctagta gattggttgg ttggtttcca tgtaccagaa ggcttaccct attagttgaa    5640
agttgaaact ttgttcccta ctcaattcct agttgtgtaa atgtatgtat atgtaatgtg    5700
```

```
tataaaacgt agtacttaaa tgactaggag tggttcttga gaccgatgag agatgggagc   5760
agaactaaag atgatgacat aattaagaac gaatttgaaa ggctcttagg tttgaatcct   5820
attcgagaat gttttgtca aagatagtgg cgattttgaa ccaaagaaaa catttaaaaa    5880
atcagtatcc ggttacgttc atgcaaatag aaagtggtct aggatctgat tgtaatttta   5940
gacttaaaga gtctcttaag attcaatcct ggctgtgtac aaaactacaa ataatatatt   6000
ttagactatt tggccttaac taaacttcca ctcattattt actgaggtta gagaatagac   6060
ttgcgaataa acacattccc gagaaatact catgatccca taattagtca gagggtatgc   6120
caatcagatc taagaacaca cattccctca aattttaatg cacatgtaat catagtttag   6180
cacaattcaa aaataatgta gtattaaaga cagaaatttg tagactttt tttggcgtta    6240 aaagaagact aagtttatac gtacatttta ttttaagtgg aaaaccgaaa ttttccatcg   6300
aaatatatga atttagtata tatatttctg caatgtacta ttttgctatt ttggcaactt   6360
tcagtggact actactttat tacaatgtgt atggatgcat gagtttgagt atacacatgt   6420
ctaaatgcat gctttgtaaa acgtaacgga ccacaaaaga ggatccatac aaatacatct   6480
catagcttcc tccattattt tccgacacaa acagagcatt ttacaacaat taccaacaac   6540
aacaaacaac aaacaacatt acaattacat ttacaattac cataccatgg cctctatcgc   6600
tatccctgct gctcttgctg gaactcttgg atacgttacc tacaatgtgg ctaaccctga   6660
tatcccagct tctgagaaag ttcctgctta cttcatgcag gttgagtact ggggacctac   6720
tatcggaact attggatacc tcctcttcat ctacttcgga aagcgtatca tgcagaacag   6780
atctcaacct ttcggactca agaacgtat gctcgtttac aacttctacc agaccttctt    6840
caacagctac tgcatctacc ttttcgttac ttctcatagg gctcagggac ttaaggtttg   6900
gggaaacatc cctgatatga ctgctaactc ttggggaatc tctcaggtta tctggcttca   6960
ctacaacaac aagtacgttg agcttctcga caccttcttc atggtgatga ggaagaagtt   7020
cgaccagctt tctttccttc acatctacca ccacactctt ctcatctggt catggttcgt   7080
tgttatgaag cttgagcctg ttggagattg ctacttcgga tcttctgtta acaccttcgt   7140
gcacgtgatc atgtactctt actacggact tgctgctctt ggagttaact gtttctggaa   7200
gaagtacatc acccagatcc agatgcttca gttctgtatc tgtgcttctc actctatcta   7260
caccgcttac gttcagaata ccgctttctg gcttccttac cttcaactct gggttatggt   7320
gaacatgttc gttctcttcg ccaacttcta ccgtaagagg tacaagtcta agggtgctaa   7380
gaagcagtga taaggcgcgc ggcgcgccgg gccgccgcca tgtgacagat cgaaggaaga   7440
aagtgtaata agacgactct cactactcga tcgctagtga ttgtcattgt tatatataat   7500
aatgttatct ttcacaactt atcgtaatgc atgtgaaact ataacacatt aatcctactt   7560
gtcatatgat aacactctcc ccatttaaaa ctcttgtcaa tttaaagata taagattctt   7620
taaatgatta aaaaaatat attataaatt caatcactcc tactaataaa ttattaatta    7680
ttatttattg attaaaaaaa tactatact aatttagtct gaatagaata attagattct    7740
agtctcatcc ccttttaaac caacttagta aacgtttttt tttttaattt tatgaagtta   7800 agttttacc ttgttttaa aaagaatcgt tcataagatg ccatgccaga acattagcta    7860
cacgttacac atagcatgca gccgcggaga attgttttc ttcgccactt gtcactccct    7920
tcaaacacct aagagcttct ctctcacagc acacacatac aatcacatgc gtgcatgcat   7980
tattacacgt gatcgccatg caaatctcct ttatagccta taaattaact catccgcttc   8040
actctttact caaaccaaaa ctcatcgata caaacaagat taaaaacata cacgaggatc   8100
```

```
ttttacaaca attaccaaca acaacaaaca acaaacaaca ttacaattac atttacaatt    8160
accataccat gcctccaagg gactcttact cttatgctgc tcctccttct gctcaacttc    8220
acgaagttga tactcctcaa gagcacgaca agaaagagct tgttatcgga gatagggctt    8280
acgatgttac caacttcgtt aagagacacc ctggtggaaa gatcattgct taccaagttg    8340
gaactgatgc taccgatgct tacaagcagt tccatgttag atctgctaag gctgacaaga    8400
tgcttaagtc tcttccttct cgtcctgttc acaagggata ctctccaaga agggctgatc    8460
ttatcgctga tttccaagag ttccaccaag aacttgaggc tgagggaatg ttcgagcctt    8520
ctcttcctca tgttgcttac agacttgctg aggttatcgc tatgcatgtt gctggtgctg    8580
ctcttatctg gcatggatac actttcgctg gaatcgctat gcttggagtt gttcagggaa    8640
gatgtggatg gcttatgcat gagggtggac attactctct cactggaaac attgctttcg    8700
acagagctat ccaagttgct tgttacggac ttggatgtgg aatgtctggt gcttggtggc    8760
gtaaccagca taacaagcac catgctactc ctcaaaagct tcagcacgat gttgatcttg    8820
ataccctttcc tctcgttgct ttccatgaga gaatcgctgc taaggttaag tctcctgcta    8880
tgaaggcttg gctttctatg caagctaagc ttttcgctcc tgttaccact cttcttgttg    8940
ctcttggatg gcagctttac cttcatccta gacacatgct caggactaag cactacgatg    9000
agcttgctat gctcggaatc agatacggac ttgttggata ccttgctgct aactacggtg    9060
ctggatacgt tctcgcttgt taccttcttt acgttcagct tggagctatg tacatcttct    9120
gcaacttcgc tgtttctcat actcacctcc ctgttgttga gcctaacgag catgctactt    9180
gggttgagta cgctgctaac cacactacta actgttctcc atcttggtgg tgtgattggt    9240
ggatgtctta ccttaactac cagatcgagc accaccttta cccttctatg cctcaattca    9300
gacaccctaa gatcgctcct agagttaagc agcttttcga gaagcacgga cttcactacg    9360
atgttagagg atacttcgag gctatggctg atactttcgc taaccttgat aacgttgccc    9420
atgctcctga gaagaaaatg cagtaatgag atcgttcaaa catttggcaa taaagtttct    9480
taagattgaa tcctgttgcc ggtcttgcga tgattatcat ataatttctg ttgaattacg    9540
ttaagcacgt aataattaac atgtaatgca tgacgttatt tatgagatgg gtttttatga    9600
ttagagtccc gcaattatac atttaatacg cgatagaaaa caaaatatag cgcgcaaact    9660
aggataaatt atcgcgcgcg gtgtcatcta tgttactaga tcggtcgatt aaaaatccca    9720
attatatttg gtctaattta gtttggtatt gagtaaaaca aattcgaacc aaaccaaaat    9780
ataaatatat agttttttata tatatgcctt taagacttttt tatagaattt tctttaaaaa    9840
atatctagaa atatttgcga ctcttctggc atgtaatatt tcgttaaata tgaagtgctc    9900
catttttatt aactttaaat aattggttgt acgatcactt tcttatcaag tgttactaaa    9960
atgcgtcaat ctctttgttc ttccatattc atatgtcaaa atctatcaaa attcttatat   10020
atctttttcg aatttgaagt gaaatttcga taatttaaaa ttaaatagaa catatcatta   10080
tttaggtatc atattgattt ttatacttaa ttactaaatt tggttaactt tgaaagtgta   10140
catcaacgaa aaattagtca aacgactaaa ataaataaat atcatgtgtt attaagaaaa   10200
ttctcctata agaatatttt aatagatcat atgtttgtaa aaaaaattaa ttttttactaa   10260
cacatatatt tacttatcaa aaatttgaca aagtaagatt aaaataatat tcatctaaca   10320
aaaaaaaaac cagaaaatgc tgaaaacccg gcaaaaccga accaatccaa accgatatag   10380
ttggtttggt ttgatttttga tataaaccga accaactcgg tccatttgca cccctaatca   10440
```

```
taatagcttt aatatttcaa gatattatta agttaacgtt gtcaatatcc tggaaatttt    10500
gcaaaatgaa tcaagcctat atggctgtaa tatgaattta aaagcagctc gatgtggtgg    10560
taatatgtaa tttacttgat tctaaaaaaa tatcccaagt attaataatt tctgctagga    10620
agaaggttag ctacgattta cagcaaagcc agaatacaaa gaaccataaa gtgattgaag    10680
ctcgaaatat acgaaggaac aaatatttt aaaaaaatac gcaatgactt ggaacaaaag    10740
aaagtgatat attttttgtt cttaaacaag catcccctct aaagaatggc agttttcctt    10800
tgcatgtaac tattatgctc ccttcgttac aaaaattttg gactactatt gggaacttct    10860
tctgaaaata gtgatagaac ccacacgagc atgtgctttc catttaattt taaaaaccaa    10920
gaaacataca tacataacat tccatcagcc tctctctctt tttattacgg ttaatgactt    10980
aaaacacatc ttattatccc atccttaaca cctagcagtg tctttatacg atctcatcga    11040
tcaccacttc aaaaccatgc agactgctgc tgcccctgga gctggcatcg gctaggctgg    11100
gtgccgcact gtcccggaag gtccctagcg acttgtttag attgatggga ccacctctca    11160
acttcctgct gctgtccctg ctgctggatg tcctgcctca tctggccgat tgcacgctcc    11220
agtcccctgc atgtgcactc gctcctcaat tgcttaagat catcgcagca gctatcgaag    11280
tgctggctct gttgccctcc tccacggcct tggttgtagt agtagctgcc gccgcccttc    11340 tggactttt cccacaggaa ccgccgaata attcgataga accacacgag catgtgcttt    11400
catttatttt aaaaaccaag aaacatacat aacatttcat cagcctctct ctctctctct    11460
ctctctctct ctctctctct ctctctctct ctctctttat tacagctgtt acactaactt    11520
aaaacacatt catctcatta ttattattat tatccatcct taacacctag cagtgtcttt    11580
gtacgatctc ataatcgatc acccccttcat caggtatcct taggcttcac tccaacgttg    11640
ttgcagttac ggaacatgta cacaccatca tggttctcaa cgaactggca agatctccaa    11700
gttttccaaa ggctaaccca catgttctca tcggtgtgtc tgtagtgctc tcccataact    11760
ttcttgatgc actcggtagc ttctctagca tggtagaatg ggatccttga aacgtagtga    11820
tggagcacat gagtctcgat gatgtcatgg aagatgattc cgaggattcc gaactctcta    11880
tcgatagtag cagcagcacc cttagcgaaa gtccactctt gagcatcgta atgaggcata    11940
gaagaatcgg tgtgctgaag gaaggtaacg aaaacaagcc agtggttaac aaggatccaa    12000
ggacagaacc atgtgatgaa gtaggccag aatccgaaaa ccttgtaagc ggtgtaaaca    12060
gaagtgaggg tagcaaggat tccaagatca gaaagaacga tgtaccagta gtccttctta    12120
tcgaaaacag ggctagaagg ccagtagtga gacttgaaga acttagaaac accagggtaa    12180
ggttgtccag tagcgttagt agcaaggtaa agagaaagtc ctccaagctg ttggaacaag    12240
agagcgaaaa cagagtagat aggagttttcc tcagcgatat cgtgaaggct ggtaacttgg    12300
tgcttctctt tgaattcctc ggcggtgtaa ggaacgaaaa ccatatctct ggtcatgtgt    12360
ccagtagcct tatggtgctt agcatgagag aacttccagc tgaagtaagg aaccataaca    12420
agagagtgga gaacccatcc aacggtatcg ttaacccatc cgtagttaga gaaagcagaa    12480
tgtccacact catgtccaag gatccagatt ccgaatccga acaagagat agagaacacg    12540 taagcagacc aagcagcgaa tctaaggaat tcgttaggga gaagagggat gtaggtaagt    12600
ccaacgtaag cgatagcaga gatagccacg atatctctca ccacgtaaga catagacttc    12660
acgagagatc tctcgtaaca gtgcttaggg atagcgtcaa ggatatcctt gatggtgtaa    12720
tctggcacct tgaaaacgtt tccgaaggta tcgatagcgg tcttttgctg cttgaaagat    12780
gcaacgtttc cagaacgcct aacggtctta gtagatccct caaggatctc agatccagac    12840
```

```
acggtaacct tagacatggt atggtaattg taaatgtaat tgtaatgttg tttgttgttt   12900
gttgttgttg gtaattgttg taaaatttt ggtggtgatt ggttctttaa ggtgtgagag   12960
tgagttgtga gttgtgtggt gggtttggtg agattgggga tggtgggttt atatagtgga   13020
gactgaggaa tggggtcgtg agtgttaact ttgcatgggc tacacgtggg ttcttttggg   13080
cttacacgta gtattattca tgcaaatgca gccaatacat atacggtatt ttaataatgt   13140
gtgggaatac aatatgccga gtattttact aattttggca atgacaagtg tacatttgga   13200
ttatcttact tggcctctct tgctttaatt tggattattt ttattctctt accttggccg   13260
ttcatattca catccctaaa ggcaagacag aattgaatgg tggccaaaaa ttaaaacgat   13320
ggatatgacc tacatagtgt aggatcaatt aacgtcgaag gaaaatactg attctctcaa   13380
gcatacggac aagggtaaat aacatagtca ccagaacata taaacaaaa agtgcagaag   13440 caagactaaa aaaattagct atggacattc aggttcatat tggaaacatc attatcctag   13500
tcttgtgacc atccttcctc ctgctctagt tgagaggcct tgggactaac gagaggtcag   13560
ttgggatagc agatccttat cctggactag ccttttctggt gtttcagagt cttcgtgccg   13620
ccgtctacat ctatctccat taggtctgaa gatgactctt cacaccaacg acgtttaagg   13680
tctctatcct actcctagct tgcaataccct ggcttgcaat acctggagca tcgtgcacga   13740
tgattggata ctgtggagga ggagtgtttg ctgatttaga gctcccggtt gggtgatttg   13800
acttcgattt cagtttaggc ttgttgaaat ttttcaggtt ccattgtgaa gcctttagag   13860
cttgagcttc cttccatgtt aatgccttga tcgaatactc ctagagaaaa gggaagtcga   13920
tctctgagta ttgaaatcga agtgcacatt ttttttcaac gtgtccaatc aatccacaaa   13980
caaagcagaa gacaggtaat ctttcatact tatactgaca agtaatagtc ttaccgtcat   14040
gcataataac gtctcgttcc ttcaagaggg gttttccgac atccataacg acccgaagcc   14100
tcatgaaagc attagggaag aacttttggt tcttcttgtc atggccttta taggtgtcag   14160
ccgagctcgc caattcccgt ccgactggct ccgcaaaata ttcgaacggc aagttatgga   14220
cttgcaacca taactccacg gtattgagca ggaccttttg tgaagactca tctcatggag   14280
cttcagaatg tggttgtcag caaaccaatg accgaaatcc atcacatgac ggacgtccag   14340
tgggtgagcg aaacgaaaca ggaagcgcct atctttcaga gtcgtgagct ccacaccgga   14400
ttccggcaac tacgtgttgg gcaggcttcg ccgtattaga gatatgttga ggcagaccca   14460
tctgtgccac tcgtacaatt acgagagttg ttttttttgt gattttccta gtttctcgtt   14520
gatggtgagc tcatattcta catcgtatgg tctctcaacg tcgtttcctg tcatctgata   14580
tcccgtcatt tgcatccacg tgcgccgcct cccgtgccaa gtccctaggt gtcatgcacg   14640
ccaaattggt ggtggtgcgg gctgcccgt gcttcttacc gatgggtgga ggttgagttt   14700
gggggtctcc gcggcgatgg tagtgggttg acggtttggt gtgggttgac ggcattgatc   14760 aattacttc ttgcttcaaa ttctttggca gaaaacaatt cattagatta gaactggaaa   14820
ccagagtgat gagacggatt aagtcagatt ccaacagagt tacatctctt aagaaataat   14880
gtaacccctt tagactttat atatttgcaa ttaaaaaaat aatttaactt ttagacttta   14940
tatatagttt taataactaa gtttaaccac tctattattt atatcgaaac tatttgtatg   15000
tctcccctct aaataaactt ggtattgtgt ttacagaacc tataatcaaa taatcaatac   15060
tcaactgaag tttgtgcagt taattgaagg gattaacggc caaaatgcac tagtattatc   15120
aaccgaatag attcacacta gatggccatt tccatcaata tcatcgccgt tcttcttctg   15180
```

| | |
|---|---|
| tccacatatc ccctctgaaa cttgagagac acctgcactt cattgtcctt attacgtgtt | 15240 |
| acaaaatgaa acccatgcat ccatgcaaac tgaagaatgg cgcaagaacc cttcccctcc | 15300 |
| atttcttatg tggcgaccat ccatttcacc atctcccgct ataaacacc cccatcactt | 15360 |
| cacctagaac atcatcacta cttgcttatc catccaaaag atacccactt ttacaacaat | 15420 |
| taccaacaac aacaaacaac aaacaacatt acaattacat ttacaattac cataccatgc | 15480 |
| cacctagcgc tgctaagcaa atgggagctt ctactggtgt tcatgctggt gttactgact | 15540 |
| cttctgctt caccagaaag gatgttgctg atagacctga tctcaccatc gttggagatt | 15600 |
| ctgtttacga tgctaaggct ttcagatctg agcatcctgg tggtgctcat ttcgtttctt | 15660 |
| tgttcggagg aagagatgct actgaggctt tcatggaata ccatagaagg gcttggccta | 15720 |
| agtctagaat gtctagattc cacgttggat ctcttgcttc tactgaggaa cctgttgctg | 15780 |
| ctgatgaggg ataccttcaa cttgtgcta ggatcgctaa gatggtgcct tctgtttctt | 15840 |
| ctggattcgc tcctgcttct tactgggtta aggctggact tatccttgga tctgctatcg | 15900 |
| ctcttgaggc ttacatgctt tacgctgaa agagacttct cccttctatc gttcttggat | 15960 |
| ggcttttcgc tcttatcggt cttaacatcc agcatgatgc taaccatggt gctttgtcta | 16020 |
| agtctgcttc tgttaacctt gctcttggac tttgtcagga ttggatcgga ggatctatga | 16080 |
| tcctttggct tcaagagcat gttgttatgc accacctcca cactaacgat gttgataagg | 16140 |
| atcctgatca aaaggctcac ggtgctctta gactcaagcc tactgatgct tggtcaccta | 16200 |
| tgcattggct tcagcatctt tacctttgc ctggtgagac tatgtacgct ttcaagcttt | 16260 |
| tgttcctcga catctctgag cttgttatgt ggcgttggga gggtgagcct atctctaagc | 16320 |
| ttgctggata cctctttatg ccttctttgc ttctcaagct taccttctgg gctagattcg | 16380 |
| ttgctttgcc tcttttacctt gctccttctg ttcatactgc tgtgtgtatc gctgctactg | 16440 |
| ttatgactgg atctttctac ctcgctttct tcttcttcat ctcccacaac ttcgagggtg | 16500 |
| ttgcttctgt tggacctgat ggatctatca cttctatgac tagaggtgct agcttcctta | 16560 |
| agagacaagc tgagacttct tctaacgttg gaggacctct tcttgctact cttaacggtg | 16620 |
| gactcaacta ccaaattgag catcacttgt tccctagagt tcaccatgga ttctacccta | 16680 |
| gacttgctcc tcttgttaag gctgagcttg aggctagagg aatcgagtac aagcactacc | 16740 |
| ctactatctg gtctaacctt gcttctaccc tcagacatat gtacgctctt ggaagaaggc | 16800 |
| ctagatctaa ggctgagtaa tgacaagctt atgtgacgtg aaataataac ggtaaaatat | 16860 |
| atgtaataat aataataata aagccacaaa gtgagaatga ggggaagggg aaatgtgtaa | 16920 |
| tgagccagta gccggtggtg ctaattttgt atcgtattgt caataaatca tgaattttgt | 16980 |
| ggttttatg tgtttttta aatcatgaat tttaaatttt ataaataat ctccaatcgg | 17040 |
| aagaacaaca ttccatatcc atgcatggat gtttctttac ccaaatctag ttcttgagag | 17100 |
| gatgaagcat caccgaacag ttctgcaact atccctcaaa agctttaaaa tgaacaacaa | 17160 |
| ggaacagagc aacgttccaa agatcccaaa cgaaacatat tatctatact aatactatat | 17220 |
| tattaattac tactgcccgg aatcacaatc cctgaatgat tcctattaac tacaagcctt | 17280 |
| gttggcggcg gagaagtgat cggcgcggcg agaagcagcg gactcggaga cgaggccttg | 17340 |
| gaagatctga gtcgaacggg cagaatcagt attttccttc gacgttaatt gatcctacac | 17400 |
| tatgtaggtc atatccatcg ttttaatttt tggccaccat tcaattctgt cttgccttta | 17460 |
| gggatgtgaa tatgaacggc caaggtaaga gaataaaaat aatccaaatt aaagcaagag | 17520 |
| aggccaagta agataatcca aatgtacact tgtcattgcc aaaattagta aaatactcgg | 17580 |

```
catattgtat tcccacacat tattaaaata ccgtatatgt attggctgca tttgcatgaa    17640
taatactacg tgtaagccca aaagaaccca cgtgtagccc atgcaaagtt aacactcacg    17700
accccattcc tcagtctcca ctatataaac ccaccatccc caatctcacc aaacccacca    17760
cacaactcac aactcactct cacaccttaa agaaccaatc accaccaaaa attttacaac    17820
aattaccaac aacaacaaac aacaaacaac attacaatta catttacaat taccatacca    17880
tgagcgctgt taccgttact ggatctgatc ctaagaacag aggatcttct agcaacaccg    17940
agcaagaggt tccaaaagtt gctatcgata ccaacggaaa cgtgttctct gttcctgatt    18000
tcaccatcaa ggacatcctt ggagctatcc ctcatgagtg ttacgagaga agattggcta    18060
cctctctcta ctacgtgttc agagatatct tctgcatgct taccaccgga taccttaccc    18120
ataagatcct ttaccctctc ctcatctctt acacctctaa cagcatcatc aagttcactt    18180
tctgggccct ttacacttac gttcaaggac ttttcggaac cggaatctgg gttctcgctc    18240
atgagtgtgg acatcaagct ttctctgatt acggaatcgt gaacgatttc gttggatgga    18300
cccttcactc ttaccttatg gttccttact tcagctggaa gtactctcat ggaaagcacc    18360
ataaggctac tggacacatg accagagata tggttttcgt tcctgccacc aaagaggaat    18420
tcaagaagtc taggaacttc ttcggtaacc tcgctgagta ctctgaggat tctccactta    18480
gaacccttta cgagcttctt gttcaacaac ttggaggatg gatcgcttac ctcttcgtta    18540
acgttacagg acaaccttac cctgatgttc cttcttggaa atggaaccac ttctggctta    18600
cctctccact tttcgagcaa agagatgctc tctacatctt cctttctgat cttggaatcc    18660
tcacccaggg aatcgttctt actctttggt acaagaaatt cggaggatgg tcccttttca    18720
tcaactggtt cgttccttac atctgggtta accactggct cgttttcatc acattccttc    18780
agcacactga tcctactatg cctcattaca acgctgagga atggactttc gctaagggtg    18840
ctgctgctac tatcgataga aagttcggat tcatcggacc tcacatcttc catgatatca    18900
tcgagactca tgtgcttcac cactactgtt ctaggatccc attctacaac gctagacctg    18960
cttctgaggc tatcaagaaa gttatgggaa agcactacag gtctagcgac agaaacatgt    19020
ggaagtcact ttggaagtct ttcaggtctt gccaatacgt tgacggtgat aacggtgttc    19080
tcatgttccg taacatcaac aactgcggag ttggagctgc tgagaagtaa tgaaggggtg    19140
atcgattatg agatcgtaca aagacactgc taggtgttaa ggatggataa taataataat    19200
aatgagatga atgtgttta agttagtgta acagctgtaa taagagaga gagagagaga    19260 gagagagaga gagagagaga gagagagaga gagaggctga tgaaatgtta tgtatgtttc    19320 ttggtttta aaataaatga aagcacatgc tcgtgtggtt ctatcgaatt attcggcggt    19380
tcctgtggga aaagtccag aagggccgcc gcagctacta ctacaaccaa ggccgtggag    19440
gagggcaaca gagccagcac ttcgatagct gctgcgatga tcttaagcaa ttgaggagcg    19500
agtgcacatg caggggactg gagcgtgcaa tcggccagat gaggcaggac atccagcagc    19560
agggacagca gcaggaagtt gagaggtggt cccatcaatc taaacaagtc gctagggacc    19620
ttccgggaca gtgcggcacc cagcctagcc gatgccagct ccaggggcag cagcagtctg    19680
catggttttg aagtggtgat cgatgagatc gtataaagac actgctaggt gttaaggatg    19740
ggataataag atgtgtttta agtcattaac cgtaataaaa agagagagag gctgatggaa    19800
tgttatgtat gtatgtttct tggtttttaa aattaaatgg aaagcacatg ctcgtgtggg    19860
ttctatctcg attaaaaatc ccaattatat ttggtctaat ttagtttggt attgagtaaa    19920
```

```
acaaattcga accaaaccaa aatataaata tatagttttt atatatatgc ctttaagact   19980
ttttatagaa ttttctttaa aaaatatcta gaaatatttg cgactcttct ggcatgtaat   20040
atttcgttaa atatgaagtg ctccattttt attaacttta aataattggt tgtacgatca   20100
ctttcttatc aagtgttact aaaatgcgtc aatctctttg ttcttccata ttcatatgtc   20160
aaaatctatc aaaattctta tatatctttt tcgaatttga agtgaaattt cgataattta   20220
aaattaaata gaacatatca ttatttaggt atcatattga tttttatact taattactaa   20280
atttggttaa ctttgaaagt gtacatcaac gaaaaattag tcaaacgact aaaataaata   20340
aatatcatgt gttattaaga aaattctcct ataagaatat tttaatagat catatgtttg   20400
taaaaaaaat taatttttac taacacatat atttacttat caaaaatttg acaaagtaag   20460
attaaaataa tattcatcta acaaaaaaaa aaccagaaaa tgctgaaaac ccggcaaaac   20520
cgaaccaatc caaaccgata tagttggttt ggtttgattt tgatataaac cgaaccaact   20580
cggtccattt gcacccctaa tcataatagc tttaatattt caagatatta ttaagttaac   20640
gttgtcaata tcctggaaat tttgcaaaat gaatcaagcc tatatggctg taatatgaat   20700
ttaaaagcag ctcgatgtgg tggtaatatg taatttactt gattctaaaa aaatatccca   20760
agtattaata atttctgcta ggaagaaggt tagctacgat ttacagcaaa gccagaatac   20820
aaagaaccat aaagtgattg aagctcgaaa tatacgaagg aacaaatatt tttaaaaaaa   20880
tacgcaatga cttggaacaa aagaaagtga tatatttttt gttcttaaac aagcatcccc   20940
tctaaagaat ggcagttttc ctttgcatgt aactattatg ctcccttcgt tacaaaaatt   21000
ttggactact attgggaact tcttctgaaa atagtcctgc aggctagtag attggttggt   21060
tggtttccat gtaccagaag gcttacccta ttagttgaaa gttgaaactt tgttccctac   21120
tcaattccta gttgtgtaaa tgtatgtata tgtaatgtgt ataaaacgta gtacttaaat   21180
gactaggagt ggttcttgag accgatgaga gatgggagca gaactaaaga tgatgacata   21240
attaagaacg aatttgaaag gctcttaggt ttgaatccta ttcgagaatg tttttgtcaa   21300
agatagtggc gattttgaac caaagaaaac atttaaaaaa tcagtatccg gttacgttca   21360
tgcaaataga aagtggtcta ggatctgatt gtaattttag acttaaagag tctcttaaga   21420
ttcaatcctg gctgtgtaca aaactacaaa taatatattt tagactattt ggccttaact   21480
aaacttccac tcattattta ctgaggttag agaatagact tgcgaataaa cacattcccg   21540
agaaatactc atgatcccat aattagtcag agggtatgcc aatcagatct aagaacacac   21600
attccctcaa atttttaatgc acatgtaatc atagtttagc acaattcaaa aataatgtag   21660
tattaaagac agaaatttgt agacttttt ttggcgttaa aagaagacta agtttatacg    21720
tacatttat tttaagtgga aaaccgaaat tttccatcga aatatatgaa tttagtatat    21780
atatttctgc aatgtactat tttgctattt tggcaacttt cagtggacta ctactttatt   21840
acaatgtgta tggatgcatg agtttgagta tacacatgtc taaatgcatg ctttgtaaaa   21900
cgtaacggac cacaaaagag gatccataca aatacatctc atagcttcct ccattatttt   21960
ccgacacaaa cagagcattt tacaacaatt accaacaaca acaaacaaca aacaacatta   22020
caattacatt tacaattacc ataccatgga atttgctcaa cctctcgttg ctatggctca   22080
agagcagtac gctgctatcg atgctgttgt tgctcctgct atcttctctg ctaccgactc   22140
tattggatgg ggactcaagc ctatctcttc tgctactaag gatctccctc tcgttgaatc   22200
tcctaccccct cttatccttt ctctcctcgc ttacttcgct atcgtggtt ctggactcgt    22260
ttaccgtaaa gtgttcccta gaaccgttaa gggacaggat cctttccttc tcaaggctct   22320
```

```
tatgctcgct cacaacgttt tccttatcgg actcagcctt tacatgtgcc tcaagctcgt   22380
ttacgaggct tacgtgaaca agtactcctt ctggggaaac gcttacaacc ctgctcaaac   22440
cgagatggct aaggtgatct ggatcttcta cgtgtccaag atctacgagt tcatggacac   22500
cttcatcatg cttctcaagg gaaacgttaa ccaggtttcc ttcctccatg tttaccacca   22560
cggatctatc tctggaatct ggtggatgat cacttatgct gctccaggtg agatgctta    22620 cttctctgct gctctcaact cttgggttca tgtgtgcatg tacacctact acttcatggc   22680
tgctgttctt cctaaggacg aaaagaccaa gagaaagtac ctttggtggg aagatacct    22740 tacccagatg caaatgttcc agttcttcat gaaccttctc caggctgttt acctcctcta   22800
ctcttcttct ccttacccta agttcattgc tcaactcctc gttgtttaca tggttaccct   22860
cctcatgctt ttcggaaact tctactacat gaagcaccac gcttctaagt gataagggcc   22920
gccgccatgt gacagatcga aggaagaaag tgtaataaga cgactctcac tactcgatcg   22980
ctagtgattg tcattgttat atataataat gttatctttc acaacttatc gtaatgcatg   23040
tgaaactata acacattaat cctacttgtc atatgataac actctcccca tttaaaactc   23100
ttgtcaattt aaagatataa gattctttaa atgattaaaa aaaatatatt ataaattcaa   23160
tcactcctac taataaatta ttaattatta tttattgatt aaaaaaatac ttatactaat   23220
ttagtctgaa tagaataatt agattctagc ctgcagggcg gccgcggatc ccatggagtc   23280
aaagattcaa atagaggacc taacagaact cgccgtaaag actggcgaac agttcataca   23340
gagtctctta cgactcaatg acaagaagaa aatcttcgtc aacatggtgg agcacgacac   23400
acttgtctac tccaaaaata tcaaagatac agtctcagaa gaccaagggg caattgagac   23460
ttttcaacaa agggtaatat ccggaaacct cctcggattc cattgcccag ctatctgtca   23520
ctttattgtg aagatagtgg aaaaggaagg tggctcctac aaatgccatc attgcgataa   23580
aggaaaggcc atcgttgaag atgcctctgc cgacagtggt cccaaagatg acccccacc    23640 cacgaggagc atcgtggaaa aagaagacgt tccaaccacg tcttcaaagc aagtggattg   23700
atgtgatatc tccactgacg taagggatga cgcacaatcc cactatcctt cgcaagaccc   23760
ttcctctata taaggaagtt catttcattt ggagagaaca cggggactg aattaaatat     23820 gagccctgag aggcgtcctg ttgaaatcag acctgctact gctgctgata tggctgctgt   23880
ttgtgatatc gtgaaccact acatcgagac ttctaccgtt aacttcagaa ctgagcctca   23940
aactcctcaa gagtggatcg atgatcttga gagactccaa gatagatacc cttggcttgt   24000
tgctgaggtt gagggtgttg ttgctggaat cgcttacgct ggaccttgga aggctagaaa   24060
cgcttacgat tggactgttg agtctaccgt ttacgtttca cacagacatc agagacttgg   24120
acttggatct acccttttaca ctcaccttct caagtctatg gaagctcagg gattcaagtc   24180
tgttgttgct gttatcggac tccctaacga tccttctgtt agacttcatg aggctcttgg   24240
atacactgct agaggaactc ttagagctgc tggatacaag cacggtggat ggcatgatgt   24300
tggattctgg caaagagatt tcgagcttcc tgctcctcct agacctgtta gaccagttac   24360
tcagatctga atttgcgtga tcgttcaaac atttggcaat aaagtttctt aagattgaat   24420
cctgttgccg gtcttgcgat gattatcata taatttctgt tgaattacgt taagcatgta   24480
ataattaaca tgtaatgcat gacgttattt atgagatggg ttttttatgat tagagtcccg   24540 caattataca tttaatacgc gatagaaaac aaaatatagc gcgcaaacta ggataaatta   24600
tcgcgcgcgg tgtcatctat gttactagat cactagtgat gtacggttaa aaccacccca   24660
```

```
gtacattaaa aacgtccgca atgtgttatt aagttgtcta agcgtcaatt tgtttacacc   24720
acaatatatc ctgccaccag ccagccaaca gctccccgac cggcagctcg gcacaaaatc   24780
accactcgat acaggcagcc catcagtcc                                     24809

<210> SEQ ID NO 6
<211> LENGTH: 26543
<212> TYPE: DNA
<213> ORGANISM: Artificial Sequence
<220> FEATURE:
<223> OTHER INFORMATION: pGA7- mod_F nucleotide sequence

<400> SEQUENCE: 6
tcctgtggtt ggcatgcaca tacaaatgga cgaacggata aaccttttca cgcccttta    60 aatatccgat tattctaata aacgctcttt tctcttaggt ttacccgcca atatatcctg   120
tcaaacactg atagtttaaa ctgaaggcgg gaaacgacaa tctgctagtg gatctcccag   180
tcacgacgtt gtaaaacggg cgggcggccg cctagaatct aattattcta ttcagactaa   240
attagtataa gtattttttt aatcaataaa tattaattaa taatttatta gtaggagtga   300
ttgaatttat aatatatttt ttttaatcat ttaaagaatc ttatatcttt aaattgacaa   360
gagttttaaa tggggagagt gttatcatat gacaagtagg attaatgtgt tatagtttca   420
catgcattac gataagttgt gaaagataac attattatat ataacaatga caatcactag   480
cgatcgagta gtgagagtcg tcttattaca ctttcttcct tcgatctgtc acatggcggc   540
ggcccgcgat cgcgataatt ctcagtgcgc cttctccgcc ttgccgttga cgtagtagtg   600
ctgcccgacc ttatccaagt tcgagaacgt cgccttccag gcgccgtaat aggacagcac   660
cttgtagttc agcccccact tcttcgcgaa cgggacgaac cgccggctca cctccggctg   720
gcgaaactgc ggcatgtccg ggaacaggtg atgaatgacc tggcagttca gatatcccat   780
caaccagttc acgtacccgc gcgacgggtc gatgtccacg gtgtgatcga ccgcgtagtt   840
cacccagctc aggtgcttat ccgagggcac gaccggagg tgcgtgtggc tcgtggagaa    900
gtgcgcgaag aggtacatgt acgcgatcca gttgccgaag gtgaaccacc agtacgcgac   960
gggccacgag tacccgtcg cgagtttaat caccgcggtc ctgacgacgt gagagacgag   1020
catccacgac gcctcctcgt agttcttctt tcgcaacacc tgccgcgggt gcaggacgta   1080
gatccagaac gcctggacga gcagcccgga ggtcaccggg acgaacgtcc acgcctgaag   1140
ccgagcccac gcgcgggaga accccctcgg ccggttgtcc tccacggcgg tgttaaaaaa   1200
cgccaccgcg ggggtcgtgt ccaggtccat gtcgtgcctc actttctgcg gcgtcgcgtg   1260
gtgcttattg tgcatctggt tccacatctc cccgctcgtg gacagcccga acccgcacgt   1320
catcgcttgg aggcgcttgt cgacgtagac ggaccccgtg agcgagttgt gcccgccctc   1380
gtgctggacc caaccgcacc gagcgccgaa gaacgcgccg tacacgacgg acgcgatgat   1440
cgggtacccg gcgtacatga gggcggtgcc gagggcgaag gtcgcgagga gctcgagtaa   1500
ccgatacgcg acgtgcgtta tcgagggctt aaagaacccg tcgcgttcga gctccgcgcg   1560
ccaccgcgcg aaatcctcca acatcggcgc gtcctcgctc tcgctgcgtt tgatctccgc   1620
ggggcgcgac ggcagcgctc tgagcatctt ccacgcctta agcgatcgca tgtggaactc   1680
cttgaacgcc tccgtggcgt ccgcgcccgt gttcgcgagc atgtagaata tcacgctgcc   1740
tcccgggtgt ttgaagtttg tgacgtcgta ctcgacgtcc tccacgcgca cccatcgcgt   1800
ctcgaacgtc gccgcgagct cgtgcggctc gagcgttttg agatcgacgg gcgcggtcga   1860
cgcgtccttg gcgtcgagcg cctccgcgga ggatttgctg cgcgtcagcg gcgatcgcgg   1920
```

```
ggacgatcgg ccgtccgtct tcggcgggca catcgtcgcg cgcgcgactt aaaccgacga   1980
cggacggacg aacctgcaac ggcgaattat caattgacgc gttgctctgt ttgtgtcgga   2040
aaataatgga ggaagctatg agatgtattt gcatggatcc tcttttgtgg tccgttacgt   2100
tttgcaaagc atgcatttag acatgtgtat actcaaactc atgcatccat acacattgta   2160
ataaagtagt agtccactga aagttgccaa aatagcaaaa tagtacattg cagaaatata   2220
tatactaaat tcatatattt cgatggaaaa tttcggtttt ccacttaaaa taaaatgtac   2280
gtataaactt agtcttcctt taacgccaaa aaaagtcta caaatttctg tctttaatac    2340
tacattattt ttgaattgtg ctaaactatg attacatgtg cattaaaatt tgagggaatg   2400
tgtgttctta gatctgattg gcatacccctc tgactaatta tgggatcatg agtatttctc  2460
gggaatgtgt ttattcgcaa gtctattctc taacctcagt aaataatgag tggaagttta   2520
gttaaggcca aatagtctaa aatatattat ttgtagtttt gtacacagcc aggattgaat   2580
cttaagagac tctttaagtc taaaattaca atcagatcct agaccacttt ctatttgcat   2640
gaacgtaacc ggatactgat ttttaaatg ttttctttgg ttcaaaatcg ccactatctt    2700
tgacaaaaac attctcgaat aggattcaaa cctaagagcc tttcaaattc gttcttaatt   2760
atgtcatcat ctttagttct gctcccatct ctcatcggtc tcaagaacca ctcctagtca   2820
tttaagtact acgttttata cgcattacat atacatacat ttacaaact aggaattgag    2880 tagggaacaa agtttcaact ttcaactaat agggtaagcc ttctggtaca tggaaaccaa   2940
ccaaccaatc tactaggcgg ccgcccgtcg ggatcttctg caagcatctc tatttcctga   3000
aggtctaacc tcgaagattt aagatttaat tacgtttata attacaaaat tgattctagt   3060
atctttaatt taatgcttat acattattaa ttaatttagt actttcaatt tgttttcaga   3120
aattatttta ctatttttta taaaataaaa gggagaaaat ggctatttaa actgaaggcg   3180
ggaaacgaca atctgctagt ggatctccca gtcacgacgt tgtaaaacgg gcgccccgcg   3240
gaaagcttgc ggccgcggta ccgcccgttc gactcagatc ttccaaggcc tcgtctccga   3300
gtccgctgct tctcgccgcg ccgatcactt ctccgccgcc aacaaggctt gtagttaata   3360
ggaatcattc agggattgtg attccgggca gtagtaatta ataatatagt attagtatag   3420
ataatatgtt tcgtttggga tctttggaac gttgctctgt tccttgttgt tcatttaaa    3480 gcttttgagg gatagttgca gaactgttcg gtgatgcttc atcctctcaa gaactagatt   3540
tgggtaaaga aacatccatg catggatatg gaatgttgtt cttccgattg gagattattt   3600
tataaaattt aaaattcatg atttaaaaaa acacataaaa accacaaaat tcatgattta   3660
ttgacaatac gatacaaaat tagcaccacc ggctactggc tcattacaca tttccccttc   3720
ccctcattct cactttgtgg ctttattatt attattatta catatatttt accgttatta   3780
tttcacgtca cataagcttg ttaattaatc attagtgagc cttctcagcc tttccgttaa   3840
cgtagtagtc ctgtcccacc ttatcaaggt tagagaaagt agccttccaa gcaccgtagt   3900
aagagagcac cttgtagttg agtccccact tcttagcgaa aggaacgaat cttctgctaa   3960
cctcaggctg tctgaattga ggcatatcag ggaagaggtg gtggataacc tgacagttaa   4020
ggtatcccat aagccagttc acgtatcctc tagaaggatc gatatcaacg gtgtgatcaa   4080
cagcgtagtt aacccaagaa aggtgcttat cagatggaac aacagggagg tgagtatgag   4140
aagtagagaa gtgagcgaaa aggtacatgt aagcgatcca gtttccgaaa gtgaaccacc   4200
agtaagcaac aggccaagag tatccagtag caagcttgat aacagcggtt ctaacaacat   4260
```

```
gagaaacgag catccaagaa gcctcttcgt agttcttctt acggagaact tgtctagggt    4320
ggagaacgta gatccagaaa gcttgaacaa gaagtccaga ggtaacagga acgaaagtcc    4380
aagcttgaag tctagcccaa gctctagaga atcctctagg tctgttatcc tcaacagcag    4440
tgttgaagaa agccacagca ggagtggtat caagatccat atcgtgtcta accttttgag    4500
gggtagcatg gtgcttgtta tgcatctggt tccacatctc accagaagta gaaagtccga    4560
atccacaagt catagcctga agtctcttgt ccacgtaaac agatccggta agagagttat    4620
gtccaccctc atgttgaacc catccacatc tagctccgaa gaaagcaccg taaacaacag    4680
aagcaatgat agggtatcca gcgtacataa gagcagttcc aagagcgaat gtagcaagaa    4740
gctcgagaag tctgtaagcc acatgggtga tagaaggctt gaagaatcca tctctctcaa    4800
gctcagcacg ccatctagcg aaatcctcaa gcataggagc atcctcagac tcagatctct    4860
tgatctcagc aggtctagaa ggcaaagctc taagcatctt ccaagccttg agagaacgca    4920
tgtggaattc tttgaaagcc tcagtagcat cagcaccagt gttagcaagc atgtagaaga    4980
tcacagatcc accagggtgc ttgaagttag tcacatcgta ctcaacgtcc tcaactctaa    5040
cccatctagt ctcgaaagta gcagcaagct catgaggctc aagagtctta agatcaacag    5100
gagcagtaga agcatcctta gcatcaagag cctcagcaga agatttagac ctggtaagtg    5160
gagatctagg agaagatctt ccatcagtct taggagggca catggtatgg taattgtaaa    5220
tgtaattgta atgttgtttg ttgtttgttg ttgttggtaa ttgttgtaaa attaattaag    5280
tgggtatctt ttggatggat aagcaagtag tgatgatgtt ctaggtgaag tgatgggggt    5340
gttttatagc gggagatggt gaaatggatg gtcgccacat aagaaatgga ggggaagggt    5400
tcttgcgcca ttcttcagtt tgcatggatg catgggtttc attttgtaac acgtaataag    5460
gacaatgaag tgcaggtgtc tctcaagttt cagagggggat atgtggacag aagaagaacg    5520
gcgatgatat tgatggaaat ggccatctag tgtgaatcta ttcggttgat aatactagtg    5580
cattttggcc gttaatccct tcaattaact gcacaaactt cagttgagta ttgattattt    5640
gattataggt tctgtaaaca caataccaag tttatttaga ggggagacat acaaatagtt    5700
tcgatataaa taatagagtg gttaaactta gttattaaaa ctatatataa agtctaaaag    5760
ttaaattatt tttttaattg caaatatata aagtctaaag gggttacatt atttcttaag    5820
agatgtaact ctgttggaat ctgacttaat ccgtctcatc actctggttt ccagttctaa    5880
tctaatgaat tgtttttctgc caaagaattt gaagcaagaa gtaaattgat caatgccgtc    5940
aacccacacc aaaccgtcaa cccactacca tcgccgcgga gacccccaaa ctcaacctcc    6000
acccatcggt aagaagcaca gggcagcccg caccaccacc aatttggcgt gcatgacacc    6060
tagggacttg gcacgggagg cggcgcacgt ggatgcaaat gacgggatat cagatgacag    6120
gaaacgacgt tgagagacca tacgatgtag aatatgagct caccatcaac gagaaactag    6180
gaaaatcaca aaaaaaacaa ctctcgtaat tgtacgagtg gcacagatgg gtctgcctca    6240
acatatctct aatacggcga agcctgccca acacgtagtt gccggaatcc ggtgtggagc    6300
tcacgactct gaaagatagg cgcttcctgt ttcgtttcgc tcacccactg gacgtccgtc    6360
atgtgatgga tttcggtcat tggtttgctg acaaccacat tctgaagctc catgagatga    6420
gtcttcacaa taggtcctgc tcaataccgt ggagttatgg ttgcaagtcc ataacttgcc    6480
gttcgaatat tttgcggagc cagtcggacg ggaattggcg agctcggctg acacctataa    6540
aggccatgac aagaagaacc aaaagttctt ccctaatgct ttcatgaggc ttcgggtcgt    6600
tatggatgtc ggaaaacccc tcttgaagga acgagacgtt attatgcatg acggtaagac    6660
```

```
tattacttgt cagtataagt atgaaagatt acctgtcttc tgctttgttt gtggattgat   6720
tggacacgtt gaaaaaaaat gtgcacttcg atttcaatac tcagagatcg acttcccttt   6780
tctctaggag tattcgatca aggcattaac atggaaggaa gctcaagctc taaaggcttc   6840
acaatggaac ctgaaaaatt tcaacaagcc taaactgaaa tcgaagtcaa atcacccaac   6900
cgggagctct aaatcagcaa acactcctcc tccacagtat ccaatcatcg tgcacgatgc   6960
tccaggtatt gcaagccagg tattgcaagc taggagtagg atagagacct taaacgtcgt   7020
tggtgtgaag agtcatcttc agacctaatg agatagatg tagacggcgg cacgaagact    7080
ctgaaacacc agaaaggcta gtccaggata aggatctgct atcccaactg acctctcgtt   7140
agtcccaagg cctctcaact agagcaggag gaaggatggt cacaagacta ggataatgat   7200
gtttccaata tgaacctgaa tgtccatagc taatttttt agtcttgctt ctgcactttt    7260
tgtttattat gttctggtga ctatgttatt tacccttgtc cgtatgcttg agggtaccct   7320
agtagattgg ttggttggtt tccatgtacc agaaggctta ccctattagt tgaaagttga   7380
aactttgttc cctactcaat tcctagttgt gtaaatgtat gtatatgtaa tgtgtataaa   7440
acgtagtact taaatgacta ggagtggttc ttgagaccga tgagagatgg gagcagaact   7500
aaagatgatg acataattaa gaacgaattt gaaaggctct taggtttgaa tcctattcga   7560
gaatgttttt gtcaaagata gtggcgattt tgaaccaaag aaaacattta aaaaatcagt   7620
atccggttac gttcatgcaa atagaaagtg gtctaggatc tgattgtaat tttagactta   7680
aagagtctct taagattcaa tcctggctgt gtacaaaact acaaataata tattttagac   7740
tatttggcct taactaaact tccactcatt atttactgag gttagagaat agacttgcga   7800
ataaacacat tcccgagaaa tactcatgat cccataatta gtcagagggt atgccaatca   7860
gatctaagaa cacacattcc ctcaaatttt aatgcacatg taatcatagt ttagcacaat   7920
tcaaaaataa tgtagtatta aagacagaaa tttgtagact ttttttggc gttaaaagaa   7980 gactaagttt atacgtacat tttatttaa gtggaaaacc gaaattttcc atcgaaatat    8040
atgaatttag tatatatatt tctgcaatgt actattttgc tattttggca actttcagtg   8100
gactactact ttattacaat gtgtatggat gcatgagttt gagtatacac atgtctaaat   8160
gcatgctttg taaaacgtaa cggaccacaa aagaggatcc atacaaatac atctcatagc   8220
ttcctccatt attttccgac acaaacagag cattttacaa caattccaa caacaacaaa     8280 caacaaacaa cattcaaatt acatttacaa ttaccatacc atggcctcta tcgctatccc   8340
tgctgctctt gctggaactc ttggatacgt tacctacaat gtggctaacc ctgatatccc   8400
agcttctgag aaagttcctg cttacttcat gcaggttgag tactggggac ctactatcgg   8460
aactattgga tacctcctct tcatctactt cggaaagcgt atcatgcaga acagatctca   8520
acctttcgga ctcaagaacg ctatgctcgt ttacaacttc taccagacct tcttcaacag   8580
ctactgcatc tacctttcg ttacttctca tagggctcag ggacttaagg tttggggaaa    8640
catccctgat atgactgcta actcttgggg aatctctcag gttatctggc ttcactacaa   8700
caacaagtac gttgagcttc tcgacaccct tcttcatggtg atgaggaaga agttcgacca   8760
gctttctttc cttcacatct accaccacac tcttctcatc tggtcatggt tcgttgttat   8820
gaagcttgag cctgttggag attgctactt cggatcttct gttaacacct tcgtgcacgt   8880
gatcatgtac tcttactacg gacttgctgc tcttggagtt aactgtttct ggaagaagta   8940
catcacccag atccagatgc ttcagttctg tatctgtgct tctcactcta tctacaccgc   9000
```

-continued

```
ttacgttcag aataccgctt tctggcttcc ttaccttcaa ctctgggtta tggtgaacat    9060
gttcgttctc ttcgccaact tctaccgtaa gaggtacaag tctaagggtg ctaagaagca    9120
gtgataaggc gcgcggcgcg ccgggccgcc gccatgtgac agatcgaagg aagaaagtgt    9180
aataagacga ctctcactac tcgatcgcta gtgattgtca ttgttatata taataatgtt    9240
atctttcaca acttatcgta atgcatgtga aactataaca cattaatcct acttgtcata    9300
tgataacact ctccccattt aaaactcttg tcaatttaaa gatataagat tctttaaatg    9360
attaaaaaaa atatattata aattcaatca ctcctactaa taaattatta attattattt    9420
attgattaaa aaaatactta tactaattta gtctgaatag aataattaga ttctagtctc    9480
atccccttttt aaaccaactt agtaaacgtt ttttttttta attttatgaa gttaagtttt    9540
taccttgttt ttaaaaagaa tcgttcataa gatgccatgc cagaacatta gctacacgtt    9600
acacatagca tgcagccgcg gagaattgtt tttcttcgcc acttgtcact cccttcaaac    9660
acctaagagc ttctctctca cagcacacac atacaatcac atgcgtgcat gcattattac    9720
acgtgatcgc catgcaaatc tcctttatag cctataaatt aactcatccg cttcactctt    9780
tactcaaacc aaaactcatc gatacaaaca agattaaaaa catacacgag gatcttttac    9840
aacaattacc aacaacaaca aacaacaaac aacattacaa ttacatttac aattaccata    9900
ccatgcctcc aagggactct tactcttatg ctgctcctcc ttctgctcaa cttcacgaag    9960
ttgatactcc tcaagagcac gacaagaaag agcttgttat cggagatagg gcttacgatg   10020
ttaccaactt cgttaagaga caccctggtg gaaagatcat tgcttaccaa gttggaactg   10080
atgctaccga tgcttacaag cagttccatg ttagatctgc taaggctgac aagatgctta   10140
agtctcttcc ttctcgtcct gttcacaagg gatactctcc aagaagggct gatcttatcg   10200
ctgatttcca agagttcacc aagcaacttg aggctgaggg aatgttcgag ccttctcttc   10260
ctcatgttgc ttacagactt gctgaggtta tcgctatgca tgttgctggt gctgctctta   10320
tctggcatgg atacactttc gctggaatcg ctatgcttgg agttgttcag ggaagatgtg   10380
gatggcttat gcatgagggt ggacattact ctctcactgg aaacattgct ttcgacagag   10440
ctatccaagt tgcttgttac ggacttggat gtggaatgtc tggtgcttgg tggcgtaacc   10500
agcataacaa gcaccatgct actcctcaaa agcttcagca cgatgttgat cttgataccc   10560
ttcctctcgt tgctttccat gagagaatcg ctgctaaggt taagtctcct gctatgaagg   10620
cttggctttc tatgcaagct aagcttttcg ctcctgttac cactcttctt gttgctcttg   10680
gatggcagct ttaccttcat cctagacaca tgctcaggac taagcactac gatgagcttg   10740
ctatgctcgg aatcagatac ggacttgttg gataccttgc tgctaactac ggtgctggat   10800
acgttctcgc ttgttacctt ctttacgttc agcttggagc tatgtacatc ttctgcaact   10860
tcgctgtttc tcatactcac ctccctgttg ttgagcctaa cgagcatgct acttgggttg   10920
agtacgctgc taaccacact actaactgtt ctccatcttg gtggtgtgat tggtggatgt   10980
cttaccttaa ctaccagatc gagcaccacc tttaccttc tatgcctcaa ttcagacacc   11040
ctaagatcgc tcctagagtt aagcagcttt tcgagaagca cggacttcac tacgatgtta   11100
gaggatactt cgaggctatg gctgatactt tcgctaacct tgataacgtt gcccatgctc   11160
ctgagaagaa aatgcagtaa tgagatcgtt caaacatttg gcaataaagt ttcttaagat   11220
tgaatcctgt tgccggtctt gcgatgatta tcatataatt tctgttgaat tacgttaagc   11280
acgtaataat taacatgtaa tgcatgacgt tatttatgag atgggttttt atgattagag   11340
tcccgcaatt atacatttaa tacgcgatag aaaacaaaat atagcgcgca aactaggata   11400
```

```
aattatcgcg cgcggtgtca tctatgttac tagatcggtc gattaaaaat cccaattata    11460
tttggtctaa tttagtttgg tattgagtaa aacaaattcg aaccaaacca aaatataaat    11520
atatagtttt tatatatatg cctttaagac tttttataga attttcttta aaaaatatct    11580
agaaatattt gcgactcttc tggcatgtaa tatttcgtta aatatgaagt gctccatttt    11640
tattaacttt aaataattgg ttgtacgatc actttcttat caagtgttac taaaatgcgt    11700
caatctcttt gttcttccat attcatatgt caaaatctat caaaattctt atatatcttt    11760
ttcgaatttg aagtgaaatt tcgataattt aaaattaaat agaacatatc attatttagg    11820
tatcatattg atttttatac ttaattacta aatttggtta actttgaaag tgtacatcaa    11880
cgaaaaatta gtcaaacgac taaaataaat aaatatcatg tgttattaag aaaattctcc    11940
tataagaata ttttaataga tcatatgttt gtaaaaaaaa ttaattttta ctaacacata    12000
tatttactta tcaaaaattt gacaaagtaa gattaaaata atattcatct aacaaaaaaa    12060
aaaccagaaa atgctgaaaa cccggcaaaa ccgaaccaat ccaaaccgat atagttggtt    12120
tggtttgatt ttgatataaa ccgaaccaac tcggtccatt tgcaccccta atcataatag    12180
ctttaatatt tcaagatatt attaagttaa cgttgtcaat atcctggaaa ttttgcaaaa    12240
tgaatcaagc ctatatggct gtaatatgaa tttaaaagca gctcgatgtg gtggtaatat    12300
gtaatttact tgattctaaa aaaatatccc aagtattaat aatttctgct aggaagaagg    12360
ttagctacga tttacagcaa agccagaata caaagaacca taaagtgatt gaagctcgaa    12420
atatacgaag gaacaaatat ttttaaaaaa atacgcaatg acttggaaca aaagaaagtg    12480 atatatttt tgttcttaaa caagcatccc ctctaaagaa tggcagtttt cctttgcatg    12540
taactattat gctcccttcg ttacaaaaat tttggactac tattgggaac ttcttctgaa    12600
aatagtgata gaacccacac gagcatgtgc tttccattta attttaaaaa ccaagaaaca    12660
tacatacata acattccatc agcctctctc tcttttattt acggttaatg acttaaaaca    12720
catcttatta tcccatcctt aacacctagc agtgtcttta tacgatctca tcgatcacca    12780
cttcaaaacc atgcagactg ctgctgcccc tggagctggc atcggctagg ctgggtgccg    12840
cactgtcccg gaaggtccct agcgacttgt ttagattgat gggaccacct ctcaacttcc    12900
tgctgctgtc cctgctgctg gatgtcctgc ctcatctggc cgattgcacg ctccagtccc    12960
ctgcatgtgc actcgctcct caattgctta agatcatcgc agcagctatc gaagtgctgg    13020
ctctgttgcc ctcctccacg gccttggttg tagtagtagc tgccgccgcc cttctggact    13080
ttttcccaca ggaaccgccg aataattcga tagaaccaca cgagcatgtg ctttcattta    13140
ttttaaaaac caagaaacat acataacatt tcatcagcct ctctctctct ctctctctct    13200
ctctctctct ctctctctct ctctctctct ttattacagc tgttacacta acttaaaaca    13260
cattcatctc attattatta ttattatcca tccttaacac ctagcagtgt ctttgtacga    13320
tctcataatc gatcacccct tcatcaggta tccttaggct tcactccaac gttgttgcag    13380
ttacggaaca tgtacacacc atcatggttc tcaacgaact ggcaagatct ccaagttttc    13440
caaaggctaa cccacatgtt ctcatcggtg tgtctgtagt gctctcccat aactttcttg    13500
atgcactcgg tagcttctct agcatggtag aatgggatcc ttgaaacgta gtgatggagc    13560
acatgagtct cgatgatgtc atggaagatg attccgagga ttccgaactc tctatcgata    13620
gtagcagcag cacccttagc gaaagtccac tcttgagcat cgtaatgagg catagaagaa    13680
tcggtgtgct gaaggaaggt aacgaaaaca agccagtggt taacaaggat ccaaggacag    13740
```

```
aaccatgtga tgaaagtagg ccagaatccg aaaaccttgt aagcggtgta aacagaagtg    13800
agggtagcaa ggattccaag atcagaaaga acgatgtacc agtagtcctt cttatcgaaa    13860
acagggctag aaggccagta gtgagacttg aagaacttag aaacaccagg gtaaggttgt    13920
ccagtagcgt tagtagcaag gtaaagagaa agtcctccaa gctgttggaa caagagagcg    13980
aaaacagagt agataggagt ttcctcagcg atatcgtgaa ggctggtaac ttggtgcttc    14040
tctttgaatt cctcggcggt gtaaggaacg aaaaccatat ctctggtcat gtgtccagta    14100
gccttatggt gcttagcatg agagaacttc cagctgaagt aaggaaccat aacaagagag    14160
tggagaaccc atccaacggt atcgttaacc catccgtagt tagagaaagc agaatgtcca    14220
cactcatgtc caaggatcca gattccgaat ccgaaacaag agatagagaa cacgtaagca    14280
gaccaagcag cgaatctaag gaattcgtta gggagaagag ggatgtaggt aagtccaacg    14340
taagcgatag cagagatagc cacgatatct ctcaccacgt aagacataga cttcacgaga    14400
gatctctcgt aacagtgctt agggatagcg tcaaggatat ccttgatggt gtaatctggc    14460
accttgaaaa cgtttccgaa ggtatcgata gcggtctttt gctgcttgaa agatgcaacg    14520
tttccagaac gcctaacggt cttagtagat ccctcaagga tctcagatcc agacacggta    14580
accttagaca tggtatggta attgtaaatg taattgtaat gttgtttgtt gtttgttgtt    14640
gttggtaatt gttgtaaaat ttttggtggt gattggttct ttaaggtgtg agagtgagtt    14700
gtgagttgtg tggtgggttt ggtgagattg gggatggtgg gtttatatag tggagactga    14760
ggaatggggt cgtgagtgtt aactttgcat gggctacacg tggttctttt tgggcttaca    14820
cgtagtatta ttcatgcaaa tgcagccaat acatatacgg tattttaata atgtgtggga    14880
atacaatatg ccgagtattt tactaatttt ggcaatgaca agtgtacatt tggattatct    14940
tacttggcct ctcttgcttt aatttggatt attttttattc tcttaccttg gccgttcata    15000
ttcacatccc taaaggcaag acagaattga atggtggcca aaaattaaaa cgatggatat    15060
gacctacata gtgtaggatc aattaacgtc gaaggaaaat actgattctc tcaagcatac    15120
ggacaagggt aaataacata gtcaccagaa cataataaac aaaaagtgca gaagcaagac    15180
taaaaaaatt agctatggac attcaggttc atattggaaa catcattatc ctagtcttgt    15240
gaccatcctt cctcctgctc tagttgagag gccttgggac taacgagagg tcagttggga    15300
tagcagatcc ttatcctgga ctagccttttc tggtgtttca gagtcttcgt gccgccgtct    15360
acatctatct ccattaggtc tgaagatgac tcttcacacc aacgacgttt aaggtctcta    15420
tcctactcct agcttgcaat acctggcttg caatacctgg agcatcgtgc acgatgattg    15480
gatactgtgg aggaggagtg tttgctgatt tagagctccc ggttgggtga tttgacttcg    15540
atttcagttt aggcttgttg aaattttttca ggttccattg tgaagccttt agagcttgag    15600
cttccttcca tgttaatgcc ttgatcgaat actcctagag aaaagggaag tcgatctctg    15660
agtattgaaa tcgaagtgca catttttttt caacgtgtcc aatcaatcca caaacaaagc    15720
agaagacagg taatctttca tacttatact gacaagtaat agtcttaccg tcatgcataa    15780
taacgtctcg ttccttcaag aggggttttc cgacatccat aacgacccga agcctcatga    15840
aagcattagg gaagaacttt tggttcttct tgtcatggcc tttataggtg tcagccgagc    15900
tcgccaattc ccgtccgact ggctccgcaa aatattcgaa cggcaagtta tggacttgca    15960
accataactc cacggtattg agcaggacct attgtgaaga ctcatctcat ggagcttcag    16020
aatgtggttg tcagcaaacc aatgaccgaa atccatcaca tgacggacgt ccagtgggtg    16080
agcgaaacga aacaggaagc gcctatcttt cagagtcgtg agctccacac cggattccgg    16140
```

```
caactacgtg ttgggcaggc ttcgccgtat tagagatatg ttgaggcaga cccatctgtg    16200
ccactcgtac aattacgaga gttgttttt ttgtgatttt cctagtttct cgttgatggt    16260
gagctcatat tctacatcgt atggtctctc aacgtcgttt cctgtcatct gatatcccgt    16320
catttgcatc cacgtgcgcc gcctcccgtg ccaagtccct aggtgtcatg cacgccaaat    16380
tggtggtggt gcgggctgcc ctgtgcttct taccgatggg tggaggttga gtttgggggt    16440
ctccgcggcg atggtagtgg gttgacggtt tggtgtgggt tgacggcatt gatcaattta    16500
cttcttgctt caaattcttt ggcagaaaac aattcattag attagaactg gaaaccagag    16560
tgatgagacg gattaagtca gattccaaca gagttacatc tcttaagaaa taatgtaacc    16620
cctttagact ttatatattt gcaattaaaa aaataattta acttttagac tttatatata    16680
gttttaataa ctaagtttaa ccactctatt atttatatcg aaactatttg tatgtctccc    16740
ctctaaataa acttggtatt gtgtttacag aacctataat caaataatca atactcaact    16800
gaagtttgtg cagttaattg aagggattaa cggccaaaat gcactagtat tatcaaccga    16860
atagattcac actagatggc catttccatc aatatcatcg ccgttcttct tctgtccaca    16920
tatcccctct gaaacttgag agacacctgc acttcattgt ccttattacg tgttacaaaa    16980
tgaaacccat gcatccatgc aaactgaaga atggcgcaag aacccttccc ctccatttct    17040
tatgtggcga ccatccattt caccatctcc cgctataaaa cacccccatc acttcaccta    17100
gaacatcatc actacttgct tatccatcca aaagataccc acttttacaa caattaccaa    17160
caacaacaaa caacaaacaa cattacaatt acatttacaa ttaccatacc atgccaccta    17220
gcgctgctaa gcaaatggga gcttctactg gtgttcatgc tggtgttact gactcttctg    17280
ctttcaccag aaaggatgtt gctgatagac ctgatctcac catcgttgga gattctgttt    17340
acgatgctaa ggctttcaga tctgagcatc ctggtggtgc tcatttcgtt tctttgttcg    17400
gaggaagaga tgctactgag gctttcatgg aataccatag aagggcttgg cctaagtcta    17460
gaatgtctag attccacgtt ggatctcttg cttctactga ggaacctgtt gctgctgatg    17520 aggatacct tcaactttgt gctaggatcg ctaagatggt gccttctgtt tcttctggat    17580
tcgctcctgc ttcttactgg gttaaggctg gacttatcct tggatctgct atcgctcttg    17640
aggcttacat gctttacgct ggaaagagac ttctcccttc tatcgttctt ggatggcttt    17700
tcgctcttat cggtcttaac atccagcatg atgctaacca tggtgctttg tctaagtctg    17760
cttctgttaa ccttgctctt ggactttgtc aggattggat cggaggatct atgatccttt    17820
ggcttcaaga gcatgttgtt atgcaccacc tccacactaa cgatgttgat aaggatcctg    17880
atcaaaaggc tcacggtgct cttagactca gcctactga tgcttggtca cctatgcatt    17940
ggcttcagca tctttacctt ttgcctggtg agactatgta cgctttcaag cttttgttcc    18000
tcgacatctc tgagcttgtt atgtggcgtt gggagggtga gcctatctct aagcttgctg    18060
gatacctctt tatgccttct ttgcttctca agcttacctt ctgggctaga ttcgttgctt    18120
tgcctcttta ccttgctcct tctgttcata ctgctgtgtg tatcgctgct actgttatga    18180
ctggatcttt ctacctcgct ttcttcttct tcatctccca caacttcgag ggtgttgctt    18240
ctgttggacc tgatggatct atcacttcta tgactagagg tgctagcttc cttaagagac    18300
aagctgagac ttcttctaac gttggaggac ctcttcttgc tactcttaac ggtggactca    18360
actaccaaat tgagcatcac ttgttcccta gagttcacca tggattctac cctagacttg    18420
ctcctcttgt taaggctgag cttgaggcta gaggaatcga gtacaagcac tacccctacta    18480
```

```
tctggtctaa ccttgcttct accctcagac atatgtacgc tcttggaaga aggcctagat    18540
ctaaggctga gtaatgacaa gcttatgtga cgtgaaataa taacggtaaa atatatgtaa    18600
taataataat aataaagcca caaagtgaga atgaggggaa ggggaaatgt gtaatgagcc    18660
agtagccggt ggtgctaatt ttgtatcgta ttgtcaataa atcatgaatt ttgtggtttt    18720
tatgtgtttt tttaaatcat gaattttaaa ttttataaaa taatctccaa tcggaagaac    18780
aacattccat atccatgcat ggatgtttct ttacccaaat ctagttcttg agaggatgaa    18840
gcatcaccga acagttctgc aactatccct caaaagcttt aaaatgaaca acaaggaaca    18900
gagcaacgtt ccaaagatcc caaacgaaac atattatcta tactaatact atattattaa    18960
ttactactgc ccggaatcac aatccctgaa tgattcctat taactacaag ccttgttggc    19020
ggcggagaag tgatcggcgc ggcgagaagc agcggactcg gagacgaggc cttggaagat    19080
ctgagtcgaa cgggcagaat cagtattttc cttcgacgtt aattgatcct acactatgta    19140
ggtcatatcc atcgttttaa tttttggcca ccattcaatt ctgtcttgcc tttagggatg    19200
tgaatatgaa cggccaaggt aagagaataa aaataatcca aattaaagca agagaggcca    19260
agtaagataa tccaaatgta cacttgtcat tgccaaaatt agtaaaatac tcggcatatt    19320
gtattcccac acattattaa aataccgtat atgtattggc tgcatttgca tgaataatac    19380
tacgtgtaag cccaaaagaa cccacgtgta gcccatgcaa agttaacact cacgacccca    19440
ttcctcagtc tccactatat aaacccacca tccccaatct caccaaaccc accacacaac    19500
tcacaactca ctctcacacc ttaaagaacc aatcaccacc aaaaatttta caacaattac    19560
caacaacaac aaacaacaaa caacattaca attacattta caattaccat accatgagcg    19620
ctgttaccgt tactggatct gatcctaaga acagaggatc ttctagcaac accgagcaag    19680
aggttccaaa agttgctatc gataccaacg gaaacgtgtt ctctgttcct gatttcacca    19740
tcaaggacat ccttggagct atccctcatg agtgttacga gagaagattg gctacctctc    19800
tctactacgt gttcagagat atcttctgca tgcttaccac cggatacctt acccataaga    19860
tcctttaccc tctcctcatc tcttacacct ctaacagcat catcaagttc actttctggg    19920 cccctttacac ttacgttcaa ggacttttcg gaaccggaat ctgggttctc gctcatgagt    19980
gtggacatca agctttctct gattacggaa tcgtgaacga tttcgttgga tggacccttc    20040
actcttacct tatggttcct tacttcagct ggaagtactc tcatggaaag caccataagg    20100
ctactggaca catgaccaga gatatggttt tcgttcctgc caccaaagag gaattcaaga    20160
agtctaggaa cttcttcggt aacctcgctg agtactctga ggattctcca cttagaaccc    20220
tttacgagct tcttgttcaa caacttggag gatggatcgc ttacctcttc gttaacgtta    20280
caggacaacc ttaccctgat gttccttctt ggaaatggaa ccacttctgg cttacctctc    20340
cacttttcga gcaaagagat gctctctaca tcttcctttc tgatcttgga atcctcaccc    20400
agggaatcgt tcttactctt tggtacaaga aattcggagg atggtcccct ttcatcaact    20460
ggttcgttcc ttacatctgg gttaaccact ggctcgtttt catcacattc cttcagcaca    20520
ctgatcctac tatgcctcat tacaacgctg aggaatggac tttcgctaag ggtgctgctg    20580
ctactatcga tagaaagttc ggattcatcg gacctcacat cttccatgat atcatcgaga    20640
ctcatgtgct tcaccactac tgttctagga tcccattcta caacgctaga cctgcttctg    20700
aggctatcaa gaaagtttat ggaaagcact acaggtctag cgacgagaac atgtggaagt    20760
cactttggaa gtctttcagg tcttgccaat acgttgacgg tgataacggt gttctcatgt    20820
tccgtaacat caacaactgc ggagttggag ctgctgagaa gtaatgaagg ggtgatcgat    20880
```

```
tatgagatcg tacaaagaca ctgctaggtg ttaaggatgg ataataataa taataatgag    20940
atgaatgtgt tttaagttag tgtaacagct gtaataaaga gagagagaga gagagagaga    21000
gagagagaga gagagagaga gagagagagg ctgatgaaat gttatgtatg tttcttggtt    21060
tttaaaataa atgaaagcac atgctcgtgt ggttctatcg aattattcgg cggttcctgt    21120
gggaaaaagt ccagaagggc cgccgcagct actactacaa ccaaggccgt ggaggagggc    21180
aacagagcca gcacttcgat agctgctgcg atgatcttaa gcaattgagg agcgagtgca    21240
catgcagggg actggagcgt gcaatcggcc agatgaggca ggacatccag cagcagggac    21300
agcagcagga agttgagagg tggtcccatc aatctaaaca agtcgctagg gaccttccgg    21360
gacagtgcgg cacccagcct agccgatgcc agctccaggg gcagcagcag tctgcatggt    21420
tttgaagtgg tgatcgatga gatcgtataa agacactgct aggtgttaag gatgggataa    21480
taagatgtgt tttaagtcat taaccgtaat aaaaagagag agaggctgat ggaatgttat    21540
gtatgtatgt ttcttggttt ttaaaattaa atggaaagca catgctcgtg tgggttctat    21600
ctcgattaaa aatcccaatt atatttggtc taatttagtt tggtattgag taaaacaaat    21660
tcgaaccaaa ccaaaatata aatatatagt ttttatatat atgcctttaa gacttttat    21720 agaatttct ttaaaaaata tctagaaata tttgcgactc ttctggcatg taatatttcg    21780
ttaaatatga agtgctccat ttttattaac tttaaataat tggttgtacg atcactttct    21840
tatcaagtgt tactaaaatg cgtcaatctc tttgttcttc catattcata tgtcaaaatc    21900
tatcaaaatt cttatatatc tttttcgaat ttgaagtgaa atttcgataa tttaaaatta    21960
aatagaacat atcattattt aggtatcata ttgatttta tacttaatta ctaaatttgg    22020
ttaactttga aagtgtacat caacgaaaaa ttagtcaaac gactaaaata aataaatatc    22080
atgtgttatt aagaaaattc tcctataaga atattttaat agatcatatg tttgtaaaaa    22140
aaattaattt ttactaacac atatatttac ttatcaaaaa tttgacaaag taagattaaa    22200
ataatattca tctaacaaaa aaaaaaccag aaaatgctga aaacccggca aaaccgaacc    22260
aatccaaacc gatatagttg gtttggtttg attttgatat aaaccgaacc aactcggtcc    22320
atttgcaccc ctaatcataa tagctttaat atttcaagat attattaagt taacgttgtc    22380
aatatcctgg aaattttgca aaatgaatca agcctatatg gctgtaatat gaatttaaaa    22440
gcagctcgat gtggtggtaa tatgtaattt acttgattct aaaaaaatat cccaagtatt    22500 ataatttct gctaggaaga aggttagcta cgatttacag caaagccaga atacaaagaa    22560
ccataaagtg attgaagctc gaaatatacg aaggaacaaa tattttaaa aaaatacgca    22620 atgacttgga acaaaagaaa gtgatatatt ttttgttctt aaacaagcat ccctctaaa    22680 gaatggcagt tttcctttgc atgtaactat tatgctccct tcgttacaaa aattttggac    22740
tactattggg aacttcttct gaaaatagtc ctgcaggcta gtagattggt tggttggttt    22800
ccatgtacca gaaggcttac cctattagtt gaaagttgaa actttgttcc ctactcaatt    22860
cctagttgtg taaatgtatg tatatgtaat gtgtataaaa cgtagtactt aaatgactag    22920
gagtggttct tgagaccgat gagagatggg agcagaacta aagatgatga cataattaag    22980
aacgaatttg aaaggctctt aggtttgaat cctattcgag aatgttttg tcaaagatag    23040 tggcgatttt gaaccaaaga aaacatttaa aaaatcagta tccggttacg ttcatgcaaa    23100
tagaaagtgg tctaggatct gattgtaatt ttagacttaa agagtctctt aagattcaat    23160
cctggctgtg tacaaaacta caaataatat attttagact atttggcctt aactaaactt    23220
```

```
ccactcatta tttactgagg ttagagaata gacttgcgaa taaacacatt cccgagaaat    23280
actcatgatc ccataattag tcagagggta tgccaatcag atctaagaac acacattccc    23340 tcaaattta atgcacatgt aatcatagtt tagcacaatt caaaataat gtagtattaa      23400 agacagaaat ttgtagactt tttttggcg ttaaaagaag actaagttta tacgtacatt     23460
ttattttaag tggaaaaccg aaattttcca tcgaaatata tgaatttagt atatatattt    23520
ctgcaatgta ctattttgct attttggcaa ctttcagtgg actactactt tattacaatg    23580
tgtatggatg catgagtttg agtatacaca tgtctaaatg catgctttgt aaaacgtaac    23640
ggaccacaaa agaggatcca tacaaataca tctcatagct tcctccatta ttttccgaca    23700
caaacagagc attttacaac aattaccaac aacaacaaac aacaaacaac attcaatta    23760 catttacaat taccatacca tggaatttgc tcaacctctc gttgctatgg ctcaagagca    23820
gtacgctgct atcgatgctg ttgttgctcc tgctatcttc tctgctaccg actctattgg    23880
atggggactc aagcctatct cttctgctac taaggatctc cctctcgttg aatctcctac    23940
ccctcttatc ctttctctcc tcgcttactt cgctatcgtt ggttctggac tcgtttaccg    24000
taaagtgttc cctagaaccg ttaagggaca ggatcctttc cttctcaagg ctcttatgct    24060
cgctcacaac gttttcctta tcggactcag cctttacatg tgcctcaagc tcgtttacga    24120
ggcttacgtg aacaagtact ccttctgggg aaacgcttac aaccctgctc aaaccgagat    24180
ggctaaggtg atctggatct tctacgtgtc caagatctac gagttcatgg acaccttcat    24240
catgcttctc aagggaaacg ttaaccaggt ttccttcctc catgtttacc accacggatc    24300
tatctctgga atctggtgga tgatcactta tgctgctcca ggtggagatg cttacttctc    24360
tgctgctctc aactcttggg ttcatgtgtg catgtacacc tactacttca tggctgctgt    24420
tcttcctaag gacgaaaaga ccaagagaaa gtaccttttgg tggggaagat accttaccca    24480
gatgcaaatg ttccagttct tcatgaacct tctccaggct gtttacctcc tctactcttc    24540
ttctccttac cctaagttca ttgctcaact cctcgttgtt tacatggtta ccctcctcat    24600
gcttttcgga aacttctact acatgaagca ccacgcttct aagtgataag gccgccgcc    24660 atgtgacaga tcgaaggaag aaagtgtaat aagacgactc tcactactcg atcgctagtg    24720
attgtcattg ttatatataa taatgttatc tttcacaact tatcgtaatg catgtgaaac    24780
tataacacat taatcctact tgtcatatga taacactctc cccatttaaa actcttgtca    24840
atttaaagat ataagattct ttaaatgatt aaaaaaaata tattataaat tcaatcactc    24900
ctactaataa attattaatt attatttatt gattaaaaaa atacttatac taatttagtc    24960
tgaatagaat aattagattc tagcctgcag ggcggccgcg gatcccatgg agtcaaagat    25020
tcaaatagag gacctaacag aactcgccgt aaagactggc gaacagttca tacagagtct    25080
cttacgactc aatgacaaga agaaaatctt cgtcaacatg gtggagcacg acacacttgt    25140
ctactccaaa aatatcaaag atacagtctc agaagaccaa agggcaattg agactttca    25200 acaaagggta atatccggaa acctcctcgg attccattgc ccagctatct gtcactttat    25260
tgtgaagata gtggaaaagg aaggtggctc ctacaaatgc catcattgcg ataaaggaaa    25320
ggccatcgtt gaagatgcct ctgccgacag tggtcccaaa gatggacccc cacccacgag    25380
gagcatcgtg gaaaagaag acgttccaac cacgtcttca aagcaagtgg attgatgtga    25440
tatctccact gacgtaaggg atgacgcaca atcccactat ccttcgcaag acccttcctc    25500
tatataagga agttcatttc atttggagag aacacggggg actgaattaa atatgagccc    25560
tgagaggcgt cctgttgaaa tcagacctgc tactgctgct gatatggctg ctgtttgtga    25620
```

```
tatcgtgaac cactacatcg agacttctac cgttaacttc agaactgagc ctcaaactcc    25680
tcaagagtgg atcgatgatc ttgagagact ccaagataga tacccttggc ttgttgctga    25740
ggttgagggt gttgttgctg gaatcgctta cgctggacct tggaaggcta gaaacgctta    25800
cgattggact gttgagtcta ccgtttacgt ttcacacaga catcagagac ttggacttgg    25860
atctacccct tacactcacc ttctcaagtc tatggaagct cagggattca agtctgttgt    25920
tgctgttatc ggactcccta acgatccttc tgttagactt catgaggctc ttggatacac    25980
tgctagagga actcttagag ctgctggata caagcacggt ggatggcatg atgttggatt    26040
ctggcaaaga gatttcgagc ttcctgctcc tctagacct gttagaccag ttactcagat    26100
ctgaatttgc gtgatcgttc aaacatttgg caataaagtt tcttaagatt gaatcctgtt    26160
gccggtcttg cgatgattat catataattt ctgttgaatt acgttaagca tgtaataatt    26220
aacatgtaat gcatgacgtt atttatgaga tgggttttta tgattagagt cccgcaatta    26280
tacatttaat acgcgataga aaacaaaata tagcgcgcaa actaggataa attatcgcgc    26340
gcggtgtcat ctatgttact agatcactag tgatgtacgg ttaaaaccac cccagtacat    26400
taaaaacgtc cgcaatgtgt tattaagttg tctaagcgtc aatttgttta caccacaata    26460
tatcctgcca ccagccagcc aacagctccc cgaccggcag ctcggcacaa aatcaccact    26520
cgatacaggc agcccatcag tcc                                           26543

<210> SEQ ID NO 7
<211> LENGTH: 23760
<212> TYPE: DNA
<213> ORGANISM: Artificial Sequence
<220> FEATURE:
<223> OTHER INFORMATION: pGA7- mod_G nucleotide sequence

<400> SEQUENCE: 7
tcctgtggtt ggcatgcaca tacaaatgga cgaacggata aaccttttca cgcccttta       60 aatatccgat tattctaata aacgctcttt tctcttaggt ttacccgcca atatatcctg     120
tcaaacactg atagtttaaa ctgaaggcgg gaaacgacaa tctgctagtg gatctcccag     180
tcacgacgtt gtaaaacggg cgccccgcgg aaagcttgcg gccgcggtac cgcccgttcg     240
actcagatct tccaaggcct cgtctccgag tccgctgctt ctcgccgcgc cgatcacttc     300
tccgccgcca acaaggcttg tagttaatag gaatcattca gggattgtga ttccgggcag     360
tagtaattaa taatatagta ttagtataga taatatgttt cgtttgggat ctttggaacg     420
ttgctctgtt ccttgttgtt catttttaaag cttttgaggg atagttgcag aactgttcgg     480
tgatgcttca tcctctcaag aactagattt gggtaaagaa acatccatgc atggatatgg     540
aatgttgttc ttccgattgg agattatttt ataaatttta aaattcatga tttaaaaaaa     600
cacataaaaa ccacaaaatt catgatttat tgacaatacg atacaaaatt agcaccaccg     660
gctactggct cattacacat ttccccttcc cctcattctc actttgtggc tttattatta     720
ttattattac atatatttta ccgttattat ttcacgtcac ataagcttgt taattaatta     780
tcactgcttc ttagcaccct tagacttgta cctcttacgg tagaagttgg cgaagagaac     840
gaacatgttc accataaccc agagttgaag gtaaggaagc cagaaagcgg tattctgaac     900
gtaagcggtg tagatagagt gagaagcaca gatacagaac tgaagcatct ggatctgggt     960
gatgtacttc ttccagaaac agttaactcc aagagcagca agtccgtagt aagagtacat    1020
gatcacgtgc acgaaggtgt taacagaaga tccgaagtag caatctccaa caggctcaag    1080
```

```
cttcataaca acgaaccatg accagatgag aagagtgtgg tggtagatgt gaaggaaaga    1140
aagctggtcg aacttcttcc tcatcaccat gaagaaggtg tcgagaagct caacgtactt    1200
gttgttgtag tgaagccaga taacctgaga gattccccaa gagttagcag tcatatcagg    1260
gatgtttccc caaaccttaa gtccctgagc cctatgagaa gtaacgaaaa ggtagatgca    1320
gtagctgttg aagaaggtct ggtagaagtt gtaaacgagc atagcgttct tgagtccgaa    1380
aggttgagat ctgttctgca tgatacgctt tccgaagtag atgaagagga ggtatccaat    1440
agttccgata gtaggtcccc agtactcaac ctgcatgaag taagcaggaa ctttctcaga    1500
agctgggata tcagggttag ccacattgta ggtaacgtat ccaagagttc cagcaagagc    1560
agcagggata gcgatagagg ccatggtatg gtaattgtaa atgtaattgt aatgttgttt    1620
gttgtttgtt gttgttggta attgttgtaa aattaattaa gtgggtatct tttggatgga    1680
taagcaagta gtgatgatgt tctaggtgaa gtgatggggg tgttttatag cgggagatgg    1740
tgaaatggat ggtcgccaca taagaaatgg aggggaaggg ttcttgcgcc attcttcagt    1800
ttgcatggat gcatgggttt cattttgtaa cacgtaataa ggacaatgaa gtgcaggtgt    1860
ctctcaagtt tcagagggga tatgtggaca gaagaagaac ggcgatgata ttgatggaaa    1920
tggccatcta gtgtgaatct attcggttga taatactagt gcattttggc cgttaatccc    1980
ttcaattaac tgcacaaact tcagttgagt attgattatt tgattatagg ttctgtaaac    2040
acaataccaa gtttatttag aggggagaca tacaaatagt ttcgtatataa ataatagagt    2100 ggttaaactt agttattaaa actatatata aagtctaaaa gttaaattat ttttttaatt    2160
gcaaatatat aaagtctaaa ggggttacat tatttcttaa gagatgtaac tctgttggaa    2220
tctgacttaa tccgtctcat cactctggtt tccagttcta atctaatgaa ttgttttctg    2280
ccaaagaatt tgaagcaaga agtaaattga tcaatgccgt caacccacac caaaccgtca    2340
acccactacc atcgccgcgg agacccccaa actcaacctc cacccatcgg taagaagcac    2400
agggcagccc gcaccaccac caatttggcg tgcatgacac ctagggactt ggcacgggag    2460
gcggcgcacg tggatgcaaa tgacgggata tcagatgaca ggaaacgacg ttgagagacc    2520
atacgatgta gaatatgagc tcaccatcaa cgagaaacta ggaaaatcac aaaaaaaaca    2580
actctcgtaa ttgtacgagt ggcacagatg ggtctgcctc aacatatctc taatacggcg    2640
aagcctgccc aacacgtagt tgccggaatc cggtgtggag ctcacgactc tgaaagatag    2700
gcgcttcctg tttcgtttcg ctcacccact ggacgtccgt catgtgatgg atttcggtca    2760
ttggtttgct gacaaccaca ttctgaagct ccatgagatg agtcttcaca ataggtcctg    2820
ctcaataccg tggagttatg gttgcaagtc cataacttgc cgttcgaata ttttgcggag    2880
ccagtcggac gggaattggc gagctcggct gacacctata aaggccatga caagaagaac    2940
caaaagttct tccctaatgc tttcatgagg cttcgggtcg ttatggatgt cggaaaaccc    3000
ctcttgaagg aacgagacgt tattatgcat gacggtaaga ctattacttg tcagtataag    3060
tatgaaagat tacctgtctt ctgctttgtt tgtggattga ttggacacgt tgaaaaaaaa    3120
tgtgcacttc gatttcaata ctcagagatc gacttcccct ttctctagga gtattcgatc    3180
aaggcattaa catggaagga agctcaagct ctaaaggctt cacaatggaa cctgaaaaat    3240
ttcaacaagc ctaaactgaa atcgaagtca aatcacccaa ccgggagctc taaatcagca    3300
aacactcctc ctcccacagta tccaatcatc gtgcacgatg ctccaggtat tgcaagccag    3360
gtattgcaag ctaggagtag gatagagacc ttaaacgtcg ttggtgtgaa gagtcatctt    3420
cagacctaat ggagatagat gtagacggcg gcacgaagac tctgaaacac cagaaggct     3480
```

```
agtccaggat aaggatctgc tatcccaact gacctctcgt tagtcccaag gcctctcaac   3540
tagagcagga ggaaggatgg tcacaagact aggataatga tgtttccaat atgaacctga   3600
atgtccatag ctaatttttt tagtcttgct tctgcacttt ttgtttatta tgttctggtg   3660
actatgttat ttaccttgt ccgtatgctt gagggtaccc tagtagattg gttggttggt   3720
ttccatgtac cagaaggctt accctattag ttgaaagttg aaactttgtt ccctactcaa   3780
ttcctagttg tgtaaatgta tgtatatgta atgtgtataa aacgtagtac ttaaatgact   3840
aggagtggtt cttgagaccg atgagagatg ggagcagaac taaagatgat gacataatta   3900
agaacgaatt tgaaaggctc ttaggtttga atcctattcg agaatgtttt tgtcaaagat   3960
agtggcgatt ttgaaccaaa gaaaacattt aaaaaatcag tatccggtta cgttcatgca   4020
aatagaaagt ggtctaggat ctgattgtaa ttttagactt aaagagtctc ttaagattca   4080
atcctggctg tgtacaaaac tacaaataat atattttaga ctatttggcc ttaactaaac   4140
ttccactcat tatttactga ggttagaaa tagacttgcg aataaacaca ttcccgagaa   4200
atactcatga tcccataatt agtcagaggg tatgccaatc agatctaaga acacacattc   4260
cctcaaattt taatgcacat gtaatcatag tttagcacaa ttcaaaaata atgtagtatt   4320
aaagacagaa atttgtagac ttttttttgg cgttaaaaga agactaagtt tatacgtaca   4380
ttttatttta agtggaaaac cgaaattttc catcgaaata tatgaattta gtatatatat   4440
ttctgcaatg tactattttg ctattttggc aactttcagt ggactactac tttattacaa   4500
tgtgtatgga tgcatgagtt tgagtataca catgtctaaa tgcatgcttt gtaaaacgta   4560
acggaccaca aaagaggatc catacaaata catctcatag cttcctccat tattttccga   4620
cacaaacaga gcattttaca acaattacca acaacaacaa acaacaaaca acattacaat   4680
tacatttaca attaccatac catggaattc gcccagcctc ttgttgctat ggctcaagag   4740
caatacgctg ctatcgatgc tgttgttgct cctgctatct tctctgctac tgattctatc   4800
ggatggggac ttaagcctat ctcttctgct actaaggact tgcctcttgt tgagtctcct   4860
acacctctca tccttttcttt gcttgcttac ttcgctatcg ttggatctgg actcgtttac   4920
agaaaggttt tccctagaac cgtgaaggga caagatccat tccttttgaa ggctcttatg   4980
cttgctcaca acgtgttcct tatcggactt tctctttaca tgtgcctcaa gcttgtgtac   5040
gaggcttacg ttaacaagta ctctttctgg ggaaacgctt acaaccctgc tcaaactgag   5100
atggctaagg ttatctggat cttctacgtg agcaagatct acgagttcat ggataccttc   5160
atcatgctcc tcaagggaaa tgttaaccag gttagcttcc ttcacgttta ccatcacgga   5220
tctatctctg gaatctggtg gatgattact tacgctgctc ctggtggtga tgcttacttc   5280
tctgctgctc ttaactcttg ggttcacgtg tgtatgtaca cctactattt tatggctgcc   5340
gtgcttccta aggacgagaa aactaagaga aagtacctct ggtggggaag atacttact    5400 caaatgcaga tgttccagtt cttcatgaac cttctccagg ctgtttacct tctctactct   5460
tcatctcctt accctaagtt tatcgctcag ctcctcgtgg tgtacatggt tactcttctc   5520
atgcttttcg gaaacttcta ctacatgaag caccacgcta gcaagtgatg aggcgcgccg   5580
ggccgccgcc atgtgacaga tcgaaggaag aaagtgtaat aagacgactc tcactactcg   5640
atcgctagtg attgtcattg ttatatataa taatgttatc tttcacaact tatcgtaatg   5700
catgtgaaac tataacacat taatcctact tgtcatatga taacactctc cccatttaaa   5760
actcttgtca atttaaagat ataagattct ttaaatgatt aaaaaaaata tattataaat   5820
```

```
tcaatcactc ctactaataa attattaatt attatttatt gattaaaaaa atacttatac    5880
taatttagtc tgaatagaat aattagattc tagtctcatc cccttttaaa ccaacttagt    5940
aaacgttttt tttttttaatt ttatgaagtt aagttttttac cttgttttta aaaagaatcg   6000
ttcataagat gccatgccag aacattagct acacgttaca catagcatgc agccgcggag    6060
aattgttttt cttcgccact tgtcactccc ttcaaacacc taagagcttc tctctcacag    6120
cacacacata caatcacatg cgtgcatgca ttattacacg tgatcgccat gcaaatctcc    6180
tttatagcct ataaattaac tcatccgctt cactctttac tcaaaccaaa actcatcgat    6240
acaaacaaga ttaaaaacat acacgaggat cttttacaac aattaccaac aacaacaaac    6300
aacaaacaac attacaatta catttacaat taccatacca tgcctccaag ggactcttac    6360
tcttatgctg ctcctccttc tgctcaactt cacgaagttg atactcctca agagcacgac    6420
aagaaagagc ttgttatcgg atagggct tacgatgtta ccaacttcgt taagagacac       6480
cctggtggaa agatcattgc ttaccaagtt ggaactgatg ctaccgatgc ttacaagcag    6540
ttccatgtta gatctgctaa ggctgacaag atgcttaagt ctcttccttc tcgtcctgtt    6600
cacaagggat actctccaag aagggctgat cttatcgctg atttccaaga gttcaccaag    6660
caacttgagg ctgagggaat gttcgagcct tctcttcctc atgttgctta cagacttgct    6720
gaggttatcg ctatgcatgt tgctggtgct gctcttatct ggcatggata cactttcgct    6780
ggaatcgcta tgcttggagt tgttcaggga agatgtggat ggcttatgca tgagggtgga    6840
cattactctc tcactggaaa cattgctttc gacagagcta tccaagttgc ttgttacgga    6900
cttgatgtg gaatgtctgg tgcttggtgg cgtaaccagc ataacaagca ccatgctact     6960
cctcaaaagc ttcagcacga tgttgatctt gataccttc ctctcgttgc tttccatgag     7020
agaatcgctc taaggttaa gtcctcctgct atgaaggctt ggctttctat gcaagctaag    7080
cttttcgctc ctgttaccac tcttcttgtt gctcttggat ggcagcttta ccttcatcct    7140
agacacatgc tcaggactaa gcactacgat gagcttgcta tgctcggaat cagatacgga    7200
cttgttggat accttgctgc taactacggt gctggatacg ttctcgcttg ttaccttctt    7260
tacgttcagc ttggagctat gtacatcttc tgcaacttcg ctgtttctca tactcacctc    7320
cctgttgttg agcctaacga gcatgctact tgggttgagt acgctgctaa ccacactact    7380
aactgttctc catcttggtg gtgtgattgg tggatgtctt accttaacta ccagatcgag    7440
caccaccttt acccttctat gcctcaattc agacacccta agatcgctcc tagagttaag    7500
cagcttttcg agaagcacgg acttcactac gatgttagag atacttcga ggctatggct    7560
gatactttcg ctaaccttga taacgttgcc catgctcctg agaagaaaat gcagtaatga    7620
gatcgttcaa acatttggca ataaagtttc ttaagattga atcctgttgc cggtcttgcg    7680
atgattatca tataatttct gttgaattac gttaagcacg taataattaa catgtaatgc    7740
atgacgttat ttatgagatg ggtttttatg attagagtcc cgcaattata catttaatac    7800
gcgatagaaa acaaaatata gcgcgcaaac taggataaat tatcgcgcgc ggtgtcatct    7860
atgttactag atcggtcgat taaaaatccc aattatattt ggtctaattt agtttggtat    7920
tgagtaaaac aaattcgaac caaaccaaaa tataaatata tagttttttat atatatgcct    7980
ttaagacttt ttatagaatt ttctttaaaa aatatctaga aatatttgcg actcttctgg   8040
catgtaatat ttcgttaaat atgaagtgct ccattttat taactttaaa taattggttg    8100
tacgatcact ttcttatcaa gtgttactaa aatgcgtcaa tctctttgtt cttccatatt    8160
catatgtcaa aatctatcaa aattcttata tatctttttc gaatttgaag tgaaatttcg    8220
```

```
ataatttaaa attaaataga acatatcatt atttaggtat catattgatt tttatactta    8280
attactaaat ttggttaact ttgaaagtgt acatcaacga aaaattagtc aaacgactaa    8340
aataaataaa tatcatgtgt tattaagaaa attctcctat aagaatattt taatagatca    8400
tatgtttgta aaaaaaatta attttttacta acacatatat ttacttatca aaaatttgac   8460
aaagtaagat taaaataata ttcatctaac aaaaaaaaaa ccagaaaatg ctgaaaaccc    8520
ggcaaaaccg aaccaatcca aaccgatata gttggtttgg tttgattttg atataaaccg    8580
aaccaactcg gtccatttgc acccctaatc ataatagctt taatatttca agatattatt    8640
aagttaacgt tgtcaatatc ctggaaattt tgcaaaatga atcaagccta tatggctgta    8700
atatgaattt aaaagcagct cgatgtggtg gtaatatgta atttacttga ttctaaaaaa    8760
atatcccaag tattaataat ttctgctagg aagaaggtta gctacgattt acagcaaagc    8820
cagaatacaa agaaccataa agtgattgaa gctcgaaata tacgaaggaa caaatatttt    8880
taaaaaaata cgcaatgact tggaacaaaa gaaagtgata tattttttgt tcttaaacaa    8940
gcatcccctc taaagaatgg cagttttcct ttgcatgtaa ctattatgct cccttcgtta    9000
caaaaatttt ggactactat tgggaacttc ttctgaaaat agtgatagaa cccacacgag    9060
catgtgcttt ccatttaatt ttaaaaacca agaaacatac atacataaca ttccatcagc    9120
ctctctctct ttttattacg gttaatgact taaaacacat cttattatcc catccttaac    9180
acctagcagt gtctttatac gatctcatcg atcaccactt caaaaccatg cagactgctg    9240
ctgcccctgg agctggcatc ggctaggctg ggtgccgcac tgtcccggaa ggtccctagc    9300
gacttgttta gattgatggg accacctctc aacttcctgc tgctgtccct gctgctggat    9360
gtcctgcctc atctggccga ttgcacgctc cagtcccctg catgtgcact cgctcctcaa    9420
ttgcttaaga tcatcgcagc agctatcgaa gtgctggctc tgttgccctc ctccacggcc    9480
ttggttgtag tagtagctgc cgccgccctt ctggactttt tcccacagga accgccgaat    9540
aattcgatag aaccacacga gcatgtgctt tcatttattt taaaaaccaa gaaacataca    9600
taacatttca tcagcctctc tctctctctc tctctctctc tctctctctc tctctctctc    9660
tctctcttta ttacagctgt tacactaact taaaacacat tcatctcatt attattatta    9720
ttatccatcc ttaacaccta gcagtgtctt tgtacgatct cataatcgat caccccttca    9780
tcaggtatcc ttaggcttca ctccaacgtt gttgcagtta cggaacatgt acacaccatc    9840
atggttctca acgaactggc aagatctcca agttttccaa aggctaaccc acatgttctc    9900
atcggtgtgt ctgtagtgct ctcccataac tttcttgatg cactcggtag cttctctagc    9960
atggtagaat gggatccttg aaacgtagtg atggagcaca tgagtctcga tgatgtcatg   10020
gaagatgatt ccgaggattc cgaactctct atcgatagta gcagcagcac ccttagcgaa   10080
agtccactct tgagcatcgt aatgaggcat agaagaatcg gtgtgctgaa ggaaggtaac   10140
gaaacaagc cagtggttaa caaggatcca aggacagaac catgtgatga agtaggcca    10200
gaatccgaaa accttgtaag cggtgtaaac agaagtgagg gtagcaagga ttccaagatc   10260
agaaagaacg atgtaccagt agtccttctt atcgaaaaca gggctagaag gccagtagtg   10320
agacttgaag aacttagaaa caccagggta aggttgtcca gtagcgttag tagcaaggta   10380
aagagaaagt cctccaagct gttggaacaa gagagcgaaa acagagtaga taggagtttc   10440
ctcagcgata tcgtgaaggc tggtaacttg gtgcttctct ttgaattcct cggcggtgta   10500
aggaacgaaa accatatctc tggtcatgtg tccagtagcc ttatggtgct tagcatgaga   10560
```

```
gaacttccag ctgaagtaag gaaccataac aagagagtgg agaacccatc caacggtatc   10620
gttaacccat ccgtagttag agaaagcaga atgtccacac tcatgtccaa ggatccagat   10680
tccgaatccg aaacaagaga tagagaacac gtaagcagac caagcagcga atctaaggaa   10740
ttcgttaggg agaagaggga tgtaggtaag tccaacgtaa gcgatagcag agatagccac   10800
gatatctctc accacgtaag acatagactt cacgagagat ctctcgtaac agtgcttagg   10860
gatagcgtca aggatatcct tgatggtgta atctggcacc ttgaaaacgt ttccgaaggt   10920
atcgatagcg gtcttttgct gcttgaaaga tgcaacgttt ccagaacgcc taacggtctt   10980
agtagatccc tcaaggatct cagatccaga cacggtaacc ttagacatgg tatggtaatt   11040
gtaaatgtaa ttgtaatgtt gtttgttgtt tgttgttgtt ggtaattgtt gtaaaatttt   11100
tggtggtgat tggttcttta aggtgtgaga gtgagttgtg agttgtgtgg tgggtttggt   11160
gagattgggg atggtgggtt tatatagtgg agactgagga atgggtcgt gagtgttaac    11220 tttgcatggg ctacacgtgg gttcttttgg gcttacacgt agtattattc atgcaaatgc   11280
agccaataca tatacggtat tttaataatg tgtgggaata caatatgccg agtatttac    11340 taattttggc aatgacaagt gtacatttgg attatcttac ttggcctctc ttgctttaat   11400
ttggattatt tttattctct taccttggcc gttcatattc acatccctaa aggcaagaca   11460
gaattgaatg gtggccaaaa attaaaacga tggatatgac ctacatagtg taggatcaat   11520
taacgtcgaa ggaaaatact gattctctca agcatacgga caagggtaaa taacatagtc   11580
accagaacat aataaacaaa aagtgcagaa gcaagactaa aaaaattagc tatggacatt   11640
caggttcata ttgaaaacat cattatccta gtcttgtgac catccttcct cctgctctag   11700
ttgagaggcc ttgggactaa cgagaggtca gttgggatag cagatcctta tcctggacta   11760
gcctttctgg tgtttcagag tcttcgtgcc gccgtctaca tctatctcca ttaggtctga   11820
agatgactct tcacaccaac gacgtttaag gtctctatcc tactcctagc ttgcaatacc   11880
tggcttgcaa tacctggagc atcgtgcacg atgattggat actgtggagg aggagtgttt   11940
gctgatttag agctcccggt tgggtgattt gacttcgatt tcagtttagg cttgttgaaa   12000 ttttttcaggt tccattgtga agcctttaga gcttgagctt ccttccatgt taatgccttg   12060
atcgaatact cctagagaaa agggaagtcg atctctgagt attgaaatcg aagtgcacat   12120 ttttttttcaa cgtgtccaat caatccacaa acaaagcaga agacaggtaa tctttcatac   12180
ttatactgac aagtaatagt cttaccgtca tgcataataa cgtctcgttc cttcaagagg   12240
ggttttccga catccataac gacccgaagc ctcatgaaag cattagggaa gaacttttgg   12300
ttcttcttgt catggccttt ataggtgtca gccgagctcg ccaattcccg tccgactggc   12360
tccgcaaaat attcgaacgg caagttatgg acttgcaacc ataactccac ggtattgagc   12420
aggacctatt gtgaagactc atctcatgga gcttcagaat gtggttgtca gcaaaccaat   12480
gaccgaaatc catcacatga cggacgtcca gtgggtgagc gaaacgaaac aggaagcgcc   12540
tatctttcag agtcgtgagc tccacaccgg attccggcaa ctacgtgttg ggcaggcttc   12600
gccgtattag agatatgttg aggcagaccc atctgtgcca ctcgtacaat tacgagagtt   12660
gttttttttg tgattttcct agtttctcgt tgatggtgag ctcatattct acatcgtatg   12720
gtctctcaac gtcgtttcct gtcatctgat atcccgtcat ttgcatccac gtgcgccgcc   12780
tcccgtgcca agtccctagg tgtcatgcac gccaaattgg tggtggtgcg ggctgccctg   12840
tgcttcttac cgatgggtgg aggttgagtt tgggggctc cgcggcgatg gtagtgggtt    12900
gacggtttgg tgtgggttga cggcattgat caatttactt cttgcttcaa attctttggc   12960
```

```
agaaaacaat tcattagatt agaactggaa accagagtga tgagacggat taagtcagat    13020
tccaacagag ttacatctct taagaaataa tgtaaccect ttagacttta tatatttgca    13080
attaaaaaaa taatttaact tttagacttt atatatagtt ttaataacta agtttaacca    13140
ctctattatt tatatcgaaa ctatttgtat gtctcccctc taaataaact tggtattgtg    13200
tttacagaac ctataatcaa ataatcaata ctcaactgaa gtttgtgcag ttaattgaag    13260
ggattaacgg ccaaaatgca ctagtattat caaccgaata gattcacact agatggccat    13320
ttccatcaat atcatcgccg ttcttcttct gtccacatat cccctctgaa acttgagaga    13380
cacctgcact tcattgtcct tattacgtgt tacaaaatga aacccatgca tccatgcaaa    13440
ctgaagaatg gcgcaagaac ccttcccctc catttcttat gtggcgacca tccatttcac    13500
catctcccgc tataaaacac ccccatcact tcacctagaa catcatcact acttgcttat    13560
ccatccaaaa gatacccact tttacaacaa ttaccaacaa caacaaacaa caaacaacat    13620
tacaattaca tttacaatta ccataccatg ccacctagcg ctgctaagca aatgggagct    13680
tctactggtg ttcatgctgg tgttactgac tcttctgctt tcaccagaaa ggatgttgct    13740
gatagacctg atctcaccat cgttggagat tctgtttacg atgctaaggc tttcagatct    13800
gagcatcctg gtggtgctca tttcgtttct ttgttcggag aagagatgc tactgaggct     13860 ttcatggaat accatagaag ggcttggcct aagtctagaa tgtctagatt ccacgttgga    13920
tctcttgctt ctactgagga acctgttgct gctgatgagg gatacctica actttgtgct    13980 aggatcgcta agatggtgcc ttctgtttct tctggattcg ctcctgcttc ttactgggtt    14040
aaggctggac ttatccttgg atctgctatc gctcttgagg cttacatgct ttacgctgga    14100
aagagacttc tcccttctat cgttcttgga tggcttttcg ctcttatcgg tcttaacatc    14160
cagcatgatg ctaaccatgg tgctttgtct aagtctgctt ctgttaaccct tgctcttgga    14220 cttttgtcagg attggatcgg aggatctatg atcctttggc ttcaagagca tgttgttatg    14280
caccacctcc acactaacga tgttgataag gatcctgatc aaaaggctca cggtgctctt    14340
agactcaagc ctactgatgc ttggtcacct atgcattggc ttcagcatct ttacctttg    14400 cctggtgaga ctatgtacgc tttcaagctt ttgttcctcg acatctctga gcttgttatg    14460
tggcgttggg agggtgagcc tatctctaag cttgctggat acctctttat gccttctttg    14520
cttctcaagc ttaccttctg ggctagattc gttgctttgc ctctttacct tgctccttct    14580
gttcatactg ctgtgtgtat cgctgctact gttatgactg gatctttcta cctcgctttc    14640
ttcttcttca tctcccacaa cttcgagggt gttgcttctg ttggacctga tggatctatc    14700
acttctatga ctagaggtgc tagcttcctt aagagacaag ctgagacttc ttctaacgtt    14760 ggaggaccctc ttcttgctac tcttaacggt ggactcaact accaaattga gcatcacttg    14820
ttccctagag ttcaccatgg attctaccct agacttgctc ctcttgttaa ggctgagctt    14880
gaggctagag gaatcgagta caagcactac cctactatct ggtctaacct tgcttctacc    14940
ctcagacata tgtacgctct tggaagaagg cctagatcta aggctgagta atgacaagct    15000
tatgtgacgt gaaataataa cggtaaaata tatgtaataa taataataat aaagccacaa    15060
agtgagaatg aggggaaggg gaaatgtgta atgagccagt agccggtggt gctaattttg    15120
tatcgtattg tcaataaatc atgaattttg tggtttttat gtgttttttt aaatcatgaa    15180
ttttaaattt tataaaataa tctccaatcg gaagaacaac attccatatc catgcatgga    15240
tgtttcttta cccaaatcta gttcttgaga ggatgaagca tcaccgaaca gttctgcaac    15300
```

```
tatccctcaa aagcttaaaa atgaacaaca aggaacagag caacgttcca aagatcccaa    15360
acgaaacata ttatctatac taatactata ttattaatta ctactgcccg gaatcacaat    15420
ccctgaatga ttcctattaa ctacaagcct tgttggcggc ggagaagtga tcggcgcggc    15480
gagaagcagc ggactcggag acgaggcctt ggaagatctg agtcgaacgg gcagaatcag    15540
tattttcctt cgacgttaat tgatcctaca ctatgtaggt catatccatc gttttaattt    15600
ttggccacca ttcaattctg tcttgccttt agggatgtga atatgaacgg ccaaggtaag    15660
agaataaaaa taatccaaat taaagcaaga gaggccaagt aagataatcc aaatgtacac    15720
ttgtcattgc caaaattagt aaaatactcg gcatattgta ttcccacaca ttattaaaat    15780
accgtatatg tattggctgc atttgcatga ataatactac gtgtaagccc aaaagaaccc    15840
acgtgtagcc catgcaaagt taacactcac gacccattc ctcagtctcc actatataaa    15900
cccaccatcc ccaatctcac caaacccacc acacaactca caactcactc tcacacctta    15960
aagaaccaat caccaccaaa aattttacaa caattaccaa caacaacaaa caacaaacaa    16020
cattacaatt acatttacaa ttaccatacc atgagcgctg ttaccgttac tggatctgat    16080
cctaagaaca gaggatcttc tagcaacacc gagcaagagg ttccaaaagt tgctatcgat    16140
accaacggaa acgtgttctc tgttcctgat ttcaccatca aggacatcct tggagctatc    16200
cctcatgagt gttacgagag aagattggct acctctctct actacgtgtt cagagatatc    16260
ttctgcatgc ttaccaccgg ataccttacc cataagatcc tttaccctct cctcatctct    16320
tacacctcta acagcatcat caagttcact ttctgggccc tttacactta cgttcaagga    16380
cttttcggaa ccggaatctg ggttctcgct catgagtgtg gacatcaagc tttctctgat    16440
tacggaatcg tgaacgattt cgttggatgg acccttcact cttaccttat ggttccttac    16500
ttcagctgga agtactctca tggaaagcac cataaggcta ctggacacat gaccagagat    16560
atggttttcg ttcctgccac caaagaggaa ttcaagaagt ctaggaactt cttcggtaac    16620
ctcgctgagt actctgagga ttctccactt agaaccctt acgagcttct tgttcaacaa    16680
cttggaggat ggatcgctta cctcttcgtt aacgttacag acaaccttac ccctgatgtt    16740
ccttcttgga aatggaacca cttctggctt acctctccac ttttcgagca aagagatgct    16800
ctctacatct tcctttctga tcttggaatc ctcacccagg gaatcgttct tactctttgg    16860
tacaagaaat tcggaggatg gtccttttc atcaactggt tcgttcctta catctgggtt    16920
aaccactggc tcgttttcat cacattcctt cagcacactg atcctactat gcctcattac    16980
aacgctgagg aatggacttt cgctaagggt gctgctgcta ctatcgatag aaagttcgga    17040
ttcatcggac ctcacatctt ccatgatatc atcgagactc atgtgcttca ccactactgt    17100
tctaggatcc cattctacaa cgctagacct gcttctgagg ctatcaagaa agttatggga    17160
aagcactaca ggtctagcga cgagaacatg tggaagtcac tttggaagtc tttcaggtct    17220
tgccaatacg ttgacggtga taacggtgtt ctcatgttcc gtaacatcaa caactgcgga    17280
gttggagctg ctgagaagta atgaaggggt gatcgattat gagatcgtac aaagacactg    17340
ctaggtgtta aggatggata ataataataa taatgagatg aatgtgtttt aagttagtgt    17400
aacagctgta ataaagagag agagagagag agagagagag agagagagag agagagagag    17460
agagaggctg atgaaatgtt atgtatgttt cttggttttt aaaataaatg aaagcacatg    17520
ctcgtgtggt tctatcgaat tattcggcgg ttcctgtggg aaaagtcca gaagggccgc    17580 cgcagctact actacaacca aggccgtgga ggagggcaac agagccagca cttcgatagc    17640
tgctgcgatg atcttaagca attgaggagc gagtgcacat gcaggggact ggagcgtgca    17700
```

```
atcggccaga tgaggcagga catccagcag cagggacagc agcaggaagt tgagaggtgg    17760
tcccatcaat ctaaacaagt cgctagggac cttccgggac agtgcggcac ccagcctagc    17820
cgatgccagc tccaggggca gcagcagtct gcatggtttt gaagtggtga tcgatgagat    17880
cgtataaaga cactgctagg tgttaaggat gggataataa gatgtgtttt aagtcattaa    17940
ccgtaataaa aagagagaga ggctgatgga atgttatgta tgtatgtttc ttggttttta    18000
aaattaaatg gaaagcacat gctcgtgtgg gttctatctc gattaaaaat cccaattata    18060
tttggtctaa tttagtttgg tattgagtaa acaaattcg aaccaaacca aaatataaat    18120
atatagtttt tatatatatg cctttaagac tttttataga atttctttta aaaaatatct    18180
agaaatattt gcgactcttc tggcatgtaa tatttcgtta aatatgaagt gctccatttt    18240
tattaacttt aaataattgg ttgtacgatc actttcttat caagtgttac taaaatgcgt    18300
caatctcttt gttcttccat attcatatgt caaaatctat caaaattctt atatatcttt    18360
ttcgaatttg aagtgaaatt tcgataattt aaaattaaat agaacatatc attatttagg    18420
tatcatattg attttttatac ttaattacta aatttggtta actttgaaag tgtacatcaa    18480
cgaaaaatta gtcaaacgac taaaataaat aaatatcatg tgttattaag aaaattctcc    18540
tataagaata ttttaataga tcatatgttt gtaaaaaaaa ttaattttta ctaacacata    18600
tatttactta tcaaaaattt gacaaagtaa gattaaaata atattcatct aacaaaaaaa    18660
aaaccagaaa atgctgaaaa cccggcaaaa ccgaaccaat ccaaaccgat atagttggtt    18720
tggtttgatt ttgatataaa ccgaaccaac tcggtccatt tgcacccccta atcataatag    18780 ctttaatatt tcaagatatt attaagttaa cgttgtcaat atcctggaaa ttttgcaaaa    18840
tgaatcaagc ctatatggct gtaatatgaa tttaaaagca gctcgatgtg gtggtaatat    18900
gtaatttact tgattctaaa aaaatatccc aagtattaat aatttctgct aggaagaagg    18960
ttagctacga tttacagcaa agccagaata caaagaacca taaagtgatt gaagctcgaa    19020
atatacgaag gaacaaatat ttttaaaaaa atacgcaatg acttggaaca aaagaaagtg    19080
atatattttt tgttcttaaa caagcatccc ctctaaagaa tggcagtttt cctttgcatg    19140
taactattat gctcccttcg ttacaaaaat tttggactac tattgggaac ttcttctgaa    19200
aatagtcctg caggctagta gattggttgg ttggttttcca tgtaccagaa ggcttaccct    19260
attagttgaa agttgaaact tgttccccta ctcaattcct agttgtgtaa atgtatgtat    19320
atgtaatgcg tataaaacgt agtacttaaa tgactaggag tggttcttga gaccgatgag    19380
agatgggagc agaactaaag atgatgacat aattaagaac gaatttgaaa ggctcttagg    19440
tttgaatcct attcgagaat gttttttgtca agatagtgg cgattttgaa ccaaagaaaa    19500
cattaaaaaa atcagtatcc ggttacgttc atgcaaatag aaagtggtct aggatctgat    19560
tgtaatttta gacttaaaga gtctcttaag attcaatcct ggctgtgtac aaaactacaa    19620
ataatatatt ttagactatt tggccttaac taaacttcca ctcattattt actgaggtta    19680
gagaatagac ttgcgaataa acacattccc gagaaatact catgatccca taattagtca    19740
gagggtatgc caatcagatc taagaacaca cattccctca aattttaatg cacatgtaat    19800
catagtttag cacaattcaa aaataatgta gtattaaaga cagaaatttg tagacttttt    19860
tttggcgtta aaggaagact aagtttatac gtacattta ttttaagtgg aaaaccgaaa    19920
ttttccatcg aaatatatga atttagtata tatatttctg caatgtacta ttttgctatt    19980
ttggcaactt tcagtggact actactttat tacaatgtgt atggatgcat gagtttgagt    20040
```

```
atacacatgt ctaaatgcat gctttgcaaa acgtaacgga ccacaaaaga ggatccatgc    20100
aaatacatct catagcttcc tccattattt tccgacacaa acagagcaga ctctagagga    20160 tcccccccgtt ttacaacaat taccaacaac aacaaacaac aaacaacatt acaattacat    20220
ttacaattac catcccaaat cggcgcgcca tgtgtcctcc taagaccgat ggaagatctt    20280
ctcctagatc tcctctcacc aggtctaagt catctgctga ggctcttgat gctaaggatg    20340
cttctaccgc tcctgttgat cttaagaccc ttgagcctca tgaacttgct gctaccttcg    20400
agactagatg ggttagggtt gaggatgttg agtacgacgt gaccaacttc aaacatcctg    20460
gtggaagcgt gatcttctac atgcttgcta acactggtgc tgatgctact gaggctttca    20520
aagaatttca catgcgtagc ctcaaggctt ggaagatgct tagagctttg ccttctagac    20580
ctgctgagat caagagatct gagtctgagg atgctcctat gcttgaggat ttcgctaggt    20640
ggagagctga acttgagagg gacggattct tcaagccttc tatcacccat gttgcttacc    20700
gtcttttgga gcttcttgct actttcgctc ttggaaccgc tcttatgtac gctggatacc    20760
ctatcattgc tagcgttgtg tacgtgcttt tcttcggagc tagatgtgga tgggttcaac    20820
atgagggtgg acacaactct cttaccggat ctgtgtacgt ggataagaga cttcaggcta    20880
tgacttgcgg attcggactt tctaccagcg gagagatgtg gaaccagatg cataacaagc    20940
accatgctac ccctcagaaa gttagacacg acatggatct tgataccact cctgctgtgg    21000 cttttcttcaa caccgctgtg gaggataata gacctagggg attctctaga gcttgggcta    21060
gacttcaagc ttggaccttc gttcctgtta cttctggact tctcgttcag gctttctgga    21120
tctacgttct ccatcctaga caggtgctca ggaagaagaa ctacgaggaa gcttcttgga    21180
tgctcgtttc tcacgttgtt agaaccgctg ttatcaagct tgctaccgga tactcttggc    21240
ctgttgctta ctggtggttc actttcggaa actggatcgc ttcatgtac ctcttcgctc    21300 acttctctac ttctcacact cacctccctg ttgttccatc tgacaagcac cttagctggg    21360
ttaactacgc tgttgatcac accgttgaca tcgatccttc tcgtggatac gttaactggc    21420
ttatgggata ccttaactgc caggttatcc accatctctt ccctgatatg cctcaattca    21480
gacagcctga ggtgtcaaga agattcgtcc ctttcgctaa gaagtgggga ctcaactaca    21540
aggtgctctc ttactacggt gcttggaagg ctactttcag caacctcgac aaagttggac    21600
agcactacta cgttaacgga aaggctgaga aggctcactg atgattaatt aaatttgggc    21660
tcgaaccggt tcgagcaagc ttatgtgacg tgaaataata acggtaaaat atatgtaata    21720
ataataataa taaagccaca aagtgagaat gaggggaagg ggaaatgtgt aatgagccag    21780
tagccggtgg tgctaatttt gtatcgtatt gtcaataaat catgaatttt gtggttttta    21840
tgtgtttttt taaatcatga attttaaatt ttataaaata atctccaatc ggaagaacaa    21900
cattccatat ccatgcatgg atgtttcttt acccaaatct agttcttgag aggatgaagc    21960
atcaccgaac agttctgcaa ctatccctca aaagctttaa aatgaacaac aaggaacaga    22020
gcaacgttcc aaagatccca aacgaaacat attatctata ctaatactat attattaatt    22080
actactgccc ggaatcacaa tccctgaatg attcctatta actacaagcc ttgttggcgg    22140
cggagaagtg atcggcgcgg cgagaagcag cggactcgga gacgaggcct tggaagatct    22200
cctgcagggc ggccgcggat cccatggagt caaagattca aatagaggac ctaacagaac    22260
tcgccgtaaa gactggcgaa cagttctatc agagtctctt acgactcaat gacaagaaga    22320
aaatcttcgt caacatggtg gagcacgaca cacttgtcta ctccaaaaat atcaaagata    22380
cagtctcaga agaccaaagg gcaattgaga cttttcaaca aagggtaata tccggaaacc    22440
```

```
tcctcggatt ccattgccca gctatctgtc actttattgt gaagatagtg gaaaaggaag    22500
gtggctccta caaatgccat cattgcgata aaggaaaggc catcgttgaa gatgcctctg    22560
ccgacagtgg tcccaaagat ggaccccccac ccacgaggag catcgtggaa aagaagacg    22620 ttccaaccac gtcttcaaag caagtggatt gatgtgatat ctccactgac gtaagggatg    22680
acgcacaatc ccactatcct tcgcaagacc cttcctctat ataaggaagt tcatttcatt    22740
tggagagaac acgggggact gaattaaata tgagccctga gaggcgtcct gttgaaatca    22800
gacctgctac tgctgctgat atggctgctg tttgtgatat cgtgaaccac tacatcgaga    22860
cttctaccgt taacttcaga actgagcctc aaactcctca agagtggatc gatgatcttg    22920
agagactcca agatagatac ccttggcttg ttgctgaggt tgagggtgtt gttgctggaa    22980
tcgcttacgc tggaccttgg aaggctagaa acgcttacga ttggactgtt gagtctaccg    23040
tttacgtttc acacagacat cagagacttg gacttggatc tacccttta c actcaccttc    23100 tcaagtctat ggaagctcag ggattcaagt ctgttgttgc tgttatcgga ctccctaacg    23160
atccttctgt tagacttcat gaggctcttg gatacactgc tagaggaact cttagagctg    23220
ctggatacaa gcacggtgga tggcatgatg ttggattctg gcaaagagat ttcgagcttc    23280
ctgctcctcc tagacctgtt agaccagtta ctcagatctg aatttgcgtg atcgttcaaa    23340
catttggcaa taaagtttct taagattgaa tcctgttgcc ggtcttgcga tgattatcat    23400
ataatttctg ttgaattacg ttaagcatgt aataattaac atgtaatgca tgacgttatt    23460
tatgagatgg ttttttatga ttagagtccc gcaattatac atttaatacg cgatagaaaa    23520
caaaatatag cgcgcaaact aggataaatt atcgcgcgcg gtgtcatcta tgttactaga    23580
tcactagtga tgtacggtta aaaccacccc agtacattaa aaacgtccgc aatgtgttat    23640
taagttgtct aagcgtcaat ttgtttacac cacaatatat cctgccacca gccagccaac    23700
agctccccga ccggcagctc ggcacaaaat caccactcga tacaggcagc ccatcagtcc    23760
```

<210> SEQ ID NO 8
<211> LENGTH: 11042
<212> TYPE: DNA
<213> ORGANISM: Artificial Sequence
<220> FEATURE:
<223> OTHER INFORMATION: pORE04+11ABGBEC_Cowpea_EPA_insert nucleotide sequence

<400> SEQUENCE: 8

```
tcctgtggtt ggcatgcaca tacaaatgga cgaacggata aacctttca cgcccttta      60 aatatccgat tattctaata aacgctcttt tctcttaggt ttacccgcca atatatcctg    120
tcaaacactg atagtttaaa ctgaaggcgg gaaacgacaa tctgctagtg gatctcccag    180
tcacgacgtt gtaaaacggg cgccctagaa tctaattatt ctattcagac taaattagta    240
taagtatttt tttaatcaat aaataataat taataattta ttagtaggag tgattgaatt    300
tataatatat ttttttttaat catttaaaga atcttatatc tttaaattga caagagtttt    360
aaatggggag agtgttatca tatcacaagt aggattaatg tgttatagtt tcacatgcat    420
tacgataagt tgtgaaagat aacattatta tatataacaa tgacaatcac tagcgatcga    480
gtagtgagag tcgtcttatt acactttctt ccttcgatct gtcacatggc ggcggcccga    540
attctcatca cttagaagcg tggtgcttca tgtagtagaa gtttccgaaa agcatgagaa    600
gagtcaccat gtacaccacg aggagctgag cgataaactt agggtaaggt gaagaagagt    660
agaggaggta cacagcctgg agaaggttca tgaagaactg gaacatttgc atctgggtga    720
```

```
ggtatcttcc ccaccagagg tactttctct tagttttctc atccttaggg agcacagcag    780
ccataaagta gtaggtgtac atgcacacgt gcacccaaga gttgagagca gcagagaaat    840
aagcatcacc acctggagca gcgtaggtga tcatccacca gattccagag atagatccgt    900
gatggtacac gtggaggaat gacacctggt tcacatttcc cttgaggagc atgatgaagg    960
tatccatgaa ctcgtagatc tttgacacgt agaaaatcca gatcaccttä gccatctcgg   1020 tctgagcagg gttgtaagcg tttccccaga aagagtactt gttcacgtaa gcctcgtaca   1080
cgagcttgag gcacatgtag agtgagagtc cgatgaggaa cacgttatga gcgagcatga   1140
gagccttgag caagaatgga tcctgtccct tcacagttct agggaacacc tttctgtaca   1200
cgagtccaga tcccacgata gcgaagtaag cgaggagaga caagataaga ggggtaggag   1260
attccacgag agggagatcc ttagtagcag aagagatagg cttgagtccc catccgatag   1320
aatcggtagc agagaagata gcaggagcca caacagcatc gatagcagcg tattgttctt   1380
gagccatagc cacgagaggc tgagcaaatt ccatgaattc tgttcttctt tactctttgt   1440
gtgactgagg tttggtctag tgctttggtc atctatatat aatgataaca acaatgagaa   1500
caagctttgg agtgatcgga gggtctagga tacatgagat tcaagtggac taggatctac   1560
accgttggat tttgagtgtg gatatgtgtg aggttaattt tacttggtaa cggccacaaa   1620
ggcctaagga gaggtgttga gacccttatc ggcttgaacc gctggaataa tgccacgtgg   1680
aagataattc catgaatctt atcgttatct atgagtgaaa ttgtgtgatg gtggagtggt   1740
gcttgctcat tttacttgcc tggtggactt ggccctttcc ttatggggaa tttatatttt   1800
acttactata gagctttcat acctttttt taccttggat ttagttaata tataatggta   1860
tgattcatga ataaaaatgg gaaatttttg aatttgtact gctaaatgca taagattagg   1920
tgaaactgtg gaatatatat ttttttcatt taaaagcaaa atttgccttt tactagaatt   1980
ataaatatag aaaatatat aacattcaaa taaaaatgaa ataagaact ttcaaaaaac   2040 agaactatgt ttaatgtgta aagattagtc gcacatcaag tcatctgtta caatatgtta   2100
caacaagtca taagcccaac aaagttagca cgtctaaata aactaaagag tccacgaaaa   2160
tattacaaat cataagccca acaaagttat tgatcaaaaa aaaaaaacgc ccaacaaagc   2220
taaacaaagt ccaaaaaaaa cttctcaagt ctccatcttc ctttatgaac attgaaaact   2280
atacacaaaa caagtcagat aaatctcttt ctgggcctgt cttcccaacc tcctacatca   2340
cttccctatc ggattgaatg ttttacttgt accttttccg ttgcaatgat attgatagta   2400
tgtttgtgaa aactaatagg gttaacaatc gaagtcatgg aatatggatt tggtccaaga   2460
ttttccgaga gctttctagt agaaagccca tcaccagaaa tttactagta aaataaatca   2520
ccaattaggt ttcttattat gtgccaaatt caatataatt atagaggata tttcaaatga   2580
aaacgtatga atgttattag taaatggtca ggtaagacat taaaaaaatc ctacgtcaga   2640
tattcaactt taaaaattcg atcagtgtgg aattgtacaa aaatttggga tctactatat   2700
atatataatg ctttacaaca cttggatttt ttttggagg ctggaatttt taatctacat   2760
atttgttttg gccatgcacc aactcattgt ttagtgtaat actttgattt tgtcaaatat   2820
atgtgttcgt gtatatttgt ataagaattt ctttgaccat atacacacac acatatatat   2880
atatatatat atattatata tcatgcactt ttaattgaaa aaataatata tatatatata   2940
gtgcattttt tctaacaacc atatatgttg cgattgatct gcaaaatac tgctagagta   3000 atgaaaaata taatctattg ctgaaattat ctcagatgtt aagattttct taaagtaaat   3060
```

```
tctttcaaat tttagctaaa agtcttgtaa taactaaaga ataatacaca atctcgacca    3120
cggaaaaaaa acacataata aatttggggc ccctagaatc taattattct attcagacta    3180
aattagtata agtattttt taatcaataa ataataatta ataatttatt agtaggagtg     3240
attgaattta taatatattt tttttaatca tttaaagaat cttatatctt taaattgaca    3300
agagttttaa atggggagag tgttatcata tcacaagtag gattaatgtg ttatagtttc    3360
acatgcatta cgataagttg tgaaagataa cattattata tataacaatg acaatcacta   3420
gcgatcgagt agtgagagtc gtcttattac actttcttcc ttcgatctgt cacatggcgg    3480
cggcccgcgg ccgctcatca gtgagccttc tcagcctttc cgttcacgta gtagtgctgt    3540
cccaccttat cgaggtttga gaaggtagcc ttccaagcac cgtagtaaga gagcaccttg    3600
tagttgagtc cccacttctt agcgaaagga acgaatcttc ttgacacctc aggctgtctg    3660
aactgtggca tatctgggaa gaggtgatgg atcacctggc agttgaggta tcccatgagc    3720
cagttcacgt aaccctaga aggatcgata tccacggtgt gatccacagc gtagttcacc     3780
caagaaaggt gcttatcaga tggcaccact gggagatggg tatgagaggt agagaagtga    3840
gcgaagaggt acatgtaagc gatccagttt ccgaaggtga accaccaata agcaacaggc    3900
caagagtatc cggtagcgag cttgataaca gcggttctca caacgtgaga cacgagcatc    3960
caagaagcct cttcgtagtt cttctttctg agcacctgtc taggatggag aacgtagatc    4020
cagaaagcct gcacgagaag tccagaagtc acaggaacga aagtccaagc ctgaagtcta    4080
gcccaagctc tagaaaatcc cctaggcctg ttatcctcaa cagcggtgtt gaagaaagcc    4140
acagcaggag tggtatcgag atccatatca tgcctcacct tttgtggggt tgcgtggtgc    4200
ttgttgtgca tctggttcca catctcacca gaggtagaaa gtccgaatcc gcaagtcata    4260
gcctggagcc tcttatccac atacacagat ccggtgagag agttatgacc accctcgtgt    4320
tgaacccatc cacatctagc tccgaagaaa gcaccgtaca ccacagaagc gataataggg    4380
tatccagcat acatgagagc agttccgaga gcgaaagtag caagaagctc gagaagtctg    4440
tatgccacgt gggtgataga aggcttgaag aatccatccc tctcaagctc agctctccac    4500
ctagcgaaat cttcgagcat aggagcatcc tcagactcag acctcttgat ctcagctggt    4560
ctagaaggca aagccctaag catcttccaa gccttgagag atctcatgtg aaattctttg    4620
aaagcctcag tagcatcagc accggtgtta gcgagcatgt agaagatcac agaaccacca    4680
gggtgcttga agttagtaac atcgtactca acatcctcaa ctctcaccca tctagtctcg    4740
aaggtagcag ccaactcatg aggctcaaga gtccttgagat ccacaggagc agtagaagca   4800
tccttagcat cgagagcctc agcagatgac ttagacctgg taagaggtga cctaggagaa    4860
gatcttccat cagtctttgg agggcacatg cggccgctgt tcttctttac tctttgtgtg    4920
actgaggttt ggtctagtgc tttggtcatc tatatataat gataacaaca atgagaacaa    4980
gctttggagt gatcggaggg tctaggatac atgagattca agtggactag gatctacacc    5040
gttggatttt gagtgtggat atgtgtgagg ttaattttac ttggtaacgg ccacaaaggc    5100
ctaaggagag gtgttgagac ccttatcggc ttgaaccgct ggaataatgc cacgtggaag    5160
ataattccat gaatcttatc gttatctatg agtgaaattg tgtgatggtg gagtggtgct    5220
tgctcatttt acttgcctgg tggacttggc cctttcctta tggggaattt atattttact    5280
tactatagag ctttcatacc ttttttttac cttggattta gttaatatat aatggtatga    5340
ttcatgaata aaaatgggaa attttgaat ttgtactgct aaatgcataa gattaggtga     5400
aactgtggaa tatatatttt tttcattaaa aagcaaaatt tgccttttac tagaattata    5460
```

```
aatatagaaa aatatataac attcaaataa aaatgaaaat aagaactttc aaaaaacaga   5520
actatgttta atgtgtaaag attagtcgca catcaagtca tctgttacaa tatgttacaa   5580
caagtcataa gcccaacaaa gttagcacgt ctaaataaac taaagagtcc acgaaaatat   5640
tacaaatcat aagcccaaca aagttattga tcaaaaaaaa aaaacgccca acaaagctaa   5700
acaaagtcca aaaaaaactt ctcaagtctc catcttcctt tatgaacatt gaaaactata   5760
cacaaaacaa gtcagataaa tctctttctg ggcctgtctt cccaacctcc tacatcactt   5820
ccctatcgga ttgaatgttt tacttgtacc ttttccgttg caatgatatt gatagtatgt   5880
ttgtgaaaac taatagggtt aacaatcgaa gtcatgaaat atggatttgg tccaagattt   5940
tccgagagct ttctagtaga aagcccatca ccagaaattt actagtaaaa taaatcacca   6000
attaggtttc ttattatgtg ccaaattcaa tataattata gaggatattt caaatgaaaa   6060
cgtatgaatg ttattagtaa atggtcaggt aagacattaa aaaaatccta cgtcagatat   6120
tcaactttaa aaattcgatc agtgtggaat tgtacaaaaa tttgggatct actatatata   6180
tataatgctt tacaacactt ggattttttt ttggaggctg aattttttaa tctacatatt   6240
tgttttggcc atgcaccaac tcattgttta gtgtaatact ttgattttgt caaatatatg   6300
tgttcgtgta tatttgtata agaatttctt tgaccatata cacacacaca tatatatata   6360
tatatatata ttatatatca tgcacttttta attgaaaaaa taatatatat atatatagtg   6420 catttttct aacaaccata tatgttgcga ttgatctgca aaaatactgc tagagtaatg   6480
aaaaatataa tctattgctg aaattatctc agatgttaag attttcttaa agtaaattct   6540
ttcaaatttt agctaaaagt cttgtaataa ctaaagaata atacacaatc tcgaccacgg   6600
aaaaaaaaca cataataaat ttgggcgcgc cgcgtattgg ctagagcagc ttgccaacat   6660
ggtggagcac gacactctcg tctactccaa gaatatcaaa gatacagtct cagaagacca   6720
aagggctatt gagacttttc aacaaagggt aatatcggga aacctcctcg gattccattg   6780
cccagctatc tgtcacttca tcaaaaggac agtagaaaag gaaggtggca cctacaaatg   6840
ccatcattgc gataaaggaa aggctatcgt tcaagatgcc tctgccgaca gtggtcccaa   6900
agatggaccc ccacccacga ggagcatcgt ggaaaaagaa gacgttccaa ccacgtcttc   6960
aaagcaagtg gattgatgtg ataacatggt ggagcacgac actctcgtct actccaagaa   7020
tatcaaagat acagtctcag aagaccaaag ggctattgag acttttcaac aaagggtaat   7080
atcgggaaac ctcctcggat tccattgccc agctatctgt cacttcatca aaaggacagt   7140
agaaaaggaa ggtggcacct acaaatgcca tcattgcgat aaaggaaagg ctatcgttca   7200
agatgcctct gccgacagtg gtcccaaaga tggaccccca cccacgagga gcatcgtgga   7260
aaaagaagac gttccaacca cgtcttcaaa gcaagtggat tgatgtgata tctccactga   7320
cgtaagggat gacgcacaat cccactatcc ttcgcaagac cttcctctat ataaggaagt   7380
tcatttcatt tggagaggac acgctgaaat caccagtctc tctctacaaa tctatctctg   7440
cgatcgcatg cctcctaggg attcttactc ttacgctgct cctccatctg ctcagctcca   7500
tgaagttgat actcctcaag agcacgataa gaaagaactc gtgatcggag atagggctta   7560
cgatgtgacc aacttcgtga agagacaccc tggtggaaag attatcgctt accaggttgg   7620
aactgatgct accgatgctt acaagcagtt ccacgtgaga tctgctaagg ctgataagat   7680
gctcaagtct ctcccatcta ggcctgtgca aagggatat tctccaagaa gggctgatct   7740
tatcgctgat ttccaagagt tcaccaagca gcttgaggct gagggaatgt tcgaaccttc   7800
```

```
tctccctcat gtggcttaca gactcgctga ggttatcgct atgcatgttg ctggtgctgc    7860
tctcatctgg cacgatata ctttcgctgg aatcgctatg ctcggagtgg ttcagggaag     7920
atgtggatgg cttatgcatg agggtggaca ctactctctc accggaaaca ttgctttcga    7980
tagggctatc caggtggcat gctatggact tggatgtgga atgtctggtg cttggtggag    8040
aaaccagcat aacaagcacc atgctacccc tcaaaagctc cagcatgatg tggatctcga    8100
tactctccct ctcgtggctt tccatgagag aatcgctgct aaggtgaagt ctcctgctat    8160
gaaggcttgg ctctctatgc aggctaagct tttcgctcct gtgactactc ttctcgttgc    8220
tcttggatgg cagctctacc tccatcctag acacatgctc aggaccaagc actacgatga    8280
gcttgctatg ctcggtatca gatacggact cgttggatac ctcgctgcta attacggtgc    8340
tggatacgtt ctcgcttgct accttcttta cgttcagctc ggagctatgt acatcttctg    8400
caacttcgct gtgtctcaca ctcatctccc tgtggttgaa cctaacgagc atgctacttg    8460
ggttgagtac gctgctaacc acactaccaa ctgctctcca tcttggtggt gtgattggtg    8520
gatgtcttac ctcaactacc agatcgagca ccacctctac ccttctatgc ctcagttcag    8580
acaccctaag atcgctccta gagtgaagca gcttttcgag aagcacggac tccactacga    8640
tgtgagagga tactttgagg ctatggctga taccttcgct aacctcgata atgtggctca    8700
cgctcctgag aagaaaatgc agtgatgagc gatcgcgatc gttcaaacat ttggcaataa    8760
agtttcttaa gattgaatcc tgttgccggt cttgcgatga ttatcatata atttctgttg    8820
aattacgtta agcatgtaat aattaacatg taatgcatga cgttatttat gagatgggtt    8880
tttatgatta gagtcccgca attatacatt taatacgcga tagaaaacaa aatatagcgc    8940
gcaaactagg ataaattatc gcgcgcggtg tcatctatgt tactagatcc ctgcagggcg    9000
tattggctag agcagcttgc caacatggtg gagcacgaca ctctcgtcta ctccaagaat    9060
atcaaagata cagtctcaga agaccaaagg gctattgaga cttttcaaca aagggtaata    9120
tcgggaaacc tcctcggatt ccattgccca gctatctgtc acttcatcaa aggacagta    9180
gaaaaggaag gtggcaccta caaatgccat cattgcgata aaggaaaggc tatcgttcaa    9240
gatgcctctg ccgacagtgg tcccaaagat ggaccccac ccacgaggag catcgtggaa     9300
aaagaagacg ttccaaccac gtcttcaaag caagtggatt gatgtgataa catggtggag    9360
cacgacactc tcgtctactc caagaatatc aaagatacag tctcagaaga ccaagggct    9420
attgagactt tcaacaaag ggtaatatcg ggaaacctcc tcggattcca ttgcccagct    9480
atctgtcact tcatcaaaag acagtagaa aaggaaggtg gcacctacaa atgccatcat    9540
tgcgataaag gaaaggctat cgttcaagat gcctctgccg acagtggtcc caaagatgga    9600
cccccaccca cgaggagcat cgtggaaaaa gaagacgttc caaccacgtc ttcaaagcaa    9660
gtggattgat gtgatatctc cactgacgta agggatgacg cacaatccca ctatccttcg    9720
caagacctc ctctatataa ggaagttcat ttcatttgga gaggacacgc tgaaatcacc     9780
agtctctctc tacaaatcta tctctctcga gatgattgaa caagatggat tgcacgcagg    9840
ttctccggcc gcttgggtgg agaggctatt cggctatgac tgggcacaac agacaatcgg    9900
ctgctctgat gccgccgtgt tccggctgtc agcgcagggg aggccggttc ttttgtcaa    9960
gaccgacctg tccggtgccc tgaatgaact tcaagacgag gcagcgcggc tatcgtggct    10020
ggccacgacg ggcgttcctt gcgcagctgt gctcgacgtt gtcactgaag cgggaaggga    10080
ctggctgcta ttgggcgaag tgccggggca ggatctcctg tcatctcacc ttgctcctgc    10140
cgagaaagta tccatcatgg ctgatgcaat gcggcggctg catacgcttg atccggctac    10200
```

```
ctgcccattc gaccaccaag cgaaacatcg catcgagcga gcacgtactc ggatggaagc    10260
cggtcttgtc gatcaggatg atctggacga agagcatcag gggctcgcgc cagccgaact    10320
gttcgccagg ctcaaggcgc gcatgcccga cggcgaggat ctcgtcgtga ctcatggcga    10380
tgcctgcttg ccgaatatca tggtggaaaa tggccgcttt tctggattca tcgactgtgg    10440
ccggctgggt gtggcggacc gctatcagga catagcgttg gctacccgtg atattgctga    10500
agagcttggc ggcgaatggg ctgaccgctt cctcgtgctt tacggtatcg ccgctcccga    10560
ttcgcagcgc atcgccttct atcgccttct tgacgagttc ttctgaaacg cgtgatcgtt    10620
caaacatttg gcaataaagt ttcttaagat tgaatcctgt tgccggtctt gcgatgatta    10680
tcatataatt tctgttgaat tacgttaagc atgtaataat taacatgtaa tgcatgacgt    10740
tatttatgag atgggttttt atgattagag tcccgcaatt atacatttaa tacgcgatag    10800
aaaacaaaat atagcgcgca aactaggata aattatcgcg cgcggtgtca tctatgttac    10860
tagatcgacg tccgtacggt taaaaccacc ccagtacatt aaaaacgtcc gcaatgtgtt    10920
attaagttgt ctaagcgtca atttgtttac accacaatat atcctgccac cagccagcca    10980
acagctcccc gaccggcagc tcggcacaaa atcaccactc gatacaggca gcccatcagt    11040
cc                                                                   11042

<210> SEQ ID NO 9
<211> LENGTH: 1254
<212> TYPE: DNA
<213> ORGANISM: Artificial Sequence
<220> FEATURE:
<223> OTHER INFORMATION: Codon-optimized open reading frame for
      expression of Lachancea kluyveri 12 desaturase in plants

<400> SEQUENCE: 9
atgagcgctg ttaccgttac tggatctgat cctaagaaca gaggatcttc tagcaacacc      60
gagcaagagg ttccaaaagt tgctatcgat accaacggaa acgtgttctc tgttcctgat     120
ttcaccatca aggacatcct tggagctatc cctcatgagt gttacgagag aagattggct     180
acctctctct actacgtgtt cagagatatc ttctgcatgc ttaccaccgg ataccttacc     240
cataagatcc tttacccctc tcctcatctc tacacctcta acagcatcat caagttcact     300
ttctgggccc tttacactta cgttcaagga cttttcggaa ccggaatctg ggttctcgct     360
catgagtgtg gacatcaagc tttctctgat tacggaatcg tgaacgattt cgttggatgg     420
acccttcact cttaccttat ggttccttac ttcagctgga gtactctca tggaaagcac     480 cataaggcta ctggacacat gaccagagat atggtttttcg ttcctgccac caagaggaa     540 ttcaagaagt ctaggaactt cttcggtaac ctcgctgagt actctgagga ttctccactt     600
agaacccttt acgagcttct tgttcaacaa cttggaggat ggatcgctta cctcttcgtt     660
aacgttacag gacaacctta ccctgatgtt ccttcttgga atggaaccca cttctggctt     720
acctctccac ttttcgagca aagagatgct ctctacatct cctttctga tcttggaatc     780 ctcacccagg gaatcgttct tactctttgg tacaagaaat cggaggatg gtcccttttc     840 atcaactggt tcgttcctta catctgggtt aaccactggc tcgttttcat cacattcctt     900
cagcacactg atcctactat gcctcattac aacgctgagg aatggacttt cgctaagggt     960
gctgctgcta ctatcgatag aaagttcgga ttcatcggac tcacatctt ccatgatatc    1020 atcgagactc atgtgcttca ccactactgt tctaggatcc cattctacaa cgctagacct    1080
gcttctgagg ctatcaagaa agttatggga aagcactaca ggtctagcga cgagaacatg    1140
```

```
tggaagtcac tttggaagtc tttcaggtct tgccaatacg ttgacggtga taacggtgtt    1200
ctcatgttcc gtaacatcaa caactgcgga gttggagctg ctgagaagta atga          1254
```

<210> SEQ ID NO 10
<211> LENGTH: 416
<212> TYPE: PRT
<213> ORGANISM: Lachancea kluyveri

<400> SEQUENCE: 10

```
Met Ser Ala Val Thr Val Thr Gly Ser Asp Pro Lys Asn Arg Gly Ser
1               5                   10                  15

Ser Ser Asn Thr Glu Gln Glu Val Pro Lys Val Ala Ile Asp Thr Asn
            20                  25                  30

Gly Asn Val Phe Ser Val Pro Asp Phe Thr Ile Lys Asp Ile Leu Gly
        35                  40                  45

Ala Ile Pro His Glu Cys Tyr Glu Arg Arg Leu Ala Thr Ser Leu Tyr
    50                  55                  60

Tyr Val Phe Arg Asp Ile Phe Cys Met Leu Thr Thr Gly Tyr Leu Thr
65                  70                  75                  80

His Lys Ile Leu Tyr Pro Leu Leu Ile Ser Tyr Thr Ser Asn Ser Ile
                85                  90                  95

Ile Lys Phe Thr Phe Trp Ala Leu Tyr Thr Tyr Val Gln Gly Leu Phe
            100                 105                 110

Gly Thr Gly Ile Trp Val Leu Ala His Glu Cys Gly His Gln Ala Phe
        115                 120                 125

Ser Asp Tyr Gly Ile Val Asn Asp Phe Val Gly Trp Thr Leu His Ser
    130                 135                 140

Tyr Leu Met Val Pro Tyr Phe Ser Trp Lys Tyr Ser His Gly Lys His
145                 150                 155                 160

His Lys Ala Thr Gly His Met Thr Arg Asp Met Val Phe Val Pro Ala
                165                 170                 175

Thr Lys Glu Glu Phe Lys Lys Ser Arg Asn Phe Phe Gly Asn Leu Ala
            180                 185                 190

Glu Tyr Ser Glu Asp Ser Pro Leu Arg Thr Leu Tyr Glu Leu Leu Val
        195                 200                 205

Gln Gln Leu Gly Gly Trp Ile Ala Tyr Leu Phe Val Asn Val Thr Gly
    210                 215                 220

Gln Pro Tyr Pro Asp Val Pro Ser Trp Lys Trp Asn His Phe Trp Leu
225                 230                 235                 240

Thr Ser Pro Leu Phe Glu Gln Arg Asp Ala Leu Tyr Ile Phe Leu Ser
                245                 250                 255

Asp Leu Gly Ile Leu Thr Gln Gly Ile Val Leu Thr Leu Trp Tyr Lys
            260                 265                 270

Lys Phe Gly Gly Trp Ser Leu Phe Ile Asn Trp Phe Val Pro Tyr Ile
        275                 280                 285

Trp Val Asn His Trp Leu Val Phe Ile Thr Phe Leu Gln His Thr Asp
    290                 295                 300

Pro Thr Met Pro His Tyr Asn Ala Glu Glu Trp Thr Phe Ala Lys Gly
305                 310                 315                 320

Ala Ala Ala Thr Ile Asp Arg Lys Phe Gly Phe Ile Gly Pro His Ile
                325                 330                 335

Phe His Asp Ile Ile Glu Thr His Val Leu His His Tyr Cys Ser Arg
            340                 345                 350
```

```
Ile Pro Phe Tyr Asn Ala Arg Pro Ala Ser Glu Ala Ile Lys Lys Val
            355                 360                 365

Met Gly Lys His Tyr Arg Ser Ser Asp Glu Asn Met Trp Lys Ser Leu
    370                 375                 380

Trp Lys Ser Phe Arg Ser Cys Gln Tyr Val Asp Gly Asp Asn Gly Val
385                 390                 395                 400

Leu Met Phe Arg Asn Ile Asn Asn Cys Gly Val Gly Ala Ala Glu Lys
                405                 410                 415

<210> SEQ ID NO 11
<211> LENGTH: 1251
<212> TYPE: DNA
<213> ORGANISM: Pichia pastoris

<400> SEQUENCE: 11
atgtctaagg ttaccgtgtc tggatctgag atccttgagg gatctactaa gaccgttagg      60
cgttctggaa acgttgcatc tttcaagcag caaaagaccg ctatcgatac cttcggaaac     120
gttttcaagg tgccagatta caccatcaag gatatccttg acgctatccc taagcactgt     180
tacgagagat ctctcgtgaa gtctatgtct acgtggtga gagatatcgt ggctatctct      240
gctatcgctt acgttggact tacctacatc cctcttctcc taacgaatt ccttagattc      300 gctgcttggt ctgcttacgt gttctctatc tcttgtttcg gattcggaat ctggatcctt     360
ggacatgagt gtggacattc tgctttctct aactacggat gggttaacga taccgttgga    420
tgggttctcc actctcttgt tatggttcct tacttcagct ggaagttctc tcatgctaag     480
caccataagg ctactggaca catgaccaga gatatggttt cgttcctta caccgccgag     540 gaattcaaag agaagcacca agttaccagc cttcacgata tcgctgagga aactcctatc     600
tactctgttt cgctctctt gttccaacag cttggaggac tttctcttta ccttgctact      660
aacgctactg acaaccttta ccctggtgtt tctaagttct tcaagtctca ctactggcct     720
tctagccctg ttttcgataa gaaggactac tggtacatcg ttctttctga tcttggaatc     780
cttgctaccc tcacttctgt ttacaccgct tacaaggttt tcggattctg gcctactttc     840
atcacatggt tctgtccttg gatccttgtt aaccactggc ttgttttcgt taccttcctt     900
cagcacaccg attcttctat gcctcattac gatgctcaag agtggacttt cgctaagggt    960
gctgctgcta ctatcgatag agagttcgga atcctcggaa tcatcttcca tgacatcatc    1020
gagactcatg tgctccatca ctacgtttca aggatcccat tctaccatgc tagagaagct    1080
accgagtgca tcaagaaagt tatgggagag cactacagac acaccgatga gaacatgtgg    1140
gttagccttt ggaaaacttg gagatcttgc cagttcgttg agaaccatga tggtgtgtac    1200
atgttccgta actgcaacaa cgttggagtg aagcctaagg atacctgatg a              1251

<210> SEQ ID NO 12
<211> LENGTH: 415
<212> TYPE: PRT
<213> ORGANISM: Pichia pastoris

<400> SEQUENCE: 12

Met Ser Lys Val Thr Val Ser Gly Ser Glu Ile Leu Glu Gly Ser Thr
1               5                   10                  15

Lys Thr Val Arg Arg Ser Gly Asn Val Ala Ser Phe Lys Gln Gln Lys
                20                  25                  30

Thr Ala Ile Asp Thr Phe Gly Asn Val Phe Lys Val Pro Asp Tyr Thr
            35                  40                  45
```

```
Ile Lys Asp Ile Leu Asp Ala Ile Pro Lys His Cys Tyr Glu Arg Ser
 50                  55                  60
Leu Val Lys Ser Met Ser Tyr Val Val Arg Asp Ile Val Ala Ile Ser
 65                  70                  75                  80
Ala Ile Ala Tyr Val Gly Leu Thr Tyr Ile Pro Leu Leu Pro Asn Glu
                 85                  90                  95
Phe Leu Arg Phe Ala Ala Trp Ser Ala Tyr Val Phe Ser Ile Ser Cys
            100                 105                 110
Phe Gly Phe Gly Ile Trp Ile Leu Gly His Glu Cys Gly His Ser Ala
            115                 120                 125
Phe Ser Asn Tyr Gly Trp Val Asn Asp Thr Val Gly Trp Val Leu His
130                 135                 140
Ser Leu Val Met Val Pro Tyr Phe Ser Trp Lys Phe Ser His Ala Lys
145                 150                 155                 160
His His Lys Ala Thr Gly His Met Thr Arg Asp Met Val Phe Val Pro
                165                 170                 175
Tyr Thr Ala Glu Glu Phe Lys Glu Lys His Gln Val Ser Leu His
            180                 185                 190
Asp Ile Ala Glu Glu Thr Pro Ile Tyr Ser Val Phe Ala Leu Leu Phe
            195                 200                 205
Gln Gln Leu Gly Gly Leu Ser Leu Tyr Leu Ala Thr Asn Ala Thr Gly
210                 215                 220
Gln Pro Tyr Pro Gly Val Ser Lys Phe Phe Lys Ser His Tyr Trp Pro
225                 230                 235                 240
Ser Ser Pro Val Phe Asp Lys Lys Asp Tyr Trp Tyr Ile Val Leu Ser
                245                 250                 255
Asp Leu Gly Ile Leu Ala Thr Leu Thr Ser Val Tyr Thr Ala Tyr Lys
            260                 265                 270
Val Phe Gly Phe Trp Pro Thr Phe Ile Thr Trp Phe Cys Pro Trp Ile
            275                 280                 285
Leu Val Asn His Trp Leu Val Phe Val Thr Phe Leu Gln His Thr Asp
290                 295                 300
Ser Ser Met Pro His Tyr Asp Ala Gln Glu Trp Thr Phe Ala Lys Gly
305                 310                 315                 320
Ala Ala Ala Thr Ile Asp Arg Glu Phe Gly Ile Leu Gly Ile Ile Phe
                325                 330                 335
His Asp Ile Ile Glu Thr His Val Leu His His Tyr Val Ser Arg Ile
            340                 345                 350
Pro Phe Tyr His Ala Arg Glu Ala Thr Glu Cys Ile Lys Lys Val Met
            355                 360                 365
Gly Glu His Tyr Arg His Thr Asp Glu Asn Met Trp Val Ser Leu Trp
370                 375                 380
Lys Thr Trp Arg Ser Cys Gln Phe Val Glu Asn His Asp Gly Val Tyr
385                 390                 395                 400
Met Phe Arg Asn Cys Asn Asn Val Gly Val Lys Pro Lys Asp Thr
                405                 410                 415

<210> SEQ ID NO 13
<211> LENGTH: 1392
<212> TYPE: DNA
<213> ORGANISM: Micromonas pusilla

<400> SEQUENCE: 13
atgtgcccgc cgaagacgga cggccgatcg tccccgcgat cgccgctgac gcgcagcaaa      60
```

```
tcctccgcgg aggcgctcga cgccaaggac gcgtcgaccg cgcccgtcga tctcaaaacg    120
ctcgagccgc acgagctcgc ggcgacgttc gagacgcgat gggtgcgcgt ggaggacgtc    180
gagtacgacg tcacaaactt caaacacccg ggaggcagcg tgatattcta catgctcgcg    240
aacacgggcg cggacgccac ggaggcgttc aaggagttcc acatgcgatc gcttaaggcg    300
tggaagatgc tcagagcgct gccgtcgcgc cccgcggaga tcaaacgcag cgagagcgag    360
gacgcgccga tgttggagga tttcgcgcgg tggcgcgcgg agctcgaacg cgacgggttc    420
tttaagccct cgataacgca cgtcgcgtat cggttactcg agctcctcgc gaccttcgcc    480
ctcggcaccg ccctcatgta cgccgggtac ccgatcatcg cgtccgtcgt gtacggcgcg    540
ttcttcggcg ctcggtgcgg ttgggtccag cacgagggcg ggcacaactc gctcacgggg    600
tccgtctacg tcgacaagcg cctccaagcg atgacgtgcg ggttcgggct gtccacgagc    660
ggggagatgt ggaaccagat gcacaataag caccacgcga cgccgcagaa agtgaggcac    720
gacatggacc tggacacgac ccccgcggtg gcgttttta acaccgccgt ggaggacaac    780
cggccgaggg ggttctcccg cgcgtgggct cggcttcagg cgtggacgtt cgtcccggtg    840
acctccgggc tgctcgtcca ggcgttctgg atctacgtcc tgcacccgcg gcaggtgttg    900
cgaaagaaga actacgagga ggcgtcgtgg atgctcgtct ctcacgtcgt caggaccgcg    960
gtgattaaac tcgcgacggg gtactcgtgg cccgtcgcgt actggtggtt caccttcggc   1020
aactggatcg cgtacatgta cctcttcgcg cacttctcca cgagccacac gcacctcccg   1080
gtcgtgccct cggataagca cctgagctgg gtgaactacg cggtcgatca caccgtggac   1140
atcgacccgt cgcgcgggta cgtgaactgg ttgatgggat atctgaactg ccaggtcatt   1200
catcacctgt tcccggacat gccgcagttt cgccagccgg aggtgagccg gcggttcgtc   1260
ccgttcgcga agaagtgggg gctgaactac aaggtgctgt cctattacgg cgcctggaag   1320
gcgacgttct cgaacttgga taaggtcggg cagcactact acgtcaacgg caaggcggag   1380
aaggcgcact ga                                                       1392

<210> SEQ ID NO 14
<211> LENGTH: 1395
<212> TYPE: DNA
<213> ORGANISM: Artificial Sequence
<220> FEATURE:
<223> OTHER INFORMATION: Codon-optimized open reading frame for
      expression of Micromonas pusilla 6-desaturase in plants (version
      1)

<400> SEQUENCE: 14
atgtgccctc ctaagactga tggaagatct tctcctagat ctccacttac caggtctaaa     60
tcttctgctg aggctcttga tgctaaggat gcttctactg ctcctgttga tcttaagact    120
cttgagcctc atgagcttgc tgctactttc gagactagat gggttagagt tgaggacgtt    180
gagtacgatg tgactaactt caagcaccct ggtggatctg tgatcttcta catgcttgct    240
aacactggtg ctgatgctac tgaggctttc aaagaattcc acatgcgttc tctcaaggct    300
tggaagatgc ttagagcttt gccttctaga cctgctgaga tcaagagatc tgagtctgag    360
gatgctccta tgcttgagga tttcgctaga tggcgtgctg agcttgagag agatggattc    420
ttcaagcctt ctatcaccca tgtggcttac agacttctcg agcttcttgc tacattcgct    480
cttggaactg ctcttatgta cgctggatac cctatcattg cttctgttgt ttacggtgct    540
ttcttcggag ctagatgtgg atgggttcaa catgagggtg gacataactc tcttaccgga    600
tctgtttacg tggacaagag acttcaggct atgacttgtg gattcggact ttctacttct    660
```

```
ggtgagatgt ggaaccagat gcataacaag caccatgcta cccctcaaaa ggttagacac      720
gatatggatc ttgataccac tcctgctgtg gctttcttca acactgctgt tgaggataac      780
agacctagag gattctctag agcttgggct agacttcaag cttggacttt cgttcctgtt      840
acctctggac ttcttgttca agcttctggg atctacgttc tccaccctag acaagttctc      900
cgtaagaaga actacgaaga ggcttcttgg atgctcgttt ctcatgttgt tagaaccgct      960
gttatcaagc ttgctactgg atactcttgg cctgttgctt actggtggtt cactttcgga     1020
aactggatcg cttacatgta cctttcgct cacttctcta cttctcatac tcacctccct      1080
gttgttccat ctgataagca cctttcttgg gttaactacg ctgttgatca caccgttgat     1140
atcgatcctt ctagaggata cgtgaactgg cttatgggat accttaactg tcaggttatc     1200
caccacctct ccctgatat gcctcaattc agacagcctg aggttagcag aagattcgtt      1260
cctttcgcta agaagtgggg actcaactac aaggtgctct cttactacgg tgcttggaag     1320
gctactttct ctaaccttga taaggtggga cagcactact acgttaacgg aaaggctgag     1380
aaggctcact aatga                                                      1395
```

<210> SEQ ID NO 15
<211> LENGTH: 1395
<212> TYPE: DNA
<213> ORGANISM: Artificial Sequence
<220> FEATURE:
<223> OTHER INFORMATION: Codon-optimized open reading frame for
      expression of Micromonas pusilla 6-desaturase in plants (version
      2)

<400> SEQUENCE: 15

```
atgtgtcctc ctaagaccga tggaagatct tctcctagat ctcctctcac caggtctaag       60
tcatctgctg aggctcttga tgctaaggat gcttctaccg ctcctgttga tcttaagacc      120
cttgagcctc atgaacttgc tgctaccttc gagactagat gggttagggt tgaggatgtt      180
gagtacgacg tgaccaactt caaacatcct ggtggaagcg tgatcttcta catgcttgct      240
aacactggtg ctgatgctac tgaggctttc aaagaatttc acatgcgtag cctcaaggct      300
tggaagatgc ttagagcttt gccttctaga cctgctgaga tcaagagatc tgagtctgag      360
gatgctccta tgcttgagga tttcgctagg tggagagctg aacttgagag ggacggattc      420
ttcaagcctt ctatcaccca tgttgcttac cgtcttttgg agcttcttgc tactttcgct      480
cttggaaccg ctcttatgta cgctggatac cctatcattg ctagcgttgt gtacggtgct      540
ttcttcggag ctagatgtgg atgggttcaa catgagggtg acacaactc tcttaccgga      600 tctgtgtacg tggataagag acttcaggct atgacttgcg gattcggact ttctaccagc      660
ggagagatgt ggaaccagat gcataacaag caccatgcta cccctcagaa agttagacac      720
gacatggatc ttgataccac tcctgctgtg gctttcttca acaccgctgt ggaggataat      780
agacctaggg gattctctag agcttgggct agacttcaag cttggacctt cgttcctgtt      840
acttctggac ttctcgttca ggcttctggg atctacgttc tccatcctag acaggtgctc      900
aggaagaaga actacgagga gcttcttgg atgctcacgt tgt tagaaccgct      960 gttatcaagc ttgctaccgg atactcttgg cctgttgctt actggtggtt cactttcgga     1020
aactggatcg cttacatgta cctcttcgct cacttctcta cttctcacac tcacctccct     1080
gttgttccat ctgacaagca ccttagctgg gttaactacg ctgttgatca caccgttgac     1140
atcgatcctt ctcgtggata cgttaactgg cttatgggat accttaactg ccaggttatc     1200
```

```
caccatctct tccctgatat gcctcaattc agacagcctg aggtgtcaag aagattcgtc    1260
cctttcgcta agaagtgggg actcaactac aaggtgctct cttactacgg tgcttggaag    1320
gctactttca gcaacctcga caaagttgga cagcactact acgttaacgg aaaggctgag    1380
aaggctcact gatga                                                     1395
```

<210> SEQ ID NO 16
<211> LENGTH: 463
<212> TYPE: PRT
<213> ORGANISM: Micromonas pusilla

<400> SEQUENCE: 16

```
Met Cys Pro Pro Lys Thr Asp Gly Arg Ser Ser Pro Arg Ser Pro Leu
1               5                   10                  15

Thr Arg Ser Lys Ser Ser Ala Glu Ala Leu Asp Ala Lys Asp Ala Ser
            20                  25                  30

Thr Ala Pro Val Asp Leu Lys Thr Leu Glu Pro His Glu Leu Ala Ala
        35                  40                  45

Thr Phe Glu Thr Arg Trp Val Arg Val Glu Asp Val Glu Tyr Asp Val
    50                  55                  60

Thr Asn Phe Lys His Pro Gly Gly Ser Val Ile Phe Tyr Met Leu Ala
65                  70                  75                  80

Asn Thr Gly Ala Asp Ala Thr Glu Ala Phe Lys Glu Phe His Met Arg
                85                  90                  95

Ser Leu Lys Ala Trp Lys Met Leu Arg Ala Leu Pro Ser Arg Pro Ala
            100                 105                 110

Glu Ile Lys Arg Ser Glu Ser Glu Asp Ala Pro Met Leu Glu Asp Phe
        115                 120                 125

Ala Arg Trp Arg Ala Glu Leu Glu Arg Asp Gly Phe Phe Lys Pro Ser
    130                 135                 140

Ile Thr His Val Ala Tyr Arg Leu Leu Glu Leu Leu Ala Thr Phe Ala
145                 150                 155                 160

Leu Gly Thr Ala Leu Met Tyr Ala Gly Tyr Pro Ile Ile Ala Ser Val
                165                 170                 175

Val Tyr Gly Ala Phe Phe Gly Ala Arg Cys Gly Trp Val Gln His Glu
            180                 185                 190

Gly Gly His Asn Ser Leu Thr Gly Ser Val Tyr Val Asp Lys Arg Leu
        195                 200                 205

Gln Ala Met Thr Cys Gly Phe Gly Leu Ser Ser Gly Glu Met Trp
    210                 215                 220

Asn Gln Met His Asn Lys His His Ala Thr Pro Gln Lys Val Arg His
225                 230                 235                 240

Asp Met Asp Leu Asp Thr Thr Pro Ala Val Ala Phe Phe Asn Thr Ala
                245                 250                 255

Val Glu Asp Asn Arg Pro Arg Gly Phe Ser Arg Ala Trp Ala Arg Leu
            260                 265                 270

Gln Ala Trp Thr Phe Val Pro Val Thr Ser Gly Leu Leu Val Gln Ala
        275                 280                 285

Phe Trp Ile Tyr Val Leu His Pro Arg Gln Val Leu Arg Lys Lys Asn
    290                 295                 300

Tyr Glu Glu Ala Ser Trp Met Leu Val Ser His Val Arg Thr Ala
305                 310                 315                 320

Val Ile Lys Leu Ala Thr Gly Tyr Ser Trp Pro Val Ala Tyr Trp Trp
                325                 330                 335
```

Phe Thr Phe Gly Asn Trp Ile Ala Tyr Met Tyr Leu Phe Ala His Phe
                340                 345                 350

Ser Thr Ser His Thr His Leu Pro Val Val Pro Ser Asp Lys His Leu
            355                 360                 365

Ser Trp Val Asn Tyr Ala Val Asp His Thr Val Asp Ile Asp Pro Ser
370                 375                 380

Arg Gly Tyr Val Asn Trp Leu Met Gly Tyr Leu Asn Cys Gln Val Ile
385                 390                 395                 400

His His Leu Phe Pro Asp Met Pro Gln Phe Arg Gln Pro Glu Val Ser
                405                 410                 415

Arg Arg Phe Val Pro Phe Ala Lys Lys Trp Gly Leu Asn Tyr Lys Val
                420                 425                 430

Leu Ser Tyr Tyr Gly Ala Trp Lys Ala Thr Phe Ser Asn Leu Asp Lys
                435                 440                 445

Val Gly Gln His Tyr Tyr Val Asn Gly Lys Ala Glu Lys Ala His
                450                 455                 460

<210> SEQ ID NO 17
<211> LENGTH: 1449
<212> TYPE: DNA
<213> ORGANISM: Ostreococcus lucimarinus

<400> SEQUENCE: 17
atgtgcgtcg aaacgaccga aggcacatcg cgaacgatgg cgaacgaacg cacgagctcg      60
tcgtcgtcgc tgagcgaagg cggaacgccg acggtgacgg tcgggatggg aagcgaagac     120
gcggggaaga agactcgaaa cgcgagcgtc acggcgtgga cgaaagagtt ggagccgcac     180
gcgatcgcga agacgttcga acggcggtac gtgacgatcg aaggcgtgga atacgatgtg     240
acggatttta agcatcccgg aggatcggtt atttattaca tgctgtcgaa cacgggagcg     300
gacgcgacgg aggcttttaa agagtttcat tatcggtcga aaaggcgcg caaggcgttg      360 gcggcgttgc cgcataagcc agtggacgcg gcgacgcggg aaccgatcga agatgaggcg     420
atgctgaagg atttcgcgca gtggcgcaag gaattggagc gtgagggatt ttttaagccc     480
tcgccggcgc acgtggcgta tcgattcgcc gagctcgcgg cgatgttcgc gctcggcacg     540
gcgttgatgc acgcgcgttg gcacgtcgct tccgtgatcg tgtactcgtg tttcttcggc     600
gcgcgatgcg gttgggtgca gcacgagggt gggcacaatt cgttgactgg aaacatttgg     660
tgggacaagc gaatccaagc cttcgccgcg gggttcggct tggcgtcgag tggcgacatg     720
tggaacaaca tgcacaacaa gcatcacgcg acgccccaaa aggtgcgaca cgatatggat     780
ctcgacacca ctcccacggt ggcgttcttc aactccgcgg ttgaagaaaa tcgcccgcgg     840
ggattcagta agttgtggtt cgcgccttca agcgtggacct tcgtgcccgt gacgtccggt     900
atggttttgt tcttctggat gttcgtcttg cacccgcgta acgcgctgcg acgcaaaagc     960
ttcgaagaag cggcttggat gttttccgcg cacgtcattc gcacggcggt tatcaaagcc    1020
gtcaccggct actcctggat cgcctcgtac ggcttgttcg cggcgacgat gtgggcgagc    1080
ggatgttact tgttcgcgca ctttccacg tctcacacgc acttggatgt cgtgccgagc    1140
gataaacacc tctcgtgggt gcgatacgcc gtcgatcaca cgatcgacat caatccgaac    1200
aacagcgtcg tcaactggtt gatgggctac ttgaactgcc aagtcatcca tcacctgttc    1260
ccggatatgc ctcagttccg ccaacccgaa gtctcccgcc gattcgtccc gtttgcgaag    1320
aagtggaact aaactacaa ggtcttgacg tattatgggg cctggaaggc gacgttcggc    1380
aacttgaacg acgtcgggaa gcactattac gtgcacggat ctcagcgcgt caaatcaaag    1440

<210> SEQ ID NO 18
<211> LENGTH: 1449
<212> TYPE: DNA
<213> ORGANISM: Artificial Sequence
<220> FEATURE:
<223> OTHER INFORMATION: Codon-optimized open reading frame for
      expression of Ostreococcus lucimarinus 6-desaturase in plants

<400> SEQUENCE: 18

```
atgtgtgttg agactactga gggaacctct agaactatgg ctaacgagag gacctcttct      60
tcttcttcac tctctgaggg tggaactcct actgttactg tgggaatggg atctgaggat     120
gctggaaaga aaccagaaa cgcttctgtt actgcttgga ccaaagagct tgagcctcac     180
gctatcgcta agaccttcga gaagatacc gttaccatcg agggtgttga gtacgatgtg     240
accgatttca acacctggg tggatctgtg atctactaca tgctctctaa cactggtgct     300
gatgctactg aggctttcaa agagttccac taccgttcta gaaggctag aaaggctctt     360
gctgctcttc ctcacaagcc tgttgatgct gctactagag agcctattga ggacgaggct     420
atgcttaagg atttcgctca gtggagaaaa gagttggaga gagagggatt cttcaagcct     480
tctcctgctc atgttgctta ccgtttcgct gaactcgctg ctatgttcgc tcttggaacc     540
gctcttatgc atgctagatg gcacgttgct agcgttatcg tgtactcctg tttcttcgga     600
gctagatgtg gatgggttca acatgagggt ggacacaact ctcttaccgg aaacatctgg     660
tgggataaga gaatccaagc tttcgctgct ggattcggac ttgcttcttc tggtgacatg     720
tggaacaaca tgcacaacaa gcaccatgct actcctcaga agtgagaca cgatatggat     780
cttgatacca ccctaccgt tgcttcttc aactctgctg tggaggaaaa cagacctagg     840
ggattctcta agctttggct cagacttcaa gcttggacct cgttcctgt acctctgga     900
atggtgctct cttctggat gttcgttctc catcctagaa cgctctccg tcgtaagtct     960
ttcgaagagg ctgcttggat gttctctgct cacgttatca gaaccgctgt tatcaaggct    1020
gttaccggat actcttggat cgctagctac ggacttttcg ctgctactat gtgggcttct    1080
ggatgctacc ttttcgctca cttctctact tctcacaccc acctcgatgt tgttccatct    1140
gataagcacc ttagctgggt taggtacgct gttgatcaca ccatcgacat caaccctaac    1200
aactctgttg tgaactggct tatgggatac cttaactgcc aggttatcca ccatctcttc    1260
cctgatatgc tcaattcag acagcctgag gtgtcaagaa gattcgtccc tttcgctaag    1320
aagtggaacc tcaactacaa ggtgctcact tactacggtg cttggaaggc tactttcgga    1380
aacctcaacg atgttggaaa gcactactac gttcacggat ctcagagagt gaagagcaag    1440
agcgcttga                                                            1449
```

<210> SEQ ID NO 19
<211> LENGTH: 482
<212> TYPE: PRT
<213> ORGANISM: Ostreococcus lucimarinus

<400> SEQUENCE: 19

```
Met Cys Val Glu Thr Thr Glu Gly Thr Ser Arg Thr Met Ala Asn Glu
1               5                   10                  15

Arg Thr Ser Ser Ser Ser Ser Leu Ser Glu Gly Gly Thr Pro Thr Val
            20                  25                  30

Thr Val Gly Met Gly Ser Glu Asp Ala Gly Lys Lys Thr Arg Asn Ala
```

```
            35                  40                  45
Ser Val Thr Ala Trp Thr Lys Glu Leu Glu Pro His Ala Ile Ala Lys
 50                  55                  60

Thr Phe Glu Arg Arg Tyr Val Thr Ile Glu Gly Val Glu Tyr Asp Val
 65                  70                  75                  80

Thr Asp Phe Lys His Pro Gly Gly Ser Val Ile Tyr Tyr Met Leu Ser
                     85                  90                  95

Asn Thr Gly Ala Asp Ala Thr Glu Ala Phe Lys Glu Phe His Tyr Arg
                    100                 105                 110

Ser Lys Lys Ala Arg Lys Ala Leu Ala Ala Leu Pro His Lys Pro Val
                    115                 120                 125

Asp Ala Ala Thr Arg Glu Pro Ile Glu Asp Glu Ala Met Leu Lys Asp
                    130                 135                 140

Phe Ala Gln Trp Arg Lys Glu Leu Glu Arg Glu Gly Phe Phe Lys Pro
145                 150                 155                 160

Ser Pro Ala His Val Ala Tyr Arg Phe Ala Glu Leu Ala Ala Met Phe
                    165                 170                 175

Ala Leu Gly Thr Ala Leu Met His Ala Arg Trp His Val Ala Ser Val
                    180                 185                 190

Ile Val Tyr Ser Cys Phe Phe Gly Ala Arg Cys Gly Trp Val Gln His
                    195                 200                 205

Glu Gly Gly His Asn Ser Leu Thr Gly Asn Ile Trp Trp Asp Lys Arg
                    210                 215                 220

Ile Gln Ala Phe Ala Ala Gly Phe Gly Leu Ala Ser Ser Gly Asp Met
225                 230                 235                 240

Trp Asn Asn Met His Asn Lys His His Ala Thr Pro Gln Lys Val Arg
                    245                 250                 255

His Asp Met Asp Leu Asp Thr Thr Pro Thr Val Ala Phe Phe Asn Ser
                    260                 265                 270

Ala Val Glu Glu Asn Arg Pro Arg Gly Phe Ser Lys Leu Trp Leu Arg
                    275                 280                 285

Leu Gln Ala Trp Thr Phe Val Pro Val Thr Ser Gly Met Val Leu Phe
                    290                 295                 300

Phe Trp Met Phe Val Leu His Pro Arg Asn Ala Leu Arg Arg Lys Ser
305                 310                 315                 320

Phe Glu Glu Ala Ala Trp Met Phe Ser Ala His Val Ile Arg Thr Ala
                    325                 330                 335

Val Ile Lys Ala Val Thr Gly Tyr Ser Trp Ile Ala Ser Tyr Gly Leu
                    340                 345                 350

Phe Ala Ala Thr Met Trp Ala Ser Gly Cys Tyr Leu Phe Ala His Phe
                    355                 360                 365

Ser Thr Ser His Thr His Leu Asp Val Val Pro Ser Asp Lys His Leu
                    370                 375                 380

Ser Trp Val Arg Tyr Ala Val Asp His Thr Ile Asp Ile Asn Pro Asn
385                 390                 395                 400

Asn Ser Val Val Asn Trp Leu Met Gly Tyr Leu Asn Cys Gln Val Ile
                    405                 410                 415

His His Leu Phe Pro Asp Met Pro Gln Phe Arg Gln Pro Glu Val Ser
                    420                 425                 430

Arg Arg Phe Val Pro Phe Ala Lys Lys Trp Asn Leu Asn Tyr Lys Val
                    435                 440                 445

Leu Thr Tyr Tyr Gly Ala Trp Lys Ala Thr Phe Gly Asn Leu Asn Asp
                    450                 455                 460
```

Val Gly Lys His Tyr Tyr Val His Gly Ser Gln Arg Val Lys Ser Lys
465                 470                 475                 480

Ser Ala

<210> SEQ ID NO 20
<211> LENGTH: 456
<212> TYPE: PRT
<213> ORGANISM: Ostreococcus lucimarinus

<400> SEQUENCE: 20

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
            85                  90                  95

Lys Ala Leu Ala Ala Leu Pro Ser Arg Pro Ala Lys Thr Ala Lys Val
        100                 105                 110

Asp Asp Ala Glu Met Leu Gln Asp Phe Ala Lys Trp Arg Lys Glu Leu
    115                 120                 125

Glu Arg Asp Gly Phe Phe Lys Pro Ser Pro Ala His Val Ala Tyr Arg
130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
    210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Leu Phe Trp Met Phe Phe Leu His Pro
        275                 280                 285

Ser Lys Ala Leu Lys Gly Gly Lys Tyr Glu Glu Leu Val Trp Met Leu
    290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

```
Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
    370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
                420                 425                 430

Ala Thr Leu Gly Asn Leu Asp Asn Val Gly Lys His Tyr Tyr Val His
            435                 440                 445

Gly Gln His Ser Gly Lys Thr Ala
    450                 455

<210> SEQ ID NO 21
<211> LENGTH: 894
<212> TYPE: DNA
<213> ORGANISM: Pyramimonas cordata

<400> SEQUENCE: 21
atggagttcg ctcagcctct tgtggctatg gcacaggagc agtatgccgc aattgacgcg      60
gtggtagccc ctgcaatttt ctcagctacc gacagcatcg ttggggtct  taagcccatt     120 agcagcgcga caaaggatct tcctctcgtt gagagtccga cgccgctcat actgagcctg     180
ttggcctatt ttgcgatcgt cggctctggg ctggtgtacc gcaaagtatt ccctcgcaca     240 gtaaagggc aagacccctt cctgctgaag gcgctcatgc ttgcgcacaa cgtgttcctc      300
attggcctca gtctatacat gtgcttgaag cttgtctacg aggcttacgt caacaagtac     360
tccttctggg aaacgcctaa caccccgca cagaccgaga tggcgaaggt catctggatt      420
ttctacgtct ccaagatcta tgagttcatg gacacgttca tcatgctctt gaagggcaac     480
gtcaaccagg tctctttcct gcatgtgtac catcatggct ccatctctgg tatctggtgg     540
atgatcacct acgctgcccc tggcggtgac gcgtacttct cggcggcgct caactcgtgg     600
gtgcacgtgt gcatgtacac gtactacttc atggcggcgg tgctgcccaa ggacgagaag     660
accaagcgca gtacctctg  gtggggccgc tacctgaccc agatgcagat gttccagttc     720
ttcatgaacc tgctccaggc ggtctacctc ctctactcct ctagccccta ccccaagttc     780
atcgcccagc tgctggtggt gtacatggtc acgctgctga tgctcttcgg caacttctac     840
tacatgaagc accacgcgag caagaagcag aagctggcca gcaagaagca gtag           894

<210> SEQ ID NO 22
<211> LENGTH: 870
<212> TYPE: DNA
<213> ORGANISM: Artificial Sequence
<220> FEATURE:
<223> OTHER INFORMATION: Codon-optimized open reading frame for
      expression of Pyramimonas cordata 6-elongase in plants (truncated
      at 3' end and encoding functional elongase) (version 1)

<400> SEQUENCE: 22
atggaattcg cccagcctct tgttgctatg gctcaagagc aatacgctgc tatcgatgct      60
gttgttgctc ctgctatctt ctctgctact gattctatcg atggggact  taagcctatc     120 tcttctgcta ctaaggactt gcctcttgtt gagtctccta cacctctcat cctttctttg     180
cttgcttact ctgctatcgt tggatctgga ctcgtttaca gaaaggtttt ccctagaacc     240
```

```
gtgaagggac aagatccatt ccttttgaag gctcttatgc ttgctcacaa cgtgttcctt    300
atcggacttt ctctttacat gtgcctcaag cttgtgtacg aggcttacgt taacaagtac    360
tctttctggg gaaacgctta caaccctgct caaactgaga tggctaaggt tatctggatc    420
ttctacgtga gcaagatcta cgagttcatg gataccttca tcatgctcct caagggaaat    480
gttaaccagg ttagcttcct tcacgtttac catcacggat ctatctctgg aatctggtgg    540
atgattactt acgctgctcc tggtggtgat gcttacttct ctgctgctct taactcttgg    600
gttcacgtgt gtatgtacac ctactatttt atggctgccg tgcttcctaa ggacgagaaa    660
actaagagaa agtacctctg gtggggaaga taccttactc aaatgcagat gttccagttc    720
ttcatgaacc ttctccaggc tgtttacctt ctctactctt catctcctta ccctaagttt    780
atcgctcagc tcctcgtggt gtacatggtt actcttctca tgcttttcgg aaacttctac    840
tacatgaagc accacgctag caagtgatga                                      870
```

`<210>` SEQ ID NO 23  
`<211>` LENGTH: 870  
`<212>` TYPE: DNA  
`<213>` ORGANISM: Artificial Sequence  
`<220>` FEATURE:  
`<223>` OTHER INFORMATION: Codon-optimized open reading frame for expression of Pyramimonas cordata 6-elongase in plants (truncated at 3' end and encoding functional elongase) (version 2)

`<400>` SEQUENCE: 23

```
atggaattcg cccagcctct tgttgctatg gctcaagagc aatacgctgc tatcgatgct    60
gttgttgctc ctgctatctt ctctgctact gattctatcg gatggggact taagcctatc   120
tcttctgcta ctaaggactt gcctcttgtt gagtctccta cacctctcat cctttctttg   180
cttgcttact tcgctatcgt tggatctgga ctcgtttaca gaaaggtttt ccctagaacc   240
gtgaagggac aagatccatt ccttttgaag gctcttatgc ttgctcacaa cgtgttcctt   300
atcggacttt ctctttacat gtgcctcaag cttgtgtacg aggcttacgt taacaagtac   360
tctttctggg gaaacgctta caaccctgct caaactgaga tggctaaggt tatctggatc   420
ttctacgtga gcaagatcta cgagttcatg gataccttca tcatgctcct caagggaaat   480
gttaaccagg ttagcttcct tcacgtttac catcacggat ctatctctgg aatctggtgg   540
atgattactt acgctgctcc tggtggtgat gcttacttct ctgctgctct taactcttgg   600
gttcacgtgt gtatgtacac ctactatttt atggctgccg tgcttcctaa ggacgagaaa   660
actaagagaa agtacctctg gtggggaaga taccttactc aaatgcagat gttccagttc   720
ttcatgaacc ttctccaggc tgtttacctt ctctactctt catctcctta ccctaagttt   780
atcgctcagc tcctcgtggt gtacatggtt actcttctca tgcttttcgg aaacttctac   840
tacatgaagc accacgctag caagtgatga                                     870
```

`<210>` SEQ ID NO 24  
`<211>` LENGTH: 870  
`<212>` TYPE: DNA  
`<213>` ORGANISM: Artificial Sequence  
`<220>` FEATURE:  
`<223>` OTHER INFORMATION: Codon-optimized open reading frame for expression of Pyramimonas cordata 6-elongase in plants (truncated at 3' end and encoding functional elongase) (version 3)

`<400>` SEQUENCE: 24

```
atggaatttg ctcaacctct cgttgctatg gctcaagagc agtacgctgc tatcgatgct    60
```

-continued

```
gttgttgctc ctgctatctt ctctgctacc gactctattg gatggggact caagcctatc    120
tcttctgcta ctaaggatct ccctctcgtt gaatctccta cccctcttat cctttctctc    180
ctcgcttact tcgctatcgt tggttctgga ctcgtttacc gtaaagtgtt ccctagaacc    240
gttaagggac aggatccttt ccttctcaag gctcttatgc tcgctcacaa cgttttcctt    300
atcggactca gcctttacat gtgcctcaag ctcgtttacg aggcttacgt gaacaagtac    360
tccttctggg gaaacgctta caaccctgct caaaccgaga tggctaaggt gatctggatc    420
ttctacgtgt ccaagatcta cgagttcatg gacaccttca tcatgcttct caagggaaac    480
gttaaccagg tttccttcct ccatgtttac caccacggat ctatctctgg aatctggtgg    540
atgatcactt atgctgctcc aggtggagat gcttacttct ctgctgctct caactcttgg    600
gttcatgtgt gcatgtacac ctactacttc atggctgctg ttcttcctaa ggacgaaaag    660
accaagagaa agtacctttg gtggggaaga taccttaccc agatgcaaat gttccagttc    720
ttcatgaacc ttctccaggc tgtttacctc ctctactctt cttctcctta ccctaagttc    780
attgctcaac tcctcgttgt ttacatggtt accctcctca tgcttttcgg aaacttctac    840
tacatgaagc accacgcttc taagtgataa                                      870
```

<210> SEQ ID NO 25
<211> LENGTH: 297
<212> TYPE: PRT
<213> ORGANISM: Pyramimonas cordata

<400> SEQUENCE: 25

```
Met Glu Phe Ala Gln Pro Leu Val Ala Met Ala Gln Glu Gln Tyr Ala
1               5                   10                  15

Ala Ile Asp Ala Val Val Ala Pro Ala Ile Phe Ser Ala Thr Asp Ser
            20                  25                  30

Ile Gly Trp Gly Leu Lys Pro Ile Ser Ser Ala Thr Lys Asp Leu Pro
        35                  40                  45

Leu Val Glu Ser Pro Thr Pro Leu Ile Leu Ser Leu Ala Tyr Phe
    50                  55                  60

Ala Ile Val Gly Ser Gly Leu Val Tyr Arg Lys Val Phe Pro Arg Thr
65                  70                  75                  80

Val Lys Gly Gln Asp Pro Phe Leu Leu Lys Ala Leu Met Leu Ala His
                85                  90                  95

Asn Val Phe Leu Ile Gly Leu Ser Leu Tyr Met Cys Leu Lys Leu Val
            100                 105                 110

Tyr Glu Ala Tyr Val Asn Lys Tyr Ser Phe Trp Gly Asn Ala Tyr Asn
        115                 120                 125

Pro Ala Gln Thr Glu Met Ala Lys Val Ile Trp Ile Phe Tyr Val Ser
    130                 135                 140

Lys Ile Tyr Glu Phe Met Asp Thr Phe Ile Met Leu Leu Lys Gly Asn
145                 150                 155                 160

Val Asn Gln Val Ser Phe Leu His Val Tyr His His Gly Ser Ile Ser
                165                 170                 175

Gly Ile Trp Trp Met Ile Thr Tyr Ala Ala Pro Gly Gly Asp Ala Tyr
            180                 185                 190

Phe Ser Ala Ala Leu Asn Ser Trp Val His Val Cys Met Tyr Thr Tyr
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
```

```
            225                 230                 235                 240
        Phe Met Asn Leu Leu Gln Ala Val Tyr Leu Leu Tyr Ser Ser Ser Pro
                        245                 250                 255

Tyr Pro Lys Phe Ile Ala Gln Leu Leu Val Val Tyr Met Val Thr Leu
                        260                 265                 270

Leu Met Leu Phe Gly Asn Phe Tyr Tyr Met Lys His His Ala Ser Lys
                        275                 280                 285

Lys Gln Lys Leu Ala Ser Lys Lys Gln
                        290                 295

<210> SEQ ID NO 26
<211> LENGTH: 288
<212> TYPE: PRT
<213> ORGANISM: Pyramimonas cordata

<400> SEQUENCE: 26

Met Glu Phe Ala Gln Pro Leu Val Ala Met Ala Gln Glu Gln Tyr Ala
 1               5                  10                  15

Ala Ile Asp Ala Val Val Ala Pro Ala Ile Phe Ser Ala Thr Asp Ser
                20                  25                  30

Ile Gly Trp Gly Leu Lys Pro Ile Ser Ser Ala Thr Lys Asp Leu Pro
            35                  40                  45

Leu Val Glu Ser Pro Thr Pro Leu Ile Leu Ser Leu Leu Ala Tyr Phe
        50                  55                  60

Ala Ile Val Gly Ser Gly Leu Val Tyr Arg Lys Val Phe Pro Arg Thr
 65                  70                  75                  80

Val Lys Gly Gln Asp Pro Phe Leu Leu Lys Ala Leu Met Leu Ala His
                85                  90                  95

Asn Val Phe Leu Ile Gly Leu Ser Leu Tyr Met Cys Leu Lys Leu Val
            100                 105                 110

Tyr Glu Ala Tyr Val Asn Lys Tyr Ser Phe Trp Gly Asn Ala Tyr Asn
        115                 120                 125

Pro Ala Gln Thr Glu Met Ala Lys Val Ile Trp Ile Phe Tyr Val Ser
    130                 135                 140

Lys Ile Tyr Glu Phe Met Asp Thr Phe Ile Met Leu Leu Lys Gly Asn
145                 150                 155                 160

Val Asn Gln Val Ser Phe Leu His Val Tyr His His Gly Ser Ile Ser
                165                 170                 175

Gly Ile Trp Trp Met Ile Thr Tyr Ala Ala Pro Gly Gly Asp Ala Tyr
            180                 185                 190

Phe Ser Ala Ala Leu Asn Ser Trp Val His Val Cys Met Tyr Thr Tyr
        195                 200                 205

Tyr Phe Met Ala Ala Val Leu Pro Lys Asp Glu Lys Thr Lys Arg Lys
    210                 215                 220

Tyr Leu Trp Trp Gly Arg Tyr Leu Thr Gln Met Gln Met Phe Gln Phe
225                 230                 235                 240

Phe Met Asn Leu Leu Gln Ala Val Tyr Leu Leu Tyr Ser Ser Ser Pro
                245                 250                 255

Tyr Pro Lys Phe Ile Ala Gln Leu Leu Val Val Tyr Met Val Thr Leu
                260                 265                 270

Leu Met Leu Phe Gly Asn Phe Tyr Tyr Met Lys His His Ala Ser Lys
                275                 280                 285

<210> SEQ ID NO 27
<211> LENGTH: 1278
```

```
<212> TYPE: DNA
<213> ORGANISM: Pavlova salina

<400> SEQUENCE: 27
atgccgccgc gcgatagcta ctcgtacgcc gccccgccgt cggcccagct gcacgaggtc    60
gataccccgc aggagcatga taagaaggag ctcgtcatcg gtgaccgcgc gtacgacgtg   120
accaactttg tgaagcgcca cccgggtggc aagatcatcg cataccaggt tggcacagat   180
gcgacggacg cgtacaagca gttccatgtg cggtctgcca aggcggacaa gatgctcaag   240
tcgctgcctt cgcgcccggt gcacaagggc tactcgcccc gccgcgctga cctcattgcc   300
gacttccagg agttcaccaa gcagctggag gcggagggca tgtttgagcc gtcgctgccg   360
cacgtggcat accgcctggc ggaggtgatc gcgatgcacg tggccggcgc cgcgctcatc   420
tggcacgggt acaccttcgc gggcattgcc atgctcggcg ttgtgcaggg cgctgcggc    480
tggctcatgc acgagggcgg ccactactcg ctcacgggca acattgcttt tgaccgtgcc   540
atccaagtcg cgtgctacgg ccttggctgc ggcatgtcgg gcgcgtggtg cgcaaccag    600
cacaacaagc accacgcgac gccgcagaag ttgcagcacg acgtcgacct cgacaccctc   660
ccgctcgtcg ccttccacga gcggatagcc gccaaggtga gagccccgc gatgaaggcg    720
tggcttagta tgcaggcgaa gctcttcgcg ccagtgacca cgctgctggt cgcgctgggc   780
tggcagctgt acctgcaccc cgcgccatat gctgcgcacca agcactacga cgagctcgcg   840
atgctcggca ttcgctacgg ccttgtcggc tacctcgcgg cgaactacgg cgcggggtac   900
gtgctcgcgt gctacctgct gtacgtgcag ctcggcgcca tgtacatctt ctgcaacttt   960
gccgtgtcgc acacacacct gccggttgtc gagcctaacg agcacgcaac gtgggtggag   1020
tacgccgcga ccacgcgac caactgctcg ccctcgtggt ggtgcgactg gtggatgtcg   1080
tacctcaact accagatcga gcaccacctc tacccgtcca tgccgcagtt ccgccacccg   1140
aagattgcgc cgcgggtgaa gcagctcttc gagaagcacg gcctgcacta cgacgtgcgt   1200
ggctacttcg aggccatggc ggacacgttt gccaaccttg caacgtcgc gcacgcgccg   1260
gagaagaaga tgcagtga                                                1278

<210> SEQ ID NO 28
<211> LENGTH: 1281
<212> TYPE: DNA
<213> ORGANISM: Artificial Sequence
<220> FEATURE:
<223> OTHER INFORMATION: Codon-optimized open reading frame for
      expression of Pavlova salina 5-desaturase in plants (version 1)

<400> SEQUENCE: 28
atgcctccaa gggactctta ctcttatgct gctcctcctt ctgctcaact tcacgaagtt    60
gatactcctc aagagcacga caagaaagag cttgttatcg gagatagggc ttacgatgtt   120
accaacttcg ttaagagaca ccctggtgga aagatcattg cttaccaagt tggaactgat   180
gctaccgatg cttacaagca gttccatgtt agatctgcta aggctgacaa gatgcttaag   240
tctcttcctt ctcgtcctgt tcacaaggga tactctccaa gagggctga tcttatcgct   300
gatttccaag agttcaccaa gcaacttgag gctgagggaa tgttcgagcc ttctcttcct   360
catgttgctt acagacttgc tgaggttatc gctatgcatg ttgctggtgc tgctcttatc   420
tggcatggat acactttcgc tggaatcgct atgcttggag ttgttcaggg aagatgtgga   480
tggcttatgc atgagggtgg acattactct ctcactggaa acattgcttt cgacagagct   540
atccaagttg cttgttacgg acttggatgt ggaatgtctg gtgcttggtg cgtaaccag    600
```

```
cataacaagc accatgctac tcctcaaaag cttcagcacg atgttgatct tgataccctt      660
cctctcgttg ctttccatga gagaatcgct gctaaggtta agtctcctgc tatgaaggct      720
tggctttcta tgcaagctaa gcttttcgct cctgttacca ctcttcttgt tgctcttgga      780
tggcagcttt accttcatcc tagacacatg ctcaggacta agcactacga tgagcttgct      840
atgctcggaa tcagatacgg acttgttgga taccttgctg ctaactacgg tgctggatac      900
gttctcgctt gttaccttct ttacgttcag cttggagcta tgtacatctt ctgcaacttc      960
gctgtttctc atactcacct ccctgttgtt gagcctaacg agcatgctac ttgggttgag     1020
tacgctgcta accacactac taactgttct ccatcttggt ggtgtgattg gtggatgtct     1080
taccttaact accagatcga gcaccacctt tacccttcta tgcctcaatt cagacaccct     1140
aagatcgctc ctagagttaa gcagcttttc gagaagcacg gacttcacta cgatgttaga     1200
ggatacttcg aggctatggc tgatactttc gctaaccttg ataacgttgc ccatgctcct     1260
gagaagaaaa tgcagtaatg a                                                1281
```

<210> SEQ ID NO 29
<211> LENGTH: 1281
<212> TYPE: DNA
<213> ORGANISM: Artificial Sequence
<220> FEATURE:
<223> OTHER INFORMATION: Codon-optimized open reading frame for
      expression of Pavlova salina 5-desaturase in plants (version 2)

<400> SEQUENCE: 29

```
atgcctccta gggactctta ctcttacgct gctcctcctt ctgctcaact tcacgaggtt       60
gacactcctc aagagcacga caagaaagag cttgttatcg agatagggc ttacgatgtg      120 accaacttcg ttaagagaca ccctggtgga aagatcattg cttaccaagt gggaactgat      180
gctaccgatg cttacaagca gttccatgtg agatctgcta aggctgacaa gatgctcaag      240
tctctccctt ctagacctgt tcacaaggga tactctccta aagagctga tcttatcgct      300 gacttccaag agttcactaa gcaacttgag gctgagggaa tgttcgaacc ttctctccct      360
catgttgctt accgtcttgc tgaggttatc gctatgcatg ttgctggtgc tgctcttatc      420
tggcacggat acactttcgc tggaatcgct atgcttggag ttgttcaggg aagatgcgga      480
tggcttatgc atgagggtgg acactactct cttaccggaa acattgcttt cgatagggct      540
atccaagttg cttgttacgg acttggatgc ggaatgtctg gtgcttggtg gagaaaccag      600
cataacaagc accatgctac tcctcaaaag ctccagcacg atgttgatct tgataccctc      660
cctctcgttg ctttccatga gagaatcgct gctaaggtta agtctcctgc tatgaaggct      720
tggctctcca tgcaagctaa actcttcgct cctgttacca ctcttcttgt tgctcttgga      780
tggcagcttt accttcaccc tagacacatg ctcagaacta agcactacga cgagcttgct      840
atgcttggta tcagatacgg acttgtggga taccttgctg ctaactacgg tgctggatac      900
gttcttgctt gctaccttct ctacgttcag cttggagcta tgtacatctt ctgcaacttc      960
gctgtttctc acactcatct ccctgttgtt gagcctaacg agcatgctac ttgggttgag     1020
tacgctgcta accacactac taactgctct ccatcttggt ggtgtgattg gtggatgagc     1080
tacctcaact accagatcga gcatcacctt tacccttcta tgcctcagtt caggcatcct     1140
aagatcgctc ctagagtgaa gcaactcttc gagaagcacg gacttcacta cgatgtgcgt     1200
ggatacttcg aggctatggc tgatactttc gctaaccteg ataacgttgc tcatgctcct     1260
gagaagaaaa tgcaatgatg a                                                1281
```

<210> SEQ ID NO 30
<211> LENGTH: 425
<212> TYPE: PRT
<213> ORGANISM: Pavlova salina

<400> SEQUENCE: 30

```
Met Pro Pro Arg Asp Ser Tyr Ser Tyr Ala Ala Pro Ser Ala Gln
1               5                   10                  15

Leu His Glu Val Asp Thr Pro Gln Glu His Asp Lys Lys Glu Leu Val
                20                  25                  30

Ile Gly Asp Arg Ala Tyr Asp Val Thr Asn Phe Val Lys Arg His Pro
                35                  40                  45

Gly Gly Lys Ile Ile Ala Tyr Gln Val Gly Thr Asp Ala Thr Asp Ala
            50                  55                  60

Tyr Lys Gln Phe His Val Arg Ser Ala Lys Ala Asp Lys Met Leu Lys
65                  70                  75                  80

Ser Leu Pro Ser Arg Pro Val His Lys Gly Tyr Ser Pro Arg Arg Ala
                85                  90                  95

Asp Leu Ile Ala Asp Phe Gln Glu Phe Thr Lys Gln Leu Glu Ala Glu
                100                 105                 110

Gly Met Phe Glu Pro Ser Leu Pro His Val Ala Tyr Arg Leu Ala Glu
            115                 120                 125

Val Ile Ala Met His Val Ala Gly Ala Ala Leu Ile Trp His Gly Tyr
130                 135                 140

Thr Phe Ala Gly Ile Ala Met Leu Gly Val Val Gln Gly Arg Cys Gly
145                 150                 155                 160

Trp Leu Met His Glu Gly Gly His Tyr Ser Leu Thr Gly Asn Ile Ala
                165                 170                 175

Phe Asp Arg Ala Ile Gln Val Ala Cys Tyr Gly Leu Gly Cys Gly Met
                180                 185                 190

Ser Gly Ala Trp Trp Arg Asn Gln His Asn Lys His His Ala Thr Pro
            195                 200                 205

Gln Lys Leu Gln His Asp Val Asp Leu Asp Thr Leu Pro Leu Val Ala
210                 215                 220

Phe His Glu Arg Ile Ala Ala Lys Val Lys Ser Pro Ala Met Lys Ala
225                 230                 235                 240

Trp Leu Ser Met Gln Ala Lys Leu Phe Ala Pro Val Thr Thr Leu Leu
                245                 250                 255

Val Ala Leu Gly Trp Gln Leu Tyr Leu His Pro Arg His Met Leu Arg
                260                 265                 270

Thr Lys His Tyr Asp Glu Leu Ala Met Leu Gly Ile Arg Tyr Gly Leu
            275                 280                 285

Val Gly Tyr Leu Ala Ala Asn Tyr Gly Ala Gly Tyr Val Leu Ala Cys
290                 295                 300

Tyr Leu Leu Tyr Val Gln Leu Gly Ala Met Tyr Ile Phe Cys Asn Phe
305                 310                 315                 320

Ala Val Ser His Thr His Leu Pro Val Val Glu Pro Asn Glu His Ala
                325                 330                 335

Thr Trp Val Glu Tyr Ala Ala Asn His Thr Thr Asn Cys Ser Pro Ser
                340                 345                 350

Trp Trp Cys Asp Trp Trp Met Ser Tyr Leu Asn Tyr Gln Ile Glu His
            355                 360                 365

His Leu Tyr Pro Ser Met Pro Gln Phe Arg His Pro Lys Ile Ala Pro
```

```
                370             375             380
Arg Val Lys Gln Leu Phe Glu Lys His Gly Leu His Tyr Asp Val Arg
385             390             395             400

Gly Tyr Phe Glu Ala Met Ala Asp Thr Phe Ala Asn Leu Asp Asn Val
            405             410             415

Ala His Ala Pro Glu Lys Lys Met Gln
            420             425

<210> SEQ ID NO 31
<211> LENGTH: 1329
<212> TYPE: DNA
<213> ORGANISM: Pyramimonas cordata

<400> SEQUENCE: 31
atgggaaagg aggcaatgc tagcgctcct actgcgaaga aggaggtgtt gatcgagggg      60
aagttttacg atgtcaccga cttcaggcac cccggtggtt cgatcatcaa gtttctctcg    120
ggttctggtg ctgacgccac cgcttcctac cgcgagttcc acgttaggtc agcgaaggca    180
gacaagttct tgaagacgct gccctcccgc gaagccactc cccaggagct gaagcaggcg    240
gttgagttct ccaagctcaa cccgccctcc gcggagagtg cctctgctcc cctgaccgac    300
cttgccaagg tggaagcgct gaacaaggac ttcgaggctt ccgtgagca gctcattcag     360
gagggcttct ttaagcccaa tatcccgcat gtggtcaagc gcatcacgga agtcgtggcg    420
atgatggccg tagcctcctg gatgatggtg cagaccaacg ctcttgttgt gaccctcgga    480
gttctgatcc gcggcattgc acagggccgg tgcggttggc ttatgcacga gggcggccac    540
tatagtctta ctgggaagat ctccattgat aggcgtctgc aggagtcaat ttacggattc    600
ggctgtggaa tgtccggcgc ctggtggcgc aaccagcaca acaagcacca cgcaaccca     660
cagaagctgc agcatgacgt cgacctggag acccttcctc tgatggcttt caacaacgct    720
gttaccgata cacgcaaggt gaagcctggt agtctccagg ctctgtggct caagtaccag    780
gccttcctct tcttccccgt gacctccctt ctggtcggcc tcggttggac caccgtcctc    840
cacccccagg cacagcttgcg caccaagcac tatttcgagc tgctctgcat ggctgctcgt    900
tacgcgagtt tcgctgctct tttcgctccc aagtacggac ttgcaggagc tgccgggctc    960
tacctcgcca ccttcgctgt cgggtgcaac tatattttca tcaacttctc ggtctctcac   1020
actcacctgc ccgtgagcgg tgcgagcgag tacctgcatt gggtcgtgta ttcggccatc   1080
cacaccacta acatcaaatc cagcatgctg tgcgattggt ggatgtcatt cctcaacttc   1140
cagatcgagc atcacctgtt cccttcaatg ccccagttcc gccacaagat tatctccccg   1200
cgtgtaaagg ccttgtttga gaagcacggt cttgtgtatg atgtgcgccc ctattggggg   1260
gccatggctg acaccttcaa gaacttgaat gacgttggca ctcacgcatc tcactccaag   1320
gcgcactag                                                            1329

<210> SEQ ID NO 32
<211> LENGTH: 442
<212> TYPE: PRT
<213> ORGANISM: Pyramimonas cordata

<400> SEQUENCE: 32

Met Gly Lys Gly Gly Asn Ala Ser Ala Pro Thr Ala Lys Lys Glu Val
1               5                   10                  15

Leu Ile Glu Gly Lys Phe Tyr Asp Val Thr Asp Phe Arg His Pro Gly
            20                  25                  30
```

Gly Ser Ile Ile Lys Phe Leu Ser Gly Ser Gly Ala Asp Ala Thr Ala
             35                  40                  45

Ser Tyr Arg Glu Phe His Val Arg Ser Ala Lys Ala Asp Lys Phe Leu
 50                  55                  60

Lys Thr Leu Pro Ser Arg Glu Ala Thr Pro Gln Glu Leu Lys Gln Ala
 65                  70                  75                  80

Val Glu Phe Ser Lys Leu Asn Pro Pro Ser Ala Glu Ser Ala Ser Ala
                     85                  90                  95

Pro Leu Thr Asp Leu Ala Lys Val Glu Ala Leu Asn Lys Asp Phe Glu
                 100                 105                 110

Ala Phe Arg Glu Gln Leu Ile Gln Glu Gly Phe Phe Lys Pro Asn Ile
                 115                 120                 125

Pro His Val Val Lys Arg Ile Thr Glu Val Val Ala Met Met Ala Val
                 130                 135                 140

Ala Ser Trp Met Met Val Gln Thr Asn Ala Leu Val Val Thr Leu Gly
145                 150                 155                 160

Val Leu Ile Arg Gly Ile Ala Gln Gly Arg Cys Gly Trp Leu Met His
                 165                 170                 175

Glu Gly Gly His Tyr Ser Leu Thr Gly Lys Ile Ser Ile Asp Arg Arg
                 180                 185                 190

Leu Gln Glu Ser Ile Tyr Gly Phe Gly Cys Gly Met Ser Gly Ala Trp
                 195                 200                 205

Trp Arg Asn Gln His Asn Lys His His Ala Thr Pro Gln Lys Leu Gln
         210                 215                 220

His Asp Val Asp Leu Glu Thr Leu Pro Leu Met Ala Phe Asn Asn Ala
225                 230                 235                 240

Val Thr Asp Arg Arg Lys Val Lys Pro Gly Ser Leu Gln Ala Leu Trp
                 245                 250                 255

Leu Lys Tyr Gln Ala Phe Leu Phe Pro Val Thr Ser Leu Leu Val
             260                 265                 270

Gly Leu Gly Trp Thr Thr Val Leu His Pro Arg His Ser Leu Arg Thr
                 275                 280                 285

Lys His Tyr Phe Glu Leu Leu Cys Met Ala Ala Arg Tyr Ala Ser Phe
         290                 295                 300

Ala Ala Leu Phe Ala Pro Lys Tyr Gly Leu Ala Gly Ala Ala Gly Leu
305                 310                 315                 320

Tyr Leu Ala Thr Phe Ala Val Gly Cys Asn Tyr Ile Phe Ile Asn Phe
                 325                 330                 335

Ser Val Ser His Thr His Leu Pro Val Ser Gly Ala Ser Glu Tyr Leu
                 340                 345                 350

His Trp Val Val Tyr Ser Ala Ile His Thr Thr Asn Ile Lys Ser Ser
             355                 360                 365

Met Leu Cys Asp Trp Trp Met Ser Phe Leu Asn Phe Gln Ile Glu His
         370                 375                 380

His Leu Phe Pro Ser Met Pro Gln Phe Arg His Lys Ile Ile Ser Pro
385                 390                 395                 400

Arg Val Lys Ala Leu Phe Glu Lys His Gly Leu Val Tyr Asp Val Arg
                 405                 410                 415

Pro Tyr Trp Gly Ala Met Ala Asp Thr Phe Lys Asn Leu Asn Asp Val
             420                 425                 430

Gly Thr His Ala Ser His Ser Lys Ala His
         435                 440

<210> SEQ ID NO 33
<211> LENGTH: 804
<212> TYPE: DNA
<213> ORGANISM: Pyramimonas cordata

<400> SEQUENCE: 33

| | | | | | | |
|---|---|---|---|---|---|---|
| atggcgtcta | ttgcgattcc | ggctgcgctg | gcagggactc | ttggttatgt | gacgtacaat | 60 |
| gtcgcaaacc | cagatattcc | tgcatccgag | aaggtgcctg | cttactttat | gcaggtcgag | 120 |
| tattgggggc | caacgattgg | gaccatcggt | tatcttctgt | tcatctactt | tggtaaacgg | 180 |
| attatgcaaa | acaggagcca | gccgtttggc | ctgaagaacg | ctatgctggt | gtacaacttc | 240 |
| tatcagactt | tcttcaactc | gtactgcata | tacctttttg | tcacgtcgca | ccgcgctcag | 300 |
| gggctgaaag | tttggggaaa | catccccgat | atgactgcca | acagctgggg | gatctcacag | 360 |
| gtgatctggc | tgcactacaa | caacaagtac | gttgagctgc | tggacacgtt | cttcatggtc | 420 |
| atgcgcaaga | agtttgacca | gctttcgttc | ctgcacattt | accatcatac | cctgttgatc | 480 |
| tggtcttggt | tcgtggtgat | gaaattggag | cccgttgggg | actgctactt | tggctctagc | 540 |
| gtcaacacgt | ttgtgcacgt | cattatgtac | tcgtactatg | gccttgccgc | gctcggggtg | 600 |
| aattgcttct | ggaagaagta | cattacgcag | attcagatgc | tgcagttctg | tatctgcgct | 660 |
| tcgcactcga | tttataccgc | ctatgtgcag | aacaccgcgt | tctggttgcc | ttacttgcag | 720 |
| ctgtgggtga | tggtgaacat | gttcgtgttg | ttcgccaact | tctatcgcaa | gcgctacaag | 780 |
| agcaagggtg | ccaagaagca | gtaa | | | | 804 |

<210> SEQ ID NO 34
<211> LENGTH: 807
<212> TYPE: DNA
<213> ORGANISM: Artificial Sequence
<220> FEATURE:
<223> OTHER INFORMATION: Codon-optimized open reading frame for
      expression of Pyramimonas cordata 5-elongase in plants (version 1)

<400> SEQUENCE: 34

| | | | | | | |
|---|---|---|---|---|---|---|
| atggcctcta | tcgctatccc | tgctgctctt | gctggaactc | ttggatacgt | tacctacaat | 60 |
| gtggctaacc | ctgatatccc | agcttctgag | aaagttcctg | cttacttcat | gcaggttgag | 120 |
| tactggggac | ctactatcgg | aactattgga | tacctcctct | tcatctactt | cggaaagcgt | 180 |
| atcatgcaga | acagatctca | accttttcgga | ctcaagaacg | ctatgctcgt | ttacaacttc | 240 |
| taccagacct | tcttcaacag | ctactgcatc | taccttttcg | ttacttctca | tagggctcag | 300 |
| ggacttaagg | tttggggaaa | catccctgat | atgactgcta | actcttgggg | aatctctcag | 360 |
| gttatctggc | ttcactacaa | caacaagtac | gttgagcttc | tcgacacctt | cttcatggtg | 420 |
| atgaggaaga | agttcgacca | gctttctttc | cttcacatct | accaccacac | tcttctcatc | 480 |
| tggtcatggt | tcgttgttat | gaagcttgag | cctgttggag | attgctactt | cggatcttct | 540 |
| gttaacacct | tcgtgcacgt | gatcatgtac | tcttactacg | gacttgctgc | tcttggagtt | 600 |
| aactgtttct | ggaagaagta | catcacccag | atccagatgc | ttcagttctg | tatctgtgct | 660 |
| tctcactcta | tctacaccgc | ttacgttcag | aataccgctt | tctggcttcc | ttaccttcaa | 720 |
| ctctgggtta | tggtgaacat | gttcgttctc | ttcgccaact | tctaccgtaa | gaggtacaag | 780 |
| tctaagggtg | ctaagaagca | gtgataa | | | | 807 |

<210> SEQ ID NO 35
<211> LENGTH: 867
<212> TYPE: DNA
<213> ORGANISM: Artificial Sequence -continued

```
<220> FEATURE:
<223> OTHER INFORMATION: Codon-optimized open reading frame for
      expression of Pyramimonas cordata 5-elongase in plants (version 2)

<400> SEQUENCE: 35
atggaatttg ctcaacctct cgttgctatg gctcaagagc agtacgctgc tatcgatgct     60
gttgttgctc ctgctatctt ctctgctacc gactctattg gatggggact caagcctatc    120
tcttctgcta ctaaggatct ccctctcgtt gaatctccta cccctcttat cctttctctc    180
ctcgcttact cgctatcgt tggttctgga ctcgtttacc gtaaagtgtt ccctagaacc     240
gttaagggac aggatccttt ccttctcaag gctcttatgc tcgctcacaa cgttttcctt    300
atcggactca gcctttacat gtgcctcaag ctcgtttacg aggcttacgt gaacaagtac    360
tccttctggg aaacgctta caaccctgct caaaccgaga tggctaaggt gatctggatc     420
ttctacgtgt ccaagatcta cgagttcatg gacaccttca tcatgcttct caagggaaac    480
gttaaccagg tttccttcct ccatgtttac caccacggat ctatctctgg aatctggtgg    540
atgatcactt atgctgctcc aggtggagat gcttacttct ctgctgctct caactcttgg    600
gttcatgtgt gcatgtacac ctactacttc atggctgctg ttcttcctaa ggacgaaaag    660
accaagagaa agtaccttttg gtggggaaga taccttaccc agatgcaaat gttccagttc    720
ttcatgaacc ttctccaggc tgttacctc ctctactctt cttctcctta ccctaagttc     780
attgctcaac tcctcgttgt ttacatggtt accctcctca tgcttttcgg aaacttctac    840
tacatgaagc accacgcttc taagtga                                        867

<210> SEQ ID NO 36
<211> LENGTH: 807
<212> TYPE: DNA
<213> ORGANISM: Artificial Sequence
<220> FEATURE:
<223> OTHER INFORMATION: Codon-optimized open reading frame for
      expression of Pyramimonas cordata 5-elongase in plants (version 3)

<400> SEQUENCE: 36
atggcttcta tcgctatccc tgctgctctt gctggaactc ttggatacgt gacctacaac     60
gtggctaacc ctgatattcc tgcttctgag aaggttccag cttacttcat gcaagtggag    120
tactggggac ctactatcgg aactatcggt tacctcctct tcatctactt cggaaagcgt    180
atcatgcaaa acagaagcca gccttttcgga cttaagaacg ctatgctcgt gtacaacttc    240
taccagacct tcttcaacag ctactgcatc tacctcttcg ttacctctca tagggctcag    300
ggacttaaag tttggggaaa catccctgat atgaccgcta actcttgggg aatctctcag    360
gttatctggc tccactacaa caacaagtac gtggagcttc tcgatacctt cttcatggtg    420
atgaggaaga agttcgacca gctttctttc cttcacatct accaccacac tcttctcatc    480
tggtcatggt tcgtggttat gaagctcgag cctgttggag attgctactt cggatctagc    540
gttaacacct tcgtgcacgt gatcatgtac tcttactacg gacttgctgc tcttggagtt    600
aactgcttct ggaagaagta catcacccag atccagatgc ttcagttctg tatctgcgct    660
tctcactcta tctacaccgc ttacgttcag aacactgctt tctggcttcc ttaccttcag    720
ctctgggtga tggttaacat gttcgtgctc ttcgctaact tctaccgtaa aggtacaag     780 agcaagggtg ctaagaagca gtgataa                                        807

<210> SEQ ID NO 37
<211> LENGTH: 267
<212> TYPE: PRT
```

<213> ORGANISM: Pyramimonas cordata

<400> SEQUENCE: 37

```
Met Ala Ser Ile Ala Ile Pro Ala Leu Ala Gly Thr Leu Gly Tyr
1               5                   10                  15

Val Thr Tyr Asn Val Ala Asn Pro Asp Ile Pro Ala Ser Glu Lys Val
            20                  25                  30

Pro Ala Tyr Phe Met Gln Val Glu Tyr Trp Gly Pro Thr Ile Gly Thr
        35                  40                  45

Ile Gly Tyr Leu Leu Phe Ile Tyr Phe Gly Lys Arg Ile Met Gln Asn
    50                  55                  60

Arg Ser Gln Pro Phe Gly Leu Lys Asn Ala Met Leu Val Tyr Asn Phe
65                  70                  75                  80

Tyr Gln Thr Phe Phe Asn Ser Tyr Cys Ile Tyr Leu Phe Val Thr Ser
                85                  90                  95

His Arg Ala Gln Gly Leu Lys Val Trp Gly Asn Ile Pro Asp Met Thr
            100                 105                 110

Ala Asn Ser Trp Gly Ile Ser Gln Val Ile Trp Leu His Tyr Asn Asn
        115                 120                 125

Lys Tyr Val Glu Leu Leu Asp Thr Phe Met Val Met Arg Lys Lys
    130                 135                 140

Phe Asp Gln Leu Ser Phe Leu His Ile Tyr His Thr Leu Leu Ile
145                 150                 155                 160

Trp Ser Trp Phe Val Met Lys Leu Glu Pro Val Gly Asp Cys Tyr
                165                 170                 175

Phe Gly Ser Ser Val Asn Thr Phe Val His Val Ile Met Tyr Ser Tyr
            180                 185                 190

Tyr Gly Leu Ala Ala Leu Gly Val Asn Cys Phe Trp Lys Lys Tyr Ile
        195                 200                 205

Thr Gln Ile Gln Met Leu Gln Phe Cys Ile Cys Ala Ser His Ser Ile
    210                 215                 220

Tyr Thr Ala Tyr Val Gln Asn Thr Ala Phe Trp Leu Pro Tyr Leu Gln
225                 230                 235                 240

Leu Trp Val Met Val Asn Met Phe Val Leu Phe Ala Asn Phe Tyr Arg
                245                 250                 255

Lys Arg Tyr Lys Ser Lys Gly Ala Lys Lys Gln
            260                 265
```

<210> SEQ ID NO 38
<211> LENGTH: 1344
<212> TYPE: DNA
<213> ORGANISM: Pavlova salina

<400> SEQUENCE: 38

```
atgcctccga gcgcggcgaa gcagatgggc gcgagcacgg gcgtgcatgc gggcgtcaca      60
gattcgtcgg ccttcacgcg caaggatgtc gccgacaggc cggacctcac gatcgtgggt     120
gacagcgtgt acgatgcgaa ggcgttccgc tccgagcatc cgggtggcgc gcactttgtg     180
tcgctgttcg gcgggcgcga tgccaccgag gcgttcatgg agtaccaccg gcgcgcctgg     240
cccaagtcgc gcatgtcgcg cttccacgtc ggctctctgg catcgaccga ggagcccgtc     300
gccgccgatg agggctacct ccagctgtgc gctcgcatcg ccaagatggt gccgtcggtc     360
agcagcgggt tcgcgccggc gtcgtactgg gtgaaggccg gctgatcct cggctccgcg     420 atcgcgctcg aggcgtacat gctgtacgcg ggcaagcgcc tgctcccgtc gatcgtgctc     480
```

```
gggtggctgt tgcgctgat tggcctgaac atccagcacg atgccaacca cggcgcgctc      540
tccaagtcgg cctcggtcaa cctggcgctc gggttgtgcc aggactggat cggcgggagc      600
atgatcctct ggctgcagga gcacgttgtc atgcaccact gcacaccaa cgacgttgac       660
aaggacccgg accagaaggc gcacggcgcc ctgcggctca agccgaccga cgcgtggagc      720
ccgatgcact ggctgcagca cctctacctg ctgcctgggg agacgatgta cgccttcaag      780
ctgctgtttc tcgacatcag cgagctggtg atgtggcggt gggagggcga gcccatcagc      840
aagctggccg ggtacctctt catgccctcg ctgctcctca agctcacctt ctgggcgcgc      900
tttgtcgcgc tgccgctgta cctcgcgccc agcgtgcaca cggcggtgtg catcgcggcg      960
acggtaatga cggggagctt ctacctcgcc ttcttcttct tcatctcgca caacttcgag     1020
ggcgtggcga gcgtcggacc ggacggcagc atcaccagca tgacgcgcgg cgcatccttc     1080
ctcaagcggc aggccgagac ctcgtccaac gtgggcggcc cgctgctcgc cacgctcaac     1140
ggcggcctca actaccaaat cgagcaccac ctcttcccca gggtgcacca cggcttctac     1200
cctcgcctcg cgccgttggt caaggcggag ctcgaggcgc gcggcattga gtacaagcac     1260
taccccacca tatggagcaa cctggcatcc acgctgaggc acatgtacgc gctcggccgc     1320
aggccgcgca gcaaggcgga gtga                                            1344
```

<210> SEQ ID NO 39
<211> LENGTH: 1347
<212> TYPE: DNA
<213> ORGANISM: Artificial Sequence
<220> FEATURE:
<223> OTHER INFORMATION: Codon-optimized open reading frame for
      expression of Pavlova salina 4-desaturase in plants (version 1)

<400> SEQUENCE: 39

```
atgccaccta gcgctgctaa gcaaatggga gcttctactg gtgttcatgc tggtgttact       60
gactcttctg ctttcaccag aaaggatgtt gctgatagac ctgatctcac catcgttgga     120
gattctgttt acgatgctaa ggctttcaga tctgagcatc ctggtggtgc tcatttcgtt     180
tctttgttcg gaggaagaga tgctactgag gctttcatgg aataccatag aagggcttgg     240
cctaagtcta gaatgtctag attccacgtt ggatctcttg cttctactga ggaacctgtt     300
gctgctgatg agggatacct tcaactttgt gctaggatcg ctaagatggt gccttctgtt     360
tcttctggat cgctcctgc ttcttactgg gttaaggctg acttatcct tggatctgct      420
atcgctcttg aggcttacat gctttacgct ggaaagagac ttctcccttc tatcgttctt     480
ggatggcttt cgctcttat cggtcttaac atccagcatg atgctaacca tggtgctttg     540
tctaagtctg cttctgttaa ccttgctctt ggactttgtc aggattggat cggaggatct     600
atgatccttt ggcttcaaga gcatgttgtt atgcaccacc tccacactaa cgatgttgat     660
aaggatcctg atcaaaaggc tcacggtgct cttagactca agcctactga tgcttggtca    720
cctatgcatt ggcttcagca tctttacctt ttgcctggtg agactatgta cgcttttcaag   780
cttttgttcc tcgacatctc tgagcttgtt atgtggcgtt gggagggtga gcctatctct   840
aagcttgctg ataccctctt tatgccttct tgcttctca gcttaccttt ctgggctaga    900
ttcgttgctt tgcctcttta ccttgctcct tctgttcata ctgctgtgtg tatcgctgct   960
actgttatga ctggatcttt ctacctcgct ttcttcttct tcatctccca caacttcgag    1020
ggtgttgctt ctgttggacc tgatggatct atcacttcta tgactagagg tgctagcttc   1080
cttaagagac aagctgagac ttcttctaac gttggaggac ctcttcttgc tactcttaac   1140
```

```
ggtggactca actaccaaat tgagcatcac ttgttcccta gagttcacca tggattctac      1200
cctagacttg ctcctcttgt taaggctgag cttgaggcta gaggaatcga gtacaagcac      1260
taccctacta tctggtctaa ccttgcttct accctcagac atatgtacgc tcttggaaga      1320
aggcctagat ctaaggctga gtaatga                                          1347

<210> SEQ ID NO 40
<211> LENGTH: 1347
<212> TYPE: DNA
<213> ORGANISM: Artificial Sequence
<220> FEATURE:
<223> OTHER INFORMATION: Codon-optimized open reading frame for
      expression of Pavlova salina 4-desaturase in plants (version 2)

<400> SEQUENCE: 40
atgcctccat ctgctgctaa acagatggga gcttctactg gtgttcacgc tggtgttacc        60
gattcttctg ctttcaccag aaaggatgtg gctgatagac ctgatcttac catcgttggt       120
gactctgtgt acgatgctaa ggctttcaga tctgagcatc ctggtggtgc tcatttcgtt       180
tcactcttcg gaggaagaga tgctactgag gctttcatgg aataccacag aagagcttgg       240
cctaagtcta ggatgtctag gttccatgtt ggatctcttg cttctaccga ggaacctgtt       300
gctgctgatg agggatacct tcagctttgt gctaggatcg ctaagatggt gccttctgtg       360
tcatctggat cgctccagc ttcttactgg gttaaggctg gacttatcct cggatctgct       420
atcgctcttg aggcttacat gctctacgct ggaaagagac ttctcccttc tatcgttctt       480
ggatggctct tcgctcttat cggacttaac atccagcatg acgctaacca tggtgctttg       540
tctaagtctg ctagcgttaa ccttgctctt ggactttgtc aggattggat cggaggatct       600
atgatccttt ggctccaaga gcatgttgtt atgcaccacc tccacaccaa cgatgttgat       660
aaggaccctg atcaaaaggc tcatggtgct cttagactca gcctaccga tgcttggtca       720 cctatgcatt ggcttcagca cctttacctt ctccctggtg aaactatgta cgcttttcaag       780 ctcctcttcc tcgatatctc tgagcttgtg atgtggagat gggagggtga acctatctct       840
aagctcgctg atacctctt catgccttct cttctcctca gcttaccttg ctgggctaga       900
ttcgttgctc ttcctcttta cctcgctcct tctgttcata ctgctgtgtg tatcgctgct       960
actgttatga ccggaagctt ctaccttgct ttcttcttct tcatcagcca caacttcgag     1020
ggtgttgctt ctgttggacc tgatggatct atcacctcta tgaccagggg agcttctttc     1080
cttaagaggc aggctgagac ttcttctaat gtgggaggac tcttcttgc tactcttaac     1140 ggtggactca actaccaaat cgagcaccac cttttcccta gagttcacca cggattctac     1200
cctagacttg ctcctcttgt gaaggctgaa cttgaggcta gaggaatcga gtacaagcac     1260
taccctacca tctggtctaa cctcgcttct accctcagac atatgtacgc tcttggaaga     1320
aggcctagat ctaaggctga gtgatga                                          1347

<210> SEQ ID NO 41
<211> LENGTH: 447
<212> TYPE: PRT
<213> ORGANISM: Pavlova salina

<400> SEQUENCE: 41

Met Pro Pro Ser Ala Ala Lys Gln Met Gly Ala Ser Thr Gly Val His
1               5                   10                  15

Ala Gly Val Thr Asp Ser Ser Ala Phe Thr Arg Lys Asp Val Ala Asp
            20                  25                  30
```

```
Arg Pro Asp Leu Thr Ile Val Gly Asp Ser Val Tyr Asp Ala Lys Ala
        35                  40                  45
Phe Arg Ser Glu His Pro Gly Gly Ala His Phe Val Ser Leu Phe Gly
 50                  55                  60
Gly Arg Asp Ala Thr Glu Ala Phe Met Glu Tyr His Arg Arg Ala Trp
 65                  70                  75                  80
Pro Lys Ser Arg Met Ser Arg Phe His Val Gly Ser Leu Ala Ser Thr
                 85                  90                  95
Glu Glu Pro Val Ala Ala Asp Glu Gly Tyr Leu Gln Leu Cys Ala Arg
                100                 105                 110
Ile Ala Lys Met Val Pro Ser Val Ser Ser Gly Phe Ala Pro Ala Ser
                115                 120                 125
Tyr Trp Val Lys Ala Gly Leu Ile Leu Gly Ser Ala Ile Ala Leu Glu
130                 135                 140
Ala Tyr Met Leu Tyr Ala Gly Lys Arg Leu Leu Pro Ser Ile Val Leu
145                 150                 155                 160
Gly Trp Leu Phe Ala Leu Ile Gly Leu Asn Ile Gln His Asp Ala Asn
                165                 170                 175
His Gly Ala Leu Ser Lys Ser Ala Ser Val Asn Leu Ala Leu Gly Leu
                180                 185                 190
Cys Gln Asp Trp Ile Gly Gly Ser Met Ile Leu Trp Leu Gln Glu His
                195                 200                 205
Val Val Met His His Leu His Thr Asn Asp Val Asp Lys Asp Pro Asp
                210                 215                 220
Gln Lys Ala His Gly Ala Leu Arg Leu Lys Pro Thr Asp Ala Trp Ser
225                 230                 235                 240
Pro Met His Trp Leu Gln His Leu Tyr Leu Leu Pro Gly Glu Thr Met
                245                 250                 255
Tyr Ala Phe Lys Leu Leu Phe Leu Asp Ile Ser Glu Leu Val Met Trp
                260                 265                 270
Arg Trp Glu Gly Glu Pro Ile Ser Lys Leu Ala Gly Tyr Leu Phe Met
                275                 280                 285
Pro Ser Leu Leu Leu Lys Leu Thr Phe Trp Ala Arg Phe Val Ala Leu
290                 295                 300
Pro Leu Tyr Leu Ala Pro Ser Val His Thr Ala Val Cys Ile Ala Ala
305                 310                 315                 320
Thr Val Met Thr Gly Ser Phe Tyr Leu Ala Phe Phe Phe Ile Ser
                325                 330                 335
His Asn Phe Glu Gly Val Ala Ser Val Gly Pro Asp Gly Ser Ile Thr
                340                 345                 350
Ser Met Thr Arg Gly Ala Ser Phe Leu Lys Arg Gln Ala Glu Thr Ser
                355                 360                 365
Ser Asn Val Gly Gly Pro Leu Leu Ala Thr Leu Asn Gly Gly Leu Asn
                370                 375                 380
Tyr Gln Ile Glu His His Leu Phe Pro Arg Val His His Gly Phe Tyr
385                 390                 395                 400
Pro Arg Leu Ala Pro Leu Val Lys Ala Glu Leu Glu Ala Arg Gly Ile
                405                 410                 415
Glu Tyr Lys His Tyr Pro Thr Ile Trp Ser Asn Leu Ala Ser Thr Leu
                420                 425                 430
Arg His Met Tyr Ala Leu Gly Arg Arg Pro Arg Ser Lys Ala Glu
                435                 440                 445
```

<210> SEQ ID NO 42
<211> LENGTH: 792
<212> TYPE: DNA
<213> ORGANISM: Isochrysis galbana

<400> SEQUENCE: 42

| | | | | | |
|---|---|---|---|---|---|
| atggccctcg | caaacgacgc | gggagagcgc | atctgggcgg | ctgtgaccga | cccggaaatc | 60 |
| ctcattggca | ccttctcgta | cttgctactc | aaaccgctgc | tccgcaattc | cgggctggtg | 120 |
| gatgagaaga | agggcgcata | caggacgtcc | atgatctggt | acaacgttct | gctggcgctc | 180 |
| ttctctgcgc | tgagcttcta | cgtgacggcg | accgccctcg | gctgggacta | tggtacgggc | 240 |
| gcgtggctgc | gcaggcaaac | cggcgacaca | ccgcagccgc | tcttccagtg | cccgtccccg | 300 |
| gtttgggact | cgaagctctt | cacatggacc | gccaaggcat | tctattactc | caagtacgtg | 360 |
| gagtacctcg | acacggcctg | gctggtgctc | aagggcaaga | gggtctcctt | ctccaggcc | 420 |
| ttccaccact | tggcgcgcc | gtgggatgtg | tacctcggca | ttcggctgca | caacgagggc | 480 |
| gtatggatct | tcatgttttt | caactcgttc | attcacacca | tcatgtacac | ctactacggc | 540 |
| ctcaccgccg | ccgggtataa | gttcaaggcc | aagccgctca | tcaccgcgat | gcagatctgc | 600 |
| cagttcgtgg | gcggcttcct | gttggtctgg | gactacatca | acgtcccctg | cttcaactcg | 660 |
| gacaaaggga | agttgttcag | ctgggctttc | aactatgcat | acgtcggctc | ggtcttcttg | 720 |
| ctcttctgcc | acttttttcta | ccaggacaac | ttggcaacga | agaaatcggc | caaggcgggc | 780 |
| aagcagctct | ag | | | | | 792 |

<210> SEQ ID NO 43
<211> LENGTH: 263
<212> TYPE: PRT
<213> ORGANISM: Isochrysis galbana

<400> SEQUENCE: 43

Met Ala Leu Ala Asn Asp Ala Gly Glu Arg Ile Trp Ala Ala Val Thr
1               5                   10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

```
Leu Ile Thr Ala Met Gln Ile Cys Gln Phe Val Gly Phe Leu Leu
            195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260
```

<210> SEQ ID NO 44
<211> LENGTH: 801
<212> TYPE: DNA
<213> ORGANISM: Emiliania huxleyi

<400> SEQUENCE: 44

```
atgctcgatc gcgcctcgtc cgacgcggcc atctggtctg cggtgtccga tccggaaatc      60
ctgatcggca ctttctccta cctgctgctc aagccgctgc tacgcaactc agggctcgtg     120
gacgagcgga aggcgcctac ccggacctcg atgatctggt acaacgtggt gctcgcgctc     180
ttctccgcga cgagcttcta cgtgactgcg accgcgctcg gtgggacaaa gggcaccggc     240
gagtggctcc gcagtctcac gggcgacagc ccgcagcagc tgtggcaatg cccgtcgagg     300
gtatgggact ccaagctgtt cctgtggacg gccaaggcct tctactactc aaagtacgtg     360
gagtacctcg acacggcgtg gctcgtcctc aaggggaaga aggtctcctt cctgcagggc     420
ttccaccact ttggcgcgcc gtgggacgtg tacctgggca ttcggctgaa gaacgagggc     480
gtgtggatct tcatgttctt caactcgttc atccacacgg tcatgtacac gtactacggc     540
ctcaccgccg cgggctacaa gatccgcggc aagccgatca tcaccgcgat gcaaataagc     600
cagttcgtcg gcggctttgt cctagtgtgg gactacatca acgtgccgtg cttccacgcc     660
gacgccgggc aggtcttcag ctgggtcttt aactatgctt acgtcggctc cgtctttctg     720
ctgttctgcc acttcttcta catggacaac atcgcgaagg ccaaggccaa gaaggccgtc     780
gctacccgca aggcgctgtg a                                              801
```

<210> SEQ ID NO 45
<211> LENGTH: 801
<212> TYPE: DNA
<213> ORGANISM: Artificial Sequence
<220> FEATURE:
<223> OTHER INFORMATION: Codon-optimized open reading frame for
      expression of Emiliania huxleyi 9-elongase in plants

<400> SEQUENCE: 45

```
atgcttgata gagcttcatc tgatgctgct atttggagcg ctgttctga tcctgagatc       60 cttatcggaa ccttctctta ccttttgctt aagcctctcc tcagaaactc tggacttgtg     120
gatgagagaa agggagctta ccgtacttct atgatctggt acaacgttgt tcttgctctc     180
ttctctgcta cctctcttta cgttactgct actgctcttg gatgggataa gggaactggt     240
gagtggctta gatctcttac tggtgattct cctcaacaac tttggcagtg cccttctaga     300
gtttgggaca gcaaactctt cttgtggact gctaagcct tctactactc aagtacgtt      360 gagtaccttg atactgcttg gcttgttctc aagggaaaga aggtttcatt cctccaggga     420
ttccatcatt tcggtgctcc atgggatgtt taccttggaa tcaggcttaa gaacgaggga     480
gtttggatct tcatgttctt caacagcttc atccacactg ttatgtacac ttactacgga     540
```

```
cttactgctg ctggatacaa gatcagagga aagcctatca tcaccgctat gcaaatctct    600
caattcgttg gtggattcgt tcttgtgtgg gactacatca acgttccttg tttccatgct    660
gatgctggac aagttttctc ttgggtgttc aactacgctt atgtgggatc tgttttcctt    720
cttttctgcc acttcttcta catggacaac attgctaagg ctaaggctaa aaaggctgtt    780
gctaccagaa aggctctttg a                                              801
```

<210> SEQ ID NO 46
<211> LENGTH: 266
<212> TYPE: PRT
<213> ORGANISM: Emiliania huxleyi

<400> SEQUENCE: 46

```
Met Leu Asp Arg Ala Ser Ser Asp Ala Ala Ile Trp Ser Ala Val Ser
1               5                   10                  15

Asp Pro Glu Ile Leu Ile Gly Thr Phe Ser Tyr Leu Leu Lys Pro
            20                  25                  30

Leu Leu Arg Asn Ser Gly Leu Val Asp Glu Arg Lys Gly Ala Tyr Arg
        35                  40                  45

Thr Ser Met Ile Trp Tyr Asn Val Val Leu Ala Leu Phe Ser Ala Thr
    50                  55                  60

Ser Phe Tyr Val Thr Ala Thr Ala Leu Gly Trp Asp Lys Gly Thr Gly
65                  70                  75                  80

Glu Trp Leu Arg Ser Leu Thr Gly Asp Ser Pro Gln Gln Leu Trp Gln
                85                  90                  95

Cys Pro Ser Arg Val Trp Asp Ser Lys Leu Phe Leu Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Lys Val Ser Phe Leu Gln Gly Phe His His Phe
    130                 135                 140

Gly Ala Pro Trp Asp Val Tyr Leu Gly Ile Arg Leu Lys Asn Glu Gly
145                 150                 155                 160

Val Trp Ile Phe Met Phe Phe Asn Ser Phe Ile His Thr Val Met Tyr
                165                 170                 175

Thr Tyr Tyr Gly Leu Thr Ala Ala Gly Tyr Lys Ile Arg Gly Lys Pro
            180                 185                 190

Ile Ile Thr Ala Met Gln Ile Ser Gln Phe Val Gly Gly Phe Val Leu
        195                 200                 205

Val Trp Asp Tyr Ile Asn Val Pro Cys Phe His Ala Asp Ala Gly Gln
    210                 215                 220

Val Phe Ser Trp Val Phe Asn Tyr Ala Tyr Val Gly Ser Val Phe Leu
225                 230                 235                 240

Leu Phe Cys His Phe Phe Tyr Met Asp Asn Ile Ala Lys Ala Lys Ala
                245                 250                 255

Lys Lys Ala Val Ala Thr Arg Lys Ala Leu
            260                 265
```

<210> SEQ ID NO 47
<211> LENGTH: 819
<212> TYPE: DNA
<213> ORGANISM: Pavlova pinguis

<400> SEQUENCE: 47

```
atggttgcgc cacccatcac gctcgagtgg ctgctttcgc cgaagctcaa ggatgcagtg    60
```

```
ttcggtgggg aggtgctcta cttctccatt gcctacctgt ttcttgcgcc catttttgaag    120 cgcacccccgt tggtggacac gcggaagggc gcgtataaga gtggtatgat cgcgtacaac    180
gtgatcatgt gcgtgttctc gctggtgtgc ttcatctgcc agctcgcagc cctgggctat    240
gacatgggct acttgcagtg ggtgcgtgac ctcacagggg acgagattgt cccctctac     300 caggacgtgt ccccgtcccc cgccttctcc aacaagctct tcaagtattc gtctattgcc    360
ttccactact ccaagtatgt tgagtacatg gacaccgcat ggctggtgat gaagggcaag    420
cccgtgtcct gctccaggg cttccaccac tttggcgccg cctgggacac ctactttggc     480
atcaccttcc agaacgaggg catctacgtg ttcgtggtgc tcaacgcctt catccacacg    540
atcatgtacg catactacgc ggccactgcg gcgggtctca agttctcact gaagttcgtc    600
atcacgctca tgcagatcac ccaattcaac gtgggcttcg taatggtgta tcactacatc    660
accctggagt acttccgcaa ctcaccggag ctcgtcttct cctacctttt caactatgcg    720
tacgtctgca cggttctcct cctcttcatg cagttcttct acatggacaa ctttggcaag    780
aagaaggccg ctgccgccgc gggcaagaag aagaagtag                            819
```

<210> SEQ ID NO 48
<211> LENGTH: 272
<212> TYPE: PRT
<213> ORGANISM: Pavlova pinguis

<400> SEQUENCE: 48

```
Met Val Ala Pro Pro Ile Thr Leu Glu Trp Leu Leu Ser Pro Lys Leu
1               5                   10                  15

Lys Asp Ala Val Phe Gly Gly Glu Val Leu Tyr Phe Ser Ile Ala Tyr
                20                  25                  30

Leu Phe Leu Ala Pro Ile Leu Lys Arg Thr Pro Leu Val Asp Thr Arg
            35                  40                  45

Lys Gly Ala Tyr Lys Ser Gly Met Ile Ala Tyr Asn Val Ile Met Cys
50                  55                  60

Val Phe Ser Leu Val Cys Phe Ile Cys Gln Leu Ala Ala Leu Gly Tyr
65                  70                  75                  80

Asp Met Gly Tyr Leu Gln Trp Val Arg Asp Leu Thr Gly Asp Glu Ile
                85                  90                  95

Val Pro Leu Tyr Gln Asp Val Ser Pro Ser Pro Ala Phe Ser Asn Lys
            100                 105                 110

Leu Phe Lys Tyr Ser Ser Ile Ala Phe His Tyr Ser Lys Tyr Val Glu
        115                 120                 125

Tyr Met Asp Thr Ala Trp Leu Val Met Lys Gly Lys Pro Val Ser Leu
130                 135                 140

Leu Gln Gly Phe His His Phe Gly Ala Ala Trp Asp Thr Tyr Phe Gly
145                 150                 155                 160

Ile Thr Phe Gln Asn Glu Gly Ile Tyr Val Phe Val Leu Asn Ala
                165                 170                 175

Phe Ile His Thr Ile Met Tyr Ala Tyr Tyr Ala Ala Thr Ala Ala Gly
            180                 185                 190

Leu Lys Phe Ser Leu Lys Phe Val Ile Thr Leu Met Gln Ile Thr Gln
        195                 200                 205

Phe Asn Val Gly Phe Val Met Val Tyr His Tyr Ile Thr Leu Glu Tyr
210                 215                 220

Phe Arg Asn Ser Pro Glu Leu Val Phe Ser Tyr Leu Phe Asn Tyr Ala
225                 230                 235                 240
```

```
Tyr Val Cys Thr Val Leu Leu Leu Phe Met Gln Phe Phe Tyr Met Asp
                245                 250                 255

Asn Phe Gly Lys Lys Lys Ala Ala Ala Ala Ala Gly Lys Lys Lys Lys
            260                 265                 270
```

<210> SEQ ID NO 49
<211> LENGTH: 840
<212> TYPE: DNA
<213> ORGANISM: Pavlova salina

<400> SEQUENCE: 49

```
atggcgactg aagggatgcc ggcgataacg ctggactggc tgctctcgcc cgggctgaag     60
gatgccgtaa ttggcgggga ggtgctctac ttttcgcttg gtatctgct gctcgagccc    120
atcctcaagc gctcaccgtt tgtggacaag cgcaagggcg cataccgcaa cggcatgatc    180
gcgtacaaca tcctcatgtg cggtttctcg ctggtatgct tcgtgtgcca gatggcggcg    240
ctcggccttg atcgcggcca cctgcagttt gtccgcgacc tcacgggcga cagcgtggtg    300
cagctctacc aggacgtgag cccatcccct gcattcgcga acaagctctt ccggtactca    360
gcggtggcgt tccactactc aaagtacgtg gagtacatgg acacagcgtg gcttgtgctg    420
aagggcaagc ccgtctcgtt cctgcagggc ttccaccact tcggcgccgc gtgggacacc    480
tactttggca tcacgtttca gaacgagggc acctacgtct ttgtgctgct caacgcattc    540
atccacacaa tcatgtacac ctactacggc gcgacggcag cgggcatcaa aatctcgatg    600
aagccgctga tcaccctcat gcagatcacg cagttcctgc tgggcttcgc gctcgtctac    660
ccgtacattg acctcggcta cttccgtgcg tcgcccgagc tcgtgtggag ctacctgttc    720
aactatgcgt acgtactcat ggtgctcttc ctcttcatgc gcttcttcta ccacgacaac    780
tttagcaagc acaagccaat ctcgcgcatc gactccagca ccgcatgaa aaccgagtag     840
```

<210> SEQ ID NO 50
<211> LENGTH: 279
<212> TYPE: PRT
<213> ORGANISM: Pavlova salina

<400> SEQUENCE: 50

```
Met Ala Thr Glu Gly Met Pro Ala Ile Thr Leu Asp Trp Leu Leu Ser
1               5                   10                  15

Pro Gly Leu Lys Asp Ala Val Ile Gly Gly Glu Val Leu Tyr Phe Ser
            20                  25                  30

Leu Gly Tyr Leu Leu Leu Glu Pro Ile Leu Lys Arg Ser Pro Phe Val
        35                  40                  45

Asp Lys Arg Lys Gly Ala Tyr Arg Asn Gly Met Ile Ala Tyr Asn Ile
    50                  55                  60

Leu Met Cys Gly Phe Ser Leu Val Cys Phe Val Cys Gln Met Ala Ala
65                  70                  75                  80

Leu Gly Leu Asp Arg Gly His Leu Gln Phe Val Arg Asp Leu Thr Gly
                85                  90                  95

Asp Ser Val Val Gln Leu Tyr Gln Asp Val Ser Pro Ser Pro Ala Phe
            100                 105                 110

Ala Asn Lys Leu Phe Arg Tyr Ser Ala Val Ala Phe His Tyr Ser Lys
        115                 120                 125

Tyr Val Glu Tyr Met Asp Thr Ala Trp Leu Val Leu Lys Gly Lys Pro
    130                 135                 140

Val Ser Phe Leu Gln Gly Phe His His Phe Gly Ala Ala Trp Asp Thr
```

```
                145                 150                 155                 160
Tyr Phe Gly Ile Thr Phe Gln Asn Glu Gly Thr Tyr Val Phe Val Leu
                    165                 170                 175
Leu Asn Ala Phe Ile His Thr Ile Met Tyr Thr Tyr Tyr Gly Ala Thr
                    180                 185                 190
Ala Ala Gly Ile Lys Ile Ser Met Lys Pro Leu Ile Thr Leu Met Gln
                    195                 200                 205
Ile Thr Gln Phe Leu Leu Gly Phe Ala Leu Val Tyr Pro Tyr Ile Asp
        210                 215                 220
Leu Gly Tyr Phe Arg Ala Ser Pro Glu Leu Val Trp Ser Tyr Leu Phe
225                 230                 235                 240
Asn Tyr Ala Tyr Val Leu Met Val Leu Phe Leu Phe Met Arg Phe Phe
                    245                 250                 255
Tyr His Asp Asn Phe Ser Lys His Lys Pro Ile Ser Arg Ile Asp Ser
                260                 265                 270
Ser Asn Arg Met Lys Thr Glu
        275

<210> SEQ ID NO 51
<211> LENGTH: 1284
<212> TYPE: DNA
<213> ORGANISM: Pavlova salina

<400> SEQUENCE: 51
```

| | | | | | |
|---|---|---|---|---|---|
| atgggacgcg | gcggagacag | cagtgggcag | gcgcatccgg | cggcggagct | ggcggtcccg | 60 |
| agcgaccgcg | cggaggtgag | caacgctgac | agcaaagcgc | tgcacatcgt | gctgtatggc | 120 |
| aagcgcgtgg | atgtgaccaa | gttccaacgc | acgcacccgg | gtggtagcaa | ggtcttccgg | 180 |
| atcttccagg | accgcgatgc | gacggagcag | ttcgagtcct | accactcgaa | gcgcgcgatc | 240 |
| aagatgatgg | agggcatgct | caagaagtct | gaggatgctc | ccgccgacac | gcccttgccc | 300 |
| tcccagtcac | cgatggggaa | ggacttcaag | gcgatgatcg | agcggcacgt | tgcagcgggt | 360 |
| tactacgatc | catgcccgct | cgatgagctg | ttcaagctca | gcctcgtgct | cctcccgacc | 420 |
| tttgcgggca | tgtacatgct | caaggcgggc | gtcggctccc | cgctctgcgg | cgccctcatg | 480 |
| gtgagctttg | gctggtacct | cgatggctgg | ctcgcgcacg | actatctgca | ccactccgtc | 540 |
| ttcaagggt | ccgtcgcacg | caccgtcggg | tggaacaacg | cggcgggcta | cttcctcggc | 600 |
| ttcgtgcagg | ggtatgcggt | cgagtggtgg | cgcgcgcggc | ataacacgca | ccacgtgtgc | 660 |
| accaatgagg | acgctcgga | ccccgacatc | aaaacggcgc | cgctgctcat | atacgtgcgc | 720 |
| aacaagccga | gcatcgccaa | gcgcctgaac | gccttccagc | gctaccagca | gtactactat | 780 |
| gtgccggtga | tggcaatcct | cgacctgtac | tggcggctcg | agtcgatcgc | ctacgtcgcg | 840 |
| atgcgcctgc | cgaagatgct | gccgcaggcc | ctcgcactcg | tcgcgcacta | cgccatcgtc | 900 |
| gcgtgggtct | ttgcgggcaa | ctaccacctg | ctcccgctcg | tgacggttct | gcgcgggttt | 960 |
| ggcactggga | tcaccgttttt | cgcgacgcac | tacggtgagg | acattctcga | gcggaccag | 1020 |
| gtgcgtcaca | tgacgctcgt | cgagcagacg | gcactcacct | cgcgcaacat | tcgggcggc | 1080 |
| tggctcgtga | acgtgctcac | cggcttcatc | tcactgcaga | cggagcacca | cctgttcccg | 1140 |
| atgatgccaa | ccggcaacct | catgactatc | cagcccgagg | tgcgcgcctt | cttcaagaag | 1200 |
| cacggacttg | agtaccgcga | gggcaacctc | attgagtgcg | tgcggcagaa | catccgtgcg | 1260 |
| cttgcattcg | agcacctgct | ttga | | | | 1284 |

<210> SEQ ID NO 52
<211> LENGTH: 427
<212> TYPE: PRT
<213> ORGANISM: Pavlova salina

<400> SEQUENCE: 52

```
Met Gly Arg Gly Gly Asp Ser Ser Gly Gln Ala His Pro Ala Ala Glu
1               5                   10                  15

Leu Ala Val Pro Ser Asp Arg Ala Glu Val Ser Asn Ala Asp Ser Lys
            20                  25                  30

Ala Leu His Ile Val Leu Tyr Gly Lys Arg Val Asp Val Thr Lys Phe
        35                  40                  45

Gln Arg Thr His Pro Gly Gly Ser Lys Val Phe Arg Ile Phe Gln Asp
    50                  55                  60

Arg Asp Ala Thr Glu Gln Phe Glu Ser Tyr His Ser Lys Arg Ala Ile
65                  70                  75                  80

Lys Met Met Glu Gly Met Leu Lys Lys Ser Glu Asp Ala Pro Ala Asp
                85                  90                  95

Thr Pro Leu Pro Ser Gln Ser Pro Met Gly Lys Asp Phe Lys Ala Met
            100                 105                 110

Ile Glu Arg His Val Ala Ala Gly Tyr Tyr Asp Pro Cys Pro Leu Asp
        115                 120                 125

Glu Leu Phe Lys Leu Ser Leu Val Leu Leu Pro Thr Phe Ala Gly Met
    130                 135                 140

Tyr Met Leu Lys Ala Gly Val Gly Ser Pro Leu Cys Gly Ala Leu Met
145                 150                 155                 160

Val Ser Phe Gly Trp Tyr Leu Asp Gly Trp Leu Ala His Asp Tyr Leu
                165                 170                 175

His His Ser Val Phe Lys Gly Ser Val Ala Arg Thr Val Gly Trp Asn
            180                 185                 190

Asn Ala Ala Gly Tyr Phe Leu Gly Phe Val Gln Gly Tyr Ala Val Glu
        195                 200                 205

Trp Trp Arg Ala Arg His Asn Thr His His Val Cys Thr Asn Glu Asp
    210                 215                 220

Gly Ser Asp Pro Asp Ile Lys Thr Ala Pro Leu Leu Ile Tyr Val Arg
225                 230                 235                 240

Asn Lys Pro Ser Ile Ala Lys Arg Leu Asn Ala Phe Gln Arg Tyr Gln
                245                 250                 255

Gln Tyr Tyr Tyr Val Pro Val Met Ala Ile Leu Asp Leu Tyr Trp Arg
            260                 265                 270

Leu Glu Ser Ile Ala Tyr Val Ala Met Arg Leu Pro Lys Met Leu Pro
        275                 280                 285

Gln Ala Leu Ala Leu Val Ala His Tyr Ala Ile Val Ala Trp Val Phe
    290                 295                 300

Ala Gly Asn Tyr His Leu Leu Pro Leu Val Thr Val Leu Arg Gly Phe
305                 310                 315                 320

Gly Thr Gly Ile Thr Val Phe Ala Thr His Tyr Gly Glu Asp Ile Leu
                325                 330                 335

Asp Ala Asp Gln Val Arg His Met Thr Leu Val Glu Gln Thr Ala Leu
            340                 345                 350

Thr Ser Arg Asn Ile Ser Gly Gly Trp Leu Val Asn Val Leu Thr Gly
        355                 360                 365

Phe Ile Ser Leu Gln Thr Glu His His Leu Phe Pro Met Met Pro Thr
    370                 375                 380
```

```
Gly Asn Leu Met Thr Ile Gln Pro Glu Val Arg Ala Phe Phe Lys Lys
385                 390                 395                 400

His Gly Leu Glu Tyr Arg Glu Gly Asn Leu Ile Glu Cys Val Arg Gln
            405                 410                 415

Asn Ile Arg Ala Leu Ala Phe Glu His Leu Leu
            420                 425

<210> SEQ ID NO 53
<211> LENGTH: 172
<212> TYPE: PRT
<213> ORGANISM: Tomato bushy stunt virus

<400> SEQUENCE: 53

Met Glu Arg Ala Ile Gln Gly Asn Asp Ala Arg Glu Gln Ala Asn Ser
1               5                   10                  15

Glu Arg Trp Asp Gly Ser Gly Gly Thr Thr Ser Pro Phe Lys Leu
            20                  25                  30

Pro Asp Glu Ser Pro Ser Trp Thr Glu Trp Arg Leu His Asn Asp Glu
            35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Ala Pro Ile Glu Val Glu Ser Asn Val Ser Arg Gly Cys
145                 150                 155                 160

Pro Glu Gly Thr Glu Thr Phe Glu Lys Glu Ser Glu
                165                 170

<210> SEQ ID NO 54
<211> LENGTH: 116
<212> TYPE: PRT
<213> ORGANISM: Tomato yellow leaf curl virus

<400> SEQUENCE: 54

Met Trp Asp Pro Leu Leu Asn Glu Phe Pro Glu Ser Val His Gly Phe
1               5                   10                  15

Arg Cys Met Leu Ala Ile Lys Tyr Leu Gln Ser Val Glu Glu Thr Tyr
            20                  25                  30

Glu Pro Asn Thr Leu Gly His Asp Leu Ile Arg Asp Leu Ile Ser Val
        35                  40                  45

Val Arg Ala Arg Asp Tyr Val Glu Ala Thr Arg Arg Tyr Asn His Phe
    50                  55                  60

His Ala Arg Leu Glu Gly Ser Pro Lys Ala Glu Leu Arg Gln Pro Ile
65                  70                  75                  80

Gln Gln Pro Cys Cys Cys Pro His Cys Pro Arg His Lys Gln Ala Thr
                85                  90                  95

Ile Met Asp Val Gln Ala His Val Pro Glu Ala Gln Asn Ile Gln Asn
            100                 105                 110
```

Val Ser Lys Pro
        115

<210> SEQ ID NO 55
<211> LENGTH: 351
<212> TYPE: PRT
<213> ORGANISM: Turnip crinkle virus

<400> SEQUENCE: 55

Met Glu Asn Asp Pro Arg Val Arg Lys Phe Ala Ser Glu Gly Ala Gln
1               5                   10                  15

Trp Ala Ile Lys Trp Gln Lys Lys Gly Trp Ser Ser Leu Thr Ser Arg
            20                  25                  30

Gln Lys Gln Thr Ala Arg Ala Ala Met Gly Ile Lys Leu Ser Pro Val
        35                  40                  45

Ala Gln Pro Val Gln Lys Val Thr Arg Leu Ser Ala Pro Val Ala Leu
    50                  55                  60

Ala Tyr Arg Glu Val Ser Thr Gln Pro Arg Val Ser Thr Ala Arg Asp
65                  70                  75                  80

Gly Ile Thr Arg Ser Gly Ser Glu Leu Ile Thr Thr Leu Lys Lys Asn
                85                  90                  95

Thr Asp Thr Glu Pro Lys Tyr Thr Thr Ala Val Leu Asn Pro Ser Glu
            100                 105                 110

Pro Gly Thr Phe Asn Gln Leu Ile Lys Glu Ala Ala Gln Tyr Glu Lys
        115                 120                 125

Tyr Arg Phe Thr Ser Leu Arg Phe Arg Tyr Ser Pro Met Ser Pro Ser
    130                 135                 140

Thr Thr Gly Gly Lys Val Ala Leu Ala Phe Asp Arg Asp Ala Ala Lys
145                 150                 155                 160

Pro Pro Pro Asn Asp Leu Ala Ser Leu Tyr Asn Ile Glu Gly Cys Val
                165                 170                 175

Ser Ser Val Pro Trp Thr Gly Phe Ile Leu Thr Val Pro Thr Asp Ser
            180                 185                 190

Thr Asp Arg Phe Val Ala Asp Gly Ile Ser Asp Pro Lys Leu Val Asn
        195                 200                 205

Phe Gly Lys Leu Ile Met Ala Thr Tyr Gly Gln Gly Ala Asn Asp Ala
    210                 215                 220

Ala Gln Leu Gly Glu Val Arg Val Glu Tyr Thr Val Gln Leu Lys Asn
225                 230                 235                 240

Arg Thr Gly Ser Thr Ser Asp Ala Gln Ile Gly Asp Phe Ala Gly Val
                245                 250                 255

Lys Asp Gly Pro Arg Leu Val Ser Trp Ser Lys Thr Lys Gly Thr Ala
            260                 265                 270

Gly Trp Glu His Asp Cys His Phe Leu Gly Thr Gly Asn Phe Ser Leu
        275                 280                 285

Thr Leu Phe Tyr Glu Lys Ala Pro Val Ser Gly Leu Glu Asn Ala Asp
    290                 295                 300

Ala Ser Asp Phe Ser Val Leu Gly Glu Ala Ala Gly Ser Val Gln
305                 310                 315                 320

Trp Ala Gly Val Lys Val Ala Glu Arg Gly Gln Ser Val Lys Met Val
                325                 330                 335

Thr Thr Glu Glu Gln Pro Arg Gly Lys Trp Gln Ala Leu Arg Ile
            340                 345                 350

<210> SEQ ID NO 56

<211> LENGTH: 303
<212> TYPE: PRT
<213> ORGANISM: Pea mosaic virus

<400> SEQUENCE: 56

Met His Gly Ile Glu Gln Pro Gln Leu Pro Leu Asp Tyr Val His Arg
1               5                   10                  15

Cys Ala Ser Thr Ser Phe Leu Leu Ala Ser Leu Asp Gly Leu Leu Ser
            20                  25                  30

Glu Ala Arg Glu Leu Ser Gly Pro Leu Ala Leu Ile Thr Ser Ser Tyr
        35                  40                  45

Tyr Leu Leu Val Ser Ile Ala Leu Cys Trp Ala Ile Pro Gly Ser Phe
50                  55                  60

Trp Tyr Arg Pro Gly Cys Trp Leu Gln Pro Val Ser Gly Arg Asn Leu
65                  70                  75                  80

Ile Phe Cys Gly Pro Thr Glu Ala Leu Gln Arg Phe Arg Leu Tyr Ala
                85                  90                  95

Ala Arg Leu Gly Leu Val Leu Ser Glu Asn Cys Pro Arg His Gly Gln
            100                 105                 110

Ser Ala Ala Ile Thr Leu Gln Ser Tyr Trp Ala Leu Pro Asn Asn Ile
        115                 120                 125

Trp Met Asp Met Ala Gln Leu Asp Leu Leu Thr Phe Ser Met Pro Ile
130                 135                 140

Ala Asn Thr Phe Ala Tyr Leu Ala Asp Cys Glu Ala Arg Phe Pro Pro
145                 150                 155                 160

Ile Val Glu Gly Val Gly Ser Ala Tyr Tyr Val Pro Thr Leu Leu Gly
                165                 170                 175

Leu Thr His Gln Asp Pro Arg Leu Tyr Leu Ala Leu Arg Arg Arg Asn
            180                 185                 190

Leu Asp Leu Ser Gly Glu Pro His Arg Val Arg Pro Gly Val Leu Glu
        195                 200                 205

Ser Met Ala Leu Leu Cys Ser Ser Val Arg Ser Thr Ser Arg Ser Arg
210                 215                 220

Gln Ile Pro Pro Leu Tyr Gly Ser Val Leu His His Val Leu Gly Leu
225                 230                 235                 240

Ala Glu Arg Asp Cys Ile Leu Phe Asp Thr Asp Ser Asn Tyr Ser Ser
                245                 250                 255

Tyr Thr His Arg Val Leu Glu Gln Asp Arg Asn Arg Ala Asp Gln Ser
            260                 265                 270

Leu Phe Ser Ile Asp Leu Glu Tyr Val His Leu Glu Leu Ile Ala
        275                 280                 285

Leu Gly Tyr Ser Asp Glu Asp Asp Glu Asp Leu Asp Asn Phe Phe
290                 295                 300

<210> SEQ ID NO 57
<211> LENGTH: 256
<212> TYPE: PRT
<213> ORGANISM: Cereal yellow dwarf virus

<400> SEQUENCE: 57

Met Phe Ile Ala Gln Pro Cys Gly Arg Val Leu Val Phe Asp Val Ala
1               5                   10                  15

Ser Arg Thr Pro Ser Phe Phe Thr Arg Tyr Ser Val Glu Leu Ser Leu
            20                  25                  30

Arg Val Leu Asp Pro Phe Phe Thr Arg Ala Val Thr Asp Phe Arg Tyr
        35                  40                  45

```
Thr Gln Asn Glu Ile Asp Leu Phe Cys Val Ser Leu Gly Phe Leu Leu
 50                  55                  60
Pro Ile Leu Leu Thr Gly Glu Ser Tyr Ser Trp Arg Gly His Leu Asn
 65                  70                  75                  80
Leu Pro Leu Ser Tyr Thr Glu Leu Leu Val Arg Trp Gly Leu Ala Val
                 85                  90                  95
Gly Tyr Phe Pro Thr Phe Ser Thr Asp Gly Asp Ile Arg Gln Asn Pro
            100                 105                 110
Glu Leu Arg Ile Asp Leu Ser Thr Met Ser Thr Arg Ser Phe Tyr Glu
        115                 120                 125
Gln Phe Leu Leu Arg Tyr Asn Thr Ser Gly Leu Ala Lys Ala Ile Val
    130                 135                 140
Gly Gln Gln Glu Cys Phe Gln Ser Gly Met Glu Ser Phe Lys Arg Phe
145                 150                 155                 160
Leu His Tyr Arg Leu Thr Cys Phe Glu Ser Cys Leu Pro Arg Pro Arg
                165                 170                 175
Trp Glu Ser Pro Leu Ala Pro Gly Pro Tyr Leu Asp Arg Ala Phe Glu
            180                 185                 190
Ala Thr Leu Leu Gly Arg Met Val Gly His Asn Gln Leu Leu Phe Thr
        195                 200                 205
Gly Leu Ser Ser Asp Ile Thr Arg Tyr Tyr Asn Glu Leu Val Val Glu
    210                 215                 220
Gly Val Pro Val Ala Phe Trp Asp Ala Ala Gly Ile Thr Leu His His
225                 230                 235                 240
Ala Gly Glu Glu Tyr Phe Ser Asn Ser Tyr Ile Gln Lys Ile Leu Gln
                245                 250                 255

<210> SEQ ID NO 58
<211> LENGTH: 519
<212> TYPE: DNA
<213> ORGANISM: Tomato bushy stunt virus

<400> SEQUENCE: 58
atggaacgag ctatacaagg aaacgacgct agggaacaag ctaacagtga acgttgggat      60
ggaggatcag gaggtaccac ttctcccttc aaacttcctg acgaaagtcc gagttggact     120
gagtggcggc tacataacga tgagacgaat tcgaatcaag ataatcccct tggtttcaag     180
gaaagctggg gtttcgggaa agttgtattt aagagatatc tcagatacga caggacggaa     240
gcttcactgc acagagtcct tggatcttgg acgggagatt cggttaacta tgcagcatct     300 cgattttcg gtttcgacca gatcggatgt acctatagta ttcggtttcg aggagttagt     360
atcaccgttt ctggagggtc gcgaactctt cagcatctct gtgagatggc aattcggtct     420
aagcaagaac tgctacagct tgccccaatc gaagtggaaa gtaatgtatc aagaggatgc     480
cctgaaggta ctgagacctt cgaaaaagaa agcgagtaa                            519

<210> SEQ ID NO 59
<211> LENGTH: 351
<212> TYPE: DNA
<213> ORGANISM: Tomato yellow leaf curl virus

<400> SEQUENCE: 59
atgtgggatc cacttctaaa tgaatttcct gaatctgttc acggatttcg ttgtatgtta      60
gctattaaat atttgcagtc cgttgaggaa acttacgagc ccaatacatt gggccacgat     120
ttaattaggg atcttatatc tgttgtaagg gcccgtgact atgtcgaagc gaccaggcga    180
```

```
tataatcatt tccacgcccg cctcgaaggt tcgccgaagg ctgaacttcg acagcccata    240
cagcagccgt gctgctgtcc ccattgtcca aggcacaaac aagcgacgat catggacgta    300
caggcccatg taccggaagc ccagaatata cagaatgtat cgaagccctg a             351
```

<210> SEQ ID NO 60
<211> LENGTH: 1056
<212> TYPE: DNA
<213> ORGANISM: Turnip crinkle virus

<400> SEQUENCE: 60

```
atggaaaatg atcctagagt ccgaaagttc gcatccgagg gcgcccaatg ggcgataaag     60
tggcagaaga agggctggtc atccctaacc agcagacaga aacagaccgc ccgcgcagcg    120
atggggatca agctctcccc tgtggcgcaa cctgtgcaga aagtgactcg actgagtgct    180
ccggtggctc tcgcctaccg cgaggtttcc acccagcctc gggtttctac tgccagggac    240
ggcataacca aagcggttc tgaactgatc acaaccctga agaagaacac tgacactgaa    300
cctaagtaca ccacagctgt gcttaaccca agcgaacccg gaacattcaa ccaactcatc    360
aaggaggcgg cccagtatga aaaataccga ttcacgtcac tcagatttag gtactctccc    420 atgagcccctt caaccaccgg gggcaaggtg gctctggcat tcgaccgaga cgctgccaaa    480
cctccgccca cgacctcgc ttccctctac aacatagagg gttgtgtatc tagcgtgccc     540
tggacagggt ttatttgac cgtcccaaca gattctactg accgctttgt ggcggatggt    600
atcagcgatc caaagcttgt caatttcggc aagctcatca tggccaccta tggccaagga    660
gccaatgatg ccgcccaact cggtgaagtg cgagtcgagt acaccgtgca gctcaagaac    720
agaactggct caaccagcga cgcccagatt ggggacttcg cgggtgttaa ggacggaccc    780
aggttggtct cgtggtccaa gaccaaggga acagctgggt gggagcacga ttgtcatttt    840
ctcggaaccg gaaacttctc gttgacactg ttctacgaga aggcgcccgt ttcggggcta    900
gaaaacgcag acgcctctga cttctcggtc ctggagaag ccgcagcagg tagtgtccaa    960
tgggctggag tgaaggtagc agaaagggga caaagcgtga aaatggtcac aactgaggag   1020
cagccaaggg gaaaatggca agcactcagg attag                             1056
```

<210> SEQ ID NO 61
<211> LENGTH: 912
<212> TYPE: DNA
<213> ORGANISM: Pea mosaic virus

<400> SEQUENCE: 61

```
atgcacggaa ttgagcagcc tcaactaccg ctagattacg ttcaccgttg cgcatcaacc     60
tccttcttgc tcgcatcact agatggcctc ctttctgaag cccgtgaact ctcagggcct    120
ctggctctca ttacttctag ctattactta cttgtttcta ttgccctctg ctgggcaatc    180
cctggatcct tctggtatag gcctggctgc tggttgcagc cagtctcagg gcggaatctc    240
atcttttgcg gccctaccga ggccttgcaa cgattccgtc tgtacgctgc cagacttggg    300
ttggtcctgt cagagaactg cccaagacac ggccaatcag cagcaatcac ccttcaatca    360
tactgggcac ttcctaacaa catctggatg gacatggccc aattggactt gctcaccttc    420
tcaatgccaa ttgctaatac atttgcctac ttggcagatt gtgaagcaag atttcctcct    480
attgttgaag gagtgggatc tgcttactat gtgccaacgc tgctcggact tactcaccaa    540
gaccccaggc tttatcttgc gcttcgcagg agaaaaccttg atcttagtgg cgaacctcat    600
```

```
agagttcgtc ctggtgtcct ggagtctatg gctttgctct gttctagtgt acgtagcaca    660
agccgttcca ggcaaattcc tcctttatat ggcagcgttt tgcaccacgt tttgggcctg    720
gccgagagag actgcatcct ctttgatacg gatagtaact actcctctta cactcatcgg    780
gttcttgaac aagaccggaa tcgggctgat cagtcattgt ttagcattga cttggaatat    840
gttcatgacc tggagcttat tgccctgggt tactctgatg aagatgatga agatcttgat    900
aacttcttct ag                                                        912
```

<210> SEQ ID NO 62  
<211> LENGTH: 771  
<212> TYPE: DNA  
<213> ORGANISM: Cereal yellow dwarf virus

<400> SEQUENCE: 62

```
atgttcatcg cccaaccttg cgggcgagtt cttgtgttcg acgtcgcctc ccgcacgcca     60
tcgttcttca ctcgttatag tgttgaactc tcgctccgtg ttctagaccc attcttcacg    120
cgagcagtaa cagatttccg atacacccaa aatgaaatcg atttattttg tgtgtctctt    180
ggctttctgt tgccaattct cctcacagga gaatcttact cttggcgcgg tcacctcaac    240 ctccccttt cttacaccga attacttgtt cgatgggggc tcgcagtggg gtacttccct    300
accttctcca ctgatggtga cattcgacag aacccagaac tccgcatcga cctgtccacc    360
atgtcaaccc gctctttcta cgagcagttc ctactcagat ataacacgag tgggttggca    420
aaagctatcg tcggacagca agagtgcttt caaagcggca tggagtcttt taaaagattc    480
ctacactacc gcctcacgtg ctttgaaagc tgccttccac gacctcgttg ggaaagtcct    540
ttggctcctg gtccttatct ggacagggct tttgaggcaa ctcttctcgg ccgtatggtc    600
ggtcataacc aactactctt taccggtttg tcttctgata tcactaggta ttataacgag    660
ttggttgtgg aaggcgtgcc ggtggctttt tgggacgctg ccggcattac tttgcatcac    720
gctggtgaag aatatttttc gaattcttac attcaaaaga ttcttcaatg a             771
```

<210> SEQ ID NO 63  
<211> LENGTH: 389  
<212> TYPE: PRT  
<213> ORGANISM: Arabidopsis thaliana

<400> SEQUENCE: 63

```
Met Val Ile Ala Ala Val Ile Val Pro Leu Gly Leu Leu Phe
 1               5                  10                  15

Ile Ser Gly Leu Ala Val Asn Leu Phe Gln Ala Val Cys Tyr Val Leu
                20                  25                  30

Ile Arg Pro Leu Ser Lys Asn Thr Tyr Arg Lys Ile Asn Arg Val Val
            35                  40                  45

Ala Glu Thr Leu Trp Leu Glu Leu Val Trp Ile Val Asp Trp Trp Ala
        50                  55                  60

Gly Val Lys Ile Gln Val Phe Ala Asp Asn Glu Thr Phe Asn Arg Met
    65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
```

```
            130                 135                 140
Lys Asp Glu Ser Thr Leu Lys Ser Gly Leu Gln Arg Leu Ser Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Ile Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
210                 215                 220

Val Thr Ile Pro Lys Thr Ser Pro Pro Thr Met Leu Arg Leu Phe
225                 230                 235                 240

Lys Gly Gln Pro Ser Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Thr
                325                 330                 335

Ile Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
        355                 360                 365

Ala Lys Pro Lys Asp Asn His His Pro Glu Ser Ser Ser Gln Thr Glu
370                 375                 380

Thr Glu Lys Glu Lys
385

<210> SEQ ID NO 64
<211> LENGTH: 281
<212> TYPE: PRT
<213> ORGANISM: Limnanthes alba

<400> SEQUENCE: 64

Met Ala Lys Thr Arg Thr Ser Ser Leu Arg Asn Arg Arg Gln Leu Lys
1               5                   10                  15

Thr Ala Val Ala Ala Thr Ala Asp Asp Asp Lys Asp Gly Ile Phe Met
            20                  25                  30

Val Leu Leu Ser Cys Phe Lys Ile Phe Val Cys Phe Ala Ile Val Leu
        35                  40                  45

Ile Thr Ala Val Ala Trp Gly Leu Ile Met Val Leu Leu Pro Trp
    50                  55                  60

Pro Tyr Met Arg Ile Arg Leu Gly Asn Leu Tyr Gly His Ile Ile Gly
65                  70                  75                  80

Gly Leu Val Ile Trp Leu Tyr Gly Ile Pro Ile Glu Ile Gln Gly Ser
                85                  90                  95

Glu His Thr Lys Lys Arg Ala Ile Tyr Ile Ser Asn His Ala Ser Pro
            100                 105                 110
```

```
Ile Asp Ala Phe Phe Val Met Trp Leu Ala Pro Ile Gly Thr Val Gly
            115                 120                 125

Val Ala Lys Lys Glu Val Ile Trp Tyr Pro Leu Leu Gly Gln Leu Tyr
130                 135                 140

Thr Leu Ala His His Ile Arg Ile Asp Arg Ser Asn Pro Ala Ala Ala
145                 150                 155                 160

Ile Gln Ser Met Lys Glu Ala Val Arg Val Ile Thr Glu Lys Asn Leu
                165                 170                 175

Ser Leu Ile Met Phe Pro Glu Gly Thr Arg Ser Gly Asp Gly Arg Leu
            180                 185                 190

Leu Pro Phe Lys Lys Gly Phe Val His Leu Ala Leu Gln Ser His Leu
                195                 200                 205

Pro Ile Val Pro Met Ile Leu Thr Gly Thr His Leu Ala Trp Arg Lys
            210                 215                 220

Gly Thr Phe Arg Val Arg Pro Val Pro Ile Thr Val Lys Tyr Leu Pro
225                 230                 235                 240

Pro Ile Asn Thr Asp Asp Trp Thr Val Asp Lys Ile Asp Asp Tyr Val
                245                 250                 255

Lys Met Ile His Asp Ile Tyr Val Arg Asn Leu Pro Ala Ser Gln Lys
            260                 265                 270

Pro Leu Gly Ser Thr Asn Arg Ser Lys
            275                 280

<210> SEQ ID NO 65
<211> LENGTH: 303
<212> TYPE: PRT
<213> ORGANISM: Saccharomyces cerevisiae

<400> SEQUENCE: 65

Met Ser Val Ile Gly Arg Phe Leu Tyr Tyr Leu Arg Ser Val Leu Val
1               5                   10                  15

Val Leu Ala Leu Ala Gly Cys Gly Phe Tyr Gly Val Ile Ala Ser Ile
            20                  25                  30

Leu Cys Thr Leu Ile Gly Lys Gln His Leu Ala Gln Trp Ile Thr Ala
            35                  40                  45

Arg Cys Phe Tyr His Val Met Lys Leu Met Leu Gly Leu Asp Val Lys
50                  55                  60

Val Val Gly Glu Glu Asn Leu Ala Lys Lys Pro Tyr Ile Met Ile Ala
65                  70                  75                  80

Asn His Gln Ser Thr Leu Asp Ile Phe Met Leu Gly Arg Ile Phe Pro
                85                  90                  95

Pro Gly Cys Thr Val Thr Ala Lys Lys Ser Leu Lys Tyr Val Pro Phe
            100                 105                 110

Leu Gly Trp Phe Met Ala Leu Ser Gly Thr Tyr Phe Leu Asp Arg Ser
            115                 120                 125

Lys Arg Gln Glu Ala Ile Asp Thr Leu Asn Lys Gly Leu Glu Asn Val
            130                 135                 140

Lys Lys Asn Lys Arg Ala Leu Trp Val Phe Pro Glu Gly Thr Arg Ser
145                 150                 155                 160

Tyr Thr Ser Glu Leu Thr Met Leu Pro Phe Lys Lys Gly Ala Phe His
                165                 170                 175

Leu Ala Gln Gln Gly Lys Ile Pro Ile Val Pro Val Val Val Ser Asn
            180                 185                 190

Thr Ser Thr Leu Val Ser Pro Lys Tyr Gly Val Phe Asn Arg Gly Cys
            195                 200                 205
```

```
Met Ile Val Arg Ile Leu Lys Pro Ile Ser Thr Glu Asn Leu Thr Lys
            210                 215                 220

Asp Lys Ile Gly Glu Phe Ala Glu Lys Val Arg Asp Gln Met Val Asp
225                 230                 235                 240

Thr Leu Lys Glu Ile Gly Tyr Ser Pro Ala Ile Asn Asp Thr Thr Leu
            245                 250                 255

Pro Pro Gln Ala Ile Glu Tyr Ala Ala Leu Gln His Asp Lys Lys Val
            260                 265                 270

Asn Lys Lys Ile Lys Asn Glu Pro Val Pro Ser Val Ser Ile Ser Asn
            275                 280                 285

Asp Val Asn Thr His Asn Glu Gly Ser Ser Val Lys Lys Met His
            290                 295                 300

<210> SEQ ID NO 66
<211> LENGTH: 373
<212> TYPE: PRT
<213> ORGANISM: Micromonas pusilla

<400> SEQUENCE: 66

Met Thr Pro Tyr Gln Trp Phe Asn Val Val Ser Ser Leu Gly Tyr Val
1               5                   10                  15

Leu Phe Thr Ala Thr Thr Ser Thr Val Thr Met Leu Val Pro Ala Ile
            20                  25                  30

Ile Leu Leu Arg Pro Val Ser Ala Asn Leu Tyr Ala Arg Cys Thr Ser
            35                  40                  45

Trp Ile Phe Ala Cys Trp Trp Thr Ser Cys Leu Phe Ile Thr Glu Arg
    50                  55                  60

Leu Asn Gly Val Lys Val Arg Val Thr Gly Asp Ala Leu Pro Leu Asn
65                  70                  75                  80

Ala Pro Leu Leu Ile Met Ser Asn His Lys Cys Asn Leu Asp Trp Met
                85                  90                  95

Phe Leu Trp Ser Ser Ala Ile Arg Thr Gly Ser Met Phe His Val Gly
            100                 105                 110

Val Phe Lys Ala Val Ala Lys Ser Glu Ile Arg Val Ile Pro Ile Phe
            115                 120                 125

Gly Trp Gly Cys Lys Leu Asn Gly Phe Ala Tyr Val Arg Arg Arg Trp
    130                 135                 140

Ser Ser Asp Ala Ser His Leu Thr Ser Trp Ile Gln Ser Gln Ile Arg
145                 150                 155                 160

Arg Arg Leu Asn Ala Asn Trp Thr Leu Ile Phe Pro Glu Gly Thr Arg
                165                 170                 175

Tyr Thr Asp Arg Asn Lys Glu Arg Ser Asp Leu Ser Cys Ala Lys Asp
            180                 185                 190

Gly Leu Glu Pro Met Ala Gly Glu Ile Leu Arg Pro Arg Thr Lys Gly
        195                 200                 205

Leu Ala Leu Leu Leu Arg Glu Ser Ala Lys Gly Gly Tyr Tyr Arg
    210                 215                 220

Lys Ile Val Asp Met Thr Ile Gln Tyr Thr Ala Asp Gly Lys Pro
225                 230                 235                 240

Leu Lys Gly Ala Ala Leu Gly Thr Arg Cys Phe Gly Gln Leu Ala Lys
                245                 250                 255

Gly Gln Leu Pro Val Ala Thr Cys His Val His Phe Asp Val Phe Ser
            260                 265                 270

His Lys Asp Val Pro Ala Gly Glu Asp Glu Asp Glu Val Glu Ala Trp
```

```
                275                 280                 285
Val Trp Lys Arg Trp Arg Lys Ala Asn Met Leu Glu Ala Cys Ala
    290                 295                 300

Ser Ala Gly Gln Phe Glu Gly Val Arg Glu Trp Ser Thr Ser Gly Thr
305                 310                 315                 320

Ala Val Pro Leu Lys Thr Gln Thr Ala Leu Arg Cys Phe Phe Val Leu
                325                 330                 335

Gln Gly Leu Val Cys Val Gly Val Ala Cys Ser Ser Thr Ala Phe Leu
                340                 345                 350

Ala Tyr Val Ala Cys Ala Ala Val Gly Ala Ala Val Ile Ala Gln Thr
                355                 360                 365

Asp Pro Ala Trp Trp
                370

<210> SEQ ID NO 67
<211> LENGTH: 314
<212> TYPE: PRT
<213> ORGANISM: Mortierella alpina

<400> SEQUENCE: 67

Met Ser Ile Gly Ser Ser Asn Pro Val Leu Leu Ala Ala Ile Pro Phe
1               5                   10                  15

Val Tyr Leu Phe Val Leu Pro Arg Val Leu Ala Phe Leu Pro Gln Lys
                20                  25                  30

Ala Gln Phe Leu Ala Lys Cys Ile Val Val Leu Ile Ala Thr Leu Ile
                35                  40                  45

Met Ser Val Ala Gly Cys Phe Ile Ser Ile Val Cys Ala Leu Leu Asp
                50                  55                  60

Lys Arg Tyr Val Ile Asn Tyr Val Val Ser Arg Leu Phe Ser Phe Leu
65                  70                  75                  80

Ala Ala Arg Pro Cys Gly Val Thr Tyr Lys Ile Val Gly Glu His
                85                  90                  95

Leu Asp Lys Tyr Pro Ala Ile Val Val Cys Asn His Gln Ser Ser Met
                100                 105                 110

Asp Met Met Val Leu Gly Arg Val Phe Pro Lys His Cys Val Val Met
                115                 120                 125

Ala Lys Lys Glu Leu Leu Tyr Phe Pro Phe Leu Gly Met Phe Met Lys
                130                 135                 140

Leu Ser Asn Ala Ile Phe Ile Asp Arg Lys Asn His Lys Lys Ala Ile
145                 150                 155                 160

Glu Ser Thr Thr Gln Ala Val Ala Asp Met Lys Lys His Asn Ser Gly
                165                 170                 175

Ile Trp Ile Phe Pro Glu Gly Thr Arg Ser Arg Leu Asp Lys Ala Asp
                180                 185                 190

Leu Leu Pro Phe Lys Lys Gly Ala Phe His Leu Ala Ile Gln Ala Gln
                195                 200                 205

Leu Pro Ile Leu Pro Ile Ile Ser Gln Gly Tyr Ser His Ile Tyr Asp
                210                 215                 220

Ser Ser Lys Arg Tyr Phe Pro Gly Gly Glu Leu Glu Ile Arg Val Leu
225                 230                 235                 240

Glu Pro Ile Pro Thr Thr Gly Leu Thr Thr Asp Asp Val Asn Asp Leu
                245                 250                 255

Met Asp Lys Thr Arg Asn Leu Met Leu Lys His Leu Lys Glu Met Asp
                260                 265                 270
```

```
Ser Gln Tyr Ser Ser Ser Thr Ala Glu Asn Gly Ser Thr His Ile Asp
            275                 280                 285

Ala Asp Ile Ala Lys Ser Thr Ala Thr Ser Ile Gly Asn Thr Asp Asp
290                 295                 300

Ala Ile Thr Lys Arg Arg Thr Pro Lys Glu
305                 310

<210> SEQ ID NO 68
<211> LENGTH: 391
<212> TYPE: PRT
<213> ORGANISM: Braccisa napus

<400> SEQUENCE: 68

Met Ala Met Ala Ala Ala Val Ile Val Pro Leu Gly Ile Leu Phe
1               5                   10                  15

Phe Ile Ser Gly Leu Val Val Asn Leu Leu Gln Ala Val Cys Tyr Val
                20                  25                  30

Leu Ile Arg Pro Leu Ser Lys Asn Thr Tyr Arg Lys Ile Asn Arg Val
            35                  40                  45

Val Ala Glu Thr Leu Trp Leu Glu Leu Val Trp Ile Val Asp Trp Trp
50                  55                  60

Ala Gly Val Lys Ile Gln Val Phe Ala Asp Asp Glu Thr Phe Asn Arg
65                  70                  75                  80

Met Gly Lys Glu His Ala Leu Val Val Cys Asn His Arg Ser Asp Ile
                85                  90                  95

Asp Trp Leu Val Gly Trp Ile Leu Ala Gln Arg Ser Gly Cys Leu Gly
            100                 105                 110

Ser Ala Leu Ala Val Met Lys Lys Ser Ser Lys Phe Leu Pro Val Ile
        115                 120                 125

Gly Trp Ser Met Trp Phe Ser Glu Tyr Leu Phe Leu Glu Arg Asn Trp
130                 135                 140

Ala Lys Asp Glu Ser Thr Leu Lys Ser Gly Leu Gln Arg Leu Asn Asp
145                 150                 155                 160

Phe Pro Arg Pro Phe Trp Leu Ala Leu Phe Val Glu Gly Thr Arg Phe
                165                 170                 175

Thr Glu Ala Lys Leu Lys Ala Ala Gln Glu Tyr Ala Ala Ser Ser Gln
            180                 185                 190

Leu Pro Val Pro Arg Asn Val Leu Ile Pro Arg Thr Lys Gly Phe Val
        195                 200                 205

Ser Ala Val Ser Asn Met Arg Ser Phe Val Pro Ala Ile Tyr Asp Met
210                 215                 220

Thr Val Ala Ile Pro Lys Thr Ser Pro Pro Thr Met Leu Arg Leu
225                 230                 235                 240

Phe Lys Gly Gln Pro Ser Val Val His Val His Ile Lys Cys His Ser
                245                 250                 255

Met Lys Asp Leu Pro Glu Ser Asp Ala Ile Ala Gln Trp Cys Arg
            260                 265                 270

Asp Gln Phe Val Ala Lys Asp Ala Leu Leu Asp Lys His Ile Ala Ala
        275                 280                 285

Asp Thr Phe Pro Gly Gln Lys Glu His Asn Ile Gly Arg Pro Ile Lys
        290                 295                 300

Ser Leu Ala Val Val Ser Trp Ala Cys Leu Leu Thr Leu Gly Ala
305                 310                 315                 320

Met Lys Phe Leu His Trp Ser Asn Leu Phe Ser Ser Leu Lys Gly Ile
                325                 330                 335
```

```
Ala Leu Ser Ala Leu Gly Leu Gly Ile Ile Thr Leu Cys Met Gln Ile
            340                 345                 350

Leu Ile Arg Ser Ser Gln Ser Glu Arg Ser Thr Pro Ala Lys Val Ala
            355                 360                 365

Pro Ala Lys Pro Lys Asp Lys His Gln Ser Gly Ser Ser Ser Gln Thr
370                 375                 380

Glu Val Glu Glu Lys Gln Lys
385                 390

<210> SEQ ID NO 69
<211> LENGTH: 390
<212> TYPE: PRT
<213> ORGANISM: Braccisa napus

<400> SEQUENCE: 69

Met Ala Met Ala Ala Val Ile Val Pro Leu Gly Ile Leu Phe Phe
1               5                   10                  15

Ile Ser Gly Leu Val Val Asn Leu Leu Gln Ala Ile Cys Tyr Val Leu
            20                  25                  30

Ile Arg Pro Leu Ser Lys Asn Thr Tyr Arg Lys Ile Asn Arg Val Val
            35                  40                  45

Ala Glu Thr Leu Trp Leu Glu Leu Val Trp Ile Val Asp Trp Trp Ala
50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
            85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
            115                 120                 125

Trp Ser Met Trp Phe Ser Glu Tyr Leu Phe Leu Glu Arg Asn Trp Ala
            130                 135                 140

Lys Asp Glu Ser Thr Leu Lys Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Val Pro Arg Asn Val Leu Ile Pro Arg Thr Lys Gly Phe Val Ser
            195                 200                 205

Ala Val Ser Asn Met Arg Ser Phe Val Pro Ala Ile Tyr Asp Met Thr
210                 215                 220

Val Ala Ile Pro Lys Thr Ser Pro Pro Thr Met Leu Arg Leu Phe
225                 230                 235                 240

Lys Gly Gln Pro Ser Val Val His Val Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
            275                 280                 285

Thr Phe Pro Gly Gln Gln Glu Gln Asn Ile Gly Arg Pro Ile Lys Ser
            290                 295                 300

Leu Ala Val Val Leu Ser Trp Ser Cys Leu Leu Ile Leu Gly Ala Met
```

```
                305                 310                 315                 320

Lys Phe Leu His Trp Ser Asn Leu Phe Ser Ser Trp Lys Gly Ile Ala
                325                 330                 335

Phe Ser Ala Leu Gly Leu Gly Ile Ile Thr Leu Cys Met Gln Ile Leu
                340                 345                 350

Ile Arg Ser Ser Gln Ser Glu Arg Ser Thr Pro Ala Lys Val Val Pro
                355                 360                 365

Ala Lys Pro Lys Asp Asn His Asn Asp Ser Gly Ser Ser Ser Gln Thr
                370                 375                 380

Glu Val Glu Lys Gln Lys
385                 390

<210> SEQ ID NO 70
<211> LENGTH: 361
<212> TYPE: PRT
<213> ORGANISM: Phytophthora infestans

<400> SEQUENCE: 70

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
                20                  25                  30

Tyr Tyr Thr Val Arg Cys Leu Val Ile Ala Val Ala Leu Thr Phe Gly
                35                  40                  45

Leu Asn Tyr Ala Arg Ala Leu Pro Glu Val Glu Ser Phe Trp Ala Leu
                50                  55                  60

Asp Ala Ala Leu Cys Thr Gly Tyr Ile Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
                100                 105                 110

Ile Leu Thr Pro Phe Glu Ser Trp Lys Leu Thr His Arg His His His
                115                 120                 125

Lys Asn Thr Gly Asn Ile Asp Arg Asp Glu Val Phe Tyr Pro Gln Arg
                130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
                180                 185                 190

Val Val Ile Ser Leu Leu Ala His Phe Phe Val Ala Gly Leu Ser Ile
                195                 200                 205

Tyr Leu Ser Leu Gln Leu Gly Leu Lys Thr Met Ala Ile Tyr Tyr Tyr
                210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
                260                 265                 270

Ile Asp Asn Leu Ser His Asn Ile Gly Thr His Gln Ile His His Leu
                275                 280                 285
```

```
Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Glu Ala Lys Ala Ala Thr
            340                 345                 350

Glu Ala Ala Ala Lys Thr Lys Ser Thr
            355                 360

<210> SEQ ID NO 71
<211> LENGTH: 418
<212> TYPE: PRT
<213> ORGANISM: Thalassiosira pseudonana

<400> SEQUENCE: 71

Met Tyr Arg Leu Thr Ser Thr Phe Leu Ile Ala Leu Ala Phe Ser Ser
1               5                   10                  15

Ser Ile Asn Ala Phe Ser Pro Gln Arg Pro Arg Thr Ile Thr Lys
            20                  25                  30

Ser Lys Val Gln Ser Thr Val Leu Pro Ile Pro Thr Lys Asp Asp Leu
        35                  40                  45

Asn Phe Leu Gln Pro Gln Leu Asp Glu Asn Asp Leu Tyr Leu Asp Asp
    50                  55                  60

Val Asn Thr Pro Pro Arg Ala Gly Thr Ile Met Lys Met Leu Pro Lys
65                  70                  75                  80

Glu Thr Phe Asn Ile Asp Thr Ala Thr Ser Leu Gly Tyr Phe Gly Met
                85                  90                  95

Asp Met Ala Ala Val Val Ser Ser Met Thr Leu Leu Asn Ala Ile Val
            100                 105                 110

Thr Ser Asp Gln Tyr His Ala Leu Pro Leu Pro Leu Gln Ala Ala Thr
        115                 120                 125

Val Ile Pro Phe Gln Leu Leu Ala Gly Phe Ala Met Trp Cys Met Trp
    130                 135                 140

Cys Ile Gly His Asp Ala Gly His Ser Thr Val Ser Lys Thr Lys Trp
145                 150                 155                 160

Ile Asn Arg Val Val Gly Glu Val Ala His Ser Val Val Cys Leu Thr
                165                 170                 175

Pro Phe Val Pro Trp Gln Met Ser His Arg Lys His His Leu Asn His
            180                 185                 190

Asn His Ile Glu Lys Asp Tyr Ser His Lys Trp Tyr Ser Arg Asp Glu
        195                 200                 205

Phe Asp Asp Ile Pro Gln Leu Tyr Lys Thr Phe Gly Tyr Asn Pro Arg
    210                 215                 220

Met Met Gln Leu Pro Phe Leu Tyr Phe Met Tyr Leu Ala Leu Gly Ile
225                 230                 235                 240

Pro Asp Gly Gly His Val Val Phe Tyr Gly Arg Met Trp Glu Gly Val
                245                 250                 255

Ser Leu Gln Lys Lys Phe Asp Ala Ala Ile Ser Val Ala Val Ser Cys
            260                 265                 270

Ala Thr Ala Gly Ser Leu Trp Met Asn Met Gly Thr Ala Asp Phe Thr
        275                 280                 285

Val Val Cys Met Val Pro Trp Leu Val Leu Ser Trp Trp Leu Phe Met
    290                 295                 300
```

```
Val Thr Tyr Leu Gln His His Ser Glu Asp Gly Lys Leu Tyr Thr Asp
305                 310                 315                 320

Glu Thr Phe Thr Phe Glu Lys Gly Ala Phe Glu Thr Val Asp Arg Ser
            325                 330                 335

Tyr Gly Lys Leu Ile Asn Arg Met Ser His His Met Met Asp Gly His
            340                 345                 350

Val Val His His Leu Phe Phe Glu Arg Val Pro His Tyr Arg Leu Glu
        355                 360                 365

Ala Ala Thr Glu Ala Leu Val Lys Gly Met Asp Glu Thr Gly Gln Lys
    370                 375                 380

His Leu Tyr Lys Tyr Ile Asp Thr Pro Asp Phe Asn Ala Glu Ile Val
385                 390                 395                 400

Asn Gly Phe Arg Asp Asn Trp Phe Leu Val Glu Glu Glu Asn Ile Lys
                405                 410                 415

Arg Glu

<210> SEQ ID NO 72
<211> LENGTH: 363
<212> TYPE: PRT
<213> ORGANISM: Pythium irregulare

<400> SEQUENCE: 72

Met Ala Ser Thr Ser Ala Ala Gln Asp Ala Pro Tyr Glu Phe Pro
1               5                   10                  15

Ser Leu Thr Glu Ile Lys Arg Ala Leu Pro Ser Glu Cys Phe Glu Ala
            20                  25                  30

Ser Val Pro Leu Ser Leu Tyr Tyr Thr Ala Arg Ser Leu Ala Leu Ala
        35                  40                  45

Gly Ser Leu Ala Val Ala Leu Ser Tyr Ala Arg Ala Leu Pro Leu Val
    50                  55                  60

Gln Ala Asn Ala Leu Leu Asp Ala Thr Leu Cys Thr Gly Tyr Val Leu
65                  70                  75                  80

Leu Gln Gly Ile Val Phe Trp Gly Phe Phe Thr Val Gly His Asp Cys
                85                  90                  95

Gly His Gly Ala Phe Ser Arg Ser His Val Leu Asn Phe Ser Val Gly
            100                 105                 110

Thr Leu Met His Ser Ile Ile Leu Thr Pro Phe Glu Ser Trp Lys Leu
        115                 120                 125

Ser His Arg His His His Lys Asn Thr Gly Asn Ile Asp Lys Asp Glu
    130                 135                 140

Ile Phe Tyr Pro Gln Arg Glu Ala Asp Ser His Pro Val Ser Arg His
145                 150                 155                 160

Leu Val Met Ser Leu Gly Ser Ala Trp Phe Ala Tyr Leu Phe Ala Gly
                165                 170                 175

Phe Pro Pro Arg Thr Met Asn His Phe Asn Pro Trp Glu Ala Met Tyr
            180                 185                 190

Val Arg Arg Val Ala Ala Val Ile Ile Ser Leu Gly Val Leu Phe Ala
        195                 200                 205

Phe Ala Gly Leu Tyr Ser Tyr Leu Thr Phe Val Leu Gly Phe Thr Thr
    210                 215                 220

Met Ala Ile Tyr Tyr Phe Gly Pro Leu Phe Ile Phe Ala Thr Met Leu
225                 230                 235                 240

Val Val Thr Thr Phe Leu His His Asn Asp Glu Glu Thr Pro Trp Tyr
                245                 250                 255
```

```
Ala Asp Ser Glu Trp Thr Tyr Val Lys Gly Asn Leu Ser Ser Val Asp
            260                 265                 270

Arg Ser Tyr Gly Ala Leu Ile Asp Asn Leu Ser His Asn Ile Gly Thr
        275                 280                 285

His Gln Ile His His Leu Phe Pro Ile Ile Pro His Tyr Lys Leu Asn
    290                 295                 300

Asp Ala Thr Ala Ala Phe Ala Lys Ala Phe Pro Glu Leu Val Arg Lys
305                 310                 315                 320

Asn Ala Ala Pro Ile Ile Pro Thr Phe Phe Arg Met Ala Ala Met Tyr
                325                 330                 335

Ala Lys Tyr Gly Val Val Asp Thr Asp Ala Lys Thr Phe Thr Leu Lys
            340                 345                 350

Glu Ala Lys Ala Ala Ala Lys Thr Lys Ser Ser
            355                 360
```